United States Patent
Hendricks et al.

(10) Patent No.: US 11,312,727 B1
(45) Date of Patent: Apr. 26, 2022

(54) MACROCYCLIC FLU ENDONUCLEASE INHIBITORS

(71) Applicant: Janssen BioPharma, Inc., South San Francisco, CA (US)

(72) Inventors: Robert Than Hendricks, San Carlos, CA (US); Antitsa Dimitrova Stoycheva, Half Moon Bay, CA (US); Jean-François Bonfanti, Andé (FR); Pierre Jean-Marie Bernard Raboisson, Wavre (BE); Jérôme Michel Claude Fortin, Igoville (FR); Guillaume Jean Maurice Mercey, Montaure (FR)

(73) Assignee: Janssen BioPharma, Inc., South San Francisco, CA (US)

( * ) Notice: Subject to any disclaimer, the term of this patent is extended or adjusted under 35 U.S.C. 154(b) by 0 days.

(21) Appl. No.: 17/284,162

(22) PCT Filed: Oct. 9, 2019

(86) PCT No.: PCT/IB2019/058591
§ 371 (c)(1),
(2) Date: Apr. 9, 2021

(87) PCT Pub. No.: WO2020/075080
PCT Pub. Date: Apr. 16, 2020

Related U.S. Application Data

(60) Provisional application No. 62/744,060, filed on Oct. 10, 2018.

(51) Int. Cl.
| | |
|---|---|
| *C07D 498/22* | (2006.01) |
| *A61P 31/16* | (2006.01) |
| *C07D 495/22* | (2006.01) |
| *C07D 498/18* | (2006.01) |
| *C07D 471/22* | (2006.01) |
| *C07D 471/18* | (2006.01) |

(52) U.S. Cl.
CPC ............ *C07D 498/22* (2013.01); *A61P 31/16* (2018.01); *C07D 471/18* (2013.01); *C07D 471/22* (2013.01); *C07D 495/22* (2013.01); *C07D 498/18* (2013.01)

(58) Field of Classification Search
CPC .. C07D 498/22; C07D 471/18; C07D 471/22; C07D 495/22
See application file for complete search history.

(56) References Cited

U.S. PATENT DOCUMENTS

2018/0057501 A1   3/2018   Jain et al.

FOREIGN PATENT DOCUMENTS

| EP | 2444400 A1 | 4/2012 |
| EP | 2620436 A1 | 7/2013 |
| WO | 2015038660 A1 | 3/2015 |

OTHER PUBLICATIONS

International Search Report and Written Opinion of the International Searching Authority for PCT Application PCT/IB2019/058591 (11 pages).

*Primary Examiner* — Susanna Moore

(57) ABSTRACT

The present invention relates to macrocyclic pyridotriazine derivatives of formula (I) and the pharmaceutically acceptable salts, solvates or polymorph thereof, and the use of such compounds as a medicament, in particular in the prevention and/or treatment of viral infections caused by viruses belonging to the Orthomyxoviridae family. The present invention furthermore relates to pharmaceutical compositions or combination preparations of the compounds, and to the compositions or preparations for use as a medicament, more preferably for the prevention or treatment of viral infections caused by viruses belonging to the Orthomyxoviridae family.

16 Claims, No Drawings
Specification includes a Sequence Listing.

SEQUENCE LISTING

<160> NUMBER OF SEQ ID NOS: 1

<210> SEQ ID NO 1
<211> LENGTH: 19
<212> TYPE: RNA
<213> ORGANISM: Artificial Sequence
<220> FEATURE:
<223> OTHER INFORMATION: fluorescent oligoribonucleotide substrate

<400> SEQUENCE: 1
auuuuguuuu uaauauuuc                                               19

MACROCYCLIC FLU ENDONUCLEASE INHIBITORS

CROSS-REFERENCE TO RELATED APPLICATIONS

This application is a national phase entry of International Application No. PCT/IB2019/058591, filed on Oct. 9, 2019, which claims priority to U.S. Provisional Patent Application No. 62/744,060, filed on Oct. 10, 2018, each of which is incorporated herein in its entirety.

SEQUENCE LISTING

The instant application contains a Sequence Listing which has been submitted electronically in ASCII format and is hereby incorporated by reference in its entirety. This ASCII copy, created on Apr. 7, 2021, is named ALP1004USPCT1_SEQ_Listing.txt and is 493 bytes in size.

FIELD OF THE INVENTION

The present invention relates to macrocyclic compounds, in particular macrocyclic pyridotriazine derivatives and the prodrugs thereof, to methods to prevent or treat influenza viral infections by using said compounds and to said compounds for use as a medicine, more preferably for use as a medicine to treat or prevent influenza viral infections. The present invention also relates to pharmaceutical compositions or combination preparations of the compounds, to the compositions or preparations for use as a medicine, more preferably for the prevention or treatment of influenza viral infections.

BACKGROUND OF THE INVENTION

Influenza is a serious public health problem with high incidence in the human population resulting in regular large-scale morbidity and mortality. According to the WHO the average global burden of annual epidemics may be on the order of 1 billion cases, 3-5 million cases of severe illness and 300,000-500,000 deaths annually. In the US, annual influenza epidemics lead to approximately 30 million outpatient visits, resulting in medical costs of $10 billion annually. Lost earnings due to illness and loss of life represent a cost of over $15 billion annually and the total US economic burden of annual influenza epidemics amounts to over $85 billion.

Pathogens that cause influenza are negative sense, single-stranded RNA viruses, which belong to the family of Orthomyxoviridae. There are three types of influenza viruses: A, B and C. Influenza A viruses are the most common form, which can spread in mammals and birds. The subtypes of influenza A are named by the types of surface proteins hemagglutinin (H) and neuraminidase (N). There are 18 different hemagglutinin and 11 known neuraminidases. Current seasonal influenza viruses found in human are mainly H1N1 and H3N2 subtypes. Influenza B viruses are usually found only in humans. They are not divided into subtypes, but can be further broken down into different strains. Circulating influenza viruses are highly variable each year, and both influenza A and B cause seasonal epidemics all over the world. Influenza C viruses give much milder symptoms, which do not cause epidemics.

All three types of viruses have similar genome structures. The genome comprises 8 segments, encoding 9-11 proteins, depending on the type. Influenza A encodes 11 proteins, which includes the surface proteins (hemagglutinin (HA) and Neuraminidase (NA), the polymerase complex, nucleoprotein (NP), membrane proteins (M1 and M2), and other proteins (NS1, NS2, NEP). The polymerase complex is a heterotrimer composed of three subunits: polymerase acid (PA), polymerase basic 1 (PB1) and polymerase basic 2 (PB2). This polymerase is responsible for replication and transcription of the viral RNA in the nuclei of infected cells. The PA subunit contains the endonuclease active site. The endonuclease activity of the PA cleaves the cellular mRNA. which is then used by the PB1 subunit as a primer for the viral mRNA synthesis.

The most effective way to prevent the disease and/or severe outcomes from the illness is vaccination. However, vaccination comes with several limitations. First, influenza vaccine may be less effective in preventing illness among the elderly, and may only reduce severity of disease and incidence of complications and deaths. In addition, influenza vaccination is most effective when circulating viruses are well-matched with vaccine viruses, and the success of vaccination is largely dependent on the good prediction of the most prevalent virus type of the season. Rapid and continual evolution of influenza viral strains through antigenic drift, coupled with the short-lived nature of vaccine-induced immune responses to current influenza vaccines, means that vaccination with seasonally appropriate strains is required every year for prevention.

The current treatment of influenza uses either direct antiviral drugs, or medicines that reduce influenza-induced symptoms. There are two classes of influenza antiviral drugs available on the market: neuraminidase inhibitors and M2 channel inhibitors.

Neuraminidase inhibitors oseltamivir or zanamivir are the primary antiviral agents recommended for the prevention and treatment of influenza. These are effective against both influenza type A and B viruses. Development of resistance to these antiviral drugs has been identified during treatment of seasonal influenza and in sporadic oseltamivir-resistant 2009 H1N1 virus, but the public health impact has been limited to date. M2 channel inhibitors, such as amantadine and rimantadine (adamantanes), are active against influenza A strains, but not influenza B strains. Adamantane resistance among circulating influenza A viruses increased rapidly worldwide beginning during 2003-2004. Therefore, amantadine and rimantadine are not recommended for antiviral treatment or chemoprophylaxis of currently circulating influenza A virus strains.

In 2009, the novel swine H1N1 strain caused an unexpected influenza pandemic as a result of reassortment of genes from human, pig, and bird's H1N1 viruses. This past pandemic, together with the ongoing circulation of highly pathogenic avian H5N1 strains and the recent emergence of the H7N9 virus, a new reassortant of avian origin isolated in China, and associated with severe respiratory disease with 40% of mortality, which could potentially adapt for human-to-human transmission, highlighted the vulnerability of the world population to novel influenza strains. Although vaccination remains the main prophylactic strategy for controlling influenza infection, to bridge the period before a new vaccine becomes available and to treat the severe influenza cases, as well as to counter the problem of viral resistance, a wider choice of anti-influenza drugs is required. Development of new influenza antivirals has therefore again become a high priority and an unmet medical need.

SUMMARY OF THE INVENTION

The present invention provides macrocyclic pyridotriazine derivatives and the prodrugs thereof, the pharmaceutically acceptable salts and solvates thereof, having activity against influenza virus, in particular influenza A and B strains.

In one aspect, the present invention provides compounds of Formula (I)

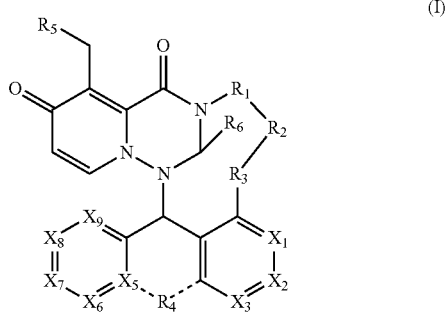

and all possible stereoisomeric forms thereof, wherein:
$R_1$ is C, —$CH_2$—$CH_2$—O—, $C_{3-6}$cycloalkyl, oxetanyl, $C_{1-3}$alkyl-cyclopropyl or $C_{1-3}$alkyl-cyclobutyl, optionally substituted by one or more substituents independently selected from, halo, oxo, $CH_2$-methoxy, $C_{1-4}$alkyl, $C_{1-6}$ cycloalkyl and tetrahydrofuran;
$R_2$ is $C_{1-6}$alkyl, $C_{1-6}$alkyl-O—, $C_{1-6}$alkyl-N—, $C_{2-6}$alkenyl, $C_{2-6}$alkenyl-O— or $C_{2-6}$alkenyl-N-optionally substituted by one or more substituents independently selected from halo, oxo or $C_{1-4}$alkyl;
$R_3$ is C or O optionally substituted by one or more substituents independently selected from halo, oxo and methyl;
or, $R_2$ and $R_3$ together form $C_{2-8}$alkenyl optionally substituted by one or more substituents independently selected from halo, oxo and methyl;
$X_1$ to $X_9$ are each N or C and wherein any of $X_1$ to $X_9$ is C, said C is optionally substituted by one or more substituents independently selected from $C_{1-4}$alkyl, $C_{3-6}$cycloalkyl, $CHF_2$, $CH_2F$, $CF_3$, $OCF_3$, $SCF_3$, $OCH_3$, $SCH_3$, S—(O)$_2$—$CH_3$ or halogen;
the dotted lines are each an optional bond;
$R_4$ is absent, —$CH_2$—$CH_2$—, —O—$CH_2$—, —S—$CH_2$—, S—(O)$_2$—$CH_2$ or cyclopropyl optionally substituted by one or more substituents independently selected from halo, oxo and methyl;
$R_5$ is H, —C(=O)Y, —($CH_2$)—O—(C=O)—Y, —($CH_2$)—O—(C=O)—O—Y, —(CHCH$_3$)—O—(C=O)—Y, —(CHCH$_3$)—O—(C=O)—O—Y, —($CH_2$)—O—(C=O)—NH—Y, —($CH_2$)—O—(C=O)C($R_7$)—NH—($R_8$);
Y is $C_{1-6}$alkyl, $C_{3-6}$cycloalkyl, aryl, heteroaryl, heterocyclyl, $C_{1-4}$alkyl-(O—$R_7$), $C_{1-4}$alkyl-N—($R_7$)($R_8$), $R_7$—O—$R_8$—O—$CH_2$;
and $R_7$ and $R_8$ are independently hydrogen or $C_{1-4}$alkyl;
$R_6$ is H, methyl or $CH_2$—O—$CH_3$;
and the pharmaceutically acceptable salts, polymorphs and solvates thereof.

The invention also relates to a pharmaceutical composition comprising a therapeutically effective amount, in particular an anti-virally effective amount, of the compound of Formula (I) or a stereoisomeric forms thereof or a prodrug thereof, a pharmaceutically acceptable salt, solvate or polymorph thereof, and one or more pharmaceutically acceptable excipients, diluents or carriers.

The invention further relates to a compound of Formula (I) or a stereoisomeric forms thereof or a prodrug thereof or a pharmaceutically acceptable salt, solvate or polymorph thereof, for use as a medicament, in particular for use in the treatment or in the prevention of influenza virus infections, particularly influenza A and/or influenza B virus infections.

Additionally, the invention relates to the use of a compound of Formula (I) or a stereoisomeric forms thereof or a prodrug thereof or a pharmaceutically acceptable salt, solvate or polymorph thereof, in combination with an additional antiviral for use in the treatment or prevention of influenza virus infections, particularly influenza A and/or influenza B virus infections.

The invention also relates to a product comprising a compound of Formula (I) or a stereoisomeric forms thereof or a prodrug thereof or a pharmaceutically acceptable salt, solvate or polymorph thereof, and an additional pharmaceutical agent, in particular an additional antiviral, as a combined preparation for simultaneous, separate or sequential use in the treatment or prevention of influenza virus infections, influenza A and/or influenza B virus infections.

DETAILED DESCRIPTION OF THE INVENTION

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

The term "about" has the meaning known to the person skilled in the art. In certain embodiments, the term "about" may be left out and the exact amount is meant. In other embodiments the term "about" means that the numerical following the term "about" is in the range of ±15%, or of ±10%, or of ±5%, or of ±1%, of said numerical value.

As used herein the term "$C_{x-y}$", where x and y are integers, refers to the number of carbon atoms in a given group. Thus, a $C_{1-6}$alkyl group contains from 1 to 6 carbon atoms, a $C_{1-4}$alkyl group contains from 1 to 4 carbon atoms, a $C_{1-3}$alkyl group contains from 1 to 3 carbon atoms, a $C_{3-6}$cycloalkyl group contains from 3 to 6 carbon atoms, and so on.

The term "alkyl" refers to a straight-chain or branched-chain saturated aliphatic hydrocarbon containing the specified number of carbon atoms.

The term "cycloalkyl" refers to a carbocyclic ring containing the specified number of carbon atoms including organic, inorganic and heterocycles.

The terms "$C_2$-$C_6$alkenyl" and "$C_2$-$C_8$alkenyl" used herein as a group or part of a group are meant to comprise straight or branched chain unsaturated hydrocarbon radicals having at least one double bond, and preferably having one double bond, and respectively from 2 to 6 and 2 to 8 carbon atoms such as ethenyl, propenyl, buten-1-yl, buten-2-yl, penten-1-yl, penten-2-yl, hexen-1-yl, hexen-2-yl, hexen-3-yl, 2-methylbuten-1-yl, hepten-1-yl, hepten-2-yl, hepten-3-yl, hepten-4-yl, 2-methylhexen-1-yl, octen-1-yl, octen-2-yl, octen-3-yl, octen-4-yl, 2-methylhepten-1-yl and the like.

The term "halo" or "halogen" is generic to fluoro, chloro, bromo and iodo.

The term "(=O)" or "oxo" forms a carbonyl moiety when attached to a carbon atom. It should be noted that an atom can only be substituted with an oxo group when the valency of that atom so permits.

It is to be understood that where compounds disclosed herein have unfilled valencies, then the valencies are to be filled with hydrogens or isotopes thereof.

It should be noted that the radical positions on any molecular moiety used in the definitions may be anywhere on such moiety as long as it is chemically stable. Radicals used in the definitions of the variables include all possible isomers unless otherwise indicated.

When any variable occurs more than one time in any constituent, each definition is independent.

The compounds of the present invention are represented herein in their neutral form, it should be clear that the charged form(s), as present in biological systems, and known to the skilled person, is/are also included within the scope of the present invention.

The term "prodrug" of a compound of the invention includes any compound that when administered to a biological system, generates the biologically active agent having the desired pharmacological effect, i.e. the antiviral activity, as a result of a biotransformation or chemical transformation (e.g. spontaneous chemical reaction(s), enzyme catalyzed chemical reaction(s), and/or metabolic chemical reaction(s)). Ideally the prodrug is pharmacologically inactive. General information on prodrugs may be found e.g. in Bundegaard, H. "Design of Prodrugs" p. 1-92, Elsevier, New York-Oxford (1985).

Several prodrug forming strategies are available in the field of antivirals and known to the skilled person. Such prodrug strategies have been reviewed, for instance, in Jones R J and Bischofberger N, Antiviral Research 1995, 27, 1-17; Sofia, MJ, Antivir Chem Chemother 2011, 22, 23-49; Bobeck D R et al. Antiviral Therapy 2010, 15, 935-950; Sofia M J, Adv Pharmacol 2013, 67, 39-73; Schultz C, Bioorg Med Chem 2003, 11, 885-898; Pertusati F et al. Antivir Chem Chemother 2012, 22, 181-203; Sofia M J et al. J Med Chem 2012, 55(6), 2481-2531; Coats S J et al. Antiviral Res 2014, 102, 119-147; Meier C and Balzarini J, Antiviral Res 2006, 71 (2-3), 282-292, incorporated by reference herein in their entirety.

Prodrugs may be prepared by modifying functional groups present on the compound in such a way that the modified functional groups are cleaved, in vivo when such prodrug is administered to a subject. The modifications typically are achieved by synthesising the parent compound with a prodrug substituent. In general, prodrugs include compounds of the invention wherein a hydroxyl, amino or phosphate group is modified.

The term "polymorph" refers to the ability of the compound of the invention to exist in more than one form or crystal structure.

The term "optionally substituted" means that the atom or radical indicated in the expression using "optionally substituted" may or may not be substituted (this means substituted or unsubstituted respectively).

The term "subject" as used herein, refers to a warm-blooded animal, preferably a mammal (e.g. cat, dog, primate or human), more preferably a human, who is or has been the object of treatment, observation or experiment.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic. p-toluenesulfonic, salicylic or naphthalene-sulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_{1-7}$alkylamine, Cyclohexylamine, Triethanolamine, ethyienediamine, and salts with amino acids such as arginine and lysine.

The term "solvates" covers any pharmaceutically acceptable solvates that the compounds of Formula (I), as well as the prodrugs and the salts thereof, are able to form. Such solvates are for example hydrates, alcoholates, e.g. ethanolates, propanolates, and the like.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of Formula (I)", or "the present compounds" or similar terms, it is meant to include the compounds of Formula (I), including the possible stereochemically isomeric forms, and their pharmaceutically acceptable salts and solvates.

As used herein, any chemical formula with bonds shown only as solid lines and not as solid or hashed wedged bonds, or otherwise indicated as having a particular configuration (e.g. R, S) around one or more atoms, contemplates each possible stereoisomer, or mixture of two or more stereoisomers.

When a stereocenter is indicated with 'RS' this means that a racemic mixture was obtained at the indicated centre, unless otherwise indicated. The stereochemical configuration for centres in some compounds may be designated "R" or "S" when the mixture(s) was separated; for some compounds, the stereochemical configuration at indicated centres has been designated as "R*", "S*", "*R" or "*S" when the absolute stereochemistry is undetermined although the compound itself has been isolated as a single stereoisomer and is enantiomerically/diastereomerically pure.

"E*", "Z*", "*E" or "*E" when shown in a compound containing a double bond refer to a double bond for which the configuration is undetermined although the compound itself has been isolated as a single stereoisomer.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%, or of 98% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary layers. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of Formula (I) can be obtained separately by conventional methods. Appropriate physical separation methods that may advantageously be employed are, for example, selective crystallization and chromatography, e.g. column chromatography.

In one embodiment, compounds of Formula (I) are provided wherein:

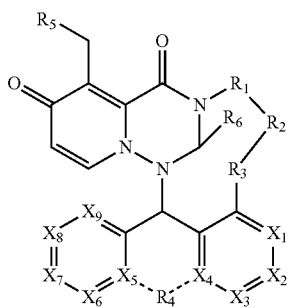

(I)

wherein:
$R_1$ is C, —$CH_2$—$CH_2$—O—, $C_{3-6}$cycloalkyl, oxetanyl, $C_{1-3}$alkyl-cyclopropyl or $C_{1-3}$alkyl-cyclobutyl, optionally substituted by one or more substituents independently selected from, halo, oxo, $CH_2$-methoxy, $C_{1-4}$alkyl, $C_{1-6}$ cycloalkyl and tetrahydrofuran;
$R_2$ is $C_{1-6}$alkyl, $C_{1-6}$alkyl-O—, $C_{1-6}$alkyl-N—, $C_{2-6}$alkenyl, $C_{2-6}$alkenyl-O— or $C_{2-6}$alkenyl-N-optionally substituted by one or more substituents independently selected from halo, oxo or $C_{1-4}$alkyl;
$R_3$ is C or O optionally substituted by one or more substituents independently selected from halo, oxo and methyl;
or, $R_2$ and $R_3$ together form $C_{2-8}$alkenyl optionally substituted by one or more substituents independently selected from halo, oxo and methyl;
$X_1$ to $X_9$ are each N or C and wherein any of $X_1$ to $X_9$ is C, said C is optionally substituted by one or more substituents independently selected from $C_{1-4}$alkyl, $C_{3-6}$cycloalkyl, $CHF_2$, $CH_2F$, $CF_3$, $OCF_3$, $SCF_3$, $OCH_3$, $SCH_3$, S—$(O)_2$—$CH_3$ or halogen;
the dotted lines are each an optional bond;
$R_4$ is absent, —$CH_2$—$CH_2$—, —O—$CH_2$—, —S—$CH_2$—, S—$(O)_2$—$CH_2$ or cyclopropyl optionally substituted by one or more substituents independently selected from halo, oxo and methyl;
$R_5$ can be a group that in vivo is capable of providing a compound of formula (I), wherein $R_5$ is H, —C(=O)Y, —($CH_2$)—O—(C=O)—Y, —($CH_2$)—O—(C=O)—O—Y, —($CHCH_3$)—O—(C=O)—Y, —($CHCH_3$)—O—(C=O)—O—Y, —($CH_2$)—O—(C=O)—NH—Y, —($CH_2$)—O—(C=O)C($R_7$)—NH—($R_8$);
Y is $C_{1-6}$alkyl, $C_{3-6}$cycloalkyl, aryl, heteroaryl, heterocyclyl, $C_{1-4}$alkyl-(O—$R_7$), $C_{1-4}$alkyl-N—($R_7$)($R_8$), $R_7$—O—$R_8$—O—$CH_2$;
and $R_7$ and $R_8$ are independently hydrogen or $C_{1-4}$alkyl;
$R_6$ is H, methyl or $CH_2$—O—$CH_3$;
and the pharmaceutically acceptable salts, polymorphs and solvates thereof.

In one embodiment, compounds of Formula (I) are provided wherein
$R_1$ is C, —$CH_2$—$CH_2$—O—, $C_{3-6}$cycloalkyl, $C_{1-3}$alkyl-cyclopropyl or $C_{1-3}$alkyl-cyclobutyl, optionally substituted by one or more substituents independently selected from, halo, oxo, $CH_2$-methoxy, $C_{1-4}$alkyl, and $C_{1-6}$ cycloalkyl;
$R_2$ is $C_{1-6}$alkyl, $C_{2-6}$alkenyl, $C_{2-6}$alkenyl-O— or $C_{2-6}$alkenyl-N— optionally substituted by one or more substituents independently selected from halo, oxo or $C_{1-4}$alkyl;
$R_3$ is C or O optionally substituted by one or more substituents independently selected from halo, oxo and methyl;
or, $R_2$ and $R_3$ together form $C_{2-8}$alkenyl optionally substituted by one or more substituents independently selected from halo, oxo and methyl;
$X_1$ to $X_9$ are each N or C and wherein any of $X_1$ to $X_9$ is C, said C is optionally substituted by one or more substituents independently selected from $C_{1-4}$alkyl, $C_{3-6}$cycloalkyl, $CHF_2$, $CH_2F$, $CF_3$, $OCF_3$, $SCF_3$, $OCH_3$, $SCH_3$, S—$(O)_2$—$CH_3$ or halogen;
$R_4$ is absent, —$CH_2$—$CH_2$— or —S—$CH_2$— optionally substituted by one or more substituents independently selected from halo, oxo and methyl;
$R_5$ is H, —C(=O)Y, —($CH_2$)—O—(C=O)—Y, —($CH_2$)—O—(C=O)—O—Y, —($CHCH_3$)—O—(C=O)—Y, —($CHCH_3$)—O—(C=O)—O—Y, —($CH_2$)—O—(C=O)—NH—Y, —($CH_2$)—O—(C=O)C($R_7$)—NH—($R_8$);
Y is $C_{1-6}$alkyl, $C_{3-6}$cycloalkyl, aryl, heteroaryl, heterocyclyl, $C_{1-4}$alkyl-(O—$R_7$), $C_{1-4}$alkyl-N—($R_7$)($R_8$), $R_7$—O—$R_8$—O—$CH_2$;
and $R_7$ and $R_8$ are independently hydrogen or $C_{1-4}$alkyl;
$R_6$ is H or methyl.

In one embodiment, compounds of Formula (I) are provided wherein
$R_1$ is C, $C_{3-6}$cycloalkyl, $C_{1-3}$alkyl-cyclopropyl or $C_{1-3}$alkyl-cyclobutyl, optionally substituted by one or more substituents independently selected from, halo, $C_{1-4}$alkyl, and $C_{1-6}$ cycloalkyl;
$R_2$ is $C_{1-6}$alkyl or $C_{2-6}$alkenyl optionally substituted by one or more substituents independently selected from halo or $C_{1-4}$alkyl;
$R_3$ is C or O optionally substituted by one or more substituents independently selected from halo and methyl;

or, $R_2$ and $R_3$ together form $C_{2-8}$alkenyl optionally substituted by one or more substituents independently selected from halo, oxo and methyl;

$X_1$ to $X_9$ are each N or C and wherein any of $X_1$ to $X_9$ is C, said C is optionally substituted by one or more substituents independently selected from $C_{1-4}$alkyl, $C_{3-6}$cycloalkyl, $CHF_2$, $CH_2F$, $CF_3$, $OCF_3$, $SCF_3$, $OCH_3$, $SCH_3$, $S-(O)_2-CH_3$ or halogen;

$R_4$ is absent or $-S-CH_2-$ optionally substituted by one or more substituents independently selected from halo and methyl;

$R_5$ is H; and $R_6$ is H or methyl.

In one embodiment, compounds of Formula (I) are provided wherein $R_1$ is C, $C_{3-6}$cycloalkyl or $C_{1-3}$alkyl-cyclopropyl, optionally substituted by one or more substituents independently selected from, halo and $C_{1-4}$alkyl;

$R_2$ is $C_{1-6}$alkyl or $C_{2-6}$alkenyl optionally substituted by one or more substituents independently selected from halo or $C_{1-4}$alkyl;

$R_3$ is C or O optionally substituted by one or more substituents independently selected from halo and methyl;

$X_1$ to $X_9$ are each N or C and wherein any of $X_1$ to $X_9$ is C, said C is optionally substituted by one or more substituents independently selected from $C_{1-4}$alkyl, $C_{3-6}$cycloalkyl, $CHF_2$, $CH_2F$, $CF_3$, $OCF_3$, $SCF_3$, $OCH_3$, $SCH_3$, $S-(O)_2-CH_3$ or halogen;

$R_4$ is absent or $-S-CH_2-$ optionally substituted by one or more substituents independently selected from halo and methyl;

$R_5$ is H; and $R_6$ is H or methyl.

In one embodiment, compounds of Formula (I) are provided wherein $R_1$ is C, $C_{3-6}$cycloalkyl or $C_{1-3}$alkyl-cyclopropyl, optionally substituted by one or more substituents independently selected from, halo and $C_{1-4}$alkyl;

$R_2$ is $C_{1-6}$alkyl or $C_{2-6}$alkenyl optionally substituted by one or more substituents independently selected from halo or $C_{1-4}$alkyl;

$R_3$ is C or O optionally substituted by one or more substituents independently selected from halo and methyl;

$X_1$ to $X_9$ are each C which is optionally substituted by one or more substituents independently selected from $C_{1-4}$alkyl, $C_{3-6}$cycloalkyl or halogen;

$R_4$ is absent or $-S-CH_2-$ optionally substituted by one or more substituents independently selected from halo and methyl;

$R_5$ is H; and $R_6$ is H or methyl.

In an embodiment, the present invention relates to those compounds of Formula (I) or any subgroup thereof as mentioned in any of the other embodiments, wherein $R_1$ is C, $-C_{3-6}$cycloalkyl, $C_{1-3}$alkyl-cyclopropyl or $C_{1-3}$alkyl-cyclobutyl, optionally substituted by one or more substituents independently selected from, halo and $C_{1-4}$alkyl.

In an embodiment, the present invention relates to those compounds of Formula (I) or any subgroup thereof as mentioned in any of the other embodiments, wherein $R_2$ is $C_{1-6}$alkyl, $C_{2-6}$alkenyl, $C_{2-6}$alkenyl-O— or $C_{2-6}$alkenyl-N— optionally substituted by one or more substituents independently selected from halo or $C_{1-4}$alkyl.

In an embodiment, the present invention relates to those compounds of Formula (I) or any subgroup thereof as mentioned in any of the other embodiments, wherein $R_3$ is C optionally substituted by one or more substituents independently selected from halo and methyl.

In an embodiment, the present invention relates to those compounds of Formula (I) or any subgroup thereof as mentioned in any of the other embodiments, wherein $R_3$ is O.

In an embodiment, the present invention relates to those compounds of Formula (I) or any subgroup thereof as mentioned in any of the other embodiments, wherein $R_2$ and $R_3$ together form $C_{2-8}$alkenyl optionally substituted by one or more substituents independently selected from halo and methyl.

In an embodiment, the present invention relates to those compounds of Formula (I) or any subgroup thereof as mentioned in any of the other embodiments, wherein $X_1$ to $X_9$ are each N.

In an embodiment, the present invention relates to those compounds of Formula (I) or any subgroup thereof as mentioned in any of the other embodiments, wherein $X_1$ to $X_9$ are each C, said C is optionally substituted by one or more substituents independently selected from $C_{1-4}$alkyl, $C_{3-6}$cycloalkyl or halogen.

In an embodiment, the present invention relates to those compounds of Formula (I) or any subgroup thereof as mentioned in any of the other embodiments, wherein $R_4$ is absent.

In an embodiment, the present invention relates to those compounds of Formula (I) or any subgroup thereof as mentioned in any of the other embodiments, wherein $R_4$ is $-CH_2-CH_2-$ optionally substituted by one or more substituents independently selected from halo and methyl;

In an embodiment, the present invention relates to those compounds of Formula (I) or any subgroup thereof as mentioned in any of the other embodiments, wherein $R_4$ is $-S-CH_2-$ optionally substituted by one or more substituents independently selected from halo and methyl.

In an embodiment, the present invention relates to those compounds of Formula (I) or any subgroup thereof as mentioned in any of the other embodiments, wherein $R_5$ is H.

In an embodiment, the present invention relates to those compounds of Formula (I) or any subgroup thereof as mentioned in any of the other embodiments, wherein $R_6$ is H.

In one embodiment, compounds of Formula (I) are provided wherein:

$R_1$ is C optionally substituted by one or more substituents independently selected from, halo and $C_{1-4}$alkyl;

$R_2$ is $C_{2-6}$alkenyl;

$R_3$ is O;

$X_1$ to $X_9$ are each C which is optionally substituted by one or more substituents independently selected from $C_{1-4}$alkyl or halogen;

$R_4$ is absent;

$R_5$ and $R_6$ are each H.

In one embodiment, compounds of Formula (I) are provided wherein $R_1$ is $C_{3-6}$cycloalkyl;

$R_2$ is $C_{2-6}$alkenyl;

$R_3$ is O;

$X_1$ to $X_9$ are each C which is optionally substituted by one or more substituents independently selected from $C_{1-4}$alkyl or halogen;

$R_4$ is absent;

$R_5$ and $R_6$ are each H.

In one embodiment, compounds of Formula (I) are provided wherein
$R_1$ is C, optionally substituted by one or more substituents independently selected from, halo and $C_{1-4}$alkyl;
$R_2$ is $C_{2-6}$alkenyl optionally substituted by one or more substituents independently selected from halo or $C_{1-4}$alkyl;
$R_3$ is O;
$X_1$ to $X_9$ are each C which is optionally substituted by one or more substituents independently selected from $C_{1-4}$alkyl, $C_{3-6}$cycloalkyl or halogen;
$R_4$ is —S—CH$_2$— optionally substituted by one or more substituents independently selected from halo and methyl;
$R_5$ and $R_6$ are each H.

In one embodiment, compounds of Formula (I) are provided wherein
$R_1$ is $C_{3-6}$cycloalkyl;
$R_2$ is $C_{1-6}$alkyl optionally substituted by one or more substituents independently selected from halo or $C_{1-4}$alkyl;
$R_3$ is O;
$X_1$ to $X_9$ are each C which is optionally substituted by one or more substituents independently selected from $C_{1-4}$alkyl, $C_{3-6}$cycloalkyl or halogen;
$R_4$ is —S—CH$_2$— optionally substituted by one or more substituents independently selected from halo and methyl;
$R_5$ and $R_6$ are each H.

In one embodiment, compounds of Formula (I) are provided wherein
$R_1$ is $C_{1-3}$alkyl-cyclopropyl optionally substituted by one or more substituents independently selected from halo and $C_{1-4}$alkyl;
$R_2$ is $C_{2-6}$alkenyl optionally substituted by one or more substituents independently selected from halo or $C_{1-4}$alkyl;
$R_3$ is O;
$X_1$ to $X_9$ are each C which is optionally substituted by one or more substituents independently selected from $C_{1-4}$alkyl, $C_{3-6}$cycloalkyl or halogen;
$R_4$ is —S—CH$_2$— optionally substituted by one or more substituents independently selected from halo and methyl;
$R_5$ and $R_6$ are each H.

In an embodiment, the present invention relates to those compounds of Formula (I) and the prodrugs thereof, the pharmaceutically acceptable salts, and the solvates thereof, or any subgroup thereof as mentioned in any of the other embodiments wherein at least 1, 2, 3, 4 or 5 of $X_1$ to $X_9$ is N.

All possible combinations of the above-indicated embodiments are considered to be embraced within the scope of this invention.

Of interest are the compounds listed below as well as the pharmaceutically acceptable acid addition salts of the following compounds:

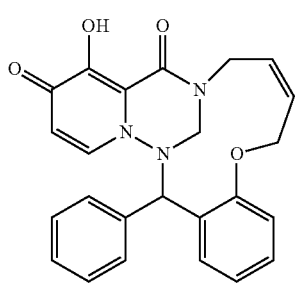

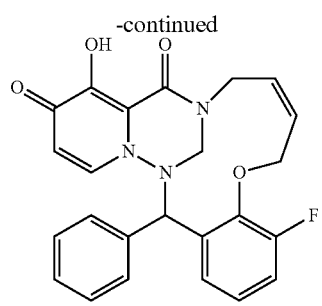

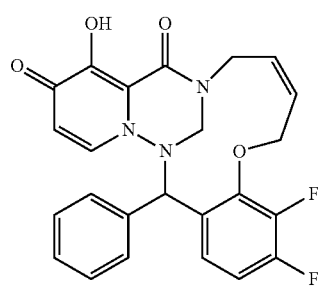

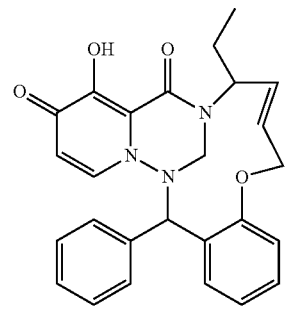

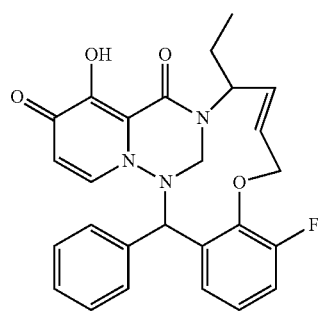

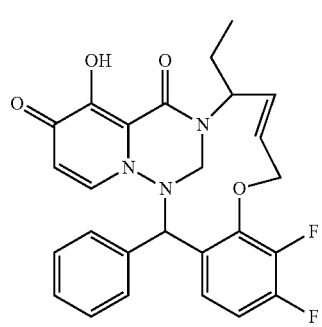

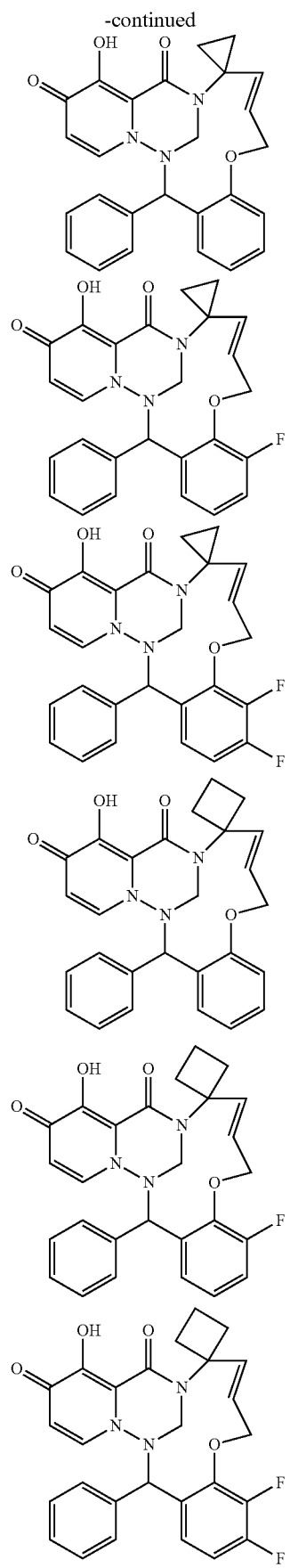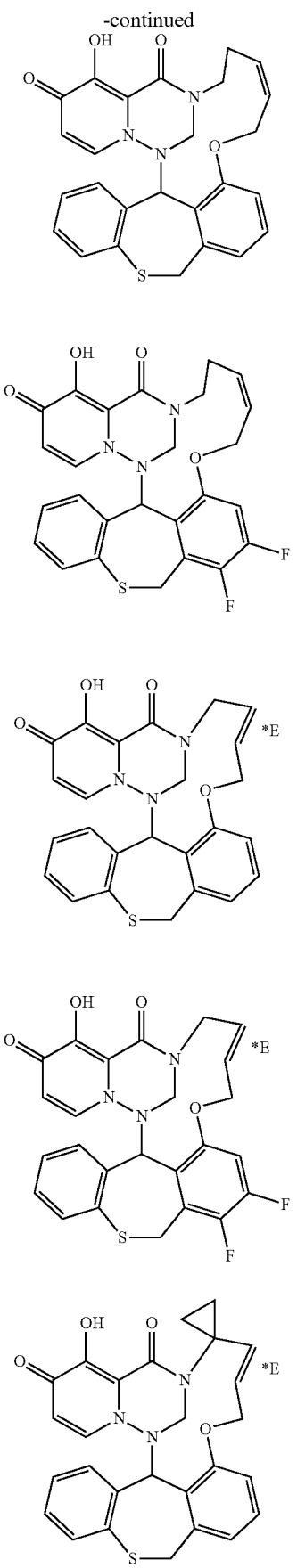

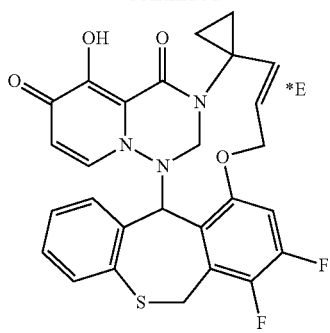

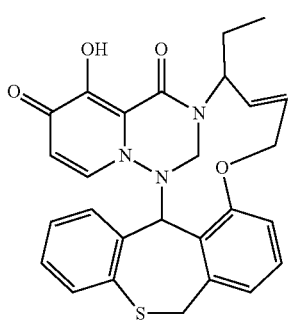

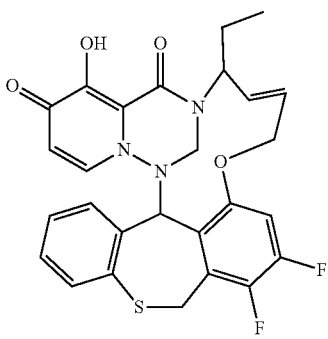

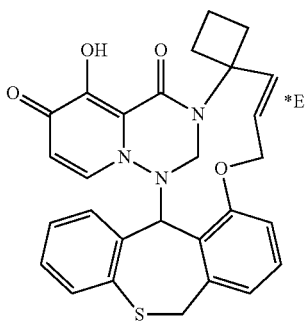

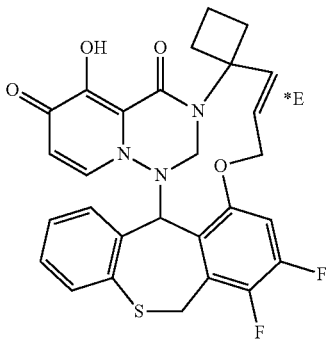

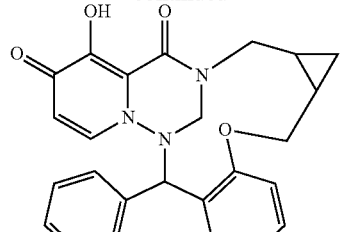

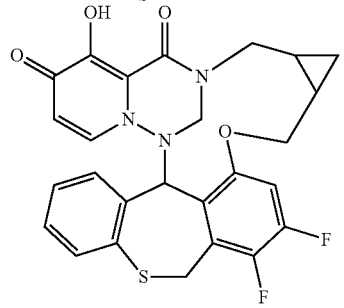

Synthetic Approaches

The compound of Formula (I) may be prepared by the methods described below, using synthetic methods known in the art of organic chemistry, or modifications and derivatizations that are familiar to those of skilled in the art. The starting materials used herein are commercially available or may be prepared by routine methods known in the art such as those methods disclosed in standard reference books. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene and P. G. M. Wuts, Protective Groups in Organic Chemistry, John Wiley & Sons, 1999, which are hereby incorporated by reference.

Compounds of Formula (I), or their pharmaceutically acceptable salts, can be prepared according to the reaction schemes discussed herein below. Unless otherwise indicated, the substituents in the schemes are defined as above. Isolation and purification of the products is accomplished by standard procedures, which are known to a chemist of ordinary skill.

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the [M+H]⁺ (protonated molecule) and/or [M−H]⁻ (deprotonated molecule). In case the compound was not directly ionizable the type of adduct is specified (i.e. [M+NH$_4$]$^+$, [M+HCOO]$^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

SFCMS-Method.
General Procedure

The SFC measurement was performed using an Analytical Supercritical fluid chromatography (SFC) system composed by a binary pump for delivering carbon dioxide (CO$_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to

| LCMS Method codes (Flow expressed in mL/min, column temperature (T) in ° C.; Run time in minutes) | | | | | | |
|---|---|---|---|---|---|---|
| Method code | Instrument | Column | Mobile phase | Gradient | Flow Col T | Run time (min) |
| LC-A - | Waters: Acquity ® UPLC ® - DAD-Quattro Micro$^{TM}$ | Waters: BEH C18 (1.7 μm, 2.1 × 100 mm) | A: 95% CH$_3$COONH$_4$ 7 mM/5% CH$_3$CN, B: CH$_3$CN | 84.2% A for 0.49 min, to 10.5% A in 2.18 min. held for 1.94 min, back to 84.2% A in 0.73 min, held for 0.73 min. | 0.343 mL/min 40° C. | 6.2 |
| LC-B - | Walers: Acquity ® H-Class - DAD and SQD2TM | Waters BEH ® C18 (1.7 μm, 2.1 × 100 mm) | A: CH$_3$COONH4 7 mM 95%/ CH$_3$CN 5%, B: CH$_3$CN | 84.2% A/15.8% B, to 10.5% A in 2.18 min held for 1.96 min, back to 84.2% A/15.8% B in 0.73 min, held for 0.49 min. | 0.343 mL/min 40° C. | 6.1 |
| LC-C - | Waters: Acquity UPLC ® - DAD and Quattro Micro ™ | YMC Triart C18 ExRS: (1.9 μm, 2.1 × 100 mm) | A: 95% CH$_3$COONH$_4$ 7 mM/5% CH$_3$CN, B: CH$_3$CN | 85% A for 0.5 min, to 15% A in 2.5 min, held for 1.6 min, back to 85% A in 0.8 min, held for 0.8 min. | 0.343 mL/min 40° C. | 6.2 |
| LC-D - | Shimadzu LCMS-2020 | Shimadzu: CORTECS C18 (2.7 μm, 2.1 × 50 mm) | A: H$_2$O/0.05% TFA, B: CH3CN/0.05% TFA | 95% A for 0.01 min, to 0% A in 1.99 min, held for 0.8 min, back to 95% A in 0.1 min, held for 0.1 or 0.25 min. | 1, 1.2 or 1.5 mL/min 40° C. | 3 or 5.2 |
| LC-E | Serie 1200 Agilent Technology | ZORBAX SB C18 1.8 μM (50 × 2.1 mm) | A: H$_2$O + 0.1% HCO$_2$H Methanol + 0.1% HCO$_2$H | 0 min: 95/5 2.5 min: 0/100 5 min: 0/100 | 0.8 mL/min 40° C. | 5 |
| LC-F | Serie 1200 Agilent Technology | ZORBAX SB C18 1.8 μM (50 × 2.1 mm) | A: H2O + 0.1% HCO2H Methanol + 0.1% HCO2H | 0 min: 60/40 10 min: 0/100 14 min: 0/100 | 0.8 mL/min 40° C. | 14 |
| LC-G | Waters: Acquity UPLC ® - DAD and Quattro Micro ™ | Peek-YMC Triart C18 ExRS: (1.9 μm, 2.1 × 100 mm) | A: 95% CH$_3$COONH$_4$ 7 mM/5% CH$_3$CN, B: CH$_3$CN | 85% A for 0.5 min, to 15% A in 2.5 min, held for 1.6 min, back to 85% A in 0.8 min, held for 0.8 min. | 0.343 mL/min 40° C. | 6.2 |

HPLC Methods
General Procedure

The HPLC measurement was performed using Analytical system from Waters comprises a modules pump-autosampler alliance 2695 and a diode array detector 996. Data acquisition and reprocess was performed with a Waters-Micromass MassLynx data system.

obtain ions allowing the identification of the compound's nominal monoisotopic molecular weight (MW). Data acquisition was performed with appropriate software.

Analytical SFC-MS Methods (Flow expressed in mL/min; column temperature (T) in ° C.; Run time in minutes, Backpressure (BPR) in bars.

| Method code | column | mobile phase | gradient | Flow Col T | Run time BPR |
|---|---|---|---|---|---|
| Method HPLC-A | Chiralpak IG 250 * 4.6 mm 5 μm | EtOH + (0.1% TFA v/v) | 100% | 1 mL/min 25° C. | 15 min |
| Method HPLC-B | Chiralpak AZ-H 250 * 4.6 mm 5 μm | EtOH + (0.1% TFA v/v) | 100% | 1 mL/min 25° C. | 15 min |

| Method code | column | mobile phase | gradient | Flow Col T | Run time BPR |
|---|---|---|---|---|---|
| Method SFC-A | Daicel Chiralcel ® OJ-3 column (3 μm, 100 × 4.6 mm) | A: CO$_2$ B: MeOH | 20% B hold 3 min, | 3.5 35 | 3 103 |
| Method SFC-B | Daicel Chiralcel ® OJ-3 column (3 μm, 100 × 4.6 mm) | A: CO$_2$ B: MeOH + 0.3% IprNH$_2$ | 20% B hold 3 min, | 3.5 35 | 3 103 |
| Method SFC-C | Daicel Chiralcel ® OJ-3 column (3 μm, 100 × 4.6 mm) | A: CO$_2$ B: MeOH + 0.3% IprNH$_2$ | 15% B hold 3 min, | 3.5 35 | 3 103 |

Melting Points

Values are either peak values or melt ranges, and are obtained with experimental uncertainties that are commonly associated with this analytical method.

DSC823e (Indicated as DSC)

For a number of compounds, melting points were determined with a DSC823e (Mettler-Toledo). Melting points were measured with a temperature gradient of 10° C./minute. Maximum temperature was 300° C.

Optical Rotations:

Optical rotations were measured on a Perkin-Elmer 341 polarimeter with a sodium lamp and reported as follows: $[\alpha]°$ ($\lambda$, c g/100 mL, solvent, T° C.).

$[\alpha]_\lambda^T = (100\alpha)/(l \times c)$: where l is the path length in dm and c is the concentration in g/100 ml for a sample at a temperature T (° C.) and a wavelength $\lambda$ (in nm). If the wavelength of light used is 589 nm (the sodium D line), then the symbol D might be used instead. The sign of the rotation (+ or −) should always be given. When using this equation, the concentration and solvent are always provided in parentheses after the rotation. The rotation is reported using degrees and no units of concentration are given (it is assumed to be g/100 ml).

EXAMPLES

Preparation of Compounds According to the Invention

Example 1: Synthesis of 4-hydroxy-16-phenyl-7,8,11,16-tetrahydro-6,17-methanobenzo[k]pyrido[1,2-b][1,2,5]triazacyclotridecine-3,5-dione (Compound 1)

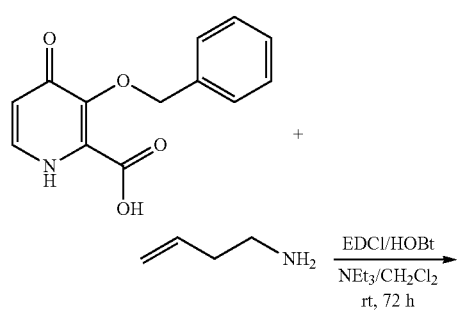

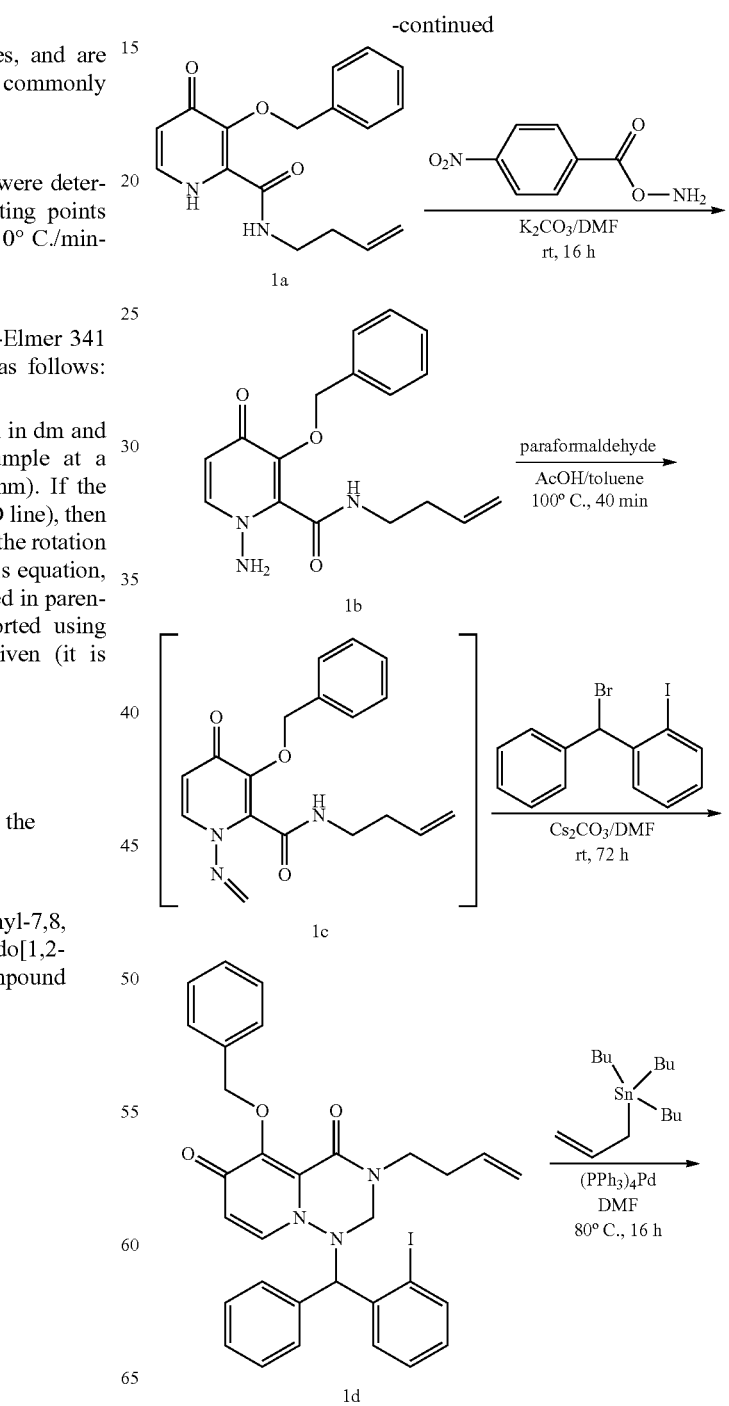

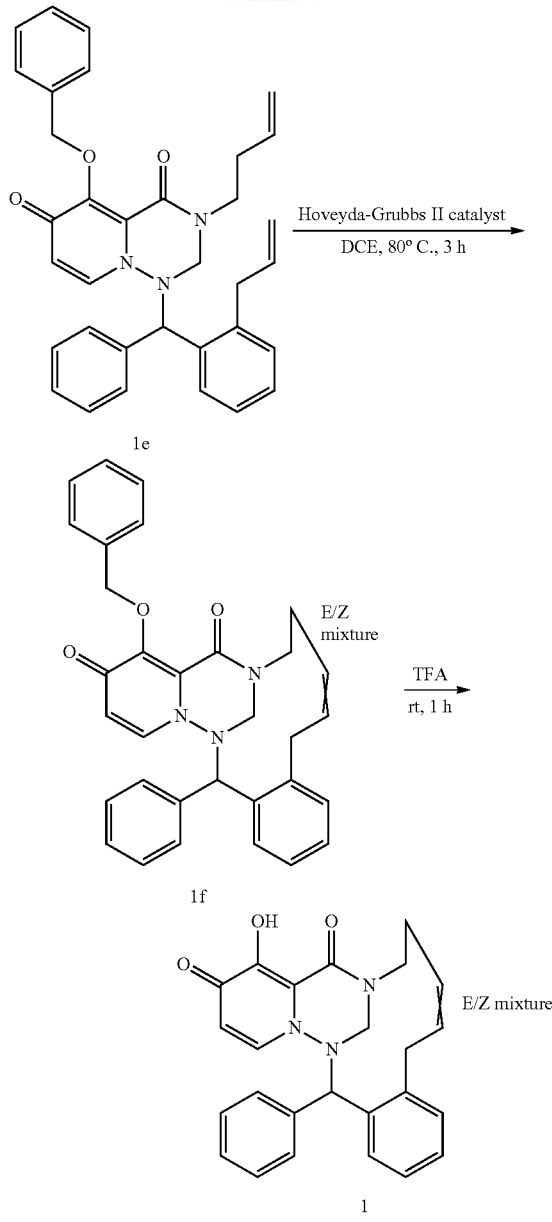

Synthesis of Intermediate 1a:

At 10° C., NEt₃ (28 mL, 0.20 mol) was added to a solution of 3-(benzyloxy)-4-oxo-1,4-dihydropyridine-2-carboxylic acid [CAS 119736-17-3] (10 g, 41 mmol), but-3-en-1-amine [CAS 2524-49-4] (4.8 mL, 53 mmol), EDCI (12 g, 61 mmol) and HOBt (8.3 g, 61 mmol) in CH₂Cl₂ (250 mL). The mixture was stirred at rt for 72 h. The mixture was poured into a mixture of water and K₂CO₃ 10% in water, and was extracted with CH₂Cl₂. The organic layer was dried over MgSO₄, filtered and the solvent was evaporated. Purification was carried out by flash chromatography over silica gel (30 μm, 300 g, CH₂Cl₂/MeOH from 100/0 to 96/4). The pure fractions were collected and concentrated under reduced pressure to give 3-(benzyloxy)-N-(but-3-en-1-yl)-4-oxo-1,4-dihydropyridine-2-carboxamide (intermediate 1a, 4.6 g).

Synthesis of Intermediate 1b:

To a DMF (240 mL) solution of 3-(benzyloxy)-N-(but-3-en-1-yl)-4-oxo-1,4-dihydropyridine-2-carboxamide (intermediate 1a, 4.6 g, 15 mmol) was suspended K₂CO₃ (6.4 g, 46 mmol). The suspension was stirred for 5 min at rt. O-(4-nitrobenzoyl)hydroxylamine [CAS 35657-36-4] (4.2 g, 23 mmol) was added and the mixture was stirred at rt for 16 h. H₂O was added and the mixture was extracted five times with CH₂Cl₂. The combined organic layers were dried over MgSO₄, filtered and the solvent was concentrated under reduced pressure. The residue was purified by flash chromatography over silica gel (30 μm, 120 g, CH₂Cl₂/MeOH from 100/0 to 95/5) to give 1-amino-3-(benzyloxy)-N-(but-3-en-1-yl)-4-oxo-1,4-dihydropyridine-2-carboxamide (intermediate 1b, 3.2 g).

Synthesis of Intermediate 1c:

A suspension of 1-amino-3-(benzyloxy)-N-(but-3-en-1-yl)-4-oxo-1,4-dihydropyridine-2-carboxamide (intermediate 1b, 620 mg, 2.0 mmol) and paraformaldehyde (59 mg, 2.0 mmol) in dry toluene (21 mL) and AcOH (ten drops) was stirred at 100° C. for 40 min. The mixture was cooled down to rt and concentrated under reduced pressure to give 3-(benzyloxy)-N-(but-3-en-1-yl)-1-(methyleneamino)-4-oxo-1,4-dihydropyridine-2-carboxamide (intermediate 1c, 643 mg), which was used as such in the next step.

Synthesis of Intermediate 1d:

Under N₂, 3-(benzyloxy)-N-(but-3-en-1-yl)-1-(methyleneamino)-4-oxo-1,4-dihydropyridine-2-carboxamide (intermediate 1c, 640 mg, 2.0 mmol) was taken up in DMF (14 mL) and Cs₂CO₃ (3.2 g, 9.8 mmol) was added at 0° C. The reaction was stirred for 1 h at 0° C. Then 1-(bromo(phenyl)methyl)-2-iodobenzene [CAS 1339630-17-9] (1.1 g, 2.9 mmol) was added and the reaction mixture was stirred at rt for 72 h. EtOAc was added and the mixture was washed 5 times with brine. The organic layer was dried over MgSO₄, filtered and concentrated under reduced pressure. Purification was carried out by flash chromatography over silica gel (30 μm, 24 g, CH₂Cl₂/MeOH from 100/0 to 98/2). The pure fractions were collected and evaporated to dryness to give 5-(benzyloxy)-3-(but-3-en-1-yl)-1-((2-iodophenyl)(phenyl)methyl)-2,3-dihydro-1H-pyrido[2,1-f][1,2,4]triazine-4,6-dione (intermediate 1d, 0.45 g).

Synthesis of Intermediate 1e:

To a solution of 5-(benzyloxy)-3-(but-3-en-1-yl)-1-((2-iodophenyl)(phenyl)methyl)-2,3-dihydro-1H-pyrido[2,1-f][1,2,4]triazine-4,6-dione (intermediate 1d, 0.45 g, 0.73 mmol) and allyltri-N-butyltin (0.27 mL, 0.88 mmol) in degassed DMF (5.6 mL) under N₂ was added (PPh₃)₄Pd (42 mg, 0.036 mmol). The mixture was stirred at 80° C. for 16 h. The mixture was partitioned between EtOAc and brine, the organic layer was separated, washed five times with brine, dried and concentrated under reduced pressure. The residue was purified by flash chromatography over silica gel (30 μm, 24 g, CH₂Cl₂/MeOH from 100/0 to 97/3) to give 1-((2-allylphenyl)(phenyl)methyl)-5-(benzyloxy)-3-(but-3-en-1-yl)-2,3-dihydro-1H-pyrido[2,1-f][1,2,4]triazine-4,6-dione (intermediate 1e, 350 mg).

Synthesis of Intermediate 1f:

A solution of 1-((2-allylphenyl)(phenyl)methyl)-5-(benzyloxy)-3-(but-3-en-1-yl)-2,3-dihydro-1H-pyrido[2,1-f][1,2,4]triazine-4,6-dione (intermediate 1e, 350 mg, 0.66 mmol) and Hoveyda-Grubbs catalyst 2$^{nd}$ generation [CAS 301224-40-8] (83 mg, 0.13 mmol) in dry DCE (52 mL) was stirred at 80° C. for 3 h. SiliaMetS® DMT (0.86 g, 0.53 mmol) was added and the mixture was stirred at rt overnight. The reaction mixture was filtered through Celite® and the filtrate was concentrated under reduced pressure. Purification was carried out by flash chromatography over silica gel (30 μm, 12 g, CH₂Cl₂/CH₃OH 100/0 to 97/3) to give 4-(benzyloxy)-16-phenyl-7,8,11,16-tetrahydro-6,17-methanobenzo[k]

pyrido[1,2-b][1,2,5]triazacyclotridecine-3,5-dione (intermediate 1f, Z/E mixture, 230 mg), which was used as such in the next step.

Synthesis of Compound 1:

TFA (0.76 mL) was added to 4-(benzyloxy)-16-phenyl-7,8,11,16-tetrahydro-6,17-methanobenzo[k]pyrido[1,2-b][1,2,5]triazacyclotridecine-3,5-dione (intermediate 1f, 50 mg, 0.099 mmol). The mixture was stirred at rt for 1 h. The mixture was concentrated under reduced pressure. The residue was purified by flash chromatography over silica gel (30 µm, 4 g, $CH_2Cl_2$/MeOH from 99/1 to 95/5) to give, after freeze drying in $CH_3CN$/water, 4-hydroxy-16-phenyl-7,8,11,16-tetrahydro-6,17-methanobenzo[k]pyrido[1,2-b][1,2,5]triazacyclotridecine-3,5-dione (Compound 1, Z/E mixture, 26 mg).

Compound 1:

major isomer (75%)

$^1$H NMR (500 MHz, DMSO-$d_6$) δ ppm 2.17 (br d, J=12.6 Hz, 1H) 2.60-2.74 (m, 1H) 2.79 (td, J=13.0, 3.6 Hz, 1H) 2.96-3.03 (m, 1H) 3.11 (br d, J=17.3 Hz, 1H) 3.69 (br dd, J=13.6, 4.4 Hz, 1H) 4.11 (d, J=13.2 Hz, 1H) 4.89-5.06 (m, 2H) 5.33 (d, J=7.6 Hz, 1H) 5.79 (s, 1H) 6.12-6.27 (m, 1H) 6.81-7.32 (m, 7H) 7.37-7.58 (m, 2H) 8.08 (d, J=7.6 Hz, 1H) 9.59-12.93 (m, 1H)

minor isomer (25%)

$^1$H NMR (500 MHz, DMSO-$d_6$) δ ppm 2.17 (br d, J=12.6 Hz, 1H) 2.60-2.74 (m, 1H) 2.79 (td, J=13.0, 3.6 Hz, 1H) 2.96-3.03 (m, 1H) 3.11 (br d, J=17.3 Hz, 1H) 3.69 (br dd, J=13.6, 4.4 Hz, 1H) 3.98-4.07 (m, 1H) 4.36 (br d, J=13.2 Hz, 1H) 4.89-5.06 (m, 1H) 5.38-5.68 (m, 3H) 6.81-7.32 (m, 7H) 7.37-7.58 (m, 2H) 7.94 (br d, J=7.3 Hz, 1H) 9.59-12.93 (m, 1H)

LC-MS (method LC-A): $R_t$ 2.68 min, MH$^+$ 414

Example 2: Synthesis of 15-hydroxy-2-phenyl-12,13,14,16-tetrahydro-11H-1(1,3)-pyrido[2,1-f][1,2,4]triazina-3(1,2)-benzenacyclononaphane-14,16-dione (Compound 2)

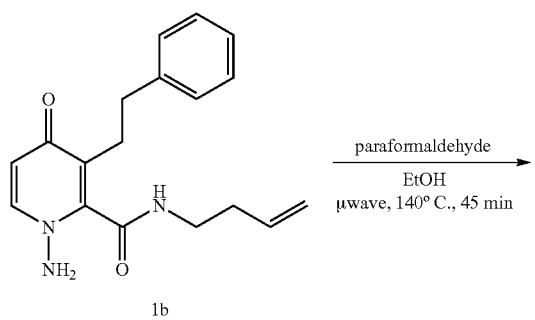

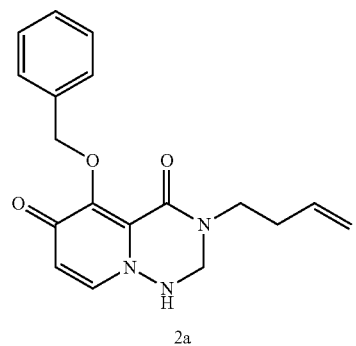

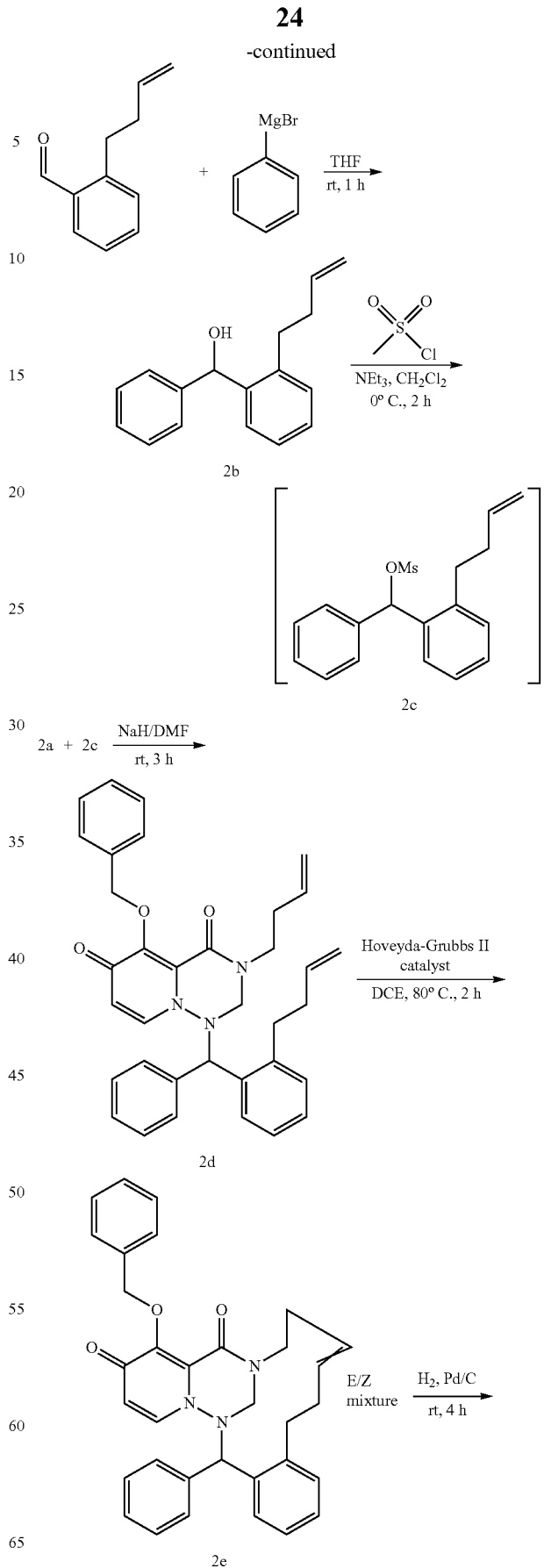

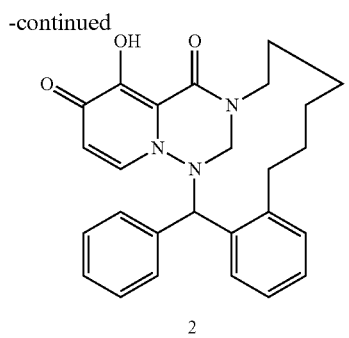

2

Synthesis of Intermediate 2a:

The reaction was split into two equal parts. 1-amino-3-(benzyloxy)-N-(but-3-en-1-yl)-4-oxo-1,4-dihydropyridine-2-carboxamide (intermediate 1b, 40.0 g, 127.65 mmol) was solubilized in EtOH (612 mL) in a warm water bath (50° C.). Paraformaldehyde (4.22 g, 140.42 mmol) was added and the resulting mixture was stirred at 140° C. for 45 min (3 min as ramp time, 600 rpm as stirring speed) in an Anton-Parr microwave oven (1700 W max power). The mixture was concentrated under vacuum (water bath at 35° C.). The residue was taken up with a minimum amount of $CH_3CN$. The precipitate was filtered off and dried under vacuum to give a first batch of 5-(benzyloxy)-3-(but-3-en-1-yl)-2,3-dihydro-1H-pyrido[2,1-f][1,2,4]triazine-4,6-dione (intermediate 2a, 30.7 g). The filtrate was concentrated under reduced pressure. Purification was carried out by flash chromatography over silica gel (15-40 μm, 330 g, $CH_2Cl_2$/$CH_3OH$: 98/2 to 95/5). The pure fractions were collected and evaporated to dryness to give a second batch of intermediate 2a (3.7 g).

Synthesis of Intermediate 2b:

At 0° C. under a $N_2$ flow, phenyl-magnesium bromide [CAS 100-58-3] (35 mL, 34.89 mmol) was added dropwise to a solution of 2-(but-3-en-1-yl)benzaldehyde [CAS 70576-29-3] (4.3 g, 26.84 mmol) in THF (30 mL). The mixture was stirred under $N_2$ at rt for 1 h. The reaction was quenched at 0° C. with a saturated aqueous solution of $NH_4Cl$ and the aqueous phase was extracted with EtOAc. The organic extracts were combined and dried over $MgSO_4$, filtered and concentrated under reduced pressure to give (2-(but-3-en-1-yl)phenyl)(phenyl)methanol (intermediate 2b, 4.2 g).

Synthesis of Intermediate 2c:

At 0° C. under a $N_2$ flow, methanesulfonyl chloride (974 μL, 12.59 mmol) was added dropwise to a solution of (2-(but-3-en-1-yl)phenyl)(phenyl)methanol (intermediate 2b, 1.5 g, 6.29 mmol) and $NEt_3$ (2.62 mL, 18.8 mmol) in $CH_2Cl_2$ (30 mL). The mixture was stirred at 0° C. for 2 h. Water was added and the mixture was extracted with $CH_2Cl_2$. The combined organic layers were dried over $MgSO_4$, filtered and concentrated under reduced pressure to give (2-(but-3-en-1-yl)phenyl)(phenyl)methyl methanesulfonate (intermediate 2c, 1.80 g), which was used as such in the next step.

Synthesis of Intermediate 2d:

At 0° C., under a $N_2$ flow, NaH (60% dispersion in oil, 145 mg, 3.78 mmol) was added to a solution of 5-(benzyloxy)-3-(but-3-en-1-yl)-2,3-dihydro-1H-pyrido[2,1-f][1,2,4]triazine-4,6-dione (intermediate 2a, 820 mg, 2.52 mmol) in DMF (10 mL). The mixture was stirred at 0° C. for 30 min (the mixture turned red), then a solution of (2-(but-3-en-1-yl)phenyl)(phenyl)methyl methanesulfonate (intermediate 2c, 1.6 g, 5.04 mmol) in DMF (6 mL) was added. The resulting mixture was stirred at rt for 3 h (reaction mixture turned yellow). The mixture was quenched with ice and extracted with EtOAc. The organic layer was dried over $MgSO_4$, filtered and concentrated under reduced pressure. Purification was carried out by flash chromatography over silica gel (15-40 μm, 80 g, $CH_2Cl_2$/$CH_3OH$:100/0 to 97/3). The pure fractions were collected and concentrated under reduced pressure to give 5-(benzyloxy)-3-(but-3-en-1-yl)-1-((2-(but-3-en-1-yl)phenyl)(phenyl)methyl)-2,3-dihydro-1H-pyrido[2,1-f][1,2,4]triazine-4,6-dione (intermediate 2d, 460 mg).

Synthesis of Intermediate 2e:

Synthesized using the procedure described for intermediate 1f yielding 15-(benzyloxy)-2-phenyl-12,13,14,16-tetrahydro-11H-1(1,3)-pyrido[2,1-f][1,2,4]triazina-3(1,2)-benzenacyclononaphan-6-ene-14,16-dione (intermediate 2e, undefined E/Z mixture, 305 mg).

Synthesis of Compound 2:

Under an atmospheric pressure of $H_2$, 15-(benzyloxy)-2-phenyl-12,13,14,16-tetrahydro-11H-1(1,3)-pyrido[2,1-f][1,2,4]triazina-3(1,2)-benzenacyclononaphan-6-ene-14,16-dione (intermediate 2e, 60 mg, 0.116 mmol) and Pd/C (10%) (61.7 mg, 0.058 mmol) in EtOAc (4 mL) were stirred at rt for 4 h. The catalyst was removed by filtration through a pad of Celite®. The Celite® was washed with EtOAc and the filtrate was concentrated under reduced pressure (45 mg). The compound was crystallized from $CH_3OH$/$Et_2O$, the precipitate was filtered off and dried to give 15-hydroxy-2-phenyl-12,13,14,16-tetrahydro-11H-1(1,3)-pyrido[2,1-f][1,2,4]triazina-3(1,2)-benzenacyclononaphane-14,16-dione (Compound 2, 32 mg).

Compound 2:

$^1$H NMR (500 MHz, DMSO-$d_6$) δ ppm 0.99-1.07 (m, 1H) 1.21 (br t, J=11.2 Hz, 1H) 1.30-1.44 (m, 2H) 1.70-1.81 (m, 2H) 1.82-1.93 (m, 1H) 2.27-2.35 (m, 1H) 2.57-2.69 (m, 1H) 2.94 (br t, J=10.7 Hz, 1H) 3.72 (br d, J=13.2 Hz, 1H) 4.40 (d, J=12.9 Hz, 1H) 5.14 (d, J=13.2 Hz, 1H) 5.40 (d, J=7.6 Hz, 1H) 5.93 (s, 1H) 7.21 (br dd, J=17.8, 9.9 Hz, 7H) 7.30-7.36 (m, 1H) 7.38-7.46 (m, 1H) 8.16 (d, J=7.3 Hz, 1H) 11.74 (br s, 1H) (1 proton under DMSO peak)

LC-MS (method LC-A): $R_t$ 2.93 min, MH$^+$ 430

Example 4: Synthesis of 4-hydroxy-16-phenyl-7,8,9,10,11,16-hexahydro-6,17-methanobenzo[k]pyrido[1,2-b][1,2,5]triazacyclotridecine-3,5-dione (Compound 4)

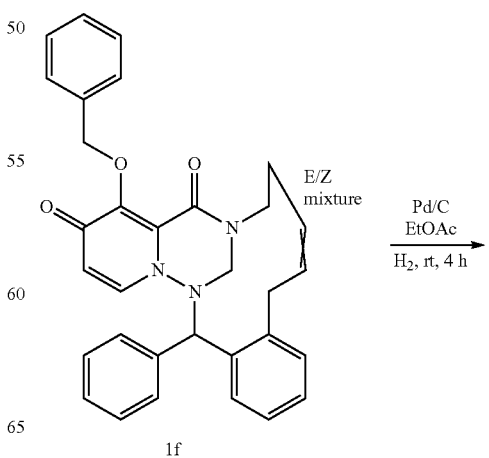

1f

-continued

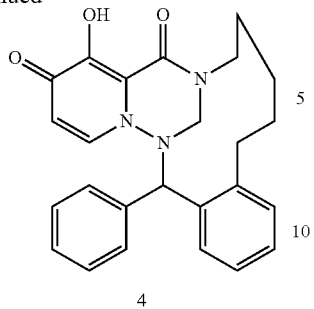

4

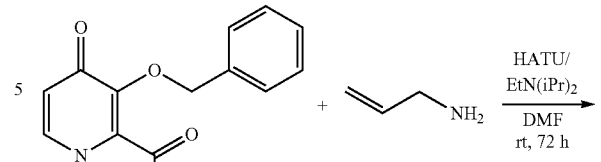

Synthesis of Compound 4:

Under an atmospheric pressure of $H_2$, 4-(benzyloxy)-16-phenyl-7,8,11,16-tetrahydro-6,17-methanobenzo[k]pyrido[1,2-b][1,2,5]triazacyclotridecine-3,5-dione (intermediate 1f, 30 mg, 0.060 mmol) and Pd/C (10%) (32 mg, 0.030 mmol) in EtOAc (1.8 mL) were stirred at rt for 4 h. The catalyst was removed by filtration through a pad of Celite®. The Celite® was washed with EtOAc and the filtrate was concentrated under reduced pressure to give, after freeze drying in $CH_3CN$/water, 4-hydroxy-16-phenyl-7,8,9,10,11,16-hexahydro-6,17-methanobenzo[k]pyrido[1,2-b][1,2,5]triazacyclotridecine-3,5-dione (Compound 4, 12 mg).

Compound 4:

$^1$H NMR (500 MHz, DMSO-$d_6$) δ ppm 0.70-0.84 (m, 1H) 1.28-1.40 (m, 1H) 1.40-1.62 (m, 2H) 1.65-1.84 (m, 1H) 1.96-2.13 (m, 1H) 2.54-2.58 (m, 1H) 2.59-2.72 (m, 2H) 3.90-4.12 (m, 1H) 4.27-4.49 (m, 1H) 5.08 (d, J=13.9 Hz, 1H) 5.53 (d, J=7.9 Hz, 1H) 5.61 (s, 1H) 7.03 (d, J=7.6 Hz, 1H) 7.17-7.47 (m, 8H) 8.00 (d, J=7.3 Hz, 1H)

LC-MS (method LC-A): $R_t$ 2.76 min, MH$^+$ 416

Example 5: Synthesis of (18R,Z)-12-hydroxy-18-phenyl-6,9-dihydro-18H-10,17-methanobenzo[b]pyrido[1,2-f][1]oxa[5,6,9]triazacyclotridecine-11,13-dione (Compound 5A) and (18S,Z)-12-hydroxy-18-phenyl-6,9-dihydro-18H-10,17-methanobenzo[b]pyrido[1,2-f][1]oxa[5,6,9]triazacyclotridecine-11,13-dione (Compound 5B)

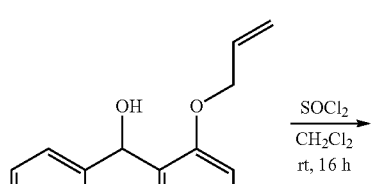

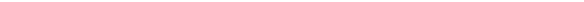

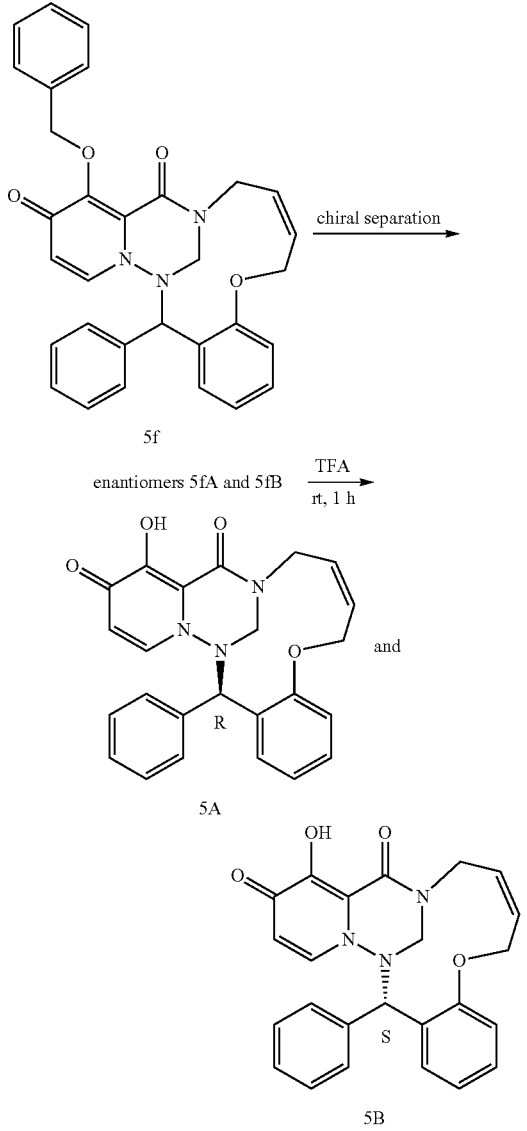

Synthesis of Intermediate 5a:

Thionyl chloride (2 mL, 27.46 mmol) was added dropwise to a solution of (2-(allyloxy)phenyl)(phenyl)methanol [CAS 1159707-76-2 (5.5 g, 27.89 mmol) in CH$_2$Cl$_2$ (56 mL) at 5° C. The mixture was stirred at 5° C. for 1 h and at rt for 16 h. The mixture was concentrated to dryness and co-evaporated with toluene to give 1-(allyloxy)-2-(chloro(phenyl)methyl)benzene (intermediate 5a, 5.9 g), which was used as such in the next step.

Synthesis of Intermediate 5b:

Under N$_2$, a mixture of 3-(benzyloxy)-4-oxo-1,4-dihydropyridine-2-carboxylic acid [CAS 119736-17-3] (20 g, 73 mmol, 90% pure), allylamine (6.6 mL, 88 mmol), HATU (42 g, 110 mmol) and N,N-diisopropylethylamine (36 mL, 220 mmol) in DMF (284 mL) was stirred at rt for 72 h. The mixture was concentrated under reduced pressure and diluted with EtOAc. The mixture was washed 5 times with brine. The organic layer was dried over MgSO$_4$, filtered and concentrated under reduced pressure. Purification was carried out by flash chromatography over silica gel (30 μm, 300 g, dry loading, CH$_2$Cl$_2$/MeOH from 100/0 to 97/3). The pure fractions were collected and evaporated to dryness to give N-allyl-3-(benzyloxy)-4-oxo-1,4-dihydropyridine-2-carboxamide (intermediate 5b, 16 g).

Synthesis of Intermediate 5c:

To a solution of N-allyl-3-(benzyloxy)-4-oxo-1,4-dihydropyridine-2-carboxamide (intermediate 5b, 13.1 g, 46.08 mmol) in DMF (250 mL) was suspended K$_2$CO$_3$ (19.1 g, 138.22 mmol). The reaction was stirred 5 min at rt. O-(4-nitrobenzoyl)hydroxylamine [CAS 35657-36-4] (12.6 g, 69.11 mmol) was added and the mixture was stirred at rt for 8 h. Water was added and the mixture was extracted five times with CH$_2$Cl$_2$. The combined organic layers were dried over MgSO$_4$, filtered and concentrated under reduced pressure. The residue was taken up with CH$_2$Cl$_2$ and the precipitate was filtered off to give N-allyl-1-amino-3-(benzyloxy)-4-oxo-1,4-dihydropyridine-2-carboxamide (intermediate 5c, 11.5 g).

Synthesis of Intermediate 5d:

N-allyl-1-amino-3-(benzyloxy)-4-oxo-1,4-dihydropyridine-2-carboxamide (intermediate 5c, 11.5 g, 38.42 mmol) was solubilized in EtOH (185 mL) using a warm water bath (50° C.). Paraformaldehyde (1.27 g, 42.26 mmol) was added and the resulting mixture was stirred at 140° C. for 45 min (3 min as ramp time, 600 rpm as stirring speed) in an Anton-Parr microwave oven (1700 W max power). The mixture was concentrated under vacuum (water bath below 35° C.). The residue was taken up with the minimum amount of CH$_3$CN. The precipitate was filtered off and dried under vacuum to give a first batch of 3-allyl-5-(benzyloxy)-2,3-dihydro-1H-pyrido[2,1-f][1,2,4]triazine-4,6-dione (intermediate 5d, 6.71 g). The filtrate was concentrated under reduced pressure (5.3 g) and was combined with another reaction (3 g) to be further purified. Purification was carried out by flash chromatography over silica gel (30 μm, 80 g, mobile phase CH$_2$Cl$_2$/MeOH from 100/0 to 95/5) yielding another batch of intermediate 5d (5 g).

Synthesis of Intermediate 5e:

Under nitrogen, 3-allyl-5-(benzyloxy)-2,3-dihydro-1H-pyrido[2,1-f][1,2,4]triazine-4,6-dione (intermediate 5d, 5.0 g, 16.06 mmol) was solubilized in DMF (80 mL) and NaH (960 mg g, 24.09 mmol) was added at 0° C. The mixture was stirred for 30 min at 0° C. Then a solution of 1-(allyloxy)-2-(chloro(phenyl)methyl)benzene (intermediate 5a, 6.0 g, 23.19 mmol) in DMF (20 mL) was added and the mixture was stirred at rt for 2 h. EtOAc was added and the mixture was washed with water. The organic layer was dried over MgSO$_4$, filtered and concentrated under reduced pressure. Purification was carried out by flash chromatography over silica gel (30 μm, 220 g, CH$_2$Cl$_2$/CH$_3$OH 100/0 to 97/3). The pure fractions were collected and evaporated to dryness to give 3-allyl-1-((2-(allyloxy)phenyl)(phenyl)methyl)-5-(benzyloxy)-2,3-dihydro-1H-pyrido[2,1-f][1,2,4]triazine-4,6-dione (intermediate 5e, 7.72 g).

Synthesis of Intermediate 5f:

A degassed solution of 3-allyl-1-((2-(allyloxy)phenyl)(phenyl)methyl)-5-(benzyloxy)-2,3-dihydro-1H-pyrido[2,1-f][1,2,4]triazine-4,6-dione (intermediate 5e, 2.0 g, 3.65 mmol) and Hoveyda-Grubbs catalyst $2^{nd}$ generation (470 mg, 0.75 mmol) in dry DCE (270 mL) was stirred at 80° C. for 2 h. SiliaMetS® DMT (9.83 g, 6.0 mmol) was added and the mixture was stirred at rt for 16 h. The reaction mixture was filtered through a pad of Celite®. The Celite® was washed with CH$_2$Cl$_2$ and the filtrate was concentrated under reduced pressure. Purification of was carried out by flash chromatography over silica gel (20-45 μm, 80 g, CH$_2$Cl$_2$/CH$_3$OH 100/0 to 96/4) to give (Z)-12-(benzyloxy)-18-phenyl-6,9-dihydro-18H-10,17-methanobenzo[b]pyrido[1,2-f]

[1]oxa[5,6,9]triazacyclotridecine-11,13-dione (intermediate 5f, Z isomer, 395 mg). This batch was combined with another one (409 mg) and the enantiomers were separated via chiral SFC (Stationary phase: Chiralcel® OD-H 5 μm 250×30 mm, Mobile phase: 60% $CO_2$, 40% EtOH) to give 314 mg of the first eluted enantiomer and 378 mg of the second eluted enantiomer. Each enantiomer was further purified via achiral SFC (Stationary phase: $NH_2$ 5 μm 150×30 mm, Mobile phase: 80% $CO_2$, 20% EtOH) to give 137 mg of enantiomer 5fA and 146 mg of enantiomer 5fB.

Synthesis of Compound 5A:

TFA (2.1 mL) was added to the enantiomer 5fA (137 mg, 0.27 mmol). The mixture was stirred at rt for 1 h and was then concentrated under reduced pressure. The residue was purified by flash chromatography over silica gel (30 μm, 4 g, $CH_2Cl_2$/MeOH from 99/1 to 95/5) to give, after freeze drying in $CH_3CN$/water, (18R,Z)-12-hydroxy-18-phenyl-6,9-dihydro-18H-10,17-methanobenzo[b]pyrido[1,2-f][1]oxa[5,6,9]triazacyclotridecine-11,13-dione (Compound 5A, 87 mg)

Synthesis of Compound 5B:

TFA (2.2 mL) was added to the enantiomer 5fB (146 mg, 0.29 mmol). The mixture was stirred at rt for 1 h and was then concentrated under reduced pressure. The residue was purified by flash chromatography over silica gel (30 μm, 4 g, $CH_2Cl_2$/MeOH from 99/1 to 95/5) to give, after freeze drying in $CH_3CN$/water, (18S,Z)-12-hydroxy-18-phenyl-6,9-dihydro-18H-10,17-methanobenzo[b]pyrido[1,2-f][1]oxa[5,6,9]triazacyclotridecine-11,13-dione (Compound 5B, 90 mg).

Compound 5A:

$^1$H NMR (400 MHz, DMSO-$d_6$) δ ppm 3.19 (br dd, J=13.9, 8.3 Hz, 1H) 4.08-4.47 (m, 2H) 4.65-4.90 (m, 2H) 5.11 (br d, J=13.6 Hz, 1H) 5.31 (s, 1H) 5.49 (d, J=7.6 Hz, 1H) 5.80-5.91 (m, 1H) 6.04-6.32 (m, 1H) 6.98-7.29 (m, 7H) 7.29-7.49 (m, 2H) 8.09 (br d, J=7.1 Hz, 1H)

LC/MS (method LC-B): $R_t$ 2.26 min, MH$^+$416

$[α]_D^{20}$: −708.58° (c 0.303, DMF)

Chiral HPLC (method HPLC-A): $R_t$ 6.61 min, chiral purity 100%.

Compound 5B:

$^1$H NMR (400 MHz, DMSO-$d_6$) δ ppm 3.19 (br dd, J=13.6, 8.1 Hz, 1H) 4.11-4.46 (m, 2H) 4.54-4.89 (m, 2H) 5.11 (br d, J=13.6 Hz, 1H) 5.31 (s, 1H) 5.48 (d, J=7.6 Hz, 1H) 5.82-5.93 (m, 1H) 6.06-6.28 (m, 1H) 7.02-7.28 (m, 7H) 7.28-7.55 (m, 2H) 8.09 (br d, J=7.6 Hz, 1H)

LC/MS (method LC-B): $R_t$ 2.25 min, MH$^+$416

$[α]_D^{20}$: +688.44° (c 0.32, DMF)

Chiral HPLC (method HPLC-A): $R_t$ 5.55 min, chiral purity 100%.

Example 6: Synthesis of (*E)-15-hydroxy-2-phenyl-12,13,14,16-tetrahydro-11H-4-oxa-1(1,3)-pyrido[2,1-f][1,2,4]triazina-3(1,3)-benzenacyclononaphan-7-ene-14,16-dione (Compound 6)

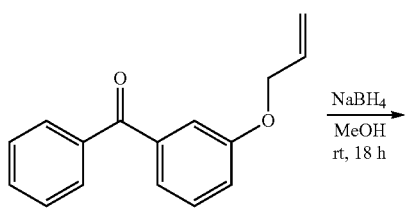

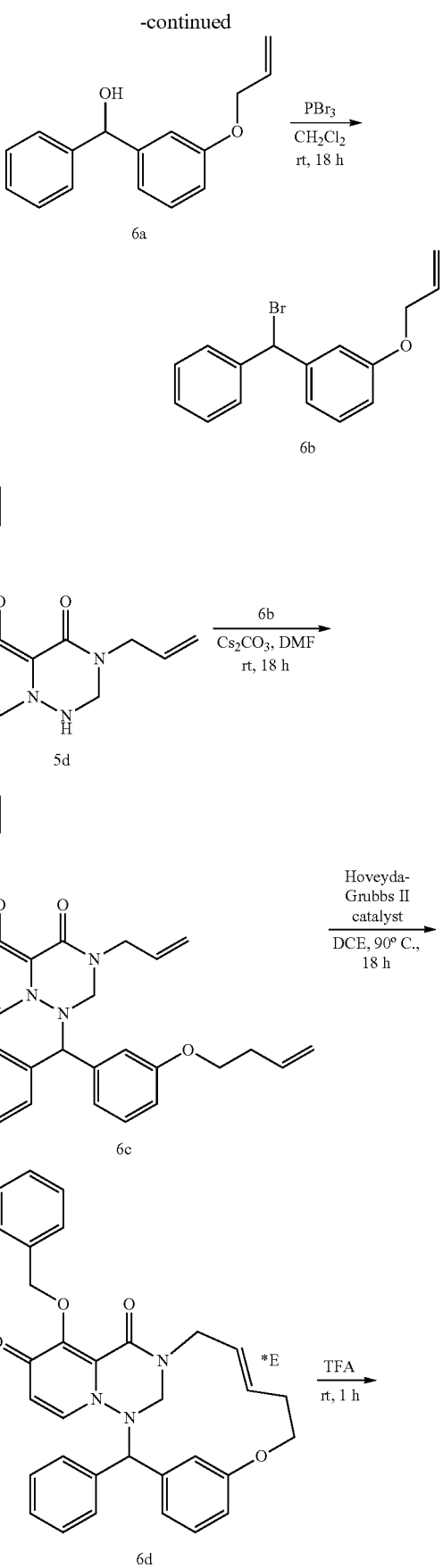

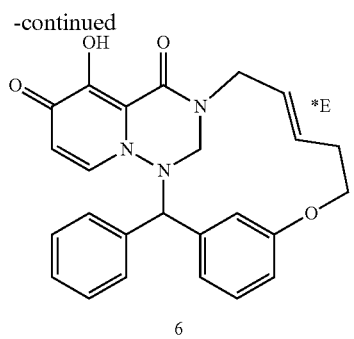

6

Synthesis of Intermediate 6a:

NaBH$_4$ (1.47 g, 38.7 mmol) was added portionwise to a solution of (3-(allyloxy)phenyl)(phenyl)methanone [CAS 93021-98-8] (7.5 g, 29.73 mmol) in MeOH (120 mL) at 0° C. The mixture was stirred at rt for 18 h. 10% NH$_4$Cl aqueous solution was added and the solution was extracted with CH$_2$Cl$_2$ twice. The combined organic layers were dried over MgSO$_4$, filtered and concentrated under reduced pressure to afford (3-(allyloxy)phenyl)(phenyl)methanol (intermediate 6a, 7.43 g).

Synthesis of Intermediate 6b:

At 0° C., under N$_2$, PBr$_3$ (261 μL, 2.75 mmol) was added dropwise to a solution of ((3-(allyloxy)phenyl)(phenyl) methanol (intermediate 6a, 700 mg, 2.75 mmol) in dry CH$_2$Cl$_2$ (8.4 mL). The mixture was warmed to rt and stirred for 18 h. The reaction was quenched with ice and the aqueous phase was extracted with CH$_2$Cl$_2$. The organic layer was washed with water, dried over MgSO$_4$, filtered and the solvent was evaporated under reduced pressure to give 1-(allyloxy)-3-(bromo(phenyl)methyl)benzene (intermediate 6b, 820 mg).

Synthesis of Intermediate 6c:

3-allyl-5-(benzyloxy)-2,3-dihydro-1H-pyrido[2,1-f][1,2, 4]triazine-4,6-dione (intermediate 5d, 470 mg, 1.51 mmol) was solubilized in DMF (10 mL) and Cs$_2$CO$_3$ (2.46 g, 7.55 mmol) was added at 0° C. The reaction mixture was stirred for 1 h at 0° C. 1-(allyloxy)-3-(bromo(phenyl)methyl)benzene (intermediate 6b, 718 mg, 2.26 mmol) was added and the mixture was stirred at rt for 18 h. Water was added and the mixture was extracted with EtOAc. The combined organic layers were washed with water, then with brine. The organic phase was dried over MgSO$_4$, filtered and concentrated under reduced pressure. Purification was carried out by flash chromatography over silica gel (15-40 μm, 40 g, CH$_2$Cl$_2$/CH$_3$OH from 100/0 to 97/3). The pure fractions were collected and evaporated to dryness to give 3-allyl-5-(benzyloxy)-1-((3-(but-3-en-1-yloxy)phenyl)(phenyl) methyl)-2,3-dihydro-1H-pyrido[2,1-f][1,2,4]triazine-4,6-dione (intermediate 6c, 0.45 g).

Synthesis of Intermediate 6d:

Prior to the reaction, the solvent was degassed by bubbling N$_2$ through. In a pressure vessel, Hoveyda-Grubbs 2$^{nd}$ generation catalyst (100.7 mg, 0.16 mmol) was added to a solution of 3-allyl-5-(benzyloxy)-1-((3-(but-3-en-1-yloxy) phenyl)(phenyl)methyl)-2,3-dihydro-1H-pyrido[2,1-f][1,2, 4]triazine-4,6-dione (intermediate 6c, 440 mg, 0.80 mmol) in DCE (66 mL) and the reaction mixture was stirred at 90° C. for 18 h. SiliaMetS® DMT (2.1 g, 1.28 mmol) was added and the mixture was stirred at rt for 48 h. The reaction mixture was filtered through Celite® and the filtrate was concentrated under reduced pressure. Purification was carried out by flash chromatography over silica gel (15-40 μm, 12 g, CH$_2$Cl$_2$/CH$_3$OH from 99/1 to 96/4). The pure fractions were collected and evaporated to dryness to give (*E)-15-(benzyloxy)-2-phenyl-12,13,14,16-tetrahydro-11H-4-oxa-1 (1,3)-pyrido[2,1-f][1,2,4]triazina-3(1,3)-benzenacyclononaphan-7-ene-14,16-dione (intermediate 6d, only one conformation for the double bond, E not fully validated, 37 mg).

Synthesis of Compound 6:

At rt, TFA (0.55 mL, 7.12 mmol) was added in one portion to (*E)-15-(benzyloxy)-2-phenyl-12,13,14,16-tetrahydro-11H-4-oxa-1(1,3)-pyrido[2,1-f][1,2,4]triazina-3(1,3)-benzenacyclononaphan-7-ene-14,16-dione (intermediate 6d, 37 mg, 0.071 mmol) and the resulting mixture was stirred at rt for 1 h. The solvent was evaporated under reduced pressure. Purification was carried out by flash chromatography over silica gel (15-40 μm, 4 g, CH$_2$Cl$_2$/CH$_3$OH 96/4). The pure fractions were collected and evaporated to dryness (12 mg). The compound was crystallized from CH$_3$OH. The precipitate was filtered off and dried under vacuum to give (E*)-15-hydroxy-2-phenyl-12,13,14,16-tetrahydro-11H-4-oxa-1 (1,3)-pyrido[2,1-f][1,2,4]triazina-3(1,3)-benzenacyclononaphan-7-ene-14,16-dione (Compound 6, 3.7 mg).

Compound 6:

$^1$H NMR (500 MHz, DMSO-d$_6$) δ ppm 3.00 (dd, J=14.0, 10.2 Hz, 1H) 3.96 (d, J=13.2 Hz, 1H) 4.07 (ddd, J=12.3, 6.0, 3.5 Hz, 1H) 4.36 (br dd, J=13.9, 3.8 Hz, 1H) 4.64 (ddd, J=11.9, 9.1, 2.4 Hz, 1H) 4.96 (d, J=13.2 Hz, 1H) 5.22 (s, 1H) 5.37-5.48 (m, 1H) 5.54 (d, J=7.9 Hz, 1H) 5.77 (ddd, J=15.2, 10.5, 4.3 Hz, 1H) 6.91 (dd, J=8.0, 1.4 Hz, 1H) 7.22 (d, J=7.9 Hz, 1H) 7.23-7.31 (m, 3H) 7.32-7.37 (m, 2H) 7.37-7.42 (m, 1H) 7.60 (br s, 2H) 11.32-12.02 (m, 1H) (2 protons under DMSO peak)

LC/MS (method LC-A): R$_t$ 2.57 min, MH$^+$430

Example 8: Synthesis of 12-hydroxy-18-phenyl-6,7, 8,9-tetrahydro-18H-10,17-methanobenzo[b]pyrido [1,2-f][1]oxa[5,6,9]triazacyclotridecine-11,13-dione (Compound 8) and its enantiomers (18R)-12-hydroxy-18-phenyl-6,7,8,9-tetrahydro-18H-10,17-methanobenzo[b]pyrido[1,2-f][1]oxa[5,6,9]triazacyclotridecine-11,13-dione (Compound 8A) and (18S)-12-hydroxy-18-phenyl-6,7,8,9-tetrahydro-18H-10,17-methanobenzo[b]pyrido[1,2-f][1]oxa[5,6, 9]triazacyclotridecine-11,13-dione (Compound 8B)

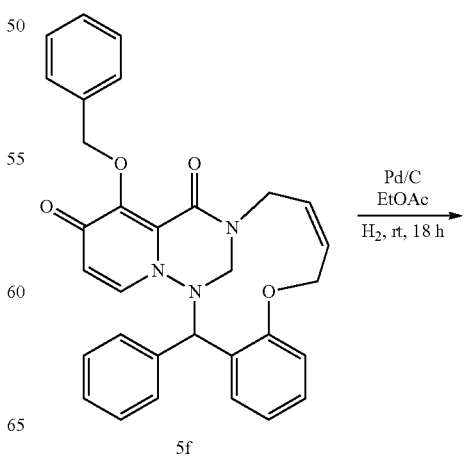

5f

-continued

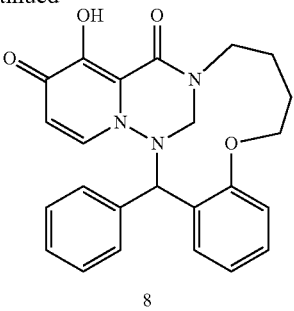

8 enantiomers 5fA and 5fB  →  Pd/C, EtOAc, H₂, rt, 18 h

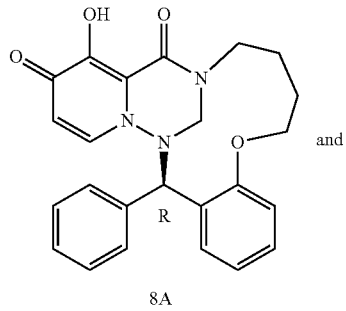

8A

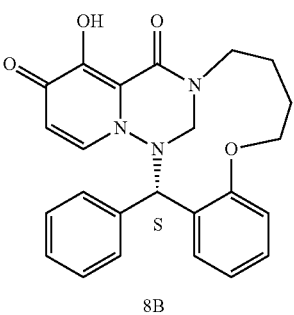

8B

Synthesis of Compound 8:

Under an atmospheric pressure of H₂, (Z)-12-(benzyloxy)-18-phenyl-6,9-dihydro-18H-10,17-methanobenzo[b]pyrido[1,2-f][1]oxa[5,6,9]triazacyclotridecine-11,13-dione (intermediate 5f, 67 mg, 0.13 mmol) and Pd/C (10%) (71 mg, 0.07 mmol) in EtOAc (3.9 mL) were stirred at rt for 18 h. The catalyst was removed by filtration through Celite®. The Celite® was washed with EtOAc, and then with CH$_2$Cl$_2$/MeOH. The filtrate was concentrated under reduced pressure. Purification was carried out by flash chromatography over silica gel (regular 30 μm, 4 g, CH$_2$Cl$_2$/CH$_3$OH from 99/1 to 97/3). The pure fractions were collected and concentrated under reduced pressure. The residue was freeze-dried in CH$_3$CN/water to give 12-hydroxy-18-phenyl-6,7,8,9-tetrahydro-18H-10,17-methanobenzo[b]pyrido[1,2-f][1]oxa[5,6,9]triazacyclotridecine-11,13-dione (Compound 8, 21 mg).

Synthesis of Compound 8A:

(18R)-12-hydroxy-18-phenyl-6,7,8,9-tetrahydro-18H-10,17-methanobenzo[b]pyrido[1,2-f][1]oxa[5,6,9]triazacyclotridecine-11,13-dione (compound 8A, 15 mg) was obtained using the procedure described for compound 8 starting from intermediate 5fA.

Synthesis of Compound 8B:

(18S)-12-hydroxy-18-phenyl-6,7,8,9-tetrahydro-18H-10,17-methanobenzo[b]pyrido[1,2-f][1]oxa[5,6,9]triazacyclotridecine-11,13-dione (compound 8B, 25 mg) was obtained using the procedure described for compound 8 starting from intermediate 5fB.

Compound 8:

$^1$H NMR (500 MHz, Chloroform-d) δ ppm 1.10-1.23 (m, 1H) 1.56-1.73 (m, 1H) 1.88-2.09 (m, 2H) 2.55 (dt, J=14.2, 3.0 Hz, 1H) 4.12-4.23 (m, 1H) 4.30-4.41 (m, 2H) 4.41-4.50 (m, 1H) 4.87 (d, J=13.2 Hz, 1H) 5.80 (br d, J=7.6 Hz, 1H) 6.04 (s, 1H) 6.82 (d, J=7.9 Hz, 1H) 7.06 (d, J=8.2 Hz, 1H) 7.18-7.25 (m, 4H) 7.31-7.48 (m, 3H) 7.88-7.96 (m, 1H)

LC/MS (method LC-A): R$_t$ 2.48 min, MH⁺418

Compound 8A:

$^1$H NMR (400 MHz, DMSO-d$_6$) δ ppm 0.97-1.16 (m, 1H) 1.50-1.66 (m, 1H) 1.75-2.00 (m, 2H) 2.67 (br s, 1H) 4.04 (br t, J=12.9 Hz, 1H) 4.13-4.29 (m, 2H) 4.38 (br d, J=12.1 Hz, 1H) 5.01 (d, J=13.1 Hz, 1H) 5.51 (d, J=7.6 Hz, 1H) 5.91 (s, 1H) 7.13-7.28 (m, 6H) 7.30-7.43 (m, 3H) 7.98 (br d, J=7.1 Hz, 1H) 11.43 (br s, 1H)

LC/MS (method LC-A): R$_t$ 2.47 min, MH⁺418

[α]$_D^{20}$: −319.13° (c 0.115, DMF)

Chiral HPLC (method HPLC-B): R$_t$ 7.75 min. chiral purity 100%.

Compound 8B:

$^1$H NMR (500 MHz, DMSO-d$_6$) δ ppm 0.99-1.13 (m, 1H) 1.52-1.65 (m, 1H) 1.75-1.99 (m, 2H) 2.64 (br s, 1H) 4.04 (br t, J=12.9 Hz, 1H) 4.18 (t, J=11.3 Hz, 1H) 4.25 (d, J=13.6 Hz, 1H) 4.38 (br d, J=12.3 Hz, 1H) 5.01 (d, J=13.6 Hz, 1H) 5.52 (d, J=7.6 Hz, 1H) 5.91 (s, 1H) 7.16-7.28 (m, 6H) 7.31-7.42 (m, 3H) 7.98 (d, J=6.6 Hz, 1H) 10.60-12.15 (m, 1H)

LC/MS (method LC-A): R$_t$ 2.47 min, MH⁺418

[α]$_D^{20}$: +296.75° (c 0.123, DMF)

Chiral HPLC (method HPLC-B): R$_t$ 5.07 min, chiral purity 100%.

Example 9: Synthesis of 15-hydroxy-2-phenyl-12,13,14,16-tetrahydro-11H-4-oxa-1(1,3)-pyrido[2,1-f][1,2,4]triazina-3(1,2)-benzenacyclononaphane-14,16-dione (Compound 9)

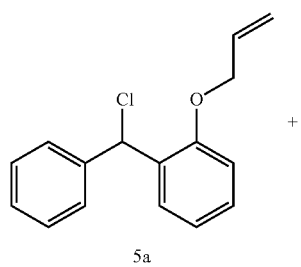

5a

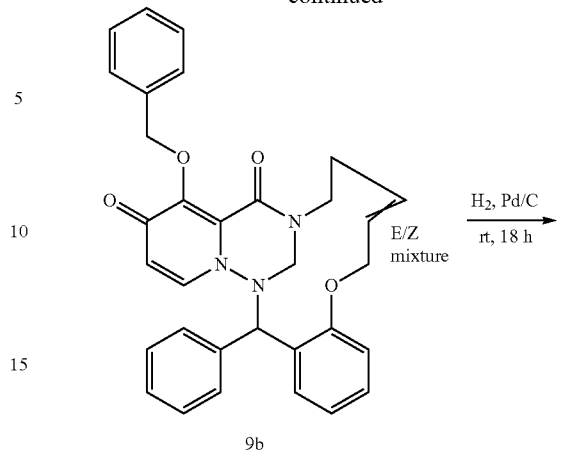

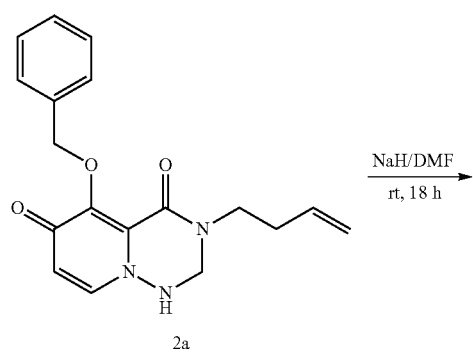

2a

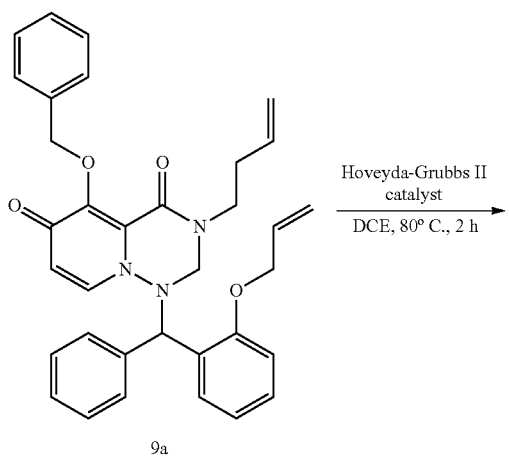

9a

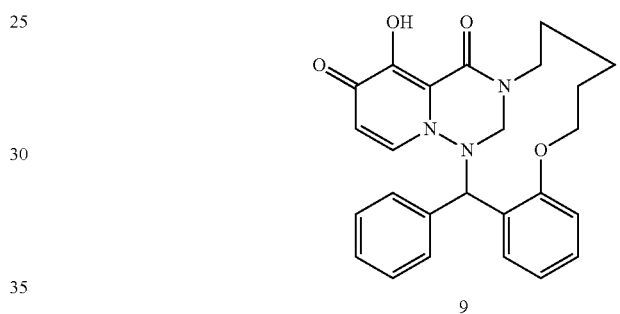

9

Synthesis of Intermediate 9a:

1-((2-(allyloxy)phenyl)(phenyl)methyl)-5-(benzyloxy)-3-(but-3-en-1-yl)-2,3-dihydro-1H-pyrido[2,1-f][1,2,4]triazine-4,6-dione (intermediate 9a, 8.4 g) was obtained using the procedure described for intermediate 5e starting from intermediate 2a.

Synthesis of Intermediate 9b:

15-(benzyloxy)-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (intermediate 9b, undefined E Z mixture, 925 mg) was obtained using the procedure described for intermediate 5f.

Synthesis of Compound 9:

15-hydroxy-2-phenyl-12,13,14,16-tetrahydro-11H-4-oxa-1(1,3)-pyrido[2,1-f][1,2,4]triazina-3(1,2)-benzenacyclononaphane-14,16-dione (compound 9, 29 mg) was obtained using the procedure described for compound 8.

Compound 9:

$^1$H NMR (500 MHz, Chloroform-d) δ ppm 0.98-1.13 (m, 1H) 1.31-1.47 (m, 1H) 1.47-1.62 (m, 1H) 1.63-1.82 (m, 1H) 1.98-2.08 (m, 1H) 2.11-2.25 (m, 1H) 2.55-2.64 (m, 1H) 3.88 (td, J=10.6, 4.3 Hz, 1H) 4.24 (d, J=13.2 Hz, 1H) 4.28-4.37 (m, 2H) 4.80 (d, J=12.9 Hz, 1H) 5.70 (br d, J=6.9 Hz, 1H) 5.98 (s, 1H) 6.73 (d, J=7.6 Hz, 1H) 6.87 (d, J=8.2 Hz, 1H) 7.07-7.12 (m, 6H) 7.18-7.29 (m, 1H) 7.89 (d, J=7.7 Hz, 1H) LC/MS (method LC-A): $R_t$ 2.60 min, MH$^+$432

Example 10: Synthesis of (2S,E)-15-hydroxy-2-phenyl-12,13,14,16-tetrahydro-11H-4-oxa-1(1,3)-pyrido[2,1-f][1,2,4]triazina-3(1,2)-benzenacyclonon-aphan-6-ene-14,16-dione (enantiomer 10A) and (2R,E)-15-hydroxy-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (Enantiomer 10 B)

(1,3)-pyrido[2,1-f][1,2,4]triazina-3(1,2)-benzenacyclonon-aphan-6-ene-14,16-dione (intermediate 10a, 648 mg).

Synthesis of Intermediates 10aA and 10aB:

The two enantiomers of intermediate 10a (1.1 g) were separated via chiral SFC (Stationary phase: Whelk O1 (S,S) 5 μm 250×21.1 mm, Mobile phase: 55% $CO_2$, 45% MeOH). The pure fractions were collected and concentrated under

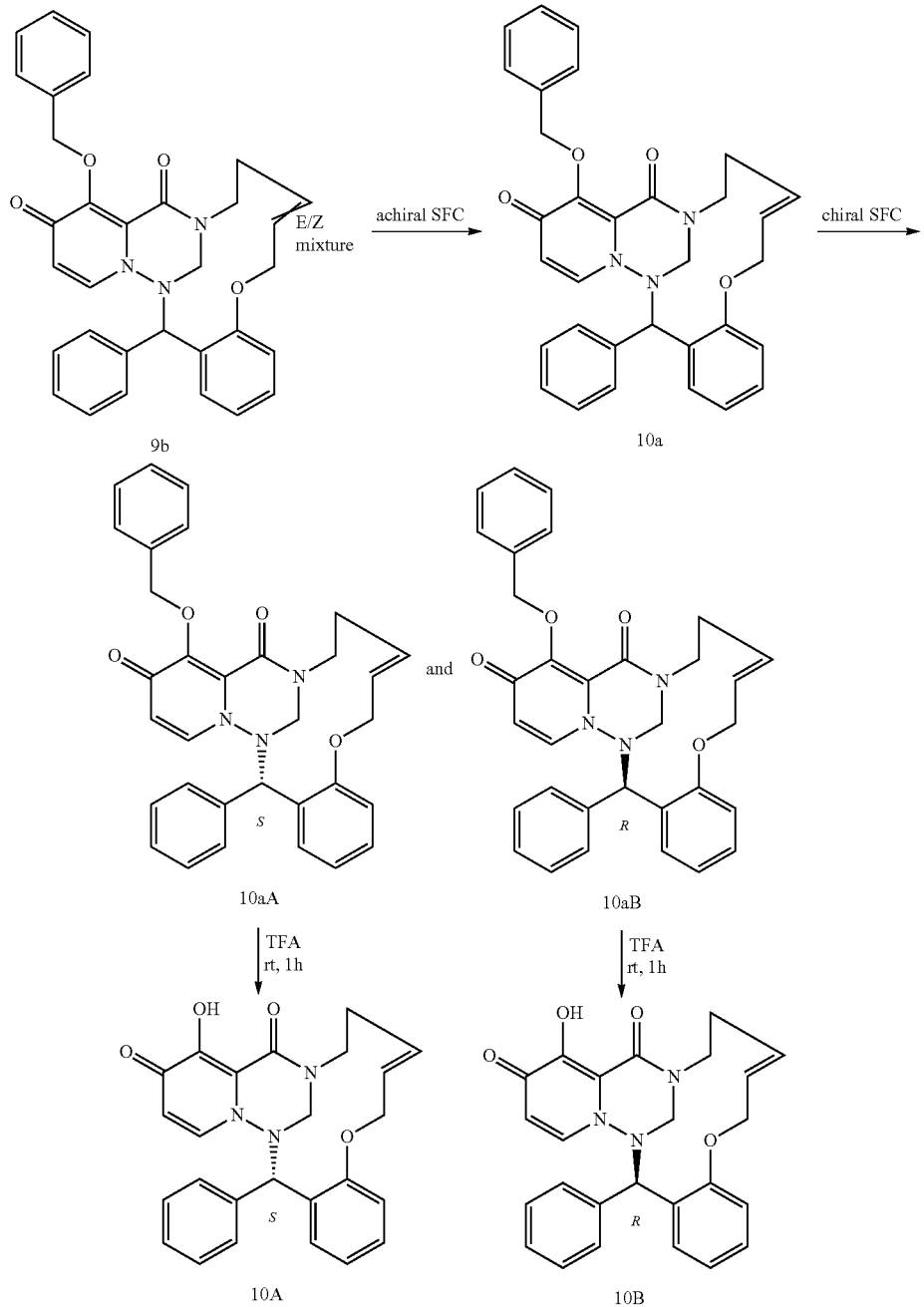

Synthesis of Intermediate 10a:

Intermediate 9b (925 mg) was purified via achiral SFC (Stationary phase: NH₂ 5 μm 150×30 mm, mobile phase: 80% $CO_2$, 20% EtOH). The pure fractions were combined and concentrated under reduced pressure to give (E)-15-(benzyloxy)-2-phenyl-12,13,14,16-tetrahydro-11H-4-oxa-1 reduced pressure to give the first eluted enantiomer (enantiomer 10aA, 470 mg) and the second eluted enantiomer (enantiomer 10aB, 487 mg).

Synthesis of Compound 10A:

(2S,E)-15-hydroxy-2-phenyl-12,13,14,16-tetrahydro-11H-4-oxa-1(1,3)-pyrido[2,1-f][1,2,4]triazina-3(1,2)-ben zenacyclononaphan-6-ene-14,16-dione (enantiomer 10A, 193 mg) was obtained using the procedure described for compound 5A.

Compound 10A:

$^1$H NMR (500 MHz, DMSO-d$_6$) δ ppm 2.22 (br d, J=12.6 Hz, 1H) 2.74-2.94 (m, 2H) 3.70-3.83 (m, 1H) 4.13-4.22 (m, 1H) 4.28 (d, J=12.9 Hz, 1H) 4.71 (dd, J=11.8, 5.2 Hz, 1H) 5.06 (d, J=12.9 Hz, 1H) 5.38 (d, J=7.6 Hz, 1H) 5.44-5.55 (m, 1H) 5.93 (s, 1H) 5.99 (ddd, J=15.3, 10.1, 5.2 Hz, 1H) 6.92-7.27 (m, 7H) 7.28-7.35 (m, 1H) 7.37-7.44 (m, 1H) 8.01 (dd, J=7.6, 1.3 Hz, 1H) 11.74 (br s, 1H)

LC/MS (method LC-B): R$_t$ 2.38 min, MH$^+$430

[α]$_D^{20}$: +409.12° (c 0.274, DMF)

MP=212° C.

Synthesis of Compound 10B:

(2R,E)-15-hydroxy-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (enantiomer 10 B, 213 mg) was obtained using the procedure described for compound 5A.

Compound 10B:

$^1$H NMR (500 MHz, DMSO-d$_6$) δ ppm 2.22 (br d, J=13.2 Hz, 1H) 2.86 (quin, J=12.4 Hz, 2H) 3.72-3.86 (m, 1H) 4.18 (t, J=11.0 Hz, 1H) 4.28 (d, J=13.2 Hz, 1H) 4.71 (dd, J=11.8, 5.2 Hz, 1H) 5.06 (d, J=12.9 Hz, 1H) 5.38 (d, J=7.6 Hz, 1H) 5.50 (td, J=10.0, 4.9 Hz, 1H) 5.93 (s, 1H) 5.99 (ddd, J=15.1, 9.8, 5.0 Hz, 1H) 6.88-7.26 (m, 7H) 7.29-7.35 (m, 1H) 7.37-7.45 (m, 1H) 8.01 (d, J=6.6 Hz, 1H) 11.57-11.88 (m, 1H)

LC/MS (method LC-B): R$_t$ 2.37 min, MH$^+$430

[α]$_D^{20}$: −433.59° (c 0.259, DMF)

MP=212° C.

Example 11: Synthesis of 15-hydroxy-2-(pyridin-2-yl)-12,13,14,16-tetrahydro-11H-1(1,3)-pyrido[2,1-f][1,2,4]triazina-3(1,2)-benzenacyclononaphane-14,16-dione (COMPOUND 11)

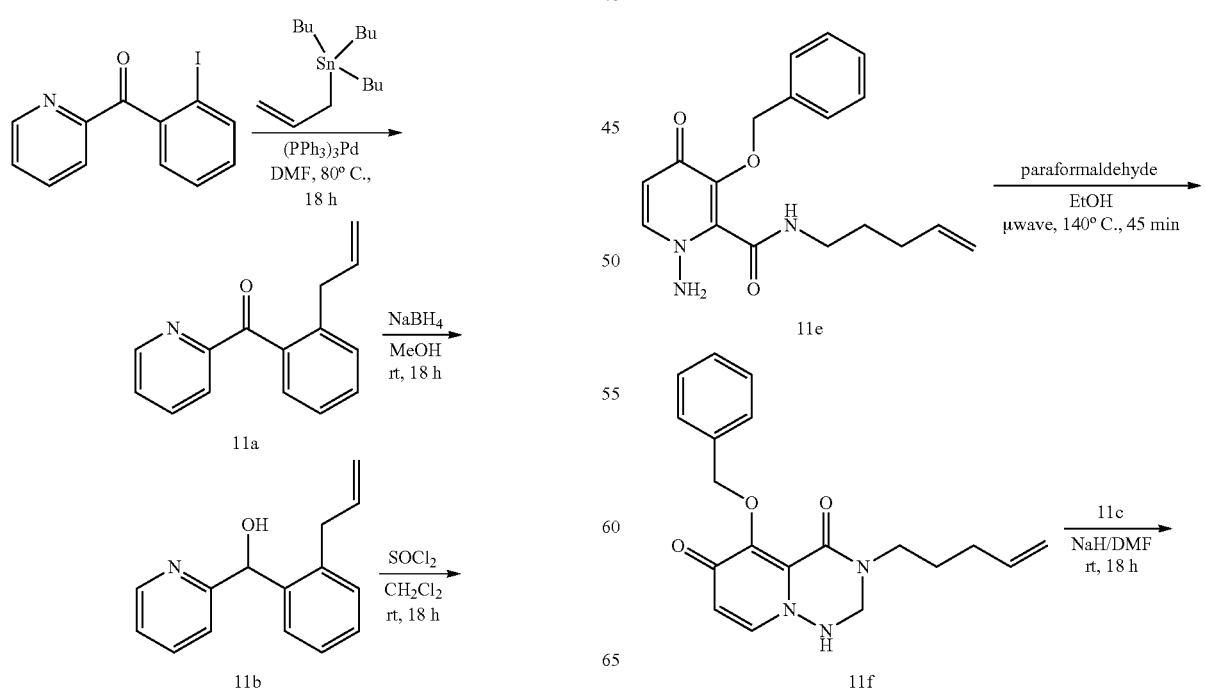

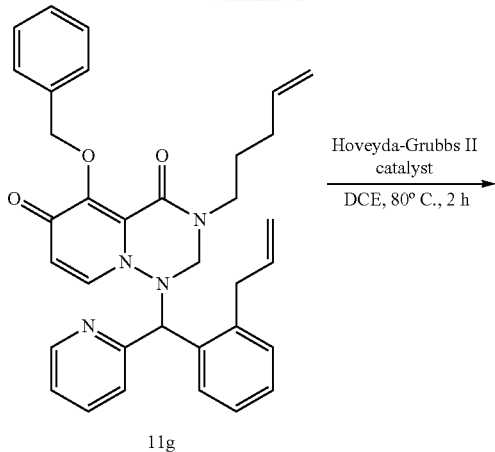

11g

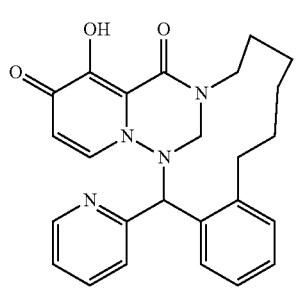

11h

[Structure]

11

Synthesis of Intermediate 11a:

To a solution of (2-iodophenyl)(pyridin-2-yl)methanone [CAS 76160-35-5] (1.5 g, 4.9 mmol) and allyltri-N-butyltin (1.8 mL, 5.8 mmol) in DMF (38 mL, degassed under nitrogen) was added $(PPh_3)_4Pd$ (0.28 g, 0.24 mmol). The mixture was stirred at 80° C. for 18 h. The mixture was partitioned between EtOAc and brine. The organic layer was washed with brine, dried over $MgSO_4$, filtered and concentrated under reduced pressure. The residue was purified by flash chromatography over silica gel (30 μm, 40 g, heptane/EtOAc from 90/10 to 80/20). The pure fractions were combined and concentrated under reduced pressure to give (2-allylphenyl)(pyridin-2-yl)methanone (intermediate 11a, 0.68 g).

Synthesis of Intermediate 11b:

$NaBH_4$ (0.23 g, 6.1 mmol) was added portionwise to a solution of (2-allylphenyl)(pyridin-2-yl)methanone (intermediate 11a, 0.68 g, 3.0 mmol) in MeOH (12 mL) at 0° C. The mixture was then stirred at 0° C. for 1.5 h then at rt for 18 h. 10% $NH_4Cl$ aqueous solution was added and the aqueous phase was extracted with $CH_2Cl_2$ twice. The combined organic extracts were dried over $MgSO_4$, filtered and concentrated under reduced pressure to afford (2-allylphenyl)(pyridin-2-yl)methanol (intermediate 11b, 0.63 g), which was used as such in the next step.

Synthesis of Intermediate 11c:

$SOCl_2$ (0.24 mL, 3.4 mmol) was added dropwise to a solution of (2-allylphenyl)(pyridin-2-yl)methanol (intermediate 11b, 0.63 g, 2.8 mmol) in $CH_2Cl_2$ (6.9 mL) at 5° C. The mixture was stirred at 5° C. for 1 h and at rt for 18 h. The solvent was evaporated to dryness and the residue co-evaporated with toluene to yield 2-((2-allylphenyl)chloromethyl)pyridine (intermediate 11c, 0.90 g), which was used as such in the next step.

Synthesis of Intermediate 11d:

3-(benzyloxy)-4-oxo-N-(pent-4-en-1-yl)-1,4-dihydropyridine-2-carboxamide (intermediate 11d, 4.7 g) was obtained using the procedure described for intermediate 1a starting from pent-4-enylamine [CAS 22537-07-1].

Synthesis of Intermediate 11e:

1-amino-3-(benzyloxy)-4-oxo-N-(pent-4-en-1-yl)-1,4-dihydropyridine-2-carboxamide (intermediate 11e, 3.9 g) was obtained using the procedure described for intermediate 1b.

Synthesis of Intermediate 11f:

5-(benzyloxy)-3-(pent-4-en-1-yl)-2,3-dihydro-1H-pyrido[2,1-f][1,2,4]triazine-4,6-dione (intermediate 11f, 5 g), used as such in the next step, was obtained using the procedure described for compound 5d.

Synthesis of Intermediate 11g:

1-((2-allylphenyl)(pyridin-2-yl)methyl)-5-(benzyloxy)-3-(pent-4-en-1-yl)-2,3-dihydro-1H-pyrido[2,1-f][1,2,4]triazine-4,6-dione (intermediate 11g, 350 mg) was obtained using the procedure described for intermediate 5e.

Synthesis of Intermediate 11h:

15-(benzyloxy)-2-(pyridin-2-yl)-12,13,14,16-tetrahydro-11H-1(1,3)-pyrido[2,1-f][1,2,4]triazina-3(1,2)-benzenacyclononaphan-5-ene-14,16-dione (intermediate 11h, undetermined mixture of E Z isomers, 200 mg), used as such in the next step, was obtained using the procedure described for intermediate 5f.

Synthesis of Compound 11:

15-hydroxy-2-(pyridin-2-yl)-12,13,14,16-tetrahydro-11H-1(1,3)-pyrido[2,1-f][1,2,4]triazina-3(1,2)-benzenacyclononaphane-14,16-dione (Compound 11, 40 mg) was obtained using the procedure described for compound 8.

Compound 11:

$^1H$ NMR (500 MHz, Chloroform-d) δ ppm 0.68-0.87 (m, 1H) 0.89-1.10 (m, 1H) 1.25-1.47 (m, 2H) 1.72-1.90 (m, 3H) 2.27-2.38 (m, 1H) 2.40-2.57 (m, 1H) 2.60-2.71 (m, 2H) 3.93 (dt, J=13.5, 4.5 Hz, 1H) 4.36 (d, J=12.9 Hz, 1H) 4.96 (d, J=12.9 Hz, 1H) 5.69 (br d, J=7.6 Hz, 1H) 6.15 (s, 1H) 6.74 (d, J=7.6 Hz, 1H) 6.98-7.16 (m, 2H) 7.29 (t, J=7.4 Hz, 1H) 7.34 (t, J=7.6 Hz, 1H) 7.42 (td, J=7.7, 1.9 Hz, 1H) 8.03 (d, J=7.7 Hz, 1H) 8.32 (d, J=4.1 Hz, 1H) LC/MS (method LC-A): $R_t$ 2.63 min, $MH^+$ 431

Example 12: Synthesis of 4-hydroxy-16-(pyridin-2-yl)-7,8,9,10,11,16-hexahydro-6,17-methanobenzo[k]pyrido[1,2-b][1,2,5]triazacyclotridecine-3,5-dione (Compound 12)

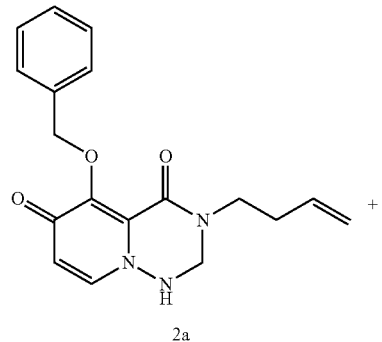
2a

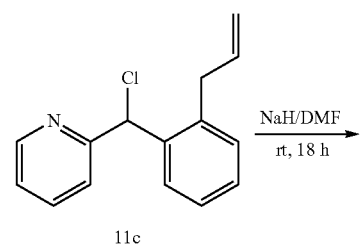
11c

NaH/DMF
rt, 18 h

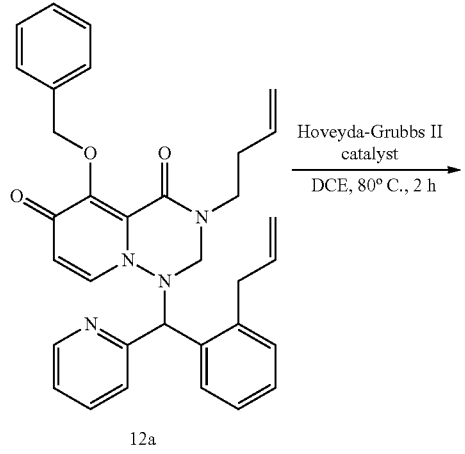
12a

Hoveyda-Grubbs II catalyst
DCE, 80° C., 2 h

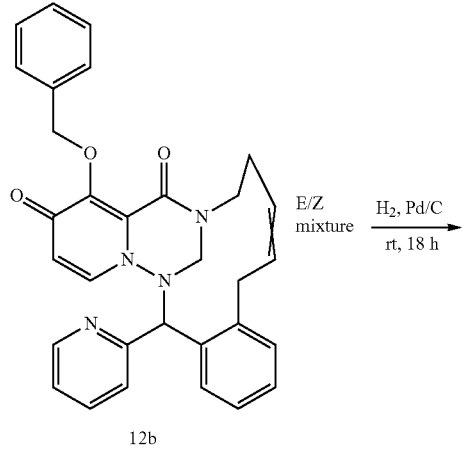
12b

E/Z mixture
H₂, Pd/C
rt, 18 h

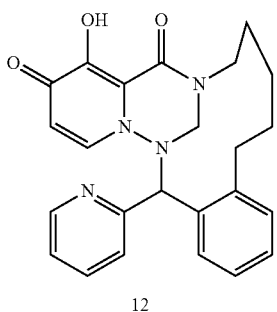 [SMILES: O=C1c2c(O)c(=O)ccn2N2CN1CCCCCc1ccccc1C2c1ccccn1]
12

Synthesis of Compound 12:

Compound 12 (8 mg) was obtained using the procedures described in example 11.

Compound 12:

$^1$H NMR (500 MHz, DMSO-d$_6$) δ ppm 0.67-0.88 (m, 1H) 1.29-1.41 (m, 1H) 1.42-1.60 (m, 2H) 1.70-1.81 (m, 1H) 1.92-2.06 (m, 1H) 2.52-2.59 (m, 1H) 2.62-2.67 (m, 1H) 2.79-2.88 (m, 1H) 3.99 (br t, J=12.8 Hz, 1H) 4.37 (d, J=13.6 Hz, 1H) 5.08 (br d, J=13.9 Hz, 1H) 5.52 (d, J=7.6 Hz, 1H) 5.82 (s, 1H) 7.05 (d, J=7.9 Hz, 1H) 7.20-7.30 (m, 2H) 7.33 (t, J=6.9 Hz, 1H) 7.41 (t, J=7.6 Hz, 1H) 7.63 (d, J=7.9 Hz, 1H) 7.71 (td, J=7.7, 1.6 Hz, 1H) 8.06 (d, J=7.6 Hz, 1H) 8.42 (d, J=4.1 Hz, 1H) 11.35 (br s, 1H) LC/MS (method LC-A): R$_t$ 2.35 min, MH$^+$415

Example 13: Synthesis of 4-hydroxy-7-methyl-15-phenyl-8,9,10,15-tetrahydro-7H-6,16-methanobenzo[j]pyrido[1,2-b][1,2,5]triazacyclododecine-3,5-dione (Compound 13)

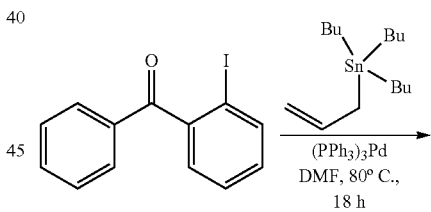

(PPh₃)₃Pd
DMF, 80° C.,
18 h

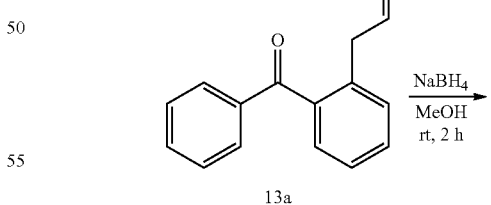
13a

NaBH₄
MeOH
rt, 2 h

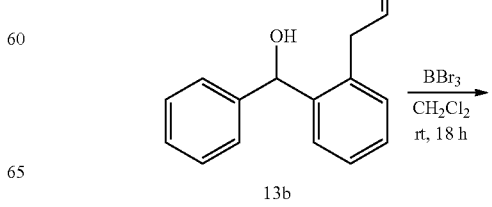
13b

BBr₃
CH₂Cl₂
rt, 18 h

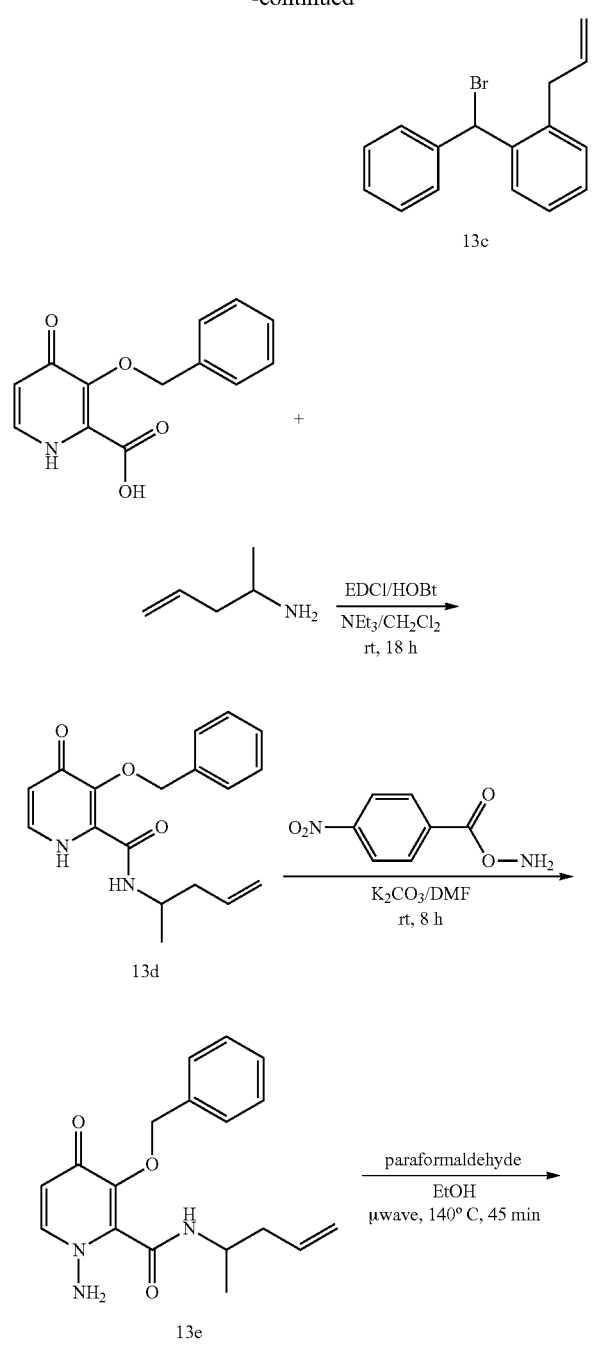

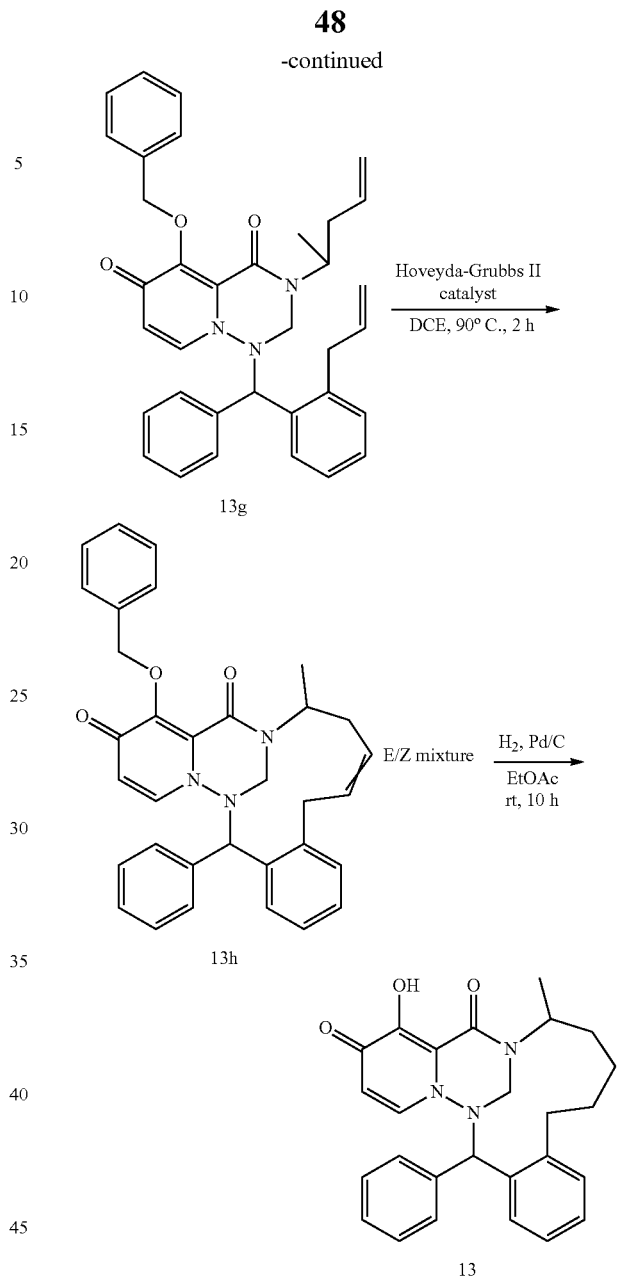

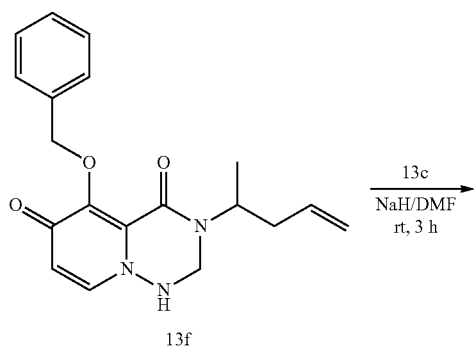

Synthesis of Intermediate 13b:

2-allylphenyl)(phenyl)methanol (intermediate 13b, 4.5 g) was obtained using the procedures described in example 11.

Synthesis of Intermediate 13c:

1-allyl-2-(bromo(phenyl)methyl)benzene (intermediate 13c, 1.28 g) was obtained using the procedure described for intermediate 6b.

Synthesis of Intermediate 13f:

5-(benzyloxy)-3-(pent-4-en-2-yl)-2,3-dihydro-1H-pyrido[2,1-f][1,2,4]triazine-4,6-dione (intermediate 13f, 1.12 g) was obtained using the procedures described for intermediate 2a.

Synthesis of Intermediate 13g:

1-((2-allylphenyl)(phenyl)methyl)-5-(benzyloxy)-3-(pent-4-en-2-yl)-2,3-dihydro-1H-pyrido[2,1-f][1,2,4]triazine-4,6-dione (intermediate 13g, 410 mg) was obtained using the procedure described for intermediate 5e.

Synthesis of Intermediate 13h:

4-(benzyloxy)-7-methyl-16-phenyl-7,8,11,16-tetrahydro-6,17-methanobenzo[k]pyrido[1,2-b][1,2,5]triazacyclotridecine-3,5-dione (undefined E/Z mixture, intermediate 13e, 140 mg) was obtained using the procedure described for intermediate 5f.

Synthesis of Compound 13:

4-hydroxy-7-methyl-15-phenyl-8,9,10,15-tetrahydro-7H-6,16-methanobenzo[j]pyrido[1,2-b][1,2,5]triazacyclododecine-3,5-dione (compound 13, 29 mg) was obtained using the procedure described for compound 8.

Compound 13:

major diastereoisomer (55%)

$^1$H NMR (500 MHz, Chloroform-d) δ ppm 0.91 (d, J=6.9 Hz, 3H) 1.17-1.73 (m, 4H) 1.87-2.14 (m, 3H) 2.46-2.75 (m, 2H) 4.45 (d, J=13.2 Hz, 1H) 4.56-4.71 (m, 2H) 5.60 (s, 1H) 5.63 (dd, J=7.6, 5.7 Hz, 1H) 6.54 (d, J=7.9 Hz, 1H) 7.08-7.18 (m, 5H) 7.20-7.37 (m, 3H) 7.87 (d, J=7.6 Hz, 1H) minor diastereoisomer (45%)

$^1$H NMR (500 MHz, Chloroform-d) δ ppm 1.17-1.73 (m, 7H) 1.87-2.14 (m, 3H) 2.46-2.75 (m, 1H) 2.72-2.80 (m, 1H) 2.81-2.93 (m, 1H) 4.28 (d, J=13.2 Hz, 1H) 4.91 (d, J=12.9 Hz, 1H) 5.63 (dd, J=7.6, 5.7 Hz, 1H) 5.71 (s, 1H) 6.63 (d, J=7.6 Hz, 1H) 7.08-7.18 (m, 5H) 7.20-7.37 (m, 3H) 7.89 (d, J=7.9 Hz, 1H) LC/MS (method LC-A): R$_t$ 2.93 min, MH$^+$430

MP>260° C.

Example 14: Synthesis of (*E)-15-hydroxy-2-phenyl-12,13,14,16-tetrahydro-11H-1(1,3)-pyrido[2,1-f][1,2,4]triazina-3(1,2)-benzenacyclononaphan-6-ene-14,16-dione (Compound 14)

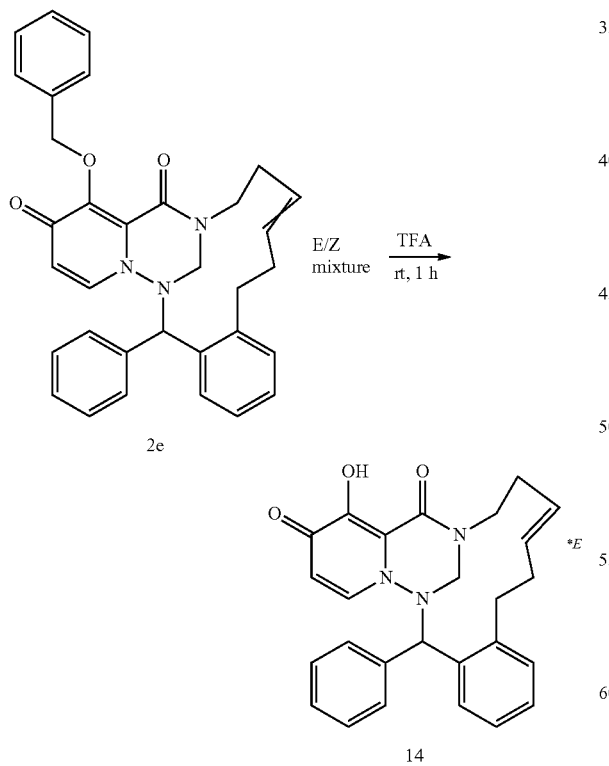

Synthesis of Compound 14:

(*E)-15-hydroxy-2-phenyl-12,13,14,16-tetrahydro-11H-1(1,3)-pyrido[2,1-f][1,2,4]triazina-3(1,2)-benzenacyclononaphan-6-ene-14,16-dione (Compound 14, 25 mg) was obtained using the procedure described for compound 5A.

Compound 14:

$^1$H NMR (500 MHz, Chloroform-d) δ ppm 1.96-2.07 (m, 1H) 2.15 (br d, J=14.2 Hz, 1H) 2.27-2.39 (m, 2H) 2.44-2.59 (m, 2H) 2.82-2.95 (m, 1H) 3.96 (dt, J=13.7, 3.9 Hz, 1H) 4.39 (d, J=12.6 Hz, 1H) 4.88 (d, J=12.6 Hz, 1H) 5.02 (ddd, J=15.0, 10.2, 4.4 Hz, 1H) 5.53 (d, J=7.6 Hz, 1H) 5.69 (ddd, J=14.9, 10.0, 5.0 Hz, 1H) 5.85 (s, 1H) 6.51 (d, J=7.9 Hz, 1H) 6.81 (br d, J=6.9 Hz, 1H) 6.98 (br s, 1H) 7.03-7.08 (m, 1H) 7.09-7.15 (m, 3H) 7.24-7.37 (m, 2H) 7.86 (d, J=7.6 Hz, 1H) LC/MS (method LC-B): R$_t$ 2.69 min, MH$^+$428

Examples 15 and 16: Synthesis of (Z)-15-hydroxy-2-(pyridin-2-yl)-12,13,14,16-tetrahydro-11H-1(1,3)-pyrido[2,1-f][1,2,4]triazina-3(1,2)-benzenacyclononaphan-5-ene-14,16-dione (Compound 15) and (E)-15-hydroxy-2-(pyridin-2-yl)-12,13,14,16-tetrahydro-11H-1(1,3)-pyrido[2,1-f][1,2,4]triazina-3(1,2)-benzenacyclononaphan-5-ene-14,16-dione (Compound 16)

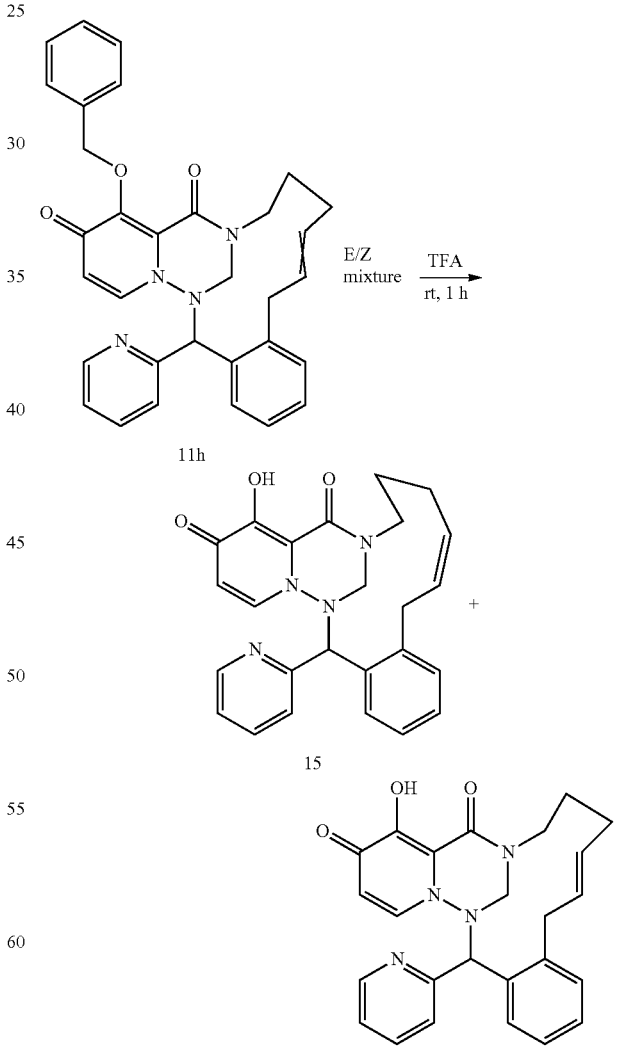

Synthesis of Compounds 15 and 16:

(Z)-15-hydroxy-2-(pyridin-2-yl)-12,13,14,16-tetrahydro-11H-1(1,3)-pyrido[2,1-f][1,2,4]triazina-3(1,2)-benzenacyclononaphan-5-ene-14,16-dione (Compound 15, 5 mg) and (E)-15-hydroxy-2-(pyridin-2-yl)-12,13,14,16-tetrahydro-11H-1(1,3)-pyrido[2,1-f][1,2,4]triazina-3(1,2)-benzenacyclononaphan-5-ene-14,16-dione (Compound 16, 12 mg) were obtained using the procedure described for compound 5A. The two isomers were separated via Reverse phase (Stationary phase: YMC-actus Triart-C18 10 µm 30×150 mm, Mobile phase: gradient from 75% formic acid 0.1%, 25% CH$_3$CN to 35% formic acid 0.1%, 65% CH$_3$CN).

Compound 15:

$^1$H NMR (500 MHz, DMSO-d$_6$) δ ppm 0.59-0.73 (m, 1H) 1.52-1.63 (m, 1H) 1.81-1.94 (m, 1H) 2.35-2.54 (m, 2H) 2.64-2.72 (m, 1H) 3.62-3.70 (m, 1H) 3.92-4.06 (m, 1H) 4.22-4.30 (m, 1H) 4.93-5.07 (m, 1H) 5.36-5.46 (m, 1H) 5.55-5.65 (m, 1H) 5.83-5.95 (m, 1H) 6.01 (s, 1H) 7.02-7.26 (m, 4H) 7.28-7.36 (m, 1H) 7.42 (d, J=7.9 Hz, 1H) 7.59 (dt, J=1.3, 7.6 Hz, 1H) 8.04 (d, J=7.9 Hz, 1H) 8.32 (d, J=3.8 Hz, 1H)

LC/MS (method LC-A): R$_t$ 2.35 min, MH$^+$429

Compound 16:

$^1$H NMR (500 MHz, DMSO-d$_6$) δ ppm 1.76-1.88 (m, 1H) 1.93-2.04 (m, 1H) 2.12-2.21 (m, 1H) 2.21-2.31 (m, 1H) 2.74-2.83 (m, 1H) 3.05-3.2 (m, 2H) 3.80-3.92 (m, 1H) 4.24 (d, J=12.6 Hz, 1H) 5.00 (d, J=12.6 Hz, 1H) 5.42 (d, J=7.6 Hz, 1H) 5.43-5.54 (m, 1H) 5.65-5.72 (m, 1H) 5.98 (s, 1H) 7.15 (d, J=6.6 Hz, 1H) 7.20 (dd, J=7.1, 5.2 Hz, 1H) 7.28-7.36 (m, 3H) 7.48 (t, J=7.3 Hz, 1H) 7.62 (td, J=7.7, 1.9 Hz, 1H) 8.29 (d, J=7.7 Hz, 1H) 8.33 (d, J=5.0 Hz, 1H) 11.78 (br s, 1H) LC/MS (method LC-A): R$_t$ 2.40 min. MH$^+$429

Example 17: Synthesis of (E)-15-hydroxy-2-phenyl-12,13,14,16-tetrahydro-11H-5-oxa-1(1,3)-pyrido[2,1-f][1,2,4]triazina-3(1,2)-benzenacyclononaphan-7-ene-14,16-dione (Compound 17)

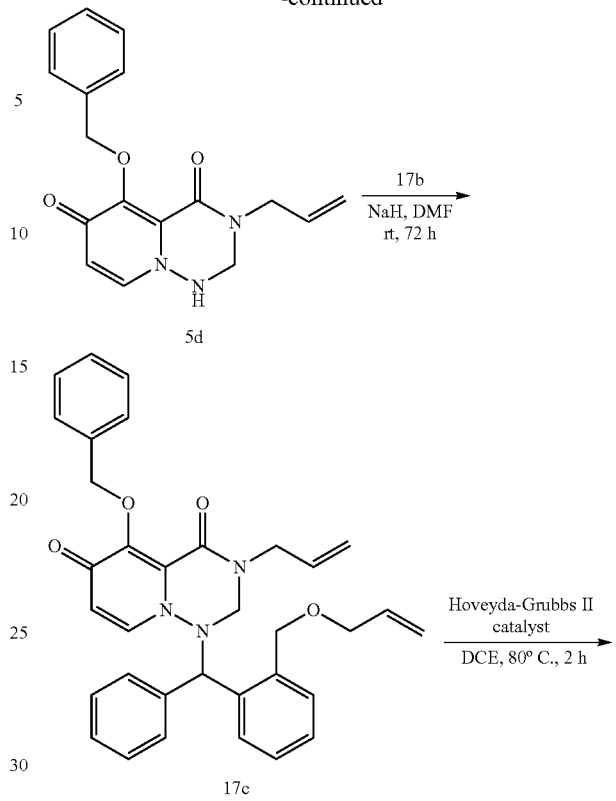

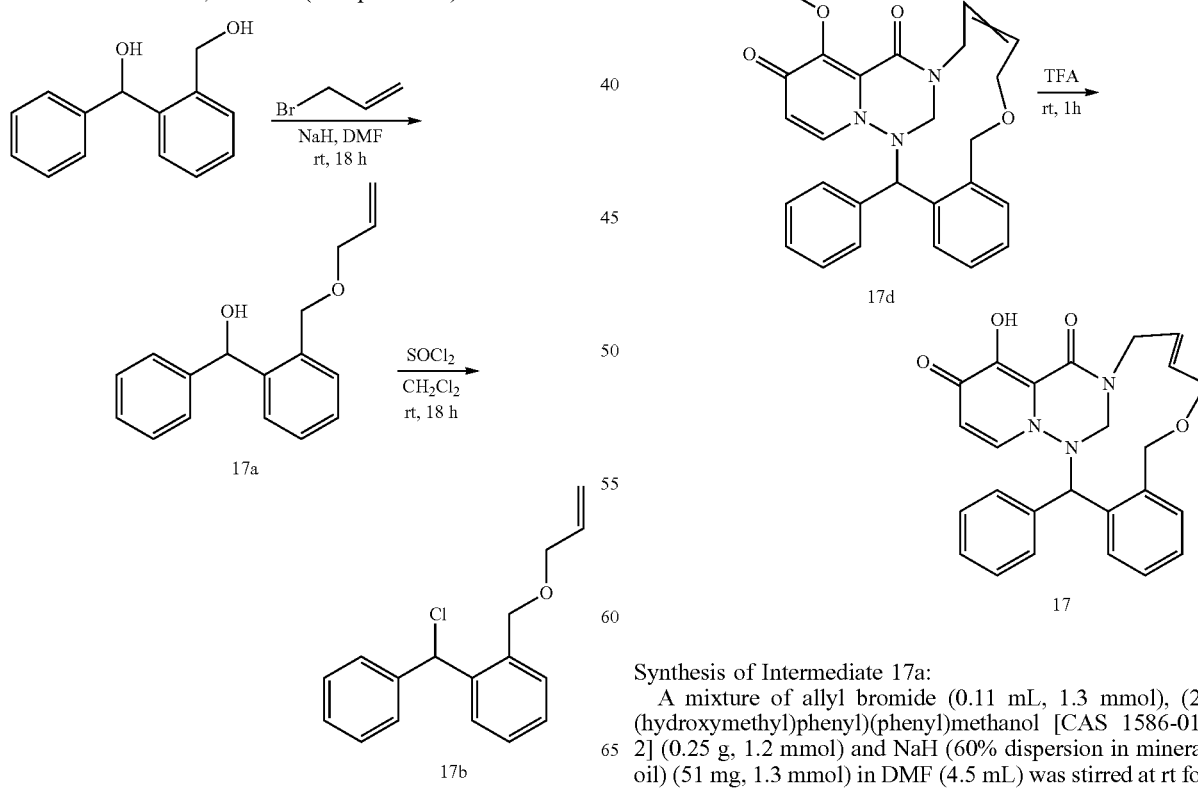

Synthesis of Intermediate 17a:

A mixture of allyl bromide (0.11 mL, 1.3 mmol), (2-(hydroxymethyl)phenyl)(phenyl)methanol [CAS 1586-01-2] (0.25 g, 1.2 mmol) and NaH (60% dispersion in mineral oil) (51 mg, 1.3 mmol) in DMF (4.5 mL) was stirred at rt for 18 h. EtOAc was added and the mixture was washed 5 times with brine. The organic layer was dried over MgSO₄, filtered and concentrated under reduced pressure. The residue was purified by flash chromatography over silica gel (30 μm, 12 g, heptane/EtOAc from 90/10 to 80/20). The pure fractions were collected and concentrated under vacuum to give (2-((allyloxy)methyl)phenyl)(phenyl)methanol (intermediate 17a, 90 mg).

Synthesis of Intermediate 17b:

SOCl₂ (31 μL, 0.043 mmol) was added dropwise to a solution of (2-((allyloxy)methyl)phenyl)(phenyl)methanol (intermediate 17a, 90 mg, 0.35 mmol) in CH₂Cl₂ (0.88 mL) at 5° C. The mixture was stirred at 5° C. for 1 h and at rt for 18 h. The solvent was evaporated to dryness and the residue co-evaporated with toluene to give 1-((allyloxy)methyl)-2-(chloro(phenyl)methyl)benzene (intermediate 17b, 90 mg), which was used as such in the next step.

Synthesis of Compound 17:

(E)-15-hydroxy-2-phenyl-12,13,14,16-tetrahydro-11H-5-oxa-1(1,3)-pyrido[2,1-f][1,2,4]triazina-3(1,2)-benzenacyclononaphan-7-ene-14,16-dione (Compound 17, 27 mg) was obtained using the procedures described in example 5.

Compound 17:
¹H NMR (500 MHz, DMSO-d₆) δ ppm (93% E, 7% Z) (spectrum of the major isomer) 3.23-3.29 (m, 1H) 3.99-4.09 (m, 2H) 4.16-4.22 (m, 1H) 4.29 (d, J=13.6 Hz, 1H) 4.46 (d, J=13.9 Hz, 1H) 4.51-4.62 (m, 1H) 5.16-5.24 (m, 1H) 5.42-5.50 (m, 2H) 5.55-5.69 (m, 1H) 6.10-6.20 (m, 1H) 7.16-7.29 (m, 6H) 7.38-7.46 (m, 2H) 7.46-7.53 (m, 1H) 8.08-8.18 (m, 1H) LC/MS (method LC-B): R_t 2.29 min, MH⁺430

Example 18: Synthesis of 12-hydroxy-18-phenyl-5,8,9,18-tetrahydro-10,17-methanobenzo[k]pyrido[1,2-b][1,2,5,9]tetraazacyclotridecine-7,11,13(6H)-trione (Compound 18)

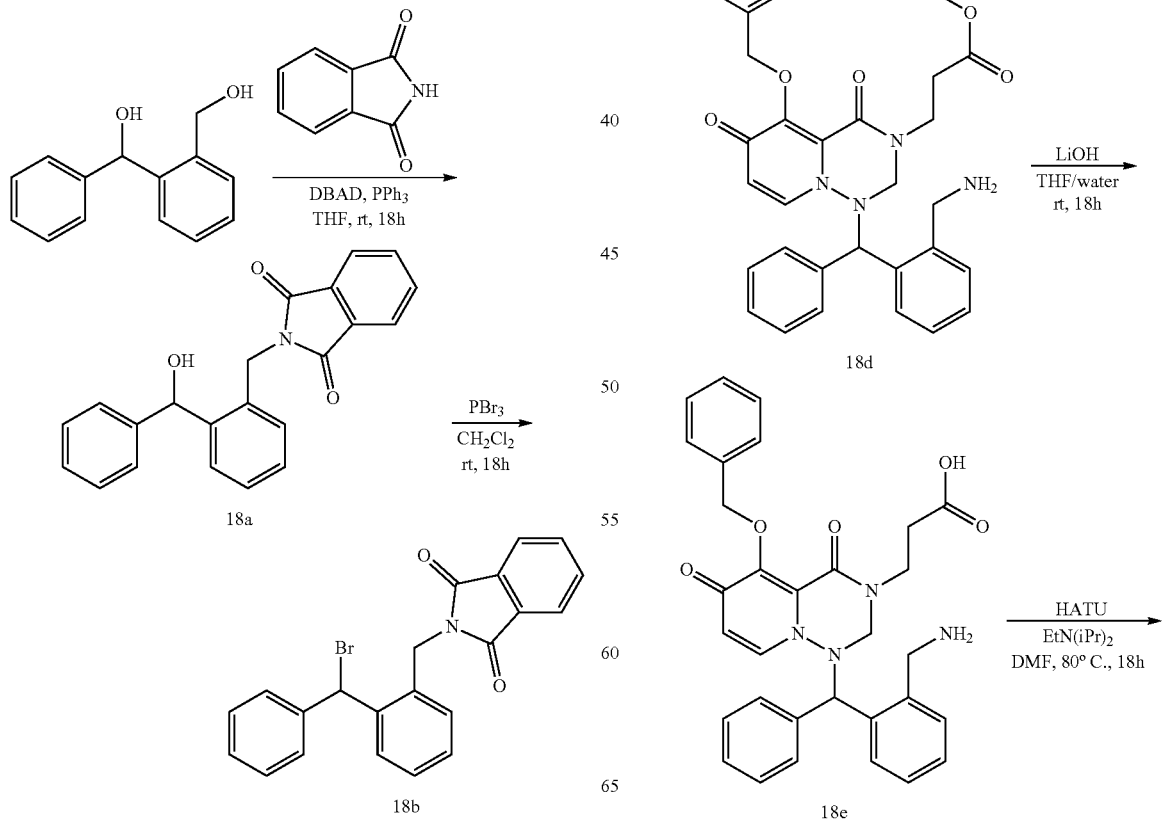

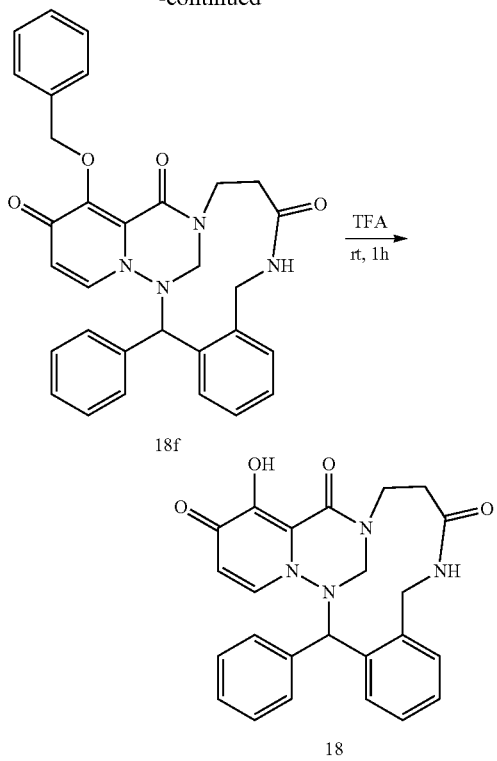

Synthesis of Intermediate 18a:

Under N₂, a solution of (2-(hydroxymethyl)phenyl)(phenyl)methanol [CAS 1586-01-2](1.5 g, 7.0 mmol), phtalimide (1.1 g, 7.7 mmol), di-tert-butyl azodicarboxylate (DBAD) (2.4 g, 11 mmol) and PPh₃ (2.8 g, 11 mmol) in dry THF (57 mL) was stirred for 18 h at rt. Celite® was added and the mixture was concentrated under recued pressure. The residue was purified by flash chromatography over silica gel (30 μm, 40 g, dry loading (Celite®), heptane/EtOAc from 90/10 to 70/30). The pure fractions were collected and concentrated under reduced pressure to give 2-(2-(hydroxy(phenyl)methyl)benzyl)isoindoline-1,3-dione (intermediate 18a, 730 mg).

Synthesis of Intermediate 18b:

At 0° C., PBr₃ (0.20 mL, 2.1 mmol) was added dropwise to a solution of 2-(2-(hydroxy(phenyl)methyl)benzyl)isoindoline-1,3-dione (intermediate 18a, 0.72 g, 2.1 mmol) in CH₂Cl₂ (6.7 mL). The mixture was warmed up to rt and stirred for 18 h. The reaction was quenched by the addition of ice and the aqueous phase was extracted with CH₂Cl₂. The organic layer was washed with water, dried over MgSO₄, filtered and the solvent was evaporated to dryness to give 2-(2-(bromo(phenyl)methyl)benzyl)isoindoline-1,3-dione (intermediate 18b, 870 mg).

Synthesis of Intermediate 18c:

Ethyl 3-(5-(benzyloxy)-1-((2-((1,3-dioxoisoindolin-2-1)methyl)phenyl)(phenyl)methyl)-4,6-dioxo-1,2,4,6-tetrahydro-3H-pyrido[2,1-f][1,2,4]triazin-3-yl)propanoate (intermediate 18c, 360 mg) was obtained using the procedure described for intermediate 1d.

Synthesis of Intermediate 18d:

A mixture of ethyl 3-(5-(benzyloxy)-1-((2-((1,3-dioxoisoindolin-2-yl)methyl)phenyl)(phenyl)methyl)-4,6-dioxo-1,2,4,6-tetrahydro-3H-pyrido[2,1-f][1,2,4]triazin-3-yl)propanoate (intermediate 18c, 0.43 g, 0.62 mmol) and hydrazine monohydrate (0.57 mL, 9.3 mmol) in EtOH (8.9 mL) was heated at 50° C. for 18 h. The mixture was cooled down to rt and concentrated to dryness with Celite®. The residue was purified by flash chromatography over silica gel (30 μm, 12 g, dry loading (Celite®), CH₂Cl₂/CH₃OH from 100/0 to 95/5). The pure fractions were collected and concentrated under reduced pressure to give ethyl 3-(1-((2-(aminomethyl)phenyl)(phenyl)methyl)-5-(benzyloxy)-4,6-dioxo-1,2,4,6-tetrahydro-3H-pyrido[2,1-f][1,2,4]triazin-3-yl)propanoate (intermediate 18d, 80 mg).

Synthesis of Intermediate 18e:

LiOH (17 mg, 0.71 mmol) was added to a mixture of ethyl 3-(1-((2-(aminomethyl)phenyl)(phenyl)methyl)-5-(benzyloxy)-4,6-dioxo-1,2,4,6-tetrahydro-3H-pyrido[2,1-f][1,2,4]triazin-3-yl)propanoate (intermediate 18d, 80 mg, 0.14 mmol) in water (0.26) and THF (1.1 mL). The reaction mixture was stirred at rt for 18 h. The solution was concentrated under vacuum and co-evaporated with toluene. Purification was performed by flash chromatography over silica gel (30 μm, 4 g, from CH₂Cl₂/CH₃OH 96/4 to 88/12). The pure fractions were collected and concentrated under reduced pressure to give 3-(1-((2-(aminomethyl)phenyl)(phenyl)methyl)-5-(benzyloxy)-4,6-dioxo-1,2,4,6-tetrahydro-3H-pyrido[2,1-f][1,2,4]triazin-3-yl)propanoic acid (intermediate 18e, 70 mg).

Synthesis of Intermediate 18f:

A mixture of 3-(1-((2-(aminomethyl)phenyl)(phenyl)methyl)-5-(benzyloxy)-4,6-dioxo-1,2,4,6-tetrahydro-3H-pyrido[2,1-f][1,2,4]triazin-3-yl)propanoic acid (intermediate 18e, 70 mg, 0.13 mmol), HATU (74 mg, 0.20 mmol) and N,N-diisopropylethylamine (86 μL, 0.52 mmol) in DMF (10 mL) was stirred at 80° C. for 18 h. EtOAc was added and the mixture was washed 5 times with brine. The organic layer was dried over MgSO₄, filtered and concentrated under reduced pressure. Purification was carried out by flash chromatography over silica gel (30 μm, 4 g, CH₂Cl₂/CH₃OH from 100/0 to 97/3). The pure fractions were collected and evaporated to dryness to give 12-(benzyloxy)-18-phenyl-5,8,9,18-tetrahydro-10,17-methanobenzo[k]pyrido[1,2-b][1,2,5,9]tetraazacyclotridecine-7,11,13(6H)-trione (intermediate 18f, 35 mg).

Synthesis of Compound 18:

12-hydroxy-18-phenyl-5,8,9,18-tetrahydro-10,17-methanobenzo[k]pyrido[1,2-b][1,2,5,9]tetraazacyclotridecine-7,11,13(6H)-trione (Compound 18, 22 mg) was obtained using the procedure described for compound 5A.

Compound 18:

¹H NMR (500 MHz, DMSO-d₆) δ ppm 2.26-2.32 (m, 1H) 2.75-2.97 (m, 1H) 2.97-3.14 (m, 1H) 3.72-3.85 (m, 2H) 3.95 (br d, J=12.6 Hz, 1H) 4.42 (br s, 1H) 5.02 (br d, J=12.6 Hz, 1H) 5.38 (br d, J=7.6 Hz, 1H) 5.88 (br s, 1H) 7.10-7.59 (m, 9H) 8.22 (br d, J=7.6 Hz, 1H) 8.75 (br s, 1H) 11.53 (br s, 1H)

LC/MS (method LC-A): R, 1.98 min, MH⁺431

Example 19: Synthesis of (*Z)-15-hydroxy-2-phenyl-12,13,14,16-tetrahydro-11H-4-oxa-1(1,3)-pyrido[2,1-f][1,2,4]triazina-3(1,2)-benzenacyclononaphan-7-ene-14,16-dione (Compound 19)

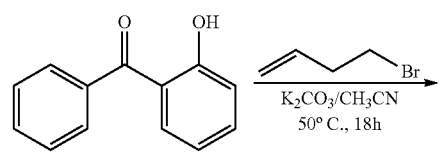

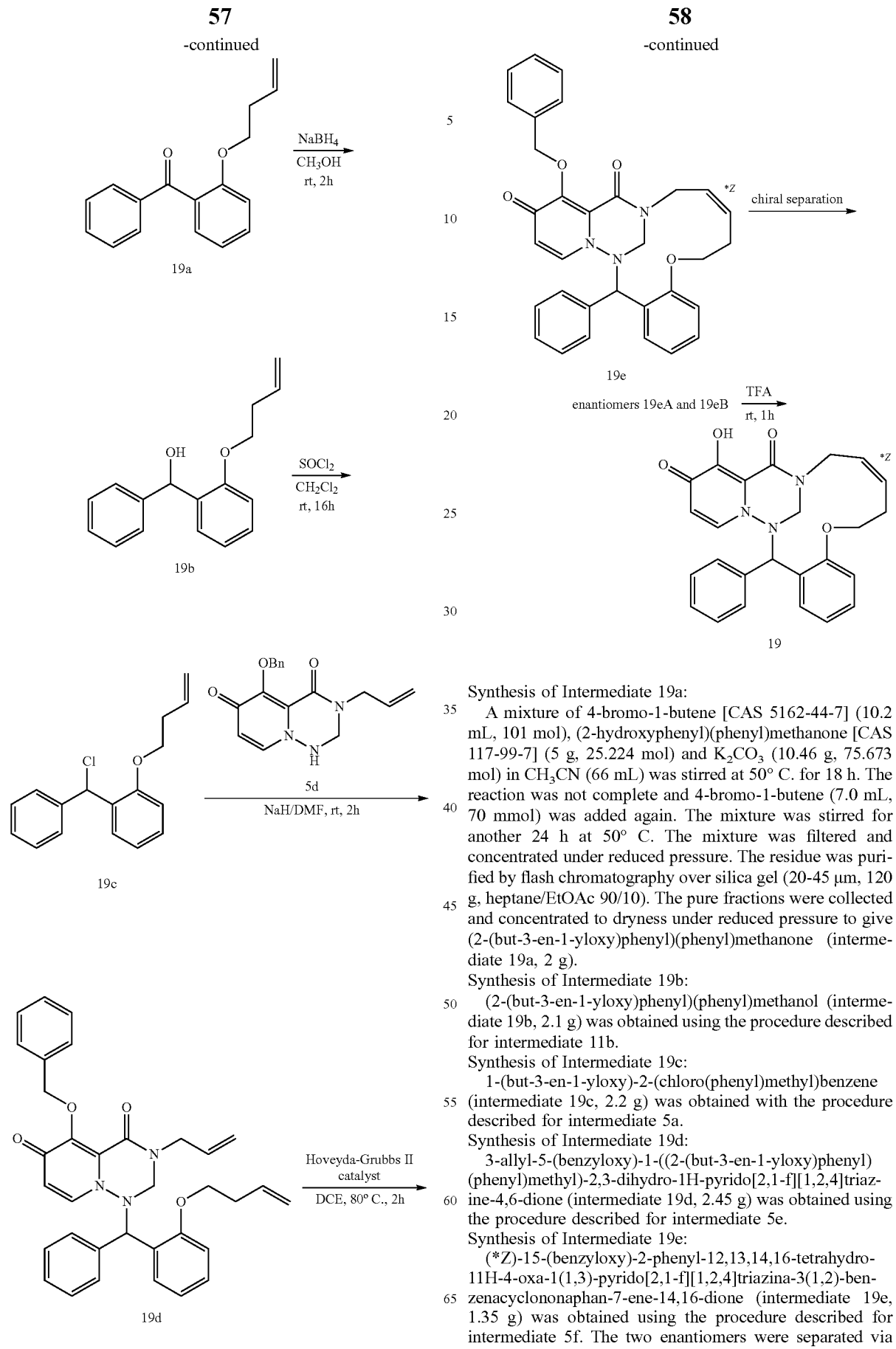

Synthesis of Intermediate 19a:

A mixture of 4-bromo-1-butene [CAS 5162-44-7] (10.2 mL, 101 mol), (2-hydroxyphenyl)(phenyl)methanone [CAS 117-99-7] (5 g, 25.224 mol) and $K_2CO_3$ (10.46 g, 75.673 mol) in $CH_3CN$ (66 mL) was stirred at 50° C. for 18 h. The reaction was not complete and 4-bromo-1-butene (7.0 mL, 70 mmol) was added again. The mixture was stirred for another 24 h at 50° C. The mixture was filtered and concentrated under reduced pressure. The residue was purified by flash chromatography over silica gel (20-45 μm, 120 g, heptane/EtOAc 90/10). The pure fractions were collected and concentrated to dryness under reduced pressure to give (2-(but-3-en-1-yloxy)phenyl)(phenyl)methanone (intermediate 19a, 2 g).

Synthesis of Intermediate 19b:

(2-(but-3-en-1-yloxy)phenyl)(phenyl)methanol (intermediate 19b, 2.1 g) was obtained using the procedure described for intermediate 11b.

Synthesis of Intermediate 19c:

1-(but-3-en-1-yloxy)-2-(chloro(phenyl)methyl)benzene (intermediate 19c, 2.2 g) was obtained with the procedure described for intermediate 5a.

Synthesis of Intermediate 19d:

3-allyl-5-(benzyloxy)-1-((2-(but-3-en-1-yloxy)phenyl)(phenyl)methyl)-2,3-dihydro-1H-pyrido[2,1-f][1,2,4]triazine-4,6-dione (intermediate 19d, 2.45 g) was obtained using the procedure described for intermediate 5e.

Synthesis of Intermediate 19e:

(*Z)-15-(benzyloxy)-2-phenyl-12,13,14,16-tetrahydro-11H-4-oxa-1(1,3)-pyrido[2,1-f][1,2,4]triazina-3(1,2)-benzenacyclononaphan-7-ene-14,16-dione (intermediate 19e, 1.35 g) was obtained using the procedure described for intermediate 5f. The two enantiomers were separated via chiral SFC (Stationary phase: Whelk 01 (S,S) 5 μm 250× 21.1 mm, Mobile phase: 60% $CO_2$, 40% MeOH) to give the first eluted enantiomer 19eA (531 mg) and the second eluted enantiomer 19eB (536 mg).

Synthesis of Compound 19:

(*Z)-15-hydroxy-2-phenyl-12,13,14,16-tetrahydro-11H-4-oxa-1(1,3)-pyrido[2,1-f][1,2,4]triazina-3(1,2)-benzenacyclononaphan-7-ene-14,16-dione (compound 19, 101 mg, racemate (full racemization occurred during this step) was obtained using the procedure described for compound 5A.

Enantiomer 19eB (270 mg, 0.52 mmol) was treated under the same conditions and gave the same compound 19 (110 mg, racemate (full racemization occurred during this step).

Compound 19:

$^1$H NMR (400 MHz, DMSO-$d_6$) δ ppm 2.29-2.44 (m, 2H) 3.19 (br dd, J=13.4, 7.8 Hz, 1H) 4.19 (d, J=13.1 Hz, 1H) 4.30 (br d, J=5.1 Hz, 2H) 4.76 (br dd, J=13.4, 6.8 Hz, 1H) 5.06 (d, J=13.6 Hz, 1H) 5.42-5.55 (m, 2H) 5.60 (s, 1H) 5.76 (s, 1H) 5.80-5.91 (m, 1H) 7.00-7.22 (m, 7H) 7.26-7.39 (m, 2H) 8.07 (d, J=7.6 Hz, 1H) 10.32-11.90 (m, 1H) LC/MS (method LC-B): $R_t$ 2.38 min. MH$^+$430

Example 20: Synthesis of (18*R,*Z)-12-hydroxy-18-(pyridin-2-yl)-6,9-dihydro-18H-10,17-methano-benzo[b]pyrido[1,2-f][1]oxa[5,6,9]triazacyclotridecine-11,13-dione (Compound 20A) and (18*S,*Z)-12-hydroxy-18-(pyridin-2-yl)-6,9-dihydro-18H-10,17-methanobenzo[b]pyrido[1,2-f][1]oxa[5,6,9] triazacyclotridecine-11,13-dione (Compound 20B)

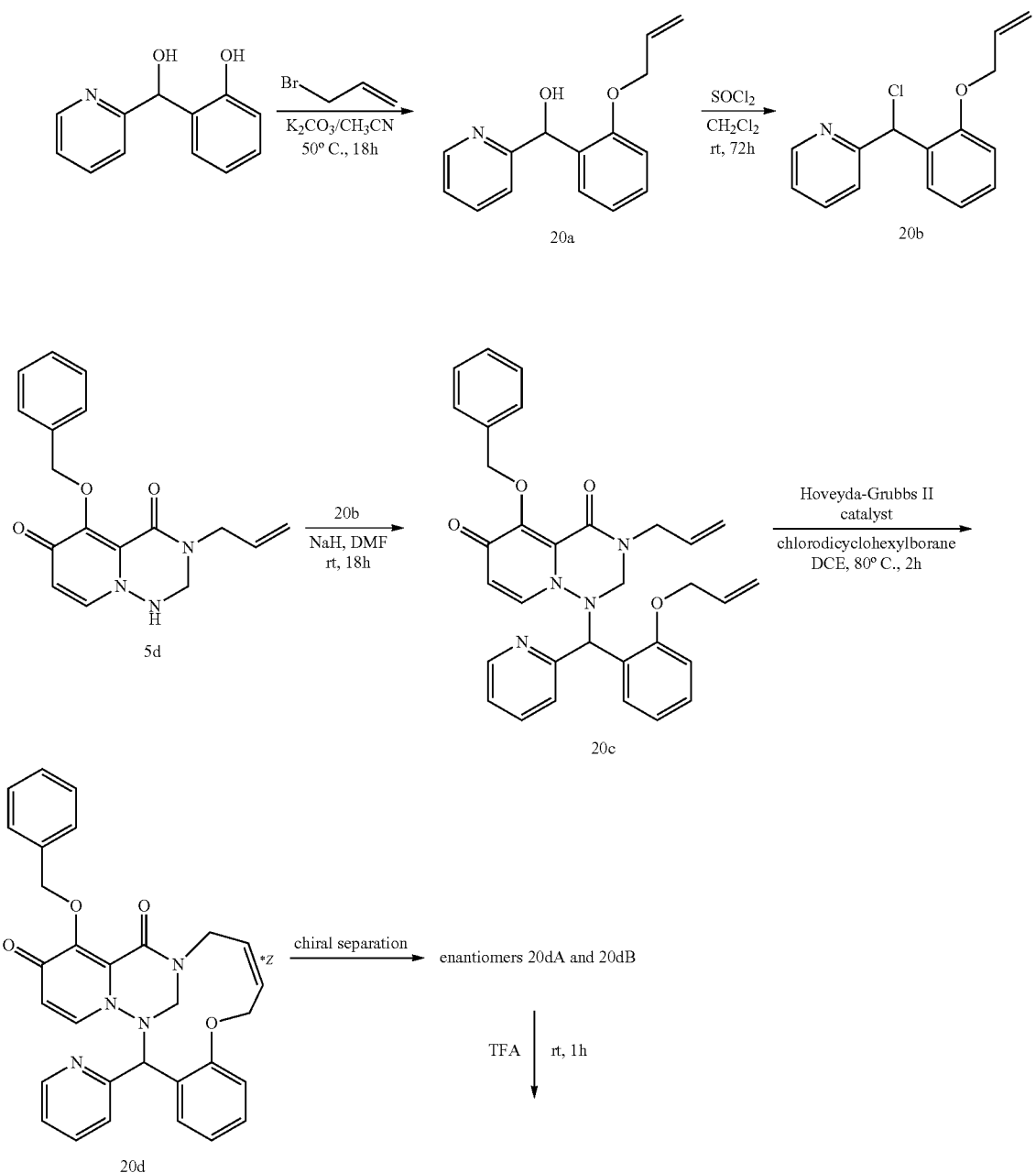

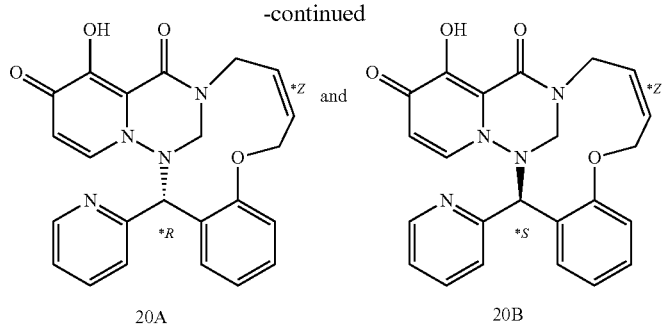

20A and 20B

Synthesis of Intermediate 20a:

A mixture of allyl bromide [CAS 106-95-6] (3.1 mL, 36 mmol), 2-(hydroxy(pyridin-2-yl)methyl)phenol [CAS 158839-52-2] (7.2 g, 36 mmol) and $K_2CO_3$ (15 g, 0.11 mol) in $CH_3CN$ (93 mL) was stirred at 50° C. for 18 h. The mixture was filtered and concentrated under reduced pressure. The residue was purified by flash chromatography over silica gel (30 μm, 120 g, heptane/EtOAc from 90/10 to 80/20). The pure fractions were collected and concentrated under reduced pressure to give (2-(allyloxy)phenyl)(pyridin-2-yl)methanol (intermediate 20a, 2.5 g).

Synthesis of Intermediate 20b:

2-((2-(allyloxy)phenyl)chloromethyl)pyridine (intermediate 20b, 1.4 g), used as such in the next step, was obtained using the procedure described for intermediate 5a.

Synthesis of Intermediate 20c:

3-allyl-1-((2-(allyloxy)phenyl)(pyridin-2-yl)methyl)-5-(benzyloxy)-2,3-dihydro-1H-pyrido[2,1-f][1,2,4]triazine-4,6-dione (intermediate 20c, 550 mg) was obtained using the procedure described for intermediate 5e.

Synthesis of Intermediate 20d:

In a sealed tube, a degassed solution of 3-allyl-1-((2-(allyloxy)phenyl)(pyridin-2-yl)methyl)-5-(benzyloxy)-2,3-dihydro-1H-pyrido[2,1-f][1,2,4]triazine-4,6-dione (intermediate 20c, 500 mg, 0.94 mmol) and chlorodicyclohexylborane (1M) [CAS 36140-1-9] (190 μL, 0.19 mmol) in DCE (64 mL) was stirred at 80° C. under $N_2$ for 1 h. Hoveyda-Grubbs catalyst $2^{nd}$ generation [CAS 301224-40-8] (120 mg, 0.19 mmol) was added and the mixture was stirred at 80° C. for 2 h. SiliaMetS® DMT (1.2 g, 0.75 mmol) was added and the mixture was stirred at rt for 18 h. The reaction mixture was filtered through Celite®. Celite® was washed with $CH_2Cl_2$ and the filtrate was concentrated under reduced pressure. Purification was carried out by flash chromatography over silica gel (30 μm, 12 g, $CH_2Cl_2/CH_3OH$ from 100/0 to 97/3). A second purification was performed via achiral SFC (Stationary phase: $NH_2$ 5 μm 150×30 mm, Mobile phase: 80% $CO_2$, 20% MeOH). The pure fractions were collected and evaporated to dryness to give (*Z)-12-(benzyloxy)-18-(pyridin-2-yl)-6,9-dihydro-18H-10,17-methanobenzo[b]pyrido[1,2-f][1]oxa[5,6,9]triazacyclotridecine-11,13-dione (intermediate 20d, 45 mg, racemate). The two enantiomers were separated via chiral SFC (Stationary phase: Chiralcel® OD-H 5 μm 250×20 mm, Mobile phase: 70% $CO_2$, 30% MeOH) to give the first eluted enantiomer 20dA (17 mg) and the second eluted enantiomer 20 dB (22 mg).

Synthesis of Compound 20A:

(18*R,*Z)-12-hydroxy-18-(pyridin-2-yl)-6,9-dihydro-18H-10,17-methanobenzo[b]pyrido[1,2-f][1]oxa[5,6,9]triazacyclotridecine-11,13-dione (compound 20A, 9 mg) was obtained using the procedure described for compound 5A.

Compound 20A:

$^1$H NMR (500 MHz, DMSO-$d_6$) δ ppm 3.09-3.16 (m, 1H) 4.16 (d, J=13.9 Hz, 1H) 4.26 (br t, J=9.3 Hz, 1H) 4.63-4.84 (m, 2H) 5.04 (d, J=13.9 Hz, 1H) 5.33-5.50 (m, 2H) 5.79-5.91 (m, 1H) 6.00-6.21 (m, 1H) 7.05 (d, J=7.9 Hz, 1H) 7.09-7.18 (m, 2H) 7.20 (br d, J=7.9 Hz, 1H) 7.23-7.31 (m, 1H) 7.31-7.43 (m, 1H) 7.56 (br t, J=7.1 Hz, 1H) 8.06 (br d, J=7.6 Hz, 1H) 8.30 (br d, J=4.1 Hz, 1H)

LC/MS (method LC-A): $R_t$ 2.11 min, MH$^+$417

$[α]_D^{20}$: −679.57° (c 0.093, DMF)

Synthesis of Compound 20B:

(18*S,*Z)-12-hydroxy-18-(pyridin-2-yl)-6,9-dihydro-18H-10,17-methanobenzo[b]pyrido[1,2-f][1]oxa[5,6,9]triazacyclotridecine-11,13-dione (compound 20B, 12 mg) was obtained using the procedure described for compound 5A.

Compound 20B:

$^1$H NMR (500 MHz, DMSO-$d_6$) δ ppm 2.98-3.16 (m, 1H) 4.16 (br d, J=13.9 Hz, 1H) 4.26 (br t, J=8.5 Hz, 1H) 4.56-4.80 (m, 2H) 5.03 (br d, J=13.6 Hz, 1H) 5.35-5.54 (m, 2H) 5.69-5.94 (m, 1H) 5.99-6.18 (m, 1H) 7.00-7.08 (m, 1H) 7.10-7.23 (m, 3H) 7.23-7.30 (m, 1H) 7.32-7.40 (m, 1H) 7.56 (br t, J=7.3 Hz, 1H) 8.06 (br d, J=7.6 Hz, 1H) 8.30 (br d, J=4.1 Hz, 1H)

LC/MS (method LC-A): $R_t$ 2.11 min, MH$^+$417

$[α]_D^{20}$: +668.13° (c 0.091, DMF)

Example 21: Synthesis of (17*R,*Z)-4-hydroxy-16-phenyl-7,10,11,16-tetrahydro-6,17-methanobenzo[k]pyrido[1,2-b][1,2,5]triazacyclotridecine-3,5-dione (Compound 21A) and (17*S,*Z)-4-hydroxy-16-phenyl-7,10,11,16-tetrahydro-6,17-methanobenzo[k]pyrido[1,2-b][1,2,5]triazacyclotridecine-3,5-dione (Compound 21B)

Synthesis of Intermediate 21a:

At 0° C. under N₂ flow, phenylmagnesium bromide [CAS 100-58-3] (35 mL, 34.89 mmol) was added dropwise to a solution of 2-(but-3-en-1-yl)benzaldehyde [CAS 70576-29-3](4.3 g, 26.84 mmol) in THF (30 mL). The mixture was stirred under N₂ at rt for 1 h. The reaction was quenched at 0° C. with a saturated aqueous solution of NH₄Cl and the

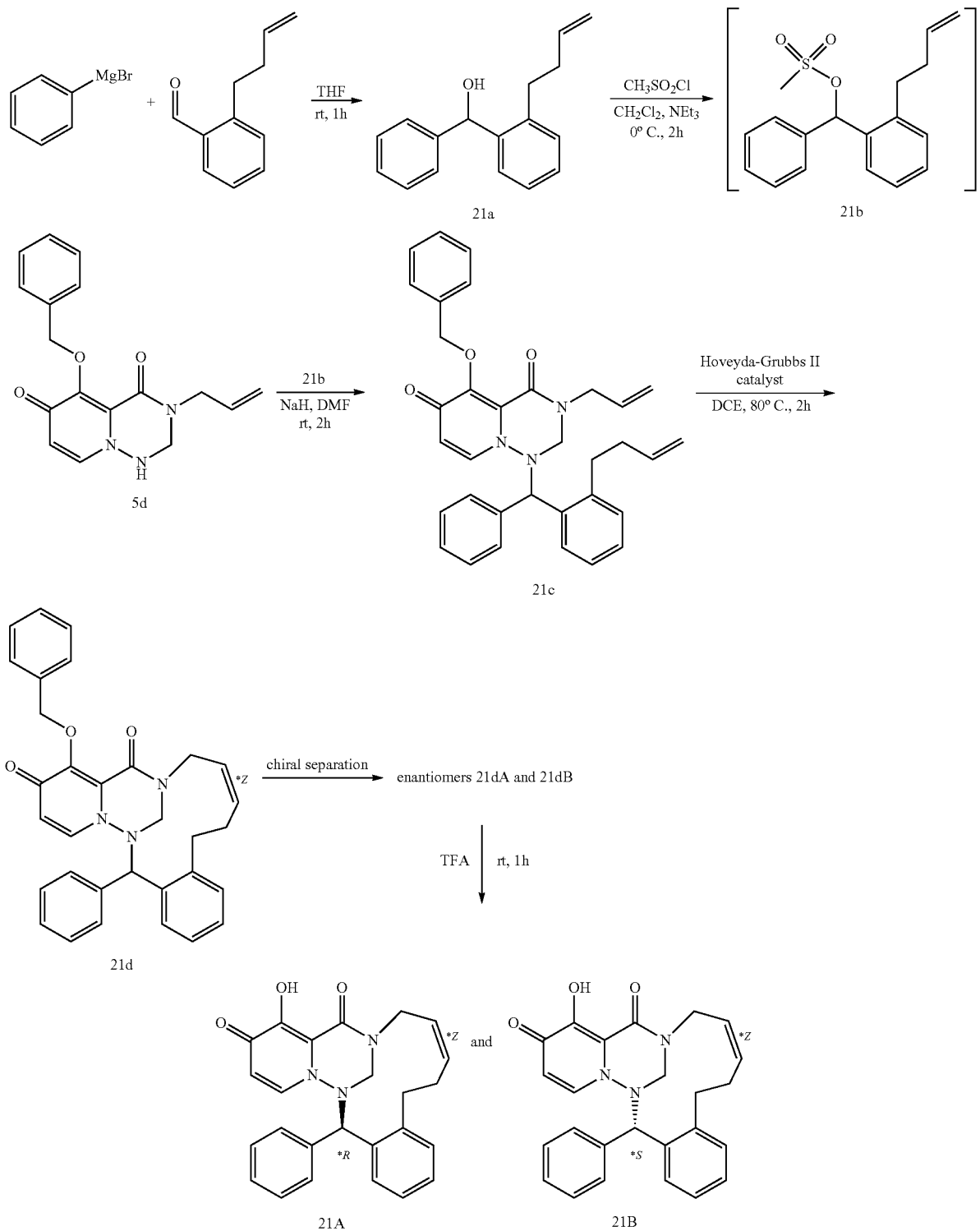

mixture was extracted with EtOAc. The combined organic layers were dried over MgSO$_4$, filtered and the solvent was concentrated under reduced pressure to give (2-(but-3-en-1-yl)phenyl)(phenyl)methanol (intermediate 21a, 4.2 g).
Synthesis of Intermediate 21b:

At 0° C. under N$_2$ flow, methanesulfonyl chloride (974 μL, 12.59 mmol) was added dropwise to a solution of (2-(but-3-en-1-yl)phenyl)(phenyl)methanol (intermediate 21a, 1.5 g, 6.29 mmol) and NEt$_3$ (2.62 mL, 18.8 mmol) in CH$_2$Cl$_2$ (30 mL). The reaction was stirred at 0° C. for 2 h. Water was added and the mixture was extracted with CH$_2$Cl$_2$. The combined organic layers were dried over MgSO$_4$, filtered and concentrated under reduced pressure to give intermediate 21b (2.1 g), which was used as such in the next step.
Synthesis of Intermediate 21c:

3-allyl-5-(benzyloxy)-1-((2-(but-3-en-1-yl)phenyl)(phenyl)methyl)-2,3-dihydro-1H-pyrido[2,1-f][1,2,4]triazine-4,6-dione (intermediate 21c, 1.08 g) was obtained using the procedure described for intermediate 5e.
Synthesis of Intermediate 21d:

(Z)-4-(benzyloxy)-16-phenyl-7,10,11,16-tetrahydro-6,17-methanobenzo[k]pyrido[1,2-b][1,2,5]triazacyclotridecine-3,5-dione (intermediate 21d, 455 mg) was obtained using the procedure described for intermediate 5f. The two enantiomers were separated via chiral SFC (Stationary phase: Chiralpak® AD-H 5 μm 250×30 mm, Mobile phase: 65% CO$_2$, 35% MeOH) to give the first eluted enantiomer 21dA (215 mg) and the second eluted enantiomer 21 dB (204 mg).
Synthesis of Compound 21A:

(17*R,*Z)-4-hydroxy-16-phenyl-7,10,11,16-tetrahydro-6,17-methanobenzo[k]pyrido[1,2-b][1,2,5]triazacyclotridecine-3,5-dione (Compound 21A, 110 mg) was obtained using the procedure described for compound 5A.
Compound 21A:
$^1$H NMR (500 MHz, DMSO-d$_6$) δ ppm 1.94-2.06 (m, 1H) 2.58-2.69 (m, 1H) 3.09 (dd, J=13.9, 7.9 Hz, 1H) 4.28 (d, J=13.6 Hz, 1H) 4.72 (dd, J=14.0, 5.2 Hz, 1H) 5.12 (d, J=13.6 Hz, 1H) 5.19 (s, 1H) 5.42-5.53 (m, 2H) 5.96 (dt, J=15.7, 7.8 Hz, 1H) 6.93-7.29 (m, 7H) 7.34 (td, J=7.4, 0.9 Hz, 1H) 7.43 (t, J=7.1 Hz, 1H) 8.07 (d, J=7.9 Hz, 1H) (2 protons under DMSO peak)
LC/MS (method LC-A): R$_t$ 2.72 min, MH$^+$414
[α]$_D^{20}$: −639.45° (c 0.365, DMF)
Synthesis of Compound 21B:

(17*S,*Z)-4-hydroxy-16-phenyl-7,10,11,16-tetrahydro-6,17-methanobenzo[k]pyrido[1,2-b][1,2,5]triazacyclotridecine-3,5-dione (Compound 21B, 110 mg) was obtained using the procedure described for compound 5A.
Compound 21B:
$^1$H NMR (500 MHz, DMSO-d$_6$) δ ppm 1.94-2.06 (m, 1H) 2.58-2.69 (m, 1H) 3.09 (dd, J=14.0, 8.0 Hz, 1H) 4.28 (d, J=13.9 Hz, 1H) 4.72 (dd, J=14.0, 5.2 Hz, 1H) 5.12 (d, J=13.6 Hz, 1H) 5.19 (s, 1H) 5.40-5.55 (m, 2H) 5.96 (dt, J=15.3, 7.8 Hz, 1H) 6.91-7.30 (m, 7H) 7.34 (td, J=7.4, 0.9 Hz, 1H) 7.40-7.48 (m, 1H) 8.07 (d, J=7.6 Hz, 1H) (2 protons under DMSO peak)
LC/MS (method LC-A): R$_t$ 2.72 min, MH$^+$414
[α]$_D^{20}$: +646.23° (c 0.365, DMF)

Example 22: Synthesis of (18*R,Z)-2-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 22A) and (18*S,Z)-2-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 22B)

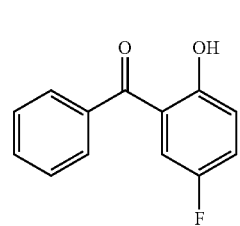

22a

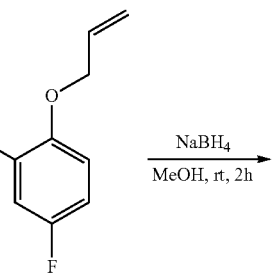

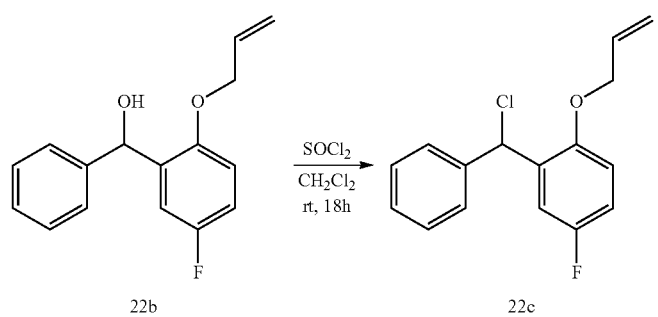

22b                                    22c

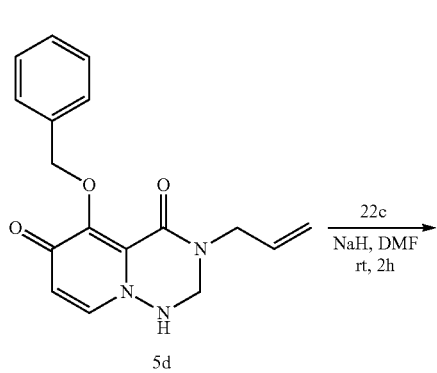

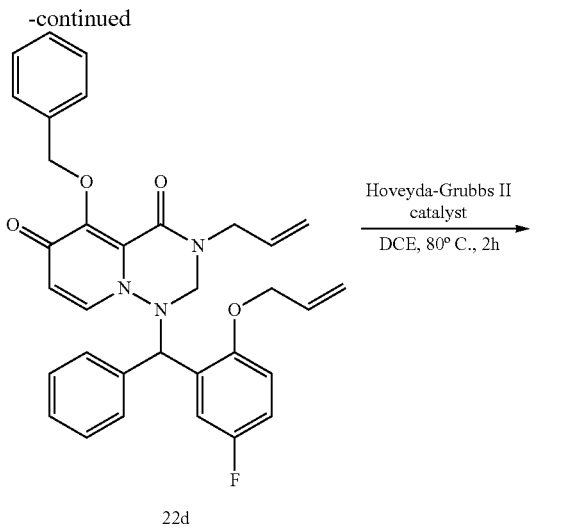

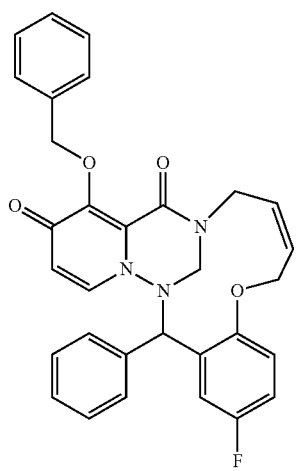

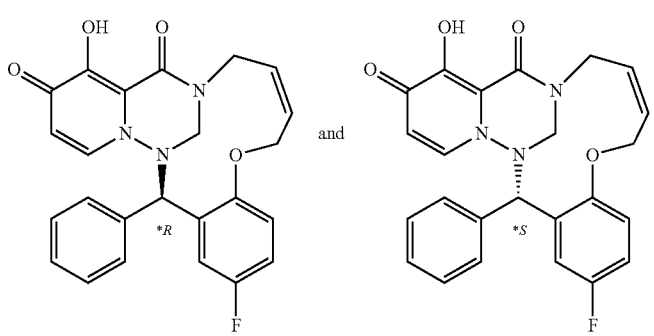

Synthesis of Intermediate 22a:

(2-(allyloxy)-5-fluorophenyl)(phenyl)methanone (intermediate 22a, 2.47 g), used as such in the next step, was obtained using the procedure described for intermediate 20a.

Synthesis of Intermediate 22b:

(2-(allyloxy)-5-fluorophenyl)(phenyl)methanol (intermediate 22b, 2.3 g), used as such in the next step, was obtained using the procedure described for intermediate 11b.

Synthesis of Intermediate 22c:

1-(allyloxy)-2-(chloro(phenyl)methyl)-4-fluorobenzene (intermediate 22c, 2.4 g) was obtained using the procedure described for intermediate 5a.

Synthesis of Intermediate 22d:

3-allyl-1-((2-(allyloxy)-5-fluorophenyl)(phenyl)methyl)-5-(benzyloxy)-2,3-dihydro-1H-pyrido[2,1-f][1,2,4]triazine-4,6-dione (intermediate 22d, 2.93 g) was obtained using the procedure described for intermediate 5e.

Synthesis of Intermediate 22e:

(*Z)-12-(benzyloxy)-2-fluoro-18-phenyl-6,9-dihydro-18H-10,17-methanobenzo[b]pyrido[1,2-f][1]oxa[5,6,9]triazacyclotridecine-11,13-dione (intermediate 22e, 780 mg) was obtained using the procedure described for intermediate 5f.

The two enantiomers were separated via chiral SFC (Stationary phase: Chiralcel® OJ-H 5 μm 250×20 mm, Mobile phase: 65% $CO_2$, 35% MeOH) to give the first eluted enantiomer 22eA (326 mg) and the second eluted enantiomer 22eB (340 mg).

Synthesis of Compound 22A:

(18*R,Z)-2-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 22A, 145 mg) was obtained using the procedure described for compound 5A.

Compound 22A:

$^1$H NMR (500 MHz, DMSO-$d_6$) δ ppm 3.19 (dd, J=13.7, 8.4 Hz, 1H) 4.30 (d, J=13.9 Hz, 2H) 4.68-4.83 (m, 2H) 5.12 (d, J=13.6 Hz, 1H) 5.28 (br s, 1H) 5.49 (d, J=7.6 Hz, 1H) 5.95 (br s, 1H) 6.06-6.23 (m, 1H) 7.06-7.30 (m, 7H) 7.33 (br d, J=7.6 Hz, 1H) 7.94 (br d, J=8.8 Hz, 1H) 10.07-11.46 (m, 1H)

LC/MS (method LC-A): $R_t$ 2.47 min, MH$^+$434

$[α]_D^{20}$: +645.02° (c 0.291, DMF)

Synthesis of Compound 22B:

(18*S,Z)-2-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 22B, 149 mg) was obtained using the procedure described for compound 5B.

Compound 22B:

$^1$H NMR (500 MHz, DMSO-$d_6$) δ ppm 3.19 (dd, J=13.6, 8.5 Hz, 1H) 4.30 (br d, J=13.9 Hz, 2H) 4.68-4.83 (m, 2H) 5.12 (d, J=13.9 Hz, 1H) 5.28 (br s, 1H) 5.49 (d, J=7.6 Hz, 1H) 5.95 (br s, 1H) 6.07-6.22 (m, 1H) 7.08-7.30 (m, 7H) 7.33 (br d, J=7.6 Hz, 1H) 7.94 (br d, J=8.5 Hz, 1H) 10.48-11.25 (m, 1H)

LC/MS (method LC-A): $R_t$ 2.47 min, MH$^+$434

$[α]_D^{20}$: −676.17° (c 0.277, DMF)

Example 23: Synthesis of (18*R)-12-hydroxy-18-phenyl-5,6,7,8,9,18-hexahydro-10,17-methanodipyrido[1,2-b:2',3'-k][1,2,5]triazacyclotridecine-11,13-dione (Compound 23A) and (18*S)-12-hydroxy-18-phenyl-5,6,7,8,9,18-hexahydro-10,17-methanodipyrido[1,2-b:2',3'-k][1,2,5]triazacyclotridecine-11,13-dione (Compound 23B)

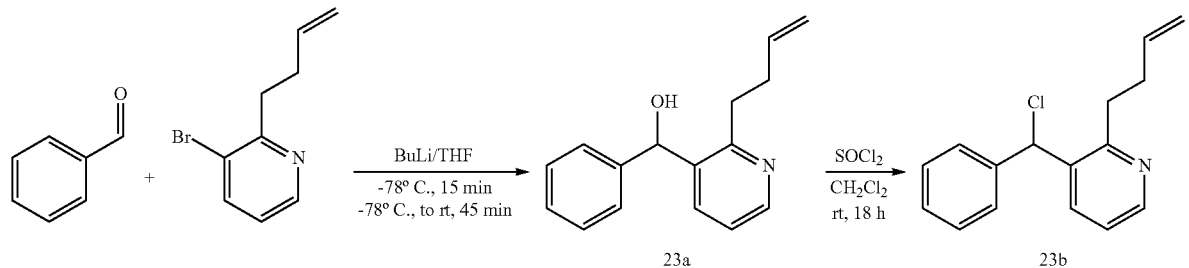

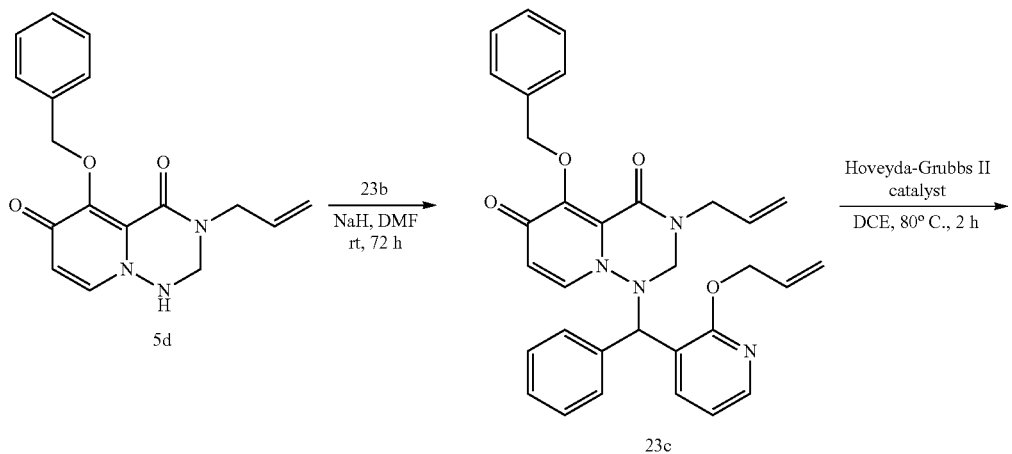

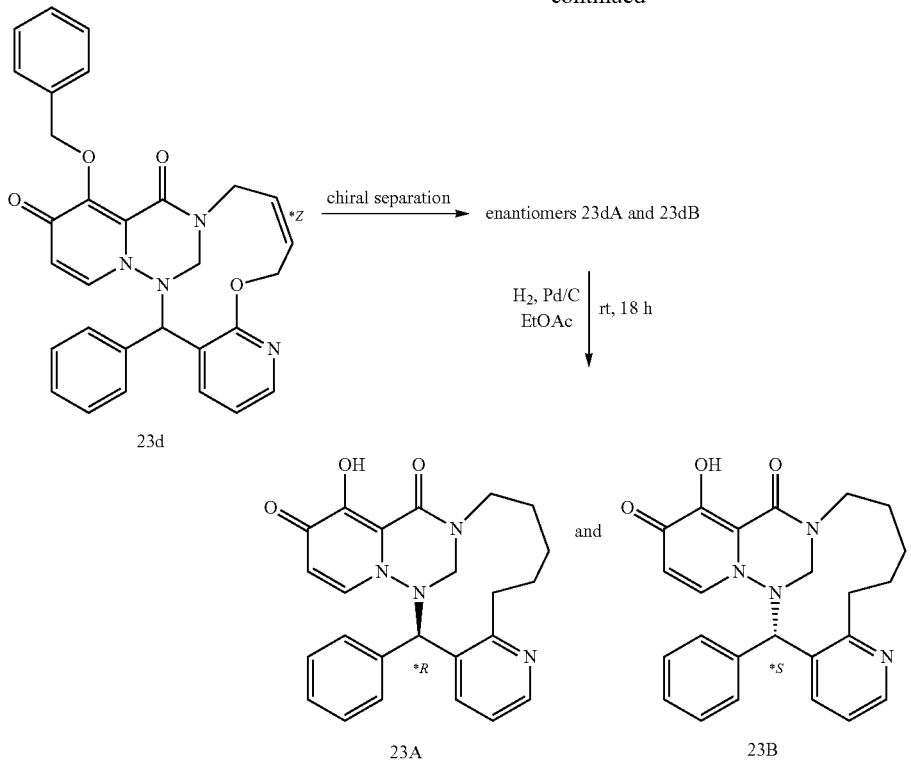

Synthesis of Intermediate 23a:

n-BuLi (1.6 M in hexane) (4.1 mL, 6.6 mmol) was added dropwise to a solution of 3-bromo-2-(but-3-en-1-yl)pyridine [CAS 1309650-05-2] (1.0 g, 4.7 mmol) in dry THF (38 mL) at −78° C. The mixture was stirred 15 min at this temperature, then benzaldehyde [CAS 100-52-7] (0.96 mL, 9.4 mmol) was added dropwise. The mixture was stirred at −78° C. for 15 min and then slowly warmed up to rt over 45 min. NH$_4$Cl 10% aqueous solution was added and the mixture was stirred at rt for 18 h. EtOAc and brine were added and the mixture was extracted with EtOAc twice. The combined organic layers were dried over MgSO$_4$, filtered and concentrated under reduced pressure. The residue was purified by flash chromatography over silica gel (30 μm, 24 g, heptane/EtOAc from 85/15 to 65/35). The pure fractions were collected and concentrated to dryness to give (2-(but-3-en-1-yl)pyridin-3-yl)(phenyl)methanol (intermediate 23a, 700 mg).

Synthesis of Intermediate 23b:

2-(but-3-en-1-yl)-3-(chloro(phenyl)methyl)pyridine (intermediate 23b, 750 mg) was obtained using the procedure described for intermediate 11c.

Synthesis of Intermediate 23c:

3-allyl-5-(benzyloxy)-1-((2-(but-3-en-1-yl)pyridin-3-yl)(phenyl)methyl)-2,3-dihydro-1H-pyrido[2,1-f][1,2,4]triazine-4,6-dione (intermediate 23c, 900 mg) was obtained using the procedure described for intermediate 11g.

Synthesis of Intermediate 23d:

(*Z)-12-(benzyloxy)-18-phenyl-5,6,9,18-tetrahydro-10,17-methanodipyrido[1,2-b:2',3'-k][1,2,5]triazacyclotridecine-11,13-dione (intermediate 23d, 510 mg) was obtained using the procedure described for intermediate 5f.

The two enantiomers were separated via chiral SFC (Stationary phase: Whelk® O1 (S,S) 5 μm 250×21.1 mm, Mobile phase: 60% CO$_2$, 40% MeOH) to give the first eluted enantiomer 23dA (190 mg) and the second eluted enantiomer 23 dB (200 mg).

Synthesis of Compound 23A:

(18*R)-12-hydroxy-18-phenyl-5,6,7,8,9,18-hexahydro-10,17-methanodipyrido[1,2-b:2',3'-k][1,2,5]triazacyclotridecine-11,13-dione (Compound 23A, 22 mg) was obtained using the procedure described for compound 8.

Compound 23A:

$^1$H NMR (500 MHz, DMSO-d$_6$) δ ppm 0.40-0.68 (m, 1H) 1.31-1.49 (m, 1H) 1.49-1.82 (m, 3H) 1.87-2.06 (m, 1H) 2.54-2.60 (m, 2H) 2.84-2.94 (m, 1H) 4.00 (br t, J=12.9 Hz, 1H) 4.27 (br d, J=13.9 Hz, 1H) 5.06 (br d, J=13.9 Hz, 1H) 5.48 (br d, J=7.3 Hz, 1H) 5.60 (s, 1H) 7.00 (br d, J=7.3 Hz, 1H) 7.19-7.55 (m, 6H) 8.37 (d, J=7.9 Hz, 1H) 8.46-8.62 (m, 1H)

LC/MS (method LC-A): R$_t$ 2.07 min, MH$^+$417

[α]$_D^{20}$: +395.06° (c 0.162, DMF)

Synthesis of Compound 23B:

(18*S)-12-hydroxy-18-phenyl-5,6,7,8,9,18-hexahydro-10,17-methanodipyrido[1,2-b:2',3'-k][1,2,5]triazacyclotridecine-11,13-dione (Compound 23B, 22 mg) was obtained using the procedure described for compound 8.

Compound 23B:

$^1$H NMR (500 MHz, DMSO-d$_6$) δ ppm 0.49-0.60 (m, 1H) 1.35-1.45 (m, 1H) 1.48-1.87 (m, 3H) 1.89-2.06 (m, 1H) 2.54-2.63 (m, 2H) 2.84-2.95 (m, 1H) 3.94-4.06 (m, 1H) 4.27 (d, J=13.9 Hz, 1H) 5.06 (br d, J=13.9 Hz, 1H) 5.49 (br d, J=7.6 Hz, 1H) 5.60 (s, 1H) 7.01 (br d, J=7.6 Hz, 1H) 7.15-7.65 (m, 6H) 8.37 (dd, J=7.9, 1.3 Hz, 1H) 8.55 (dd, J=4.7, 1.6 Hz, 1H)

LC/MS (method LC-A): R$_t$ 2.07 min, MH$^+$417

[α]$_D^{20}$: −385.58° (c 0.215, DMF)

Example 24: Synthesis of (18*R,*Z)-12-hydroxy-18-phenyl-5,6,9,18-tetrahydro-10,17-methanodipyrido[1,2-b:2',3'-k][1,2,5]triazacyclotridecine-11,13-dione (Compound 24A) and (18*S,*Z)-12-hydroxy-18-phenyl-5,6,9,18-tetrahydro-10,17-methanodipyrido[1,2-b:2',3'-k][1,2,5]triazacyclotridecine-11,13-dione (Compound 24B)

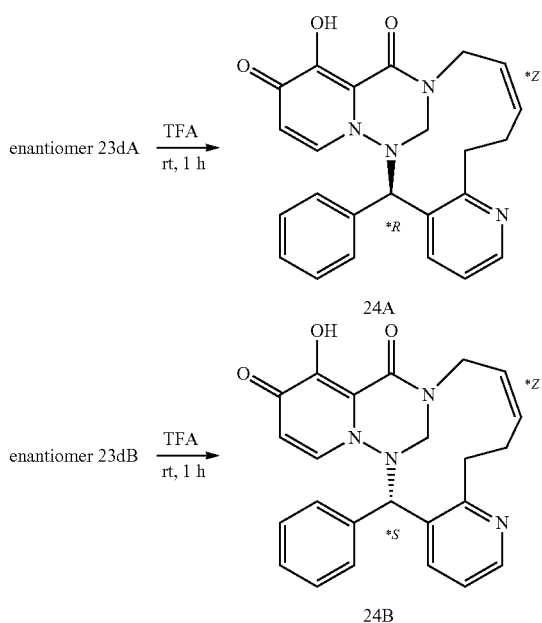

Synthesis of Compound 24A:
(18*R,*Z)-12-hydroxy-18-phenyl-5,6,9,18-tetrahydro-10,17-methanodipyrido[1,2-b:2',3'-k][1,2,5]triazacyclotridecine-11,13-dione (Compound 24A, TFA salt, 115 mg) was obtained using the procedure described for compound 5A.
Compound 24A:
$^1$H NMR (500 MHz, DMSO-d$_6$) δ ppm 2.15-2.28 (m, 1H) 2.59-2.84 (m, 3H) 2.98-3.19 (m, 1H) 4.24 (d, J=13.9 Hz, 1H) 4.67-4.84 (m, 1H) 5.14 (d, J=13.9 Hz, 1H) 5.24 (s, 1H) 5.52 (d, J=7.9 Hz, 1H) 5.55-5.69 (m, 1H) 6.02 (dt, J=15.1, 7.6 Hz, 1H) 7.00-7.46 (m, 6H) 7.67 (br dd, J=7.6, 5.0 Hz, 1H) 8.53-8.83 (m, 2H)
LC/MS (method LC-A): R$_t$ 2.02 min. MH$^+$415
[α]$_D^{20}$: +572.76° (c 0.279, DMF)

Synthesis of Compound 24B:
(18*S,*Z)-12-hydroxy-18-phenyl-5,6,9,18-tetrahydro-10,17-methanodipyrido[1,2-b:2',3'-k][1,2,5]triazacyclotridecine-11,13-dione (Compound 24B, TFA salt, 99 mg) was obtained using the procedure described for compound 5A.
Compound 24B:
$^1$H NMR (500 MHz, DMSO-d$_6$) δ ppm 2.16-2.29 (m, 1H) 2.57-2.86 (m, 3H) 3.07 (dd, J=14.0, 8.0 Hz, 1H) 4.24 (d, J=13.6 Hz, 1H) 5.14 (d, J=13.9 Hz, 1H) 4.69-4.82 (m, 1H) 5.24 (s, 1H) 5.52 (d, J=7.9 Hz, 1H) 5.55-5.74 (m, 1H) 6.02 (dt, J=15.3, 7.5 Hz, 1H) 7.13-7.40 (m, 6H) 7.68 (br dd, J=7.6, 5.4 Hz, 1H) 8.61-8.81 (m, 2H)
LC/MS (method LC-A): R$_t$ 2.02 min, MH$^+$417
[α]$_D^{20}$: −550.53° (c 0.378, DMF)

Example 25: Synthesis of (18*R,Z)-2-fluoro-18-(3-fluorophenyl)-12-hydroxy-6,9-dihydro-18H-10,17-methanobenzo[b]pyrido[1,2-f][1]oxa[5,6,9]triazacyclotridecine-11,13-dione (Compound 25A) and (18*S,Z)-2-fluoro-18-(3-fluorophenyl)-12-hydroxy-6,9-dihydro-18H-10,17-methanobenzo[b]pyrido[1,2-f][1]oxa[5,6,9]triazacyclotridecine-11,13-dione (Compound 25B)

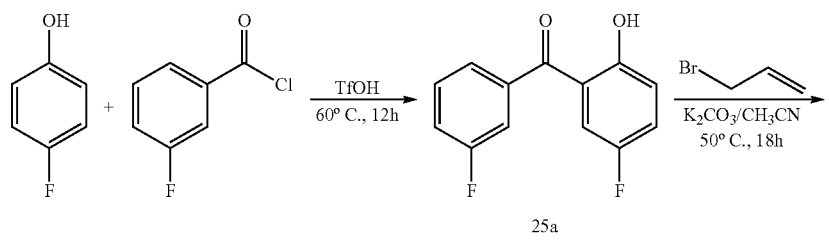

25a

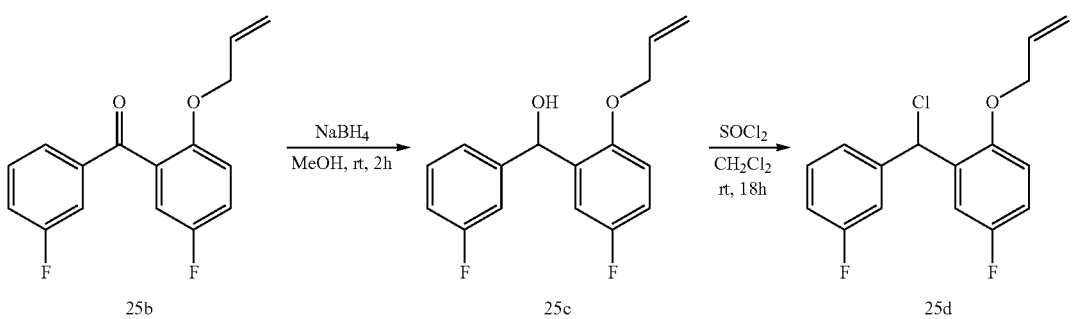

25b    25c    25d

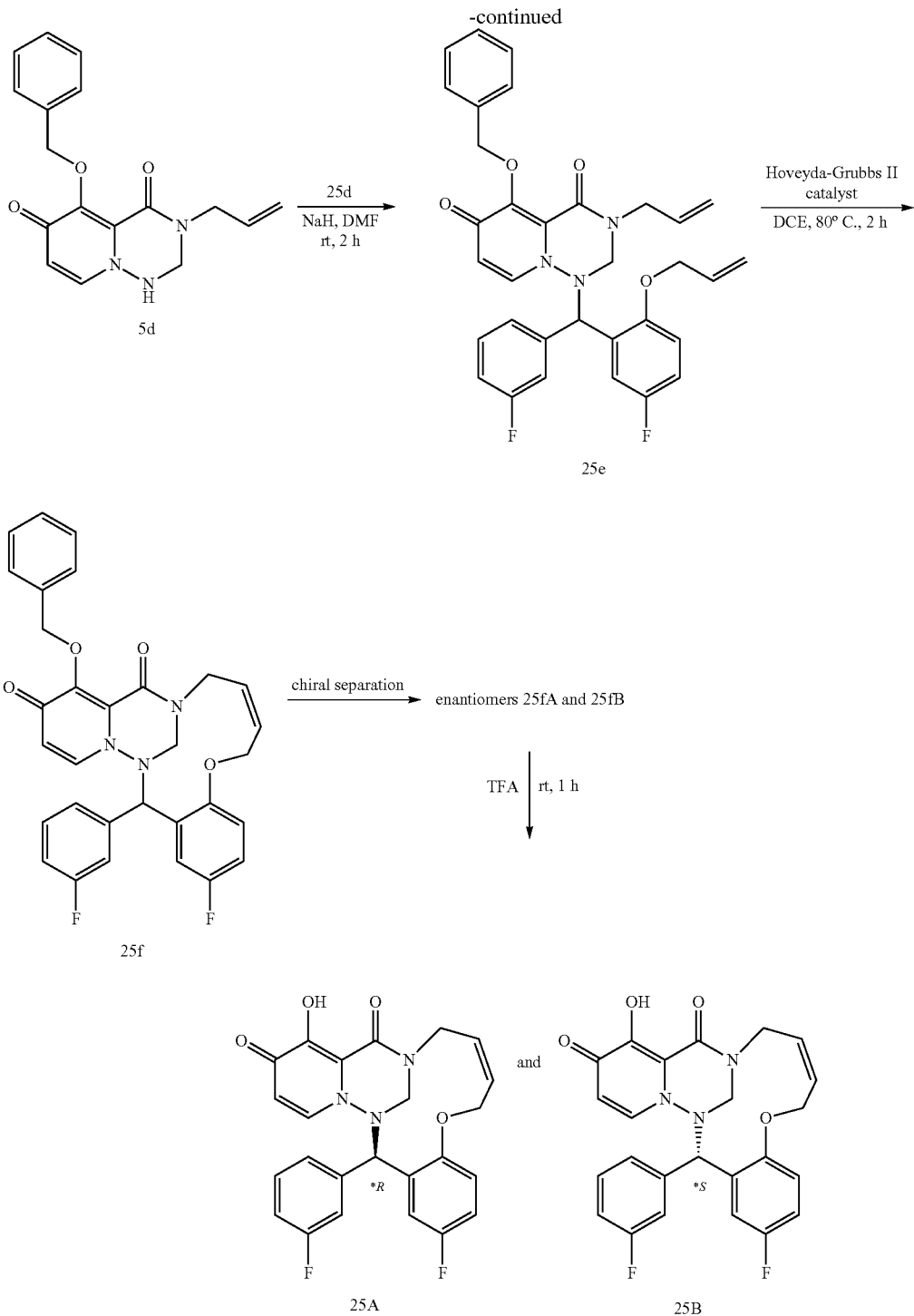

Synthesis of Intermediate 25a:
4-fluorophenol [CAS 371-41-5] (1.5 g, 13.38 mmol) and 3-fluorobenzoyl chloride (1.64 mL, 13.38 mmol) were dissolved in triflic acid (50 mL) at 0° C. The reaction mixture was warmed up to rt and stirred at 60° C. for 12 h. After cooling down to rt, the mixture was poured into a cold solution of water (250 mL) and EtOAc. The organic layer was separated, dried over MgSO$_4$, filtered and concentrated under vacuum to give (5-fluoro-2-hydroxyphenyl)(3-fluorophenyl)methanone (intermediate 25a, 3.2 g).

Synthesis of Intermediate 25f:
(Z)-12-(benzyloxy)-2-fluoro-18-(3-fluorophenyl)-6,9-dihydro-18H-10,17-methanobenzo[b]pyrido[1,2-f][1]oxa[5,6,9]triazacyclotridecine-11,13-dione (intermediate 25f, 740 mg) was obtained using the procedures described in example 22. The two enantiomers were separated via chiral SFC (Stationary phase: Chiralcel® OJ-H 5 μm 250×30 mm, Mobile phase: 75% CO$_2$, 25% MeOH) to give the first eluted enantiomer 25fA (313 mg) and the second eluted enantiomer 25fB (316 mg).

Synthesis of Compound 25A:

(18*R,Z)-2-fluoro-18-(3-fluorophenyl)-12-hydroxy-6,9-dihydro-18H-10,17-methanobenzo[b]pyrido[1,2-f][1]oxa[5,6,9]triazacyclotridecine-11,13-dione (Compound 25A, 162 mg) was obtained using the procedure described for compound 5A.

Compound 25A:

$^1$H NMR (400 MHz, DMSO-d$_6$) δ ppm 3.18 (br dd, J=13.6, 8.1 Hz, 1H) 4.28 (br d, J=13.6 Hz, 2H) 4.66-4.83 (m, 2H) 5.12 (d, J=13.6 Hz, 1H) 5.30 (br s, 1H) 5.57 (d, J=7.6 Hz, 1H) 5.95 (br s, 1H) 6.13 (br s, 1H) 6.88-7.17 (m, 3H) 7.19-7.33 (m, 3H) 7.44 (br d, J=7.6 Hz, 1H) 7.96 (br d, J=9.6 Hz, 1H)

LC/MS (method LC-A): R$_t$ 2.52 min, MH$^+$452

[α]$_D^{20}$: +615.66° (c 0.281, DMF)

Chiral HPLC (method HPLC-B): R$_t$ 4.33 min, chiral purity 100%.

Synthesis of Compound 25B:

(18*S,Z)-2-fluoro-18-(3-fluorophenyl)-12-hydroxy-6,9-dihydro-18H-10,17-methanobenzo[b]pyrido[1,2-f][1]oxa[5,6,9]triazacyclotridecine-11,13-dione (Compound 25B, 162 mg) was obtained using the procedure described for compound 5B.

Compound 25B:

$^1$H NMR (400 MHz, DMSO-d$_6$) δ ppm 3.10-3.22 (m, 1H) 4.28 (br d, J=13.1 Hz, 2H) 4.66-4.83 (m, 2H) 5.12 (br d, J=13.6 Hz, 1H) 5.30 (br s, 1H) 5.56 (br d, J=7.6 Hz, 1H) 5.95 (br s, 1H) 6.14 (br s, 1H) 6.92-7.17 (m, 3H) 7.18-7.34 (m, 3H) 7.44 (br d, J=5.1 Hz, 1H) 7.96 (br d, J=9.1 Hz, 1H) 10.04-11.58 (m, 1H)

LC/MS (method LC-A): R$_t$ 2.52 min, MH$^+$452

[α]$_D^{20}$: −642.59° (c 0.277, DMF)

Chiral HPLC (method HPLC-B): R$_t$ 5.71 min, chiral purity 100%.

Example 26: Synthesis of (18*R,*Z)-12-hydroxy-18-(pyridin-3-yl)-6,9-dihydro-18H-10,17-methanobenzo[b]pyrido[1,2-f][1]oxa[5,6,9]triazacyclotridecine-11,13-dione (Compound 26A) and (18*S,*Z)-12-hydroxy-18-(pyridin-3-yl)-6,9-dihydro-18H-10,17-methanobenzo[b]pyrido[1,2-f][1]oxa[5,6,9]triazacyclotridecine-11,13-dione (Compound 26B)

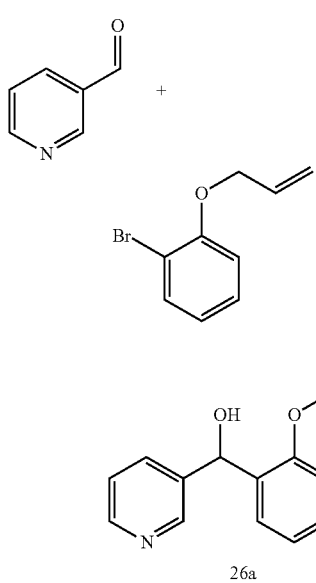

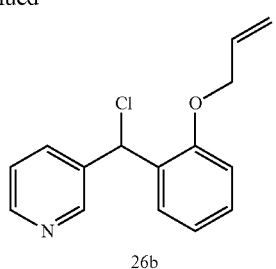

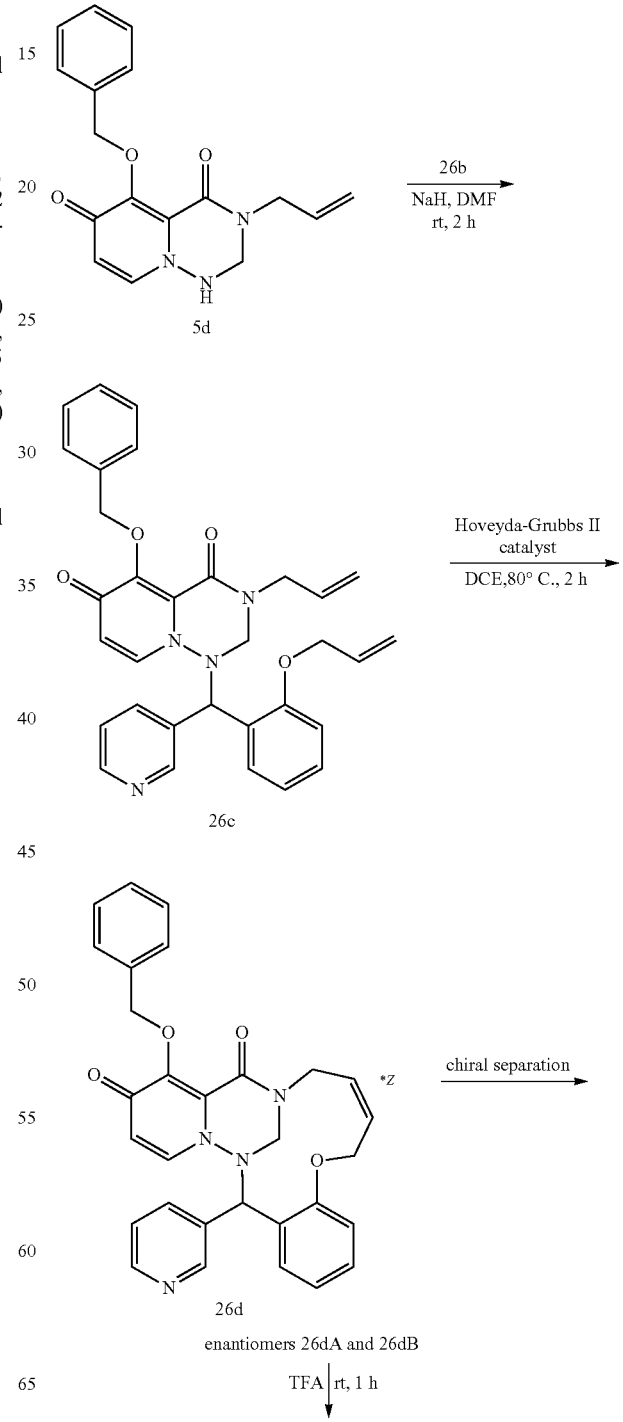

-continued

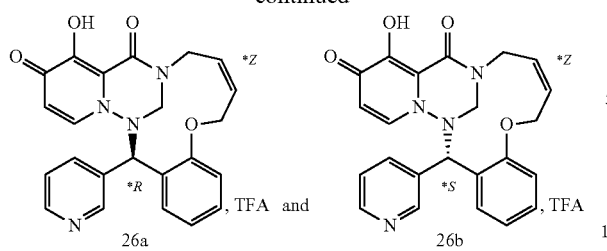

Synthesis of Intermediate 26a:

(2-(allyloxy)phenyl)(pyridin-3-yl)methanol (intermediate 26a, 1.25 g) was obtained using the procedure described for intermediate 23a.

Synthesis of Intermediate 26d:

(*Z)-12-(benzyloxy)-18-(pyridin-3-yl)-6,9-dihydro-18H-10,17-methanobenzo[b]pyrido[1,2-f][1]oxa[5,6,9]triazacyclotridecine-11,13-dione (intermediate 26d, 350 mg) was obtained using the procedures described in example 5 starting from intermediates 26b (synthesized as 5a) and 5d.

The two enantiomers were separated via chiral SFC (Stationary phase: Whelk® 01 (S,S) 5 µm 250×21.1 mm, Mobile phase: 40% $CO_2$, 60% EtOH) to give the first eluted enantiomer 26dA (93 mg) and the second eluted enantiomer 26 dB (99 mg).

Synthesis of Compound 26A:

(18*R,*Z)-12-hydroxy-18-(pyridin-3-yl)-6,9-dihydro-18H-10,17-methanobenzo[b]pyrido[1,2-f][1]oxa[5,6,9]triazacyclotridecine-11,13-dione (Compound 26A, TFA salt, 65 mg) was obtained using the procedure described for compound 5A.

Compound 26A:

$^1$H NMR (500 MHz, DMSO-$d_6$) δ ppm 3.16-3.24 (m, 1H) 4.12-4.40 (m, 2H) 4.68-4.95 (m, 2H) 5.15 (d, J=13.6 Hz, 1H) 5.39 (br s, 1H) 5.55 (d, J=7.6 Hz, 1H) 5.88-5.98 (m, 1H) 6.10-6.22 (m, 1H) 7.18-7.32 (m, 2H) 7.32-7.53 (m, 3H) 7.70 (br s, 1H) 8.14 (br d, J=7.6 Hz, 1H) 8.26-8.51 (m, 2H)

LC/MS (method LC-A): $R_t$ 2.04 min, MH$^+$417

$[α]_D^{20}$: −673.64° (c 0.129, DMF)

Chiral HPLC (method HPLC-B): $R_t$ 10.26 min, chiral purity 100%.

Synthesis of Compound 26B:

(18*S,*Z)-12-hydroxy-18-(pyridin-3-yl)-6,9-dihydro-18H-10,17-methanobenzo[b]pyrido[1,2-f][1]oxa[5,6,9]triazacyclotridecine-11,13-dione (Compound 26B, TFA salt, 63 mg) was obtained using the procedure described for compound 5B.

Compound 26B:

$^1$H NMR (500 MHz, DMSO-$d_6$) δ ppm 3.15-3.23 (m, 1H) 4.16-4.52 (m, 2H) 4.71-4.93 (m, 2H) 5.15 (br d, J=13.9 Hz, 1H) 5.39 (br s, 1H) 5.55 (br d, J=7.6 Hz, 1H) 5.87-5.99 (m, 1H) 6.10-6.24 (m, 1H) 7.15-7.30 (m, 2H) 7.30-7.54 (m, 3H) 7.69 (br s, 1H) 8.14 (br d, J=7.3 Hz, 1H) 8.27-8.49 (m, 2H)

LC/MS (method LC-A): $R_t$ 2.04 min, MH$^+$417

$[α]_D^{20}$: +655.46° (c 0.119, DMF)

Chiral HPLC (method HPLC-B): $R_t$ 7.63 min, chiral purity 100%.

Example 27: Synthesis of (18*R,*Z)-12-hydroxy-18-phenyl-6,9-dihydro-18H-10,17-methanodipyrido[3,2-b:1',2'-f][1]oxa[5,6,9]triazacyclotridecine-11,13-dione (Compound 27A) and (18*S,*Z)-12-hydroxy-18-phenyl-6,9-dihydro-18H-10,17-methanodipyrido[3,2-b:1',2'-f][1]oxa[5,6,9]triazacyclotridecine-11,13-dione (Compound 27B)

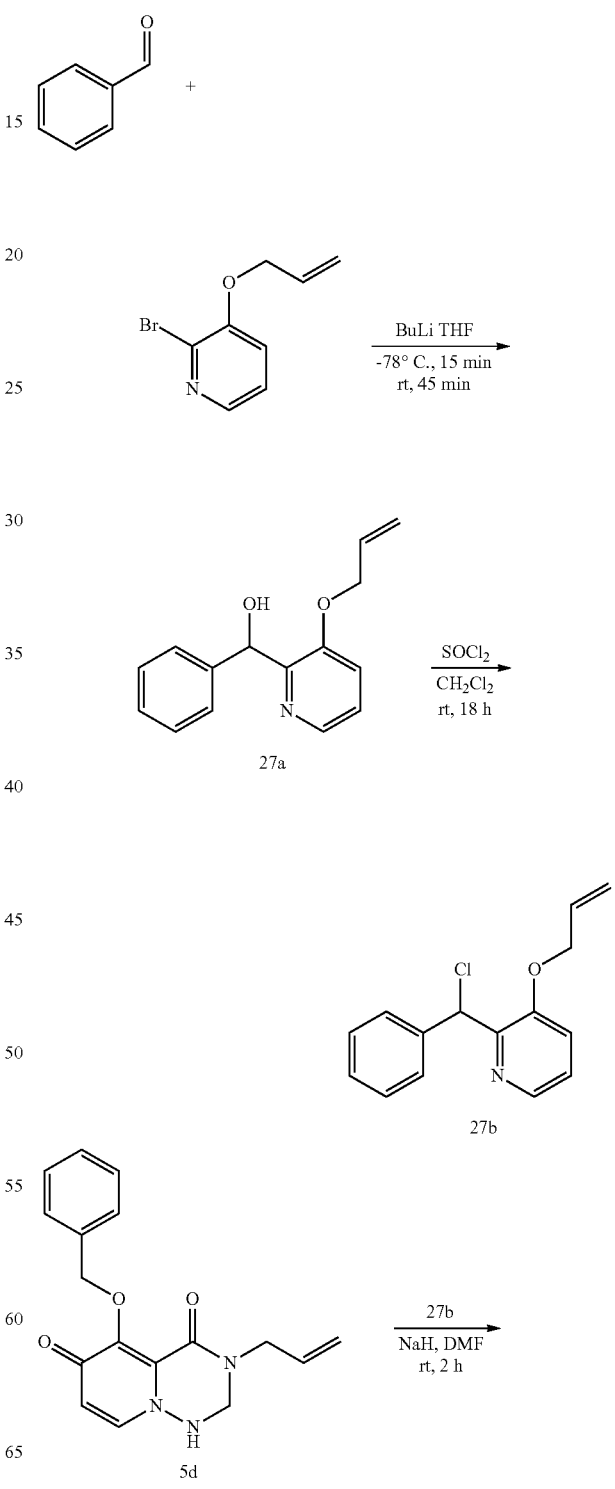

-continued

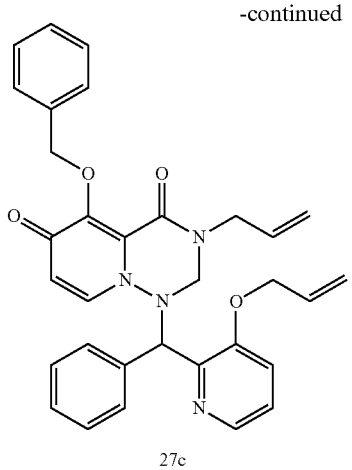

27c

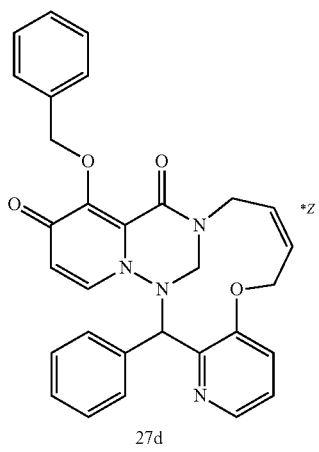

27d
enantiomers 27dA and 27dB

TFA | rt, 1 h

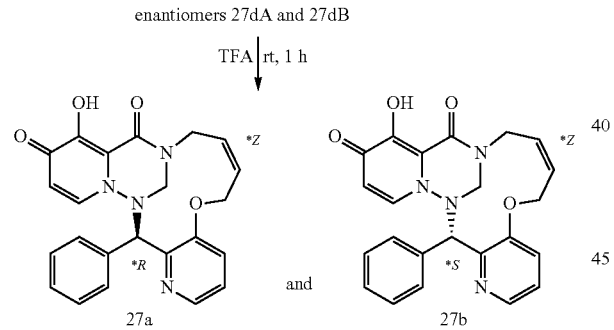

27a and 27b

Synthesis of Intermediate 27a:
(3-(allyloxy)pyridin-2-yl)(phenyl)methanol (intermediate 27a, 1.9 g) was obtained using the procedure described for intermediate 23a, starting from 3-(allyloxy)-2-bromopyridine [CAS 123552-77-2].

Synthesis of Intermediate 27d:
(*Z)-12-(benzyloxy)-18-phenyl-6,9-dihydro-18H-10,17-methanodipyrido[3,2-b:1',2'-f][1]oxa[5,6,9]triazacyclotridecine-11,13-dione (intermediate 27d, 0.136 g) was obtained using the procedures described in example 20 starting from intermediates 27b (synthesized as 5a) and 5d.

The two enantiomers were separated via chiral SFC (Stationary phase: Chiralcel® OD-H 5 µm 250×30 mm, Mobile phase: 70% $CO_2$, 30% EtOH) to give the first eluted enantiomer 27dA (65 mg) and the second eluted enantiomer 27 dB (61 mg).

Synthesis of Compound 27A: ((18*R,*Z)-12-hydroxy-18-phenyl-6,9-dihydro-18H-10,17-methanodipyrido[3,2-b:1', 2'-f][1]oxa[5,6,9]triazacyclotridecine-11,13-dione (Compound 27A, TFA salt, 28 mg) was obtained using the procedure described for compound 24A.

Compound 27A:
$^1$H NMR (500 MHz, DMSO-$d_6$) δ ppm 3.13-3.21 (m, 1H) 4.18 (d, J=13.9 Hz, 1H) 4.26 (br t, J=10.1 Hz, 1H) 4.78 (dd, J=14.3, 4.6 Hz, 1H) 4.89 (br dd, J=11.0, 6.3 Hz, 1H) 5.13 (d, J=13.9 Hz, 1H) 5.41 (s, 1H) 5.47 (d, J=7.9 Hz, 1H) 5.68-5.79 (m, 1H) 6.22 (dt, J=15.5, 7.5 Hz, 1H) 6.98 (d, J=7.9 Hz, 1H) 7.15-7.38 (m, 5H) 7.48 (dd, J=8.2, 4.4 Hz, 1H) 7.69 (d, J=8.2 Hz, 1H) 8.48-8.61 (m, 1H) 11.06 (br s, 1H)

LC/MS (method LC-A): $R_t$ 2.01 min, MH$^+$417

$[α]_D^{20}$: −700.93° (c 0.107, DMF)

Chiral HPLC (method HPLC-B): $R_t$ 6.75 min, chiral purity 100%.

Synthesis of Compound 27B:
((18*S,*Z)-12-hydroxy-18-phenyl-6,9-dihydro-18H-10,17-methanodipyrido[3,2-b:1',2'-f][1]oxa[5,6,9]triazacyclotridecine-11,13-dione (Compound 27B, TFA salt, 31 mg) was obtained using the procedure described for compound 24B.

Compound 27B:
$^1$H NMR (500 MHz, DMSO-$d_6$) δ ppm 3.10-3.19 (m, 1H) 4.18 (d, J=13.9 Hz, 1H) 4.26 (br t, J=10.1 Hz, 1H) 4.78 (dd, J=14.5, 4.7 Hz, 1H) 4.89 (br dd, J=11.0, 6.0 Hz, 1 H) 5.13 (d, J=13.9 Hz, 1H) 5.35 (s, 1H) 5.47 (d, J=7.6 Hz, 1H) 5.64-5.86 (m, 1H) 6.22 (dt, J=15.3, 7.50 Hz, 1H) 6.98 (d, J=7.60 Hz, 1H) 7.10-7.43 (m, 5H) 7.43-7.52 (m, 1H) 7.69 (d, J=8.2 Hz, 1H) 8.57 (d, J=3.8 Hz, 1H)

LC/MS (method LC-A): $R_t$ 2.01 min, MH$^+$417

$[α]D^{20}$: +665.54° (c 0.148, DMF)

Chiral HPLC (method HPLC-B): $R_t$ 5.28 min, chiral purity 100%.

Example 28: Synthesis of (Compound 28A) and (Compound 28B)

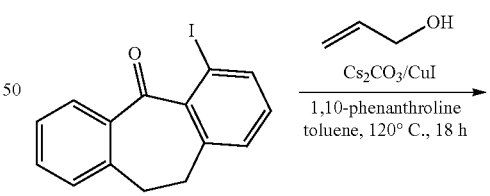

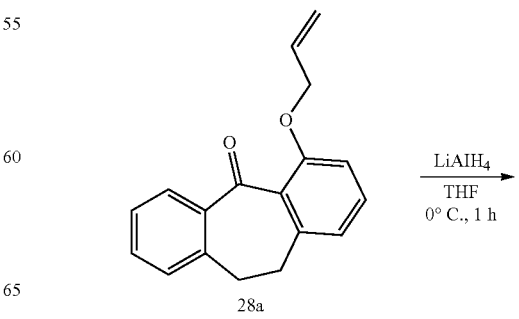

28a

83
-continued

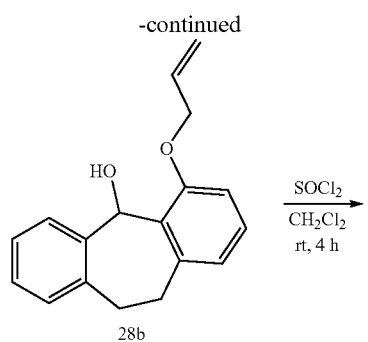
28b

SOCl₂
CH₂Cl₂
rt, 4 h
→

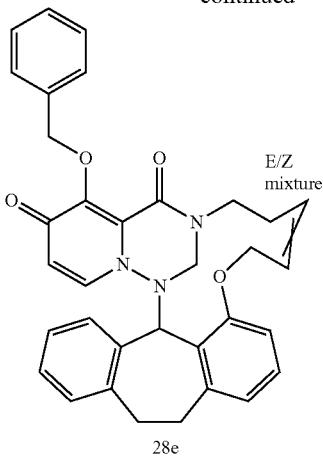
28c

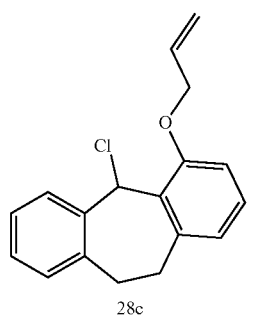
2a

28c
NaH, DMF
rt, 2 h
→

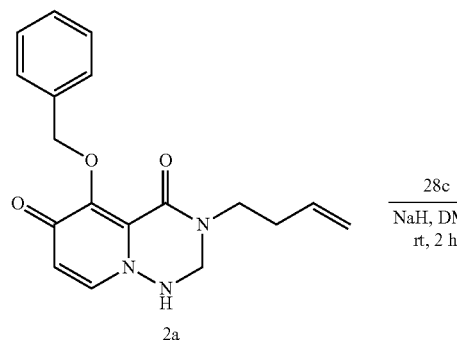
28d

Hoveyda-Grubbs II catalyst
DCE, 80° C., 2 h
→

84
-continued

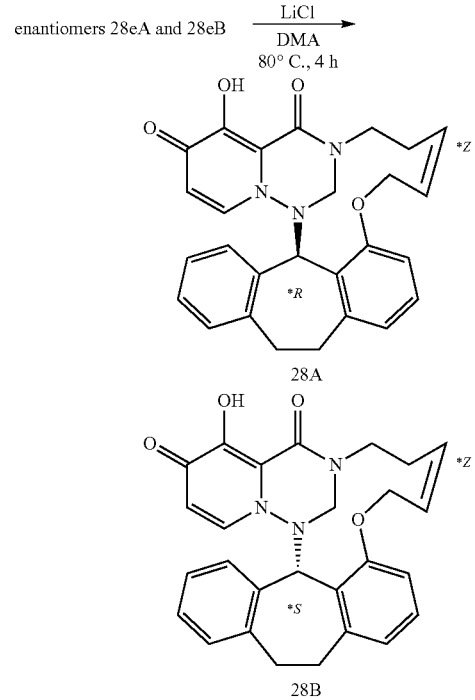
28e
enantiomers 28eA and 28eB chiral separation →

LiCl
DMA
80° C., 4 h
→

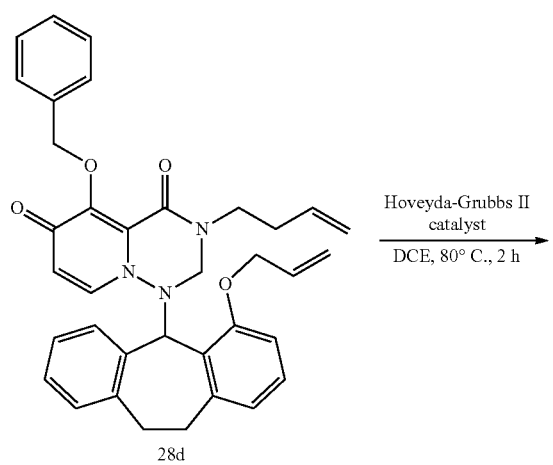
28A
28B

Synthesis of Intermediate 28a:

The reaction was performed in a sealed tube.

A mixture of 4-iodo-10,11-dihydro-5H-dibenzo[α,d][7]annulen-5-one [CAS 70911-04-5] (7.8 g, 23.34 mmol), 2-propen-1-ol [CAS 107-18-6] (3.19 mL, 46.68 mmol), CuI (444 mg, 2.33 mmol), 1,10-phenanthroline [CAS 5144-89-8] (841 mg, 4.66 mmol) and Cs₂CO₃ (15.2 g, 46.68 mmol) in toluene (20 mL) was stirred vigorously at 120° C. for 18 h. The mixture was cooled down to rt and poured into water. The mixture was diluted with EtOAc and then filtered through a pad of Celite®. The Celite® was washed with EtOAc. The two layers were separated and the organic phase was dried over MgSO₄, filtered and concentrated under reduced pressure. Purification was carried out by flash chromatography over silica gel (15-40 μm, 80 g, Heptane/EtOAc from 90/10 to 80/20). The pure fractions were collected and evaporated to dryness (batch 1, m=3.4 g). The fractions containing impurities were combined and purified again by flash chromatography over silica gel (15-40 μm, 40 g, Heptane/EtOAc 95/5). The pure fractions were collected and evaporated to dryness (batch 2, m=0.6 g). The two batches were combined to give 4-(allyloxy)-10,11-dihydro-5H-dibenzo[α,d][7]annulen-5-one (intermediate 28a, 4 g).

Synthesis of Intermediate 28b:

At 0° C. under $N_2$ flow, $LiAlH_4$ (1M in THF) (17.7 mL, 17.7 mmol) was added dropwise to a solution of 4-(allyloxy)-10,11-dihydro-5H-dibenzo[α,d][7]annulen-5-one (intermediate 28a, 3.9 g, 14.76 mmol) in THF (80 mL). The mixture was stirred at 0° C. for 1 h and quenched with EtOAc and diluted with water. The mixture was filtered through Celite®. The organic phase was separated, dried over $MgSO_4$, filtered and concentrated under reduced pressure to give 4-(allyloxy)-10,11-dihydro-5H-dibenzo[α,d][7]annulen-5-ol (intermediate 28b, 3.8 g).

Synthesis of Intermediate 28c:

At 0° C., $SOCl_2$ (1.22 mL, 16.89 mmol) was added dropwise to a solution of 4-(allyloxy)-10,11-dihydro-5H-dibenzo[α,d][7]annulen-5-ol (intermediate 28b, 3.75 g, 14.08 mmol) in $CH_2Cl_2$ (70 mL). The reaction was stirred at 0° C. for 30 min and then at rt for 4 h. The mixture was concentrated to dryness, taken up with toluene and concentrated again to give 4-(allyloxy)-5-chloro-10,11-dihydro-5H-dibenzo[α,d][7]annulene (intermediate 28c, 4.2 g), which was used as such in the next step.

Synthesis of Intermediate 28d:

1-(4-(allyloxy)-10,11-dihydro-5H-dibenzo[α,d][7]annulen-5-yl)-5-(benzyloxy)-3-(but-3-en-1-yl)-2,3-dihydro-1H-pyrido[2,1-f][1,2,4]triazine-4,6-dione (intermediate 28d, 5.55 g) was obtained using the procedure described for intermediate 5e.

Synthesis of Intermediate 28e:

Intermediate 28e (undefined E Z mixture, 620 mg) was obtained using the procedure described for intermediate 5f. The two enantiomers were separated via chiral SFC (Stationary phase: Whelk-O1 (S,S) 5 μm 250×21.2 mm, Mobile phase: 45% $CO_2$, 55% MeOH) to give the first eluted enantiomer (215 mg, undefined E Z mixture) and the second eluted enantiomer (230 mg, undefined E Z mixture). The first eluted enantiomer was further purified via chiral SFC (Stationary phase: Chiralcel® OD-H 5 μm 250×30 mm, Mobile phase: 60% $CO_2$, 40% MeOH) to give enantiomer 28eA (139 mg, pure *Z isomer). The second eluted enantiomer was further purified via chiral SFC (Stationary phase: Chiralpak® AD-H 5 μm 250×30 mm, Mobile phase: 60% $CO_2$, 40% MeOH) to give enantiomer 28eB (129 mg, pure *Z isomer).

Synthesis of Compound 28A:

LiCl (54 mg, 1.27 mmol) was added to a solution of 28eA (139 mg, 0.26 mmol) in DMA (1.44 mL) and the reaction was stirred at 80° C. for 4 h. The mixture was cooled to rt and HCl 0.5N in ice was added. The aqueous layer was extracted with $CH_2Cl_2$. The combined organic layers were washed 3 times with HCl 0.5N, dried over $MgSO_4$, filtered and concentrated under reduced pressure. Purification was carried out by flash chromatography over silica gel (15-40 μm, 4 g, $CH_2Cl_2/CH_3OH$ from 99/1 to 97/3). The pure fractions were collected and evaporated to dryness to give, after freeze-drying in 10 mL of CH3CN/water (2/8), Compound 28A (65 mg).

Compound 28A:

$^1H$ NMR (500 MHz, DMSO-$d_6$) δ ppm 2.18 (br d, J=14.2 Hz, 1H) 2.28-2.40 (m, 1H) 2.70-2.79 (m, 1H) 2.85 (br d, J=14.2 Hz, 1H) 2.89-3.00 (m, 1H) 4.18-4.32 (m, 2H) 4.37-4.49 (m, 2H) 4.53-4.62 (m, 1H) 4.82 (d, J=12.9 Hz, 1H) 5.42 (d, J=7.6 Hz, 1H) 5.91-6.01 (m, 2H) 6.05-6.14 (m, 1H) 6.49 (d, J=7.6 Hz, 1H) 6.83 (t, J=7.3 Hz, 1H) 6.92 (d, J=7.3 Hz, 1H) 6.96 (d, J=8.2 Hz, 1H) 7.04-7.12 (m, 2H) 7.13-7.20 (m, 1H) 7.29 (t, J=7.9 Hz, 1H) (1 proton under the peak of water)

LC/MS (method LC-C): $R_t$ 2.92 min, MH$^+$456

$[α]_D^{20}$: +291.23° (c, 0.285 DMF)

Chiral HPLC (method HPLC-B): $R_t$ 6.16 min, chiral purity 100%.

Synthesis of Compound 28B:

Compound 28B (59 mg) was obtained using the procedure described for compound 28A.

Compound 28B:

$^1H$ NMR (500 MHz, DMSO-$d_6$) δ ppm 2.19 (br s, 1H) 2.27-2.39 (m, 1H) 2.71-2.77 (m, 1H) 2.84 (br d, J=14.2 Hz, 1H) 2.89-3.00 (m, 1H) 4.18-4.29 (m, 2H) 4.36-4.48 (m, 2H) 4.53-4.63 (m, 1H) 4.82 (d, J=12.9 Hz, 1H) 5.41 (d, J=7.6 Hz, 1H) 5.91-6.01 (m, 2H) 6.04-6.13 (m, 1H) 6.49 (d, J=7.3 Hz, 1H) 6.83 (t, J=7.1 Hz, 1H) 6.92 (d, J=7.6 Hz, 1H) 6.96 (d, J=8.2 Hz, 1H) 7.04-7.12 (m, 2H) 7.15 (d, J=7.6 Hz, 1H) 7.28 (t, J=7.9 Hz, 1H) (1 proton under the peak of water)

LC/MS (method LC-C): $R_t$ 2.92 min, MH$^+$456

$[α]_D^{20}$: −285.33° (c 0.3, DMF)

Chiral HPLC (method HPLC-B): $R_t$ 8.52 min, chiral purity 100%.

Example 29: Synthesis of (9*R, 18*R, E)-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 29AA), (9*S, 18*R, E)-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 29AB), (9*R, 18*S, E)-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 29BA) and (9*S, 18*S, E)-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 29BB)

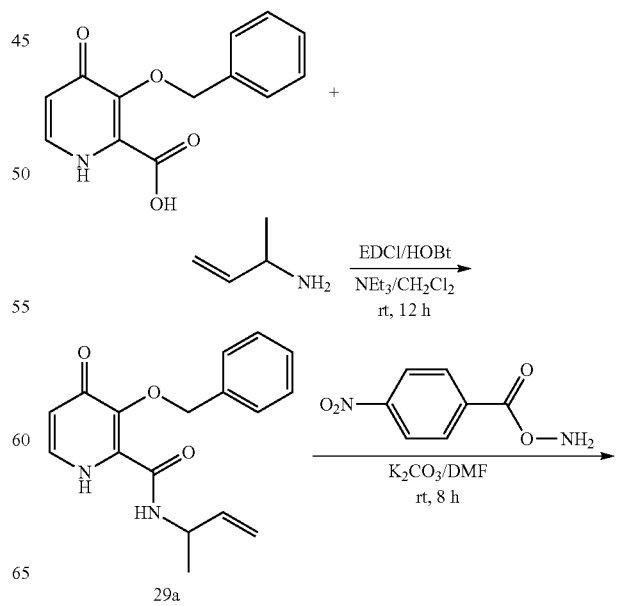

29a

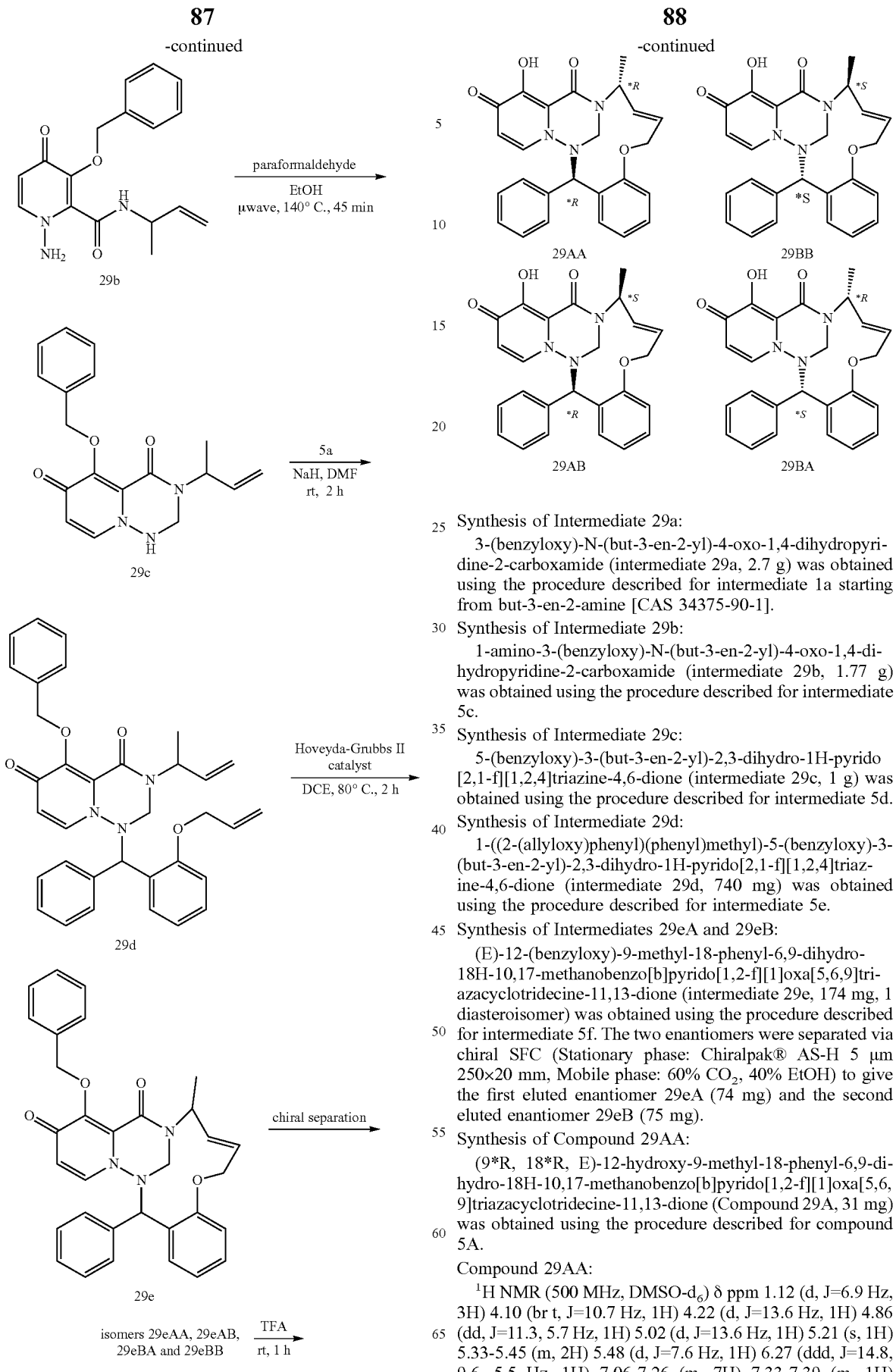

Synthesis of Intermediate 29a:
3-(benzyloxy)-N-(but-3-en-2-yl)-4-oxo-1,4-dihydropyridine-2-carboxamide (intermediate 29a, 2.7 g) was obtained using the procedure described for intermediate 1a starting from but-3-en-2-amine [CAS 34375-90-1].

Synthesis of Intermediate 29b:
1-amino-3-(benzyloxy)-N-(but-3-en-2-yl)-4-oxo-1,4-dihydropyridine-2-carboxamide (intermediate 29b, 1.77 g) was obtained using the procedure described for intermediate 5c.

Synthesis of Intermediate 29c:
5-(benzyloxy)-3-(but-3-en-2-yl)-2,3-dihydro-1H-pyrido[2,1-f][1,2,4]triazine-4,6-dione (intermediate 29c, 1 g) was obtained using the procedure described for intermediate 5d.

Synthesis of Intermediate 29d:
1-((2-(allyloxy)phenyl)(phenyl)methyl)-5-(benzyloxy)-3-(but-3-en-2-yl)-2,3-dihydro-1H-pyrido[2,1-f][1,2,4]triazine-4,6-dione (intermediate 29d, 740 mg) was obtained using the procedure described for intermediate 5e.

Synthesis of Intermediates 29eA and 29eB:
(E)-12-(benzyloxy)-9-methyl-18-phenyl-6,9-dihydro-18H-10,17-methanobenzo[b]pyrido[1,2-f][1]oxa[5,6,9]triazacyclotridecine-11,13-dione (intermediate 29e, 174 mg, 1 diasteroisomer) was obtained using the procedure described for intermediate 5f. The two enantiomers were separated via chiral SFC (Stationary phase: Chiralpak® AS-H 5 μm 250×20 mm, Mobile phase: 60% $CO_2$, 40% EtOH) to give the first eluted enantiomer 29eA (74 mg) and the second eluted enantiomer 29eB (75 mg).

Synthesis of Compound 29AA:
(9*R, 18*R, E)-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 29A, 31 mg) was obtained using the procedure described for compound 5A.

Compound 29AA:
$^1$H NMR (500 MHz, DMSO-$d_6$) δ ppm 1.12 (d, J=6.9 Hz, 3H) 4.10 (br t, J=10.7 Hz, 1H) 4.22 (d, J=13.6 Hz, 1H) 4.86 (dd, J=11.3, 5.7 Hz, 1H) 5.02 (d, J=13.6 Hz, 1H) 5.21 (s, 1H) 5.33-5.45 (m, 2H) 5.48 (d, J=7.6 Hz, 1H) 6.27 (ddd, J=14.8, 9.6, 5.5 Hz, 1H) 7.06-7.26 (m, 7H) 7.33-7.39 (m, 1H)

7.40-7.47 (m, 1H) 8.09 (dd, J=7.7, 1.4 Hz, 1H) 9.92-12.00 (m, 1H)

LC/MS (method LC-A): $R_t$ 2.56 min, MH$^+$430

$[\alpha]_D^{20}$: +608.99° (c 0.178, DMF)

Chiral HPLC (method HPLC-B): $R_t$ 5.70 min, chiral purity 100%.

Synthesis of Compound 29BB:

(9*S, 18*S, E)-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 29B, 27 mg) was obtained using the procedure described for compound 5A.

Compound 29BB:

$^1$H NMR (500 MHz, DMSO-d$_6$) δ ppm 1.12 (d, J=6.9 Hz, 3H) 4.10 (t, J=10.7 Hz, 1H) 4.22 (d, J=13.6 Hz, 1H) 4.87 (dd, J=11.3, 5.4 Hz, 1H) 5.02 (d, J=13.6 Hz, 1H) 5.21 (s, 1H) 5.34-5.45 (m, 2H) 5.48 (d, J=7.6 Hz, 1H) 6.27 (ddd, J=14.8, 9.6, 5.5 Hz, 1H) 7.05-7.25 (m, 7H) 7.33-7.40 (m, 1H) 7.41-7.47 (m, 1H) 8.09 (dd, J=7.7, 1.4 Hz, 1H) 10.34-11.93 (m, 1H)

LC/MS (method LC-A): $R_t$ 2.56 min, MH$^+$430

$[\alpha]_D^{20}$: −608.94° (c 0.179, DMF)

Chiral HPLC (method HPLC-B): $R_t$ 6.68 min, chiral purity 100%.

Synthesis of Compound 29AB:

(9*S, 18*R, E)-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 29A, 31 mg) was obtained using the procedure described for compound 5A.

Compound 29AB:

$^1$H NMR (500 MHz, DMSO-d$_6$) δ ppm 1.74 (d, J=6.9 Hz, 3H) 3.65-3.73 (m, 1H) 4.17 (d, J=13.9 Hz, 1H) 4.49-4.56 (m, 1H) 4.58 (br t, J=10.1 Hz, 1H) 5.14 (d, J=13.9 Hz, 1H) 5.44 (s, 1H) 5.48 (d, J=7.6 Hz, 1H) 5.71-5.85 (m, 1H) 6.37-6.48 (m, 1H) 7.06-7.21 (m, 5H) 7.26 (d, J=7.9 Hz, 1H) 7.31-7.37 (m, 2H) 7.36-7.43 (m, 1H) 8.14 (dd, J=7.88, 1.26 Hz, 1H) 10.09-10.66 (m, 1H).

LC/MS (method LC-C): $R_t$ 2.66 min, MH$^+$430

$[\alpha]_D^{20}$: −737.35° (c 0.166, DMF)

Chiral HPLC (method HPLC-A): $R_t$ 7.59 min, chiral purity 100%.

Synthesis of Compound 29BA:

(9*R, 18*S, E)-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 29A, 31 mg) was obtained using the procedure described for compound 5A.

Compound 29BA:

$^1$H NMR (500 MHz, DMSO-d$_6$) δ ppm 1.74 (d, J=6.9 Hz, 3H) 3.64-3.77 (m, 1H) 4.17 (d, J=13.9 Hz, 1H) 4.49-4.63 (m, 2H) 5.16 (d, J=13.87 Hz, 1H) 5.43-5.50 (m, 2H) 5.73-5.90 (m, 1H) 6.42 (br dd, J=15.29, 9.93 Hz, 1H) 7.06-7.20 (m, 5H) 7.26 (d, J=7.88 Hz, 1H) 7.30-7.36 (m, 2H) 7.36-7.45 (m, 1H) 8.14 (d, J=6.62 Hz, 1H) 10.05-10.89 (m, 1H)

LC/MS (method LC-C): $R_t$ 2.66 min, MH$^+$430

$[\alpha]_D^{20}$: +728.18° (c 0.22, DMF)

Chiral HPLC (method HPLC-A): $R_t$ 5.18 min. chiral purity 100%.

Example 30: Synthesis of (18*R)-2-fluoro-12-hydroxy-18-phenyl-6,7,8,9-tetrahydro-18H-10,17-methanobenzo[b]pyrido[1,2-f][1]oxa[5,6,9]triazacyclotridecine-11,13-dione (Compound 30A) and (18*S)-2-fluoro-12-hydroxy-18-phenyl-6,7,8,9-tetrahydro-18H-10,17-methanobenzo[b]pyrido[1,2-f][1]oxa[5,6,9]triazacyclotridecine-11,13-dione (Compound 30B)

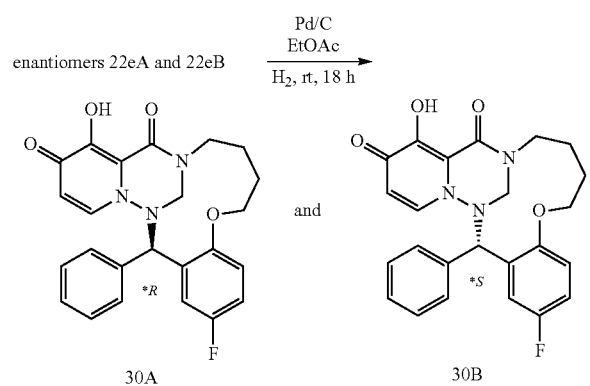

Synthesis of Compound 30A:

(18*R)-2-fluoro-12-hydroxy-18-phenyl-6,7,8,9-tetrahydro-18H-10,17-methanobenzo[b]pyrido[1,2-f][1]oxa[5,6,9]triazacyclotridecine-11,13-dione (Compound 30A, 24 mg) was obtained using the procedure described for compound 8 starting from intermediate 22eA.

Compound 30A:

$^1$H NMR (500 MHz, DMSO-d$_6$) δ ppm 1.12 (q, J=12.4 Hz, 1H) 1.52-1.65 (m, 1H) 1.75-1.97 (m, 2H) 2.61-2.69 (m, 1H) 4.05 (br t, J=12.6 Hz, 1H) 4.13 (t, J=11.5 Hz, 1H) 4.32-4.42 (m, 2H) 5.02 (d, J=13.6 Hz, 1H) 5.52 (d, J=7.9 Hz, 1H) 5.86 (s, 1H) 7.15-7.43 (m, 8H) 7.81 (dd, J=9.3, 3.0 Hz, 1H) 11.37 (br s, 1H)

LC/MS (method LC-C): $R_t$ 2.61 min, MH$^+$436

$[\alpha]_D^{20}$: +314.16° (c 0.113, DMF)

Chiral HPLC (method HPLC-B): $R_t$ 7.86 min, chiral purity 100%.

Synthesis of Compound 30B:

(18*S)-2-fluoro-12-hydroxy-18-phenyl-6,7,8,9-tetrahydro-18H-10,17-methanobenzo[b]pyrido[1,2-f][1]oxa[5,6,9]triazacyclotridecine-11,13-dione (compound 30B, 28 mg) was obtained using the procedure described for compound 8 starting from intermediate 22eB.

Compound 30B:

$^1$H NMR (500 MHz, DMSO-d$_6$) δ ppm 1.04-1.18 (m, 1H) 1.52-1.67 (m, 1H) 1.74-1.99 (m, 2H) 2.61-2.70 (m, 1H) 4.05 (br t, J=12.8 Hz, 1H) 4.13 (br t, J=11.3 Hz, 1H) 4.31-4.42 (m, 2H) 5.02 (d, J=13.6 Hz, 1H) 5.52 (d, J=7.9 Hz, 1H) 5.86 (s, 1H) 7.15-7.45 (m, 8H) 7.81 (dd, J=9.3, 2.7 Hz, 1H) 11.36 (br s, 1H)

LC/MS (method LC-C): $R_t$ 2.61 min, MH$^+$436

$[\alpha]_D^{20}$: −312.59° (c 0.143, DMF)

Chiral HPLC (method HPLC-B): $R_t$ 4.76 min, chiral purity 100%.

Example 31: Synthesis of (19bR,Z)-4-hydroxy-8,9,15,19b-tetrahydro-7H,14H-13,12-(epiprop[1]en[1]yl[3]ylidene)-6,20-methanobenzo[3,4]cyclohepta[1,2-1]pyrido[1,2-b][1,2,5]triazacyclotridecine-3,5-dione (Compound 31B)

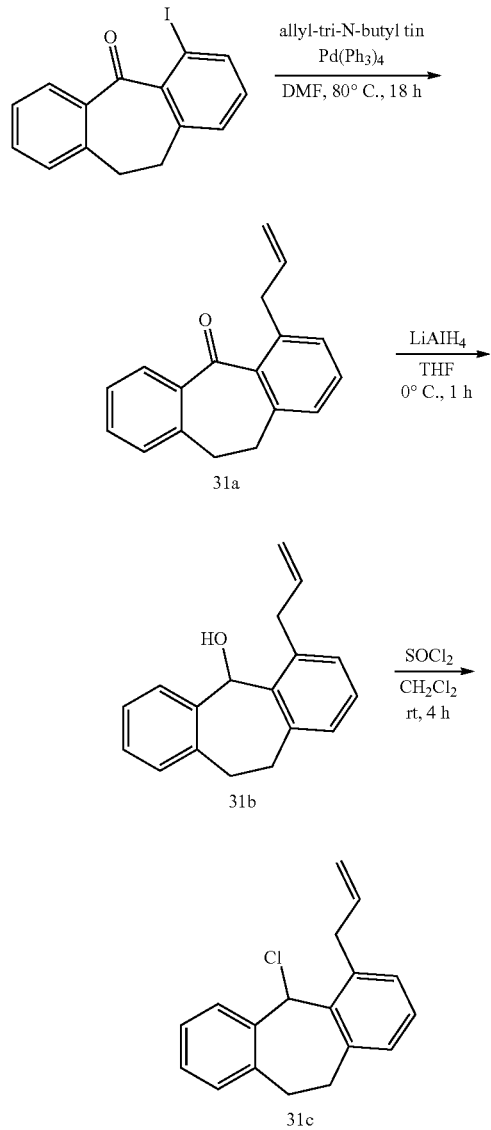

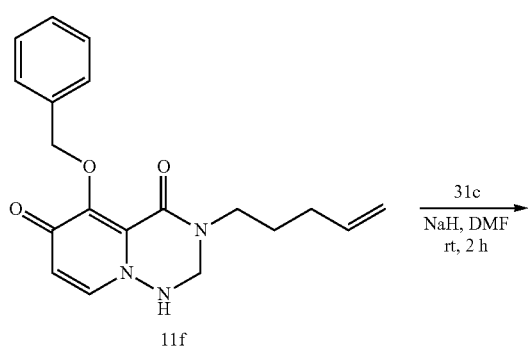

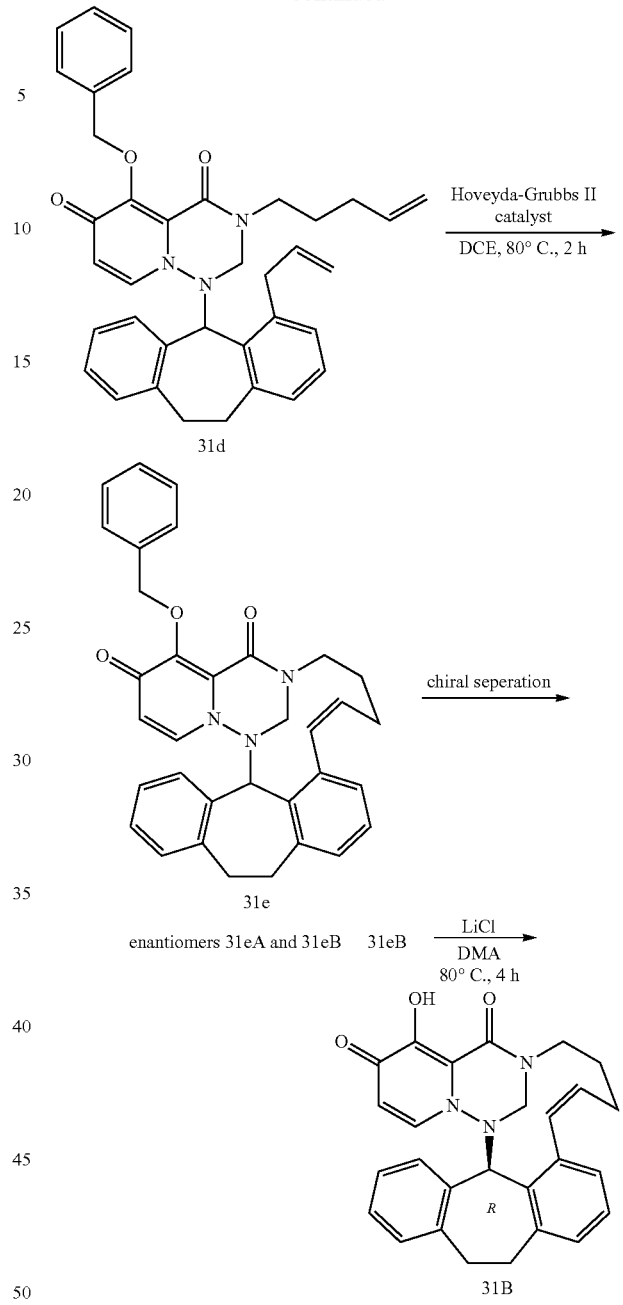

Synthesis of Intermediate 31a:
4-allyl-10,11-dihydro-5H-dibenzo[α,d][7]annulen-5-one (intermediate 31a, 1.24 g) was obtained using the procedure described for intermediate 11a.

Synthesis of Intermediate 31b:
4-allyl-10,11-dihydro-5H-dibenzo[α,d][7]annulen-5-ol (intermediate 31b, 1.29 g) was obtained using the procedure described for intermediate 28b.

Synthesis of Intermediate 31c:
4-allyl-5-chloro-10,11-dihydro-5H-dibenzo[α,d][7]annulene (intermediate 31c, 1.27 g) was obtained using the procedure described for intermediate 28c.

Synthesis of Intermediate 31d:
1-(4-allyl-10,11-dihydro-5H-dibenzo[α,d][7]annulen-5-yl)-5-(benzyloxy)-3-(pent-4-en-1-yl)-2,3-dihydro-1H- pyrido[2,1-f][1,2,4]triazine-4,6-dione (intermediate 31d, 1.07 g) was obtained using the procedure described for intermediate 28d starting from intermediate 11f.

Synthesis of Intermediate 31e:

Intermediate 31e (138 mg, racemate of the Z isomer) was obtained using the procedure described for intermediate 5f. The two enantiomers were separated via chiral SFC (Stationary phase: Chiralpak® AS-H 5 µm 250×20 mm, Mobile phase: 70% $CO_2$, 30% MeOH) to give the first eluted enantiomer 31eA (68 mg) and the second eluted enantiomer 31eB (63 mg).

Synthesis of Compound 31B:

(19bR,Z)-4-hydroxy-8,9,15,19b-tetrahydro-7H,14H-13, 12-(epiprop[1]en[1]yl[3]ylidene)-6,20-methanobenzo[3,4]cyclohepta[1,2-1]pyrido[1,2-b][1,2,5]triazacyclotridecine-3,5-dione (compound 31B, 20 mg) was obtained using the procedure described for compound 28A.

Compound 31B:

$^1$H NMR (500 MHz, DMSO-$d_6$) δ ppm 1.50-1.64 (m, 1H) 1.92-2.22 (m, 3H) 2.53-2.65 (m, 1H) 2.73 (dt, J=14.1, 4.3 Hz, 1H) 2.90 (ddd, J=17.8, 13.1, 5.0 Hz, 1H) 3.45-3.57 (m, 1H) 3.62-3.74 (m, 1H) 3.98 (d, J=12.9 Hz, 1H) 4.22 (td, J=13.6, 5.0 Hz, 1H) 4.78 (d, J=12.9 Hz, 1H) 5.34 (s, 1H) 5.40 (d, J=7.9 Hz, 1H) 5.87 (td, J=10.5, 4.9 Hz, 1H) 6.33 (d, J=11.0 Hz, 1H) 6.50 (d, J=7.6 Hz, 1H) 6.78 (d, J=7.6 Hz, 1H) 6.83 (t, J=7.3 Hz, 1H) 6.91 (d, J=6.9 Hz, 1H) 7.07-7.18 (m, 2H) 7.20-7.28 (m, 2H) 11.82 (br s, 1H)

LC/MS (method LC-C): $R_t$ 3.18 min, MH$^+$440

$[α]_D^{20}$: −206.93° (c 0.202, DMF)

Example 32: Synthesis of (18*R)-2-fluoro-18-(3-fluorophenyl)-12-hydroxy-6,7,8,9-tetrahydro-18H-10,17-methanobenzo[b]pyrido[1,2-f][1]oxa[5,6,9]triazacyclotridecine-11,13-dione (compound 32A) and (18*S)-2-fluoro-18-(3-fluorophenyl)-12-hydroxy-6,7,8,9-tetrahydro-18H-10,17-methanobenzo[b]pyrido[1,2-f][1]oxa[5,6,9]triazacyclotridecine-11,13-dione (Compound 32B)

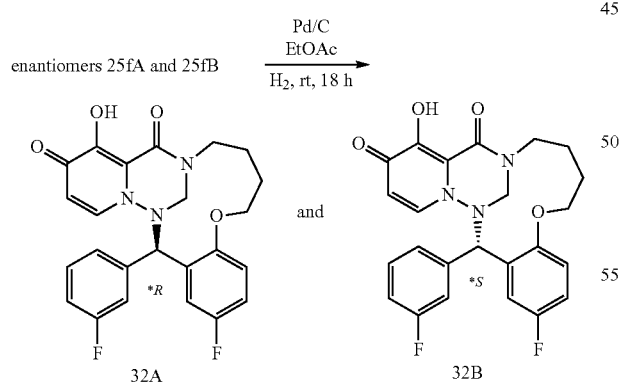

Synthesis of Compound 32A:

(18*R)-2-fluoro-18-(3-fluorophenyl)-12-hydroxy-6,7,8,9-tetrahydro-18H-10,17-methanobenzo[b]pyrido[1,2-f][1]oxa[5,6,9]triazacyclotridecine-11,13-dione (Compound 32A, 24 mg) was obtained using the procedure described for compound 8 starting from intermediate 25fA.

Compound 32A:

$^1$H NMR (500 MHz, DMSO-$d_6$) δ ppm 0.96-1.09 (m, 1H) 1.51 (br d, J=9.8 Hz, 1H) 1.68-1.90 (m, 2H) 2.54-2.62 (m, 1H) 3.98 (brt, J=12.9 Hz, 1H) 4.06 (brt, J=11.2 Hz, 1H) 4.23-4.36 (m, 2H) 4.96 (d, J=13.6 Hz, 1H) 5.54 (d, J=7.6 Hz, 1H) 5.83 (s, 1H) 6.98-7.34 (m, 7H) 7.78 (dd, J=9.3, 2.7 Hz, 1H) 11.42 (s, 1H)

LC/MS (method LC-C): $R_t$ 2.66 min, MH$^+$454

$[α]_D^{20}$: +261.02° (c 0.118, DMF)

Chiral HPLC (method HPLC-B): $R_t$ 4.19 min, chiral purity 100%.

Synthesis of Compound 32B:

(18*S)-2-fluoro-18-(3-fluorophenyl)-12-hydroxy-6,7,8,9-tetrahydro-18H-10,17-methanobenzo[b]pyrido[1,2-f][1]oxa[5,6,9]triazacyclotridecine-11,13-dione (Compound 32B, 16 mg) was obtained using the procedure described for compound 8 starting from intermediate 25fB.

Compound 32B:

$^1$H NMR (500 MHz, DMSO-$d_6$) δ ppm 0.93-1.11 (m, 1H) 1.51 (br d, J=10.7 Hz, 1H) 1.68-1.91 (m, 2H) 2.55-2.58 (m, 1H) 3.98 (brt, J=12.9 Hz, 1H) 4.06 (brt, J=11.3 Hz, 1H) 4.22-4.38 (m, 2H) 4.95 (br d, J=13.6 Hz, 1H) 5.53 (br d, J=7.9 Hz, 1H) 5.83 (s, 1H) 6.94-7.38 (m, 7H) 7.78 (dd, J=9.3, 2.4 Hz, 1H) 11.32 (br s, 1H)

LC/MS (method LC-C): $R_t$ 2.66 min, MH$^+$454

$[α]_D^{20}$: −297.35° (c 0.113, DMF)

Chiral HPLC (method HPLC-B): $R_t$ 8.38 min, chiral purity 100%.

Example 33: Synthesis of (19b*R,Z)-4-hydroxy-7,10,15,19b-tetrahydro-14H-13,12-(epiprop[1]en[1]yl[3]ylidene)-6,20-methanobenzo[3,4]cyclohepta[1,2-c]pyrido[1,2-f][1]oxa[5,6,9]triazacyclotridecine-3,5-dione (Compound 33A) and (19b*S,Z)-4-hydroxy-7,10,15,19b-tetrahydro-14H-13,12-(epiprop[1]en[1]yl[3]ylidene)-6,20-methanobenzo[3,4]cyclohepta[1,2-c]pyrido[1,2-f][1]oxa[5,6,9]triazacyclotridecine-3,5-dione (Compound 33B)

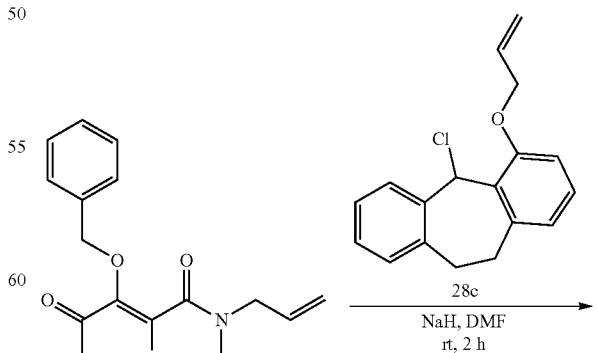

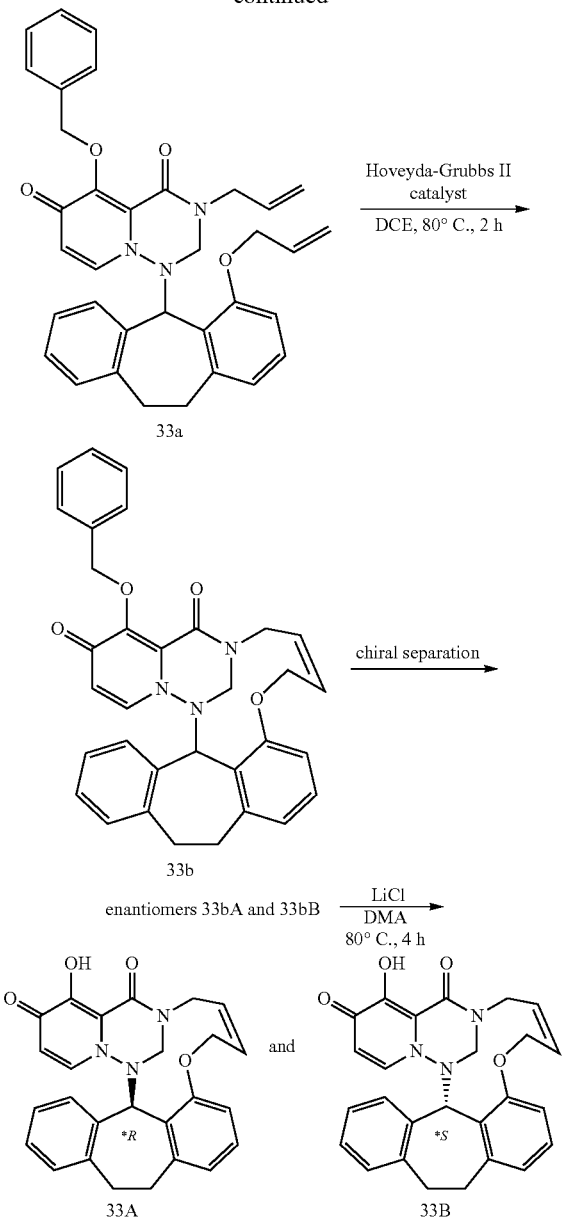

Synthesis of Intermediate 33a:

3-allyl-1-(4-(allyloxy)-10,11-dihydro-5H-dibenzo[α,d][7]annulen-5-yl)-5-(benzyloxy)-2,3-dihydro-1H-pyrido[2,1-f][1,2,4]triazine-4,6-dione (intermediate 33a, 3.1 g) was obtained using the procedure described for intermediate 5e starting from intermediate 5d.

Synthesis of Intermediate 33b:

(Z)-4-(benzyloxy)-7,10,15,19b-tetrahydro-14H-13,12-(epiprop[1]en[1]yl[3]ylidene)-6,20-methanobenzo[3,4]cyclohepta[1,2-c]pyrido[1,2-f][1]oxa[5,6,9]triazacyclotridecine-3,5-dione (intermediate 33b, 117 mg) was obtained using the procedure described for intermediate 5f. A second purification was done via reverse phase (Stationary phase: YMC-actus Triart C18 10 μm 30×150 mm, Mobile phase: Gradient from 55% NH$_4$HCO$_3$ 0.2%, 45% CH$_3$CN to 35% NH$_4$HCO$_3$ 0.2%, 65% CH$_3$CN).

The two enantiomers were separated via chiral SFC (Stationary phase: Whelk-O1 (S,S) 5 μm 250×21.2 mm, Mobile phase: 45% CO$_2$, 55% MeOH) to give the first eluted enantiomer 33bA (42 mg) and the second eluted enantiomer 33bB (49 mg).

Synthesis of Compound 33A:

(19b*R,Z)-4-hydroxy-7,10,15,19b-tetrahydro-14H-13,12-(epiprop[1]en[1]yl[3]ylidene)-6,20-methanobenzo[3,4]cyclohepta[1,2-c]pyrido[1,2-f][1]oxa[5,6,9]triazacyclotridecine-3,5-dione (Compound 33A, 22 mg) was obtained using the procedure described for compound 28A.

Compound 33A:

$^1$H NMR (500 MHz, DMSO-d$_6$) δ ppm 2.77-2.85 (m, 1H) 2.95 (ddd, J=16.9, 12.8, 3.8 Hz, 1H) 3.61 (dt, J=17.1, 4.5 Hz, 1H) 3.78 (br dd, J=13.4, 8.4 Hz, 1H) 4.08-4.20 (m, 2H) 4.26 (d, J=12.9 Hz, 1H) 4.61 (dd, J=10.7, 6.6 Hz, 1H) 4.75 (dd, J=10.6, 6.8 Hz, 1H) 4.97 (d, J=13.2 Hz, 1H) 5.44 (d, J=7.9 Hz, 1H) 5.94 (s, 1H) 6.30-6.37 (m, 1H) 6.39-6.47 (m, 1H) 6.51 (d, J=7.6 Hz, 1H) 6.81-6.90 (m, 1H) 6.95 (d, J=7.3 Hz, 1H) 7.04-7.11 (m, 2H) 7.12-7.22 (m, 2H) 7.32 (t, J=7.9 Hz, 1H)

LC/MS (method LC-C): R$_t$ 2.80 min, MH$^+$442

$[\alpha]_D^{20}$: +307.89° (c 0.190, DMF)

Chiral HPLC (method HPLC-B): R$_t$ 5.31 min, chiral purity 100%.

Synthesis of Compound 33B:

(19b*S,Z)-4-hydroxy-7,10,15,19b-tetrahydro-14H-13,12-(epiprop[1]en[1]yl[3]ylidene)-6,20-methanobenzo[3,4]cyclohepta[1,2-c]pyrido[1,2-f][1]oxa[5,6,9]triazacyclotridecine-3,5-dione (Compound 33B, 20 mg) was obtained using the procedure described for compound 28A.

Compound 33B:

$^1$H NMR (500 MHz, DMSO-d$_6$) δ ppm 2.77-2.85 (m, 1H) 2.94 (ddd, J=16.9, 12.8, 3.8 Hz, 1H) 3.60 (dt, J=17.2, 4.7 Hz, 1H) 3.77 (br dd, J=13.6, 8.2 Hz, 1H) 4.08-4.18 (m, 2H) 4.25 (d, J=12.9 Hz, 1H) 4.60 (dd, J=10.7, 6.6 Hz, 1H) 4.74 (dd, J=10.7, 6.6 Hz, 1H) 4.96 (d, J=12.9 Hz, 1H) 5.43 (d, J=7.9 Hz, 1H) 5.93 (s, 1H) 6.33 (dt, J=10.6, 6.5 Hz, 1H) 6.38-6.46 (m, 1H) 6.51 (d, J=7.6 Hz, 1H) 6.86 (t, J=6.9 Hz, 1H) 6.94 (d, J=7.6 Hz, 1H) 7.07 (dd, J=7.7, 4.6 Hz, 2H) 7.12-7.20 (m, 2H) 7.32 (t, J=7.9 Hz, 1H)

LC/MS (method LC-C): R$_t$ 2.80 min, MH$^+$442

$[\alpha]_D^{20}$: −327.83° (c 0.212, DMF)

Chiral HPLC (method HPLC-B): R$_t$ 7.10 min, chiral purity 100%.

Example 34: Synthesis of (18*R)-12-hydroxy-18-phenyl-5,6,7,8,9,18-hexahydro-10,17-methanodipyrido[1,2-b:4',3'-k][1,2,5]triazacyclotridecine-11,13-dione (Compound 34A) and (18*S)-12-hydroxy-18-phenyl-5,6,7,8,9,18-hexahydro-10,17-methanodipyrido[1,2-b:4',3'-k][1,2,5]triazacyclotridecine-11,13-dione (Compound 34B)

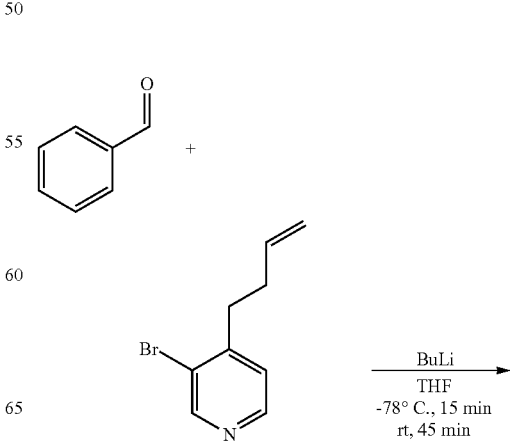

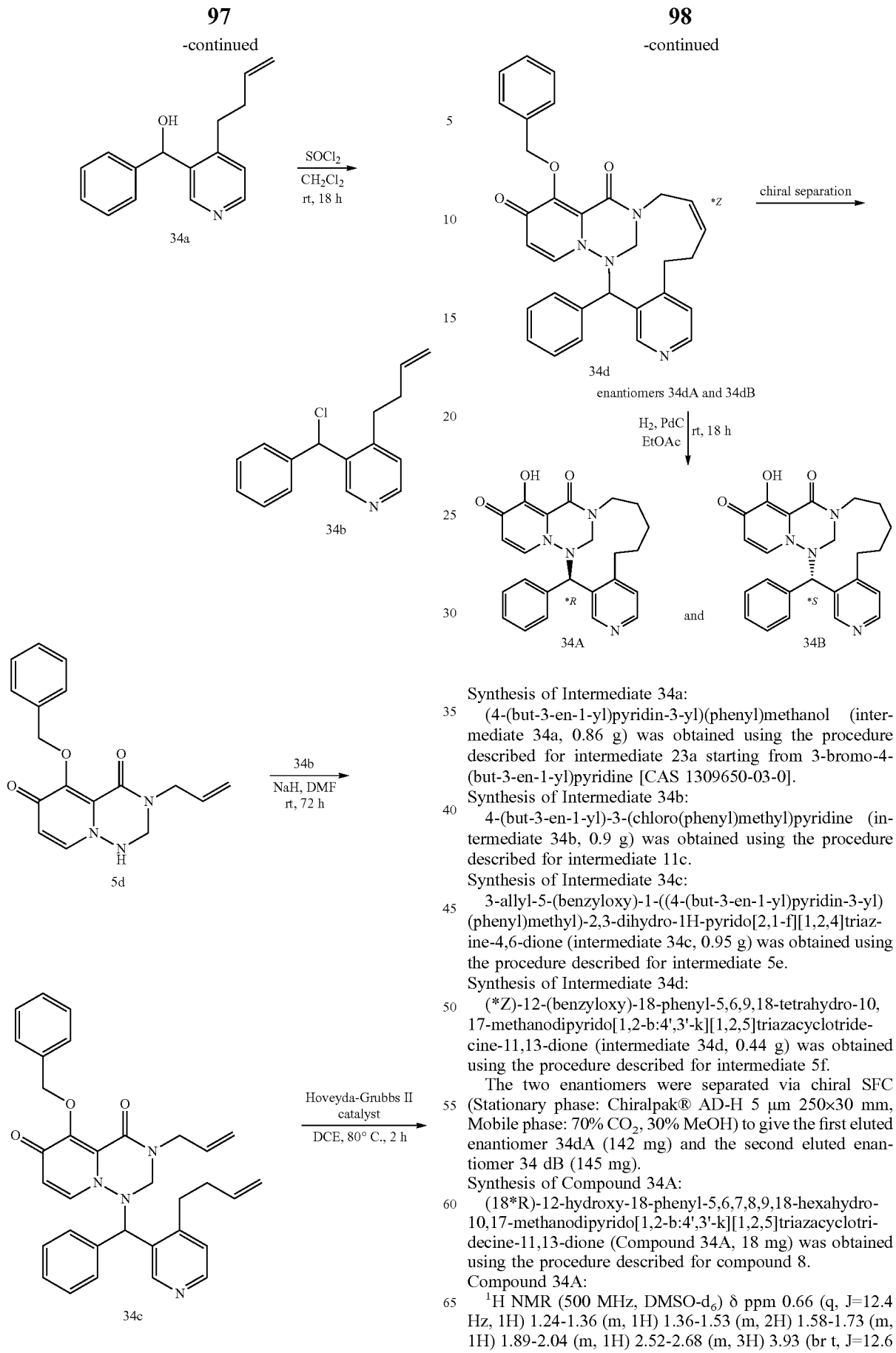

Synthesis of Intermediate 34a:
(4-(but-3-en-1-yl)pyridin-3-yl)(phenyl)methanol (intermediate 34a, 0.86 g) was obtained using the procedure described for intermediate 23a starting from 3-bromo-4-(but-3-en-1-yl)pyridine [CAS 1309650-03-0].

Synthesis of Intermediate 34b:
4-(but-3-en-1-yl)-3-(chloro(phenyl)methyl)pyridine (intermediate 34b, 0.9 g) was obtained using the procedure described for intermediate 11c.

Synthesis of Intermediate 34c:
3-allyl-5-(benzyloxy)-1-((4-(but-3-en-1-yl)pyridin-3-yl)(phenyl)methyl)-2,3-dihydro-1H-pyrido[2,1-f][1,2,4]triazine-4,6-dione (intermediate 34c, 0.95 g) was obtained using the procedure described for intermediate 5e.

Synthesis of Intermediate 34d:
(*Z)-12-(benzyloxy)-18-phenyl-5,6,9,18-tetrahydro-10,17-methanodipyrido[1,2-b:4',3'-k][1,2,5]triazacyclotridecine-11,13-dione (intermediate 34d, 0.44 g) was obtained using the procedure described for intermediate 5f.

The two enantiomers were separated via chiral SFC (Stationary phase: Chiralpak® AD-H 5 μm 250×30 mm, Mobile phase: 70% $CO_2$, 30% MeOH) to give the first eluted enantiomer 34dA (142 mg) and the second eluted enantiomer 34 dB (145 mg).

Synthesis of Compound 34A:
(18*R)-12-hydroxy-18-phenyl-5,6,7,8,9,18-hexahydro-10,17-methanodipyrido[1,2-b:4',3'-k][1,2,5]triazacyclotridecine-11,13-dione (Compound 34A, 18 mg) was obtained using the procedure described for compound 8.

Compound 34A:
$^1$H NMR (500 MHz, DMSO-d$_6$) δ ppm 0.66 (q, J=12.4 Hz, 1H) 1.24-1.36 (m, 1H) 1.36-1.53 (m, 2H) 1.58-1.73 (m, 1H) 1.89-2.04 (m, 1H) 2.52-2.68 (m, 3H) 3.93 (br t, J=12.6

Hz, 1H) 4.36 (d, J=13.9 Hz, 1H) 5.02 (br d, J=13.9 Hz, 1H) 5.42 (br d, J=7.6 Hz, 1H) 5.58 (s, 1H) 7.00 (br d, J=7.6 Hz, 1H) 7.16-7.44 (m, 6H) 8.42 (d, J=5.0 Hz, 1H) 9.13 (s, 1H) 11.37 (br s, 1H)

LC/MS (method LC-C): $R_t$ 2.18 min, MH$^+$417

$[\alpha]_D^{20}$: −342.02° (c 0.119, DMF)

Synthesis of Compound 34B:

(18*S)-12-hydroxy-18-phenyl-5,6,7,8,9,18-hexahydro-10,17-methanodipyrido[1,2-b:4',3'-k][1,2,5]triazacyclotridecine-11,13-dione (Compound 34B, 18 mg) was obtained using the procedure described for compound 8.

Compound 34B:

$^1$H NMR (500 MHz, DMSO-d$_6$) δ ppm 0.57-0.73 (m, 1H) 1.23-1.58 (m, 3H) 1.58-1.72 (m, 1H) 1.90-2.04 (m, 1H) 2.47-2.53 (m, 2H) 2.60-2.75 (m, 1H) 3.93 (brt, J=12.6 Hz, 1H) 4.36 (d, J=13.9 Hz, 1H) 5.02 (br d, J=13.9 Hz, 1H) 5.42 (br d, J=7.6 Hz, 1H) 5.58 (s, 1H) 7.00 (br d, J=7.6 Hz, 1H) 7.07-7.56 (m, 6H) 8.42 (d, J=5.0 Hz, 1H) 9.13 (s, 1H) 11.29 (br s, 1H)

LC/MS (method LC-C): $R_t$ 2.18 min, MH$^+$417

$[\alpha]_D^{20}$: +342.28° (c 0.149, DMF)

Example 35: Synthesis of (18*R,*Z)-12-hydroxy-18-phenyl-5,6,9,18-tetrahydro-10,17-methanodipyrido[1,2-b:4',3'-k][1,2,5]triazacyclotridecine-11,13-dione (Compound 35A) and (18*S,*Z)-12-hydroxy-18-phenyl-5,6,9,18-tetrahydro-10,17-methanodipyrido[1,2-b:4',3'-k][1,2,5]triazacyclotridecine-11,13-dione (Compound 35B)

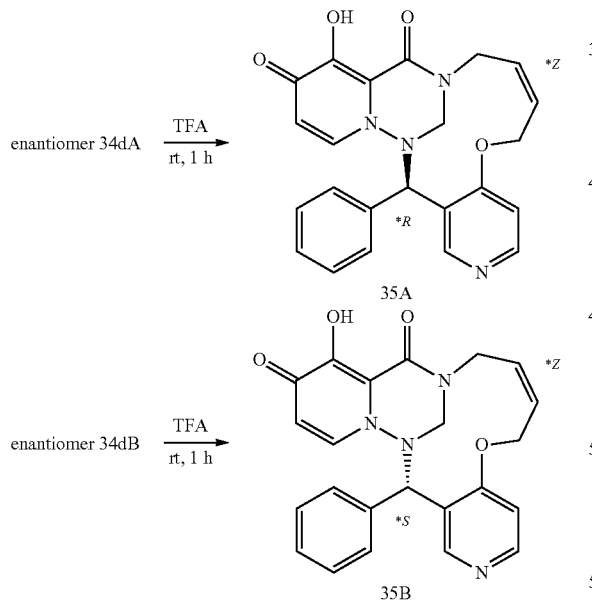

Synthesis of Compound 35A:

(18*R,*Z)-12-hydroxy-18-phenyl-5,6,9,18-tetrahydro-10,17-methanodipyrido[1,2-b:4',3'-k][1,2,5]triazacyclotridecine-11,13-dione (Compound 35A, 77 mg) was obtained using the procedure described for compound 5A.

Compound 35A:

$^1$H NMR (400 MHz, DMSO-d$_6$) δ ppm 1.85-2.18 (m, 1H) 2.54-2.72 (m, 3H) 2.95-3.17 (m, 1H) 4.34 (d, J=14.2 Hz, 1H) 4.71 (br dd, J=14.2, 5.1 Hz, 1H) 5.14 (d, J=13.6 Hz, 1H) 5.25 (s, 1H) 5.45 (d, J=7.6 Hz, 1H) 5.48-5.71 (m, 1H) 5.81-6.18 (m, 1H) 6.92-7.47 (m, 7H) 8.50 (d, J=4.6 Hz, 1H) 9.28 (s, 1H)

LC/MS (method LC-C): $R_t$ 2.10 min, MH$^+$415

$[\alpha]_D^{20}$: −592.86° (c 0.140, DMF)

Chiral HPLC (method HPLC-A): $R_t$ 4.58 min, chiral purity 100%.

Synthesis of Compound 35B:

(18*S,*Z)-12-hydroxy-18-phenyl-5,6,9,18-tetrahydro-10,17-methanodipyrido[1,2-b:4',3'-k][1,2,5]triazacyclotridecine-11,13-dione (Compound 35B, 71 mg) was obtained using the procedure described for compound 5A.

Compound 35B:

$^1$H NMR (400 MHz, DMSO-d$_6$) δ ppm 1.96-2.20 (m, 1H) 2.53-2.69 (m, 3H) 2.94-3.20 (m, 1H) 4.34 (d, J=13.6 Hz, 1H) 4.71 (br dd, J=13.6, 5.1 Hz, 1H) 5.14 (d, J=13.6 Hz, 1H) 5.25 (s, 1H) 5.45 (d, J=7.6 Hz, 1H) 5.51-5.65 (m, 1H) 5.96 (dt, J=15.4, 7.5 Hz, 1H) 7.13-7.33 (m, 7H) 8.50 (d, J=4.6 Hz, 1H) 9.28 (s, 1H)

LC/MS (method LC-C): $R_t$ 2.10 min, MH$^+$415

$[\alpha]_D^{20}$: +600° (c 0.112, DMF)

Chiral HPLC (method HPLC-A): $R_t$ 6.07 min, chiral purity 100%.

Example 36: Synthesis of (18*R,Z)-18-(2-fluorophenyl)-12-hydroxy-6,9-dihydro-18H-10,17-methanobenzo[b]pyrido[1,2-f][1]oxa[5,6,9]triazacyclotridecine-11,13-dione (Compound 36A) and (18*S,Z)-18-(2-fluorophenyl)-12-hydroxy-6,9-dihydro-18H-10,17-methanobenzo[b]pyrido[1,2-f][1]oxa[5,6,9]triazacyclotridecine-11,13-dione (Compound 36B)

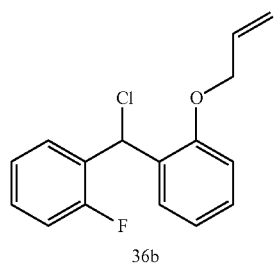

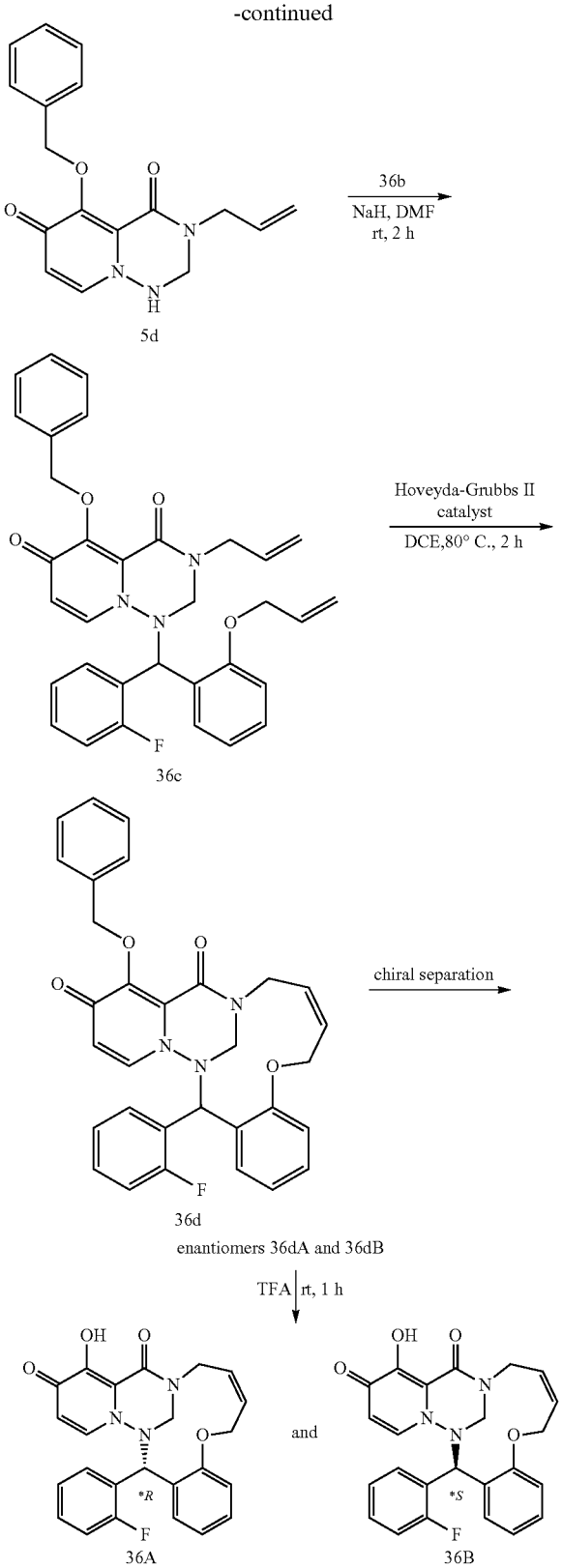

14.08 mmol) in dry THF (25 mL). The mixture was stirred 15 min at this temperature then 2-fluorobenzaldehyde [CAS 446-52-6] (1.78 mL, 16.90 mmol) was added dropwise. The mixture was stirred at −78° C. for 1 h, and then slowly warmed up to 0° C. over 45 min. The reaction was quenched with NH₄Cl 10% aqueous solution and the aqueous phase was extracted with EtOAc. The organic layer was washed with brine, dried over MgSO₄, filtered and concentrated under reduced pressure. The residue was dissolved in EtOH (50 mL) and SiliaMetS® diamine (1.8 g, 2.816 mmol) was added. The mixture was stirred at rt for 4 h and then filtered. The filtrate was concentrated under reduced pressure. Purification was carried out by flash chromatography over silica gel (15-40 μm, 80 g, heptane/EtOAc from 95/5 to 80/20). The pure fractions were collected and concentrated to dryness to give (2-(allyloxy)phenyl)(2-fluorophenyl)methanol (intermediate 36a, 2 g).

Synthesis of Intermediate 36d:

(Z)-12-(benzyloxy)-18-(2-fluorophenyl)-6,9-dihydro-18H-10,17-methanobenzo[b]pyrido[1,2-f][1]oxa[5,6,9]triazacyclotridecine-11,13-dione (intermediate 36d, 460 mg) was obtained using the procedures described in example 5 starting from intermediates 36b (synthesized as 5a) and 5d.

The two enantiomers were separated via chiral SFC (Stationary phase: Chiralcel® OD-H 5 μm 250×30 mm, Mobile phase: 60% CO₂, 40% EtOH) to give the first eluted enantiomer 36dA (195 mg) and the second eluted enantiomer 36 dB (195 mg).

Synthesis of Compound 36A:

(18*R,Z)-18-(2-fluorophenyl)-12-hydroxy-6,9-dihydro-18H-10,17-methanobenzo[b]pyrido[1,2-f][1]oxa[5,6,9]triazacyclotridecine-11,13-dione (Compound 36A, 62 mg) was obtained using the procedure described for compound 5A.

Compound 36A:

¹H NMR (500 MHz, DMSO-d₆) δ ppm 3.22 (br dd, J=13.9, 8.5 Hz, 1H) 4.23 (br d, J=13.9 Hz, 1H) 4.33 (br s, 1H) 4.70-4.84 (m, 2H) 5.12 (d, J=13.9 Hz, 1H) 5.53 (d, J=7.6 Hz, 1H) 5.88 (br s, 1H) 5.97 (br s, 1H) 6.03-6.14 (m, 1H) 6.99 (br t, J=9.3 Hz, 1H) 7.09 (brt, J=7.4 Hz, 1H) 7.15-7.33 (m, 3H) 7.34-7.39 (m, 1H) 7.44 (q, J=8.0 Hz, 2H) 8.12 (br d, J=7.3 Hz, 1H) 10.47-11.36 (m, 1H)

LC/MS (method LC-C): R$_t$ 2.48 min, MH⁺434

[α]$_D^{20}$: −672.67° (c 0.3, DMF)

Chiral HPLC (method HPLC-A): R$_t$ 5.04 min, chiral purity 100%.

Synthesis of Compound 36B:

(18*S,Z)-18-(2-fluorophenyl)-12-hydroxy-6,9-dihydro-18H-10,17-methanobenzo[b]pyrido[1,2-f][1]oxa[5,6,9]triazacyclotridecine-11,13-dione (Compound 36B, 95 mg) was obtained using the procedure described for compound 5A.

Compound 36B:

¹H NMR (500 MHz, DMSO-d₆) δ ppm 3.22 (br dd, J=13.9, 8.5 Hz, 1H) 4.23 (d, J=13.6 Hz, 1H) 4.33 (br s, 1H) 4.69-4.86 (m, 2H) 5.12 (d, J=13.9 Hz, 1H) 5.53 (d, J=7.6 Hz, 1H) 5.88 (br s, 1H) 5.97 (br s, 1H) 6.08 (dt, J=15.1, 7.3 Hz, 1H) 6.99 (t, J=9.1 Hz, 1H) 7.09 (t, J=7.6 Hz, 1H) 7.20-7.32 (m, 3H) 7.33-7.39 (m, 1H) 7.44 (q, J=8.0 Hz, 2H) 8.12 (br d, J=7.3 Hz, 1H) 10.33-11.43 (m, 1H)

LC/MS (method LC-C): R$_t$ 2.48 min, MH⁺434

[α]$_D^{20}$: +606.82° (c 0.264, DMF)

Chiral HPLC (method HPLC-B): R$_t$ 6.87 min, chiral purity 100%.

Synthesis of Intermediate 36a:

Under N₂ flow at −78° C., n-BuLi (1.6 M in hexane) (9.7 mL, 15.49 mmol) was added dropwise to a solution of 1-(allyloxy)-2-bromobenzene [CAS 60333-75-7] (3.0 g, Example 37: Synthesis of (1*R,13Z)-7-hydroxy-16-oxa-23-thia-2,3,10-triazahexacyclo[15.12.1.1²,¹⁰.0³,⁸.0²¹,³⁰.0²⁴,²⁹]hentriaconta-4,7,13,17,19,21(30),24(29),25,27-nonaene-6,9-dione (Compound 37A), (1*S,13Z)-7-hydroxy-16-oxa-23-thia-2,3,10-triazahexacyclo[15.12.1.1²,¹⁰.0³,⁸.0²¹,³⁰.0²⁴,²⁹]hentriaconta-4,7,13,17,19,21(30),24(29),25,27-nonaene-6,9-dione (Compound 37B), (1*R,13E)-7-hydroxy-16-oxa-23-thia-2,3,10-triazahexacyclo[15.12.1.1²,¹⁰.0³,⁸.0²¹,³⁰.0²⁴,²⁹]hentriaconta-4,7,13,17,19,21(30),24(29),25,27-nonaen-9-one (Compound 37C) and (1*S,13E)-7-hydroxy-16-oxa-23-thia-2,3,10-triazahexacyclo[15.12.1.1²,¹⁰.0³,⁸.0²¹,³⁰.0²⁴,²⁹]hentriaconta-4,7,13,17,19,21(30),24(29),25,27-nonaene-6,9-dione (Compound 37D)

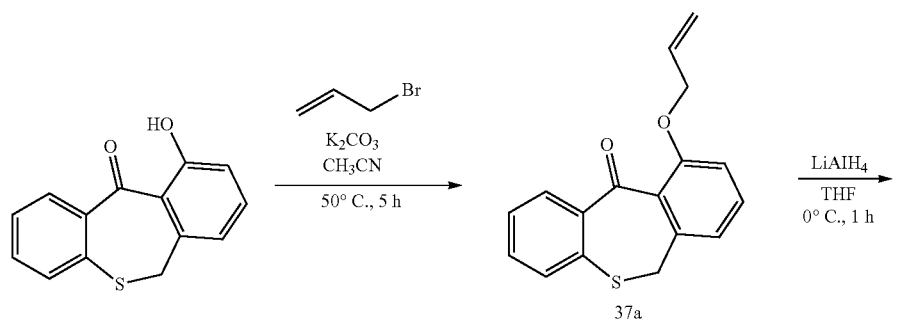

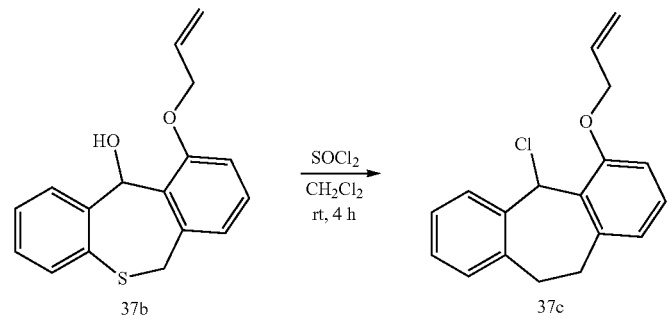

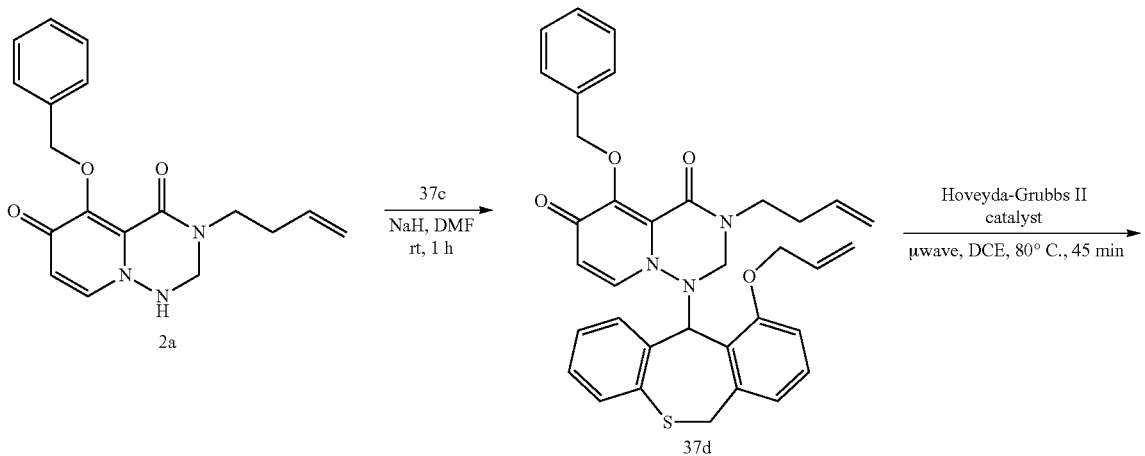

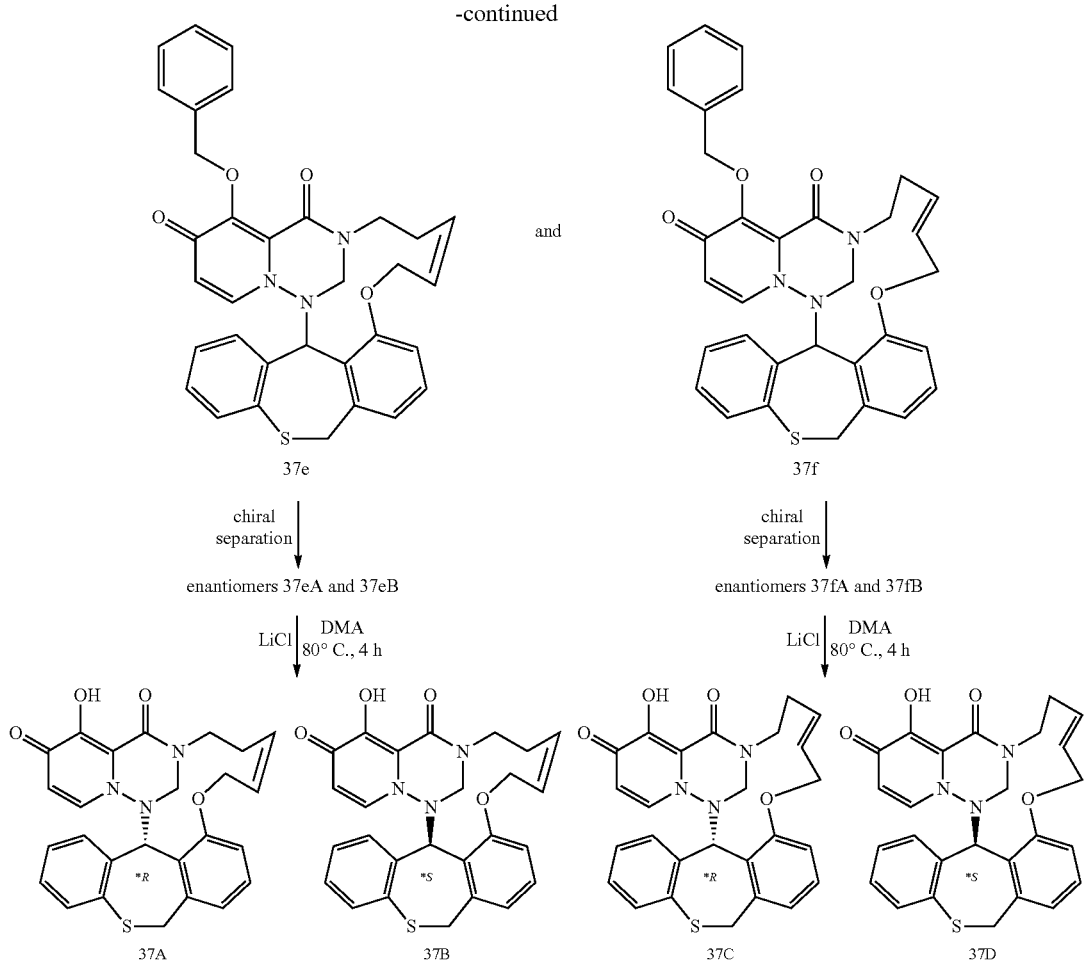

Synthesis of Intermediate 37a:

A mixture of 10-hydroxydibenzo[b,e]thiepin-11(6H)-one [CAS 1370250-54-6] (10.8 g, 44.57 mmol), allyl bromide [CAS 106-95-6] (6.7 mL, 46.80 mmol) and $K_2CO_3$ (18.5 g, 133.72 mmol) in $CH_3CN$ (150 mL) was stirred at 50° C. for 5 h. The mixture was cooled down to rt and concentrated under reduced pressure. The residue was taken up with EtOAc and water. The two layers were separated. The organic phase was washed with water, dried over $MgSO_4$, filtered and concentrated under reduced pressure to give 10-(allyloxy)dibenzo[b,e]thiepin-11(6H)-one (intermediate 37a, 12 g).

Synthesis of Intermediate 37b:

At 0° C. under $N_2$, $LiAlH_4$ (1M in THF) (51 mL, 51.0 mmol) was added dropwise to a solution of 10-(allyloxy)dibenzo[b,e]thiepin-11(6H)-one (intermediate 37a 12.0 g, 42.49 mmol) in THF (200 mL). The mixture was stirred at 0° C. for 1 h, diluted with EtOAc, and then quenched by the dropwise addition of water. The mixture was filtered through Celite®. The two layers were decanted. The organic layer was washed with water and brine, dried over $MgSO_4$, filtered and the solvent was concentrated under reduced pressure to give 10-(allyloxy)-6,11-dihydrodibenzo[b,e]thiepin-11-ol (intermediate 37b, 12.2 g). The compound was used as such in the next step.

Synthesis of Intermediate 37c:

At 0° C., $SOCl_2$ (1.5 mL, 2.28 mmol) was added dropwise to a solution of 10-(allyloxy)-6,11-dihydrodibenzo[b,e]thi- epin-11-ol (intermediate 37b, 4.8 g, 16.88 mmol) in $CH_2Cl_2$ (86 mL). The mixture was stirred at 0° C. for 30 min, then at rt for 4 h. The solution was concentrated to dryness. The residue was taken up with toluene and concentrated again to give 10-(allyloxy)-11-chloro-6,11-dihydrodibenzo[b,e]thi- epine (intermediate 37c, 5.11 g), which was used as such in the next step.

Synthesis of Intermediate 37d:

Under $N_2$ and at 0° C., NaH (60% dispersion in mineral oil) (1.23 g, 30.75 mmol) was added to a solution of 5-(benzyloxy)-3-(but-3-en-1-yl)-2,3-dihydro-1H-pyrido[2,1-f][1,2,4]triazine-4,6-dione (intermediate 2a, 6.67 g, 20.50 mmol) in DMF (100 mL). The mixture was stirred for 30 min at 0° C. 10-(allyloxy)-11-chloro-6,11-dihydrodibenzo [b,e]thiepine (intermediate 37c, 7.45 g, 24.60 mmol) in DMF (50 mL) was added dropwise and the mixture was stirred at rt for 1 h. The mixture was poured in water/ice (500 mL). The precipitate was filtered off and washed with water. The precipitate was taken up with $CH_2Cl_2$, dried over $MgSO_4$, filtered and the solvent was concentrated under reduced pressure. Purification was carried out by flash chromatography over silica gel (20-45 μm, 120 g, $CH_2Cl_2$/ $CH_3OH$ from 99/1 to 96/4. The pure fractions were collected and concentrated to dryness to give a first batch of 1-(10-(allyloxy)-6,11-dihydrodibenzo[b,e]thiepin-11-yl)-5-(ben- zyloxy)-3-(but-3-en-1-yl)-2,3-dihydro-1H-pyrido[2,1-f][1, 2,4]triazine-4,6-dione (intermediate 37d, 8.75 g). Other fractions containing the desired product were combined (2 g) and a second purification was carried out by flash chromatography over silica gel (15-40 µm, 80 g, CH$_2$Cl$_2$/EtOAc from 85/15 to 75/25). The pure fractions were collected and concentrated to dryness to give a second batch of intermediate 37d (1.15 g).

Synthesis of Intermediates 37e and 37f:

The reaction was performed in an Anton-Paar microwave oven on two batches in parallel. A degassed solution of 1-(10-(allyloxy)-6,11-dihydrodibenzo[b,e]thiepin-11-yl)-5-(benzyloxy)-3-(but-3-en-1-yl)-2,3-dihydro-1H-pyrido[2,1-f][1,2,4]triazine-4,6-dione (intermediate 37d, 2×4.1 g, 13.86 mmol) and Hoveyda-Grubbs catalyst 2$^{nd}$ generation [CAS 301224-40-8] (2×0.87 g, 2.77 mmol) in dry DCE (2×500 mL) was stirred at 80° C. for 25 min. The mixture was cooled down to rt and SiliaMetS® DMT (2×9 g, 11.09 mmol) was added and the mixture was stirred at rt for 4 h. The reaction mixture was filtered through Celite®, the Celite® was washed with CH$_2$Cl$_2$ and the filtrate was concentrated under reduced pressure. Purification was carried out by flash chromatography over silica gel (30 µm, 330 g, CH$_2$Cl$_2$/CH$_3$OH from 99.5/0.5 to 96/4)). A second purification was performed by flash chromatography over silica gel (15 µm, 120 g, Toluene/iPrOH 92/8), and then two other purifications were carried out by flash chromatography over silica gel (15 µm, 120 g, Toluene/iPrOH 93/7) to give intermediate 37e (1.23 g, Z isomer) and intermediate 37f (320 mg, E isomer).

The two enantiomers of intermediate 37e were separated via chiral SFC (Stationary phase: Whelk-O1 (S,S) 5 µm 250×21.2 mm, Mobile phase: 45% CO$_2$, 55% EtOH+10% CH$_2$Cl$_2$) to give the first eluted enantiomer 37eA (530 mg) and the second eluted enantiomer 37eB (520 mg).

The two enantiomers of intermediate 37f were separated via chiral SFC (Stationary phase: Whelk-O1 (S,S) 5 µm 250×21.2 mm, Mobile phase: 45% CO$_2$, 55% EtOH+10% CH$_2$Cl$_2$) to give the first eluted enantiomer 37fA (134 mg) and the second eluted enantiomer 37fB (133 mg).

Synthesis of Compound 37A:

LiCl (199 mg, 4.70 mmol) was added to a solution of enantiomer 37eA (530 mg, 0.94 mmol) in DMA (5 mL) and the mixture was stirred at 80° C. for 4 h. The mixture was cooled down to rt and a mixture of ice and an aqueous solution of HCl 0.5 N was added. The aqueous layer was extracted with CH$_2$Cl$_2$. The organic phase was washed 3 times with an aqueous solution of HCl 0.5 N, dried over MgSO$_4$, filtered and concentrated under reduced pressure. Purification was carried out by flash chromatography over silica gel (15-40 µm, 12 g, CH$_2$Cl$_2$/CH$_3$OH from 99/1 to 97/3). The pure fractions were collected and concentrated to dryness to give after freeze-drying from water/CH$_3$CN (8/2) compound 37A (187 mg).

Compound 37A:

$^1$H NMR (500 MHz, DMSO-d$_6$) δ ppm 2.11-2.31 (m, 2H) 2.85 (br d, J=14.2 Hz, 1H) 3.82 (d, J=13.2 Hz, 1H) 4.19-4.33 (m, 2H) 4.52 (d, J=6.9 Hz, 2H) 4.95 (d, J=13.2 Hz, 1H) 5.56 (d, J=7.9 Hz, 1H) 5.71 (d, J=13.2 Hz, 1H) 5.97 (td, J=10.6, 3.9 Hz, 1H) 6.04-6.15 (m, 2H) 6.58 (d, J=7.3 Hz, 1H) 6.78-6.85 (m, 1H) 7.05 (d, J=8.2 Hz, 3H) 7.08-7.14 (m, 1H) 7.24 (d, J=7.6 Hz, 1H) 7.37 (t, J=7.9 Hz, 1H) 11.52-11.97 (m, 1H)

LC/MS (method LC-C): R$_t$ 2.76 min, MH$^+$474

[α]$_D^{20}$: +189.43° (c 0.331, DMF)

Chiral HPLC (method HPLC-B): R$_t$ 6.36 min, chiral purity 100%.

Synthesis of Compound 37B:

LiCl (194 mg, 4.57 mmol) was added to a solution of enantiomer 37eB (515 mg, 0.91 mmol) in DMA (5 mL) and the mixture was stirred at 80° C. for 4 h. The mixture was cooled down to rt and a mixture of ice and an aqueous solution of HCl 0.5 N was added. The aqueous layer was extracted with CH$_2$Cl$_2$. The organic phase was washed 3 times with an aqueous solution of HCl 0.5 N, dried over MgSO$_4$, filtered and concentrated under reduced pressure. Purification was carried out by flash chromatography over silica gel (15-40 µm, 12 g, CH$_2$Cl$_2$/CH$_3$OH from 99/1 to 97/3). The pure fractions were collected and concentrated to dryness to give after freeze-drying from water/CH$_3$CN (8/2) compound 37B (255 mg).

Compound 37B:

$^1$H NMR (500 MHz, DMSO-d$_6$) δ ppm 2.12-2.31 (m, 2H) 2.85 (br d, J=14.2 Hz, 1H) 3.82 (d, J=13.2 Hz, 1H) 4.20-4.35 (m, 2H) 4.52 (d, J=7.3 Hz, 2H) 4.95 (d, J=13.2 Hz, 1H) 5.56 (d, J=7.6 Hz, 1H) 5.71 (d, J=13.2 Hz, 1H) 5.92-6.01 (m, 1H) 6.04-6.13 (m, 2H) 6.58 (d, J=6.9 Hz, 1H) 6.81 (td, J=7.4, 1.3 Hz, 1H) 7.05 (d, J=8.5 Hz, 3H) 7.08-7.14 (m, 1H) 7.24 (d, J=7.6 Hz, 1H) 7.37 (t, J=7.9 Hz, 1H) 11.56-11.91 (m, 1H)

LC/MS (method LC-C): R$_t$ 2.76 min, MH$^+$474

[α]$_D^{20}$: −184.01° (c 0.344, DMF)

Chiral HPLC (method HPLC-B): R$_t$ 9.80 min, chiral purity 100%.

Synthesis of Compound 37C:

Compound 37C (67 mg) was obtained using the procedure described for compound 37A.

Compound 37C:

$^1$H NMR (500 MHz, DMSO-d$_6$) δ ppm 2.15-2.23 (m, 1H) 2.76-2.85 (m, 2H) 3.74-3.82 (m, 1H) 3.85 (d, J=13.2 Hz, 1H) 4.16 (d, J=12.9 Hz, 1H) 4.43-4.51 (m, 1H) 4.74 (dd, J=11.7, 5.4 Hz, 1H) 5.01 (d, J=12.9 Hz, 1H) 5.50-5.60 (m, 2H) 5.67 (d, J=13.2 Hz, 1H) 5.86 (s, 1H) 5.92 (ddd, J=15.1, 9.7, 5.5 Hz, 1H) 6.80-6.90 (m, 2H) 7.01-7.07 (m, 1H) 7.08-7.16 (m, 2H) 7.18-7.27 (m, 2H) 7.37 (t, J=7.9 Hz, 1H) 11.94 (br s, 1H)

LC/MS (method LC-C): R$_t$ 2.73 min, MH$^+$474

[α]$_D^{20}$: +280.56° (c 0.252, DMF)

Chiral HPLC (method HPLC-B): R$_t$ 6.34 min, chiral purity 100%.

Synthesis of Compound 37D:

Compound 37D (67 mg) was obtained using the procedure described for compound 37A.

Compound 37D:

$^1$H NMR (500 MHz, DMSO-d$_6$) δ ppm 2.13-2.25 (m, 1H) 2.75-2.90 (m, 2H) 3.72-3.82 (m, 1H) 3.85 (br d, J=13.2 Hz, 1H) 4.15 (br d, J=12.9 Hz, 1H) 4.47 (br t, J=10.9 Hz, 1H) 4.74 (br dd, J=11.7, 5.4 Hz, 1H) 5.00 (br d, J=12.9 Hz, 1H) 5.49-5.60 (m, 2H) 5.67 (br d, J=13.2 Hz, 1H) 5.86 (s, 1H) 5.92 (ddd, J=15.2, 9.5, 5.2 Hz, 1H) 6.78-6.90 (m, 2H) 7.00-7.07 (m, 1H) 7.07-7.16 (m, 2H) 7.22 (dd, J=16.9, 8.0 Hz, 2H) 7.37 (t, J=7.7 Hz, 1H) 11.91 (br s, 1H)

LC/MS (method LC-C): R$_t$ 2.73 min, MH$^+$474

[α]$_D^{20}$: −280.56° (c 0.324, DMF)

Chiral HPLC (method HPLC-B): R$_t$ 8.17 min, chiral purity 99.25%.

Example 38: Synthesis of (18*R,Z)-12-hydroxy-8-methyl-18-phenyl-6,9-dihydro-18H-10,17-methanobenzo[b]pyrido[1,2-f][1]oxa[5,6,9]triazacyclotridecine-11,13-dione (Compound 38A) and (18*S,Z)-12-hydroxy-8-methyl-18-phenyl-6,9-dihydro-18H-10,17-methanobenzo[b]pyrido[1,2-f][1]oxa[5,6,9]triazacyclotridecine-11,13-dione (Compound 38B)

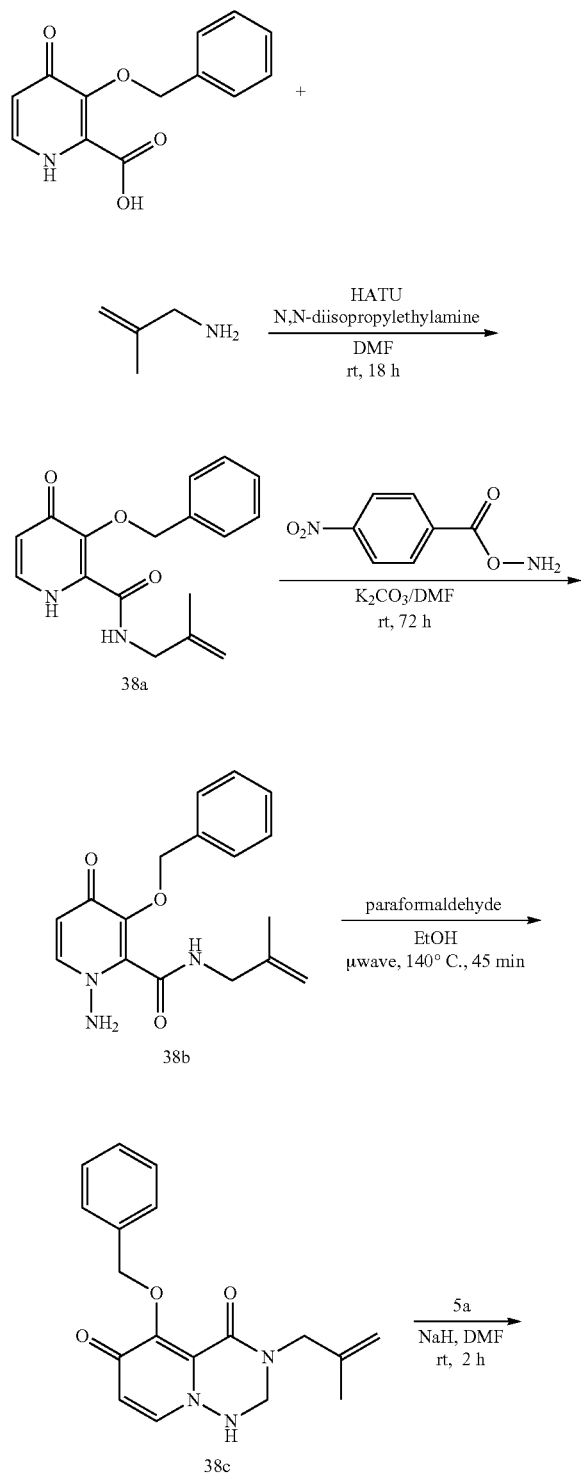

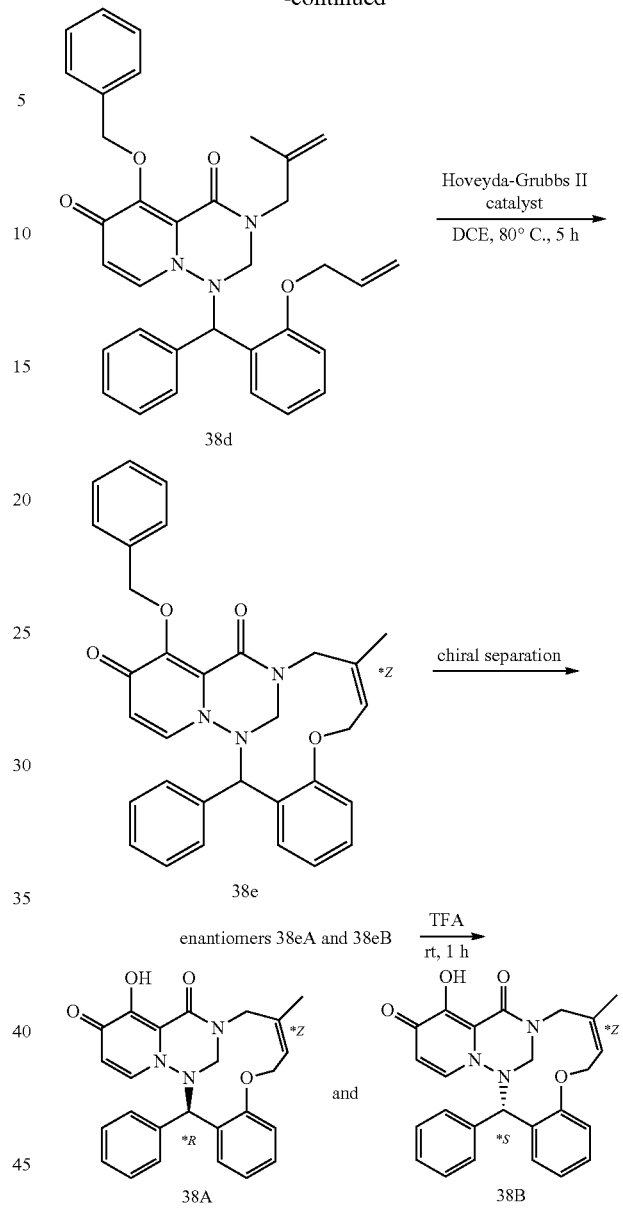

Synthesis of Intermediate 38a:
3-(benzyloxy)-N-(2-methylallyl)-4-oxo-1,4-dihydropyridine-2-carboxamide (intermediate 38a, 4.4 g) was obtained using the procedure described for intermediate 5b starting from 2-methylprop-2-en-1-amine [CAS 2878-14-0].

Synthesis of Intermediate 38b:
1-amino-3-(benzyloxy)-N-(2-methylallyl)-4-oxo-1,4-dihydropyridine-2-carboxamide (intermediate 38b, 2.7 g) was obtained using the procedure described for intermediate 5c.

Synthesis of Intermediate 38c:
5-(benzyloxy)-3-(2-methylallyl)-2,3-dihydro-1H-pyrido[2,1-f][1,2,4]triazine-4,6-dione (intermediate 38c, 1.8 g) was obtained using the procedure described for intermediate 5d.

Synthesis of Intermediate 38d:
1-((2-(allyloxy)phenyl)(phenyl)methyl)-5-(benzyloxy)-3-(2-methylallyl)-2,3-dihydro-1H-pyrido[2,1-f][1,2,4]triazine-4,6-dione (intermediate 38d, 1.2 g) was obtained using the procedure described for intermediate 5e.

Synthesis of Intermediate 38e:

(*Z)-12-(benzyloxy)-8-methyl-18-phenyl-6,9-dihydro-18H-10,17-methanobenzo[b]pyrido[1,2-f][1]oxa[5,6,9]triazacyclotridecine-11,13-dione (intermediate 38e, 420 mg) was obtained using the procedure described for intermediate 5f.

The two enantiomers were separated via chiral SFC (Stationary phase: Chiralpak® AS-H 5 µm 250×20 mm, Mobile phase: 45% $CO_2$, 55% EtOH) to give the first eluted enantiomer 38eA (134 mg) and the second eluted enantiomer 38eB (145 mg).

Synthesis of Compound 38A:

(18*R,*Z)-12-hydroxy-8-methyl-18-phenyl-6,9-dihydro-18H-10,17-methanobenzo[b]pyrido[1,2-f][1]oxa[5,6,9]triazacyclotridecine-11,13-dione (Compound 38A, 80 mg) was obtained using the procedure described for compound 5A.

Compound 38A:

$^1$H NMR (400 MHz, DMSO-$d_6$) δ ppm 1.57 (br s, 3H) 3.09 (d, J=14.2 Hz, 1H) 4.16 (d, J=13.6 Hz, 1H) 4.40-4.59 (m, 1H) 4.68-4.83 (m, 1H) 4.88 (d, J=14.2 Hz, 1H) 5.12 (d, J=13.1 Hz, 1H) 5.34 (s, 1H) 5.49 (d, J=7.6 Hz, 1H) 5.85 (br t, J=7.8 Hz, 1H) 6.94-7.51 (m, 9H) 8.08 (br d, J=7.1 Hz, 1H)

LC/MS (method LC-C): $R_t$ 2.62 min, MH$^+$430

$[α]_D^{20}$: +657.75° (c 0.213, DMF)

Chiral HPLC (method HPLC-B): $R_t$ 5.57 min, chiral purity 100%.

Synthesis of Compound 38B:

(18*S,*Z)-12-hydroxy-8-methyl-18-phenyl-6,9-dihydro-18H-10,17-methanobenzo[b]pyrido[1,2-f][1]oxa[5,6,9]triazacyclotridecine-11,13-dione (Compound 38B, 80 mg) was obtained using the procedure described for compound 5A.

Compound 38B:

$^1$H NMR (400 MHz, DMSO-$d_6$) δ ppm 1.56 (br s, 3H) 3.09 (d, J=14.2 Hz, 1H) 4.16 (d, J=13.6 Hz, 1H) 4.51 (dd, J=11.6, 9.1 Hz, 1H) 4.77 (dd, J=12.1, 7.1 Hz, 1H) 4.89 (br d, J=14.2 Hz, 1H) 5.12 (d, J=13.6 Hz, 1H) 5.34 (s, 1H) 5.48 (d, J=7.6 Hz, 1H) 5.85 (br t, J=7.8 Hz, 1H) 7.11-7.28 (m, 7H) 7.31-7.42 (m, 2H) 8.07 (br d, J=7.6 Hz, 1H)

LC/MS (method LC-C): $R_t$ 2.62 min, MH$^+$430

$[α]_D^{20}$: −687.4° (c 0.246, DMF)

Chiral HPLC (method HPLC-B): $R_t$ 7.04 min, chiral purity 100%.

Example 39: Synthesis of (9R,18S,E)-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 39AA) and (9S,18R,E)-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 39BB) and (9S,18S,E)-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 39AB) and (9R,18R,E)-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 39BA)

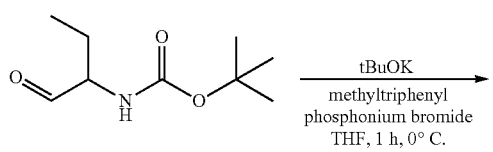

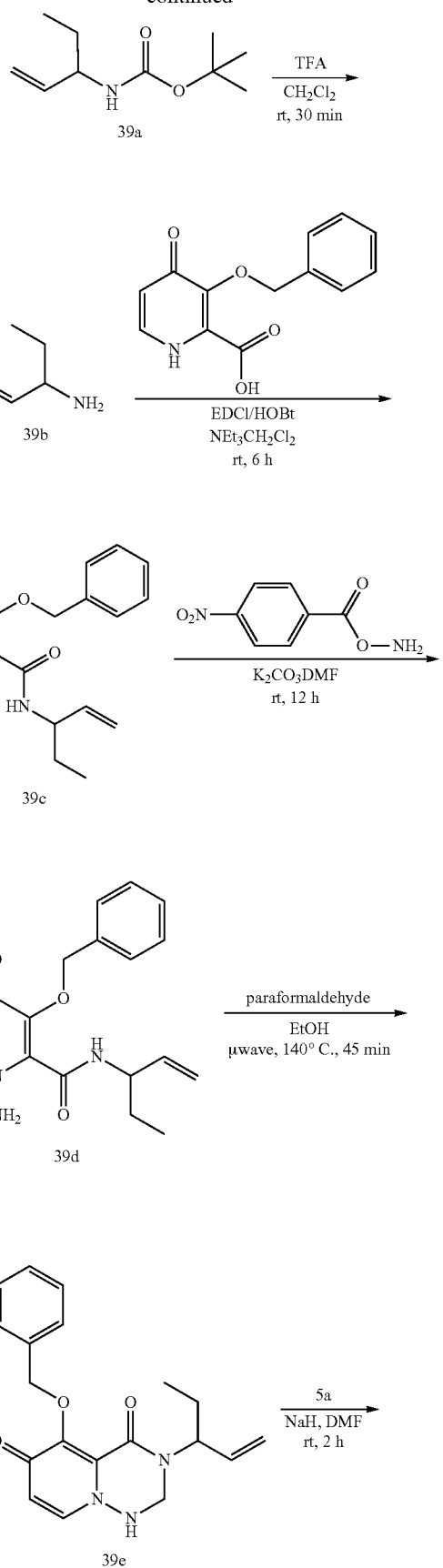

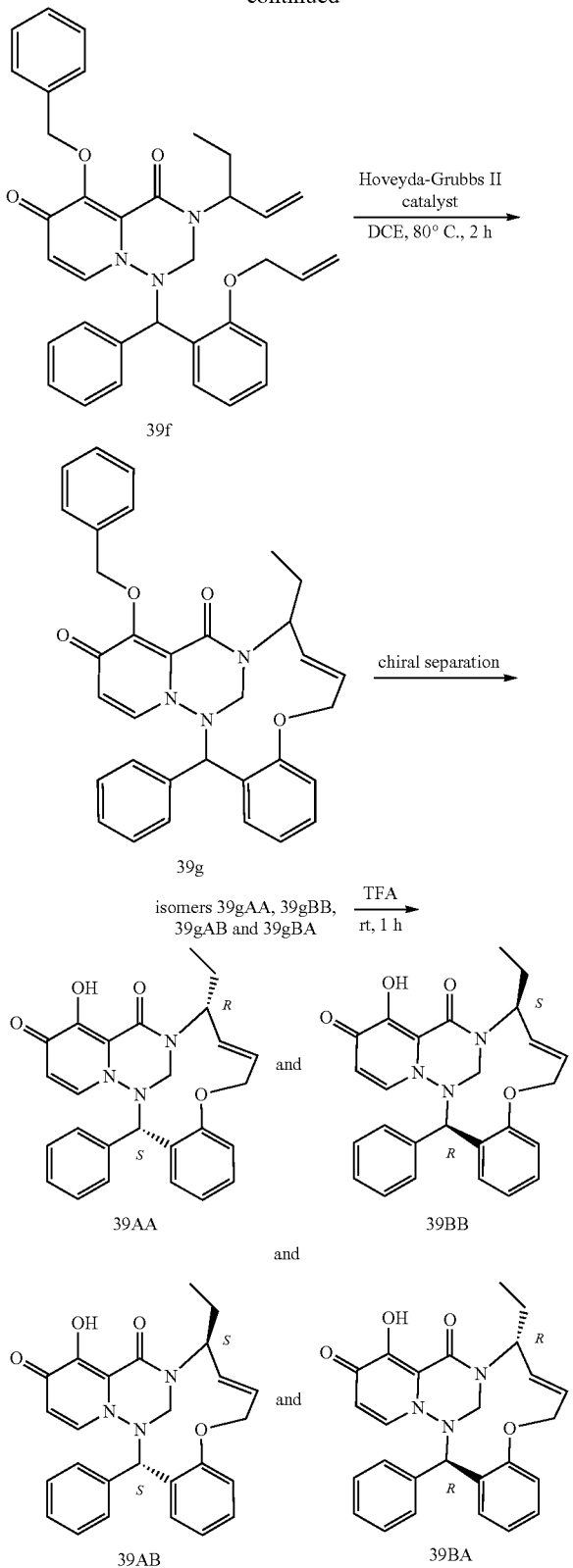

Synthesis of Intermediate 39a:
To a suspension of methyltriphenylphosphonium bromide [CAS 1779-49-3] (36.0 g, 100.94 mmol) in THF (300 mL) at 0° C. was added tBuOK (9.7 g, 86.52 mmol) portionwise. The resulting bright yellow suspension was stirred at 0° C. for 30 min. A solution of tert-butyl (1-oxobutan-2-yl)carbamate [CAS 346690-97-9] (13.5 g, 72.10 mmol) in THF (100 mL) was then added dropwise. The resulting pale-yellow mixture was stirred for 1 h at 0° C., and the reaction was quenched by the addition of acetone (50 mL). The suspension was diluted with hexane, dried over $Na_2SO_4$, filtered and concentrated under reduced pressure. The residue was purified by flash column chromatography over silica gel (petroleum ether/EtOAc from 100:0 to 90:10) to give tert-butyl pent-1-en-3-ylcarbamate (intermediate 39a, 6.5 g).

Synthesis of Intermediate 39b:
A solution of tert-butyl pent-1-en-3-ylcarbamate (intermediate 39a, 6.5 g, 35.09 mmol) in $CH_2Cl_2$/TFA (1:1) (60 mL) was stirred at rt for 30 min. The solution was concentrated under reduced pressure and co-evaporated twice with toluene. The residue was purified by flash chromatography over silica gel ($CH_2Cl_2$/MeOH from 100:0 to 80:20) to give pent-1-en-3-amine (intermediate 39b, 2.8 g).

Synthesis of Intermediate 39c:
3-(benzyloxy)-4-oxo-N-(pent-1-en-3-yl)-1,4-dihydropyridine-2-carboxamide (intermediate 39c, 6.1 g) was obtained using the procedure described for intermediate 1a.

Synthesis of Intermediate 39d:
1-amino-3-(benzyloxy)-4-oxo-N-(pent-1-en-3-yl)-1,4-dihydropyridine-2-carboxamide (intermediate 39d, 3.5 g) was obtained using the procedure described for intermediate 5c.

Synthesis of Intermediate 39e:
5-(benzyloxy)-3-(pent-1-en-3-yl)-2,3-dihydro-1H-pyrido[2,1-f][1,2,4]triazine-4,6-dione (intermediate 39e, 830 mg) was obtained using the procedure described for intermediate 5d.

Synthesis of Intermediate 39f:
1-((2-(allyloxy)phenyl)(phenyl)methyl)-5-(benzyloxy)-3-(pent-1-en-3-yl)-2,3-dihydro-1H-pyrido[2,1-f][1,2,4]triazine-4,6-dione (intermediate 39f, 980 mg) was obtained using the procedure described for intermediate 5e.

Synthesis of Intermediate 39g:
A degassed solution of 1-((2-(allyloxy)phenyl)(phenyl)methyl)-5-(benzyloxy)-3-(pent-1-en-3-yl)-2,3-dihydro-1H-pyrido[2,1-f][1,2,4]triazine-4,6-dione (intermediate 39f, 1.0 g, 1.78 mmol) and Hoveyda-Grubbs catalyst $2^{nd}$ generation [CAS 301224-40-8] (223 mg, 0.36 mmol) in dry DCE (135 mL) was stirred at 80° C. for 2 h. The reaction mixture was concentrated under reduced pressure and the residue was purified by flash chromatography over silica gel (120 g, $CH_2Cl_2$/MeOH from 100:0 to 98:2). The compound was purified again by flash chromatography over silica gel (petroleum ether/EtOAc from 100:0 to 0:100) and by reverse phase chromatography (C18: 40 μm, 45 g, $H_2O$/MeOH from 70:30 to 0:100) to give (E)-12-(benzyloxy)-9-ethyl-18-phenyl-6,9-dihydro-18H-10,17-methanobenzo[b]pyrido[1,2-f][1]oxa[5,6,9]triazacyclotridecine-11,13-dione (intermediate 39g, 580 mg).

The 4 isomers (780 mg batch) were separated. A first separation via achiral SFC (Stationary phase: diethylaminopropyl 5 μm 150×30 mm, Mobile phase: 90% $CO_2$, 10% MeOH) delivered fraction 1 (460 mg) and fraction 2 (196 mg). Isomers of fraction 1 were separated via chiral SFC (Stationary phase: Chiralpak® IC 5 μm 250×30 mm, Mobile phase: 40% $CO_2$, 60% MeOH) to give isomer 39gAA (203 mg) and isomer 39gBB (217 mg). Isomers of fraction 2 were separated via chiral SFC (Stationary phase: Chiralpak® IC 5 μm 250×21.2 mm, Mobile phase: 40% $CO_2$, 60% MeOH) to give isomer 39gAB (48 mg) and fraction 3 (65 mg). Fraction 3 was purified by chiral SFC (Stationary phase:

Chiralpak® IA 5 µm 250×20 mm, Mobile phase: 70% $CO_2$, 30% EtOH) to give isomer 39gBA (35 mg).
Synthesis of Compound 39AA:
(9R,18S,E)-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 39AA, 95 mg) was obtained using the procedure described for compound 5A.
Compound 39AA:
$^1$H NMR (500 MHz, DMSO-$d_6$) δ ppm 0.81 (t, J=7.4 Hz, 3H) 1.36-1.56 (m, 2H) 4.09 (t, J=10.9 Hz, 1H) 4.19 (d, J=13.6 Hz, 1H) 4.87 (dd, J=11.3, 5.7 Hz, 1H) 5.03 (d, J=13.6 Hz, 1H) 5.16 (q, J=7.3 Hz, 1H) 5.22 (s, 1H) 5.35 (br dd, J=15.8, 6.6 Hz, 1H) 5.48 (d, J=7.6 Hz, 1H) 6.30 (ddd, J=15.8, 10.1, 5.7 Hz, 1H) 7.10-7.26 (m, 7H) 7.33-7.39 (m, 1H) 7.40-7.47 (m, 1H) 8.08 (dd, J=7.7, 1.4 Hz, 1H) 11.13 (br s, 1H)
LC/MS (method LC-C): $R_t$ 2.83 min, MH$^+$444
$[\alpha]_D^{20}$: +617.94° (c 0.301, DMF)
Chiral HPLC (method HPLC-B): $R_t$ 5.64 min, chiral purity 100%.
Synthesis of Compound 39BB:
(9S,18R,E)-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 39BB, 77 mg) was obtained using the procedure described for compound 5A.
Compound 39BB:
$^1$H NMR (500 MHz, DMSO-$d_6$) δ ppm 0.81 (t, J=7.3 Hz, 3H) 1.36-1.56 (m, 2H) 4.09 (t, J=10.7 Hz, 1H) 4.19 (d, J=13.2 Hz, 1H) 4.87 (dd, J=11.5, 5.5 Hz, 1H) 5.03 (d, J=13.2 Hz, 1H) 5.16 (q, J=7.3 Hz, 1H) 5.22 (s, 1H) 5.35 (br dd, J=15.6, 6.5 Hz, 1H) 5.48 (d, J=7.9 Hz, 1H) 6.30 (ddd, J=15.8, 10.1, 5.4 Hz, 1H) 7.11-7.24 (m, 7H) 7.33-7.39 (m, 1H) 7.41-7.47 (m, 1H) 8.08 (dd, J=7.7, 1.4 Hz, 1H) 11.11 (br s, 1H)
LC/MS (method LC-C): $R_t$ 2.83 min, MH$^+$444
$[\alpha]_D^{20}$: −592.57° (c 0.296, DMF)
Chiral HPLC (method HPLC-B): $R_t$ 6.66 min, chiral purity 99.06%.
Synthesis of Compound 39AB:
(9S,18S,E)-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 39AB, 26 mg) was obtained using the procedure described for compound 5A.
Compound 39AB:
$^1$H NMR (500 MHz, DMSO-$d_6$) δ ppm 0.85 (t, J=7.4 Hz, 3H) 2.07-2.18 (m, 1H) 2.25-2.35 (m, 1H) 3.39-3.47 (m, 1H) 4.17 (d, J=13.9 Hz, 1H) 4.50-4.64 (m, 2H) 5.17 (d, J=13.9 Hz, 1H) 5.46 (s, 1H) 5.48 (d, J=7.6 Hz, 1H) 5.80 (ddd, J=15.1, 9.5, 5.4 Hz, 1H) 6.38 (br dd, J=15.0, 9.9 Hz, 1H) 7.02-7.23 (m, 5H) 7.26 (d, J=7.9 Hz, 1H) 7.30-7.36 (m, 2H) 7.37-7.43 (m, 1H) 8.13 (dd, J=7.7, 1.4 Hz, 1H)
LC/MS (method LC-C): $R_t$ 2.86 min, MH$^+$444
$[\alpha]_D^{20}$: +675.96° (c 0.208, DMF)
Chiral HPLC (method HPLC-A): $R_t$ 5.00 min, chiral purity 100%.
Synthesis of Compound 39BA:
(9R,18R,E)-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 39BA, 18 mg) was obtained using the procedure described for compound 5A.
Compound 39BA:
$^1$H NMR (500 MHz, DMSO-$d_6$) δ ppm 0.85 (t, J=7.4 Hz, 3H) 2.06-2.19 (m, 1H) 2.26-2.34 (m, 1H) 3.39-3.48 (m, 1H) 4.17 (d, J=14.2 Hz, 1H) 4.48-4.66 (m, 2H) 5.17 (d, J=13.9 Hz, 1H) 5.46 (s, 1H) 5.48 (d, J=7.6 Hz, 1H) 5.80 (ddd, J=15.0, 9.3, 5.4 Hz, 1H) 6.38 (br dd, J=15.0, 9.9 Hz, 1H) 7.02-7.21 (m, 5H) 7.26 (d, J=8.2 Hz, 1H) 7.30-7.36 (m, 2H) 7.37-7.44 (m, 1H) 8.13 (dd, J=7.6, 1.6 Hz, 1H)
LC/MS (method LC-C): $R_t$ 2.86 min, MH$^+$444
$[\alpha]_D^{20}$: −725.74° (c 0.202, DMF)
Chiral HPLC (method HPLC-A): $R_t$ 6.02 min, chiral purity 100%.

Example 40: Synthesis of (17*R)-4-hydroxy-16-(pyridin-2-yl)-7,8,9,10,11,16-hexahydro-6,17-methanobenzo[k]pyrido[1,2-b][1,2,5]triazacyclotridecine-3,5-dione (Compound 40A) and ((17*S)-4-hydroxy-16-(pyridin-2-yl)-7,8,9,10,11,16-hexahydro-6,17-methanobenzo[k]pyrido[1,2-b][1,2,5]triazacyclotridecine-3,5-dione (Compound 40B)

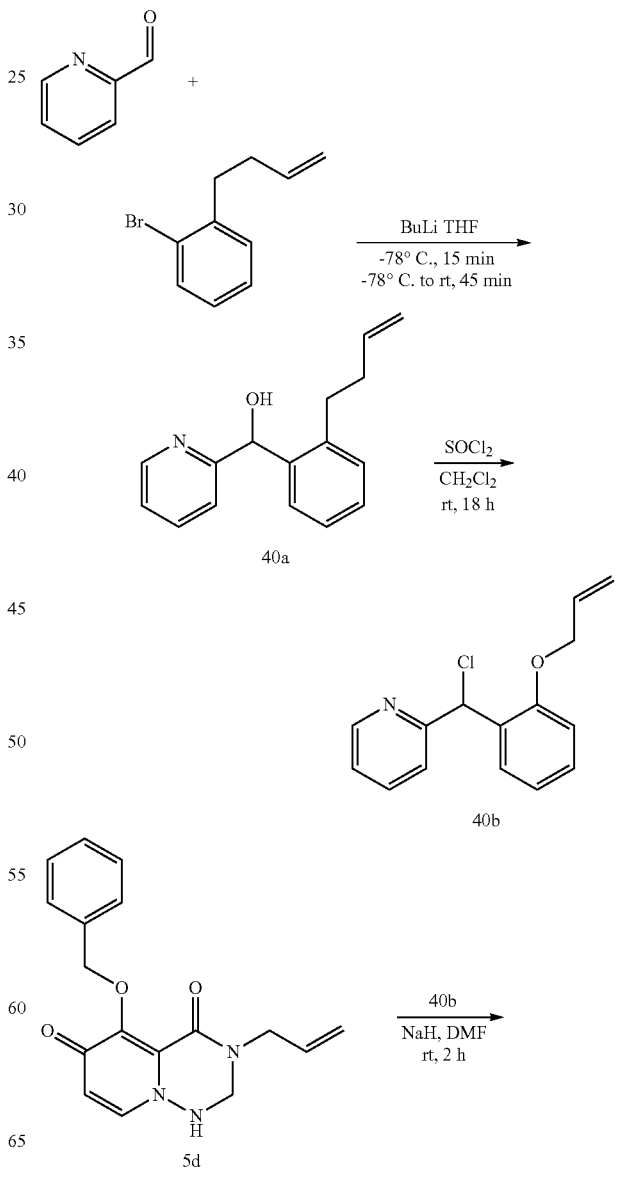

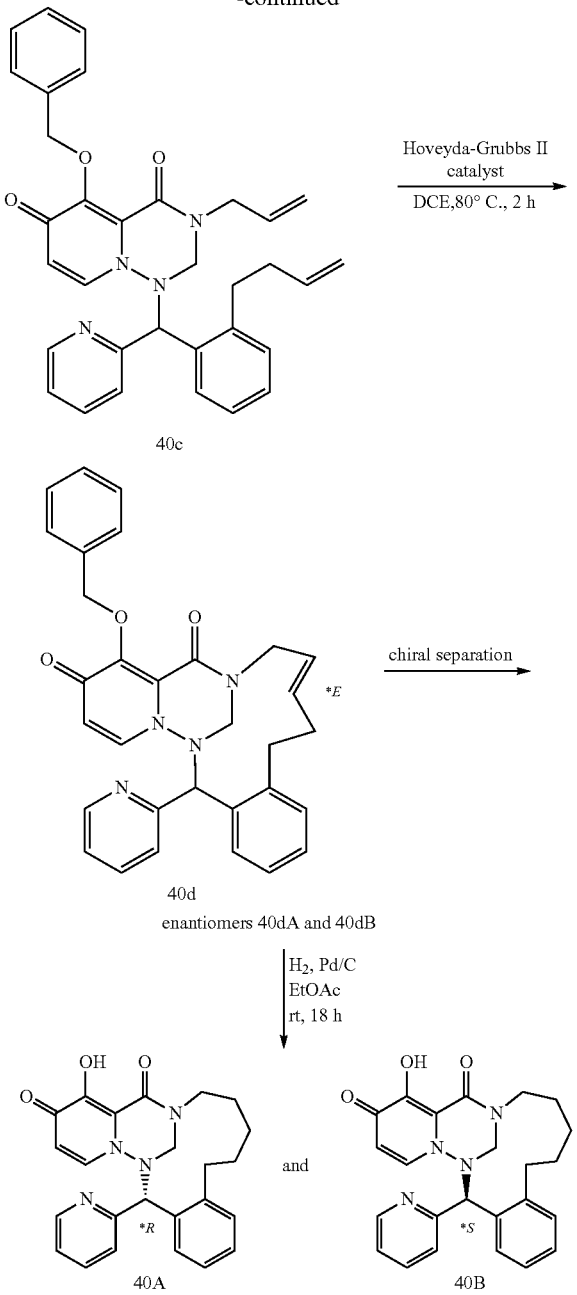

Synthesis of Intermediate 40d:
(*Z)-4-(benzyloxy)-16-(pyridin-2-yl)-7,10,11,16-tetrahydro-6,17-methanobenzo[k]pyrido[1,2-b][1,2,5]triazacyclotridecine-3,5-dione (intermediate 40d, 900 mg) was obtained using the procedure described for intermediate 5f. The compound was used as such for the separation of the two enantiomers via chiral SFC (Stationary phase: Chiralpak® AD-H 5 μm 250×30 mm, Mobile phase: 60% $CO_2$, 40% MeOH) to give the first eluted enantiomer 40dA (353 mg) and the second eluted enantiomer 40 dB (345 mg).

Synthesis of Compound 40A:
(17*R)-4-hydroxy-16-(pyridin-2-yl)-7,8,9,10,11,16-hexahydro-6,17-methanobenzo[k]pyrido[1,2-b][1,2,5]triazacyclotridecine-3,5-dione (Compound 40A, 79 mg) was obtained using the procedure described for compound 8.

Compound 40A:
$^1$H NMR (500 MHz, DMSO-$d_6$) δ ppm 0.62-0.81 (m, 1H) 1.22-1.32 (m, 1H) 1.35-1.59 (m, 2H) 1.60-1.79 (m, 1H) 1.79-2.10 (m, 1H) 2.45-2.55 (m, 1H) 2.52-2.66 (m, 1H) 2.69-2.86 (m, 1H) 3.92 (br t, J=12.9 Hz, 1H) 4.29 (d, J=13.6 Hz, 1H) 5.00 (br d, J=13.6 Hz, 1H) 5.44 (br d, J=7.6 Hz, 1H) 5.75 (s, 1H) 6.97 (br d, J=7.9 Hz, 1H) 7.11-7.22 (m, 2H) 7.25 (t, J=7.1 Hz, 1H) 7.34 (t, J=7.4 Hz, 1H) 7.55 (d, J=7.9 Hz, 1H) 7.59-7.69 (m, 1H) 7.99 (d, J=7.6 Hz, 1H) 8.34 (d, J=4.1 Hz, 1H) 11.29 (br s, 1H)

LC/MS (method LC-C): $R_t$ 2.54 min. MH$^+$417
$[α]_D^{20}$: −445.38° (c 0.119, DMF)
Chiral HPLC (method HPLC-B): $R_t$ 4.30 min, chiral purity 100%.

Synthesis of Compound 40B:
(17*S)-4-hydroxy-16-(pyridin-2-yl)-7,8,9,10,11,16-hexahydro-6,17-methanobenzo[k]pyrido[1,2-b][1,2,5]triazacyclotridecine-3,5-dione (Compound 40B, 76 mg) was obtained using the procedure described for compound 8.

Compound 40B:
$^1$H NMR (500 MHz, DMSO-$d_6$) δ ppm 0.78 (br q, J=12.6 Hz, 1H) 1.28-1.38 (m, 1H) 1.40-1.56 (m, 2H) 1.63-1.84 (m, 1H) 1.94-2.10 (m, 1H) 2.51-2.57 (m, 1H) 2.64 (br d, J=13.6 Hz, 1H) 2.83 (br t, J=11.7 Hz, 1H) 3.99 (br t, J=12.9 Hz, 1H) 4.36 (d, J=13.6 Hz, 1H) 5.08 (br d, J=13.6 Hz, 1H) 5.52 (d, J=7.6 Hz, 1H) 5.82 (s, 1H) 7.05 (d, J=7.6 Hz, 1H) 7.16-7.51 (m, 4H) 7.52-7.76 (m, 2H) 8.06 (d, J=7.6 Hz, 1H) 8.41 (br d, J=4.4 Hz, 1H) 11.31 (br s, 1H)

LC/MS (method LC-C): $R_t$ 2.54 min, MH$^+$417
$[α]_D^{20}$: +410.05° (c 0.189, DMF)
Chiral HPLC (method HPLC-B): $R_t$ 4.97 min, chiral purity 100%.

Example 41: Synthesis of (18*R,Z)-2,3-difluoro-12-hydroxy-18-phenyl-6,9-dihydro-18$_H$-10,17-methanobenzo[b]pyrido[1,2-f][1]oxa[5,6,9]triazacyclotridecine-11,13-dione (Compound 41A) and (18*S,Z)-2,3-difluoro-12-hydroxy-18-phenyl-6,9-dihydro-18$_H$-10,17-methanobenzo[b]pyrido[1,2-f][1]oxa[5,6,9]triazacyclotridecine-11,13-dione (Compound 41B)

Synthesis of Intermediate 40a:
(2-(but-3-en-1-yl)phenyl)(pyridin-2-yl)methanol (intermediate 40a, 880 mg)) was obtained using the procedure described for intermediate 23a starting from (2-(but-3-en-1-yl)phenyl)(pyridin-2-yl)methanol [CAS 1121-60-4] (9.948 mmol) and 1-bromo-2-(but-3-en-1-yl)benzene [CAS 71813-50-8] (6.63 mmol).

Synthesis of Intermediate 40b:
2-((2-(but-3-en-1-yl)phenyl)chloromethyl)pyridine (intermediate 40b, 950 mg) was obtained using the procedure described for intermediate 11c.

Synthesis of Intermediate 40c:
3-allyl-5-(benzyloxy)-1-((2-(but-3-en-1-yl)phenyl)(pyridin-2-yl)methyl)-2,3-dihydro-1H-pyrido[2,1-f][1,2,4]triazine-4,6-dione (intermediate 40c, 920 mg) was obtained using the procedure described for intermediate 11g.

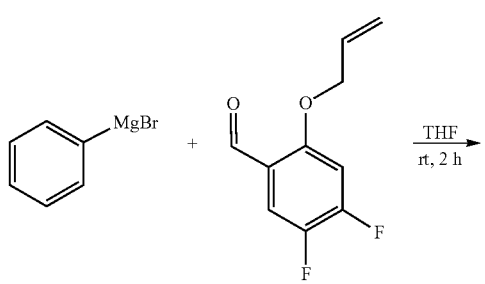

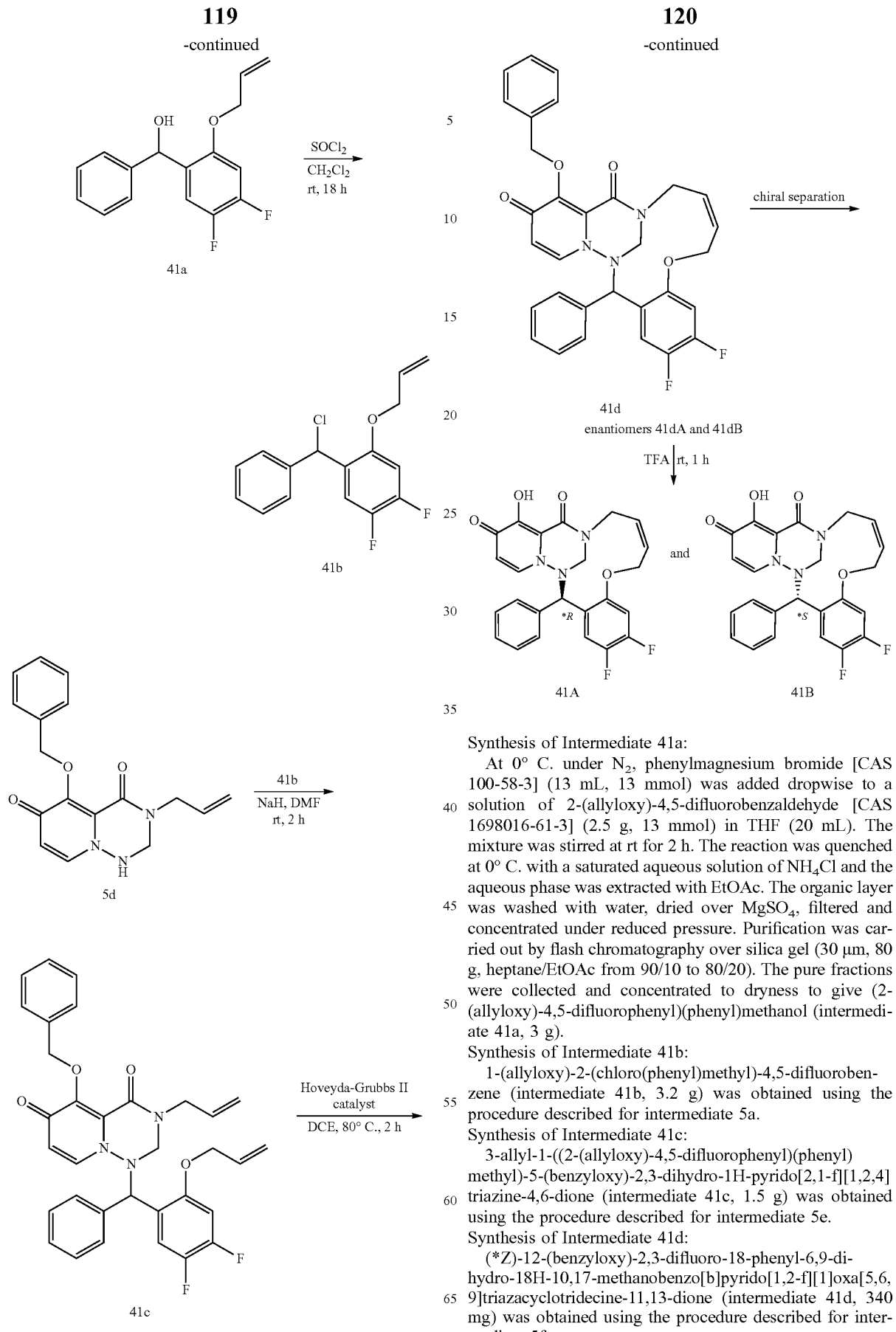

Synthesis of Intermediate 41a:

At 0° C. under N₂, phenylmagnesium bromide [CAS 100-58-3] (13 mL, 13 mmol) was added dropwise to a solution of 2-(allyloxy)-4,5-difluorobenzaldehyde [CAS 1698016-61-3] (2.5 g, 13 mmol) in THF (20 mL). The mixture was stirred at rt for 2 h. The reaction was quenched at 0° C. with a saturated aqueous solution of NH₄Cl and the aqueous phase was extracted with EtOAc. The organic layer was washed with water, dried over MgSO₄, filtered and concentrated under reduced pressure. Purification was carried out by flash chromatography over silica gel (30 μm, 80 g, heptane/EtOAc from 90/10 to 80/20). The pure fractions were collected and concentrated to dryness to give (2-(allyloxy)-4,5-difluorophenyl)(phenyl)methanol (intermediate 41a, 3 g).

Synthesis of Intermediate 41b:

1-(allyloxy)-2-(chloro(phenyl)methyl)-4,5-difluorobenzene (intermediate 41b, 3.2 g) was obtained using the procedure described for intermediate 5a.

Synthesis of Intermediate 41c:

3-allyl-1-((2-(allyloxy)-4,5-difluorophenyl)(phenyl)methyl)-5-(benzyloxy)-2,3-dihydro-1H-pyrido[2,1-f][1,2,4]triazine-4,6-dione (intermediate 41c, 1.5 g) was obtained using the procedure described for intermediate 5e.

Synthesis of Intermediate 41d:

(*Z)-12-(benzyloxy)-2,3-difluoro-18-phenyl-6,9-dihydro-18H-10,17-methanobenzo[b]pyrido[1,2-f][1]oxa[5,6,9]triazacyclotridecine-11,13-dione (intermediate 41d, 340 mg) was obtained using the procedure described for intermediate 5f.

The two enantiomers were separated via chiral SFC (Stationary phase: Chiralcel® OJ-H 5 µm 250×30 mm, Mobile phase: 65% CO$_2$, 35% MeOH) to give the first eluted enantiomer 41dA (141 mg) and the second eluted enantiomer 41 dB (129 mg).

Synthesis of Compound 41A:
18*R,Z)-2,3-difluoro-12-hydroxy-18-phenyl-6,9-dihydro-18H-10,17-methanobenzo[b]pyrido[1,2-f][1]oxa[5,6,9]triazacyclotridecine-11,13-dione (Compound 41A, 75 mg) was obtained using the procedure described for intermediate 5A.

Compound 41A:
$^1$H NMR (500 MHz, DMSO-d$_6$) δ ppm 3.00-3.13 (m, 1H) 4.20-4.35 (m, 2H) 4.57-4.79 (m, 2H) 5.03 (d, J=13.9 Hz, 1H) 5.11-5.24 (m, 1H) 5.42 (d, J=7.6 Hz, 1H) 5.85-6.01 (m, 1H) 6.01-6.17 (m, 1H) 6.99-7.20 (m, 5H) 7.26 (br d, J=7.6 Hz, 1H) 7.35-7.45 (m, 1H) 8.12 (br t, J=10.6 Hz, 1H)

LC/MS (method LC-C): R$_t$ 2.64 min, MH$^+$452
[α]$_D^{20}$: +562.39° (c 0.234, DMF)
Chiral HPLC (method HPLC-A): R$_t$ 4.37 min, chiral purity 100%.

Synthesis of Compound 41B:
18*S,Z)-2,3-difluoro-12-hydroxy-18-phenyl-6,9-dihydro-1$^{8H}$-10,17-methanobenzo[b]pyrido[1,2-f][1]oxa[5,6,9]triazacyclotridecine-11,13-dione (Compound 41B, 66 mg) was obtained using the procedure described for intermediate 5A.

Compound 41B:
$^1$H NMR (500 MHz, DMSO-d$_6$) δ ppm 3.07-3.13 (m, 1H) 4.10-4.43 (m, 2H) 4.46-4.78 (m, 2H) 5.03 (d, J=13.9 Hz, 1H) 5.18 (br s, 1H) 5.42 (d, J=7.57 Hz, 1H) 5.79-6.22 (m, 2H) 7.05-7.19 (m, 5H) 7.26 (br d, J=7.3 Hz, 1H) 7.40 (br dd, J=11.8, 7.4 Hz, 1H) 8.12 (br t, J=10.6 Hz, 1H)

LC/MS (method LC-C): R$_t$ 2.64 min, MH$^+$452
[α]$_D^{20}$: −660.41° (c 0.245, DMF)
Chiral HPLC (method HPLC-A): R$_t$ 5.36 min, chiral purity 100%.

Example 42: Synthesis of (18*R,Z)-3-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 42A) and (18*S,Z)-3-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 42B)

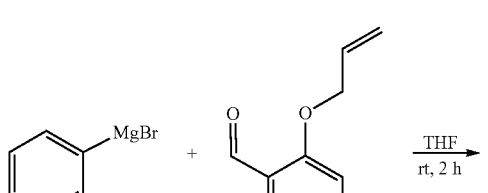

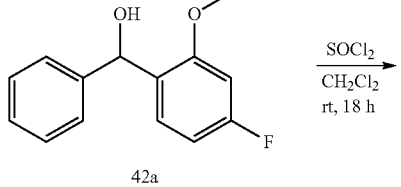

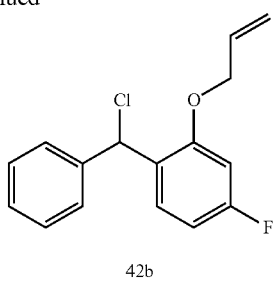

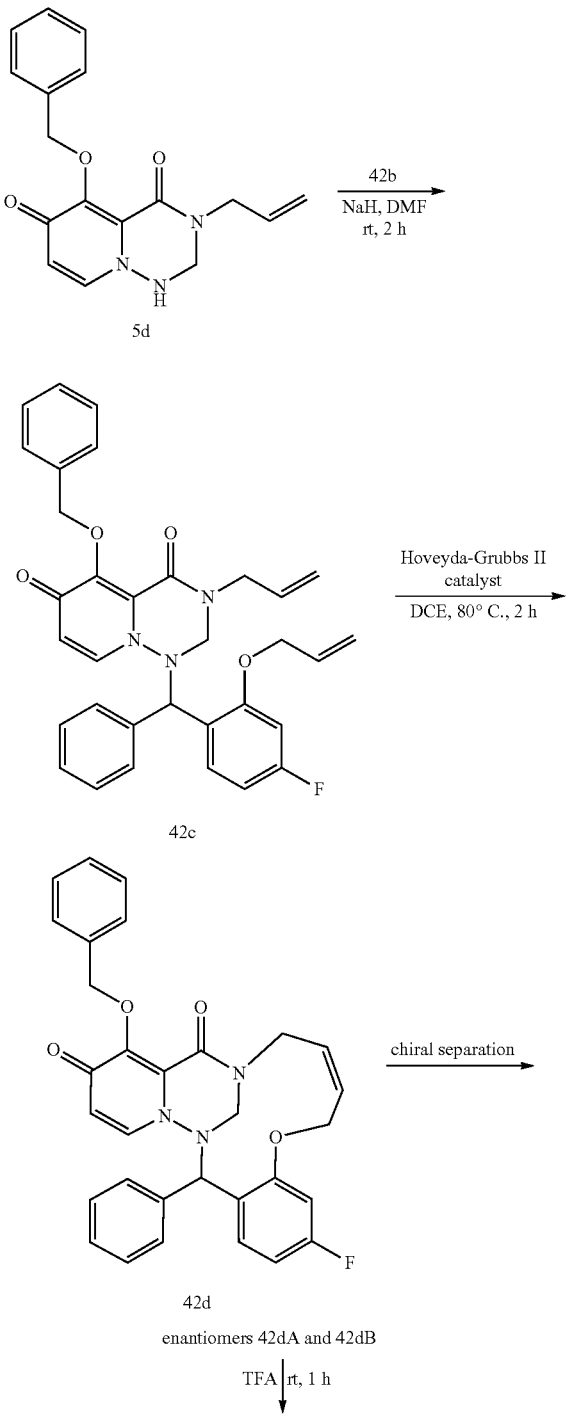

-continued

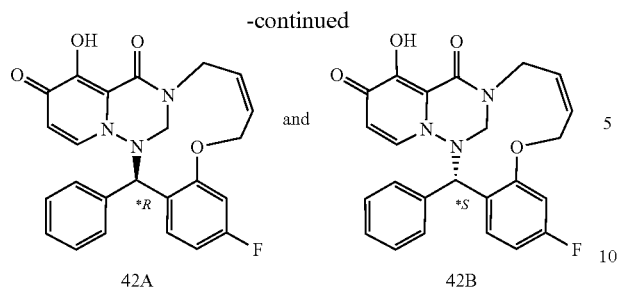

Synthesis of Intermediate 42a:
(2-(allyloxy)-4-fluorophenyl)(phenyl)methanol (intermediate 42a, 2.4 g) was obtained using the procedure described for intermediate 41a starting from 2-(allyloxy)-4-fluorobenzaldehyde [CAS 1207288-81-0] (11.655 mmol) and phenylmagnesiumbromide [CAS 100-58-3].

Synthesis of Intermediate 42b:
2-(allyloxy)-1-(chloro(phenyl)methyl)-4-fluorobenzene (intermediate 42b, 2.6 g) was obtained using the procedure described for intermediate 5a.

Synthesis of Intermediate 42c:
3-allyl-1-((2-(allyloxy)-4-fluorophenyl)(phenyl)methyl)-5-(benzyloxy)-2,3-dihydro-1H-pyrido[2,1-f][1,2,4]triazine-4,6-dione (intermediate 42c, 2.05 g) was obtained using the procedure described for intermediate 5e.

Synthesis of Intermediate 42d:
(Z)-12-(benzyloxy)-3-fluoro-18-phenyl-6,9-dihydro-18H-10,17-methanobenzo[b]pyrido[1,2-f][1]oxa[5,6,9]triazacyclotridecine-11,13-dione (intermediate 42d, 330 mg) was obtained using the procedure described for intermediate 5f.

The two enantiomers were separated via chiral SFC (Stationary phase: Chiralcel® OJ-H 5 μm 250×30 mm, Mobile phase: 55% CO₂, 45% EtOH) to give the first eluted enantiomer (146 mg) and the second eluted enantiomer (128 mg). The two enantiomers were further purified by flash chromatography over silica gel (15-40 μm, 4 g, CH₂Cl₂/CH₃OH 98/2). The pure fractions were collected and concentrated to dryness to give enantiomer 42dA (120 mg) and enantiomer 42 dB (90 mg).

Synthesis of Compound 42A:
(18*R,Z)-3-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 42A, 62 mg) was obtained using the procedure described for compound 5A.

Compound 42A:
¹H NMR (500 MHz, DMSO-d₆) δ ppm 3.19 (br dd, J=13.9, 8.5 Hz, 1H) 4.23 (d, J=13.9 Hz, 1H) 4.39 (br t, J=8.4 Hz, 1H) 1H) 4.69-4.83 (m, 2H) 5.10 (d, J=13.9 Hz, 1H) 5.27 (s, 1H) 5.48 (d, J=7.9 Hz, 1H) 5.98 (br s, 1H) 6.08-6.22 (m, 1H) 7.04-7.29 (m, 8H) 8.14 (t, J=7.7 Hz, 1H)
LC/MS (method LC-C): R$_t$ 2.56 min, MH⁺434
[α]$_D$²⁰: +613.19° (c 0.235, DMF)
Chiral HPLC (method HPLC-B): R$_t$ 4.88 min, chiral purity 100%.

Synthesis of Compound 42B:
(18*S,Z)-3-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 42B, 52 mg) was obtained using the procedure described for compound 5A.

Compound 42B:
¹H NMR (500 MHz, DMSO-d₆) δ ppm 3.19 (br dd, J=13.7, 8.4 Hz, 1H) 4.23 (d, J=13.9 Hz, 1H) 4.39 (br t, J=8.4 Hz, 1H) 4.71-4.82 (m, 2H) 5.10 (d, J=13.9 Hz, 1H) 5.27 (s, 1H) 5.48 (d, J=7.9 Hz, 1H) 5.98 (br s, 1H) 6.08-6.20 (m, 1H) 7.06-7.29 (m, 8H) 8.14 (t, J=7.6 Hz, 1H)
LC/MS (method LC-C): R$_t$ 2.56 min, MH⁺434
[α]$_D$²⁰: −645.56° (c 0.248, DMF)
Chiral HPLC (method HPLC-B): R$_t$ 6.18 min, chiral purity 100%.

Example 43: Synthesis of (17S,E)-4-hydroxy-16-(pyridin-2-yl)-7,10,11,16-tetrahydro-6,17-methanobenzo[k]pyrido[1,2-b][1,2,5]triazacyclotridecine-3,5-dione (Compound 43A) and (17R,E)-4-hydroxy-16-(pyridin-2-yl)-7,10,11,16-tetrahydro-6,17-methanobenzo[k]pyrido[1,2-b][1,2,5]triazacyclotridecine-3,5-dione (Compound 43B)

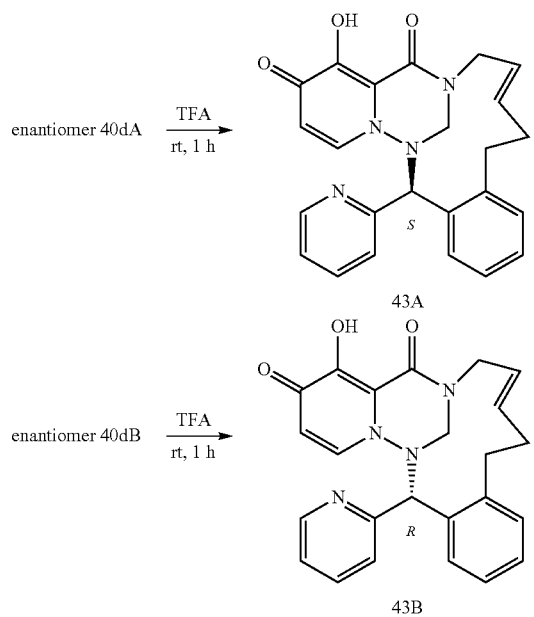

Synthesis of Compound 43A:
(17S,E)-4-hydroxy-16-(pyridin-2-yl)-7,10,11,16-tetrahydro-6,17-methanobenzo[k]pyrido[1,2-b][1,2,5]triazacyclotridecine-3,5-dione (Compound 43A, 150 mg) was obtained using the procedure described for compound 5A.

Compound 43A:
¹H NMR (400 MHz, DMSO-d₆) δ ppm 1.89-2.11 (m, 1H) 2.50-2.60 (m, 3H) 3.05-3.14 (m, 1H) 4.29 (br d, J=13.6 Hz, 1H) 4.51-4.83 (m, 1H) 5.13 (br d, J=13.6 Hz, 1H) 5.29-5.59 (m, 3H) 5.92 (dt, J=15.16, 7.6 Hz, 1H) 7.03-7.25 (m, 3H) 7.33 (brt, J=7.1 Hz, 1H) 7.37-7.51 (m, 2H) 7.52-7.80 (m, 1H) 8.11 (br d, J=8.1 Hz, 1H) 8.34 (br d, J=4.0 Hz, 1H)
LC/MS (method LC-B): R$_t$ 2.42 min, MH⁺415
[α]$_D$²⁰: −724.29° (c 0.140, DMF)
Chiral HPLC (method HPLC-A): R$_t$ 4.67 min, chiral purity 100%.

Synthesis of Compound 43B:
(17R,E)-4-hydroxy-16-(pyridin-2-yl)-7,10,11,16-tetrahydro-6,17-methanobenzo[k]pyrido[1,2-b][1,2,5]triazacyclotridecine-3,5-dione (Compound 43B, 147 mg) was obtained using the procedure described for compound 5A.

Compound 43B:
¹H NMR (400 MHz, DMSO-d₆) δ ppm 1.92-2.16 (m, 1H) 2.53-2.74 (m, 3H) 2.97-3.16 (m, 1H) 4.29 (br d, J=13.6 Hz, 1H) 4.71 (br dd, J=13.6, 4.6 Hz, 1H) 5.13 (br d, J=13.6 Hz, 1H) 5.32-5.60 (m, 3H) 5.92 (dt, J=15.28, 7.8 Hz, 1H) 7.07-7.27 (m, 3H) 7.33 (br t, J=7.1 Hz, 1H) 7.37-7.50 (m, 2H) 7.64 (br t, J=7.3 Hz, 1H) 8.11 (br d, J=7.6 Hz, 1H) 8.34 (br d, J=4.0 Hz, 1H)

LC/MS (method LC-B): $R_t$ 2.42 min, MH$^+$415

$[\alpha]_D^{20}$: +685.48° (c 0.124, DMF)

Chiral HPLC (method HPLC-A): $R_t$ 5.40 min, chiral purity 100%.

Example 44: Synthesis of (18*R,*Z)-12-hydroxy-7-methyl-18-phenyl-6,9-dihydro-18H-10,17-methano-benzo[b]pyrido[1,2-f][1]oxa[5,6,9]triazacyclotride-cine-11,13-dione (Compound 44A) and (18*S,*Z)-12-hydroxy-7-methyl-18-phenyl-6,9-dihydro-18H-10,17-methanobenzo[b]pyrido[1,2-f][1]oxa[5,6,9]triazacyclotridecine-11,13-dione (Compound 44B)

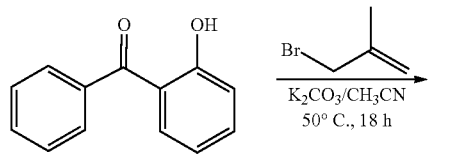

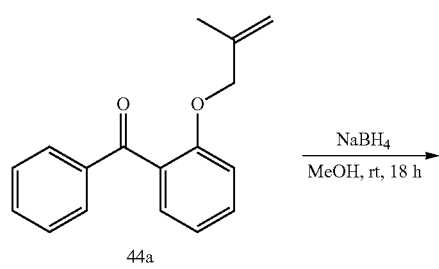

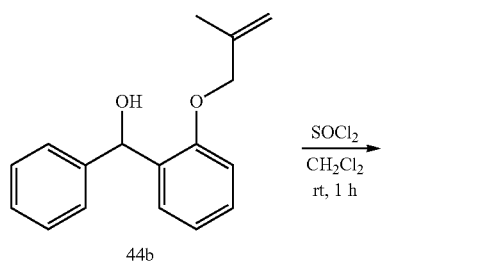

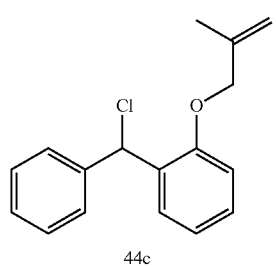

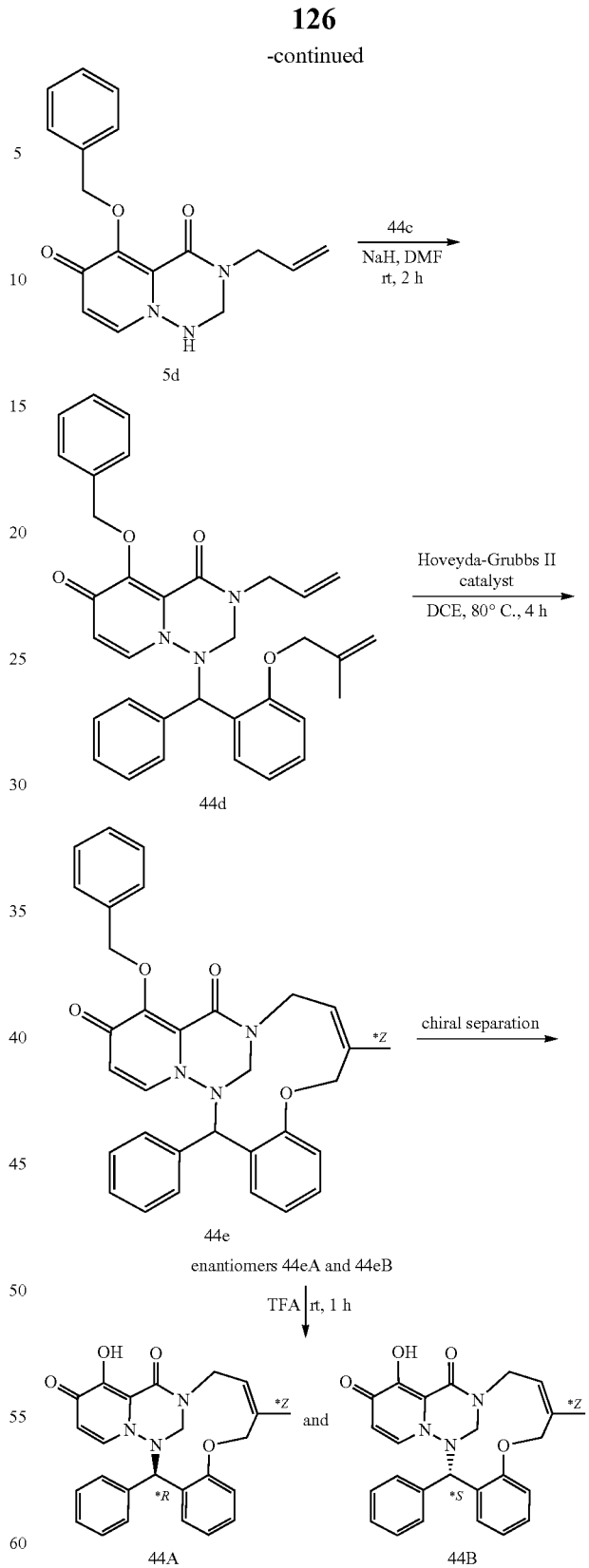

Synthesis of Intermediate 44a:

(2-((2-methylallyl)oxy)phenyl)(phenyl)methanone (intermediate 44a, 5.1 g) was obtained using the procedure described for intermediate 20a starting from (2-hydroxyphenyl)(phenyl)methanone [CAS 117-99-7] (20.179 mmol) and 3-bromo-2-methylprop-1-ene [CAS 1458-98-6] (22.197 mmol).

Synthesis of Intermediate 44b:

(2-((2-methylallyl)oxy)phenyl)(phenyl)methanol (intermediate 44b, 5.2 g) was obtained using the procedure described for intermediate 11b.

Synthesis of Intermediate 44c:

1-(chloro(phenyl)methyl)-2-((2-methylallyl)oxy)benzene (intermediate 44c, 1.3 g) was obtained using the procedure described for intermediate 5a.

Synthesis of Intermediate 44d:

3-allyl-5-(benzyloxy)-1-((2-((2-methylallyl)oxy)phenyl)(phenyl)methyl)-2,3-dihydro-1H-pyrido[2,1-f][1,2,4]triazine-4,6-dione (intermediate 44d, 1.7 g) was obtained using the procedure described for intermediate 5e.

Synthesis of Intermediate 44e:

(*Z)-12-(benzyloxy)-7-methyl-18-phenyl-6,9-dihydro-18H-10,17-methanobenzo[b]pyrido[1,2-f][1]oxa[5,6,9]triazacyclotridecine-11,13-dione (intermediate 44e, 500 mg) was obtained using the procedure described for intermediate 5f.

The two enantiomers were separated via chiral SFC (Stationary phase: Chiralcel® OD-H 5 µm 250×30 mm, Mobile phase: 55% CO$_2$, 45% EtOH) to give the first eluted enantiomer 44eA (194 mg) and the second eluted enantiomer 44eB (202 mg).

Synthesis of Compound 44A:

(18*R,*Z)-12-hydroxy-7-methyl-18-phenyl-6,9-dihydro-18H-10,17-methanobenzo[b]pyrido[1,2-f][1]oxa[5,6,9]triazacyclotridecine-11,13-dione (Compound 44A, 115 mg) was obtained using the procedure described for intermediate 5A.

Compound 44A:

$^1$H NMR (500 MHz, DMSO-d$_6$) δ ppm 1.97 (s, 3H) 3.28 (br dd, J=13.9, 7.6 Hz, 1H) 4.17-4.23 (m, 2H) 4.72 (d, J=11.0 Hz, 1H) 4.95 (br dd, J=14.0, 7.4 Hz, 1H) 5.07 (d, J=13.6 Hz, 1H) 5.14 (s, 1H) 5.42 (br t, 7.3 Hz, 1H) 5.47 (d, J=7.6 Hz, 1H) 7.02-7.26 (m, 7H) 7.29-7.40 (m, 1H) 7.38-7.51 (m, 1H) 8.13 (dd, J=7.6, 1.26 Hz, 1H)

LC/MS (method LC-C): R$_t$ 2.63 min, MH$^+$430

$[α]_D^{20}$: −784.62° (c 0.117, DMF)

Chiral HPLC (method HPLC-B): R$_t$ 6.56 min. chiral purity 100%.

Synthesis of Compound 44B:

(18*S,*Z)-12-hydroxy-7-methyl-18-phenyl-6,9-dihydro-18H-10,17-methanobenzo[b]pyrido[1,2-f][1]oxa[5,6,9]triazacyclotridecine-11,13-dione (Compound 44B, 109 mg) was obtained using the procedure described for intermediate 5A.

Compound 44B:

$^1$H NMR (500 MHz, DMSO-d$_6$) δ ppm 1.97 (s, 3H) 3.24-3.32 (m, 1H) 4.13-4.36 (m, 2H) 4.72 (d, J=11.0 Hz, 1H) 4.95 (dd, J=14.0, 7.4 Hz, 1H) 5.00-5.17 (m, 2H) 5.42 (br t, J=7.3 Hz, 1H) 5.46-5.52 (m, 1H) 6.80-7.28 (m, 7H) 7.32-7.39 (m, 1H) 7.38-7.78 (m, 1H) 8.13 (dd, J=7.57, 1.26 Hz, 1H)

LC/MS (method LC-C): R$_t$ 2.63 min, MH$^+$430

$[α]_D^{20}$: +687.07° (c 0.147, DMF)

Chiral HPLC (method HPLC-B): R$_t$ 5.00 min. chiral purity 100%.

Example 45: Synthesis of (18*R,Z)-18-(3,4-difluorophenyl)-12-hydroxy-6,9-dihydro-18H-10,17-methanobenzo[b]pyrido[1,2-f][1]oxa[5,6,9]triazacyclotridecine-11,13-dione (Compound 45A) and (18*S,Z)-18-(3,4-difluorophenyl)-12-hydroxy-6,9-dihydro-18H-10,17-methanobenzo[b]pyrido[1,2-f][1]oxa[5,6,9]triazacyclotridecine-11,13-dione (Compound 45B)

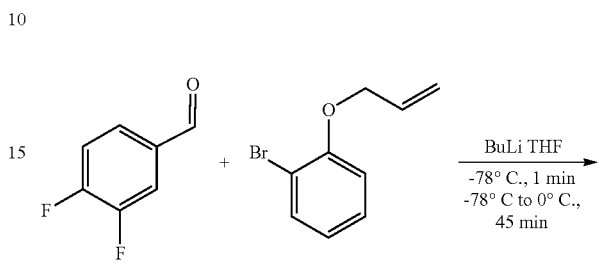

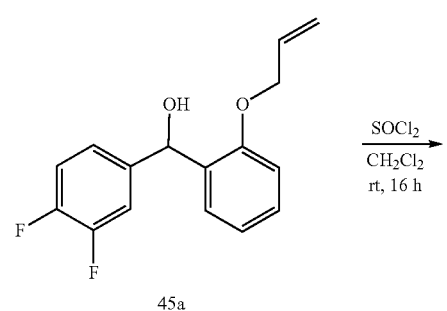

45a

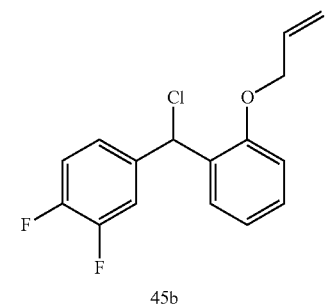

45b

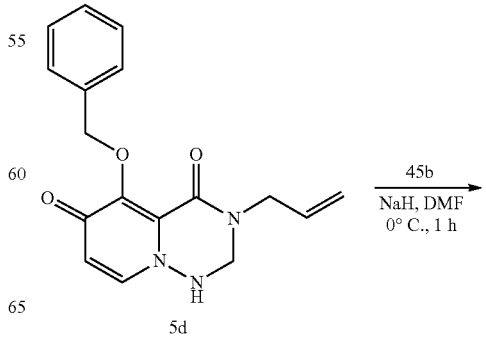

5d

129
-continued

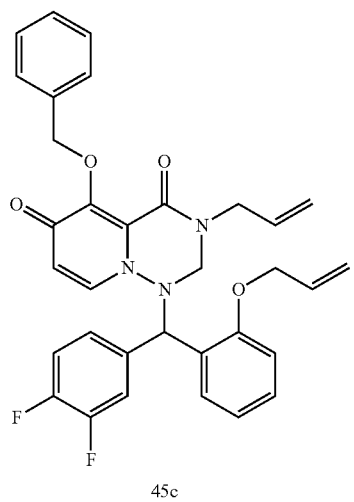

45c

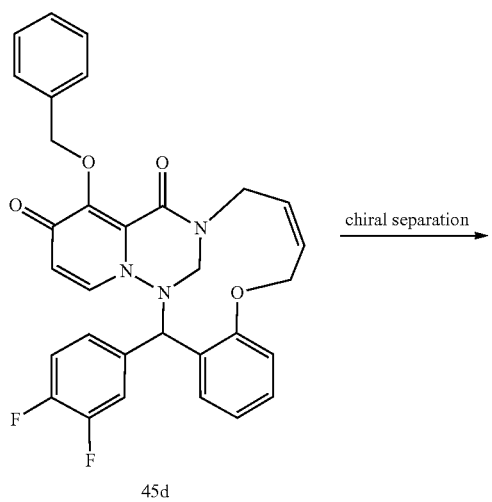

45d enantiomers 45dA and 45bB

TFA | rt, 1 h

130
-continued

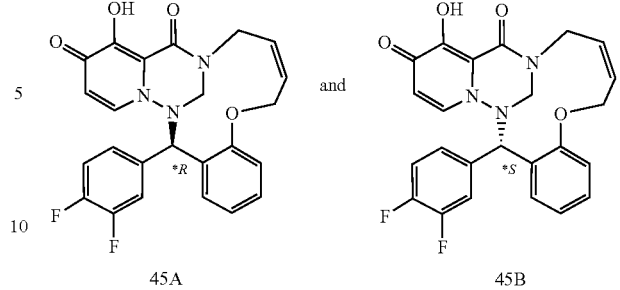

45A and 45B

Synthesis of Intermediate 45d:

(Z)-12-(benzyloxy)-18-(3,4-difluorophenyl)-6,9-dihydro-18H-10,17-methanobenzo[b]pyrido[1,2-f][1]oxa[5,6,9]triazacyclotridecine-11,13-dione (intermediate 45d, 130 mg) was obtained using the procedures described in example 5. The two enantiomers were separated via chiral SFC (Stationary phase: Chiralcel® OD-H 5 μm 250×20 mm, Mobile phase: 85% $CO_2$, 15% MeOH) to give the first eluted enantiomer 45dA (49 mg) and the second eluted enantiomer 45 dB (47 mg).

Synthesis of Compound 45A:

(18*R,Z)-18-(3,4-difluorophenyl)-12-hydroxy-6,9-dihydro-18H-10,17-methanobenzo[b]pyrido[1,2-f][1]oxa[5,6,9]triazacyclotridecine-11,13-dione (Compound 45A, 26 mg) was obtained using the procedure described for compounds 5A.

Compound 45A:

$^1$H NMR (500 MHz, DMSO-$d_6$) δ ppm 3.11 (br dd, J=13.7, 8.4 Hz, 1H) 4.13 (d, J=13.6 Hz, 1H) 4.18-4.39 (m, 1H) 4.63-4.76 (m, 2H) 5.04 (d, J=13.9 Hz, 1H) 5.25 (s, 1H) 5.56 (d, J=7.6 Hz, 1H) 5.59-5.93 (m, 1H) 5.93-6.20 (m, 1H) 6.94 (br s, 1H) 7.15-7.24 (m, 2H) 7.25-7.40 (m, 4H) 8.01 (br d, J=7.6 Hz, 1H)

LC/MS (method LC-C): $R_t$ 2.60 min, MH$^+$452

$[α]_D^{20}$: +609.39° (c 0.181, DMF)

Chiral HPLC (method HPLC-B): $R_t$ 4.55 min, chiral purity 100%.

Synthesis of Compound 45B:

(18*S,Z)-18-(3,4-difluorophenyl)-12-hydroxy-6,9-dihydro-18H-10,17-methanobenzo[b]pyrido[1,2-f][1]oxa[5,6,9]triazacyclotridecine-11,13-dione (Compound 45B, 25 mg) was obtained using the procedure described for compounds 5A.

Compound 45B:

$^1$H NMR (500 MHz, DMSO-$d_6$) δ ppm 3.11 (br dd, J=13.9, 8.2 Hz, 1H) 4.13 (d, J=13.6 Hz, 1H) 4.18-4.29 (m, 1H) 4.64-4.76 (m, 2H) 5.04 (d, J=13.6 Hz, 1H) 5.25 (s, 1H) 5.56 (d, J=7.6 Hz, 1H) 5.72-5.85 (m, 1H) 6.03-6.14 (m, 1H) 6.94 (br s, 1H) 7.15-7.23 (m, 2H) 7.25-7.40 (m, 4H) 8.02 (br d, J=7.9 Hz, 1H)

LC/MS (method LC-C): $R_t$ 2.60 min, MH$^+$452

$[α]_D^{20}$: −634.06° (c 0.138, DMF)

Chiral HPLC (method HPLC-B): $R_t$ 6.17 min, chiral purity 100%.

Example 46: Synthesis of (21R,Z)-16-hydroxy-6, 10,13,21a-tetrahydro-7,8-(epiprop[1]en[1]yl[3] ylidene)-14,21-methanobenzo[6,7]thiepino[4,5-c] pyrido[1,2-f][1]oxa[5,6,9]triazacyclotridecine-15,17-dione (Compound 46A), (21S,Z)-16-hydroxy-6,10, 13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (compound 46B), (17R,E)-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1] oxa[5,6,9]triazacyclotridecine-11,13-dione (compound 46C) and (17S,E)-12-hydroxy-2,6,9, 17a-tetrahydro-3,4-(epiprop[1]en[1]yl[3]ylidene)-10, 17-methanobenzo[6,7]thiepino[4,5-c]pyrido[1,2-f] [1]oxa[5,6,9]triazacyclotridecine-11,13-dione (Compound 46D)

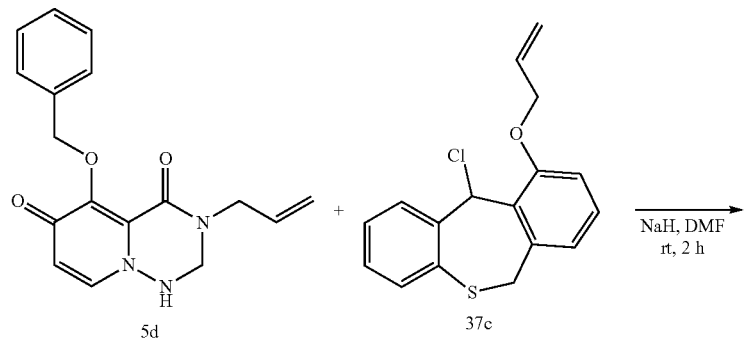

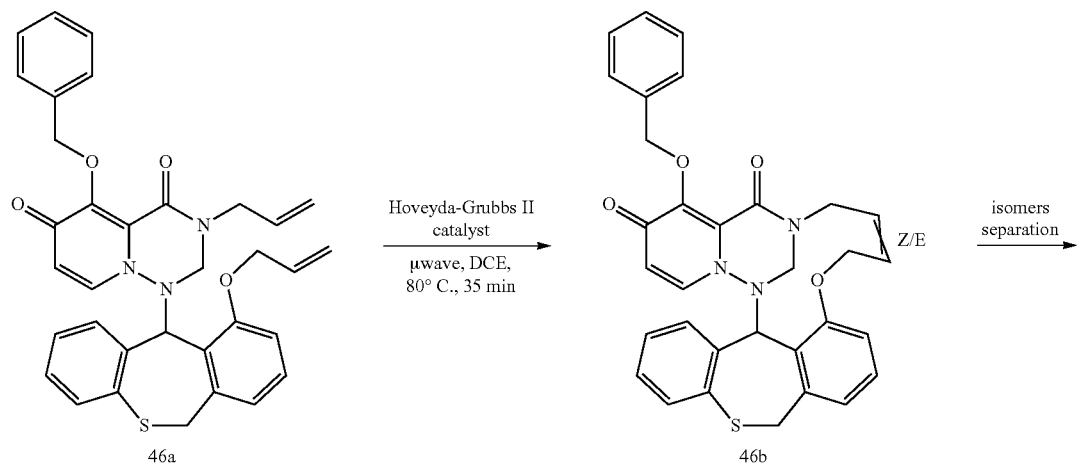

-continued

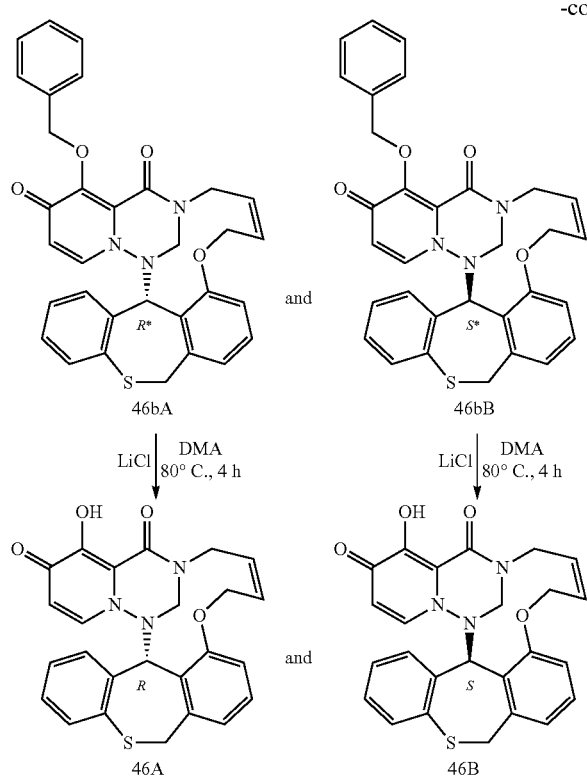

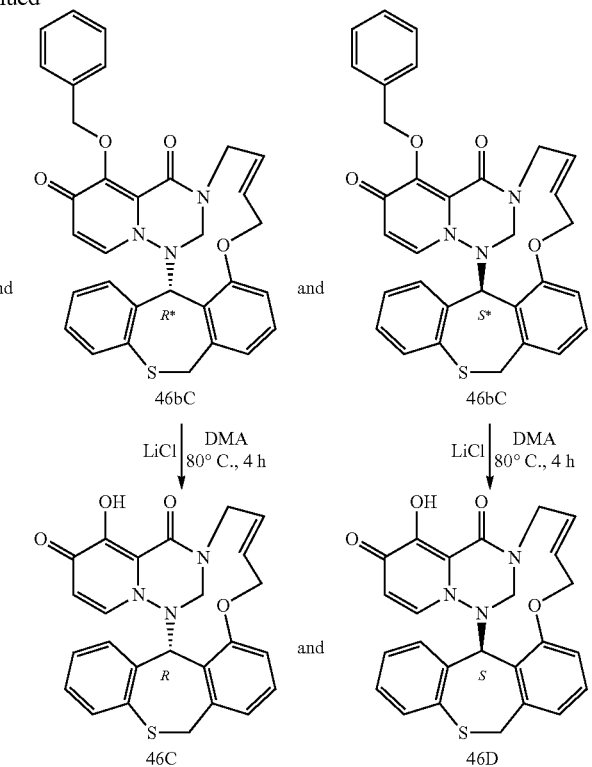

Synthesis of Intermediate 46a:

Under N₂, at 0° C., NaH (60% dispersion in mineral oil) (2.11 g, 52.74 mmol) was added to a solution of 3-allyl-5-(benzyloxy)-2,3-dihydro-1H-pyrido[2,1-f][1,2,4]triazine-4,6-dione (intermediate 5d, 10.95 g, 35.16 mmol) in DMF (250 mL). The mixture was stirred for 30 min at 0° C. 10-(allyloxy)-11-chloro-6,11-dihydrodibenzo[b,e]thiepine (intermediate 37c, 11.18 g, 36.92 mmol) in DMF (50 mL) was added and the mixture was stirred at rt for 2 h. The reaction was quenched by the addition of ice and water. The mixture was extracted with EtOAc and the combined organic layers were washed with water, dried over MgSO₄, filtered and concentrated to dryness. The residue was taken up with a minimum amount of EtOAc. The precipitate was filtered off and dried to give a first batch of 3-allyl-1-(10-(allyloxy)-6,11-dihydrodibenzo[b,e]thiepin-11-yl)-5-(benzyloxy)-2,3-dihydro-1H-pyrido[2,1-f][1,2,4]triazine-4,6-dione (intermediate 46a, 12.5 g). The flitrate was concentrated under reduced pressure. Purification of the residue was carried out by flash chromatography over silica gel (30 μm, 220 g, CH₂Cl₂/CH₃OH from 99/1 to 96/4). The fractions containing the expected compound were collected and concentrated to dryness. This fraction was taken up with EtOAc and the precipitate was filtered off to give a second batch of intermediate 46a (2.65 g).

Synthesis of Intermediate 46b:

The reaction was performed in an Anton-Paar microwave oven in 4 batches of 3.47 g of intermediate 46a.

A degassed solution of 3-allyl-1-(10-(allyloxy)-6,11-dihydrodibenzo[b,e]thiepin-11-yl)-5-(benzyloxy)-2,3-dihydro-1H-pyrido[2,1-f][1,2,4]triazine-4,6-dione (intermediate 46a,13.9 g, 24.06 mmol) and Hoveyda-Grubbs catalyst 2$^{nd}$ generation [CAS 301224-40-8] (3.0 g, 4.81 mmol) in dry DCE (1.5 L) was stirred at 80° C. for 35 min. SiliaMetS® DMT (31.5 g, 19.25 mmol) was added and the mixture was stirred at rt for 18 h. The reaction mixture was filtered through Celite®. The Celite® was washed with CH₂Cl₂ and the filtrate was concentrated under reduced pressure. Purification was carried out by flash chromatography over silica gel (30 μm, 330 g, CH₂Cl₂/CH₃OH from 99.5/0.5 to 97/3). A second purification was carried out by flash chromatography over silica gel (15 μm, 120 g, Toluene/iPrOH 93/7). The pure fractions were collected and concentrated under reduced pressure to afford 16-(benzyloxy)-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (mixture of Z and E isomers, intermediate 46b, 1.98 g).

The isomers were separated via chiral SFC (Stationary phase: Chiralcel® OJ-H 5 μm 250×30 mm, Mobile phase: 65% CO₂, 35% MeOH) to give the first eluted isomer 46bA (460 mg), a mixture of 46bB and 46bC (790 mg) and finally the last eluted isomer 46bB (340 mg). The isomers 46bB (382 mg) and 46bC (306 mg) were separated via chiral SFC (Stationary phase: Chiralpak® AS-H 5 μm 250×20 mm, Mobile phase: 40% CO₂, 60% MeOH).

Synthesis of Compound 46A:

(21R,Z)-16-hydroxy-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (Compound 46A, 258 mg) was obtained using the procedure described for Compound 37A.

Compound 46A:

$^1$H NMR (500 MHz, DMSO-d₆) δ ppm 3.75-3.86 (m, 2H) 4.15-4.26 (m, 1H) 4.32 (d, J=13.2 Hz, 1H) 4.51-4.58 (m, 1H) 4.85 (dd, J=10.6, 6.8 Hz, 1H) 5.02 (d, J=13.2 Hz, 1H) 5.61 (d, J=7.9 Hz, 1H) 5.72 (d, J=13.9 Hz, 1H) 6.08 (s, 1H) 6.29 (dt, J=10.5, 7.2 Hz, 1H) 6.37-6.43 (m, 1H) 6.57 (d, J=6.9 Hz, 1H) 6.81 (t, J=7.4 Hz, 1H) 7.01-7.14 (m, 3H) 7.20 (d, J=8.1 Hz, 1H) 7.26 (d, J=7.7 Hz, 1H) 7.40 (t, J=7.9 Hz, 1H)

LC/MS (method LC-C): R$_t$ 2.66 min, MH$^+$460

[α]$_D^{20}$: +252.22° (c 0.293, DMF)

Synthesis of Compound 46B:

(21S,Z)-16-hydroxy-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (Compound 46B, 235 mg) was obtained using the procedure described for Compound 37A.

Compound 46B:

$^1$H NMR (500 MHz, DMSO-d$_6$) δ ppm 3.75-3.86 (m, 2H) 4.18 (dd, J=13.6, 7.6 Hz, 1H) 4.32 (d, J=13.2 Hz, 1H) 4.55 (dd, J=10.7, 7.9 Hz, 1H) 4.85 (dd, J=10.4, 6.9 Hz, 1H) 5.02 (d, J=13.2 Hz, 1H) 5.61 (d, J=7.6 Hz, 1H) 5.72 (d, J=13.9 Hz, 1H) 6.08 (s, 1H) 6.29 (dt, J=10.6, 7.3 Hz, 1H) 6.37-6.43 (m, 1H) 6.57 (d, J=6.9 Hz, 1H) 6.81 (t, J=7.5 Hz, 1H) 7.06-7.14 (m, 3H) 7.20 (d, J=8.1 Hz, 1H) 7.26 (d, J=7.7 Hz, 1H) 7.40 (t, J=7.9 Hz, 1H)

LC/MS (method LC-C): R$_t$ 2.66 min, MH$^+$460

[α]$_D^{20}$: −271.76° (c 0.262, DMF)

Synthesis of Compound 46C:

(17R,E)-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 46C, 155 mg) was obtained using the procedure described for Compound 37A.

Compound 46C:

$^1$H NMR (500 MHz, DMSO-d$_6$) δ ppm 3.17 (dd, J=14.0, 8.4 Hz, 1H) 3.87 (d, J=13.6 Hz, 1H) 4.25 (d, J=13.9 Hz, 1H) 4.41-4.51 (m, 1H) 4.70-4.83 (m, 2H) 5.15 (d, J=13.6 Hz, 1H) 5.41 (s, 1H) 5.61 (d, J=7.9 Hz, 1H) 5.82 (d, J=13.2 Hz, 1H) 5.90-6.01 (m, 1H) 6.17-6.27 (m, 1H) 6.77-6.82 (m, 1H) 6.82-6.88 (m, 1H) 7.00-7.06 (m, 1H) 7.07-7.13 (m, 1H) 7.19 (d, J=7.6 Hz, 1H) 7.23 (d, J=8.2 Hz, 1H) 7.34 (d, J=7.9 Hz, 1H) 7.37-7.44 (m, 1H) 11.26 (br s, 1H)

LC/MS (method LC-C): R$_t$ 2.56 min, MH$^+$460

[α]$_D^{20}$: +513.07° (c 0.306, DMF)

Chiral HPLC (method HPLC-B): R$_t$ 7.30 min, chiral purity 100%

Synthesis of Compound 46D:

(17S,E)-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (compound 46D, 160 mg) was obtained using the procedure described for compound 37A.

Compound 46D:

$^1$H NMR (500 MHz, DMSO-d$_6$) δ ppm 3.17 (dd, J=14.0, 8.4 Hz, 1H) 3.87 (d, J=13.6 Hz, 1H) 4.25 (d, J=13.9 Hz, 1H) 4.43-4.50 (m, 1H) 4.73-4.81 (m, 2H) 5.15 (d, J=13.9 Hz, 1H) 5.41 (s, 1H) 5.61 (d, J=7.6 Hz, 1H) 5.82 (d, J=13.6 Hz, 1H) 5.91-6.00 (m, 1H) 6.22 (dt, J=15.5, 7.7 Hz, 1H) 6.79-6.88 (m, 2H) 7.04 (d, J=7.8 Hz, 1H) 7.10 (t, J=7.5 Hz, 1H) 7.19 (d, J=7.4 Hz, 1H) 7.23 (d, J=8.1 Hz, 1H) 7.34 (d, J=7.6 Hz, 1H) 7.40 (t, J=7.9 Hz, 1H) 11.23 (br s, 1H)

LC/MS (method LC-C): R$_t$ 2.56 min, MH$^+$460

[α]$_D^{20}$: −512.94° (c 0.255, DMF)

Chiral HPLC (method HPLC-B): R$_t$ 8.94 min, chiral purity 100%

Example 47: Synthesis of (18*R,Z)-18-(4-fluorophenyl)-12-hydroxy-6,9-dihydro-18H-10,17-methanobenzo[b]pyrido[1,2-f][1]oxa[5,6,9]triazacyclotridecine-11,13-dione (Compound 47A) and (18*S,Z)-18-(4-fluorophenyl)-12-hydroxy-6,9-dihydro-18H-10,17-methanobenzo[b]pyrido[1,2-f][1]oxa[5,6,9]triazacyclotridecine-11,13-dione (Compound 47B)

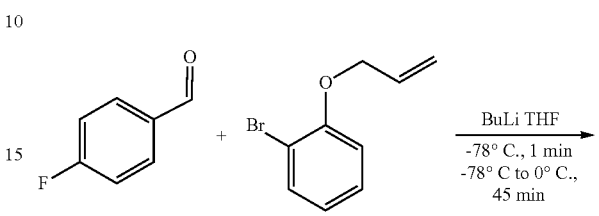

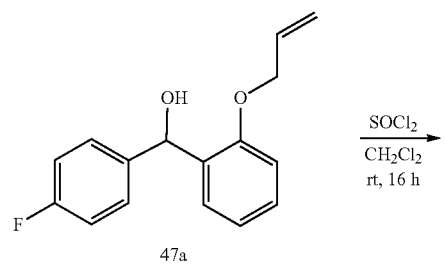

47a

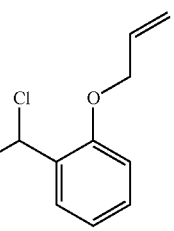

47b

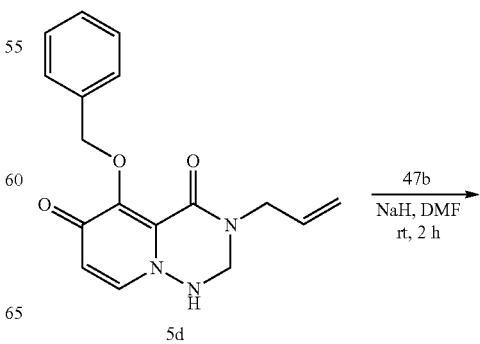

5d

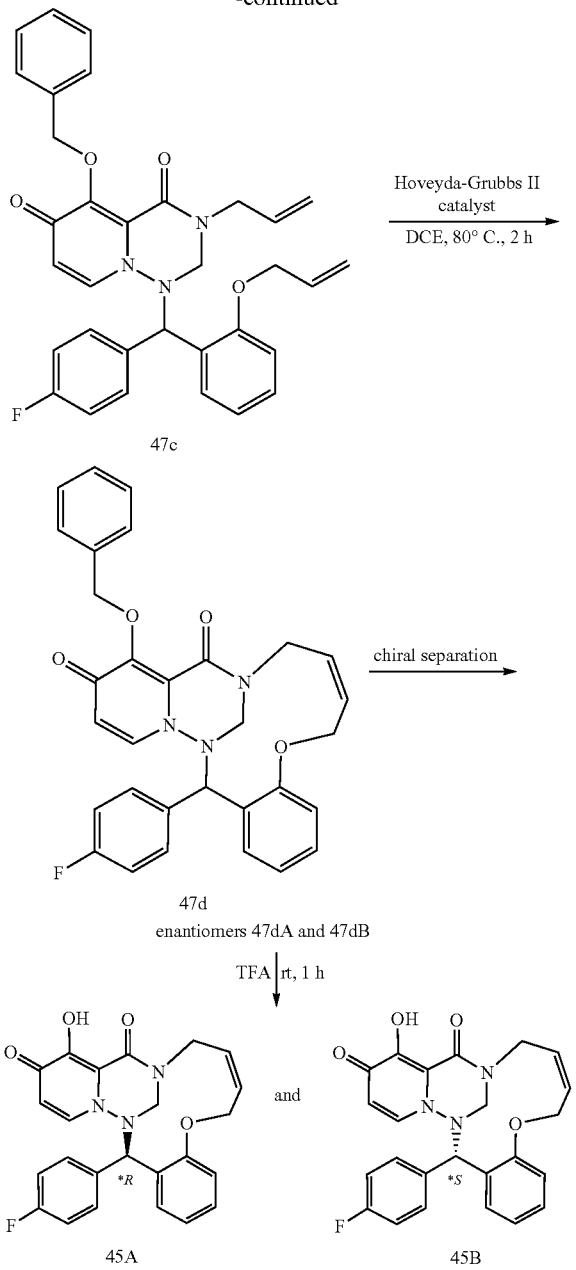

47c 47d
enantiomers 47dA and 47dB

TFA | rt, 1 h 45A and 45B

Synthesis of Intermediate 47d:

(Z)-12-(benzyloxy)-18-(4-fluorophenyl)-6,9-dihydro-18H-10,17-methanobenzo[b]pyrido[1,2-f][1]oxa[5,6,9]triazacyclotridecine-11,13-dione (intermediate 47d, 130 mg) was obtained using the procedures described in example 5. The two enantiomers were separated via chiral SFC (Stationary phase: Chiralcel® OJ-H 5 μm 250×30 mm, Mobile phase: 75% $CO_2$, 25% MeOH) to give the first eluted enantiomer 47dA (242 mg) and the second eluted enantiomer 47 dB (243 mg).

Synthesis of Compound 47A:

(18*R,Z)-18-(4-fluorophenyl)-12-hydroxy-6,9-dihydro-18H-10,17-methanobenzo[b]pyrido[1,2-f][1]oxa[5,6,9]triazacyclotridecine-11,13-dione (Compound 47A, 100 mg) was obtained using the procedure described for Compound 5A.

Compound 47A:

$^1$H NMR (500 MHz, DMSO-$d_6$) δ ppm 3.19 (dd, J=13.9, 8.5 Hz, 1H) 4.20-4.32 (m, 2H) 4.72-4.81 (m, 2H) 5.11 (d, J=13.6 Hz, 1H) 5.32 (s, 1H) 5.56 (d, J=7.6 Hz, 1H) 5.82-5.94 (m, 1H) 6.09-6.19 (m, 1H) 7.02 (br t, J=8.7 Hz, 2H) 7.20-7.33 (m, 4H) 7.30-7.37 (m, 1H) 7.42 (t, J=7.7 Hz, 1H) 8.08 (br d, J=7.6 Hz, 1H) 10.94 (br s, 1H)

LC/MS (method LC-C): $R_t$ 2.52 min, MH$^+$434

$[α]_D^{20}$: +685.14° (c 0.148, DMF)

Chiral HPLC (method HPLC-B): $R_t$ 4.89 min, chiral purity 100%.

Synthesis of Compound 47B:

(18*S,Z)-18-(4-fluorophenyl)-12-hydroxy-6,9-dihydro-18H-10,17-methanobenzo[b]pyrido[1,2-f][1]oxa[5,6,9]triazacyclotridecine-11,13-dione (Compound 47B, 113 mg) was obtained using the procedure described for Compound 5A.

Compound 47B:

$^1$H NMR (500 MHz, DMSO-$d_6$) δ ppm 3.19 (br dd, J=13.9, 8.5 Hz, 1H) 4.22 (d, J=13.6 Hz, 1H) 4.25-4.37 (m, 1H) 4.70-4.82 (m, 2H) 5.11 (d, J=13.9 Hz, 1H) 5.32 (s, 1H) 5.56 (d, J=7.6 Hz, 1H) 5.85-5.95 (m, 1H) 6.09-6.19 (m, 1H) 7.02 (br t, J=8.5 Hz, 2H) 7.12-7.27 (m, 4H) 7.30-7.37 (m, 1H) 7.38-7.47 (m, 1H) 8.08 (br d, J=7.3 Hz, 1H) 10.90 (br s, 1H)

LC/MS (method LC-C): $R_t$ 2.52 min, MH$^+$434

$[α]_D^{20}$: −706.56° (c 0.122, DMF)

Chiral HPLC (method HPLC-B): $R_t$ 5.85 min, chiral purity 100%.

Example 48: Synthesis of Compounds 48, 48A and 48B

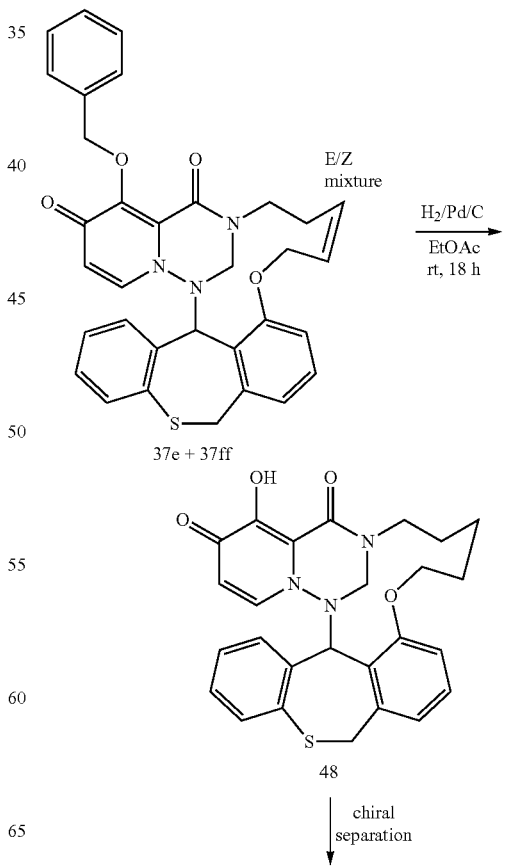

37e + 37ff

H$_2$/Pd/C
EtOAc
rt, 18 h

48 chiral separation

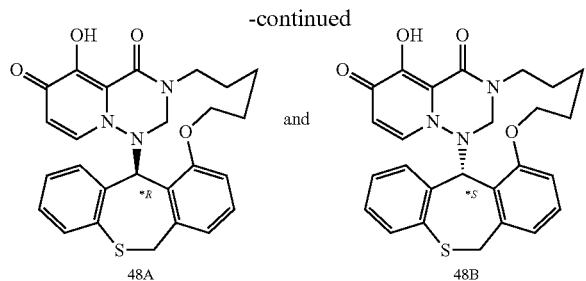

Synthesis of Compound 48:

Under an atmospheric pressure of H₂, a mixture of intermediates 37e+37f (undefined Z/E mixture, 222 mg, 0.39 mmol) and Pd/C (10%) (210 mg, 0.197 mmol) in EtOAc (12 mL) was stirred at rt for 18 h. The catalyst was removed by filtration through Celite®. The Celite® was washed with EtOAc and then with CH₂Cl₂/CH₃OH. The filtrate was concentrated under reduced pressure. The residue was purified by chromatography over silica gel (15 µm, 12 g, CH₂Cl₂/CH₃OH from 99/1 to 93/7) to give, after freeze-drying in CH₃CN/water, Compound 48 (112 mg).

The two enantiomers were separated via chiral HPLC (Stationary phase: Chiralpak® IG, 20 µm, 250 g, Mobile phase: EtOH+0.1% TFA) to give, after freeze-drying in water/CH₃CN (2/8), the first eluted enantiomer 48A (33 mg) and the second eluted enantiomer 48B (34 mg).

Compound 48A:

¹H NMR (500 MHz, DMSO-d₆) δ ppm 1.16-1.30 (m, 1H) 1.36-1.44 (m, 1H) 1.55-1.70 (m, 2H) 1.82-1.93 (m, 1H) 2.04-2.16 (m, 1H) 2.82 (br d, J=13.6 Hz, 1H) 3.82-3.91 (m, 2H) 4.13 (br t, J=12.6 Hz, 1H) 4.29 (d, J=13.2 Hz, 1H) 4.33-4.40 (m, 1H) 5.01 (d, J=13.2 Hz, 1H) 5.65 (d, J=7.9 Hz, 1H) 5.87 (d, J=13.6 Hz, 1H) 6.05 (s, 1H) 6.73 (d, J=7.6 Hz, 1H) 6.84 (t, J=7.3 Hz, 1H) 6.99-7.08 (m, 3H) 7.08-7.15 (m, 1H) 7.36 (t, J=7.9 Hz, 1H) 7.46 (d, J=7.6 Hz, 1H) 11.82 (br s, 1H)

LC/MS (method LC-C): R$_t$ 2.85 min, MH⁺476

[α]$_D^{20}$: +174.8° (c 0.127, DMF)

Compound 48B:

¹H NMR (500 MHz, DMSO-d₆) δ ppm 1.20-1.29 (m, 1H) 1.36-1.44 (m, 1H) 1.55-1.71 (m, 2H) 1.82-1.93 (m, 1H) 2.05-2.16 (m, 1H) 2.82 (br d, J=13.9 Hz, 1H) 3.81-3.90 (m, 2H) 4.13 (br t, J=12.5 Hz, 1H) 4.29 (d, J=13.6 Hz, 1H) 4.33-4.40 (m, 1H) 5.01 (d, J=13.6 Hz, 1H) 5.64 (d, J=7.6 Hz, 1H) 5.87 (d, J=13.6 Hz, 1H) 6.05 (s, 1H) 6.73 (d, J=7.3 Hz, 1H) 6.84 (t, J=7.4 Hz, 1H) 7.00-7.07 (m, 3H) 7.08-7.13 (m, 1H) 7.36 (t, J=7.9 Hz, 1H) 7.46 (d, J=7.6 Hz, 1H) 11.81 (br s, 1H)

LC/MS (method LC-C): R$_t$ 2.84 min, MH⁺476

[α]$_D^{20}$: −184° (c 0.125, DMF)

Example 49: Synthesis of (18R,Z)-11,13-dioxo-18-phenyl-6,9,11,13-tetrahydro-18H-10,17-methano-benzo[b]pyrido[1,2-f][1]oxa[5,6,9]triazacyclotride-cin-12-yl isobutyrate (Compound 49)

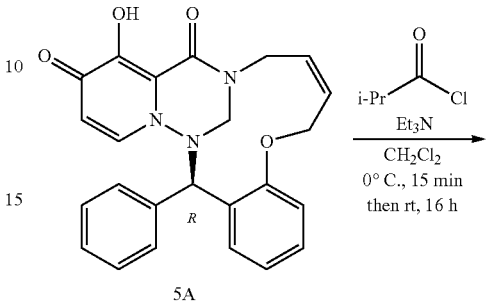

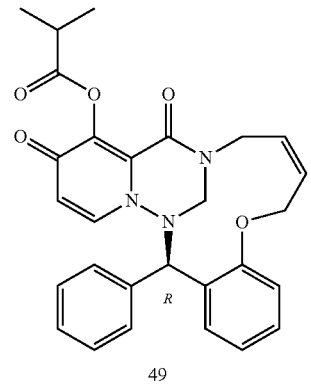

Synthesis of Compound 49:

Et₃N (45.2 µL, 325 µmol) was added to a solution of compound 5A (90.0 mg, 217 µmol) in CH₂Cl₂ (9 mL) at 0° C. The reaction mixture was stirred at 0° C. for 15 min and isobutyryl chloride [CAS 79-30-1] (27.2 µL, 0.26 mmol) was added dropwise. The reaction mixture was stirred at rt overnight. The mixture was evaporated under vacuum. Purification was carried out by flash chromatography over silica gel (30 µm, 12 g, CH₂Cl₂/MeOH 99/1). The residue was taken up in CH₃CN/MeOH. The solid was filtered off and dried under vacuum at 65° C. overnight to give (18R,Z)-11,13-dioxo-18-phenyl-6,9,11,13-tetrahydro-18H-10,17-methanobenzo[b]pyrido[1,2-f][1]oxa[5,6,9]triazacyclotridecin-12-yl isobutyrate (compound 49, 71 mg).

Compound 49:

¹H NMR (500 MHz, DMSO-d₆) δ ppm 8.10 (br d, J=7.6 Hz, 1H), 7.41-7.46 (m, 1H), 7.35 (t, J=7.3 Hz, 1H), 7.28-7.38 (m, 1H), 7.24 (d, J=7.9 Hz, 1H), 7.16-7.22 (m, 3H), 7.10 (br s, 2H), 6.02-6.15 (m, 1H), 5.92 (br s, 1H), 5.76 (s, 1H), 5.68 (br d, J=7.3 Hz, 1H), 5.31 (s, 1H), 5.14 (d, J=13.9 Hz, 1H), 4.70-4.75 (m, 1H), 4.68 (br dd, J=13.9, 4.7 Hz, 1H), 4.26-4.35 (m, 1H), 4.22 (d, J=13.9 Hz, 1H), 3.16 (dd, J=13.6, 8.5 Hz, 1H), 2.77 (spt, J=7.0 Hz, 1H), 1.24 (br d, J=6.9 Hz, 6H).

LC/MS (method LC-A): R$_t$ 2.71 min, MH⁺486

[α]$_D^{20}$: −628.76° (c 0.153, DMF)

Chiral SFC (method SFC-A): R$_t$ 1.62 min, chiral purity 100%.

Example 50: Synthesis of 12-hydroxy-6-methyl-18-phenyl-5,8,9,18-tetrahydro-10,17-methanobenzo[k]pyrido[1,2-b][1,2,5,9]tetraazacyclotridecine-7,11,13(6H)-trione (Compound 50)

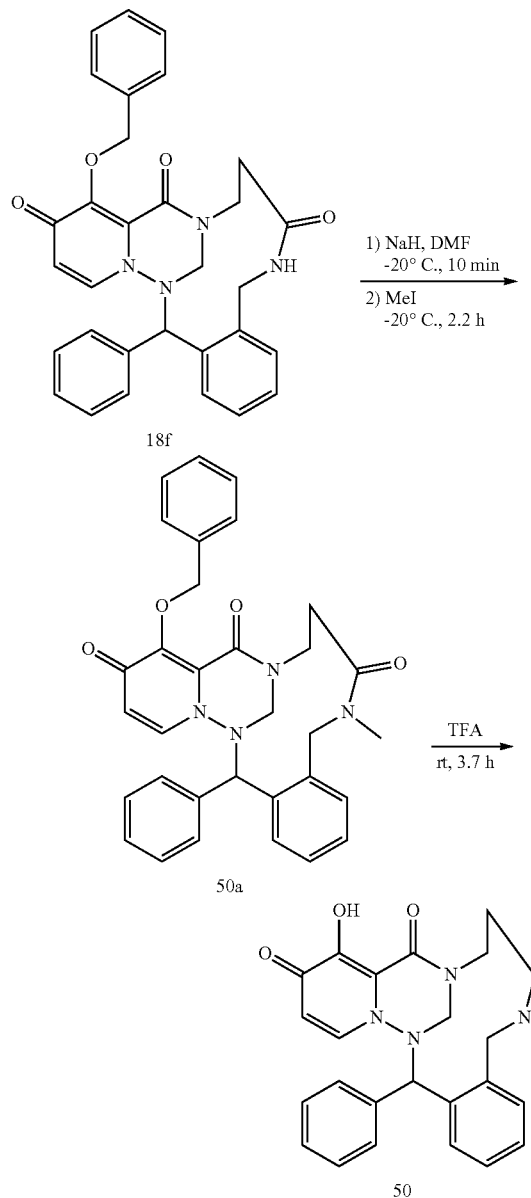

(benzyloxy)-6-methyl-18-phenyl-5,8,9,18-tetrahydro-10,17-methanobenzo[k]pyrido[1,2-b][1,2,5,9]tetraazacyclotridecine-7,11,13(6H)-trione (intermediate 50a, 214 mg).

Synthesis of Compound 50:

Intermediate 50a (214 mg, 0.40 mmol) was dissolved in TFA (3.1 mL, 40.0 mmol) and the reaction mixture was stirred at rt for 3h45. The reaction mixture was concentrated under vacuum and co-evaporated with toluene (twice). Purification was carried out by flash chromatography on silica-C18 (H₂O/MeOH from 100/0 to 0/100). A second purification was performed by flash chromatography on silica-C18 (H₂O/MeOH from 100/0 to 0/100). The residue was lyophilized (dioxane/H₂O) and purified a last time by flash chromatography on silica-C18 (H₂O/MeOH from 100/0 to 0/100) to give 12-hydroxy-6-methyl-18-phenyl-5,8,9,18-tetrahydro-10,17-methanobenzo[k]pyrido[1,2-b][1,2,5,9]tetraazacyclotridecine-7,11,13(6H)-trione (compound 50, 74 mg).

Compound 50:

$^1$H NMR (400 MHz, DMSO-$d_6$) δ ppm 11.65 (m, 1H), 8.36 (d, J=7.8 Hz, 1H), 7.50-7.64 (m, 1H), 7.43 (d, J=7.6 Hz, 1H), 7.29-7.41 (m, 4H), 7.14-7.23 (m, 3H), 5.82 (s, 1H), 5.56 (d, J=13.7 Hz, 1H), 5.43 (d, J=7.6 Hz, 1H), 5.09 (d, J=13.1 Hz, 1H), 3.99 (d, J=13.1 Hz, 1H), 3.74-3.86 (m, 1H), 3.41 (br d, J=13.7 Hz, 1H), 3.08-3.21 (m, 3H), 2.86 (s, 3H)

Example 51: Synthesis of (18*R,Z)-12-hydroxy-18-phenyl-6,9-dihydro-18H-10,17-methanobenzo[b]pyrido[1,2-f][1]oxa[5,6,9]triazacyclotridecine-11,13-dione (Compound 51A) and (18*S,Z)-12-hydroxy-18-phenyl-6,9-dihydro-18H-10,17-methanobenzo[b]pyrido[1,2-f][1]oxa[5,6,9]triazacyclotridecine-11,13-dione (Compound 51B)

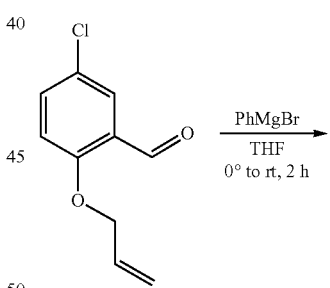

Synthesis of Intermediate 50a:

Under nitrogen atmosphere, to a suspension of intermediate 18f (208 mg, 0.40 mmol) in anhydrous DMF (8 mL) at −20° C. was added NaH (60% dispersion in mineral oil, 24 mg, 0.60 mmol). The reaction mixture was stirred at −20° C. for 10 min. Iodomethane (37 µL, 0.60 mmol) was added and the reaction mixture was stirred at −20° C. for 2h10. The reaction was quenched by the careful addition of water. The aqueous phase was extracted with EtOAc (3 times). The combined organic extracts were washed with brine, dried over Na₂SO₄, filtered and concentrated in vacuo. The crude mixture was purified by flash chromatography on silica gel (40 g, CH₂Cl₂/MeOH from 100/0 to 90/10) to afford 12-

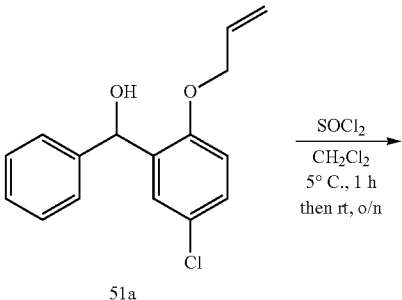

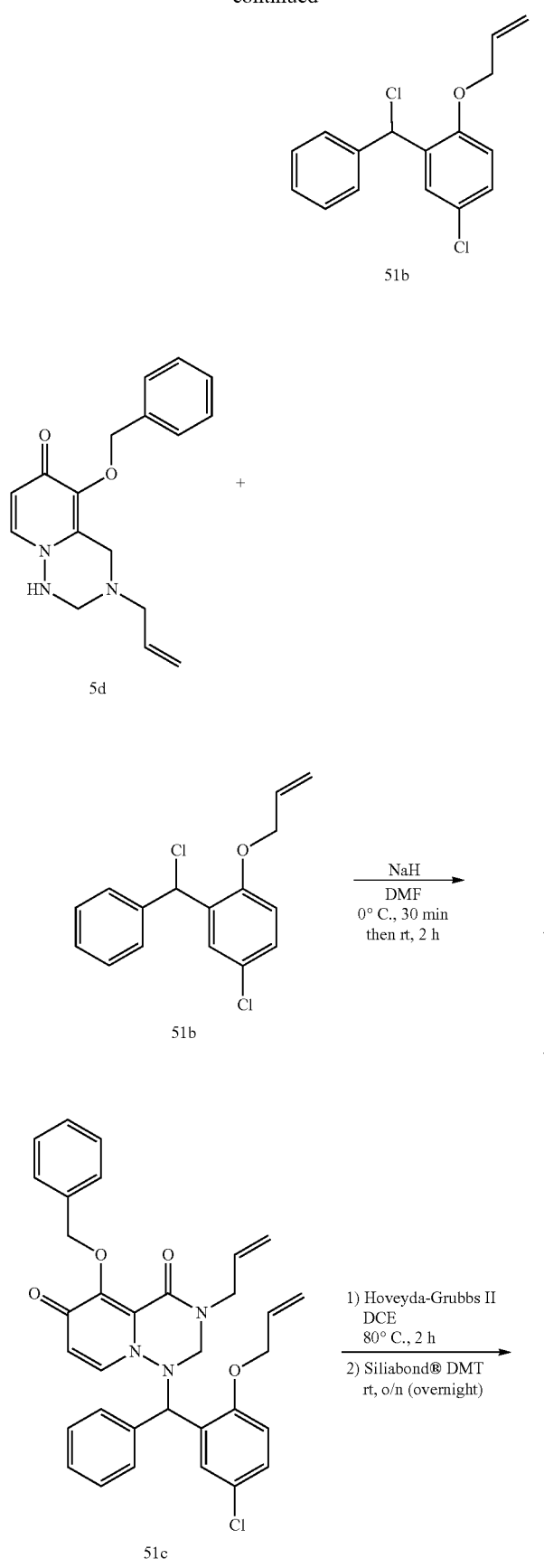

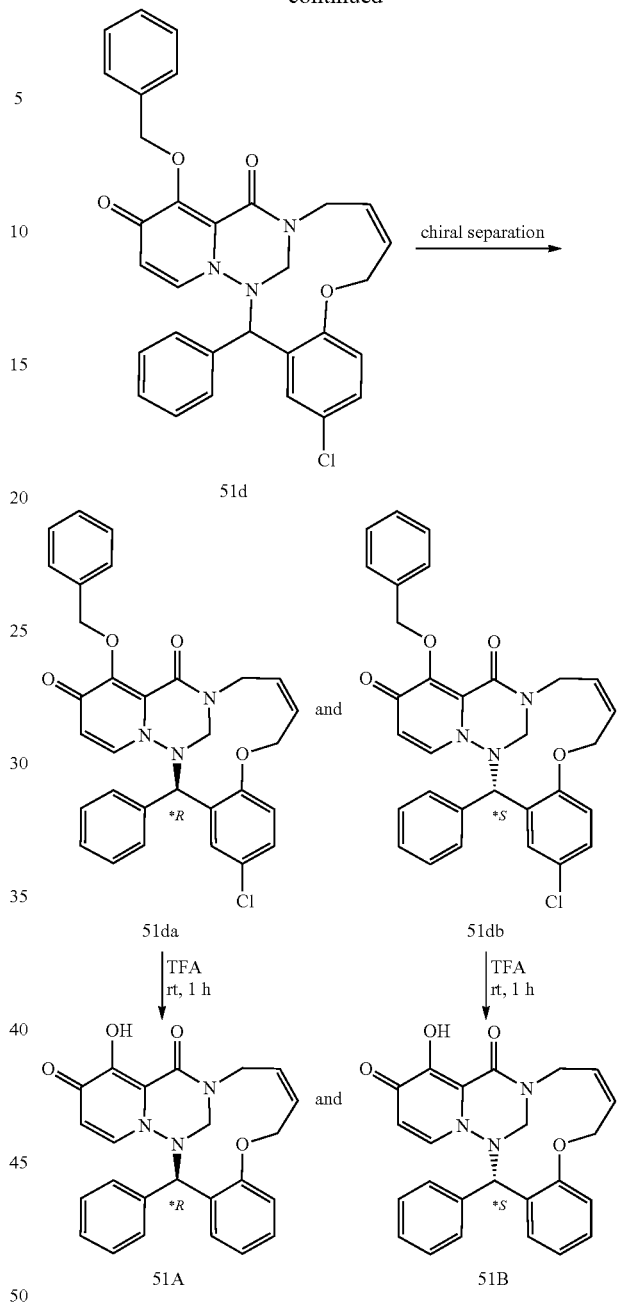

Synthesis of Intermediate 51a:
  (2-(allyloxy)-5-chlorophenyl)(phenyl)methanol (intermediate 51a, 2.63 g) was obtained using the procedure described for intermediate 21a. The desired intermediate 51a was purified by flash chromatography over silica gel (20-45 μm, 120 g, heptane/EtOAc 90/10).

Synthesis of Intermediate 51b:
  1-(allyloxy)-4-chloro-2-(chloro(phenyl)methyl)benzene (intermediate 51b, 2.2 g) was obtained using the procedure described for intermediate 5a.

Synthesis of Intermediate 51c:
  3-allyl-1-((2-(allyloxy)-5-chlorophenyl)(phenyl)methyl)-5-(benzyloxy)-2,3-dihydro-1H-pyrido[2,1-f][1,2,4]triazine-4,6-dione (intermediate 51c, 1.74 g) was obtained using the procedure described for intermediate 5e.

145

Synthesis of Intermediates 51d, 51da and 51db:

(Z)-12-(benzyloxy)-2-chloro-18-phenyl-6,9-dihydro-18H-10,17-methanobenzo[b]pyrido[1,2-f][1]oxa[5,6,9]triazacyclotridecine-11,13-dione (intermediate 51d, 374 mg) was obtained using the procedure described for intermediate 5f. A second purification was performed by preparative LC (Stationary phase: irregular bare silica 40 g, Mobile phase: heptane/MeOH/EtOAc 60/5/35).

The enantiomers (330 mg) were separated via chiral SFC (Stationary phase: Chiracel OJ-H 5 μm 250*30 mm, Mobile phase: 75% $CO_2$, 25% MeOH) to afford the first eluted enantiomer 51da (113 mg) and the second eluted enantiomer 51db (115 mg).

Synthesis of Compound 51A:

(18*R,Z)-12-hydroxy-18-phenyl-6,9-dihydro-18H-10,17-methanobenzo[b]pyrido[1,2-f][1]oxa[5,6,9]triazacyclotridecine-11,13-dion (compound 51A, 60 mg) was obtained using the procedure described for compound 5A.

Compound 51A:

$^1$H NMR (500 MHz, DMSO-$d_6$) δ ppm 8.16 (d, J=1.9 Hz, 1H), 7.46 (dd, J=8.8, 2.5 Hz, 1H), 7.37 (br d, J=7.6 Hz, 1H), 7.28 (d, J=8.8 Hz, 1H), 7.20 (br d, J=2.2 Hz, 3H), 7.09-7.22 (m, 2H), 6.08-6.19 (m, 1H), 5.97 (br s, 1H), 5.47 (d, J=7.6 Hz, 1H), 5.29 (s, 1H), 5.13 (d, J=13.9 Hz, 1H), 4.71-4.81 (m, 2H), 4.31-4.37 (m, 1H), 4.29 (d, J=13.6 Hz, 1H), 3.20 (br dd, J=13.7, 8.4 Hz, 1H).

LC/MS (method LC-C): Rt 2.70 min, MH$^+$450

$[\alpha]_D^{20}$: +809.44° (c 0.119, DMF)

Chiral HPLC (method HPLC-B): Rt 5.28 min, chiral purity 100%

Synthesis of Compound 51B:

(18*S,Z)-12-hydroxy-18-phenyl-6,9-dihydro-18H-10,17-methanobenzo[b]pyrido[1,2-f][1]oxa[5,6,9]triazacyclotridecine-11,13-dione (compound 51B, 52 mg) was obtained using the procedure described for compound 5A.

Compound 51B:

$^1$H NMR (400 MHz, DMSO-$d_6$) δ ppm 8.16 (d, J=2.0 Hz, 1H), 7.46 (dd, J=8.8, 2.8 Hz, 1H), 7.38 (br d, J=7.6 Hz, 1H), 7.28 (d, J=8.6 Hz, 1H), 7.10-7.24 (m, 5H), 6.08-6.20 (m, 1H), 5.98 (br s, 1H), 5.47 (d, J=7.6 Hz, 1H), 5.29 (s, 1H), 5.13 (d, J=14.1 Hz, 1H), 4.70-4.82 (m, 2H), 4.24-4.37 (m, 1H), 4.29 (d, J=13.6 Hz, 1H), 3.17-3.25 (m, 1H).

LC/MS (method LC-C): Rt 2.70 min, MH$^+$450

$[\alpha]_D^{20}$: −785.86° (c 0.151, DMF)

Chiral HPLC (method HPLC-B): Rt 6.42 min, chiral purity 100%

Example 52: Synthesis of (16*R,*Z)-4-hydroxy-16-(pyridin-4-yl)-7,10,11,16-tetrahydro-6,17-methanobenzo[k]pyrido[1,2-b][1,2,5]triazacyclotridecine-3,5-dione (Compound 52A) and (16*S,*Z)-4-hydroxy-16-(pyridin-4-yl)-7,10,11,16-tetrahydro-6,17-methanobenzo[k]pyrido[1,2-b][1,2,5]triazacyclotridecine-3,5-dione (Compound 52B)

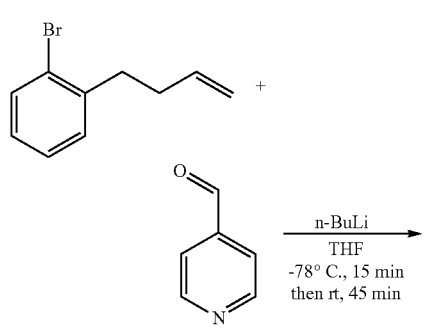

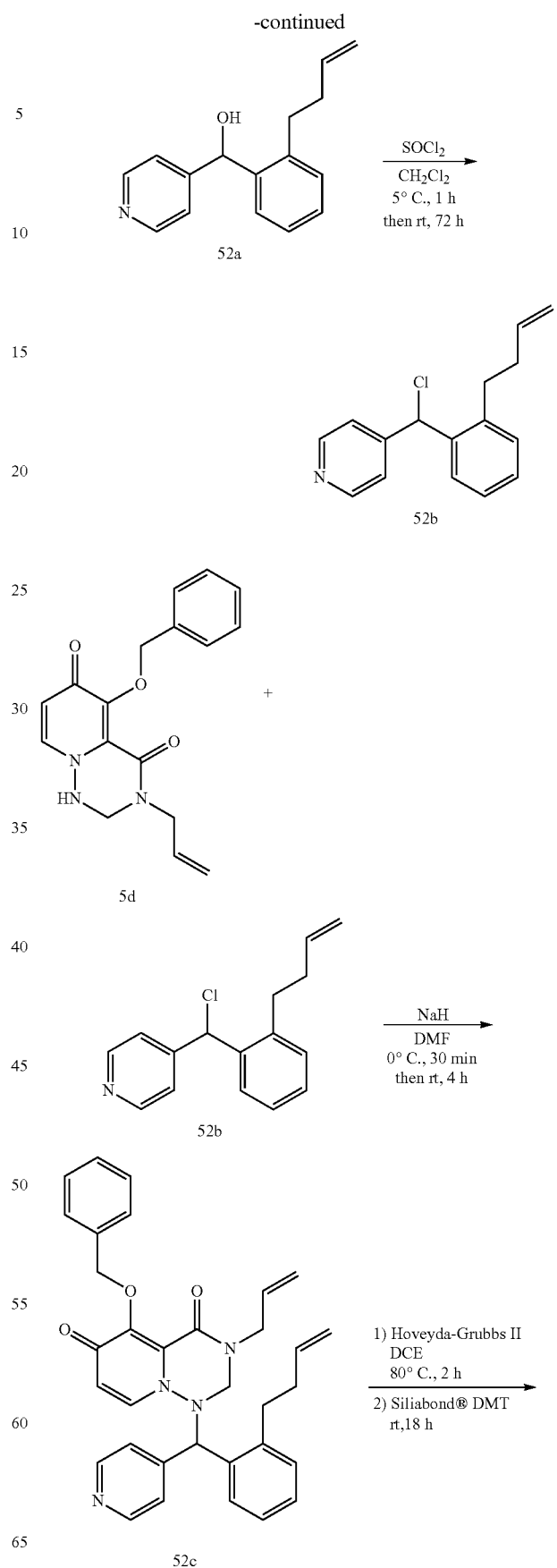

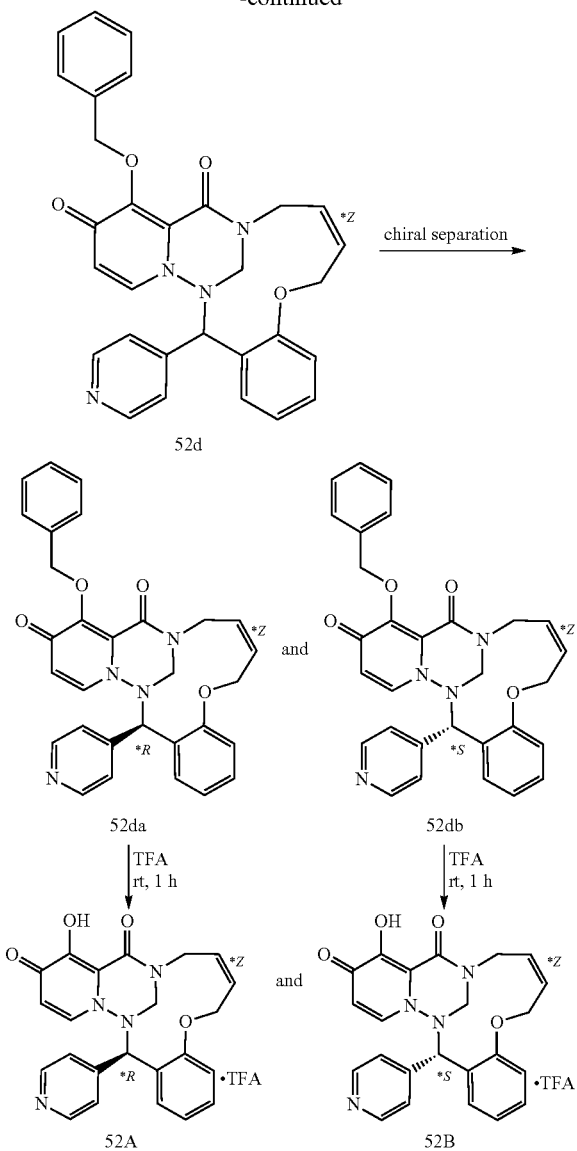

Synthesis of Intermediate 52a:

(2-(but-3-en-1-yl)phenyl)(pyridin-4-yl)methanol (intermediate 52a, 1.4 g) was obtained using the procedure described for intermediate 23a. Crude intermediate 52a was purified by preparative LC (Stationary phase: regular SiOH 30 μm 40 g, Mobile phase: CH₂Cl₂/MeOH from 100/0 to 98/2).

Synthesis of Intermediate 52b:

4-((2-(but-3-en-1-yl)phenyl)chloromethyl)pyridine (intermediate 52b, 1.4 g) was obtained using the procedure described for intermediate 5a. Following the co-evaporation with toluene, the residue was suspended in EtOAc and the organic phase was washed with a 10% aqueous solution of K₂CO₃, dried over MgSO₄, filtered and concentrated to afford intermediate 52b.

Synthesis of Intermediate 52c:

3-allyl-5-(benzyloxy)-1-((2-(but-3-en-1-yl)phenyl)(pyridin-4-yl)methyl)-2,3-dihydro-1H-pyrido[2,1-f][1,2,4]triazine-4,6-dione (intermediate 52c, 0.26 g) was obtained using the procedure described for intermediate 5e.

Synthesis of Intermediate 52d:

(*Z)-4-(benzyloxy)-16-(pyridin-4-yl)-7,10,11,16-tetrahydro-6,17-methanobenzo[k]pyrido[1,2-b][1,2,5]triazacyclotridecine-3,5-dione (intermediate 52d, 97 mg) was obtained using the procedure described for intermediate 5f.

The enantiomers were separated via chiral SFC (Stationary phase: Whelk-O1 (S,S) 5 μm 250*21.2 mm, Mobile phase: 40% CO₂, 60% EtOH) to afford the first eluted enantiomer 52da (37 mg) and the second eluted enantiomer 52db (37 mg).

Synthesis of Compound 52A:

(16*R,*Z)-4-hydroxy-16-(pyridin-4-yl)-7,10,11,16-tetrahydro-6,17-methanobenzo[k]pyrido[1,2-b][1,2,5]triazacyclotridecine-3,5-dione, trifluoroacetic acid (compound 52A, 23 mg) was obtained using the procedure described for compound 5A.

Compound 52A:

¹H NMR (400 MHz, DMSO-d₆) δ ppm 8.39 (d, J=5.1 Hz, 2H), 8.09 (d, J=7.6 Hz, 1H), 7.45 (t, J=7.3 Hz, 1H), 7.36 (t, J=7.6 Hz, 1H), 7.26-7.33 (m, 3H), 7.22 (d, J=7.6 Hz, 1H), 5.94-6.06 (m, 1H), 5.51 (d, J=7.6 Hz, 1H), 5.41-5.49 (m, 1H), 5.23 (s, 1H), 5.13 (d, J=13.6 Hz, 1H), 4.71 (br dd, J=14.1, 5.1 Hz, 1H), 4.28 (d, J=13.6 Hz, 1H), 3.08 (br dd, J=13.9, 7.8 Hz, 1H), 2.58-2.66 (m, 1H), 2.53-2.57 (m, 2H), 1.93-2.05 (m, 1H).

LC/MS (method LC-C): R_t 2.29 min, MH⁺415

[α]_D²⁰: +546.88° (c 0.083, DMF)

Chiral HPLC (method HPLC-B): Rt 4.99 min, chiral purity 100%

Synthesis of Compound 52B:

(16*S,*Z)-4-hydroxy-16-(pyridin-4-yl)-7,10,11,16-tetrahydro-6,17-methanobenzo[k]pyrido[1,2-b][1,2,5]triazacyclotridecine-3,5-dione, trifluoroacetic acid (compound 52B, 23 mg) was obtained using the procedure described for compound 5A.

Compound 52B:

¹H NMR (400 MHz, DMSO-d₆) δ ppm 8.39 (d, J=5.1 Hz, 2H), 8.09 (d, J=7.6 Hz, 1H), 7.45 (t, J=7.3 Hz, 1H), 7.36 (t, J=7.6 Hz, 1H), 7.31 (br d, J=7.6 Hz, 3H), 7.22 (d, J=7.6 Hz, 1H), 5.93-6.06 (m, 1H), 5.51 (d, J=7.6 Hz, 1H), 5.41-5.49 (m, 1H), 5.23 (s, 1H), 5.13 (d, J=13.6 Hz, 1H), 4.71 (br dd, J=14.1, 5.1 Hz, 1H), 4.28 (d, J=13.6 Hz, 1H), 3.08 (br dd, J=13.9, 7.8 Hz, 1H), 2.52-2.65 (m, 3H), 1.94-2.05 (m, 1H).

LC/MS (method LC-C): Rt 2.29 min, MH⁺415

[α]D²⁰: −547.15° (c0.118, DMF)

Chiral HPLC (method HPLC-B): Rt 5.92 min, chiral purity 100%

Example 53: Synthesis of (21a*R,Z)-16-hydroxy-6,10,13,21a-tetrahydro-7,8-(epiprop[1]en[1]yl[3]ylidene)-14,21-methanobenzo[6,7]oxepino[4,5-c]pyrido[1,2-f][1]oxa[5,6,9]triazacyclotridecine-15,17-dione (Compound 53A) and (21a*S,Z)-16-hydroxy-6,10,13,21a-tetrahydro-7,8-(epiprop[1]en[1]yl[3]ylidene)-14,21-methanobenzo[6,7]oxepino[4,5-c]pyrido[1,2-f][1]oxa[5,6,9]triazacyclotridecine-15,17-dione (Compound 53B)

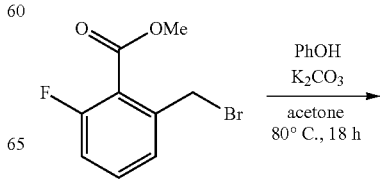

-continued

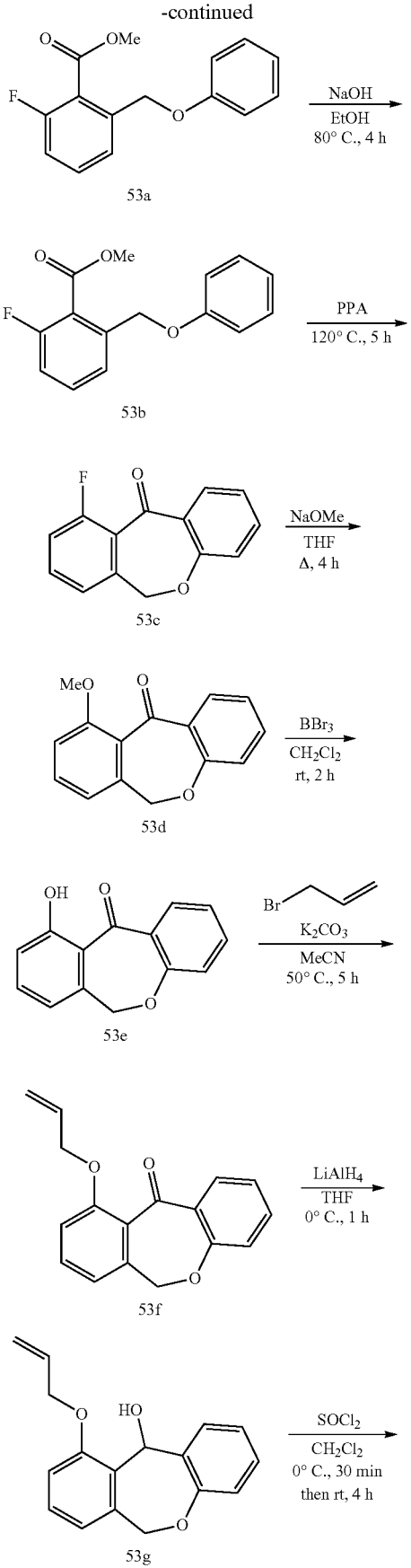

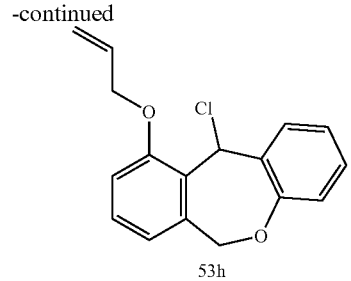

Synthesis of Intermediate 53a:
Methyl 2-(bromomethyl)-6-fluorobenzoate [CAS 197516-58-8] (15.0 g, 60.7 mmol) was dissolved in acetone (230 mL). Phenol (5.71 g, 60.7 mmol) and $K_2CO_3$ (12.6 g, 91.1 mmol) were added and the reaction mixture was stirred at 80° C. for 18 h. The mixture was filtered and the solvent was evaporated under vacuum. Purification was carried out by flash chromatography over silica gel (20-45 µm, 220 g, liquid injection ($CH_2Cl_2$/heptane), heptane/EtOAc 90/10,). The pure fractions were collected and evaporated to dryness to afford methyl 2-fluoro-6-(phenoxymethyl)benzoate (intermediate 53a, 5.55 g).

Synthesis of Intermediate 53b:
A mixture of intermediate 53a (5.50 g, 21.1 mmol) and sodium hydroxide (2N in $H_2O$, 52.8 mL, 106 mmol) in EtOH (98.7 mL) was stirred at 80° C. for 4 h. The mixture was diluted with water and acidified until pH 2 with HCl. The aqueous phase was extracted with EtOAc. The combined organic extracts were dried over $MgSO_4$, filtered and concentrated under vacuum to afford 2-fluoro-6-(phenoxymethyl)benzoic acid (intermediate 53b, 5.24 g).

Synthesis of Intermediate 53c:
Intermediate 53b (5.24 g, 21.3 mmol) was added to polyphosphoric acid (8.30 g). The reaction mixture was stirred at 120° C. for 5 h. Iced water was added and the aqueous phase was extracted with EtOAc. The organic phase was dried over $MgSO_4$, filtered and evaporated under vacuum. Purification was carried out by flash chromatography over silica gel (20-45 µm, 80 g, $CH_2Cl_2$ 100%). The pure fractions were collected and evaporated to dryness to afford 10-fluorodibenzo[b,e]oxepin-11(6H)-one (intermediate 53c, 3.2 g).

Synthesis of Intermediate 53d:
Intermediate 53c (2.70 g, 11.8 mmol) was dissolved in THF (5.7 mL) and a solution of sodium methoxide (5.4 M, 13.8 mL, 74.5 mmol) was added. The reaction mixture was stirred under reflux for 4 h. An aqueous solution of HCl was added and the mixture was extracted with EtOAc. The organic phase was washed with water and brine, dried over $MgSO_4$, filtered and the solvent was evaporated under vacuum. The residue was diluted with $CH_2Cl_2$ and few drops of heptane were added. The precipitated was filtered off and dried under vacuum to afford 10-methoxydibenzo[b,e]oxepin-11(6H)-one (intermediate 53d, 1 g).

Synthesis of Intermediate 53e:
To a solution of intermediate 53d (1.00 g, 4.16 mmol) in $CH_2Cl_2$ (10 mL) at 0° C. was added boron tribromide (8.32 mL, 8.32 mmol) dropwise. The reaction mixture was stirred at rt for 2 h. A saturated aqueous solution of sodium bicarbonate was added while the temperature of the mixture was maintained at 0° C. The mixture was warmed up to rt. Brine was added and the mixture was extracted with $CH_2Cl_2$. The organic phase was washed with brine, dried over $MgSO_4$, filtered and the solvent was evaporated under vacuum. The residue was taken up in $Et_2O$. The solid was filtered off and dried under vacuum to afford 10-hydroxydibenzo[b,e]oxepin-11(6H)-one (intermediate 53e, 220 mg).

Synthesis of Intermediate 53f:

10-(allyloxy)dibenzo[b,e]oxepin-11(6H)-one (intermediate 53f, 1.05 g) was obtained using the procedure described for intermediate 37a.

Synthesis of Intermediate 53g:

10-(allyloxy)-6,11-dihydrodibenzo[b,e]oxepin-11-ol (intermediate 53g, 1.0 g) was obtained using the procedure described for intermediate 28b.

Synthesis of Intermediate 53h:

10-(allyloxy)-11-chloro-6,11-dihydrodibenzo[b,e]
oxepine (intermediate 53h, 1.0 g) was obtained using the procedure described for 5a.

Synthesis of Intermediate 53i:

3-allyl-1-(10-(allyloxy)-6,11-dihydrodibenzo[b,e]oxepin-11-yl)-5-(benzyloxy)-2,3-dihydro-1H-pyrido[2,1-f][1,2,4]triazine-4,6-dione (intermediate 53i, 1.21 g) was obtained using the procedure described for intermediate 5e.

Synthesis of Intermediate 53j:

(Z)-16-(benzyloxy)-6,10,13,21a-tetrahydro-7,8-(epiprop[1]en[1]yl[3]ylidene)-14,21-methanobenzo[6,7]oxepino[4,5-c]pyrido[1,2-f][1]oxa[5,6,9]triazacyclotridecine-15,17-dione (intermediate 53j, 141 mg) was obtained using the procedure described for intermediate 5f.

The enantiomers were separated via chiral SFC (Stationary phase: CHIRALPAK AD-H 5 μm 250*30 mm, Mobile phase: 50% $CO_2$, 50% EtOH) to give the first eluted enantiomer 53jA (38 mg) and the second eluted enantiomer 53jB (52 mg).

Synthesis of Compound 53A:

LiCl (15.1 mg, 0.36 mmol) was added to a solution of intermediate 53jA (38.0 mg, 71.2 μmol) in DMA (0.4 mL) and the mixture was stirred at 80° C. for 4 h. The mixture was cooled to rt and evaporated in vacuo. Purification was carried out by flash chromatography over silica gel (15-40 μm, 4 g, $CH_2Cl_2$/MeOH from 99/1 to 97.5/2.5). The pure fractions were collected and evaporated to dryness. The residue was freeze-dried ($H_2O$/$CH_3CN$ 4/1) to afford (21a*R,Z)-16-hydroxy-6,10,13,21a-tetrahydro-7,8-(epiprop[1]en[1]yl[3]ylidene)-14,21-methanobenzo[6,7]oxepino[4,5-c]pyrido[1,2-f][1]oxa[5,6,9]triazacyclotridecine-15,17-dione (compound 53A, 24 mg).

Compound 53A:

$^1$H NMR (400 MHz, DMSO-$d_6$) δ ppm 11.66 (br s, 1H), 7.46 (t, J=7.8 Hz, 1H), 7.30 (d, J=7.6 Hz, 1H), 7.26 (d, J=8.1 Hz, 1H), 7.19 (t, J=7.8 Hz, 1H), 7.13 (d, J=7.1 Hz, 1H), 6.83 (d, J=8.1 Hz, 1H), 6.62 (t, J=7.3 Hz, 1H), 6.33-6.46 (m, 3H), 6.29 (d, J=12.6 Hz, 1H), 5.76 (s, 1H), 5.55 (d, J=7.6 Hz, 1H), 4.97 (d, J=12.6 Hz, 1H), 4.96 (d, J=13.6 Hz, 1H), 4.75-4.83 (m, 1H), 4.66 (dd, J=10.6, 6.1 Hz, 1H), 4.25 (d, J=13.1 Hz, 1H), 4.11 (dd, J=13.1, 7.6 Hz, 1H), 3.80 (br dd, J=13.1, 7.6 Hz, 1H).

LC/MS (method LC-C): Rt 2.55 min, MH$^+$444

[α]$_D^{20}$: -66.67° (c 0.108, DMF)

Chiral HPLC (method HPLC-B): Rt 6.89 min, chiral purity 100%

Synthesis of Compound 53B:

(21a*S,Z)-16-hydroxy-6,10,13,21a-tetrahydro-7,8-(epiprop[1]en[1]yl[3]ylidene)-14,21-methanobenzo[6,7]oxepino[4,5-c]pyrido[1,2-f][1]oxa[5,6,9]triazacyclotridecine-15,17-dione (compound 53B, 53 mg) was obtained using the procedure described for compound 53A.

Compound 53B:

$^1$H NMR (500 MHz, DMSO-$d_6$) δ ppm 7.46 (t, J=7.7 Hz, 1H), 7.31 (br d, J=7.6 Hz, 1H), 7.26 (d, J=8.5 Hz, 1H), 7.19 (br t, J=7.6 Hz, 1H), 7.14 (d, J=7.3 Hz, 1H), 6.83 (d, J=8.2 Hz, 1H), 6.57-6.66 (m, 1H), 6.25-6.47 (m, 4H), 5.76 (s, 1H), 5.56 (br d, J=7.3 Hz, 1H), 4.97 (br d, J=12.6 Hz, 2H), 4.79 (br dd, J=10.6, 6.5 Hz, 1H), 4.66 (br dd, J=10.4, 6.6 Hz, 1H), 4.26 (br d, J=13.2 Hz, 1H), 4.11 (br dd, J=13.4, 7.4 Hz, 1H), 3.80 (br dd, J=12.8, 8.0 Hz, 1H).

LC/MS (method LC-C): Rt 2.55 min, MH$^+$444

[α]$_D^{20}$: +46.88° (c 0.109, DMF)

Chiral HPLC (method HPLC-B): Rt 5.52 min, chiral purity 100%

Example 54: Synthesis of (*Z)-4-hydroxy-15-phenyl-8,15-dihydro-7H-6,16-methanobenzo[j]pyrido[1,2-b][1,2,5]triazacyclododecine-3,5-dione (compound 54), (16*R,*Z)-4-hydroxy-16-phenyl-7,8,9,16-tetrahydro-6,17-methanobenzo[k]pyrido[1,2-b][1,2,5]triazacyclotridecine-3,5-dione (Compound 54A) and (16*S,*Z)-4-hydroxy-16-phenyl-7,8,9,16-tetrahydro-6,17-methanobenzo[k]pyrido[1,2-b][1,2,5]triazacyclotridecine-3,5-dione (Compound 54B)

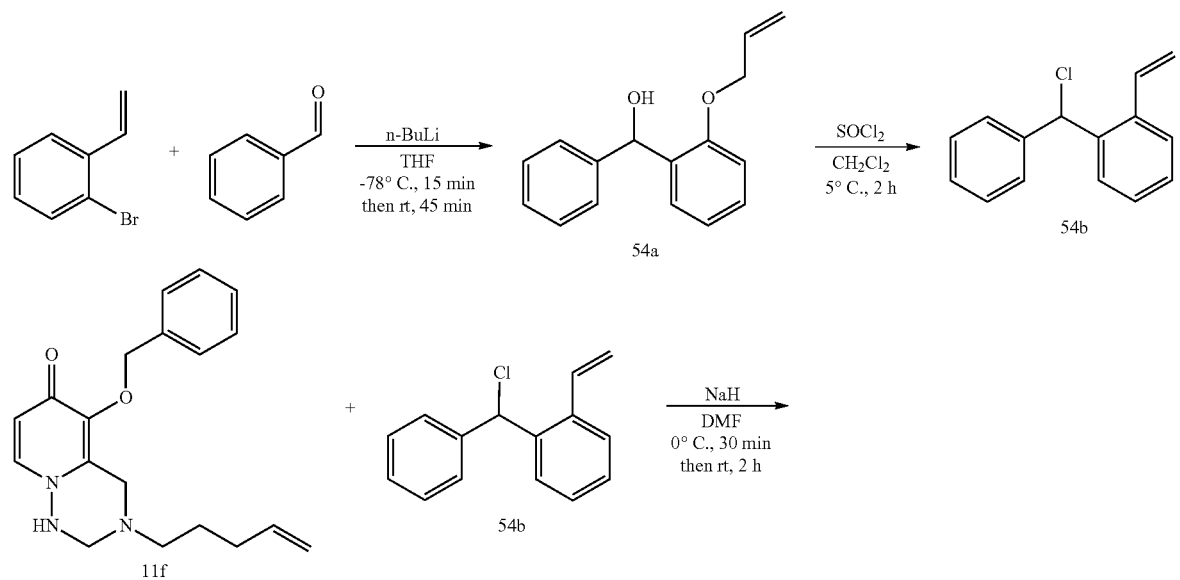

-continued
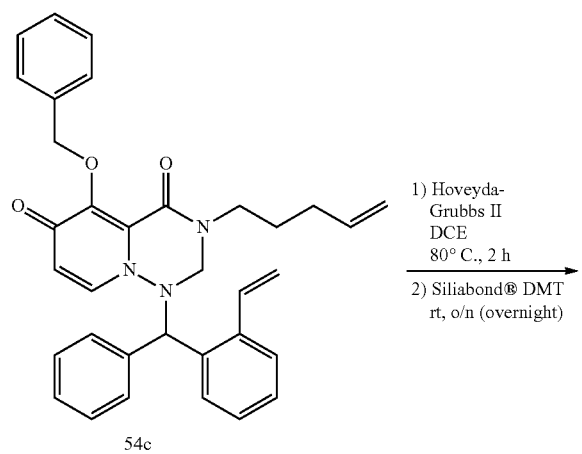
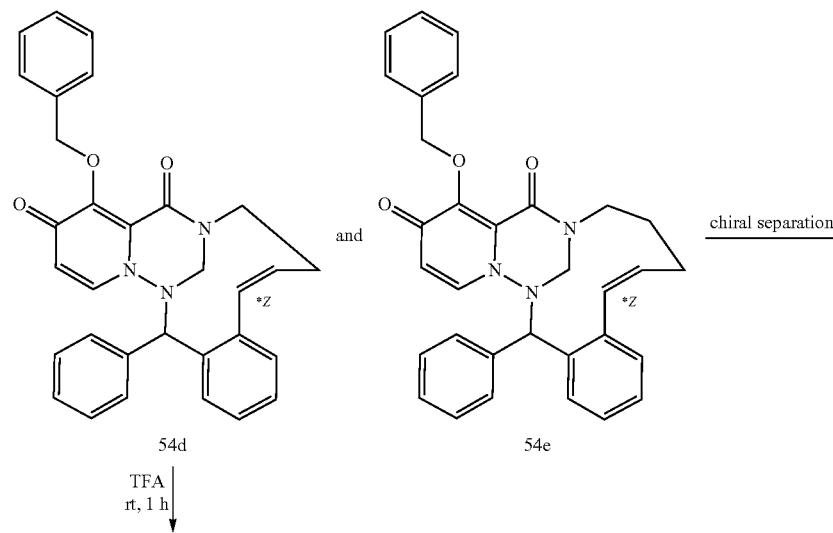
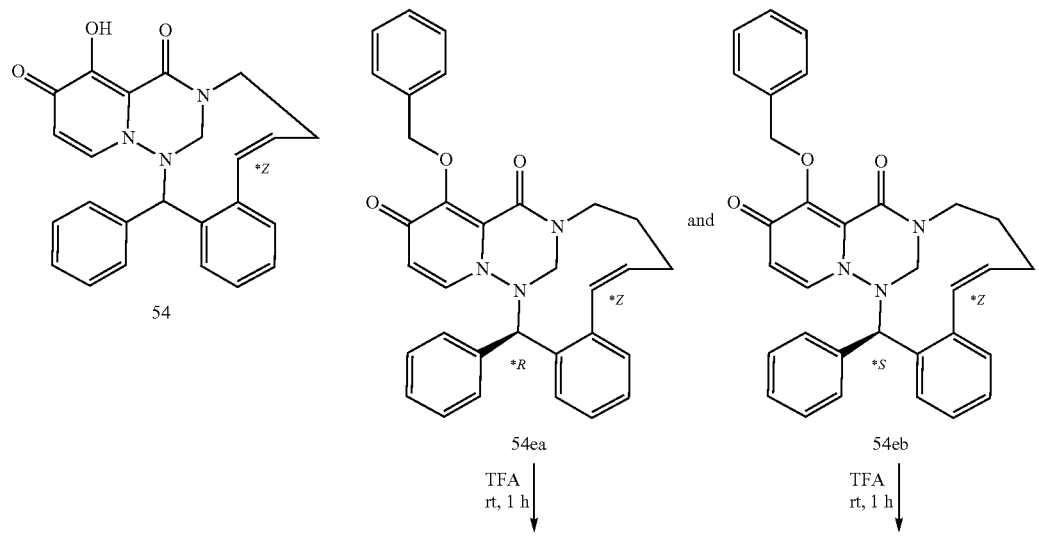

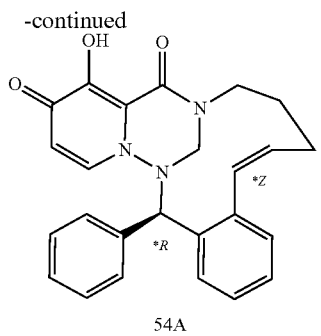
54A

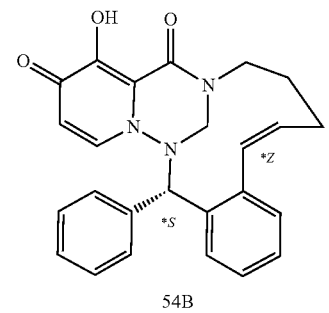
54B

Synthesis of Intermediate 54a:
phenyl(2-vinylphenyl)methanol (intermediate 54a, 2.9 g) was obtained using the procedure described for intermediate 23a.

Synthesis of Intermediate 54b:
1-(chloro(phenyl)methyl)-2-vinylbenzene (intermediate 54b, 54 mg) was obtained using the procedure described for intermediate 5a.

Synthesis of Intermediate 54c:
5-(benzyloxy)-3-(pent-4-en-1-yl)-1-(phenyl(2-vinylphenyl)methyl)-2,3-dihydro-1H-pyrido[2,1-f][1,2,4]triazine-4,6-dione (intermediate 54c, 0.85 g) was obtained using the procedure described for intermediate 2d.

Synthesis of Intermediates 54d, 54e:
(*Z)-4-(benzyloxy)-16-phenyl-7,8,9,16-tetrahydro-6,17-methanobenzo[k]pyrido[1,2-b][1,2,5]triazacyclotridecine-3,5-dione (intermediate 54e) and (*Z)-4-(benzyloxy)-15-phenyl-8,15-dihydro-7H-6,16-methanobenzo[j]pyrido[1,2-b][1,2,5]triazacyclododecine-3,5-dione (intermediate 54d) were obtained using the procedure described for intermediate 1f. Purification was carried out by flash chromatography over silica gel (30 μm, 40 g, CH$_2$Cl$_2$/MeOH from 100/0 to 98/2). A second purification was performed via reverse phase (Stationary phase: YMC-actus Triart C18 10 μm 30*150 mm, Mobile phase gradient: aq. 0.2% NH$_4$HCO$_3$/CH$_3$CN from 55/45 to 30/70) to afford intermediate 54e (64 mg) and intermediate 54d (30 mg). The enantiomers 54ea and 54eb were separated via chiral SFC (Stationary phase: Chiralpak AS-H 5 μm 250*20 mm, Mobile phase: 50% CO$_2$, 50% EtOH) to afford the first eluted enantiomer 54ea (26 mg) and the second eluted enantiomer 54eb (26 mg).

Synthesis of Compound 54:
(*Z)-4-hydroxy-15-phenyl-8,15-dihydro-7H-6,16-methanobenzo[j]pyrido[1,2-b][1,2,5]triazacyclododecine-3,5-dione (compound 54, 17 mg) was obtained using the procedure described for compound 1.

Compound 54:
$^1$H NMR (500 MHz, DMSO-d$_6$) δ ppm 11.60 (br s, 1H), 8.06 (d, J=7.9 Hz, 1H), 7.49 (t, J=7.6 Hz, 1H), 7.32-7.43 (m, 2H), 7.35 (br t, J=7.6 Hz, 1H), 7.28 (d, J=7.9 Hz, 1H), 7.21-7.27 (m, 3H), 7.07 (d, J=7.6 Hz, 1H), 6.39 (br d, J=11.0 Hz, 1H), 5.94 (br td, J=10.9, 4.1 Hz, 1H), 5.58 (s, 1H), 5.49 (d, J=7.6 Hz, 1H), 5.03 (d, J=12.9 Hz, 1H), 4.25 (d, J=12.9 Hz, 1H), 3.80 (br d, J=13.9 Hz, 1H), 2.70 (br t, J=12.5 Hz, 1H), 2.23 (br t, J=13.2 Hz, 1H), 1.84-2.03 (m, 2H), 1.70-1.81 (m, 1H).

LC/MS (method LC-C): Rt 2.72 min. MH$^+$400

Synthesis of Compound 54A:
(16*R,*Z)-4-hydroxy-16-phenyl-7,8,9,16-tetrahydro-6,17-methanobenzo[k]pyrido[1,2-b][1,2,5]triazacyclotridecine-3,5-dione (compound 54A, 17 mg) was obtained using the procedure described for compound 1.

$^1$H NMR (500 MHz, DMSO-d$_6$) δ ppm 11.60 (br s, 1H), 8.06 (d, J=7.9 Hz, 1H), 7.49 (t, J=7.6 Hz, 1H), 7.32-7.43 (m, 2H), 7.35 (br t, J=7.6 Hz, 1H), 7.28 (d, J=7.9 Hz, 1H), 7.21-7.27 (m, 3H), 7.07 (d, J=7.6 Hz, 1H), 6.39 (br d, J=11.0 Hz, 1H), 5.94 (br td, J=10.9, 4.1 Hz, 1H), 5.58 (s, 1H), 5.49 (d, J=7.6 Hz, 1H), 5.03 (d, J=12.9 Hz, 1H), 4.25 (d, J=12.9 Hz, 1H), 3.80 (br d, J=13.9 Hz, 1H), 2.70 (br t, J=12.5 Hz, 1H), 2.23 (br t, J=13.2 Hz, 1H), 1.84-2.03 (m, 2H), 1.70-1.81 (m, 1H).

LC/MS (method LC-C): Rt 2.90 min, MH$^+$414

$[α]_D^{20}$: +336.18° (c 0.105, DMF)

Chiral HPLC (method HPLC-A): R$_t$ 5.02 min, chiral purity 100%

Synthesis of Compound 54B:
(16*S,*Z)-4-hydroxy-16-phenyl-7,8,9,16-tetrahydro-6,17-methanobenzo[k]pyrido[1,2-b][1,2,5]triazacyclotridecine-3,5-dione (compound 54B, 15 mg) was obtained using the procedure described for compound 1.

Compound 54B:
$^1$H NMR (500 MHz, DMSO-d$_6$) δ ppm 11.63 (br s, 1H), 8.06 (d, J=7.9 Hz, 1H), 7.49 (t, J=7.6 Hz, 1H), 7.33-7.44 (m, 2H), 7.35 (br t, J=7.4 Hz, 1H), 7.28 (d, J=7.9 Hz, 1H), 7.20-7.27 (m, 3H), 7.07 (d, J=7.6 Hz, 1H), 6.39 (br d, J=11.0 Hz, 1H), 5.94 (td, J=10.8, 4.3 Hz, 1H), 5.58 (s, 1H), 5.49 (d, J=7.6 Hz, 1H), 5.03 (d, J=13.2 Hz, 1H), 4.25 (d, J=12.9 Hz, 1H), 3.80 (br d, J=14.2 Hz, 1H), 2.70 (br t, J=12.5 Hz, 1H), 2.23 (br t, J=12.5 Hz, 1H), 1.85-2.03 (m, 2H), 1.71-1.82 (m, 1H).

LC/MS (method LC-C): Rt 2.89 min, MH$^+$414

$[α]_D^{20}$: −311.96° (c 0.092, DMF)

Chiral HPLC (method HPLC-A): R$_t$ 6.17 min, chiral purity 100%

Example 55: Synthesis of 15-hydroxy-2-phenyl-12,13,14,16-tetrahydro-11H-4-oxa-1(1,3)-pyrido[2,1-f][1,2,4]triazina-3(1,2)-benzenacyclodecaphane-14,16-dione (Compound 55)

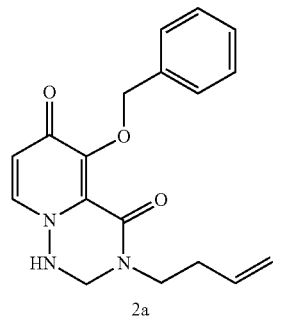

2a

+

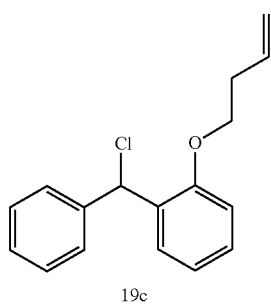

19c

NaH
DMF rt, 2 h

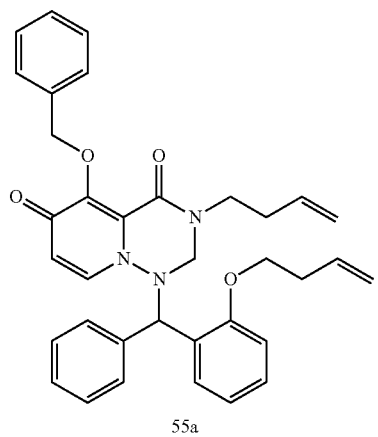

55a

1) Hoveyda-Grubbs II
DCE
80° C., 2 h

2) Siliabond ® DMT
rt o/n

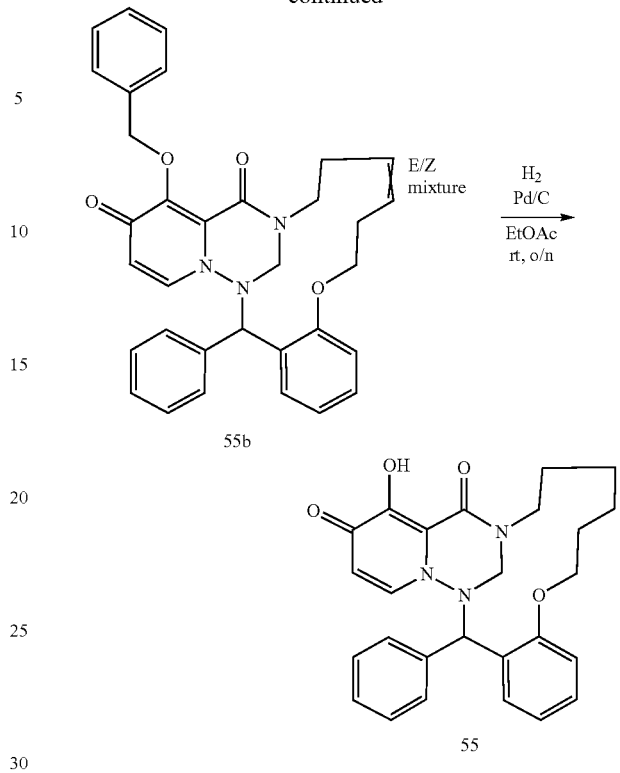

Synthesis of Intermediate 55a:

5-(benzyloxy)-3-(but-3-en-1-yl)-1-((2-(but-3-en-1-yloxy)phenyl)(phenyl)methyl)-2,3-dihydro-1H-pyrido[2,1-f][1,2,4]triazine-4,6-dione (intermediate 55a, 3.52 g) was obtained using the procedure described for intermediate 2d.

Synthesis of Intermediate 55b:

(E/Z)-15-(benzyloxy)-2-phenyl-12,13,14,16-tetrahydro-11H-4-oxa-1(1,3)-pyrido[2,1-f][1,2,4]triazina-3(1,2)-benzenacyclodecaphan-7-ene-14,16-dione (intermediate 55b, mixture of E and Z isomers, 1.46 g) was obtained using the procedure described for intermediate 1f.

Synthesis of Compound 55:

15-hydroxy-2-phenyl-12,13,14,16-tetrahydro-11H-4-oxa-1(1,3)-pyrido[2,1-f][1,2,4]triazina-3(1,2)-benzenacyclodecaphane-14,16-dione (compound 55, 74.7 mg) was obtained using the procedure described for compound 2. Compound 55 was purified by flash chromatography over silica gel (30 μm, 4 g, $CH_2Cl_2/CH_3OH$ from 99:1 to 97:3). The pure fractions were collected and evaporated to dryness. The residue was taken up in $Et_2O$ and the solid was filtered off to give compound 55.

Compound 55:

$^1$H NMR (500 MHz, DMSO-$d_6$) δ ppm 11.60 (br s, 1H), 8.05 (dd, J=7.7, 1.1 Hz, 1H), 7.30-7.36 (m, 1H), 7.16-7.29 (m, 6H), 7.14 (t, J=7.4 Hz, 1H), 6.99 (d, J=8.2 Hz, 1H), 5.76 (s, 1H), 5.44 (d, J=7.6 Hz, 1H), 5.04 (d, J=13.2 Hz, 1H), 4.34 (dd, J=11.7, 5.4 Hz, 1H), 4.28 (d, J=13.2 Hz, 1H), 4.05-4.12 (m, 1H), 3.97-4.05 (m, 1H), 2.78 (br d, J=13.9 Hz, 1H), 1.77-1.94 (m, 3H), 1.52-1.65 (m, 2H), 1.42-1.52 (m, 1H), 1.19-1.32 (m, 2H).

LC/MS (method LC-C): $R_t$ 2.95 min, MH$^+$446 m.p. 294.35° C.

Example 56: Synthesis of (18*R,*Z)-12-hydroxy-18-phenyl-5,6,9,18-tetrahydro-10,17-methano-dipyrido[1,2-b:3',4'-k][1,2,5]triazacyclotridecine-11,13-dione (Compound 56A) and (18*S,*Z)-12-hydroxy-18-phenyl-5,6,9,18-tetrahydro-10,17-methanodipyrido[1,2-b:3',4'-k][1,2,5]triazacyclotridecine-11,13-dione (Compound 56B)
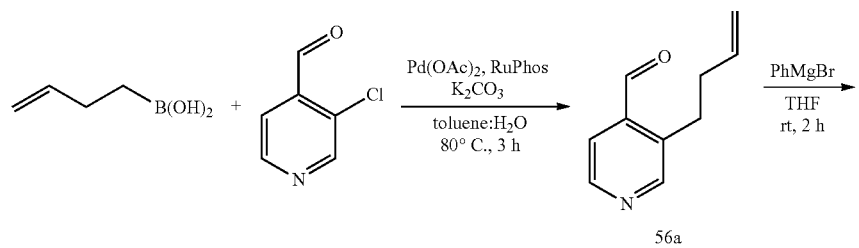
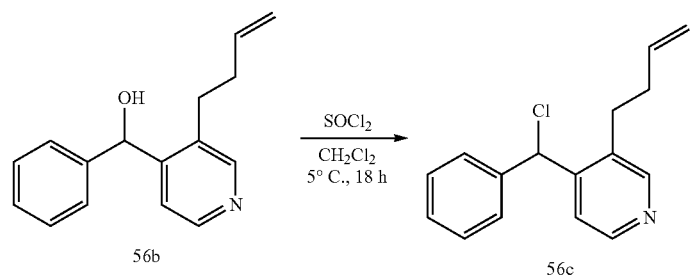
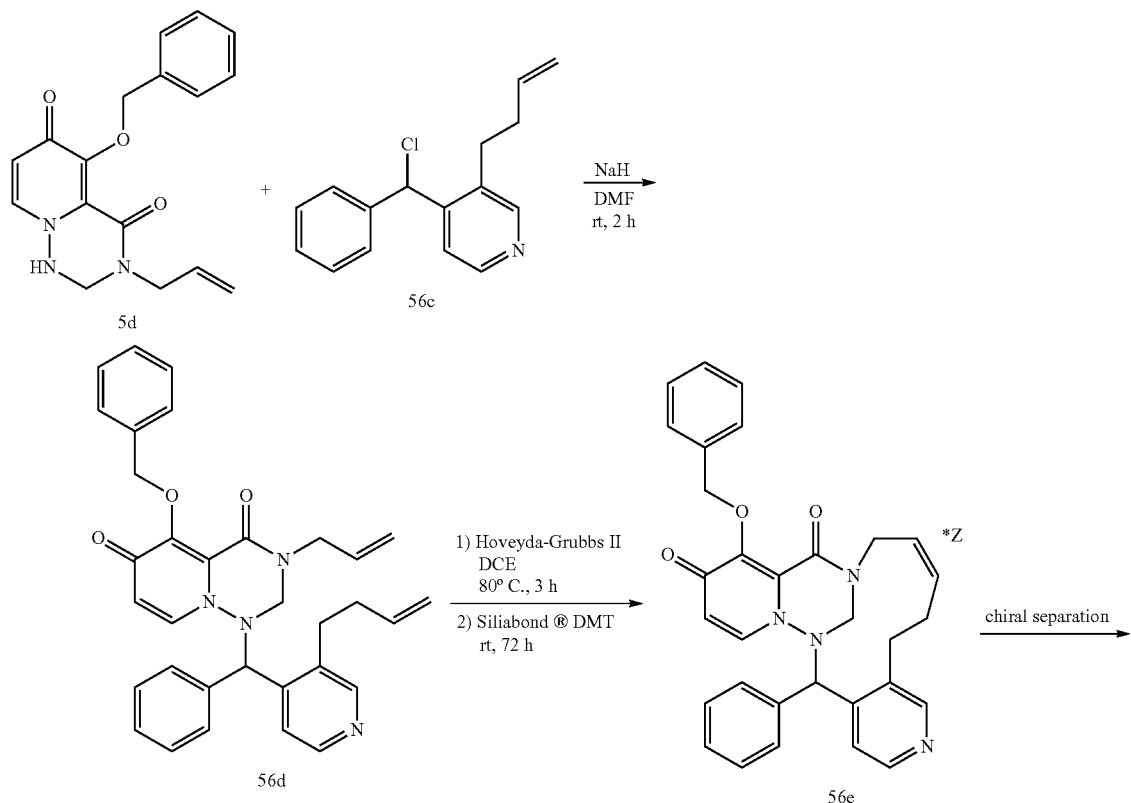

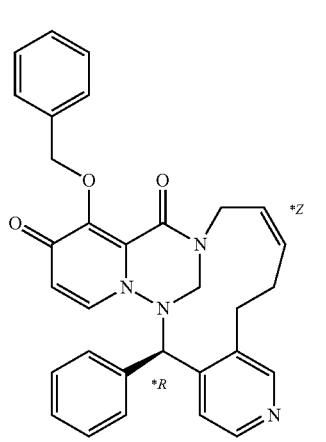

56ea

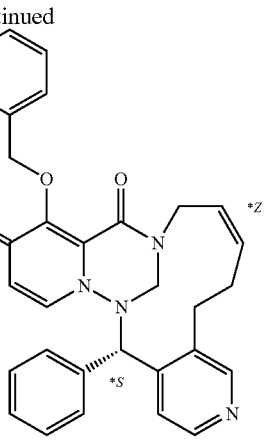

56eb

TFA
CH₂Cl₂
rt, 1 h

TFA
CH₂Cl₂
rt, 1 h

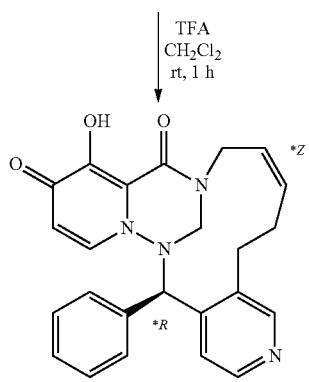

56A

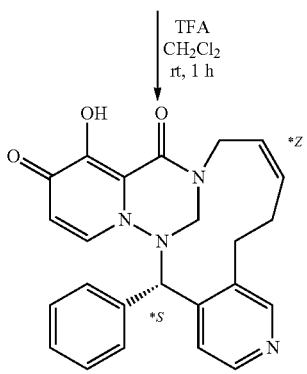

56A

Synthesis of Intermediate 56a:

A mixture of 3-chloroisonicotinaldehyde [CAS72990-37-5] (3.00 g, 21.2 mmol), but-3-en-1-ylboronic acid (2.65 g, 26.5 mmol) and K₂CO₃ (8.79 g, 63.6 mmol) in toluene (79 mL) and water (11 mL) was degassed under nitrogen. Pd(OAc)₂ (0.24 g, 1.06 mmol) and RuPhos (0.99 g, 2.12 mmol) were added and the reaction mixture was stirred at 80° C. for 3 h. A 1M aqueous solution of NaOH (150 mL) was added and the mixture was extracted with EtOAc (twice). The organic phase was dried over MgSO₄, filtered and concentrated in vacuo. Purification was carried out by flash chromatography over silica gel (30 μm, 80 g, heptane/EtOAc from 85/15 to 65/35) to afford 3-(but-3-en-1-yl)isonicotinaldehyde (intermediate 56a, 2.0 g).

Synthesis of Intermediate 56b:

(3-(but-3-en-1-yl)pyridin-4-yl)(phenyl)methanol (intermediate 56b, 2.4 g) was obtained using the procedure described for intermediate 2b.

Synthesis of Intermediate 56c:

3-(but-3-en-1-yl)-4-(chloro(phenyl)methyl)pyridine (intermediate 56c, 2.4 g) was obtained using the procedure described for intermediate 5a.

Synthesis of Intermediate 56d:

3-allyl-5-(benzyloxy)-1-((3-(but-3-en-1-yl)pyridin-4-yl)(phenyl)methyl)-2,3-dihydro-1H-pyrido[2,1-f][1,2,4]triazine-4,6-dione (intermediate 56d, 3.4 g) was obtained using the procedure described for intermediate 2d.

Synthesis of Intermediate 56e:

(*Z)-12-(benzyloxy)-18-phenyl-5,6,9,18-tetrahydro-10,17-methanodipyrido[1,2-b:3',4'-k][1,2,5]triazacyclotridecine-11,13-dione (intermediate 56e, 1.2 g) was obtained using the procedure described for intermediate 1f.

The enantiomers were separated via chiral SFC (Stationary phase: Whelk-O1 (S,S) 5 μm 250*21.2 mm, Mobile phase: 45% CO₂, 55% MeOH) to afford the first eluted enantiomer 56ea (325 mg) and the second eluted enantiomer 56eb (394 mg) containing impurities. Intermediate 56eb was purified again via chiral SFC (Stationary phase: Whelk-O1 (S,S) 5 μm 250*21.2 mm, Mobile phase: 45% CO₂, 55% MeOH) to give pure intermediate 56eb (316 mg).

Synthesis of Compound 56A:

(18*R,*Z)-12-(benzyloxy)-18-phenyl-5,6,9,18-tetrahydro-10,17-methanodipyrido[1,2-b:3',4'-k][1,2,5]triazacyclotridecine-11,13-dione (compound 56A, 198 mg) was obtained using the procedure described for compound 1.

Compound 56A:

$^1$H NMR (400 MHz, DMSO-d₆) δ ppm 8.61 (d, J=5.1 Hz, 1H), 8.42 (s, 1H), 8.03 (d, J=5.1 Hz, 1H), 7.11-7.30 (br s, 5H), 7.17 (d, J=7.6 Hz, 1H), 6.00 (br ddd, J=15.3, 8.7, 6.3 Hz, 1H), 5.42-5.55 (m, 1H), 5.46 (d, J=7.6 Hz, 1H), 5.11-5.19 (m, 2H), 4.73 (br dd, J=14.1, 5.1 Hz, 1H), 4.26 (d, J=13.6 Hz, 1H), 3.08 (br dd, J=13.9, 7.8 Hz, 1H), 2.65 (br d, J=10.1 Hz, 2H), 2.41-2.48 (m, 1H), 1.93-2.06 (m, 1H).

LC/MS (method LC-C): Rt 2.03 min, MH⁺415

[α]$_D^{20}$: +631.35° (c 0.114, DMF)

Chiral HPLC (method HPLC-A): R$_t$ 5.96 min, chiral purity 100%

Synthesis of Compound 56B:

TFA (4.8 mL, 62.6 mmol) was added to intermediate 56eb (316 mg, 0.63 mmol). The mixture was stirred at rt for 1 h.

The mixture was concentrated in vacuo. Purification was carried out by preparative LC (regular SiOH, 30 μm, 12 g, CH$_2$Cl$_2$/MeOH from 99/1 to 95/5). The residue was taken up in CH$_2$Cl$_2$ (4.0 mL) and Si-piperidine silicycle (0.56 g, 0.75 mmol) was added and the mixture was stirred at rt for 18 h. The mixture was filtered, dried and freeze-dried in CH$_3$CN/water to give (18*S,*Z)-12-hydroxy-18-phenyl-5,6,9,18-tetrahydro-10,17-methanodipyrido[1,2-b:3',4'-k][1,2,5]triazacyclotridecine-11,13-dione (compound 56B, 180 mg). Compound 56B:

$^1$H NMR (400 MHz, DMSO-d$_6$) δ ppm 8.62 (d, J=5.1 Hz, 1H), 8.42 (s, 1H), 8.03 (d, J=5.1 Hz, 1H), 7.09-7.31 (m, 6H), 5.93-6.06 (m, 1H), 5.42-5.55 (m, 1H), 5.46 (d, J=7.6 Hz, 1H), 5.11-5.20 (m, 2H), 4.73 (br dd, J=13.6, 5.1 Hz, 1H), 4.26 (d, J=13.6 Hz, 1H), 3.08 (br dd, J=13.9, 7.8 Hz, 1H), 2.65 (br d, J=10.1 Hz, 2H), 2.42-2.49 (m, 1H), 1.93-2.06 (m, 1H).

LC/MS (method LC-C): R$_t$ 2.03 min, MH$^+$415
[α]$_D^{20}$: −673.18° (c 0.097, DMF)
Chiral HPLC (method HPLC-A): Rt 5.40 min, chiral purity 100%

Example 57: Synthesis of (16*R,E)-13-fluoro-4-hydroxy-16-(pyridin-2-yl)-7,10,11,16-tetrahydro-6,17-methanobenzo[k]pyrido[1,2-b][1,2,5]triazacyclotridecine-3,5-dione (Compound 57A) and (16*S,E)-13-fluoro-4-hydroxy-16-(pyridin-2-yl)-7,10,11,16-tetrahydro-6,17-methanobenzo[k]pyrido[1,2-b][1,2,5]triazacyclotridecine-3,5-dione (Compound 57B)

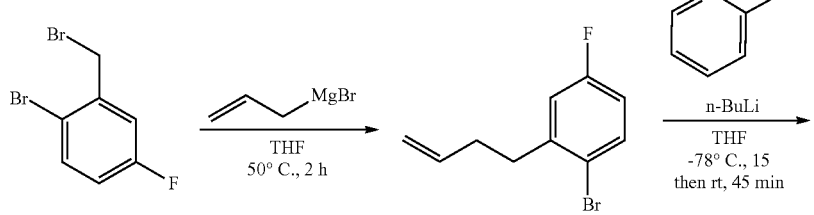

57a

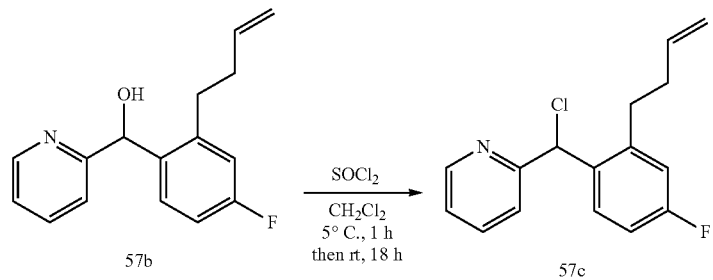

57b        57c

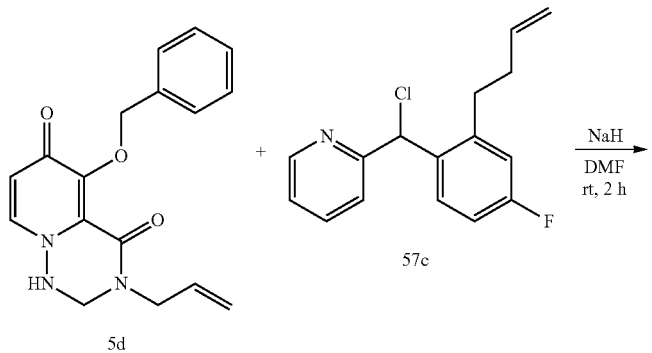

5d

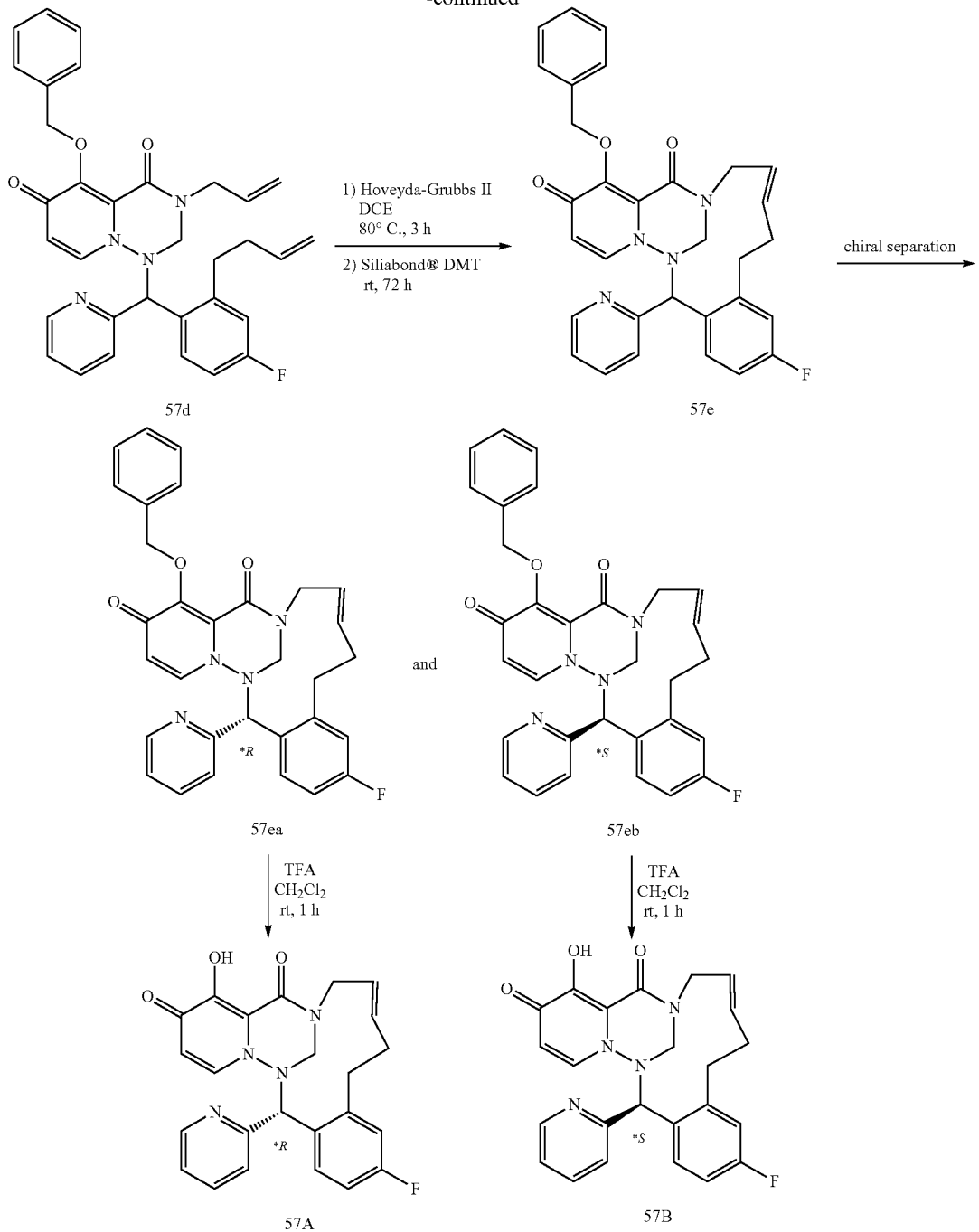

Synthesis of Intermediate 57a:

Under nitrogen atmosphere, allylmagnesium bromide (1.0 M, 17 mL, 17.0 mmol) was added slowly at 0° C. to a solution of 1-bromo-2-(bromomethyl)-4-fluorobenzene [CAS 112399-50-5] (3.00 g, 11.2 mmol) in anhydrous THF (27 mL). The reaction mixture was stirred at 50° C. for 2 h. The reaction was quenched by the addition of a 10% aqueous solution of NH$_4$Cl and the mixture was extracted with EtOAc. The organic phase was washed with brine, dried over MgSO$_4$, filtered and evaporated in vacuo to afford 1-bromo-2-(but-3-en-1-yl)-4-fluorobenzene (intermediate 57a, 2.5 g).

Synthesis of Intermediate 57b (2-(but-3-en-1-yl)-4-fluorophenyl)(pyridin-2-yl)methanol (intermediate 57b, 1.8 g) was obtained using the procedure described for intermediate 23a. Crude intermediate 57b was purified by preparative LC (Stationary phase: regular SiOH 30 µm, 40 g, Mobile phase: CH$_2$Cl$_2$/MeOH from 100/0 to 98/2).

Synthesis of Intermediate 57c 2-((2-(but-3-en-1-yl)-4-fluorophenyl)chloromethyl)pyridine (intermediate 57c, 1.9 g) was obtained using the procedure described for intermediate 5a.

Synthesis of Intermediate 57d 3-allyl-5-(benzyloxy)-1-((2-(but-3-en-1-yl)-4-fluorophenyl)(pyridin-2-yl)methyl)-2,3-dihydro-1H-pyrido[2,1-f][1,2,4]triazine-4,6-dione (intermediate 57d, 0.90 g) was obtained using the procedure described for intermediate 2d.

Synthesis of Intermediate 57e (E)-4-(benzyloxy)-13-fluoro-16-(pyridin-2-yl)-7,10,11,16-tetrahydro-6,17-methanobenzo[k]pyrido[1,2-b][1,2,5]triazacyclotridecine-3,5-dione (intermediate 57e, 620 mg) was obtained using the procedure described for intermediate 1f.

The enantiomers were separated via chiral SFC (Stationary phase: CHIRALPAK AD-H 5 μm, 250*30 mm, Mobile phase: 60% $CO_2$, 40% EtOH) to afford the first eluted enantiomer 57ea (287 mg) and the second eluted enantiomer 57eb (298 mg).

Synthesis of Compound 57A:

(16*R,E)-13-fluoro-4-hydroxy-16-(pyridin-2-yl)-7,10,11,16-tetrahydro-6,17-methanobenzo[k]pyrido[1,2-b][1,2,5]triazacyclotridecine-3,5-dione (compound 57A, 190 mg) was obtained using the procedure described for compound 1.

Compound 57A:

$^1$H NMR (500 MHz, DMSO-$d_6$) δ ppm 8.37 (br d, J=4.1 Hz, 1H), 8.16 (dd, J=8.7, 6.1 Hz, 1H), 7.66 (td, J=7.7, 1.6 Hz, 1H), 7.40 (d, J=7.9 Hz, 1H), 7.27 (td, J=8.5, 2.8 Hz, 1H), 7.22 (dd, J=6.8, 4.9 Hz, 1H), 7.16 (d, J=7.9 Hz, 1H), 7.10 (dd, J=10.1, 2.5 Hz, 1H), 5.94 (br dt, J=15.2, 7.7 Hz, 1H), 5.50-5.59 (m, 1H), 5.52 (d, J=7.6 Hz, 1H), 5.37 (s, 1H), 5.14 (d, J=13.9 Hz, 1H), 4.71 (br dd, J=13.9, 5.0 Hz, 1H), 4.30 (d, J=13.6 Hz, 1H), 3.11 (dd, J=14.0, 8.0 Hz, 1H), 2.56-2.67 (m, 3H), 2.01-2.14 (m, 1H).

LC/MS (method LC-C): Rt 2.47 min, MH$^+$433

$[α]_D^{20}$: −658.94° (c 0.104, DMF)

Chiral HPLC (method HPLC-A): Rt 4.97 min, chiral purity 100%

Synthesis of Compound 57B:

(16*S,E)-13-fluoro-4-hydroxy-16-(pyridin-2-yl)-7,10,11,16-tetrahydro-6,17-methanobenzo[k]pyrido[1,2-b][1,2,5]triazacyclotridecine-3,5-dione (compound 57B, 187 mg) was obtained using the procedure described for compound 1.

Compound 57B:

$^1$H NMR (500 MHz, DMSO-$d_6$) δ ppm 8.36 (d, J=4.1 Hz, 1H), 8.15 (dd, J=8.8, 6.3 Hz, 1H), 7.65 (td, J=7.7, 1.6 Hz, 1H), 7.40 (d, J=7.9 Hz, 1H), 7.27 (td, J=8.6, 2.7 Hz, 1H), 7.22 (dd, J=6.9, 5.0 Hz, 1H), 7.15 (d, J=7.6 Hz, 1H), 7.10 (dd, J=10.1, 2.8 Hz, 1H), 5.94 (dt, J=15.4, 7.7 Hz, 1H), 5.49-5.58 (m, 1H), 5.51 (d, J=7.6 Hz, 1H), 5.37 (s, 1H), 5.13 (d, J=13.6 Hz, 1H), 4.71 (dd, J=14.0, 4.9 Hz, 1H), 4.29 (d, J=13.9 Hz, 1H), 3.10 (dd, J=13.9, 8.2 Hz, 1H), 2.54-2.66 (m, 3H), 2.02-2.13 (m, 1H).

LC/MS (method LC-C): R$_t$ 2.47 min, MH$^+$433

$[α]_D^{20}$: +588.55° (c 0.131, DMF)

Chiral HPLC (method HPLC-A): Rt 5.64 min, chiral purity 100%

Example 58: Synthesis of (16*R,E)-13,14-difluoro-4-hydroxy-16-(pyridin-2-yl)-7,10,11,16-tetrahydro-6,17-methanobenzo[k]pyrido[1,2-b][1,2,5]triazacyclotridecine-3,5-dione (Compound 58A) and (16*SE)-13,14-difluoro-4-hydroxy-16-(pyridin-2-yl)-7,10,11,16-tetrahydro-6,17-methanobenzo[k]pyrido[1,2-b][1,2,5]triazacyclotridecine-3,5-dione (Compound 58B)

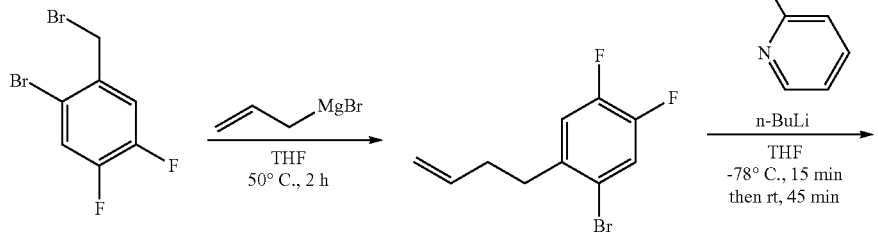

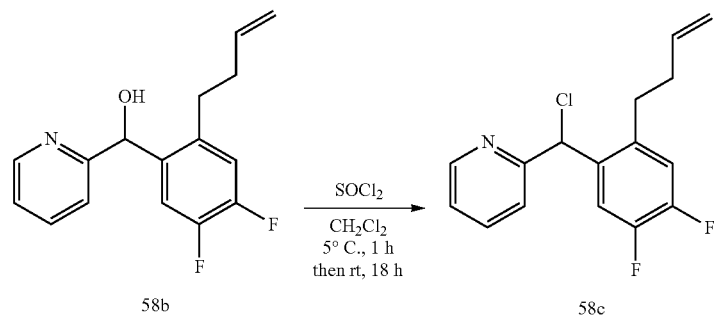

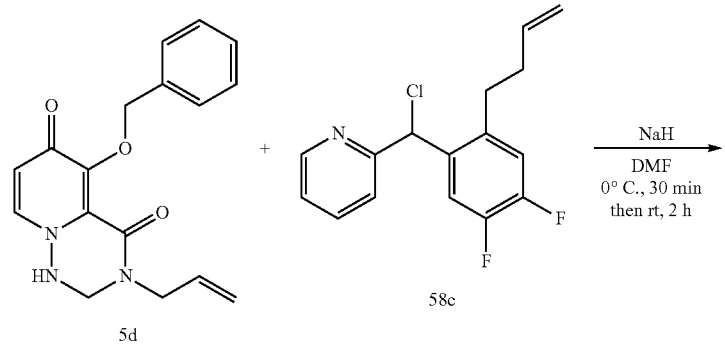
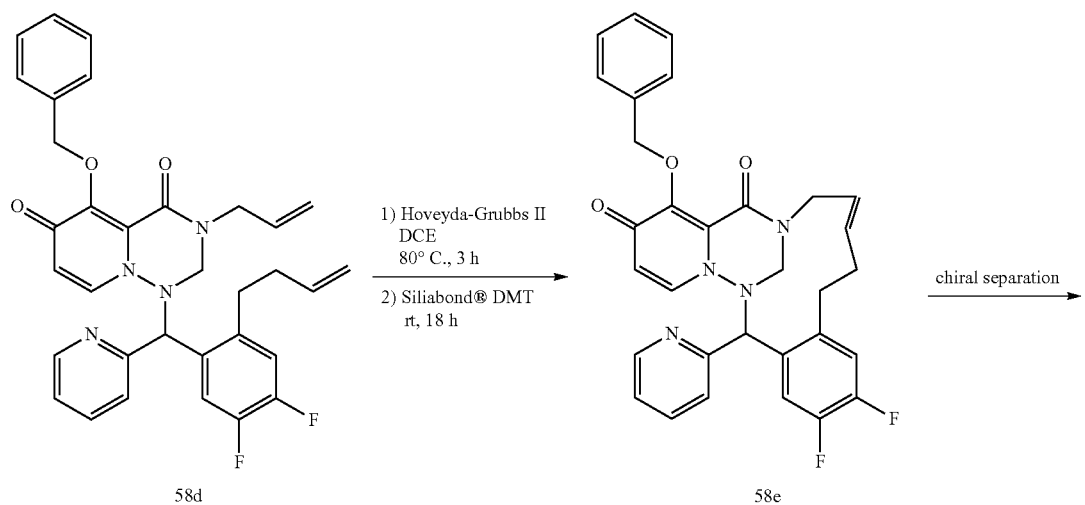
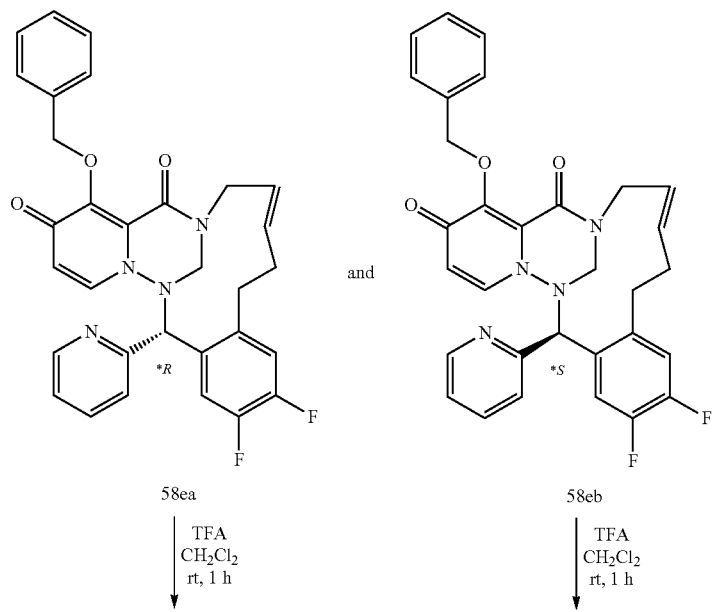

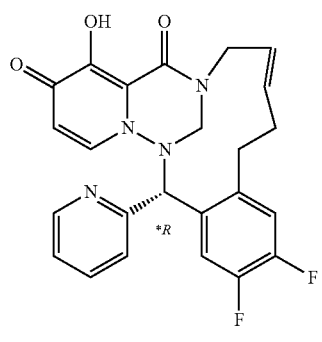

58A

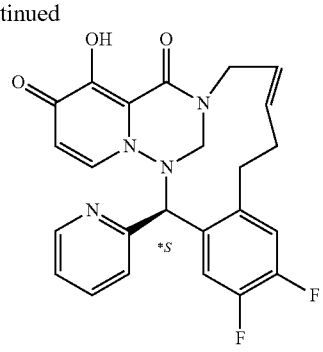

58B

Synthesis of Intermediate 58a:

1-Bromo-2-(but-3-en-1-yl)-4,5-difluorobenzene (intermediate 58a, 2.5 g) was obtained using the procedure described for intermediate 57a.

Synthesis of Intermediate 58b (2-(But-3-en-1-yl)-4,5-difluorophenyl)(pyridin-2-yl)methanol (intermediate 58b, 0.72 g) was obtained using the procedure described for intermediate 23a.

Synthesis of Intermediate 58c 2-((2-(But-3-en-1-yl)-4,5-difluorophenyl)chloromethyl)pyridine (intermediate 58c, 770 mg) was obtained using the procedure described for intermediate 5a.

Synthesis of Intermediate 58d 3-allyl-5-(benzyloxy)-1-((2-(but-3-en-1-yl)-4,5-difluorophenyl)(pyridin-2-yl)methyl)-2,3-dihydro-1H-pyrido[2,1-f][1,2,4]triazine-4,6-dione (intermediate 58d, 0.71 g) was obtained using the procedure described for intermediate 2d.

Synthesis of Intermediate 58e (E)-4-(benzyloxy)-13,14-difluoro-16-(pyridin-2-yl)-7,10,11,16-tetrahydro-6,17-methanobenzo[k]pyrido[1,2-b][1,2,5]triazacyclotridecine-3,5-dione (intermediate 58e, 0.57 g) was obtained using the procedure described for intermediate 1f.

The enantiomers were separated via chiral SFC (Stationary phase: CHIRALPAK AD-H 5 μm, 250*30 mm, Mobile phase: 60% CO$_2$, 40% EtOH) to afford the first eluted enantiomer 58ea (234 mg) and the second eluted enantiomer 58eb (228 mg).

Synthesis of Compound 58A:

(16*R,E)-13,14-difluoro-4-hydroxy-16-(pyridin-2-yl)-7,10,11,16-tetrahydro-6,17-methanobenzo[k]pyrido[1,2-b][1,2,5]triazacyclotridecine-3,5-dione (compound 58A, 145 mg) was obtained using the procedure described for compound 1.

Compound 58A:

$^1$H NMR (500 MHz, DMSO-d$_6$) δ ppm 8.39 (d, J=4.1 Hz, 1H), 8.12 (dd, J=12.6, 8.5 Hz, 1H), 7.67 (td, J=7.7, 1.6 Hz, 1H), 7.45 (d, J=7.9 Hz, 2H), 7.35 (dd, J=11.8, 8.4 Hz, 1H), 7.24 (dd, J=7.1, 5.2 Hz, 1H), 7.20 (d, J=7.6 Hz, 1H), 5.94 (dt, J=15.4, 7.6 Hz, 1H), 5.54-5.64 (m, 1H), 5.50 (d, J=7.9 Hz, 1H), 5.35 (s, 1H), 5.13 (d, J=13.6 Hz, 1H), 4.71 (br dd, J=13.9, 5.0 Hz, 1H), 4.35 (d, J=13.6 Hz, 1H), 3.09 (dd, J=13.9, 8.2 Hz, 1H), 2.53-2.63 (m, 3H), 2.01-2.13 (m, 1H).

LC/MS (method LC-C): Rt 2.59 min, MH$^+$451

$[α]_D^{20}$: −602.11° (c 0.161, DMF)

Chiral HPLC (method HPLC-A): Rt 4.47 min. chiral purity 100%

Synthesis of Compound 58B:

(16*S,E)-13,14-difluoro-4-hydroxy-16-(pyridin-2-yl)-7,10,11,16-tetrahydro-6,17-methanobenzo[k]pyrido[1,2-b][1,2,5]triazacyclotridecine-3,5-dione (compound 58B, 145 mg) was obtained using the procedure described for compound 1.

Compound 58B:

$^1$H NMR (500 MHz, DMSO-d$_6$) δ ppm 8.39 (br d, J=4.4 Hz, 1H), 8.12 (dd, J=12.3, 8.5 Hz, 1H), 7.67 (br td, J=7.6, 1.4 Hz, 1H), 7.42-7.48 (m, 2H), 7.35 (br dd, J=11.7, 8.5 Hz, 1H), 7.24 (dd, J=6.9, 5.0 Hz, 1H), 7.20 (d, J=7.6 Hz, 1H), 5.94 (dt, J=15.3, 7.5 Hz, 1H), 5.55-5.64 (m, 1H), 5.51 (d, J=7.9 Hz, 1H), 5.35 (s, 1H), 5.13 (d, J=13.9 Hz, 1H), 4.71 (br dd, J=13.9, 5.0 Hz, 1H), 4.35 (d, J=13.9 Hz, 1H), 3.09 (br dd, J=13.9, 8.2 Hz, 1H), 2.53-2.63 (m, 3H), 2.02-2.13 (m, 1H).

LC/MS (method LC-C): Rt 2.59 min, MH$^+$451

$[α]_D^{20}$: +618.82° (c 0.085, DMF)

Chiral HPLC (method HPLC-A): Rt 5.16 min, chiral purity 100%

Example 59: Synthesis of (18*R,Z)-4-fluoro-18-(3-fluorophenyl)-12-hydroxy-6,9-dihydro-18H-10,17-methanobenzo[b]pyrido[1,2-f][1]oxa[5,6,9]triazacyclotridecine-11,13-dione (Compound 59A) and (18*S,Z)-4-fluoro-18-(3-fluorophenyl)-12-hydroxy-6,9-dihydro-18H-10,17-methanobenzo[b]pyrido[1,2-f][1]oxa[5,6,9]triazacyclotridecine-11,13-dione (Compound 59B)
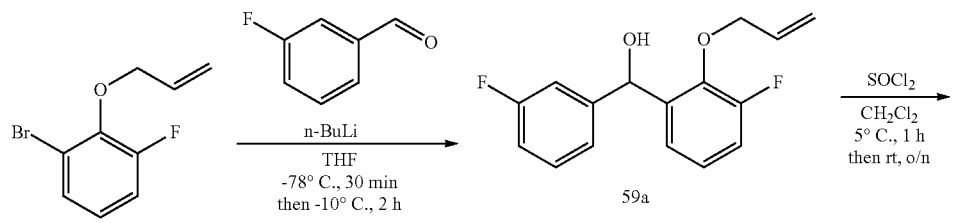
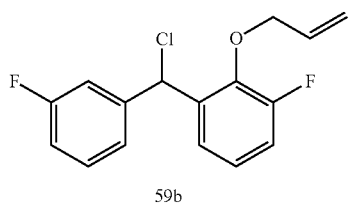
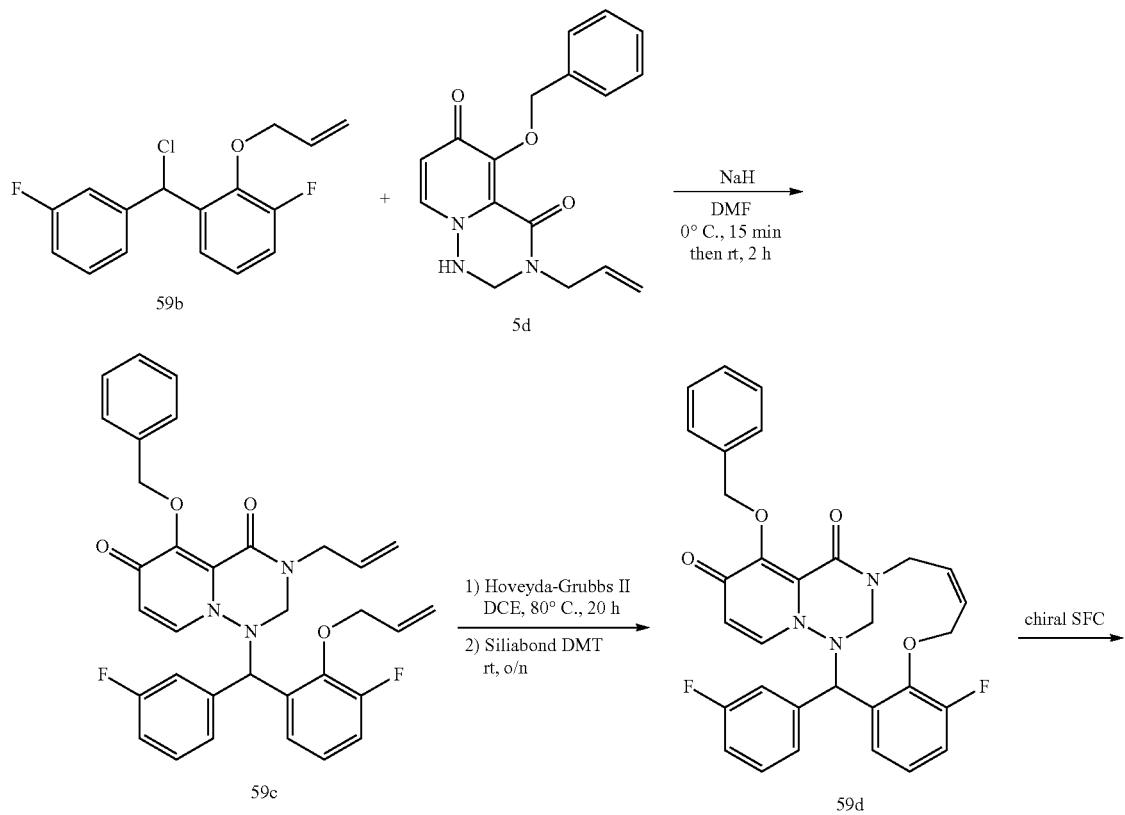

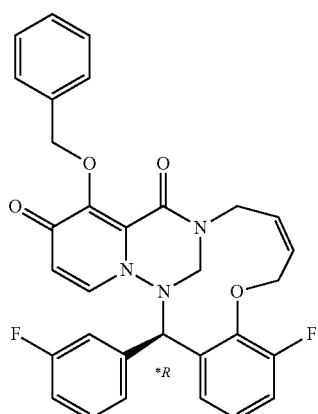

59da

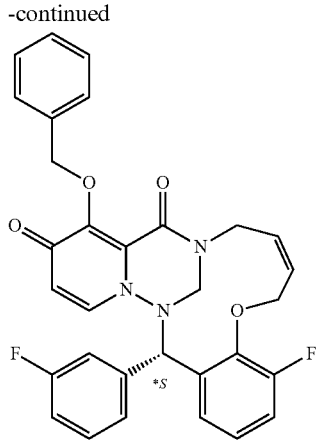

and

59db

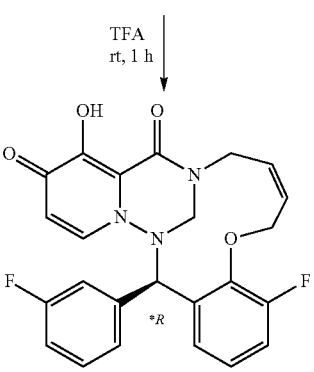

59A

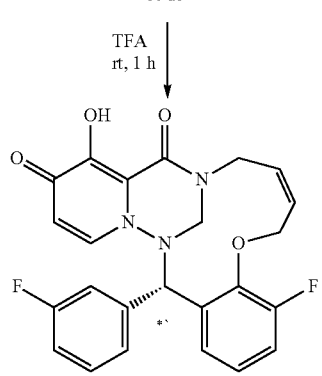

59B

Synthesis of Intermediate 59a:

2-(allyloxy)-1-bromo-3-fluorobenzene [CAS 1010422-27-1] (5.00 g, 21.6 mmol) was dissolved in anhydrous THF (50 mL). The reaction mixture was cooled to −78° C. and n-BuLi (2.5 M, 9.1 mL, 22.7 mmol) was added dropwise. After 15 min 3-fluorobenzaldehyde (2.82 g, 22.7 mmol) was added. The reaction mixture was stirred at −78° C. for 45 min and slowly warmed to −10° C. over 2 h. The reaction was quenched by addition of a saturated aqueous of NH$_4$Cl (50 mL). The aqueous phase was extracted with EtOAc (twice). The combined organic extracts were dried over Na$_2$SO$_4$, filtered and concentrated in vacuo. Purification was carried out by flash chromatography (80 g, petroleum ether/EtOAc from 100/0 to 85/15) to afford (2-(allyloxy)-3-fluorophenyl)(3-fluorophenyl)methanol (intermediate 59a, 3.2 g).

Synthesis of Intermediate 59b 2-(allyloxy)-1-(chloro(3-fluorophenyl)methyl)-3-fluorobenzene ene (intermediate 59b, 3.4 g) was obtained using the procedure described for intermediate 5a.

Synthesis of Intermediate 59c 3-allyl-1-((2-(allyloxy)-3-fluorophenyl)(3-fluorophenyl)methyl)-5-(benzyloxy)-2,3-dihydro-1H-pyrido[2,1-f][1,2,4]triazine-4,6-dione (intermediate 59c, 960 mg) was obtained using the procedure reported for intermediate 2d.

Synthesis of Intermediate 59d

A degassed solution of intermediate 59c (1.00 g, 1.76 mmol) and Hoveyda-Grubbs second generation catalyst (220 mg, 0.35 mmol) in anhydrous DCE (90 mL) was stirred at 80° C. for 2 h. The reaction mixture was concentrated in vacuo. The residue was purified by flash chromatography (120 g, CH$_2$Cl$_2$/MeOH from 100/0 to 98/2). The residue was dissolved in CH$_2$Cl$_2$ (60 mL) and siliabond DMT (4.61 g, 0.28 mmol) was added. The mixture was stirred at rt overnight. The reaction mixture was filtered through Celite®. The filter-cake was washed with CH$_2$Cl$_2$ and the filtrate was evaporated under reduced pressure. Purification was carried out by flash chromatography (80 g, CH$_2$Cl$_2$/MeOH from 100/0 to 98/2). A second purification was performed by flash chromatography C18 (45 g, H$_2$O/MeOH from 70/30 to 0/100). The residue was purified a last time by flash chromatography (40 g, CH$_2$Cl$_2$/MeOH from 100/0 to 98/2) to afford (Z)-12-(benzyloxy)-4-fluoro-18-(3-fluorophenyl)-6,9-dihydro-18H-10,17-methanobenzo[b]pyrido[1,2-f][1]oxa[5,6,9]triazacyclotridecine-11,13-dione (intermediate 59d, 130 mg).

The enantiomers were separated by chiral SFC (Stationary phase: CHIRALPAK AD-H 5 μm 250*30 mm, Mobile phase: 65% CO$_2$, 35% EtOH) to give the first eluted enantiomer 59da (39 mg) and the second eluted enantiomer 59db (46 mg).

Synthesis of Compound 59A:

(18*R,Z)-4-fluoro-18-(3-fluorophenyl)-12-hydroxy-6,9-dihydro-18H-10,17-methanobenzo[b]pyrido[1,2-f][1]oxa[5,6,9]triazacyclotridecine-11,13-dione (compound 59A, 25 mg) was obtained using the procedure described for compound 1.

Compound 59A:

$^1$H NMR (500 MHz, DMSO-d$_6$) δ ppm 7.92 (br d, J=7.6 Hz, 1H), 7.32-7.45 (m, 3H), 7.20-7.28 (m, 1H), 7.04-7.15

(m, 2H), 7.00 (br s, 1H), 6.26 (br s, 1H), 5.95 (br s, 1H), 5.56 (d, J=7.6 Hz, 1H), 5.31 (br s, 1H), 5.15 (d, J=13.9 Hz, 1H), 4.81 (br dd, J=13.4, 4.3 Hz, 2H), 4.26 (d, J=13.9 Hz, 1H), 4.21 (br s, 1H), 3.20 (br dd, J=13.9, 7.9 Hz, 1H).

LC/MS (method LC-C): $R_t$ 2.63 min, MH$^+$452

$[\alpha]_D^{20}$: −667.62° (c 0.104, DMF)

Chiral HPLC (method HPLC-B): $R_t$ 5.90 min, chiral purity 100%

Synthesis of Compound 59B:

(18*S,Z)-4-fluoro-18-(3-fluorophenyl)-12-hydroxy-6,9-dihydro-18H-10,17-methanobenzo[b]pyrido[1,2-f][1]oxa[5,6,9]triazacyclotridecine-11,13-dione (compound 59B, 28 mg) was obtained using the procedure described for compound 1.

Compound 59B:

$^1$H NMR (500 MHz, DMSO-d$_6$) δ ppm 7.92 (br d, J=7.6 Hz, 1H), 7.32-7.45 (m, 3H), 7.19-7.28 (m, 1H), 7.03-7.14 (m, 2H), 7.00 (br s, 1H), 6.26 (br s, 1H), 5.94 (br s, 1H), 5.57 (d, J=7.6 Hz, 1H), 5.31 (br s, 1H), 5.15 (d, J=13.9 Hz, 1H), 4.81 (br dd, J=13.6, 4.4 Hz, 2H), 4.26 (d, J=13.9 Hz, 1H), 4.20 (br s, 1H), 3.21 (br dd, J=13.9, 7.9 Hz, 1H).

LC/MS (method LC-C): Rt 2.63 min, MH$^+$452

$[\alpha]_D^{20}$: +592.34° (c 0.102, DMF)

Chiral HPLC (method HPLC-B): Rt 4.56 min, chiral purity 100%

Example 60: Synthesis of (*Z)-15-hydroxy-2-phenyl-12,13,14,16-tetrahydro-11H-4-oxa-1(1,3)-pyrido[2,1-f][1,2,4]triazina-3(1,2)-benzenacyclodecaphan-8-ene-14,16-dione (Compound 60)

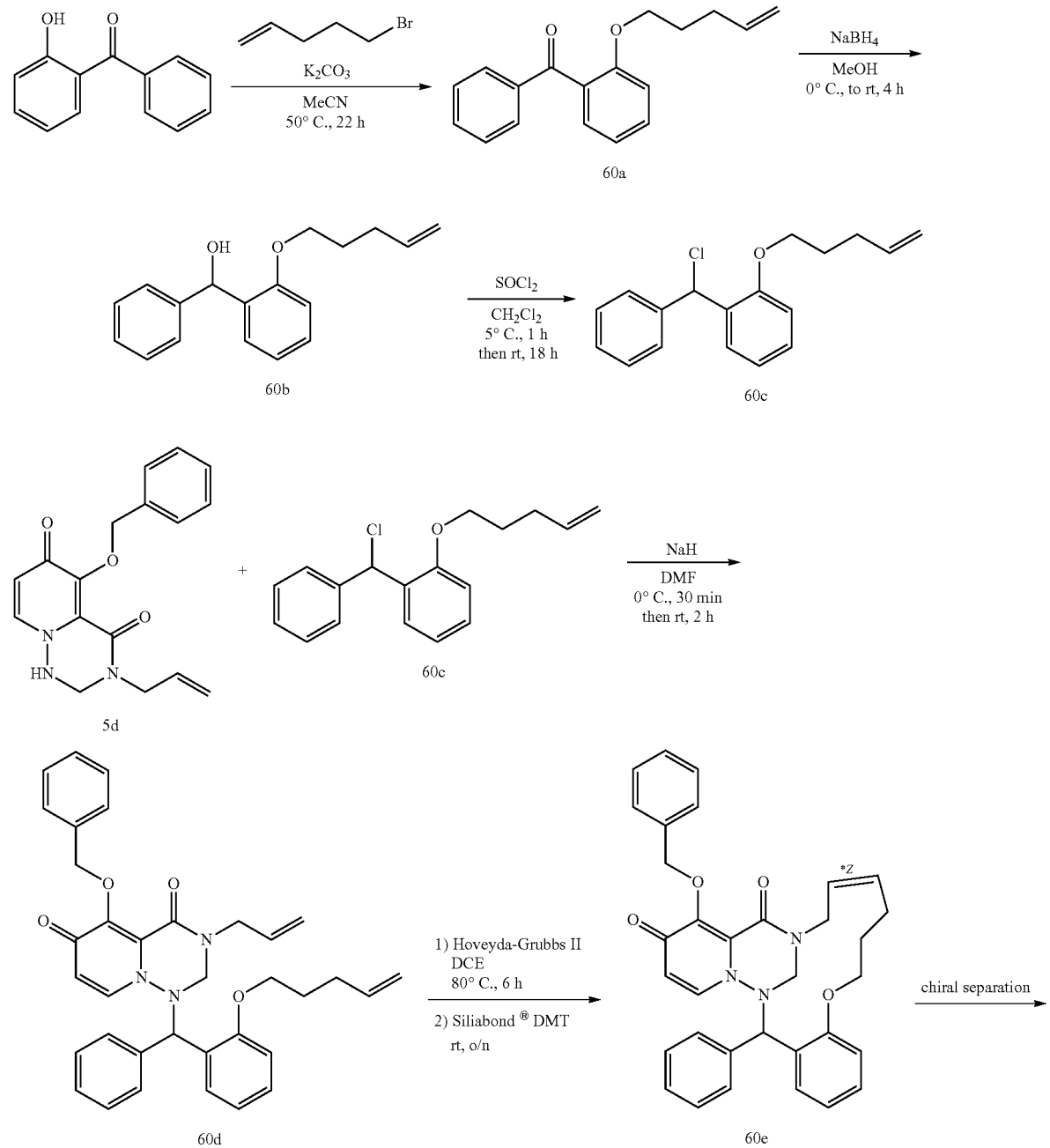

-continued

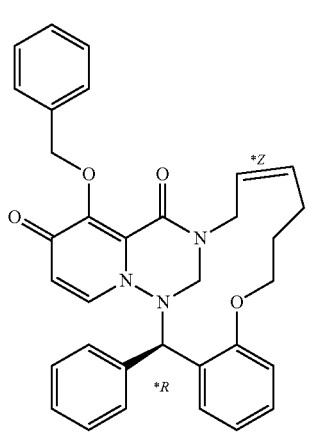
60ea *R and

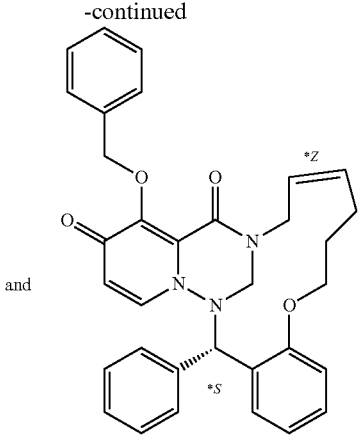
60eb *S

TFA
CH$_2$Cl$_2$
rt, 1 h

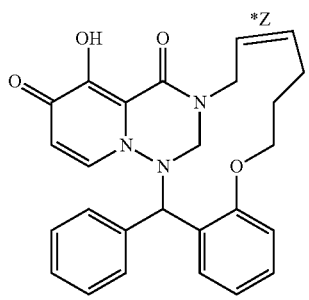
60

Synthesis of Intermediate 60a:

(2-(pent-4-en-1-yloxy)phenyl)(phenyl)methanone (intermediate 60a, 6.91 g) was obtained using the procedure described for intermediate 19a.

Synthesis of Intermediate 60b:

(2-(pent-4-en-1-yloxy)phenyl)(phenyl)methanol (intermediate 60b, 7.71 g) was obtained using the procedure described for intermediate 11b.

Synthesis of Intermediate 60c:

1-(chloro(phenyl)methyl)-2-(pent-4-en-1-yloxy)benzene (intermediate 60c, 3.5 g) was obtained using the procedure described for intermediate 5a.

Synthesis of Intermediate 60d:

3-allyl-5-(benzyloxy)-1-((2-(pent-4-en-1-yloxy)phenyl)(phenyl)methyl)-2,3-dihydro-1H-pyrido[2,1-f][1,2,4]triazine-4,6-dione (intermediate 60d, 2.0 g) was obtained using the procedure described for intermediate 2d.

Synthesis of Intermediate 60e:

(*Z)-15-(benzyloxy)-2-phenyl-12,13,14,16-tetrahydro-11H-4-oxa-1(1,3)-pyrido[2,1-f][1,2,4]triazina-3(1,2)-benzenacyclodecaphan-8-ene-14,16-dione (intermediate 60e, 872 mg) was obtained using the procedure described for intermediate 1f.

The enantiomers were separated via chiral SFC (Stationary phase: Welk-O1 (S,S) 5 µm 250*21.2 mm, Mobile phase: 50% CO$_2$, 50% MeOH) to afford the first eluted enantiomer 60ea (414 mg) and the second eluted enantiomer 60eb (389 mg).

Synthesis of Compound 60:

(*Z)-15-hydroxy-2-phenyl-12,13,14,16-tetrahydro-11H-4-oxa-1(1,3)-pyrido[2,1-fj][1,2,4]triazina-3(1,2)-benzenacyclodecaphan-8-ene-14,16-dione (compound 60, 120 mg) was obtained using the procedure described for compound 1. Racemization occurred during the reaction leading to the synthesis of racemic compound 60. Racemization was also observed when starting from enantiomer 60eb.

Compound 60:

$^1$H NMR (500 MHz, DMSO-d$_6$) δ ppm 11.40 (br s, 1H), 8.09 (br d, J=6.9 Hz, 1H), 7.28-7.36 (m, 2H), 7.18 (br s, 5H), 7.11 (br t, J=7.4 Hz, 1H), 6.94 (d, J=8.2 Hz, 1H), 5.82-5.89 (m, 1H), 5.81 (s, 1H), 5.54 (br dd, J=16.2, 4.6 Hz, 1H), 5.46 (d, J=7.6 Hz, 1H), 5.12 (d, J=13.2 Hz, 1H), 4.42 (br d, J=15.8 Hz, 1H), 4.21 (d, J=12.9 Hz, 1H), 4.02-4.16 (m, 1H), 3.24 (br dd, J=15.6, 7.1 Hz, 2H), 2.38-2.45 (m, 2H), 2.18-2.29 (m, 1H), 1.89-1.98 (m, 1H), 1.74-1.84 (m, 1H).

LC/MS (method LC-C): R$_t$ 2.84 min, MH$^+$444

Example 61: Synthesis of (18*R,Z)-4-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 61A) and (18*S,Z)-4-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 61B)
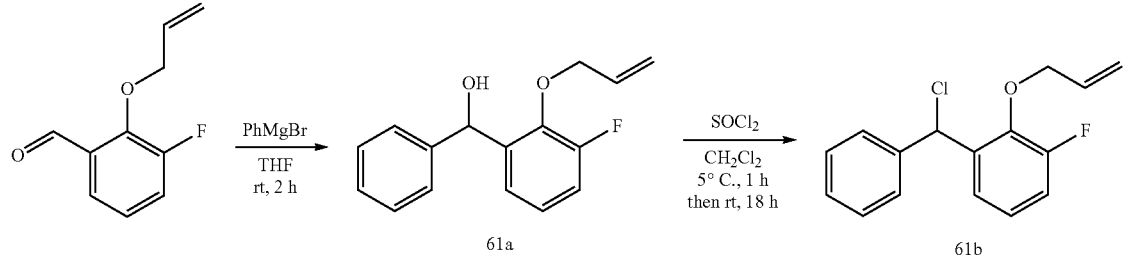
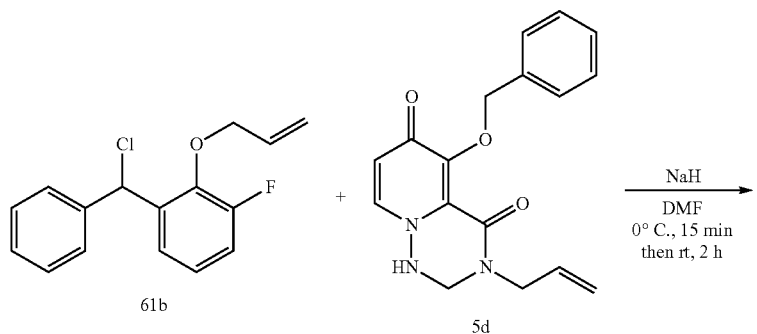
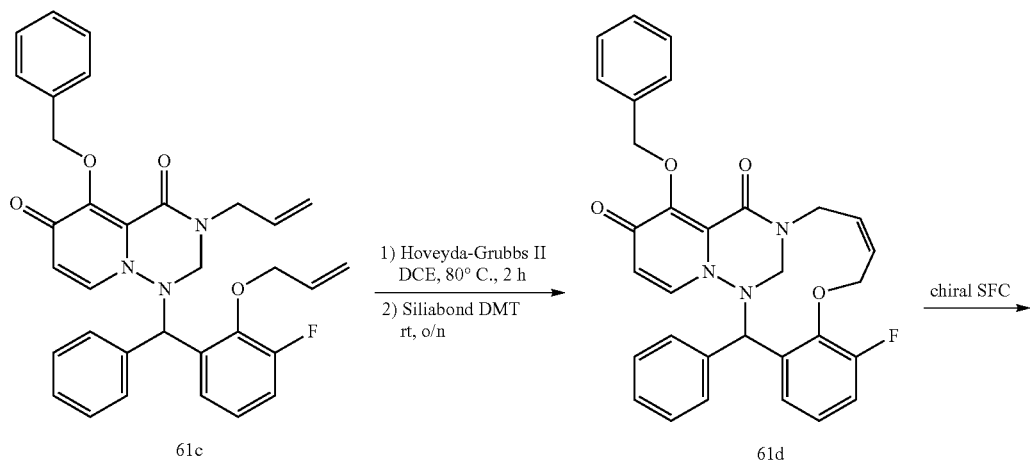

183

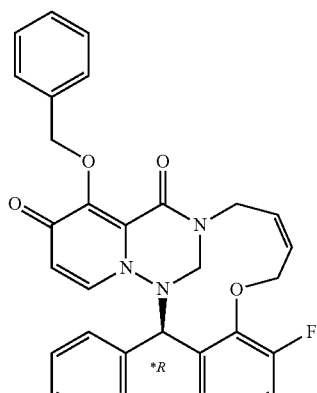

61da

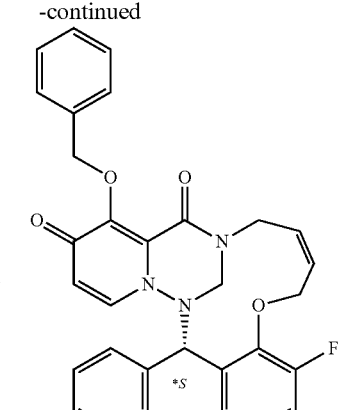

and

61db

TFA
rt, 1 h ↓

TFA
rt, 1 h ↓

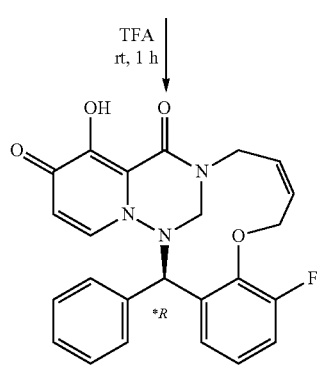

61A

184

-continued

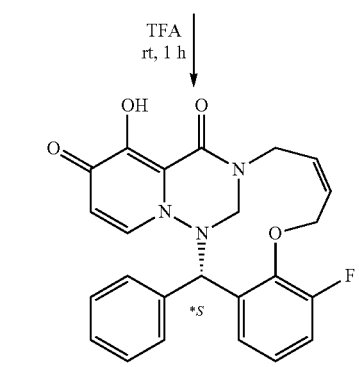

61B

Synthesis of Intermediate 61a:

(2-(allyloxy)-3-fluorophenyl)(phenyl)methanol (intermediate 61a, 2.8 g) was obtained using the procedure described for intermediate 2b. Crude intermediate 61a was purified by flash chromatography over silica gel (30 µm, 80 g, heptane/EtOAc 90/10).

Synthesis of Intermediate 61b 2-(allyloxy)-1-(chloro(phenyl)methyl)-3-fluorobenzene (intermediate 61b, 3.0 g) was obtained using the procedure described for intermediate 5a.

Synthesis of Intermediate 61c 3-allyl-1-((2-(allyloxy)-3-fluorophenyl)(phenyl)methyl)-5-(benzyloxy)-2,3-dihydro-1H-pyrido[2,1-f][1,2,4]triazine-4,6-dione (intermediate 61c, 0.65 g) was obtained using the procedure described for intermediate 2d.

Synthesis of Intermediate 61d (Z)-12-(benzyloxy)-4-fluoro-18-phenyl-6,9-dihydro-18H-10,17-methanobenzo[b]pyrido[1,2-f][1]oxa[5,6,9]triazacyclotridecine-11,13-dione (intermediate 61d, 0.50 g) was obtained using the procedure described for intermediate 1f.

The enantiomers were separated via chiral SFC (Stationary phase: CHIRALPAK IC 5 µm 250*30 mm, Mobile phase: 40% CO$_2$, 60% (MeOH/CH$_2$Cl$_2$ 90/10) to afford the first eluted enantiomer 61da (250 mg) and the second eluted enantiomer 61db (250 mg).

Synthesis of Compound 61A:

(18*R,Z)-4-fluoro-12-hydroxy-18-phenyl-6,9-dihydro-18H-10,17-methanobenzo[b]pyrido[1,2-f][1]oxa[5,6,9]tri-azacyclotridecine-11,13-dione (compound 61A, 90 mg) was obtained using the procedure described for compound 1.

Compound 61A:

$^1$H NMR (400 MHz, DMSO-d$_6$) δ ppm 7.91 (br d, J=7.6 Hz, 1H), 7.30-7.45 (m, 2H), 7.03-7.25 (m, 6H), 6.22 (br s, 1H), 5.94 (br s, 1H), 5.48 (d, J=8.1 Hz, 1H), 5.28 (s, 1H), 5.14 (d, J=13.6 Hz, 1H), 4.70-4.86 (m, 2H), 4.27 (d, J=13.6 Hz, 1H), 4.21 (br s, 1H), 3.21 (br dd, J=13.9, 7.8 Hz, 1H).

LC/MS (method LC-C): Rt 2.58 min, MH$^+$434

$[α]_D^{20}$: 676.19° (c 0.157, DMF)

Chiral HPLC (method HPLC-B): Rt 7.89 min, chiral purity 99.25%

Synthesis of Compound 61B:

(18*S,Z)-4-fluoro-12-hydroxy-18-phenyl-6,9-dihydro-18H-10,17-methanobenzo[b]pyrido[1,2-f][1]oxa[5,6,9]tri-azacyclotridecine-11,13-dione (compound 61B, 105 mg) was obtained using the procedure described for compound 1.

Compound 61B:

$^1$H NMR (400 MHz, DMSO-d$_6$) δ ppm 7.91 (br d, J=7.6 Hz, 1H), 7.31-7.44 (m, 2H), 7.05-7.26 (m, 6H), 6.22 (br s, 1H), 5.94 (br s, 1H), 5.48 (d, J=7.6 Hz, 1H), 5.28 (s, 1H), 5.14 (d, J=13.6 Hz, 1H), 4.74-4.86 (m, 2H), 4.27 (d, J=14.1 Hz, 1H), 4.21 (br s, 1H), 3.21 (br dd, J=13.9, 7.8 Hz, 1H).

LC/MS (method LC-C): R$_t$ 2.57 min, MH$^+$434

$[α]_D^{20}$: +671.76° (c 0.131, DMF)

Chiral HPLC (method HPLC-B): R$_t$ 6.10 min, chiral purity 100%

Example 62: Synthesis of (((18R,Z)-11,13-dioxo-18-phenyl-6,9,11,13-tetrahydro-18H-10,17-methanobenzo[b]pyrido[1,2-f][1]oxa[5,6,9]triazacyclotridecin-12-yl)oxy)methyl methyl carbonate (Compound 62)

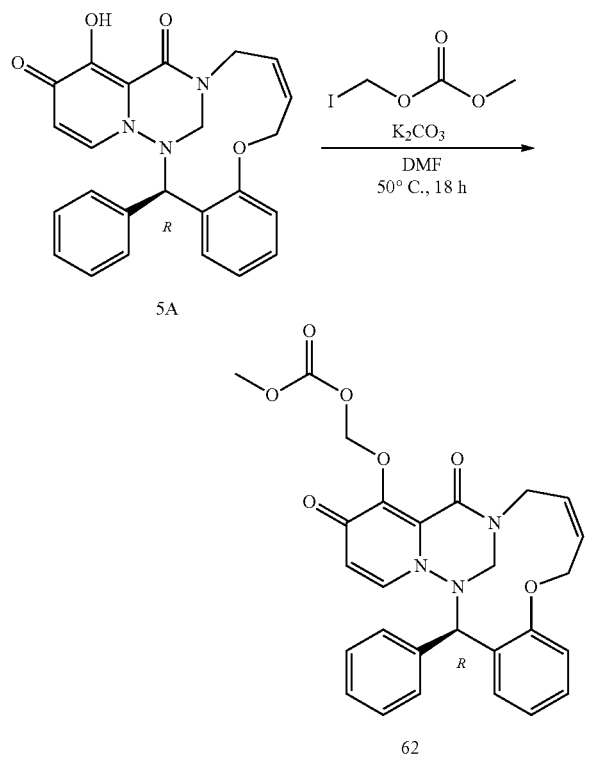

Iodomethyl methyl carbonate [69862-08-4] (200 mg, 0.94 mmol) was added dropwise to a suspension of compound 5A (260 mg, 0.63 mmol) and $K_2CO_3$ (173 mg, 1.25 mmol) in DMF (4.8 mL). The reaction mixture was stirred at 50° C. for 18 h. The reaction mixture was diluted with water and EtOAc. The organic phase was washed with brine (5 times), dried over $MgSO_4$, filtered and evaporated in vacuo. Purification was carried out by flash chromatography over silica gel (30 µm, 12 g, $CH_2Cl_2/CH_3OH$ from 100/0 to 98/2). The residue was freeze-dried ($CH_3CN$/water) to give (((18R,Z)-11,13-dioxo-18-phenyl-6,9,11,13-tetrahydro-18H-10,17-methanobenzo[b]pyrido[1,2-f][1]oxa[5,6,9]triazacyclotridecin-12-yl)oxy)methyl methyl carbonate (compound 62, 130 mg).

Compound 62:

$^1$H NMR (400 MHz, DMSO-$d_6$) δ ppm 8.09 (br d, J=7.6 Hz, 1H), 7.40-7.46 (m, 1H), 7.35 (br t, J=7.4 Hz, 1H), 7.30 (d, J=7.6 Hz, 1H), 7.24 (d, J=8.1 Hz, 1H), 7.16-7.21 (m, 3H), 7.04-7.16 (m, 2H), 6.05-6.16 (m, 1H), 5.91 (br s, 1H), 5.74 (d, J=6.1 Hz, 1H), 5.68 (d, J=8.1 Hz, 1H), 5.54 (d, J=6.6 Hz, 1H), 5.30 (s, 1H), 5.08 (d, J=13.6 Hz, 1H), 4.63-4.78 (m, 2H), 4.27-4.35 (m, 1H), 4.19 (d, J=14.1 Hz, 1H), 3.78 (s, 3H), 3.16 (dd, J=13.6, 8.6 Hz, 1H).

LC/MS (method LC-A): Rt 2.52 min, MH$^+$504

$[α]_D^{20}$: −625.81° (c 0.155, DMF)

Example 63: Synthesis of (18*R,Z)-18-(3-fluorophenyl)-12-hydroxy-6,9-dihydro-18H-10,17-methanobenzo[b]pyrido[1,2-f][1]oxa[5,6,9]triazacyclotridecine-11,13-dione (Compound 63A) and (18*S,Z)-18-(3-fluorophenyl)-12-hydroxy-6,9-dihydro-18H-10,17-methanobenzo[b]pyrido[1,2-f][1]oxa[5,6,9]triazacyclotridecine-11,13-dione (Compound 63B)

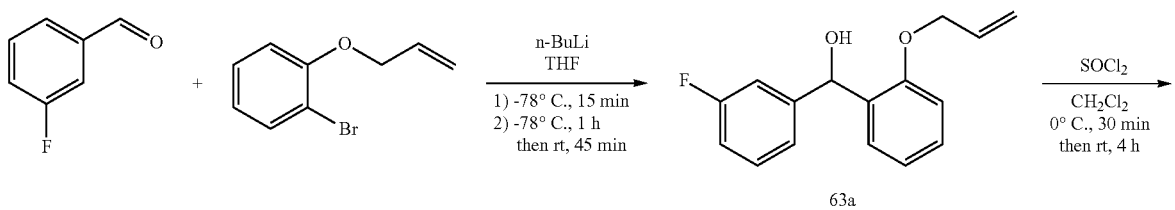

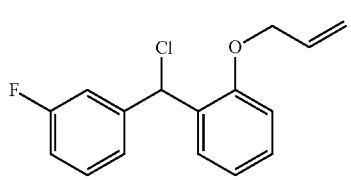

63b

-continued
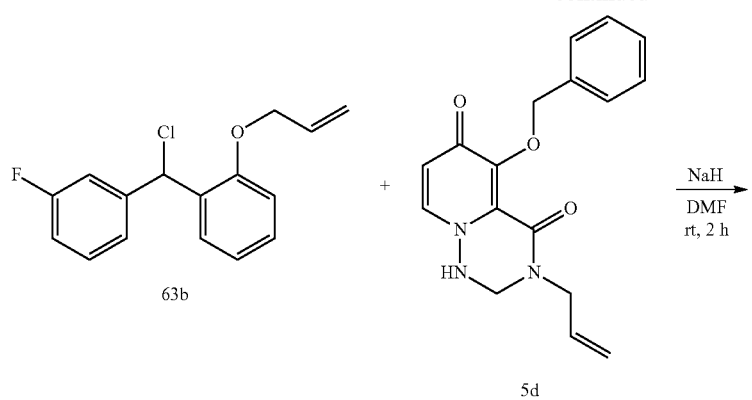
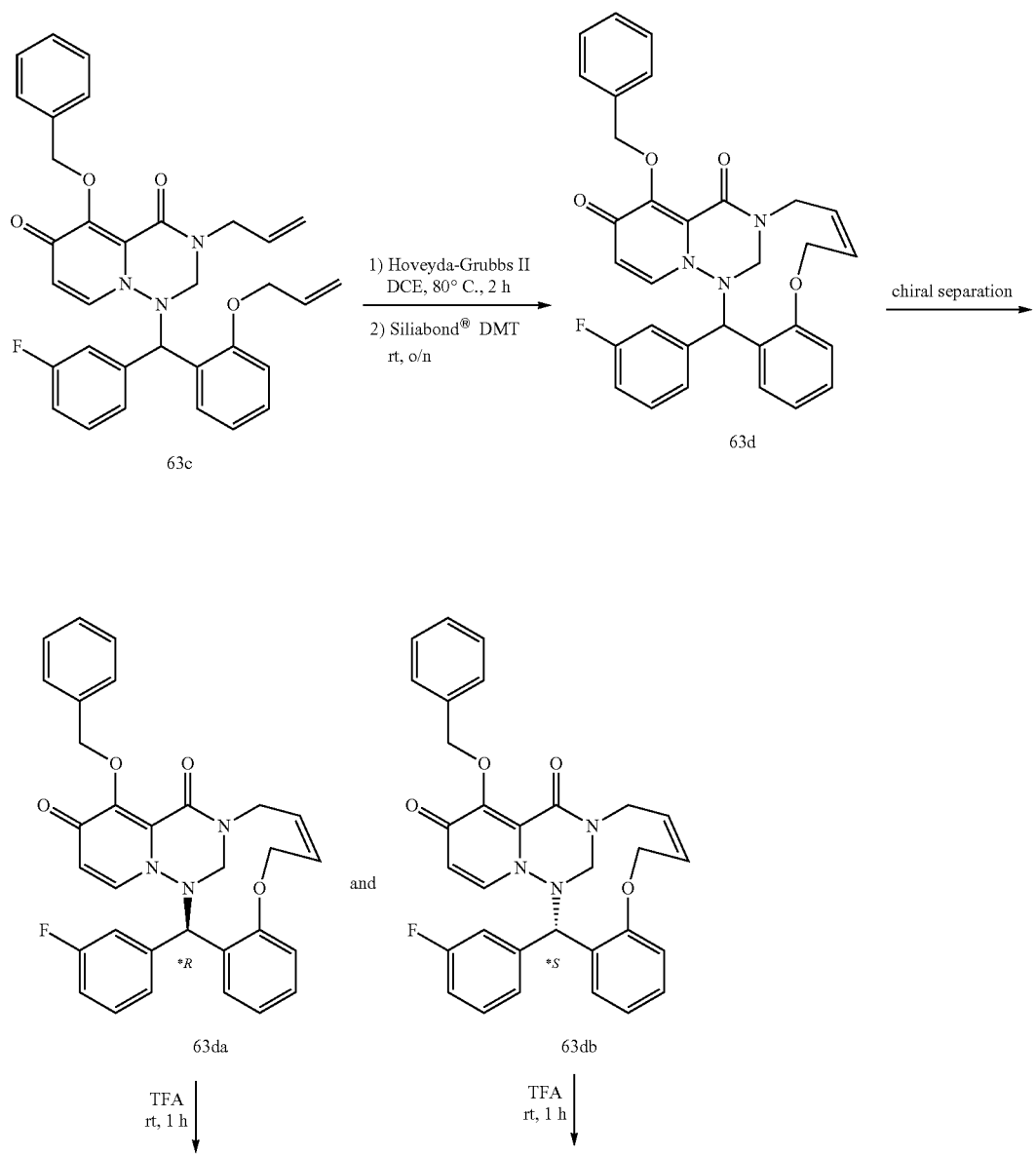

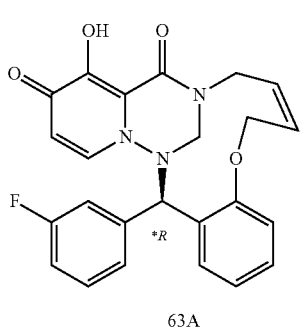

63A

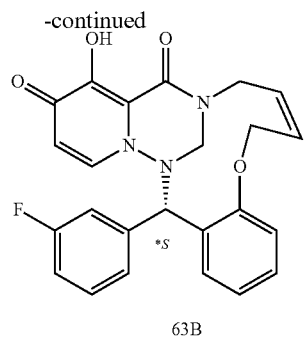

63B

Synthesis of Intermediate 63a:

(2-(allyloxy)phenyl)(3-fluorophenyl)methanol (intermediate 63a, 2.64 g) was obtained using the procedure described for intermediate 23a.

Synthesis of Intermediate 63b:

1-(allyloxy)-2-(chloro(3-fluorophenyl)methyl)benzene (intermediate 63b, 3.00 g) was obtained using the procedure described for intermediate 5a.

Synthesis of Intermediate 63c:

3-allyl-1-((2-(allyloxy)phenyl)(3-fluorophenyl)methyl)-5-(benzyloxy)-2,3-dihydro-1H-pyrido[2,1-f][1,2,4]triazine-4,6-dione (intermediate 63c, 3.3 g) was obtained using the procedure described for intermediate 2d.

Synthesis of Intermediate 63d:

(Z)-12-(benzyloxy)-18-(3-fluorophenyl)-6,9-dihydro-18H-10,17-methanobenzo[b]pyrido[1,2-f][1]oxa[5,6,9]triazacyclotridecine-11,13-dione (intermediate 63d, 560 mg) was obtained using the procedure described for intermediate 1f. Crude intermediate 63d was purified by flash chromatography over silica gel (15-40 µm, 40 g, $CH_2Cl_2/CH_3OH$ from 100/0 to 97/3). A second purification was performed via preparative LC (Stationary phase: irregular bare silica 40 g, Mobile phase: heptane/$CH_3OH$/EtOAc 42/8/50).

The enantiomers were separated by chiral SFC (Stationary phase: CHIRACEL OJ-H 5 µm 250*30 mm, Mobile phase: 80% $CO_2$, 20% MeOH) to afford the first eluted enantiomer 63da (242 mg) and the second eluted enantiomer 63db (232 mg).

Synthesis of Compound 63A (18*R,Z)-18-(3-fluorophenyl)-12-hydroxy-6,9-dihydro-18H-10,17-methanobenzo[b]pyrido[1,2-f][1]oxa[5,6,9]triazacyclotridecine-11,13-dione (compound 63A, 73 mg) was obtained using the procedure described for compound 1. After purification by flash chromatography, compound 63A was crystallized from $CH_3CN$ and $Et_2O$.

Compound 63A:

$^1$H NMR (500 MHz, DMSO-$d_6$) δ ppm 10.96 (br s, 1H), 8.10 (br d, J=7.6 Hz, 1H), 7.40-7.46 (m, 1H), 7.32-7.39 (m, 2H), 7.19-7.26 (m, 2H), 6.90-7.12 (m, 3H), 6.09-6.21 (m, 1H), 5.88 (br s, 1H), 5.56 (d, J=7.6 Hz, 1H), 5.34 (s, 1H), 5.11 (d, J=13.9 Hz, 1H), 4.70-4.82 (m, 2H), 4.25-4.35 (m, 1H), 4.22 (d, J=13.6 Hz, 1H), 3.19 (br dd, J=13.7, 8.4 Hz, 1H).

LC/MS (method LC-C): Rt 2.55 min, MH$^+$434

[α]$D^{20}$: +660.6° (c 0.214, DMF)

Chiral HPLC (method HPLC-B): Rt 5.07 min, chiral purity 100%

Synthesis of Compound 63B:

(18*S,Z)-18-(3-fluorophenyl)-12-hydroxy-6,9-dihydro-18H-10,17-methanobenzo[b]pyrido[1,2-f][1]oxa[5,6,9]triazacyclotridecine-11,13-dione (compound 63B, 70 mg) was obtained using the procedure described for compound 1. After purification by flash chromatography, compound 63B was crystallized from $CH_3CN$ and $Et_2O$.

Compound 63B:

$^1$H NMR (400 MHz, DMSO-$d_6$) δ ppm 10.96 (br s, 1H), 8.09 (br d, J=7.6 Hz, 1H), 7.40-7.46 (m, 1H), 7.30-7.39 (m, 2H), 7.17-7.28 (m, 2H), 6.90-7.12 (m, 3H), 6.09-6.23 (m, 1H), 5.89 (br s, 1H), 5.56 (d, J=7.6 Hz, 1H), 5.34 (s, 1H), 5.11 (d, J=13.6 Hz, 1H), 4.69-4.83 (m, 2H), 4.29 (br t, J=7.6 Hz, 1H), 4.22 (d, J=14.1 Hz, 1H), 3.18 (dd, J=13.9, 8.3 Hz, 1H).

LC/MS (method LC-C): Rt 2.55 min, MH$^+$434

[α]$_D^{20}$: -643.49° (c 0.281, DMF)

Chiral HPLC (method HPLC-B): Rt 6.65 min, chiral purity 100%

Example 65: Synthesis of (2*R,*Z)-15-hydroxy-2-phenyl-12,13,14,16-tetrahydro-11H-4-oxa-1(1,3)-pyrido[2,1-f][1,2,4]triazina-3(1,2)-benzenacyclodecaphan-7-ene-14,16-dione (Compound 65A), (2*S,*Z)-15-hydroxy-2-phenyl-12,13,14,16-tetrahydro-11H-4-oxa-1(1,3)-pyrido[2,1-f][1,2,4]triazina-3(1,2)-benzenacyclodecaphan-7-ene-14,16-dione (Compound 65B), (2*R,*E)-15-hydroxy-2-phenyl-12,13,14,16-tetrahydro-11H-4-oxa-1(1,3)-pyrido[2,1-f][1,2,4]triazina-3(1,2)-benzenacyclodecaphan-7-ene-14,16-dione (Compound 65C) and (2*S,*E)-15-hydroxy-2-phenyl-12,13,14,16-tetrahydro-11H-4-oxa-1(1,3)-pyrido[2,1-f][1,2,4]triazina-3(1,2)-benzenacyclodecaphan-7-ene-14,16-dione (Compound 65D)

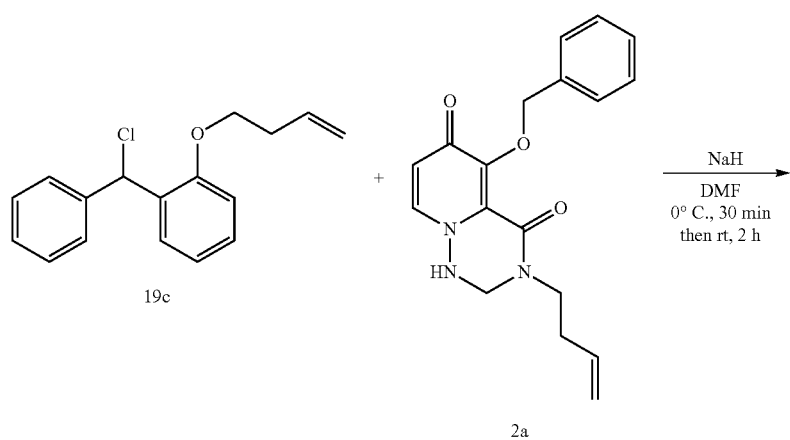

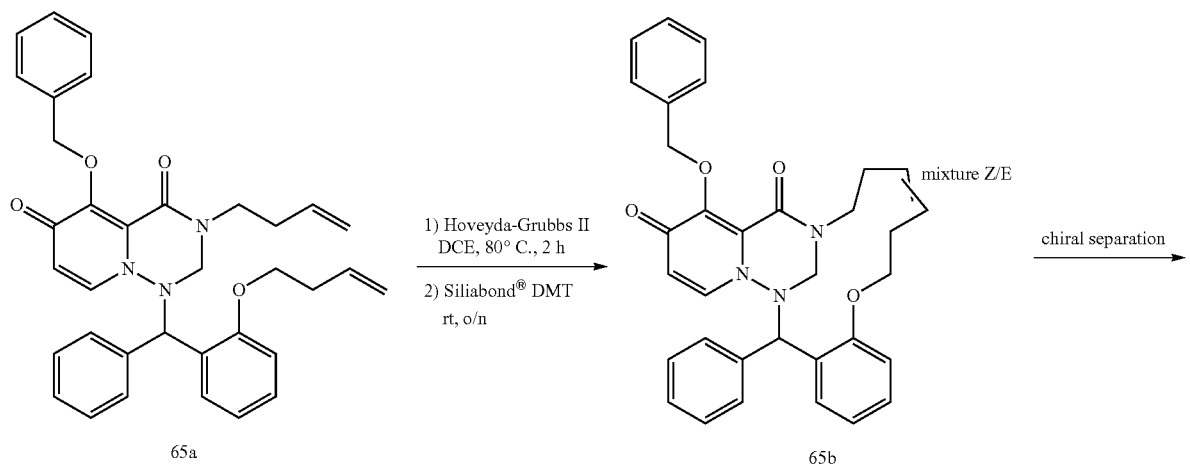

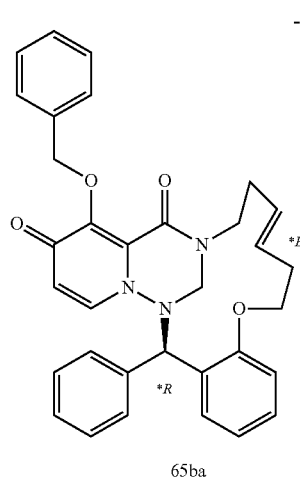

65ba

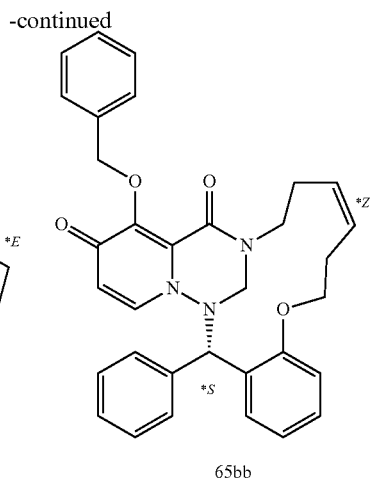

65bb

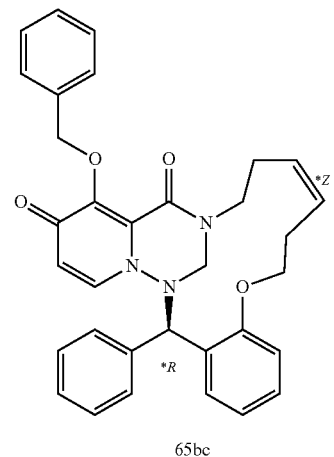

65bc

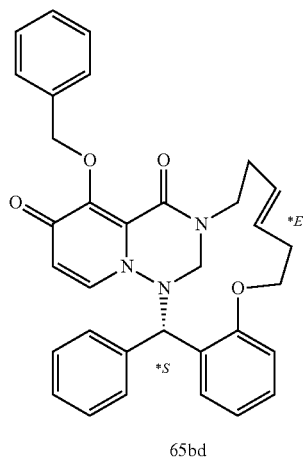

65bd

Synthesis of Intermediate 65a:
5-(benzyloxy)-3-(but-3-en-1-yl)-1-((2-(but-3-en-1-yloxy)phenyl)(phenyl)methyl)-2,3-dihydro-1H-pyrido[2,1-f][1,2,4]triazine-4,6-dione (intermediate 65a, 3.52 g) was obtained using the procedure described for intermediate 2d.

Synthesis of Intermediate 65b:
(E/Z)$_{15}$-(benzyloxy)-2-phenyl-12,13,14,16-tetrahydro-11H-4-oxa-1(1,3)-pyrido[2,1-f][1,2,4]triazina-3(1,2)-benzenacyclodecaphan-7-ene-14,16-dione (intermediate 65b) was obtained using the procedure described for intermediate 1f. Crude intermediate 65b was purified by flash chromatography over silica gel (30 μm, 80 g, CH$_2$Cl$_2$/CH$_3$OH from 97/3 to 95/5) to afford 1.46 g of intermediate 65b.

The enantiomers were separated via chiral SFC (Stationary phase: Whelk-O1 (S,S) 5 μm 250*21.2 mm, Mobile phase: 50% CO$_2$, 50% EtOH (10% CH$_2$Cl$_2$)) to afford a first fraction of enantiomers 65ba and 65bc (546 mg) as a mixture of E and Z isomers and a second fraction of enantiomers 65bb and 65bd (531 mg) as a mixture of E and Z isomers. The isomers 65ba and 65bc were separated via chiral SFC (Stationary phase: Chiralpak AD-H 5 μm 250*30 mm, Mobile phase: 75% CO$_2$, 25% EtOH) to afford intermediate 65ba (371 mg) and intermediate 65bc (128 mg).

The isomers 65bb and 65bd were separated via achiral SFC (Stationary phase: AMINO 5 μm 150*30 mm, Mobile phase: 85% CO$_2$, 15% (MeOH/DCM: 80/20) to afford intermediate 65bb (326 mg) and intermediate 65bd (148 mg).

Synthesis of Compound 65A:

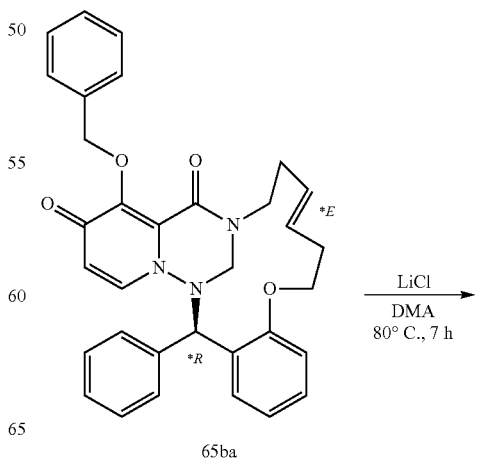

65ba

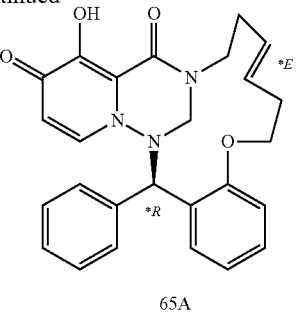

65A (2*R,*Z)-15-hydroxy-2-phenyl-12,13,14,16-tetrahydro-11H-4-oxa-1(1,3)-pyrido[2,1-fj][1,2,4]triazina-3(1,2)-benzenacyclodecaphan-7-ene-14,16-dione (compound 65A, 101 mg) was obtained using the procedure described for compound 28A.

Compound 65A:

$^1$H NMR (500 MHz, DMSO-d$_6$) δ ppm 8.00 (dd, J=7.7, 1.1 Hz, 1H), 7.33 (td, J=8.8, 1.6 Hz, 1H), 7.09-7.19 (m, 6H), 7.06 (d, J=8.2 Hz, 1H), 7.00 (br s, 1H), 5.85 (s, 1H), 5.59-5.68 (m, 1H), 5.36 (d, J=7.9 Hz, 1H), 5.10-5.17 (m, 1H), 5.08 (d, J=12.9 Hz, 1H), 4.39 (br dt, J=11.6, 3.3 Hz, 1H), 4.26 (d, J=12.9 Hz, 1H), 4.06 (td, J=11.3, 2.7 Hz, 1H), 3.75 (br d, J=13.2 Hz, 1H), 2.85-2.93 (m, 1H), 2.75-2.85 (m, 1H), 2.37-2.45 (m, 1H), 2.20-2.27 (m, 1H), 2.12-2.20 (m, 1H).

LC/MS (method LC-C): Rt 2.78 min, MH$^+$444

[α]$_D^{20}$: +339.11° (c 0.225, DMF)

Synthesis of Compound 65B:

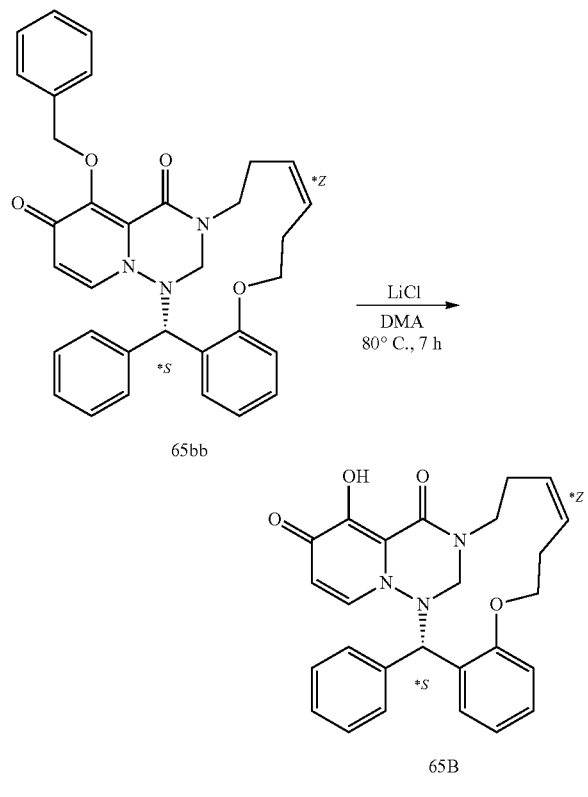

65bb

65B (2*S,*Z)-15-hydroxy-2-phenyl-12,13,14,16-tetrahydro-11H-4-oxa-1(1,3)-pyrido[2,1-f][1,2,4]triazina-3(1,2)-benzenacyclodecaphan-7-ene-14,16-dione (compound 65B, 46 mg) was obtained using the procedure described for compound 28A.

Compound 65B:

$^1$H NMR (500 MHz, DMSO-d$_6$) δ ppm 7.96 (dd, J=7.6, 1.0 Hz, 1H), 7.33-7.39 (m, 1H), 7.10-7.23 (m, 7H), 7.07 (d, J=7.6 Hz, 1H), 5.73 (br t, J=9.9 Hz, 1H), 5.58-5.65 (m, 1H), 5.57 (s, 1H), 5.42 (d, J=7.9 Hz, 1H), 5.06 (d, J=13.2 Hz, 1H), 4.63 (br d, J=12.0 Hz, 1H), 4.36 (d, J=13.2 Hz, 1H), 4.22-4.29 (m, 1H), 3.89 (br t, J=11.7 Hz, 1H), 2.40-2.48 (m, 1H), 1.84-2.06 (m, 3H).

LC/MS (method LC-C): R$_t$ 2.79 min, MH$^+$444

[α]$_D^{20}$: −324.51° (c 0.204, DMF)

Chiral HPLC (method HPLC-B): R$_t$ 4.59 min, chiral purity 100%

Synthesis of Compound 65C:

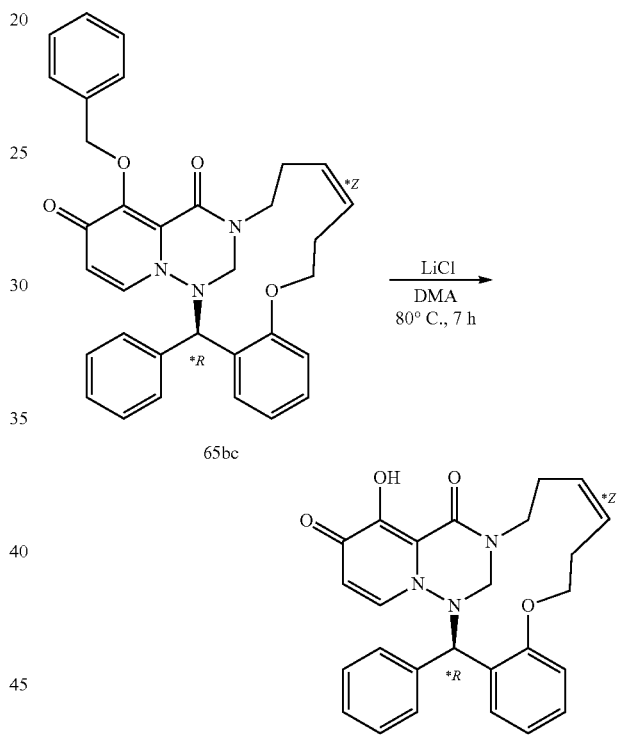

65C (2*R,*E)-15-hydroxy-2-phenyl-12,13,14,16-tetrahydro-11H-4-oxa-1(1,3)-pyrido[2,1-f][1,2,4]triazina-3(1,2)-benzenacyclodecaphan-7-ene-14,16-dione (compound 65C, 45 mg) was obtained using the procedure described for compound 28A.

Compound 65C:

$^1$H NMR (500 MHz, DMSO-d$_6$) δ ppm 7.96 (d, J=6.9 Hz, 1H), 7.33-7.38 (m, 1H), 7.11-7.20 (m, 6H), 7.07 (d, J=7.6 Hz, 1H), 6.95-7.04 (br s, 1H), 5.72 (br t, J=9.9 Hz, 1H), 5.58-5.64 (m, 1H), 5.57 (s, 1H), 5.41 (d, J=7.6 Hz, 1H), 5.05 (d, J=13.2 Hz, 1H), 4.62 (br d, J=12.3 Hz, 1H), 4.35 (d, J=13.2 Hz, 1H), 4.21-4.29 (m, 1H), 3.88 (br t, J=12.0 Hz, 1H), 2.78 (br d, J=14.2 Hz, 1H), 2.40-2.47 (m, 1H), 1.99-2.06 (m, 1H), 1.83-1.98 (m, 2H).

LC/MS (method LC-C): Rt 2.80 min, MH$^+$444

[α]$_D^{20}$: +315.85° (c 0.183, DMF)

Synthesis of Compound 65D:

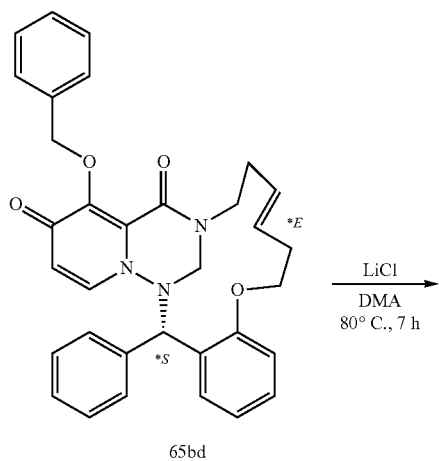

(2*S,*E)-15-hydroxy-2-phenyl-12,13,14,16-tetrahydro-11H-4-oxa-1(1,3)-pyrido[2,1-f][1,2,4]triazina-3(1,2)-benzenacyclodecaphan-7-ene-14,16-dione (compound 65D, 116 mg) was obtained using the procedure described for compound 28A.

Compound 65D:

$^1$H NMR (500 MHz, DMSO-$d_6$) δ ppm 8.00 (br d, J=7.6 Hz, 1H), 7.30-7.38 (m, 1H), 7.10-7.20 (m, 6H), 7.07 (br d, J=8.2 Hz, 1H), 6.93-7.05 (m, 1H), 5.86 (s, 1H), 5.60-5.69 (m, 1H), 5.37 (d, J=7.9 Hz, 1H), 5.11-5.18 (m, 1H), 5.09 (d, J=12.9 Hz, 1H), 4.37-4.44 (m, 1H), 4.26 (d, J=12.9 Hz, 1H), 4.06 (td, J=11.3, 2.4 Hz, 1H), 3.76 (br d, J=13.2 Hz, 1H), 2.86-2.94 (m, 1H), 2.76-2.85 (m, 1H), 2.35-2.46 (m, 1H), 2.21-2.28 (m, 1H), 2.17 (br d, J=15.1 Hz, 1H).

LC/MS (method LC-C): Rt 2.81 min, MH+444

$[\alpha]_D^{20}$: −345.29° (c 0.223, DMF)

Chiral HPLC (method HPLC-B): Rt 4.86 min, chiral purity 100%

Example 67: Synthesis of (2*R,*Z)-15-hydroxy-2-phenyl-12,13,14,16-tetrahydro-11H-4-oxa-1(1,3)-pyrido[2,1-f][1,2,4]triazina-3(1,2)-benzenacyclodecaphan-6-ene-14,16-dione (Compound 67A), (2*S,*Z)-15-hydroxy-2-phenyl-12,13,14,16-tetrahydro-11H-4-oxa-1(1,3)-pyrido[2,1-f][1,2,4]triazina-3(1,2)-benzenacyclodecaphan-6-ene-14,16-dione (Compound 67B)

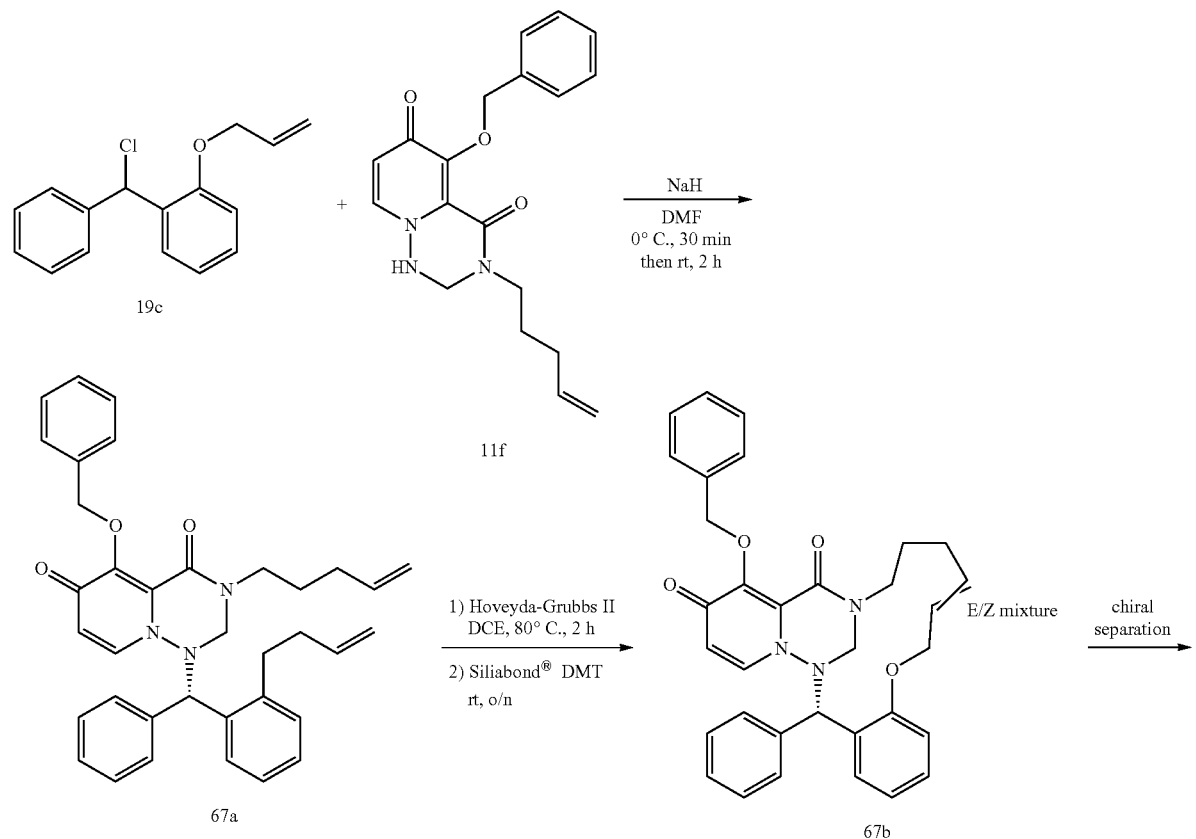

-continued

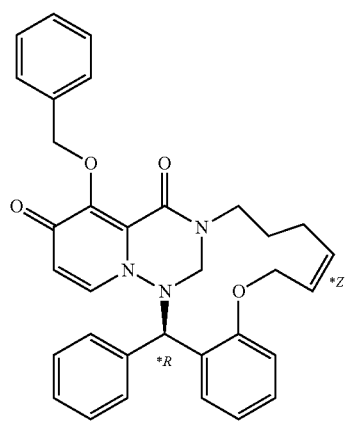

67ba

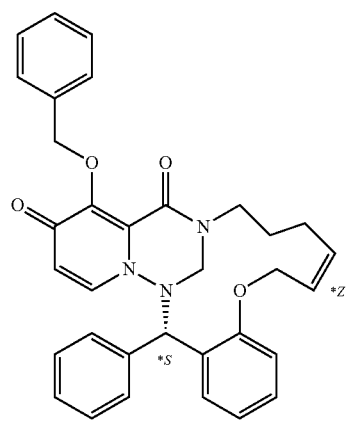

67bb

LiCl
DMA
80° C., 5 h

LiCl
DMA
80° C., 5 h

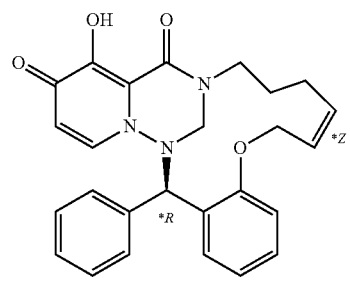

67A

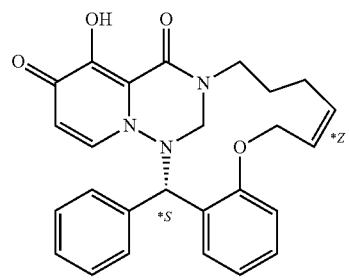

67B

Synthesis of Intermediate 67a:
1-((2-(allyloxy)phenyl)(phenyl)methyl)-5-(benzyloxy)-3-(pent-4-en-1-yl)-2,3-dihydro-1H-pyrido[2,1-f][1,2,4]triazine-4,6-dione (intermediate 67a, 3.7 g) was obtained using the procedure described for intermediate 2d.

Synthesis of Intermediate 67b:
(E/Z)15-(benzyloxy)-2-phenyl-12,13,14,16-tetrahydro-11H-4-oxa-1(1,3)-pyrido[2,1-f][1,2,4]triazina-3(1,2)-benzenacyclodecaphan-6-ene-14,16-dione (intermediate 67b, mixture of Z and E isomers, 900 mg) was obtained using the procedure described for intermediate 1f.

The isomers were separated via chiral SFC (Stationary phase: Whelk-O1 (S,S) 5 μm 250*21.2 mm, Mobile phase: 45% $CO_2$, 55% MeOH) to afford the first eluted enantiomer 67ba (335 mg) and the second eluted enantiomer 67bb (331 mg).

Synthesis of Compound 67A:
(2*R,*Z)-15-(benzyloxy)-2-phenyl-12,13,14,16-tetrahydro-11H-4-oxa-1(1,3)-pyrido[2,1-f][1,2,4]triazina-3(1,2)-benzenacyclodecaphan-6-ene-14,16-dione (compound 67A, 95 mg) was obtained using the procedure described for compound 28A.

Compound 67A:
$^1$H NMR (500 MHz, DMSO-$d_6$) δ ppm 7.91 (br d, J=6.9 Hz, 1H), 7.28 (br t, J=7.4 Hz, 1H), 7.16-7.44 (m, 5H), 7.11

(t, J=7.4 Hz, 1H), 7.07 (d, J=7.9 Hz, 1H), 6.84 (d, J=8.2 Hz, 1H), 5.78 (s, 1H), 5.54-5.68 (m, 2H), 5.48 (d, J=7.6 Hz, 1H), 5.01 (d, J=13.2 Hz, 1H), 4.92 (br d, J=15.4 Hz, 1H), 4.57 (br dd, J=15.1, 5.0 Hz, 1H), 4.45 (br d, J=13.2 Hz, 1H), 4.07 (br t, J=13.1 Hz, 1H), 2.78-2.88 (m, 1H), 2.73 (br d, J=13.9 Hz, 1H), 1.79-1.89 (m, 1H), 1.37 (br t, J=13.1 Hz, 1H), 0.55 (q, J=13.0 Hz, 1H).

LC/MS (method LC-A): Rt 2.85 min, MH$^+$444

Chiral HPLC (method HPLC-B): Rt 4.89 min, chiral purity 100%

Synthesis of Compound 67B:

(2*S,*Z)-15-hydroxy-2-phenyl-12,13,14,16-tetrahydro-11H-4-oxa-1(1,3)-pyrido[2,1-f][1,2,4]triazina-3(1,2)-benzenacyclodecaphan-6-ene-14,16-dione (compound 67B, 141 mg) was obtained using the procedure described for compound 28A.

Compound 67B:

$^1$H NMR (500 MHz, DMSO-d$_6$) δ ppm 7.91 (dd, J=7.6, 1.3 Hz, 1H), 7.25-7.30 (m, 1H), 7.15-7.37 (m, 5H), 7.11 (t, J=7.6 Hz, 1H), 7.07 (d, J=7.6 Hz, 1H), 6.84 (d, J=8.5 Hz, 1H), 5.78 (s, 1H), 5.55-5.67 (m, 2H), 5.48 (d, J=7.6 Hz, 1H), 5.01 (d, J=13.6 Hz, 1H), 4.92 (br dd, J=15.3, 1.7 Hz, 1H), 4.57 (dd, J=15.1, 5.4 Hz, 1H), 4.45 (d, J=13.6 Hz, 1H), 4.07 (br t, J=12.9 Hz, 1H), 2.78-2.88 (m, 1H), 2.73 (br d, J=14.2 Hz, 1H), 1.84 (br t, J=12.8 Hz, 1H), 1.37 (br t, J=13.2 Hz, 1H), 0.55 (q, J=13.7 Hz, 1H).

LC/MS (method LC-A): Rt 2.85 min, MH$^+$444

Chiral HPLC (method HPLC-B): Rt 5.26 min, chiral purity 100%

Example 69: Synthesis of (23b*R)-6-hydroxy-10,11,12,13,18,23b-hexahydro-9H-1,8-methano[1]benzothiepino[5,4,3-lm]pyrido[2,1-i][1,7,10,11]benzoxatriazacyclotetradecine-5,7-dione (Compound 69A), (23b*S)-6-hydroxy-10,11,12,13,18,23b-hexahydro-9H-1,8-methano[1]benzothiepino[5,4,3-lm]pyrido[2,1-i][1,7,10,11]benzoxatriazacyclotetradecine-5,7-dione (Compound 69B)

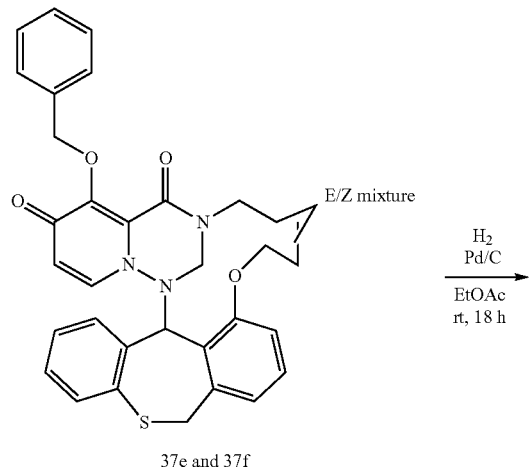

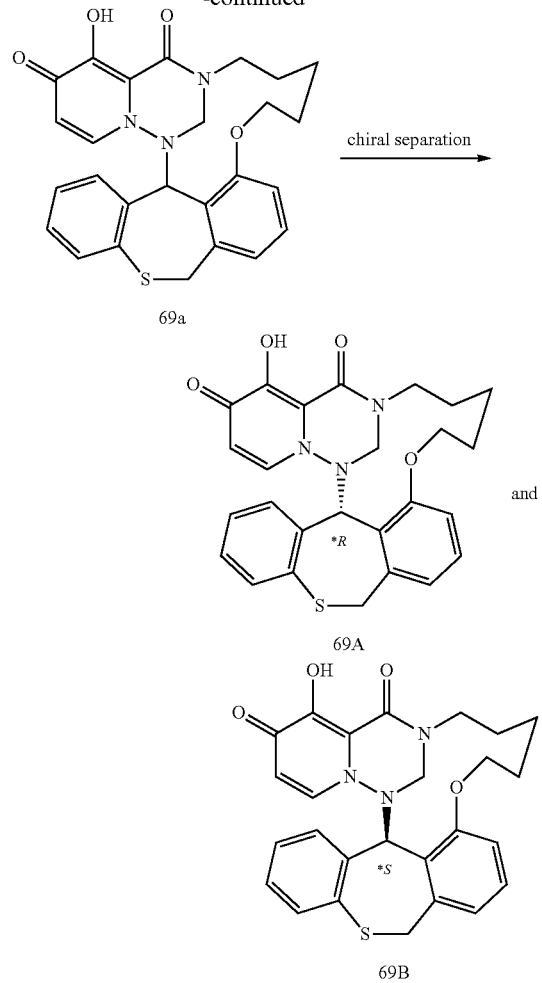

Synthesis of Intermediate 69a:

6-hydroxy-10,11,12,13,18,23b-hexahydro-9H-1,8-methano[1]benzothiepino[5,4,3-lm]pyrido[2,1-i][1,7,10,11]benzoxatriazacyclotetradecine-5,7-dione (intermediate 69a, 190 mg) was obtained using the procedure described for compound 2. Purification was carried out by flash chromatography over silica gel (15 μm, 12 g, CH$_2$Cl$_2$/MeOH from 99/1 to 93/7) to afford intermediate 69a (112 mg) as a mixture of enantiomers.

Synthesis of Compounds 69A and 69B:

The enantiomers 69A and 69B were separated via Prep Chiral HPLC (Stationary phase: Daicel Chiralpak IG 20 μm 250 gram, Mobile phase: Ethanol+0.1% TFA) to afford the first eluted enantiomer 69A (49 mg) and the second eluted enantiomer 69B (49 mg). Enantiomer 69A was freeze-dried (water/CH$_3$CN, 4/1) overnight to give (23b*R)-6-hydroxy-10,11,12,13,18,23b-hexahydro-9H-1,8-methano[1]benzothiepino[5,4,3-lm]pyrido[2,1-i][1,7,10,11]benzoxatriazacyclotetradecine-5,7-dione (compound 69A, 33 mg).

Enantiomer 69B was freeze-dried (water/CH$_3$CN, 4/1) overnight to give (23b*S)-6-hydroxy-10,11,12,13,18,23b-hexahydro-9H-1,8-methano[1]benzothiepino[5,4,3-lm]pyrido[2,1-i][1,7,10,11]benzoxatriazacyclotetradecine-5,7-dione (compound 69B, 34 mg).

Compound 69A:

$^1$H NMR (500 MHz, DMSO-d$_6$) δ ppm 11.80 (br s, 1H), 7.46 (d, J=7.6 Hz, 1H), 7.36 (t, J=7.9 Hz, 1H), 7.08-7.13 (m, 1H), 7.00-7.07 (m, 3H), 6.84 (t, J=7.3 Hz, 1H), 6.73 (d, J=7.6 Hz, 1H), 6.05 (s, 1H), 5.87 (d, J=13.6 Hz, 1H), 5.65 (d, J=7.9 Hz, 1H), 5.01 (d, J=13.2 Hz, 1H), 4.37 (br dd, J=9.0, 6.8 Hz, 1H), 4.29 (d, J=13.2 Hz, 1H), 4.13 (br t, J=12.6 Hz, 1H), 3.81-3.90 (m, 2H), 2.82 (br d, J=13.6 Hz, 1H), 2.05-2.15 (m, 1H), 1.82-1.93 (m, 1H), 1.55-1.70 (m, 2H), 1.35-1.45 (m, 1H), 1.15-1.29 (m, 1H).

LC/MS (method LC-A): Rt 2.85 min, MH+476

$[\alpha]_D^{20}$: +174.8° (c 0.127, DMF)

Compound 69B:

1H NMR (500 MHz, DMSO-$d_6$) δ ppm 11.84 (br s, 1H), 7.46 (d, J=7.6 Hz, 1H), 7.36 (t, J=7.9 Hz, 1H), 7.08-7.13 (m, 1H), 6.99-7.08 (m, 3H), 6.84 (t, J=7.4 Hz, 1H), 6.73 (d, J=7.3 Hz, 1H), 6.05 (s, 1H), 5.87 (d, J=13.6 Hz, 1H), 5.64 (d, J=7.6 Hz, 1H), 5.01 (d, J=13.6 Hz, 1H), 4.36 (br dd, J=9.1, 6.6 Hz, 1H), 4.29 (d, J=13.6 Hz, 1H), 4.13 (br t, J=13.4 Hz, 1H), 3.81-3.90 (m, 2H), 2.82 (br d, J=13.9 Hz, 1H), 2.05-2.15 (m, 1H), 1.81-1.93 (m, 1H), 1.55-1.70 (m, 2H), 1.35-1.45 (m, 1H), 1.20-1.29 (m, 1H).

LC/MS (method LC-A): Rt 2.84 min, MH+476

$[\alpha]_D^{20}$: −184° (c 0.125, DMF)

Example 70: Synthesis of (18*R,*Z)-2,3-difluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (Compound 70A), (18*S,*Z)-2,3-difluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (Compound 70B)

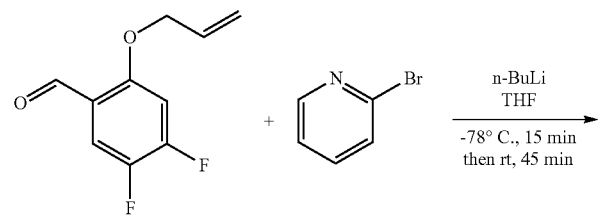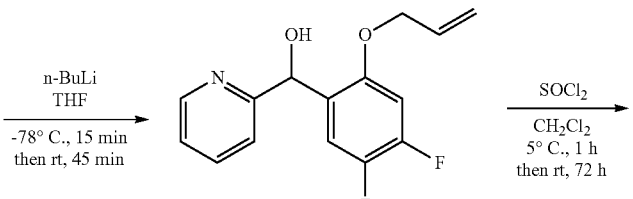

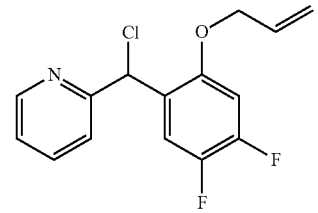

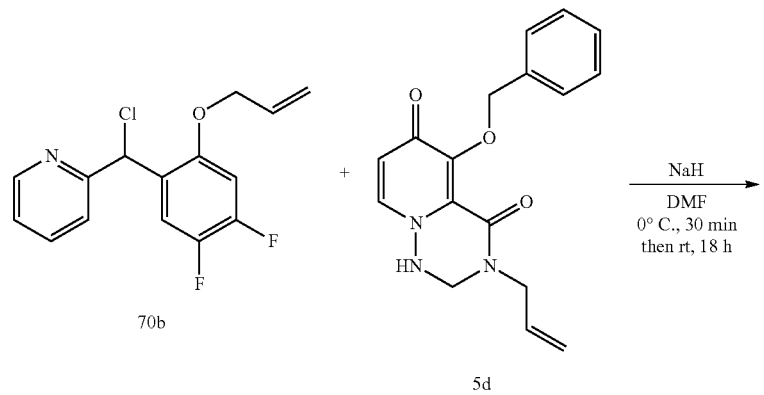

-continued

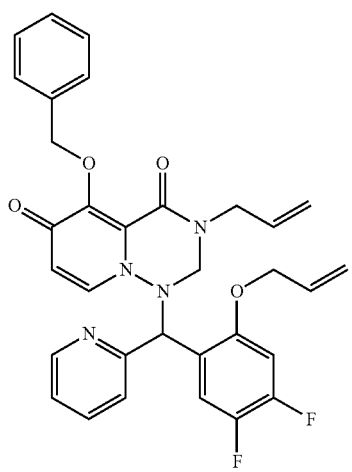

70c

1) Hoveyda-Grubbs II
DCE, 80° C., 3 h

2) Siliabond® DMT
rt, 18 h

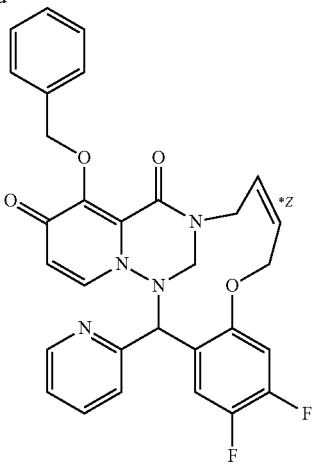

70d chiral separation

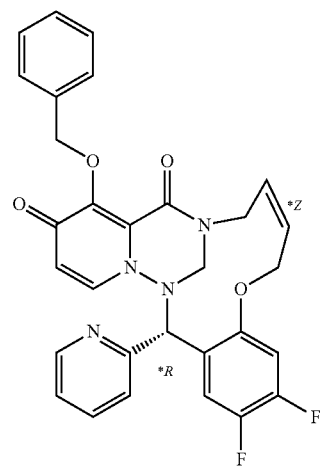

70da and

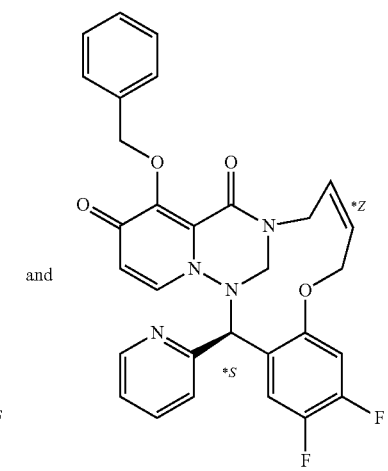

70db

TFA
rt, 1 h

TFA
rt, 1 h

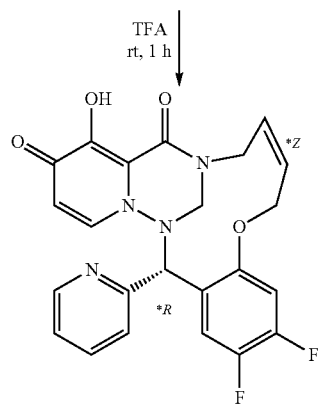

70A

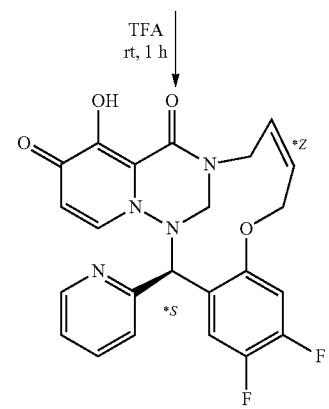

70B

Synthesis of Intermediate 70a:
(2-(allyloxy)-4,5-difluorophenyl)(pyridin-2-yl)methanol (intermediate 70a, 2.2 g) was obtained using the procedure described for intermediate 23a. Crude intermediate 70a was purified by preparative LC (Stationary phase: regular SiOH, 30 μm, Interchim® 120 g, Mobile phase: CH$_2$Cl$_2$/MeOH from 100/0 to 99/1).

Synthesis of Intermediate 70b:
2-((2-(allyloxy)-4,5-difluorophenyl)chloromethyl)pyridine (intermediate 70b, 2.3 g) was obtained using the procedure described for intermediate 5a.

Synthesis of Intermediate 70c:
3-allyl-1-((2-(allyloxy)-4,5-difluorophenyl)(pyridin-2-yl)methyl)-5-(benzyloxy)-2,3-dihydro-1H-pyrido[2,1-f][1,2,4]

triazine-4,6-dione (intermediate 70c, 1.5g) was obtained using the procedure described for intermediate 2d.
Synthesis of Intermediate 70d:
(*Z)-12-(benzyloxy)-2,3-difluoro-18-(pyridin-2-yl)-6,9-dihydro-18H-10,17-methanobenzo[b]pyrido[1,2-f][1]oxa[5,6,9]triazacyclotridecine-11,13-dione (intermediate 70d, 0.68 g) was obtained using the procedure described for intermediate 1f. A second purification was performed via reverse phase (Stationary phase: YMC-actus Triart C18 10 μm 30*150 mm, Mobile phase: 0.2% aq.NH$_4$CO$_3$/CH$_3$CN from 65/35 to 25/75) to afford 0.36 g of intermediate 70d.

The enantiomers were separated via chiral SFC (Stationary phase: CHIRALPAK IC 5 μm 250*30 mm, Mobile phase: 40% CO$_2$, 60% (MeOH+20% DCM) to afford the first eluted enantiomer 70da (163 mg) and the second eluted enantiomer 70db (163 mg).
Synthesis of Compound 70A:
(18*R,*Z)-2,3-difluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (compound 70A, 91 mg) was obtained using the procedure described for compound 1.
Compound 70A:
$^1$H NMR (500 MHz, DMSO-d$_6$) δ ppm 8.41 (br d, J=4.1 Hz, 1H), 8.14 (br t, J=10.7 Hz, 1H), 7.65 (td, J=7.6, 1.3 Hz, 1H), 7.48 (br dd, J=11.7, 7.3 Hz, 1H), 7.28 (d, J=7.9 Hz, 1H), 7.24 (dd, J=6.9, 5.0 Hz, 1H), 7.19 (br d, J=7.6 Hz, 1H), 6.11-6.21 (m, 1H), 6.05 (br s, 1H), 5.55 (d, J=7.6 Hz, 1H), 5.45 (s, 1H), 5.11 (d, J=13.9 Hz, 1H), 4.79 (br dd, J=13.6, 4.4 Hz, 1H), 4.73 (dd, J=10.7, 7.3 Hz, 1H), 4.36-4.44 (m, 1H), 4.32 (d, J=13.9 Hz, 1H), 3.18 (br dd, J=13.6, 8.5 Hz, 1H).
LC/MS (method LC-A): Rt 2.37 min, MH$^+$453
[α]$_D^{20}$: +628.83° (c 0.111, DMF)
Chiral HPLC (method HPLC-B): R$_t$ 4.38 min, chiral purity 100%
Synthesis of Compound 70B:
(18*S,*Z)-2,3-difluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (compound 70B, 94 mg) was obtained using the procedure described for compound 1.
Compound 70B:
$^1$H NMR (500 MHz, DMSO-d$_6$) δ ppm 8.41 (br d, J=3.8 Hz, 1H), 8.14 (br t, J=10.6 Hz, 1H), 7.65 (td, J=7.6, 1.3 Hz, 1H), 7.48 (br dd, J=11.8, 7.4 Hz, 1H), 7.27 (br d, J=7.6 Hz, 1H), 7.24 (dd, J=7.1 Hz, 1H), 7.17 (br d, J=7.6 Hz, 1H), 6.11-6.21 (m, 1H), 6.05 (br s, 1H), 5.51 (d, J=7.6 Hz, 1H), 5.45 (br s, 1H), 5.11 (d, J=13.9 Hz, 1H), 4.79 (br dd, J=13.7, 4.3 Hz, 1H), 4.73 (br dd, J=10.1, 7.6 Hz, 1H), 4.36-4.44 (m, 1H), 4.32 (d, J=13.9 Hz, 1H), 3.18 (br dd, J=13.6, 8.5 Hz, 1H).
LC/MS (method LC-A): Rt 2.36 min, MH$^+$453
[α]$_D^{20}$: −609.82° (c 0.163, DMF)
Chiral HPLC (method HPLC-B): Rt 4.71 min, chiral purity 100%

Example 71: Synthesis of (18*R,*Z)-3-fluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (Compound 71A), (18*S,*Z)-3-fluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (Compound 71B)

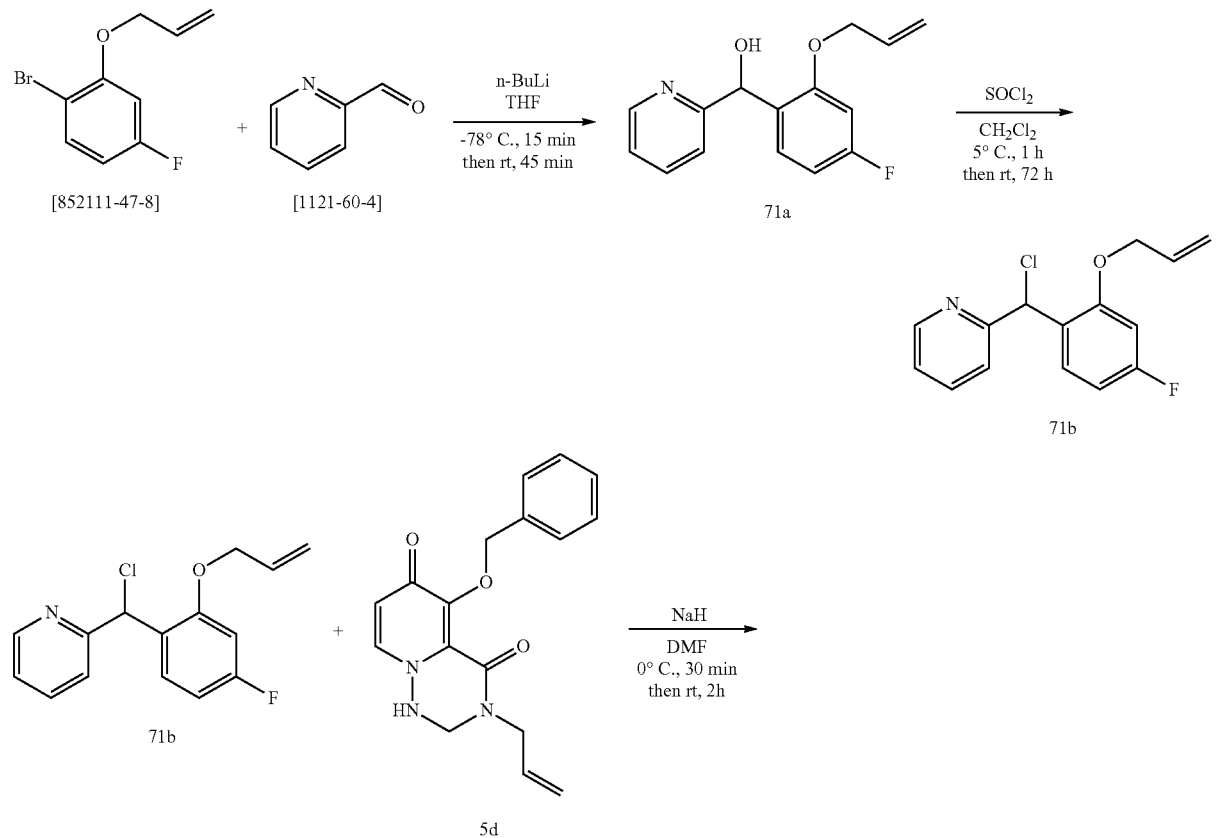

-continued

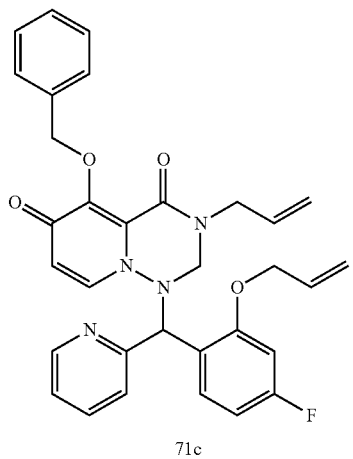

71c

1) Hoveyda-Grubbs II
DCE, 80° C., 3 h

2) Siliabond® DMT
rt, 18 h

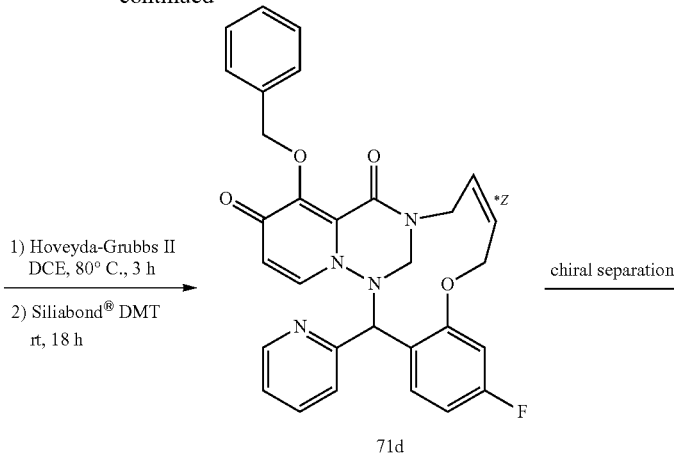

71d chiral separation

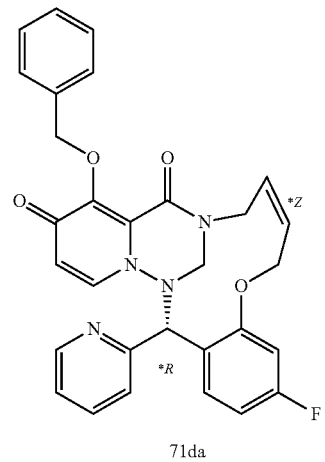

71da and

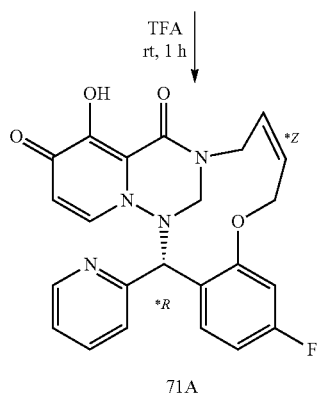

71db

TFA
rt, 1 h

TFA
rt, 1 h

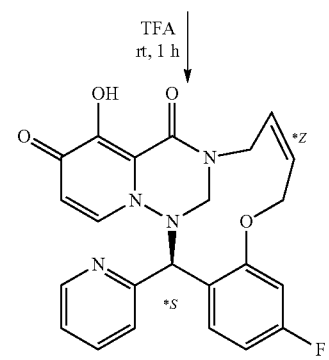

71A

71B

Synthesis of Intermediate 71a:

(2-(allyloxy)-4-fluorophenyl)(pyridin-2-yl)methanol (intermediate 71a, 0.26 g) was obtained using the procedure described for intermediate 23a. Crude intermediate 71a was purified by preparative LC (Stationary phase: regular SiOH, 30 µm, 80 g Interchim®, Mobile phase: $CH_2Cl_2$).

Synthesis of Intermediate 71b:

2-((2-(allyloxy)-4-fluorophenyl)chloromethyl)pyridine (intermediate 71b, 280 mg) was obtained using the procedure described for intermediate 5a.

Synthesis of Intermediate 71c:

3-allyl-1-((2-(allyloxy)-4-fluorophenyl)(pyridin-2-yl)methyl)-5-(benzyloxy)-2,3-dihydro-1H-pyrido[2,1-f][1,2,4]triazine-4,6-dione (intermediate 71c, 0.43 g) was obtained using the procedure described for intermediate 2d.

Synthesis of Intermediate 71d:

(*Z)-12-(benzyloxy)-3-fluoro-18-(pyridin-2-yl)-6,9-dihydro-18H-10,17-methanobenzo[b]pyrido[1,2-f][1]oxa[5,6,9]triazacyclotridecine-11,13-dione (intermediate 71d, 0.17 g) was obtained using the procedure described for intermediate 1f. Purification was carried out by flash chromatography over silica gel (30 µm, 24 g, $CH_2Cl_2$/MeOH from 100/0 to 98/2). A second purification via Reverse phase (Stationary phase: YMC-actus Triart C18 10 µm 30*150 mm, Mobile phase: 0.2% aq.$NH_4HCO_3$/$CH_3CN$ from 75/25 to 35/65) was performed yielding 80 mg of 71d. The enantiomers were separated by chiral SFC (Stationary phase: Chiralcel OD-H 5 μm 250×21.2 mm, Mobile phase: 60% $CO_2$, 40% EtOH) to give the first eluted enantiomer 71da (40 mg) and the second eluted enantiomer 71db (39 mg).

Synthesis of Compound 71A:

(18*R,*Z)-3-fluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (compound 71A, 18 mg) was obtained using the procedure described for compound 1.

Compound 71A:

$^1$H NMR (500 MHz, DMSO-$d_6$) δ ppm 8.32 (br d, J=4.1 Hz, 1H), 8.06-8.14 (m, 1H), 7.56 (td, J=7.7, 1.6 Hz, 1H), 7.09-7.19 (m, 4H), 7.04 (d, J=7.9 Hz, 1H), 6.03-6.12 (m, 1H), 5.92 (br s, 1H), 5.42 (d, J=7.9 Hz, 1H), 5.39 (s, 1H), 5.02 (d, J=13.9 Hz, 1H), 4.64-4.74 (m, 2H), 4.35 (br dd, J=10.1, 8.2 Hz, 1H), 4.16 (d, J=13.9 Hz, 1H), 3.09-3.15 (m, 1H).

LC/MS (method LC-C): Rt 2.24 min, MH$^+$435

$[α]_D^{20}$: −666.96° (c 0.115, DMF)

Chiral HPLC (method HPLC-B): Rt 5.50 min. chiral purity 100%

Synthesis of Compound 71B:

(18*R,*Z)-3-fluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (compound 71B, 20 mg) was obtained using the procedure described for compound 1.

Compound 71B:

$^1$H NMR (500 MHz, DMSO-$d_6$) δ ppm 8.32 (br d, J=3.8 Hz, 1H), 8.10 (br t, J=8.0 Hz, 1H), 7.56 (br t, J=7.4 Hz, 1H), 7.09-7.20 (m, 4H), 7.04 (d, J=7.6 Hz, 1H), 6.03-6.12 (m, 1H), 5.93 (br s, 1H), 5.42 (d, J=7.6 Hz, 1H), 5.39 (s, 1H), 5.02 (br d, J=13.6 Hz, 1H), 4.63-4.75 (m, 2H), 4.35 (br dd, J=9.9, 8.0 Hz, 1H), 4.16 (br d, J=13.9 Hz, 1H), 3.09-3.16 (m, 1H).

LC/MS (method LC-C): Rt 2.24 min, MH$^+$435

$[α]_D^{20}$: +647.77° (c 0.156, DMF)

Chiral HPLC (method HPLC-B): Rt 5.07 min, chiral purity 100%

Example 72: Synthesis of (18*R,Z)-3-chloro-12-hydroxy-18-phenyl-6,9-dihydro-18H-10,17-methanobenzo[b]pyrido[1,2-f][1]oxa[5,6,9]triazacyclotridecine-11,13-dione (Compound 72A), (18*S,Z)-3-chloro-12-hydroxy-18-phenyl-6,9-dihydro-18H-10,17-methanobenzo[b]pyrido[1,2-f][1]oxa[5,6,9]triazacyclotridecine-11,13-dione (Compound 72B)

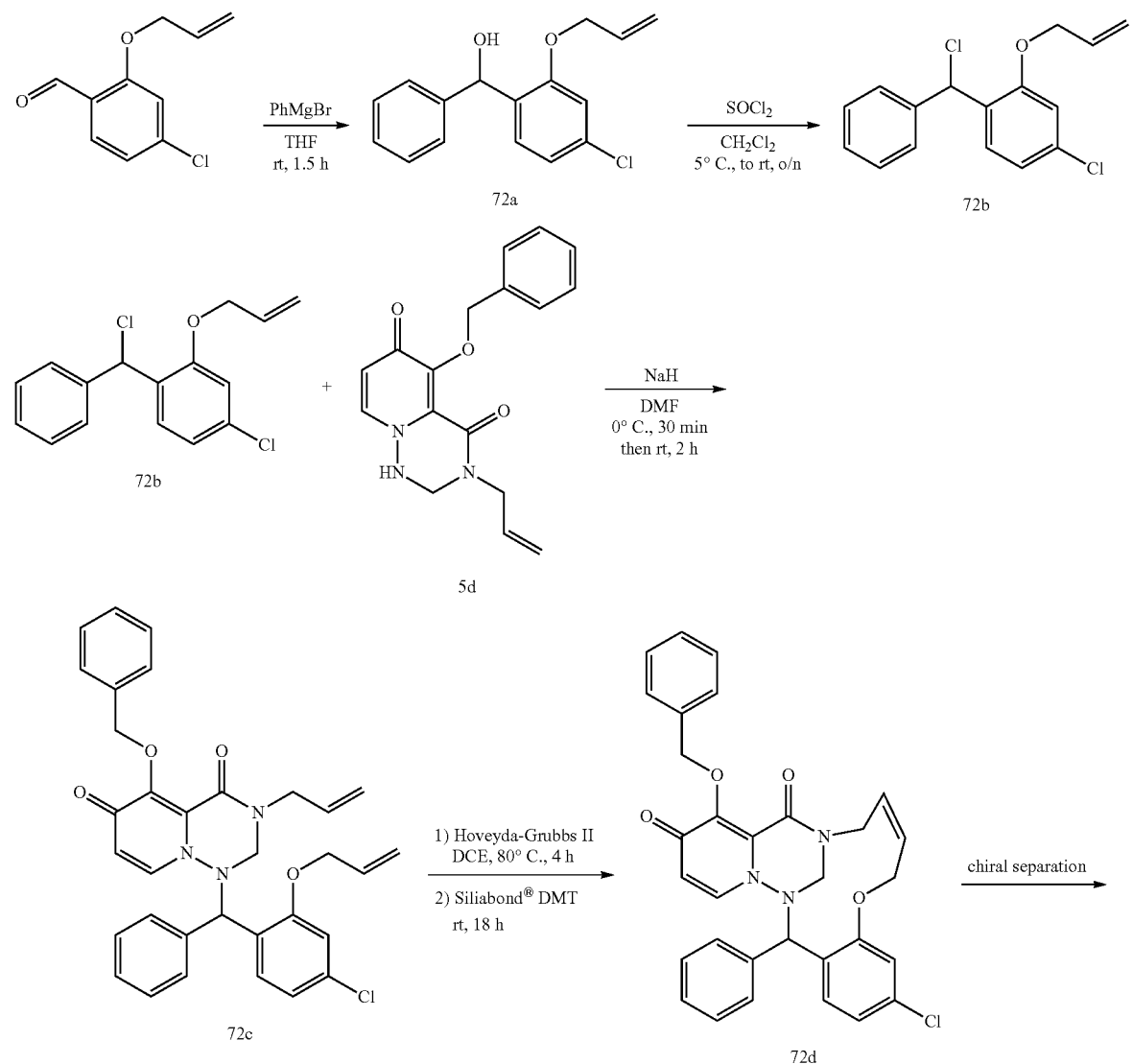

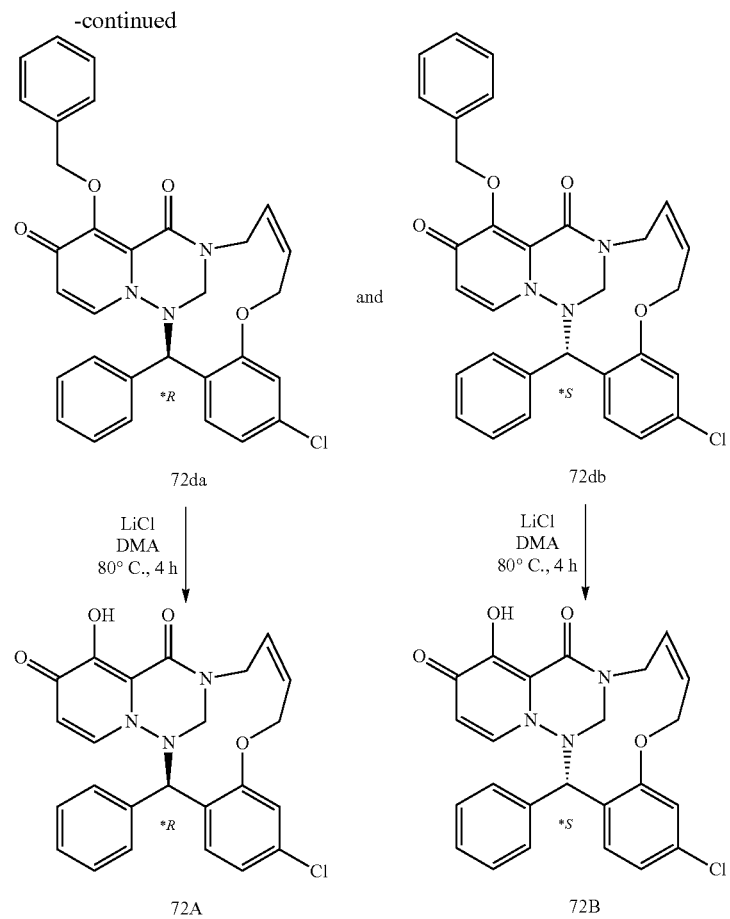

Synthesis of Intermediate 72a:

(2-(allyloxy)-4-chlorophenyl)(phenyl)methanol (intermediate 72a, 5.00 g) was obtained using the procedure described for intermediate 2b. Crude intermediate 72a was purified by flash column chromatography on silica gel (15-40 μm, 120 g, heptane/EtOAc from 90/10 to 80/20).

Synthesis of Intermediate 72b:

2-(allyloxy)-4-chloro-1-(chloro(phenyl)methyl)benzene (intermediate 72b, 2.3 g) was obtained using the procedure described for intermediate 5a.

Synthesis of Intermediate 72c:

3-allyl-1-((2-(allyloxy)-4-chlorophenyl)(phenyl)methyl)-5-(benzyloxy)-2,3-dihydro-1H-pyrido[2,1-f][1,2,4]triazine-4,6-dione (intermediate 72c, 2.5 g) was obtained using the procedure described for intermediate 2d.

Synthesis of Intermediate 72d:

(Z)-12-(benzyloxy)-3-chloro-18-phenyl-6,9-dihydro-18H-10,17-methanobenzo[b]pyrido[1,2-f][1]oxa[5,6,9]triazacyclotridecine-11,13-dione (intermediate 72d, 1.8 g) was obtained using the procedure described for intermediate 1f. Crude intermediate 72d was purified by flash chromatography over silica gel (20-45 μm, 20 g, $CH_2Cl_2/CH_3OH$ from 99/1 to 97/3) to afford intermediate 72d (380 mg). The enantiomers were separated via chiral SFC (Stationary phase: CHIRACEL OJ-H 5 μm 250*30 mm, Mobile phase: 70% $CO_2$, 30% $CH_3OH$) to give the first eluted enantiomer 72da (140 mg) and the second eluted enantiomer 72db (135 mg).

Synthesis of Compound 72A (18*R,Z)-3-chloro-12-hydroxy-18-phenyl-6,9-dihydro-18H-10,17-methanobenzo[b]pyrido[1,2-f][1]oxa[5,6,9]triazacyclotridecine-11,13-dione (compound 72A, 54 mg) was obtained using the procedure described for compound 28A. Compound 72A:

$^1$H NMR (500 MHz, DMSO-$d_6$) δ ppm 8.13 (d, J=8.2 Hz, 1H), 7.41-7.45 (m, 1H), 7.39-7.41 (m, 1H), 7.25 (br d, J=7.9 Hz, 1H), 7.06-7.22 (m, 5H), 6.11-6.20 (m, 1H), 5.99 (br s, 1H), 5.49 (d, J=7.6 Hz, 1H), 5.28 (s, 1H), 5.10 (d, J=13.9 Hz, 1H), 4.72-4.82 (m, 2H), 4.35-4.44 (m, 1H), 4.25 (d, J=13.9 Hz, 1H), 3.20 (br dd, J=13.9, 8.5 Hz, 1H).

LC/MS (method LC-C): Rt 2.79 min, MH$^+$450

$[α]_D^{20}$: +685.35° (c 0.198, DMF)

Chiral HPLC (method HPLC-B): Rt 5.39 min, chiral purity 100%

Synthesis of Compound 72B:

(18*S,Z)-3-chloro-12-hydroxy-18-phenyl-6,9-dihydro-18H-10,17-methanobenzo[b]pyrido[1,2-f][1]oxa[5,6,9]triazacyclotridecine-11,13-dione (compound 72B, 56 mg) was obtained using the procedure described for compound 28A. Compound 72B:

$^1$H NMR (500 MHz, DMSO-$d_6$) δ ppm 8.12 (d, J=8.2 Hz, 1H), 7.42 (dd, J=8.5, 1.9 Hz, 1H), 7.39-7.41 (m, 1H), 7.24 (br d, J=7.6 Hz, 1H), 7.09-7.22 (m, 5H), 6.10-6.20 (m, 1H), 5.98 (br s, 1H), 5.48 (d, J=7.6 Hz, 1H), 5.27 (s, 1H), 5.10 (d, J=13.6 Hz, 1H), 4.71-4.83 (m, 2H), 4.36-4.44 (m, 1H), 4.24 (d, J=13.9 Hz, 1H), 3.19 (br dd, J=13.9, 8.5 Hz, 1H).

LC/MS (method LC-C): Rt 2.79 min, MH$^+$450

$[α]_D^{20}$: −692.86° (c 0.210, DMF)

Chiral HPLC (method HPLC-B): Rt 7.11 min, chiral purity 100%

Example 73: Synthesis of (11*Z)-6-hydroxy-10,16,17,21b-tetrahydro-9H-1,8-methanobenzo[4,5]cyclohepta[1,2,3-op]pyrido[1,2-c][2,3,6]benzotriazacyclododecine-5,7-dione (Compound 73)
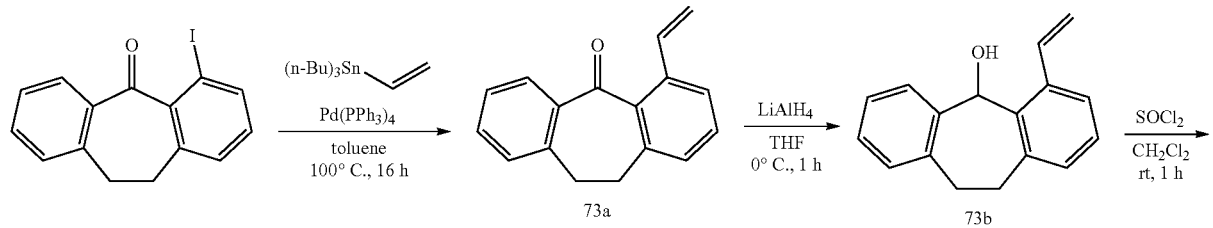
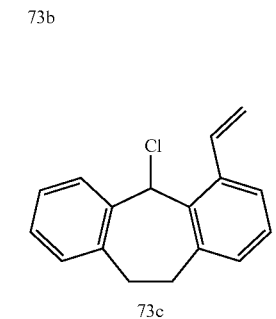
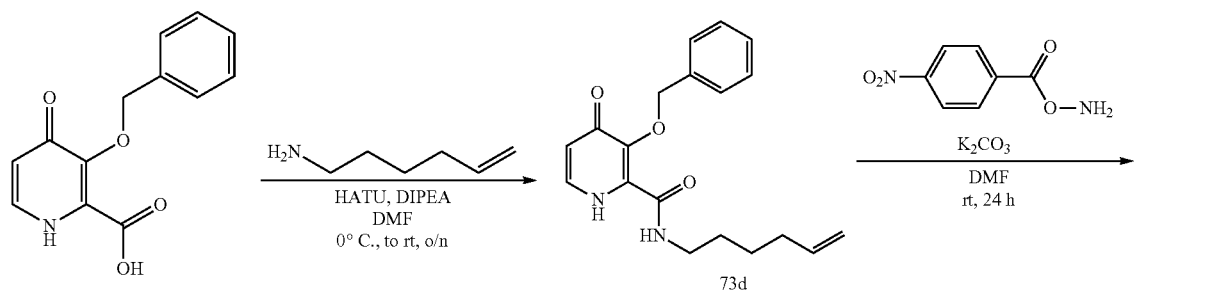
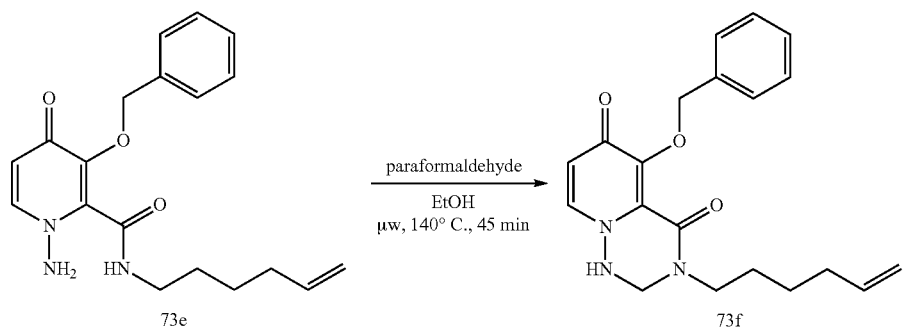
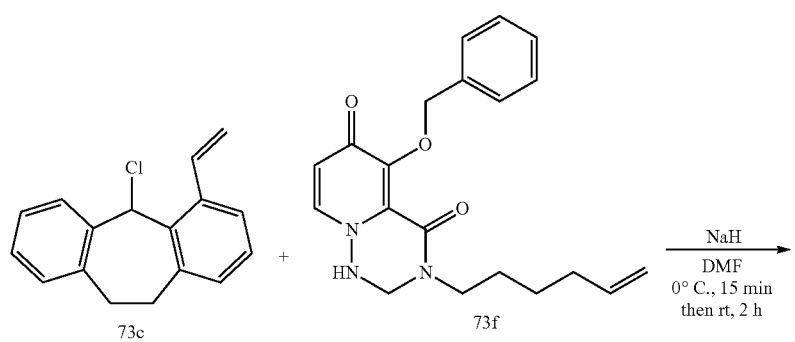

-continued
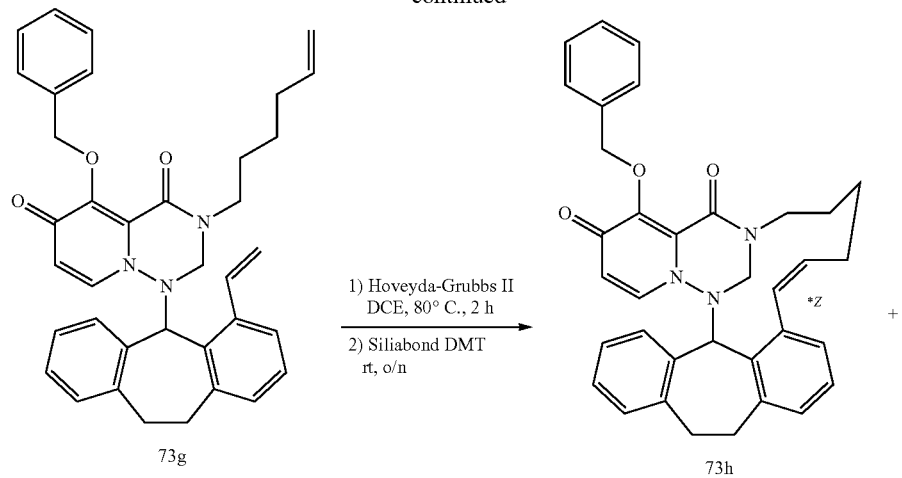
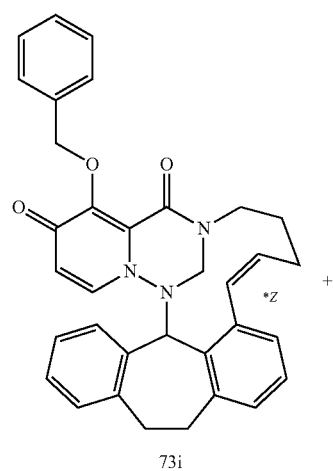
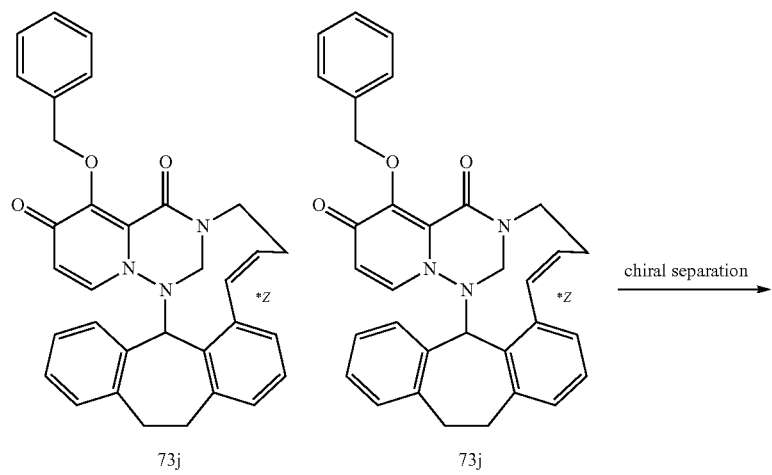
chiral separation →

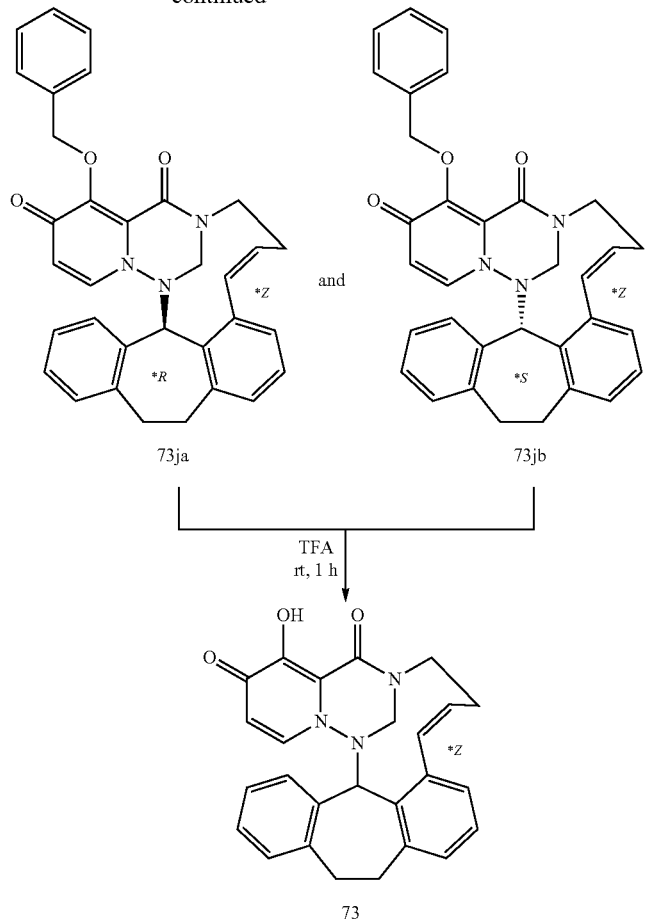

Synthesis of Intermediate 73a:

To a stirred solution of 4-iodo-10,11-dihydro-5H-dibenzo[α,d][7]annulen-5-one [CAS 70911-04-5] (3.40 g, 10.2 mmol) and Pd(PPh$_3$)$_4$ (1.18 g, 1.02 mmol) in toluene (146 mL) was added tributyl(vinyl)tin (8.9 mL, 30.5 mmol). The reaction mixture was stirred at 100° C. for 16 h. The mixture was concentrated in vacuo. The residue was extracted with CH$_2$Cl$_2$, washed with water, dried over Na$_2$SO$_4$, filtered and concentrated in vacuo. Purification was carried out by flash column chromatography over silica gel (petroleum ether/EtOAc from 100/0 to 90/10) to afford 4-vinyl-10,11-dihydro-5H-dibenzo[α,d][7]annulen-5-one (intermediate 73a, 2.15 g).

Synthesis of Intermediate 73b:

Intermediate 73a (1.50 g, 6.40 mmol) was dissolved in anhydrous THF (30 mL) under nitrogen atmosphere. The solution was cooled to 0° C. and LiAlH$_4$ (1.0 M in THF, 6.4 mL, 6.40 mmol) was added dropwise. The reaction mixture was stirred at 0° C. for 1 h. The reaction was quenched by the careful addition of water (250 μL), then a 15% aqueous solution of NaOH and water (750 μL) were added. The precipitate was filtered over Celite®. The filter-cake was washed with EtOAc. The filtrate was dried over Na$_2$SO$_4$, filtered and concentrated in vacuo to afford 4 4-vinyl-10,11-dihydro-5H-dibenzo[α,d][7]annulen-5-ol (intermediate 73b, 1.51 g).

Synthesis of Intermediate 73c:

5-chloro-4-vinyl-10,11-dihydro-5H-dibenzo[α,d][7]annulene (intermediate 73c, 1.63 g) was obtained using the procedure described for intermediate 5a.

Synthesis of Intermediate 73d:

3-(benzyloxy)-N-(hex-5-en-1-yl)-4-oxo-1,4-dihydropyridine-2-carboxamide (intermediate 73d, 5.7 g) was obtained using the procedure described for intermediate 5b.

Synthesis of Intermediate 73e:

To a solution of intermediate 73d (5.70 g, 17.5 mmol) in anhydrous DMF (200 mL) was suspended K$_2$CO$_3$ (7.24 g, 52.4 mmol) at rt. The mixture was stirred for 5 min. O-(4-Nitrobenzoyl)hydroxylamine (4.77 g, 26.2 mmol) was added and the reaction mixture was stirred at rt for 24 h. The reaction mixture was diluted with water. The mixture was extracted with CH$_2$Cl$_2$ (3 times), dried over Na$_2$SO$_4$, filtered and concentrated in vacuo. The residue was taken up in EtOAc. The precipitate was filtered off and dried under vacuum to afford 1-amino-3-(benzyloxy)-N-(hex-5-en-1-yl)-4-oxo-1,4-dihydropyridine-2-carboxamide (intermediate 73e, 4.6 g).

Synthesis of Intermediate 73f:

Paraformaldehyde (223 mg, 7.41 mmol) was added to a solution of intermediate 73e (2.30 g, 3.34 mmol) in EtOH (15 mL). The reaction mixture was stirred at 140° C. for 45 min in a microwave oven. The mixture was concentrated in vacuo. The crude mixture was purified by flash chromatography over silica gel (220 g, CH$_2$Cl$_2$/MeOH from 100/0 to 90/10) to afford 5-(benzyloxy)-3-(hex-5-en-1-yl)-2,3-dihydro-1H-pyrido[2,1-f][1,2,4]triazine-4,6-dione (intermediate 73f, 1.9 g).

Synthesis of Intermediate 73g:

5-(benzyloxy)-3-(hex-5-en-1-yl)-1-(4-vinyl-10,11-dihydro-5H-dibenzo[α,d][7]annulen-5-yl)-2,3-dihydro-1H-pyrido[2,1-f][1,2,4]triazine-4,6-dione (intermediate 73g, 170 mg) was obtained using the procedure described for intermediate 2d.

Synthesis of Intermediates 73h, 73i and 73j

A mixture of (13*Z)-6-(benzyloxy)-10,11,12,18,19,23b-hexahydro-9H-1,8-methanobenzo[4,5]cyclohepta[1,2,3-qr]pyrido[1,2-c][2,3,6]benzotriazacyclotetradecine-5,7-dione (intermediate 73h), (12*Z)-6-(benzyloxy)-9,10,11,17,18,22b-hexahydro-1,8-methanobenzo[4,5]cyclohepta[1,2,3-pq]pyrido[1,2-c][2,3,6]benzotriazacyclotridecine-5,7-dione (intermediate 73i) and (11*Z)-6-(benzyloxy)-10,16,17,21b-tetrahydro-9H-1,8-methanobenzo[4,5]cyclohepta[1,2,3-op]pyrido[1,2-c][2,3,6]benzotriazacyclododecine-5,7-dione (intermediate 73j) was obtained using the procedure described for intermediate 59d.

The mixture of intermediates 73h, 73i and 73j (300 mg) was purified via reverse phase (Stationary phase: YMC-actus Triart C18 10 μm 30*150 mm, Mobile phase Gradient: from 45% 0.2% aq. NH$_4$HCO$_3$/MeCN from 45/55 to 25/75) to afford intermediate 73j (65 mg), intermediate 73i (118 mg) and intermediate 73h (25 mg).

The enantiomers of 73j were separated via chiral SFC (Stationary phase: Whelk-O1 (S,S) 5 μm 250*21.2 mm, Mobile phase: 50% CO$_2$, 50% MeOH) to afford the first eluted enantiomer 73ja (30 mg) and the second eluted enantiomer 73jb (35 mg).

Synthesis of Compound 73:

((11*Z)-6-hydroxy-10,16,17,21b-tetrahydro-9H-1,8-methanobenzo[4,5]cyclohepta[1,2,3-op]pyrido[1,2-c][2,3,6]benzotriazacyclododecine-5,7-dione (compound 73, 6 mg) was obtained using the procedure described for compound 1. Racemization occurred during the reaction and was also observed when starting from intermediate 73jb.

Compound 73:

$^1$H NMR (500 MHz, DMSO-d$_6$) δ ppm 7.21-7.29 (m, 2H), 7.06-7.16 (m, 2H), 6.89 (br dd, J=7.1, 0.8 Hz, 1H), 6.85 (br d, J=7.6 Hz, 1H), 6.80 (br t, J=7.1 Hz, 1H), 6.64 (d, J=10.7 Hz, 1H), 6.40 (d, J=7.6 Hz, 1H), 5.86 (td, J=11.1, 4.6 Hz, 1H), 5.52 (s, 1H), 5.40 (br d, J=7.3 Hz, 1H), 4.76 (br d, J=13.6 Hz, 1H), 4.24-4.40 (m, 2H), 4.16 (br d, J=13.6 Hz, 1H), 3.46-3.54 (m, 1H), 2.85-2.94 (m, 1H), 2.67-2.76 (m, 2H), 2.14-2.25 (m, 1H), 2.03 (br d, J=14.8 Hz, 1H).

LC/MS (method LC-C): R$_t$ 2.92 min, MH$^+$426

Example 74: Synthesis of (18*R,Z)-3,4-difluoro-12-hydroxy-18-phenyl-6,9-dihydro-18H-10,17-methanobenzo[b]pyrido[1,2-f][1]oxa[5,6,9]triazacyclotridecine-11,13-dione (Compound 74A), (18*S,Z)-3,4-difluoro-12-hydroxy-18-phenyl-6,9-dihydro-18H-10,17-methanobenzo[b]pyrido[1,2-f][1]oxa[5,6,9]triazacyclotridecine-11,13-dione (Compound 74B)

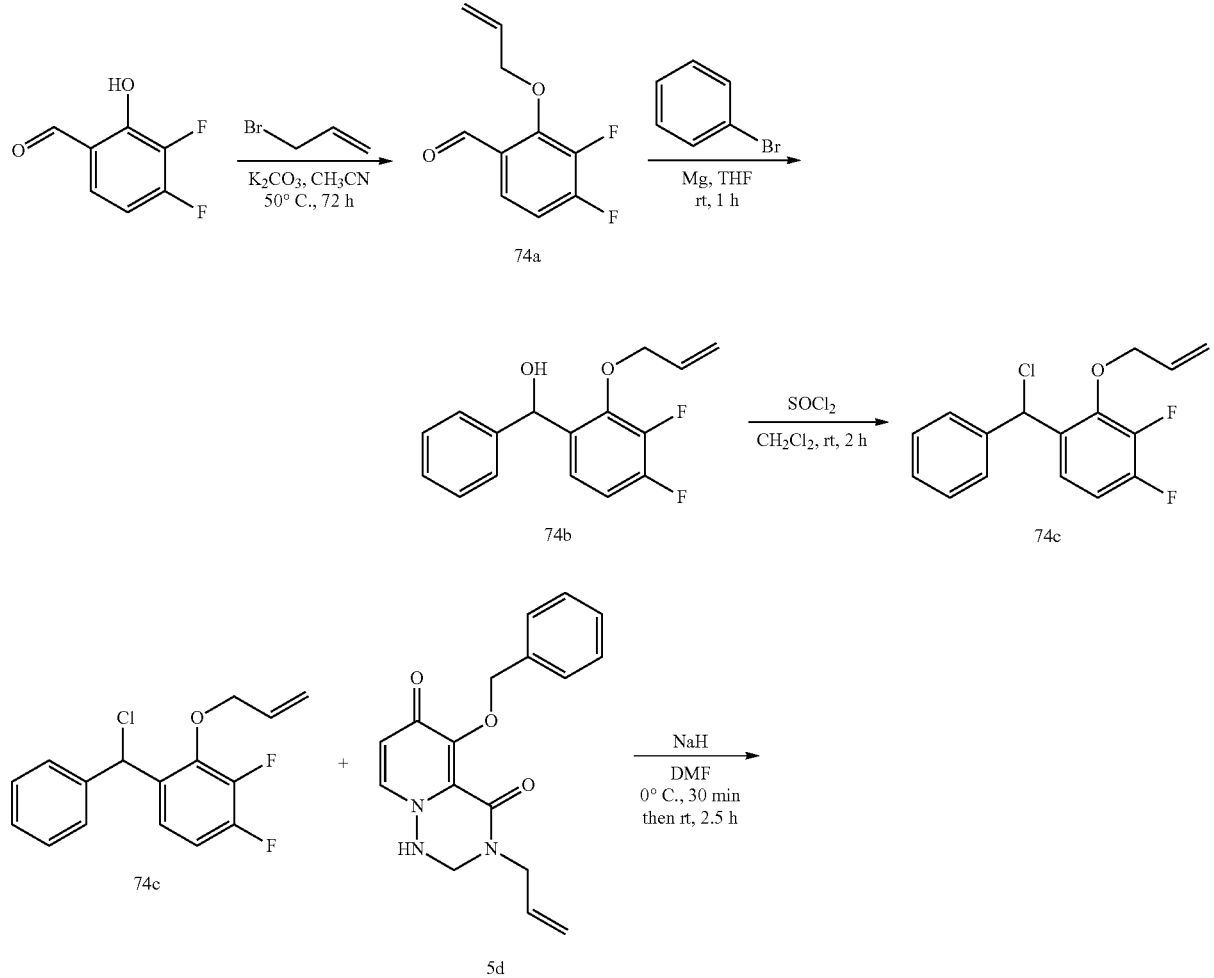

-continued

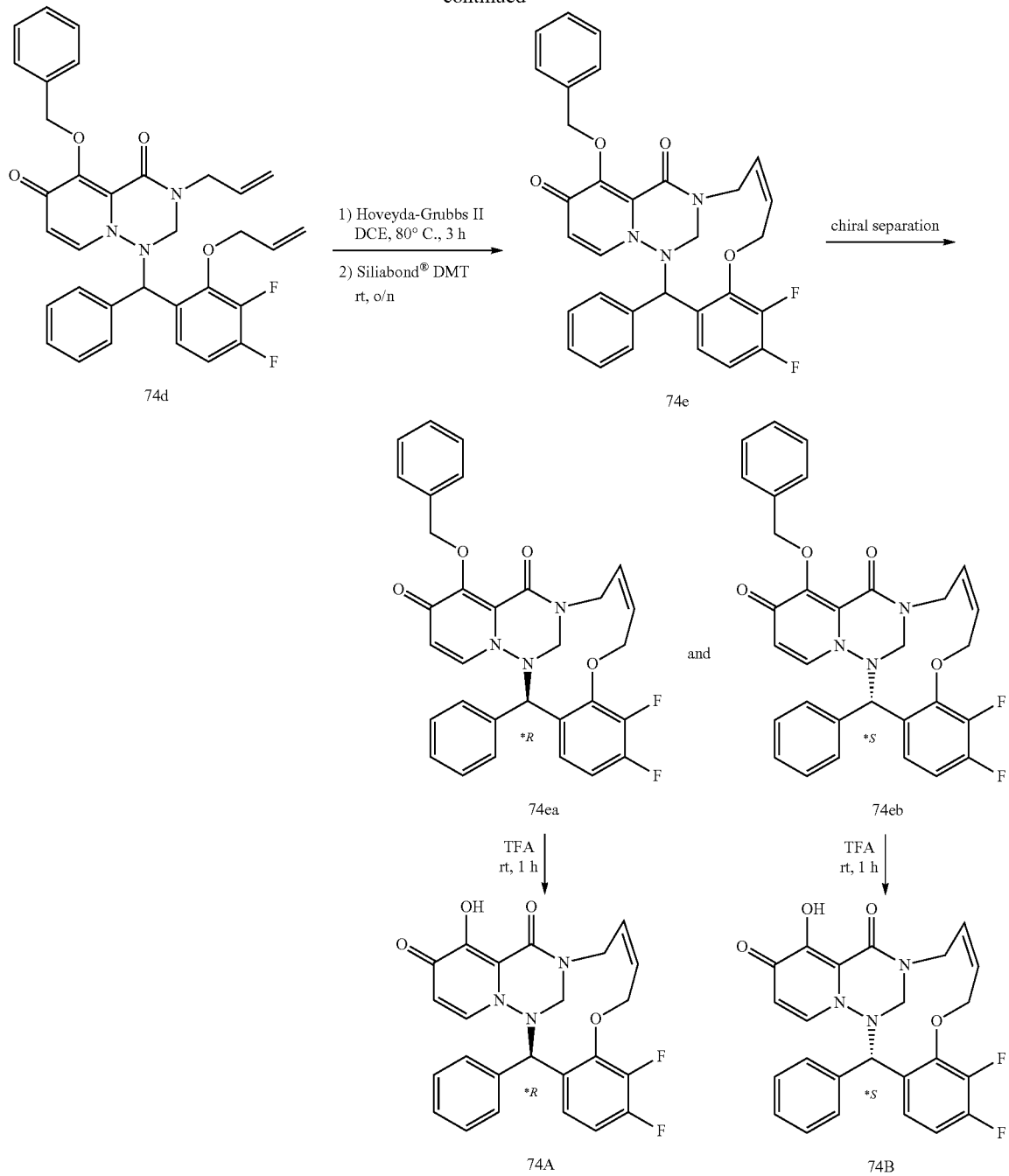

Synthesis of Intermediate 74a:
A mixture of allyl bromide (16.4 mL, 189.748 mmol), 3,4-difluoro-2-hydroxybenzaldehyde [CAS 502762-95-0] (20 g, 126.5 mmol), $K_2CO_3$ (34.97 g, 253 mmol) in $CH_3CN$ (330 mL) was stirred at 50° C. for 72 h. The reaction was filtered and the filtrate was concentrated under reduced pressure. The residue was taken up with EtOAc and filtered. The filtrate was washed with water, dried over $MgSO_4$, filtered and the solvent was evaporated to give 2-(allyloxy)-3,4-difluorobenzaldehyde (intermediate 74a, 24.6 g).

Synthesis of Intermediate 74b:
Under a $N_2$ flow, bromobenzene (7.56 mL, 72.161 mmol) in THE (50 mL) was added dropwise to a suspension of Mg (1.76 g) in THE (25 mL). The temperature was kept under 40° C. with an ice-bath and the mixture was stirred under $N_2$ until Mg disappearance. Under $N_2$ flow, this solution was added dropwise at 0° C. to a solution of 2-(allyloxy)-3,4-difluorobenzaldehyde (intermediate 74a, 11 g, 55.508 mmol) in THF (50 mL). The resulting mixture was stirred at rt for 1 h. The reaction was cooled down to 0° C., was quenched with $NH_4Cl$ 10% in water and extracted with EtOAc. The organic layer was washed with water, dried over $MgSO_4$, filtered and the solvent was concentrated under reduced pressure. Purification was carried out by flash chromatography over silica gel (220 g 30 μm, eluent Heptane/EtOAc 95/5 to 80/20). The pure fractions were collected and evaporated to dryness to give (2-(allyloxy)-3,4-difluorophenyl)(phenyl)methanol (intermediate 74b, 11 g).
Synthesis of Intermediate 74c:

SOCl$_2$ (2.98 mL, 40.979 mmol) was added dropwise to a solution of (2-(allyloxy)-3,4-difluorophenyl)(phenyl)methanol (intermediate 74b, 9.44 g, 34.149 mmol) in CH$_2$Cl$_2$ (84 mL) at 5° C. The mixture was stirred at 5° C. for 45 mn and at rt for 2h. The solvent was evaporated to dryness and coevaporated with toluene to give 2-(allyloxy)-1-(chloro (phenyl)methyl)-3,4-difluorobenzene (intermediate 74c, 10.7 g), used as such in the next step.
Synthesis of Intermediate 74d:

3-allyl-1-((2-(allyloxy)-3,4-difluorophenyl)(phenyl) methyl)-5-(benzyloxy)-2,3-dihydro-1H-pyrido[2,1-f][1,2,4] triazine-4,6-dione (intermediate 74d, 1.7 g) was obtained using the procedure described for intermediate 2d.
Synthesis of Intermediate 74e:

(Z)-12-(benzyloxy)-3,4-difluoro-18-phenyl-6,9-dihydro-18H-10,17-methanobenzo[b]pyrido[1,2-f][1]oxa[5,6,9]triazacyclotridecine-11,13-dione (intermediate 74e, 1.3 g) was obtained using the procedure described for intermediate 1f. The enantiomers were separated via chiral SFC (Stationary phase: CHIRACEL OJ-H 5 μm 250*30 mm, Mobile phase: 80% CO$_2$, 20% MeOH) to afford the first eluted enantiomer 74ea (561 mg) and the second eluted enantiomer 74eb (564 mg).
Synthesis of compound 74A:

(18*R,Z)-3,4-difluoro-12-hydroxy-18-phenyl-6,9-dihydro-18H-10,17-methanobenzo[b]pyrido[1,2-f][1]oxa[5,6,9]triazacyclotridecine-11,13-dione (compound 74A) was obtained using the procedure described for compound 1. Crude compound 74A was purified by preparative LC (regular SiOH 30 μm, 24 g, CH$_2$Cl$_2$/MeOH from 99/1 to 95/5). The residue (370 mg) was triturated in Et$_2$O. The solid was filtered off and dried under vacuum to give compound 74A (311 mg).

Compound 74A:
$^1$H NMR (500 MHz, DMSO-d$_6$) δ ppm 7.94 (br t, J=6.3 Hz, 1H), 7.50 (q, J=8.5 Hz, 1H), 7.01-7.29 (m, 6H), 6.25 (br s, 1H), 6.04 (br s, 1H), 5.49 (d, J=7.9 Hz, 1H), 5.22 (br s, 1H), 5.13 (d, J=13.6 Hz, 1H), 4.78-4.91 (m, 2H), 4.27 (br d, J=13.9 Hz, 2H), 3.20 (br dd, J=13.9, 7.9 Hz, 1H).

LC/MS (method LC-C): Rt 2.68 min, MH$^+$452

$[α]_D^{20}$: +607.43° (c 0.202, DMF)

Chiral HPLC (method HPLC-B): Rt 5.38 min, chiral purity 100%

Synthesis of Compound 74B:

(18*S,Z)-3,4-difluoro-12-hydroxy-18-phenyl-6,9-dihydro-18H-10,17-methanobenzo[b]pyrido[1,2-f][1]oxa[5,6,9]triazacyclotridecine-11,13-dione (compound 74B) was obtained using the procedure described for compound 1. Crude compound 74B was purified by preparative LC (regular SiOH 30 μm, 24 g, CH$_2$Cl$_2$/MeOH from 99/1 to 95/5). The residue (375 mg) was triturated in Et$_2$O. The solid was filtered off and dried under vacuum to give compound 74B (320 mg).

Compound 74B:
$^1$H NMR (500 MHz, DMSO-d$_6$) δ ppm 7.94 (br t, J=6.1 Hz, 1H), 7.50 (q, J=8.5 Hz, 1H), 7.00-7.29 (m, 6H), 6.25 (br s, 1H), 6.04 (br s, 1H), 5.49 (d, J=7.6 Hz, 1H), 5.22 (br s, 1H), 5.13 (d, J=13.6 Hz, 1H), 4.79-4.90 (m, 2H), 4.27 (d, J=13.9 Hz, 2H), 3.20 (br dd, J=13.9, 8.2 Hz, 1H).

LC/MS (method LC-C): Rt 2.68 min, MH$^+$452

$[α]_D^{20}$: −634.65° (c 0.127, DMF)

Chiral HPLC (method HPLC-B): Rt 8.39 min. chiral purity 100%

Example 75: Synthesis of (18*R,Z)-4-chloro-12-hydroxy-18-phenyl-6,9-dihydro-18H-10,17-methanobenzo[b]pyrido[1,2-f][1]oxa[5,6,9]triazacyclotridecine-11,13-dione (Compound 75A), (18*S,Z)-4-chloro-12-hydroxy-18-phenyl-6,9-dihydro-18H-10, 17-methanobenzo[b]pyrido[1,2-f][1]oxa[5,6,9] triazacyclotridecine-11,13-dione (Compound 75B)

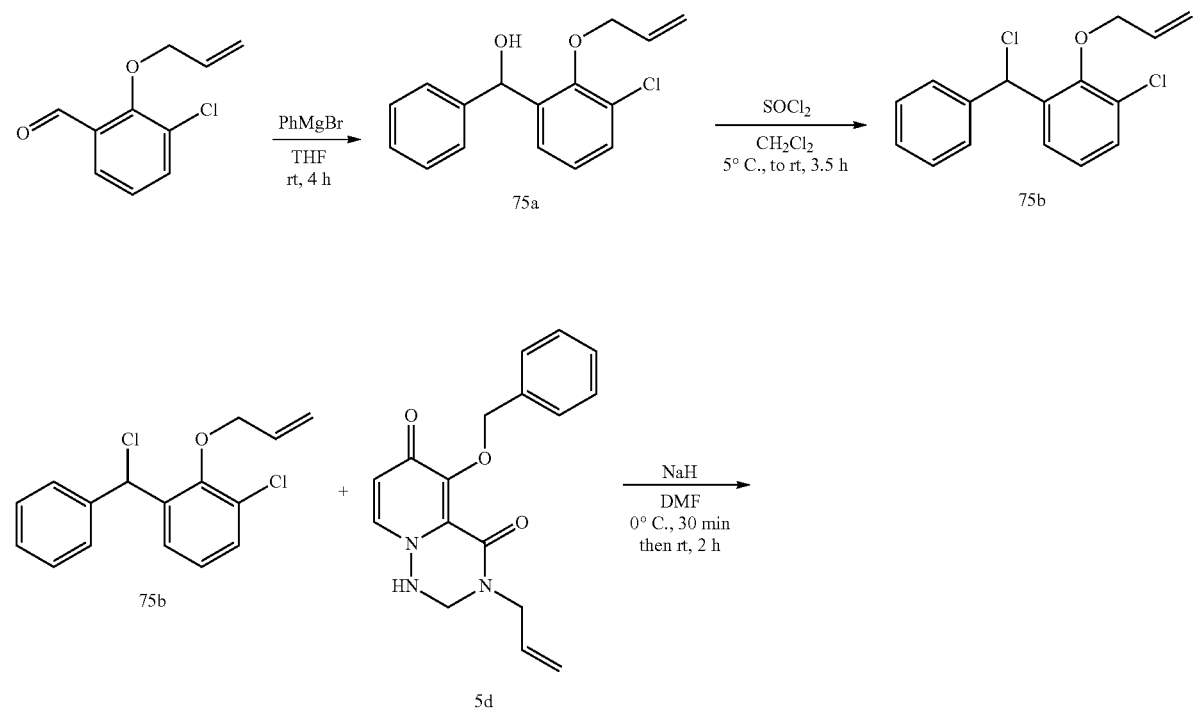

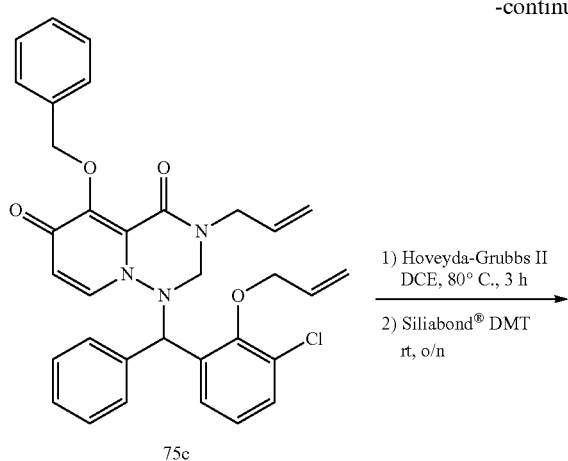

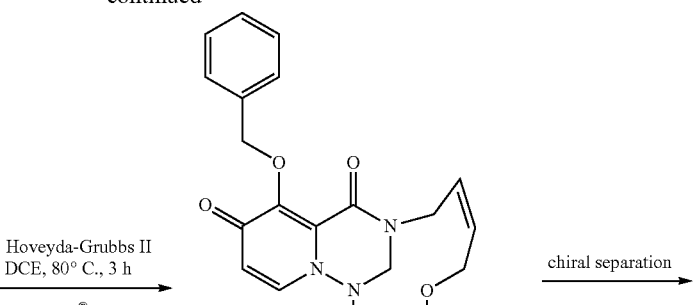

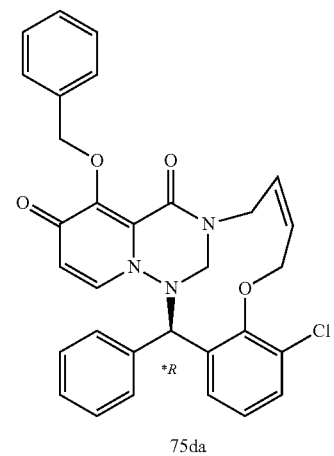

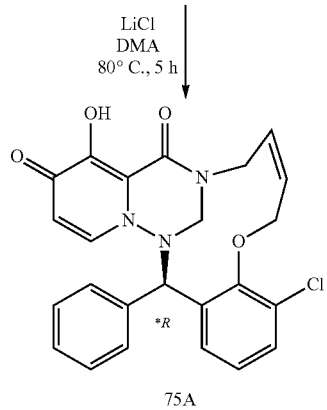

Synthesis of Intermediate 75a:
(2-(allyloxy)-3-chlorophenyl)(phenyl)methanol (intermediate 75a, 4.7 g) was obtained using the procedure described for intermediate 2b. Crude intermediate 75a was purified by flash chromatography over silica gel (15-40 μm, 220 g, heptane/EtOAc from 90/10 to 80/20).

Synthesis of Intermediate 75b:
2-(allyloxy)-1-chloro-3-(chloro(phenyl)methyl)benzene (intermediate 75b, 2.00 g) was obtained using the procedure described for intermediate 5a.

Synthesis of Intermediate 75c:
3-allyl-1-((2-(allyloxy)-3-chlorophenyl)(phenyl)methyl)-5-(benzyloxy)-2,3-dihydro-1H-pyrido[2,1-f][1,2,4]triazine-4,6-dione (intermediate 75c, 3.7 g) was obtained using the procedure described for intermediate 2d.

Synthesis of Intermediate 75d:
(Z)-12-(benzyloxy)-4-chloro-18-phenyl-6,9-dihydro-18H-10,17-methanobenzo[b]pyrido[1,2-f][1]oxa[5,6,9]triazacyclotridecine-11,13-dione (intermediate 75d, 2.23 g) was obtained using the procedure described for intermediate 1f.

The enantiomers were separated via chiral SFC (Stationary phase: Chiralpak IC 5 μm 250*21.2 mm, Mobile phase: 40% CO₂, 60% (MeOH/CH₂Cl₂, 80/20) to afford the first elute enantiomer 75da (1.01 g) and the second eluted enantiomer 75db (916 mg).

Synthesis of Compound 75A:

(18*R,Z)-4-chloro-12-hydroxy-18-phenyl-6,9-dihydro-18H-10,17-methanobenzo[b]pyrido[1,2-f][1]oxa[5,6,9]triazacyclotridecine-11,13-dione (compound 75A, 187 mg) was obtained using the procedure described for compound 28A.

Compound 75A:

$^{1}$H NMR (500 MHz, DMSO-d$_6$) δ ppm 8.01 (br d, J=7.6 Hz, 1H), 7.50 (dd, J=8.0, 1.4 Hz, 1H), 7.35 (t, J=8.0 Hz, 1H), 6.95-7.22 (m, 6H), 6.19 (br s, 1H), 5.82 (br s, 1H), 5.41 (d, J=7.9 Hz, 1H), 5.23 (br s, 1H), 5.09 (d, J=13.6 Hz, 1H), 4.69-4.81 (m, 2H), 4.24 (br d, J=13.9 Hz, 2H), 3.14 (br dd, J=14.0, 7.7 Hz, 1H).

LC/MS (method LC-C): R$_t$ 2.74 min, MH$^+$450

$[α]_D^{20}$: +606.45° (c 0.248, DMF)

Synthesis of Compound 75B:

(18*S,Z)-4-chloro-12-hydroxy-18-phenyl-6,9-dihydro-18H-10,17-methanobenzo[b]pyrido[1,2-f][1]oxa[5,6,9]triazacyclotridecine-11,13-dione (compound 75B, 226 mg) was obtained using the procedure described for compound 28A.

Compound 75B:

$^{1}$H NMR (500 MHz, DMSO-d$_6$) δ ppm 8.08 (br d, J=7.6 Hz, 1H), 7.57 (dd, J=7.9, 0.9 Hz, 1H), 7.42 (t, J=7.9 Hz, 1H), 7.00-7.27 (m, 6H), 6.27 (br s, 1H), 5.90 (br s, 1H), 5.49 (d, J=7.6 Hz, 1H), 5.31 (br s, 1H), 5.17 (d, J=13.6 Hz, 1H), 4.76-4.88 (m, 2H), 4.32 (br d, J=13.9 Hz, 2H), 3.22 (br dd, J=14.2, 7.6 Hz, 1H).

LC/MS (method LC-C): Rt 2.74 min, MH$^+$450

$[α]_D^{20}$: −623.19° (c 0.276, DMF)

Example 76: Synthesis of (16*R,E)-12-fluoro-16-(6-fluoropyridin-2-yl)-4-hydroxy-7,10,11,16-tetrahydro-6,17-methanobenzo[k]pyrido[1,2-b][1,2,5]triazacyclotridecine-3,5-dione (Compound 76A), (16*S,E)-12-fluoro-16-(6-fluoropyridin-2-yl)-4-hydroxy-7,10,11,16-tetrahydro-6,17-methanobenzo[k]pyrido[1,2-b][1,2,5]triazacyclotridecine-3,5-dione (Compound 76B)

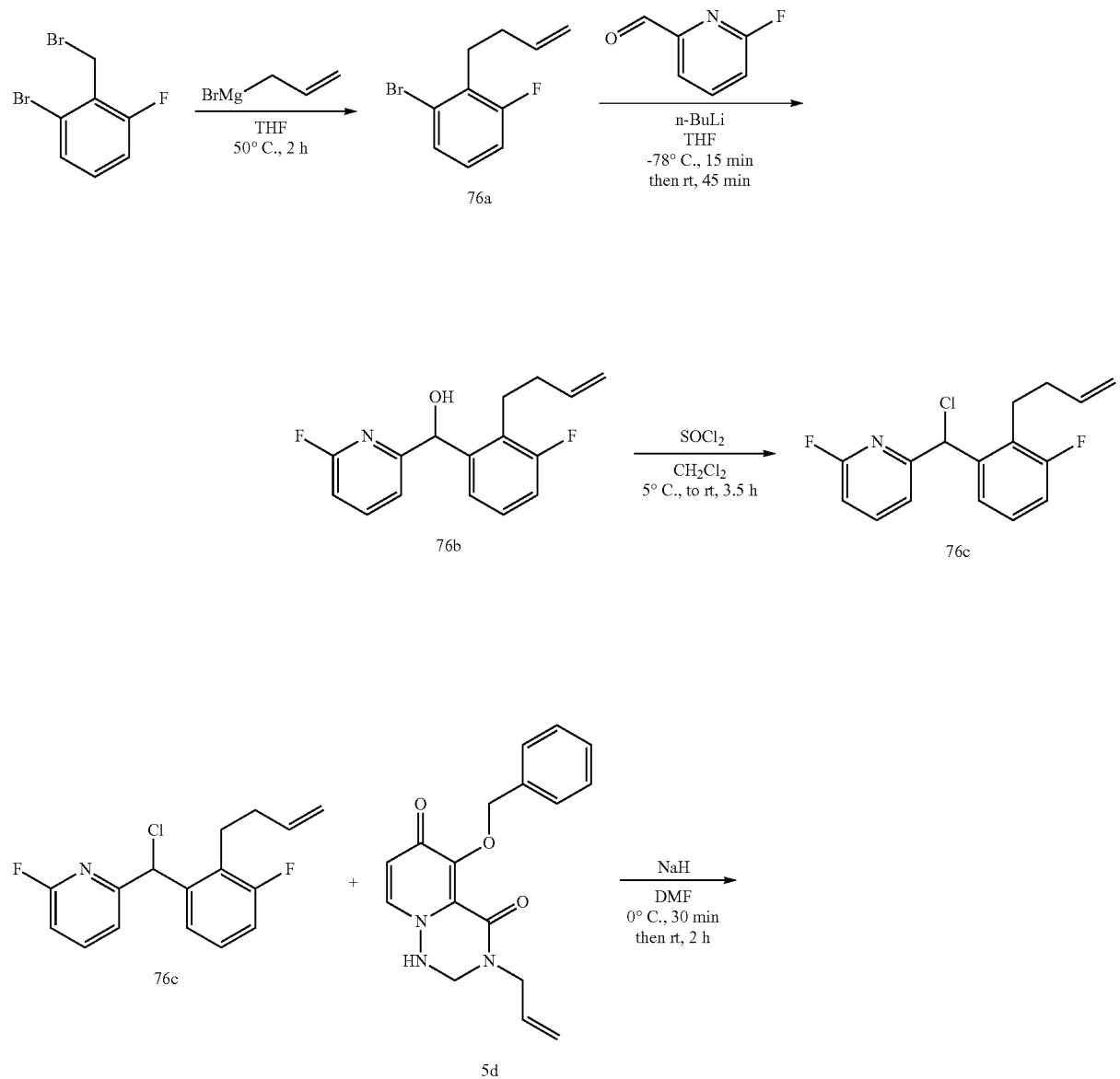

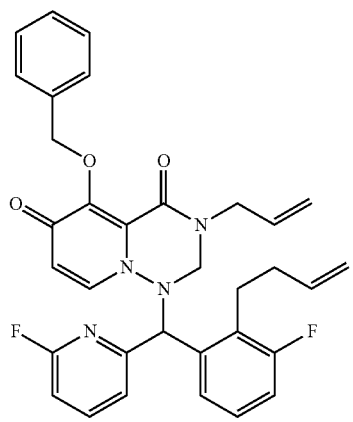

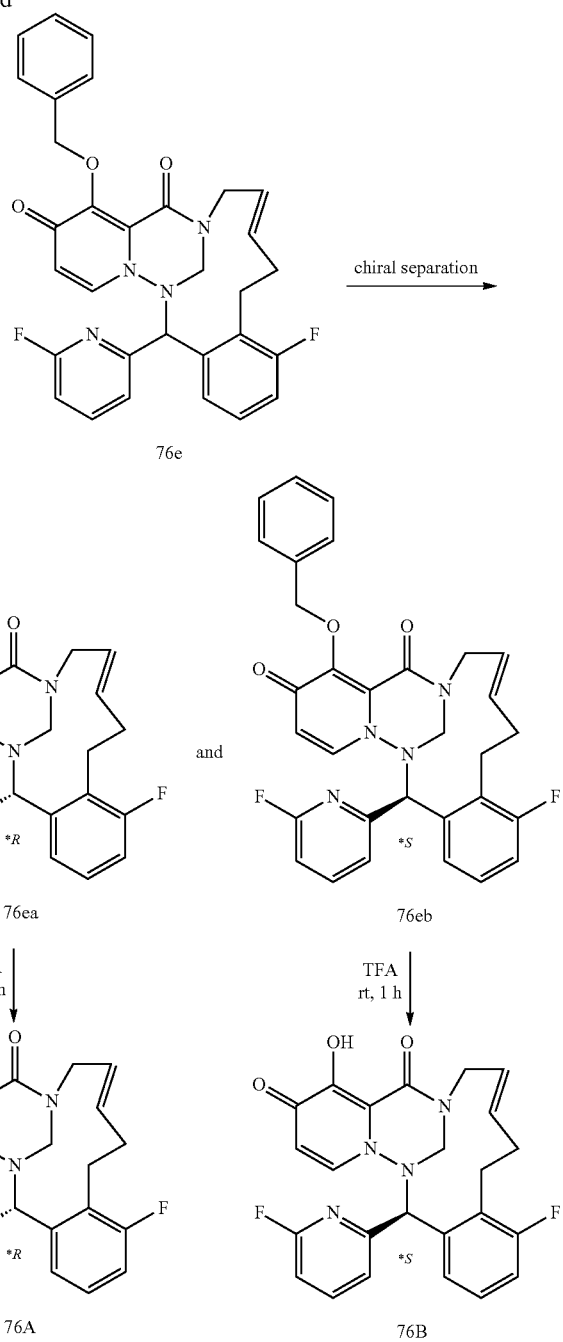

Synthesis of Intermediate 76a:

Under nitrogen atmosphere, allylmagnesium bromide (1.0 M, 28.0 mL, 28 mmol) was added slowly to a solution of 1-bromo-2-(bromomethyl)-3-fluorobenzene [CAS 1548-81-8] (5.00 g, 18.7 mmol) in anhydrous THF (46 mL) at 0° C. The reaction mixture was stirred at 50° C. for 2 h. The reaction was quenched by the addition of a 10% aqueous solution of $NH_4Cl$. The mixture was extracted with EtOAc. The combined organic extracts were washed with brine, dried over $MgSO_4$, filtered and evaporated in vacuo to afford 1-bromo-2-(but-3-en-1-yl)-3-fluorobenzene (intermediate 76a, 4.00 g).

Synthesis of Intermediate 76b:

(2-(but-3-en-1-yl)-3-fluorophenyl)(6-fluoropyridin-2-yl)methanol (intermediate 76b, 1.1 g) was obtained using the procedure described for intermediate 23a.

Synthesis of Intermediate 76c:

2-((2-(but-3-en-1-yl)-3-fluorophenyl)chloromethyl)-6-fluoropyridine (intermediate 76c, 1.2 g) was obtained using the procedure described for intermediate 5a.

Synthesis of Intermediate 76d:

3-allyl-5-(benzyloxy)-1-((2-(but-3-en-1-yl)-3-fluorophenyl)(6-fluoropyridin-2-yl)methyl)-2,3-dihydro-1H-pyrido[2,1-f][1,2,4]triazine-4,6-dione (intermediate 76d, 0.37 g) was obtained using the procedure described for intermediate 2d.

Synthesis of Intermediate 76e:

(E)-4-(benzyloxy)-12-fluoro-16-(6-fluoropyridin-2-yl)-7,10,11,16-tetrahydro-6,17-methanobenzo[k]pyrido[1,2-b][1,2,5]triazacyclotridecine-3,5-dione (intermediate 76e, 176 mg) was obtained using the procedure described for intermediate 1f.

The enantiomers were separated via chiral SFC (Stationary phase: Chiralcel OD-H 5 μm 250×21.2 mm, Mobile phase: 60% $CO_2$, 40% MeOH) to afford the first eluted enantiomer 76ea (70 mg) and the second eluted enantiomer 76eb (72 mg).

Synthesis of Compound 76A:

(16*R,E)-4-(benzyloxy)-12-fluoro-16-(6-fluoropyridin-2-yl)-7,10,11,16-tetrahydro-6,17-methanobenzo[k]pyrido[1,2-b][1,2,5]triazacyclotridecine-3,5-dione (compound 76A, 41 mg) was obtained using the procedure described for compound 1.

Compound 76A:

$^1$H NMR (500 MHz, DMSO-$d_6$) δ ppm 7.88 (d, J=7.9 Hz, 1H), 7.79 (q, J=7.9 Hz, 1H), 7.41-7.48 (m, 1H), 7.33 (dd, J=7.6, 1.9 Hz, 1H), 7.16 (t, J=9.1 Hz, 1H), 7.08 (d, J=7.9 Hz, 1H), 6.97-7.02 (m, 1H), 5.94 (br dt, J=15.1, 7.9 Hz, 1H), 5.50 (d, J=7.9 Hz, 1H), 5.42-5.48 (m, 1H), 5.24 (s, 1H), 5.07 (d, J=13.9 Hz, 1H), 4.65 (dd, J=14.2, 5.0 Hz, 1H), 4.18 (d, J=13.6 Hz, 1H), 3.03 (dd, J=13.9, 7.9 Hz, 1H), 2.74 (br d, J=13.9 Hz, 1H), 2.50-2.56 (m, 1H), 2.34 (br t, J=12.9 Hz, 1H), 1.91-2.00 (m, 1H).

LC/MS (method LC-C): $R_t$ 2.74 min, MH$^+$451

$[α]_D^{20}$: +556.00° (c 0.150, DMF)

Synthesis of compound 76B:

16*S,E)-12-fluoro-16-(6-fluoropyridin-2-yl)-4-hydroxy-7,10,11,16-tetrahydro-6,17-methanobenzo[k]pyrido[1,2-b][1,2,5]triazacyclotridecine-3,5-dione (compound 76B, 40 mg) was obtained using the procedure described for compound 1.

Compound 76B:

$^1$H NMR (500 MHz, DMSO-$d_6$) δ ppm 7.96 (d, J=7.9 Hz, 1H), 7.87 (q, J=8.1 Hz, 1H), 7.48-7.55 (m, 1H), 7.41 (dd, J=7.3, 1.9 Hz, 1H), 7.24 (t, J=9.0 Hz, 1H), 7.16 (d, J=7.9 Hz, 1H), 7.07 (dd, J=8.2, 2.2 Hz, 1H), 6.02 (dt, J=15.5, 7.8 Hz, 1H), 5.57 (d, J=7.6 Hz, 1H), 5.49-5.56 (m, 1H), 5.32 (s, 1H), 5.15 (d, J=13.6 Hz, 1H), 4.73 (dd, J=13.9, 5.0 Hz, 1H), 4.26 (d, J=13.6 Hz, 1H), 3.10 (dd, J=13.9, 7.9 Hz, 1H), 2.81 (br d, J=13.6 Hz, 1H), 2.57-2.63 (m, 1H), 2.41 (br t, J=12.8 Hz, 1H), 1.98-2.08 (m, 1H).

LC/MS (method LC-C): $R_t$ 2.74 min, MH$^+$451

$[α]_D^{20}$: −550.00° (c 0.166, DMF)

Example 77: Synthesis of (7E,19*R)-3-fluoro-13-hydroxy-19-phenyl-9,10-dihydro-6H,19H-11,18-methanobenzo[2,1-i][1,7,10,11]benzoxatriazacyclotetradecine-12,14-dione (Compound 77A), (7E,19*R)-3-fluoro-13-hydroxy-19-phenyl-9,10-dihydro-6H,19H-11,18-methanopyrido[2,1-i][1,7,10,11]benzoxatriazacyclotetradecine-12,14-dione (Compound 77B)

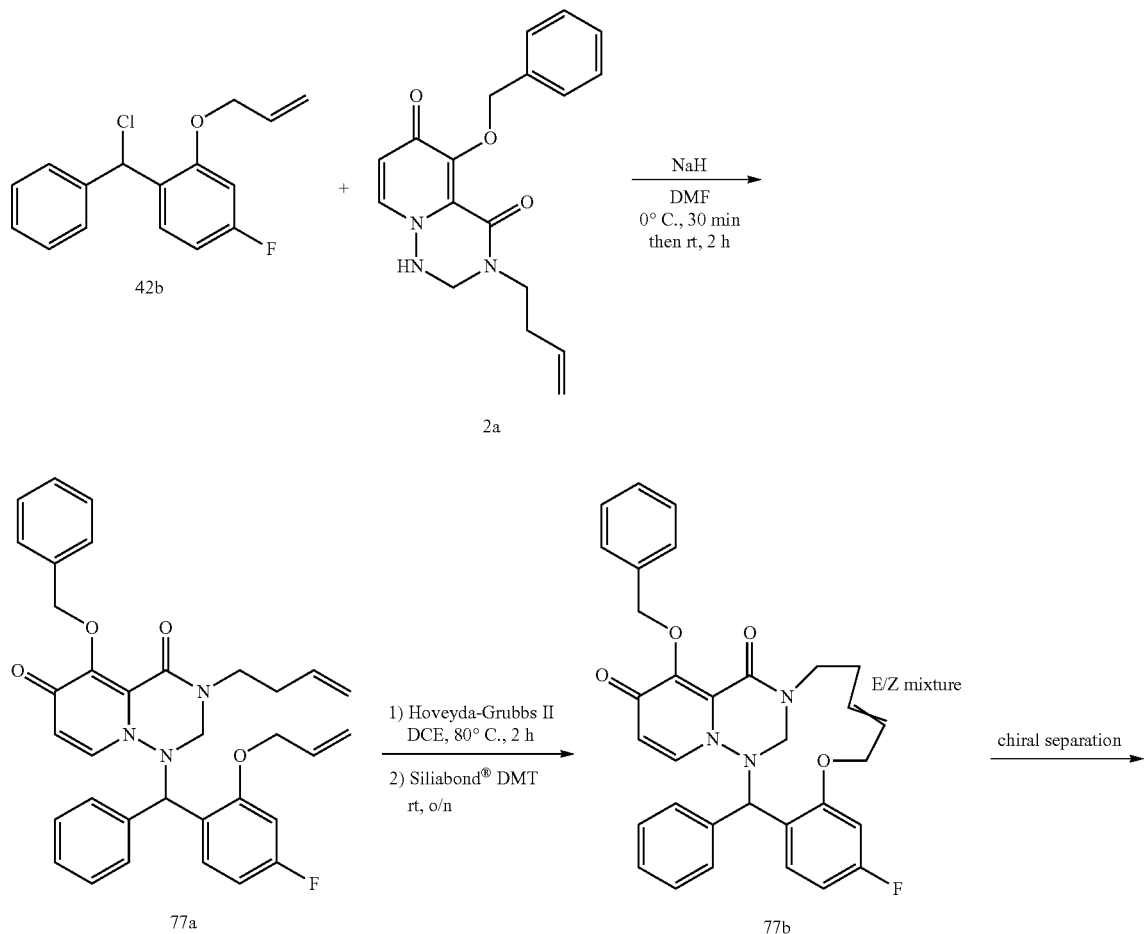

-continued

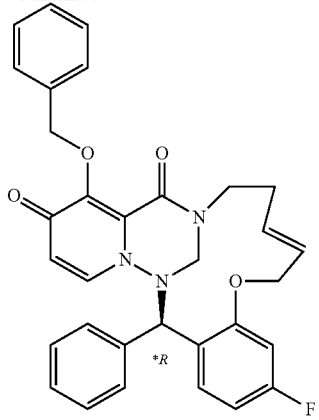

77ba

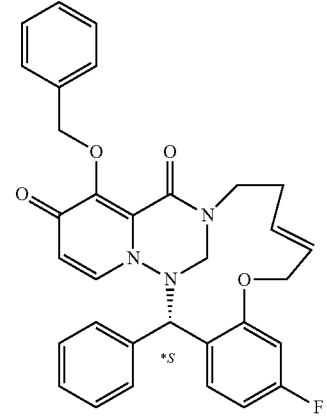

77bb

TFA | rt, 1 h

TFA | rt, 1 h

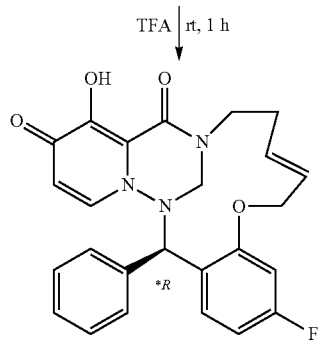

77A

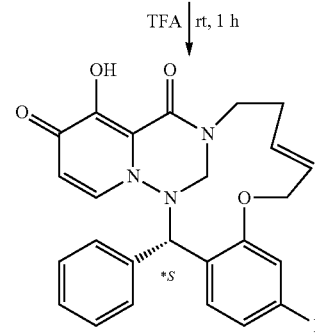

77B

Synthesis of Intermediate 77a:

1-((2-(allyloxy)-4-fluorophenyl)(phenyl)methyl)-5-(benzyloxy)-3-(but-3-en-1-yl)-2,3-dihydro-1H-pyrido[2,1-f][1,2,4]triazine-4,6-dione (intermediate 77a, 3.6 g) was obtained using the procedure described for intermediate 2d.

Synthesis of Intermediate 77b:

(E/Z)-15-(benzyloxy)-34-fluoro-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (intermediate 77b, mixture of Z and E isomers, 760 mg) was obtained using the procedure described for intermediate 1f. Crude intermediate 77b (3.27 g) was purified by flash chromatography over silica gel (20-45 µm, 120 g, $CH_2Cl_2$/MeOH from 99/1 to 92/8). The residue (1.47 g) was purified a second time by flash chromatography over silica gel (20-45 µm, 40 g, toluene/i-PrOH 95/5) to afford intermediate 77b.

The isomers were separated via chiral SFC (Stationary phase: CHIRALPAK AD-H 5 µm 250*30 mm, Mobile phase: 75% $CO_2$, 25% EtOH) to afford the first eluted enantiomer 77ba (253 mg) and the second eluted enantiomer 77b (271 mg). The enantiomer 77bb was re-purified via chiral SFC (Stationary phase: CHIRALPAK AD-H 5 µm 250*30 mm, Mobile phase: 77% $CO_2$, 23% EtOH) to deliver 234 mg of pure enantiomer 77bb.

Synthesis of Compound 77A:

(7E,19*R)-3-fluoro-13-hydroxy-19-phenyl-9,10-dihydro-6H,19H-11,18-methanopyrido[2,1-i][1,7,10,11]benzoxatriazacyclotetradecine-12,14-dione (compound 77A, 137 mg) was obtained using the procedure for compound 1.

Compound 77A:

$^1$H NMR (500 MHz, DMSO-$d_6$) δ ppm 11.72 (br s, 1H), 8.04 (dd, J=8.8, 6.9 Hz, 1H), 6.99-7.30 (m, 8H), 5.99 (ddd, J=15.5, 9.9, 5.2 Hz, 1H), 5.86 (s, 1H), 5.57 (ddd, J=15.2, 10.2, 4.6 Hz, 1H), 5.38 (d, J=7.6 Hz, 1H), 5.03 (d, J=12.9 Hz, 1H), 4.70 (dd, J=11.8, 5.2 Hz, 1H), 4.27 (d, J=12.9 Hz, 1H), 4.23 (dd, J=12.0, 10.4 Hz, 1H), 3.78 (br dt, J=13.2, 3.5 Hz, 1H), 2.84-2.94 (m, 1H), 2.78-2.86 (m, 1H), 2.24 (br d, J=12.9 Hz, 1H).

LC/MS (method LC-C): Rt 2.71 min, MH$^+$448

$[α]_D^{20}$: +420.73° (c 0.193, DMF)

Chiral HPLC (method HPLC-B): R$_t$ 4.30 min, chiral purity 100%

Synthesis of Compound 77B:

(7E,19*S)-3-fluoro-13-hydroxy-19-phenyl-9,10-dihydro-6H,19H-11,18-methanopyrido[2,1-i][1,7,10,11]benzoxatriazacyclotetradecine-12,14-dione (compound 77B, 102 mg) was obtained using the procedure for compound 1.

Compound 77B:

$^1$H NMR (500 MHz, DMSO-$d_6$) δ ppm 11.73 (br s, 1H), 8.04 (dd, J=8.5, 7.3 Hz, 1H), 7.00-7.26 (m, 8H), 5.99 (ddd, J=15.4, 9.9, 5.2 Hz, 1H), 5.86 (s, 1H), 5.57 (ddd, J=14.8, 10.1, 4.4 Hz, 1H), 5.38 (d, J=7.6 Hz, 1H), 5.03 (d, J=12.9 Hz, 1H), 4.70 (dd, J=11.8, 5.2 Hz, 1H), 4.27 (d, J=12.9 Hz, 1H), 4.24 (dd, J=11.7, 10.1 Hz, 1H), 3.78 (dt, J=13.2, 3.5 Hz, 1H), 2.86-2.94 (m, 1H), 2.77-2.86 (m, 1H), 2.23 (br d, J=12.9 Hz, 1H).

LC/MS (method LC-C): Rt 2.72 min, MH$^+$478

$[α]_D^{20}$: −411.24° (c 0.169, DMF)

Chiral HPLC (method HPLC-B): Rt 5.38 min. chiral purity 99.3%

Example 78: Synthesis of (16*R,E)-16-(6-fluoro-pyridin-2-yl)-4-hydroxy-7,10,11,16-tetrahydro-6,17-methanobenzo[k]pyrido[1,2-b][1,2,5]triazacyclotri-decine-3,5-dione (Compound 78A), (16*S,E)-16-(6-fluoropyridin-2-yl)-4-hydroxy-7,10,11,16-tetrahydro-6,17-methanobenzo[k]pyrido[1,2-b][1,2,5]triazacyclotridecine-3,5-dione (Compound 78B)
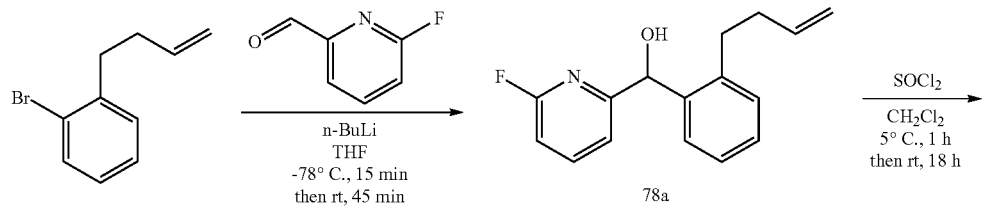
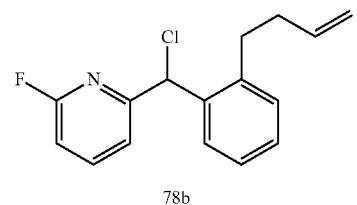
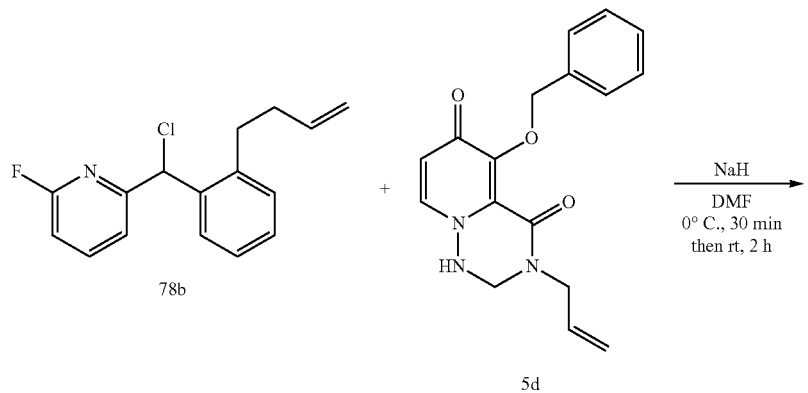
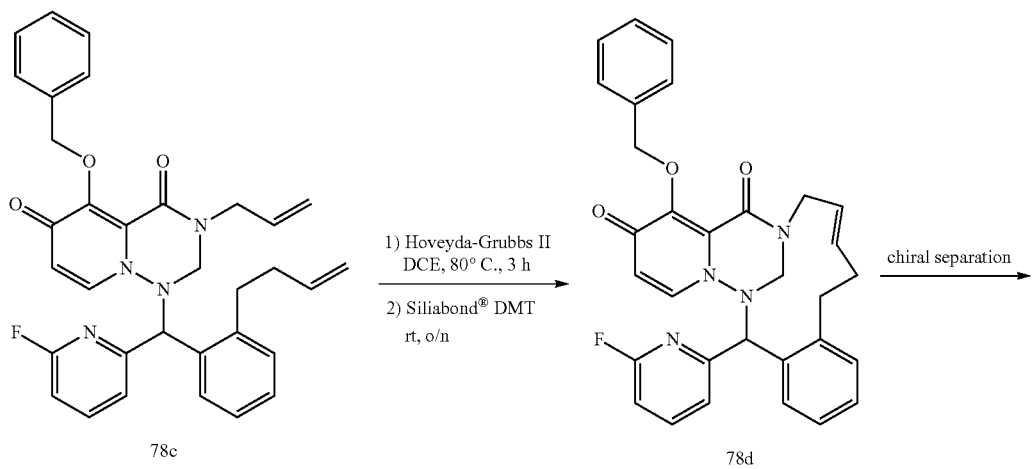

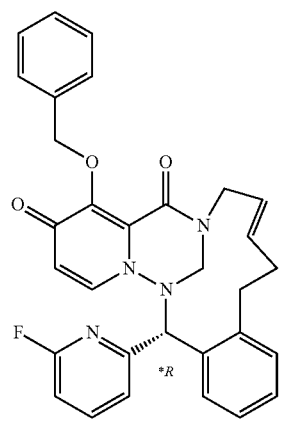

78da

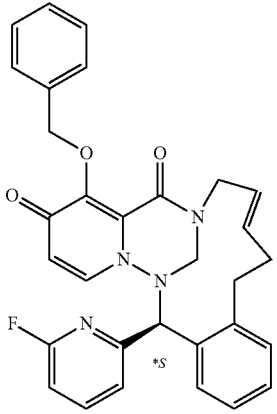

78db and

TFA rt, 1 h ↓       TFA rt, 1 h ↓

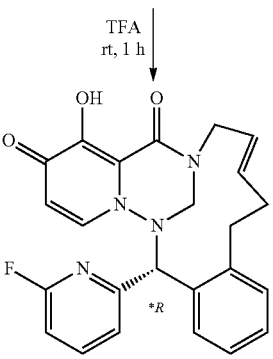

78A

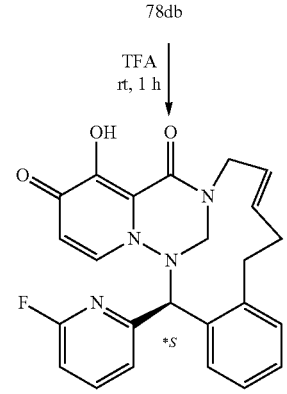

78B

Synthesis of Intermediate 78a:
(2-(but-3-en-1-yl)phenyl)(6-fluoropyridin-2-yl)methanol (intermediate 78a, 1.6 g) was obtained using the procedure described for intermediate 23a.

Synthesis of Intermediate 78b:
2-((2-(but-3-en-1-yl)phenyl)chloromethyl)-6-fluoropyridine (intermediate 78b, 1.7 g) was obtained using the procedure described for intermediate 5a.

Synthesis of Intermediate 78c:
3-allyl-5-(benzyloxy)-1-((2-(but-3-en-1-yl)phenyl)(6-fluoropyridin-2-yl)methyl)-2,3-dihydro-1H-pyrido[2,1-f][1,2,4]triazine-4,6-dione (intermediate 78c, 1.07 g) was obtained using the procedure described for intermediate 2d.

Synthesis of Intermediate 78d:
(E)-4-(benzyloxy)-16-(6-fluoropyridin-2-yl)-7,10,11,16-tetrahydro-6,17-methanobenzo[k]pyrido[1,2-b][1,2,5]triazacyclotridecine-3,5-dione (intermediate 78d, 0.50 g) was obtained using the procedure described for intermediate 1f.

The enantiomers were separated via chiral SFC (Stationary phase: CHIRALPAK AD-H 5 μm 250*30 mm, Mobile phase: 60% CO$_2$, 40% EtOH) to afford the first eluted enantiomer 78da (197 mg) and the second eluted enantiomer 78db (211 mg).

Synthesis of compound 78A:
(16*R,E)-16-(6-fluoropyridin-2-yl)-4-hydroxy-7,10,11,16-tetrahydro-6,17-methanobenzo[k]pyrido[1,2-b][1,2,5]triazacyclotridecine-3,5-dione (compound 78A, 132 mg) was obtained using the procedure described for compound 1.

Compound 78A:
$^1$H NMR (500 MHz, DMSO-d$_6$) δ ppm 8.08 (dd, J=7.9, 0.9 Hz, 1H), 7.85 (q, J=8.2 Hz, 1H), 7.30-7.48 (m, 3H), 7.23 (dd, J=7.6, 0.9 Hz, 1H), 7.17 (d, J=7.9 Hz, 1H), 7.04 (dd, J=8.0, 2.4 Hz, 1H), 5.90-5.98 (m, 1H), 5.59 (d, J=7.6 Hz, 1H), 5.43-5.51 (m, 1H), 5.31 (s, 1H), 5.13 (d, J=13.9 Hz, 1H), 4.70 (dd, J=14.2, 5.0 Hz, 1H), 4.27 (d, J=13.6 Hz, 1H), 3.09 (dd, J=14.0, 8.0 Hz, 1H), 2.52-2.67 (m, 3H), 1.98-2.07 (m, 1H).

LC/MS (method LC-C): Rt 2.67 min, MH$^+$433

$[\alpha]_D^{20}$: −591.76° (c 0.182, DMF)

Chiral HPLC (method HPLC-B): R$_t$ 5.43 min. chiral purity 100%

Synthesis of Compound 78B:
(16*S,E)-16-(6-fluoropyridin-2-yl)-4-hydroxy-7,10,11,16-tetrahydro-6,17-methanobenzo[k]pyrido[1,2-b][1,2,5]triazacyclotridecine-3,5-dione (compound 78B, 134 mg) was obtained using the procedure described for compound 1.

Compound 78B:
$^1$H NMR (500 MHz, DMSO-d$_6$) δ ppm 8.08 (d, J=7.9 Hz, 1H), 7.85 (q, J=8.1 Hz, 1H), 7.30-7.48 (m, 3H), 7.23 (d, J=7.6 Hz, 1H), 7.17 (d, J=7.6 Hz, 1H), 7.04 (dd, J=8.2, 2.2 Hz, 1H), 5.89-5.99 (m, 1H), 5.57 (d, J=7.6 Hz, 1H), 5.42-5.51 (m, 1H), 5.31 (s, 1H), 5.13 (d, J=13.6 Hz, 1H), 4.70 (dd, J=14.0, 5.2 Hz, 1H), 4.26 (d, J=13.9 Hz, 1H), 3.09 (dd, J=13.9, 7.9 Hz, 1H), 2.52-2.67 (m, 3H), 1.98-2.07 (m, 1H).

LC/MS (method LC-C): R$_t$ 2.67 min, MH$^+$433

$[\alpha]_D^{20}$: +598.59° (c 0.142, DMF)

Chiral HPLC (method HPLC-B): R$_t$ 6.04 min, chiral purity 100%

Example 79: Synthesis of (18'S,E)-12'-hydroxy-18'-phenyl-6'H,18'H-spiro[cyclopropane-1,9'-[10,17]methanobenzo[b]pyrido[1,2-f][1]oxa[5,6,9]triazacyclotridecine]-11',13'-dione (Compound 79A), (18'R,E)-12'-hydroxy-18'-phenyl-6'H,18'H-spiro[cyclopropane-1,9'-[10,17]methanobenzo[b]pyrido[1,2-f][1]oxa[5,6,9]triazacyclotridecine]-11',13'-dione (Compound 79B)
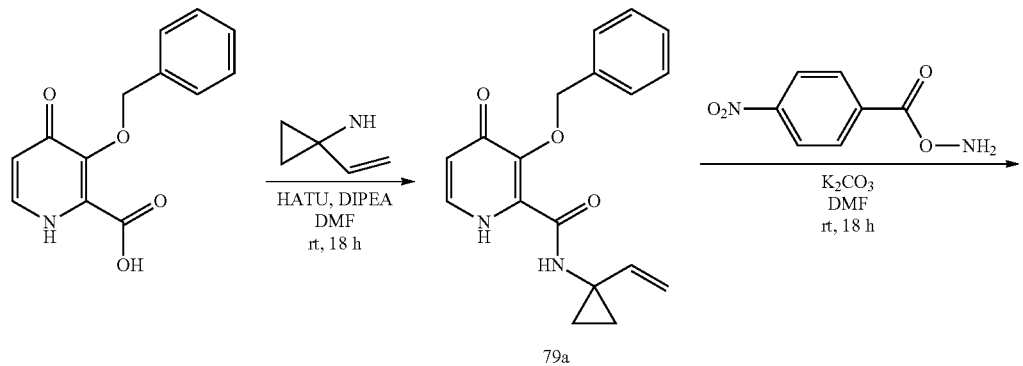
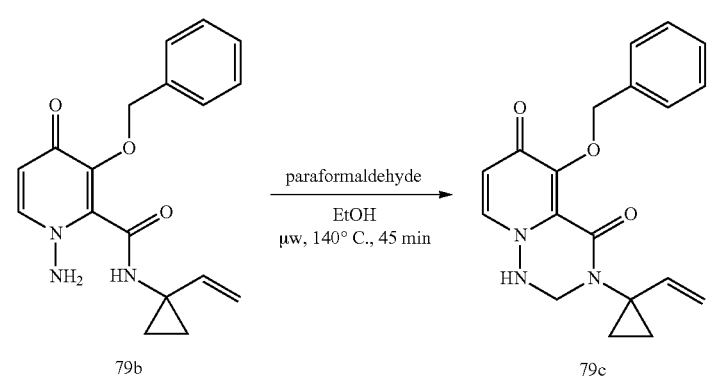
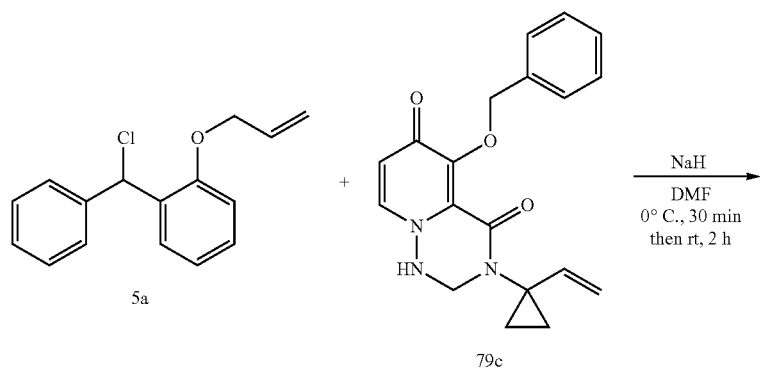

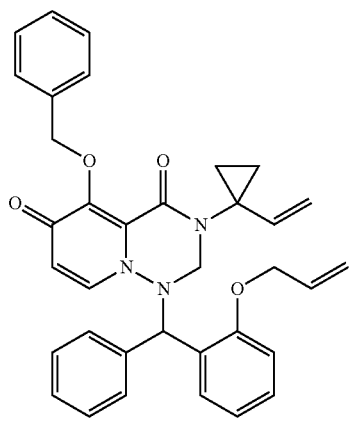

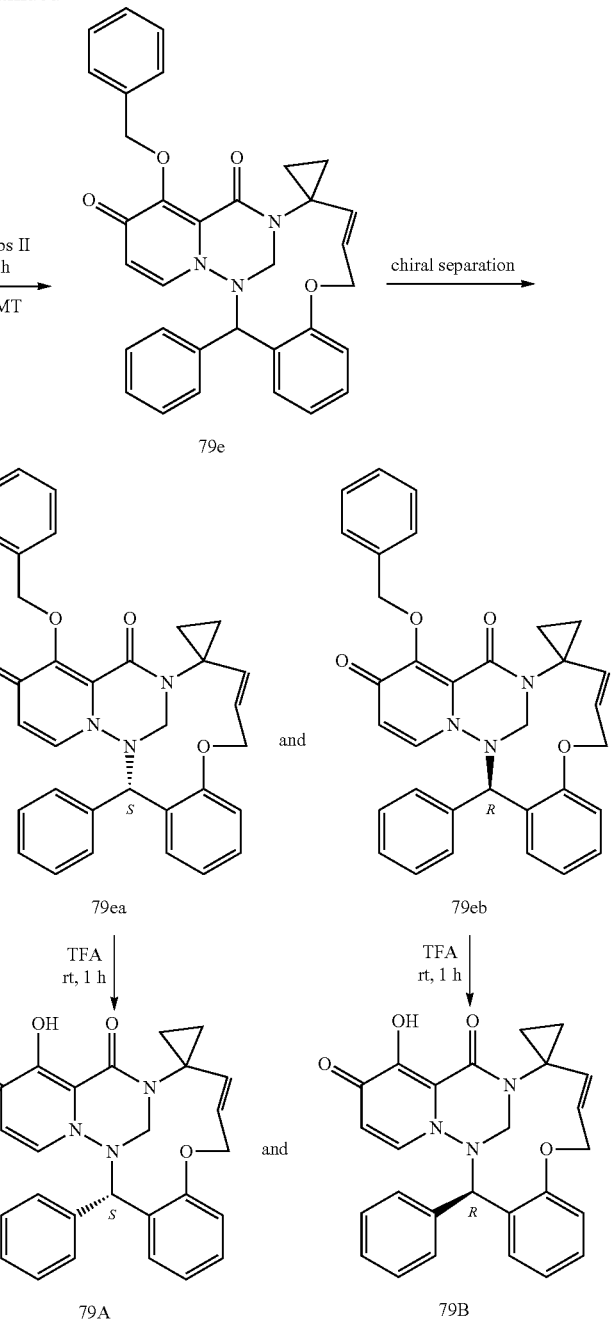

Synthesis of Intermediate 79a:
3-(benzyloxy)-4-oxo-N-(1-vinylcyclopropyl)-1,4-dihydropyridine-2-carboxamide (intermediate 79a, 3.0 g) was obtained using the procedure described for intermediate 5b.

Synthesis of Intermediate 79b:
1-amino-3-(benzyloxy)-4-oxo-N-(1-vinylcyclopropyl)-1,4-dihydropyridine-2-carboxamide (intermediate 79b, 1.1 g) was obtained using the procedure described for intermediate 1b. Crude intermediate 79b was purified by trituration in CH$_2$Cl$_2$.

Synthesis of Intermediate 79c:
In a microwave vial, a mixture of intermediate 79b (1.10 g, 3.38 mmol) and paraformaldehyde (0.10 g, 3.38 mmol) in EtOH (12 mL) was stirred at 140° C. using a single mode microwave (Biotage Initiator EXP 60) with a power output ranging from 0 to 400 W for 45 min. The reaction mixture was filtered to afford a first fraction of 5-(benzyloxy)-3-(1-vinylcyclopropyl)-2,3-dihydro-1H-pyrido[2,1-f][1,2,4]triazine-4,6-dione (intermediate 79c, 0.35 g) and the filtrate was concentrated in vacuo to deliver a second fraction of intermediate 79c (0.63 g).

Synthesis of Intermediate 79d:
1-((2-(allyloxy)phenyl)(phenyl)methyl)-5-(benzyloxy)-3-(1-vinylcyclopropyl)-2,3-dihydro-1H-pyrido[2,1-f][1,2,4]triazine-4,6-dione (intermediate 79d, 0.49 g) was obtained using the procedure described for intermediate 2d.

245

Synthesis of Intermediate 79e:

(E)-12'-(benzyloxy)-18'-phenyl-6'H,18'H-spiro[cyclopropane-1,9'-[10,17]methanobenzo[b]pyrido[1,2-f][1]oxa[5,6,9]triazacyclotridecine]-11',13'-dione (intermediate 79e, 0.18 g) was obtained using the procedure described for intermediate 1f.

The enantiomers were separated via chiral SFC (Stationary phase: AS 5 μm 250*20 mm, Mobile phase: 45% $CO_2$, 55% EtOH) to afford the first eluted enantiomer 79ea (73 mg) and the second eluted enantiomer 79eb (74 mg).

Synthesis of Compound 79A:

(18'S,E)-12'-hydroxy-18'-phenyl-6'H,18'H-spiro[cyclopropane-1,9'-[10,17]methanobenzo[b]pyrido[1,2-f][1]oxa[5,6,9]triazacyclotridecine]-11',13'-dione (compound 79A, 40 mg) was obtained using the procedure described for compound 1.

Compound 79A:

$^1$H NMR (500 MHz, DMSO-$d_6$) δ ppm 8.06 (dd, J=7.7, 1.4 Hz, 1H), 7.41 (td, J=7.8, 1.6 Hz, 1H), 7.35 (td, J=7.4, 1.0 Hz, 1H), 7.15-7.28 (m, 7H), 6.23 (br dt, J=15.2, 7.7 Hz, 1H), 5.78 (br d, J=15.1 Hz, 1H), 5.50 (d, J=7.6 Hz, 1H), 5.40 (s, 1H), 5.09 (d, J=13.6 Hz, 1H), 4.82 (dd, J=11.0, 6.3 Hz, 1H), 4.24 (br dd, J=10.7, 9.1 Hz, 1H), 4.18 (d, J=13.6 Hz, 1H), 1.45-1.52 (m, 1H), 1.12-1.19 (m, 1H), 0.82-0.88 (m, 1H), 0.67-0.75 (m, 1H).

LC/MS (method LC-C): Rt 2.71 min, MH$^+$442

$[α]_D^{20}$: +569.7° (c 0.132, DMF)

Chiral HPLC (method HPLC-B): Rt 6.06 min, chiral purity 100%

Synthesis of Compound 79B:

(18'R,E)-12'-hydroxy-18'-phenyl-6'H,18'H-spiro[cyclopropane-1,9'-[10,17]methanobenzo[b]pyrido[1,2-f][1]oxa[5,6,9]triazacyclotridecine]-11',13'-dione (compound 79B, 40 mg) was obtained using the procedure described for compound 1.

Compound 79B:

$^1$H NMR (500 MHz, DMSO-$d_6$) δ ppm 8.06 (dd, J=7.9, 1.6 Hz, 1H), 7.41 (td, J=7.6, 1.3 Hz, 1H), 7.35 (td, J=7.6, 1.0 Hz, 1H), 7.16-7.28 (m, 7H), 6.18-6.27 (m, 1H), 5.78 (br d, J=15.8 Hz, 1H), 5.50 (d, J=7.6 Hz, 1H), 5.40 (s, 1H), 5.09 (d, J=13.6 Hz, 1H), 4.82 (dd, J=11.0, 6.3 Hz, 1H), 4.24 (dd, J=10.9, 9.0 Hz, 1H), 4.18 (d, J=13.6 Hz, 1H), 1.45-1.52 (m, 1H), 1.12-1.19 (m, 1H), 0.82-0.88 (m, 1H), 0.68-0.74 (m, 1H).

LC/MS (method LC-C): Rt 2.70 min, MH$^+$442

$[α]_D^{20}$: −572.27° (c 0.154, DMF)

Chiral HPLC (method HPLC-B): Rt 6.68 min, chiral purity 100%

Example 80: Synthesis of ((1a*S,8*S,17a*S)-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (Compound 80AA), (1a*R,8*R,17a*R)-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (Compound 80BB), (1a*R,8*S,17a*R)-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (Compound 80AB) and (1a*S,8*R,17a*S)-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (Compound 80BA)

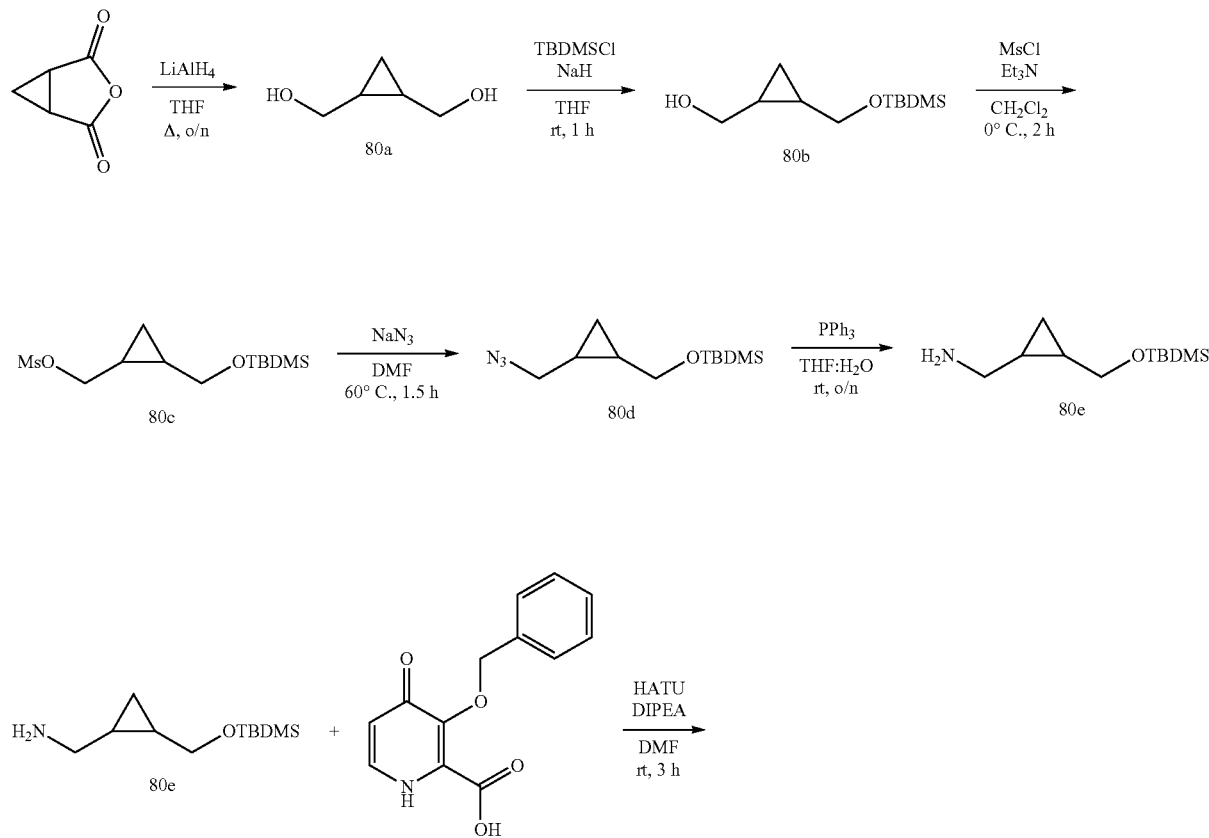

-continued
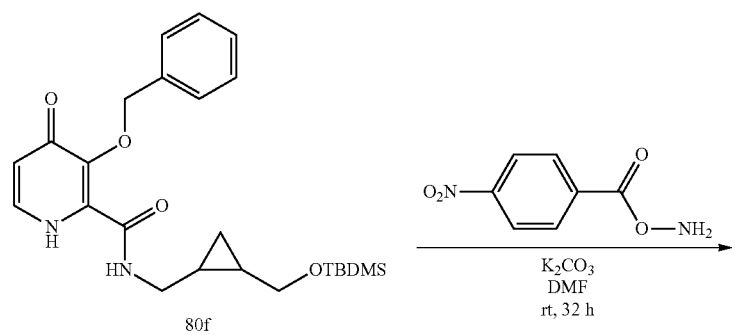
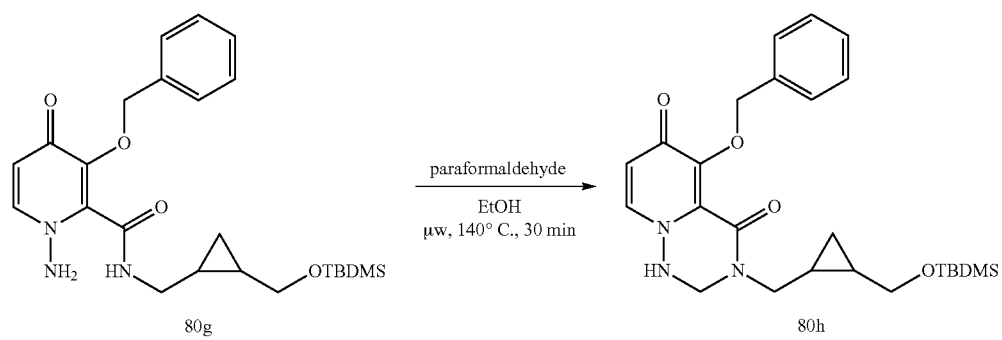
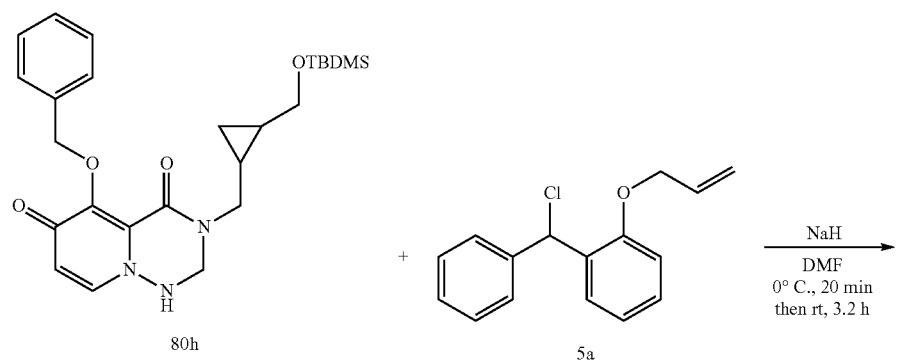
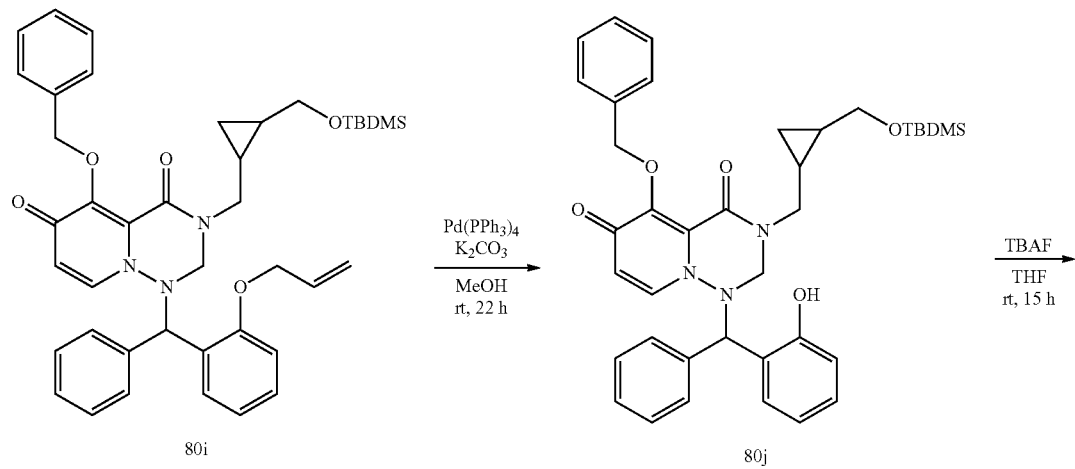

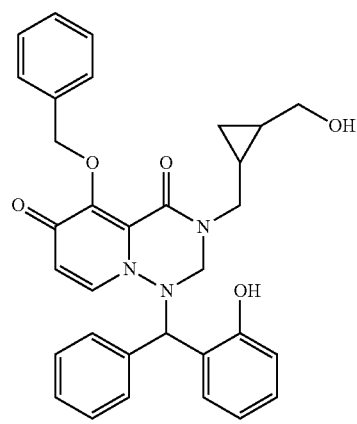
80k
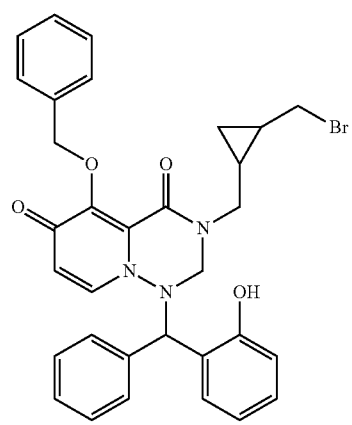
80l
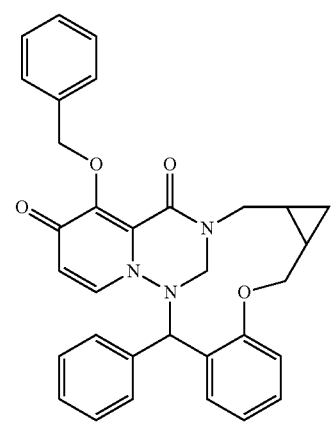
80m
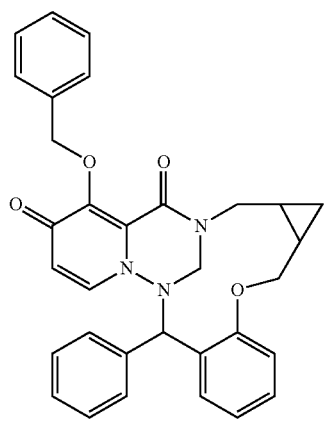
80m
chiral separation

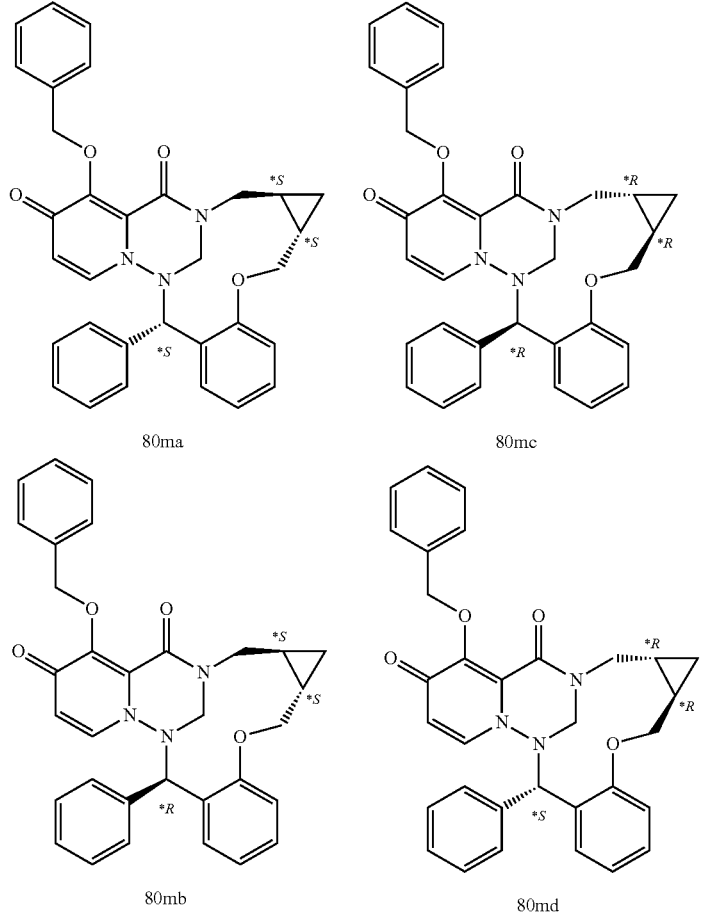

80ma    80mc

80mb    80md

Synthesis of Intermediate 80a:

Under nitrogen atmosphere, to a solution of 3-oxabicyclo [3.1.0]hexane-2,4-dione [CAS 5617-74-3] (6.51g, 58.1 mmol) in anhydrous THF (195 mL) at 0° C. was added dropwise LiAlH₄ (1.0 M in THF, 87.1 mL, 87.1 mmol). The reaction mixture was stirred under reflux overnight. The reaction mixture was cooled to 0° C. and the reaction was quenched by the addition of Et₂O and water. The mixture was filtered over a pad of Celite®. The solid was suspended in THE and stirred under reflux for 16 h. The mixture was filtered and the solid was washed with hot THE (twice) and acetone. The filtrates were combined and concentrated in vacuo to afford cyclopropane-1,2-diyldimethanol (intermediate 80a, 5.93 g).

Synthesis of Intermediate 80b:

To a solution of intermediate 80a (5.93 g, 58.1 mmol) in anhydrous THE (120 mL) at 0° C. under nitrogen atmosphere was added NaH (60% dispersion in mineral oil, 2.79 g, 69.7 mmol). The reaction mixture was stirred at rt for 45 min and TBDMSCl (8.75 g, 58.1 mmol) was added. The reaction mixture was stirred at rt for 2 h. The reaction mixture was diluted with Et₂O and washed with a saturated aqueous solution of NH₄Cl and brine. The aqueous layer was back extracted with Et₂O. The combined organic extracts were dried over Na₂SO₄, filtered and concentrated in vacuo. Purification was carried out by flash chromatography over silica gel (220 g, petroleum ether/EtOAc from 100/0 to 0/100) afforded (2-(((tert-butyldimethylsilyl)oxy)methyl)cyclopropyl)methanol (intermediate 80b, 9.81 g).

Synthesis of Intermediate 80c:

To a solution of intermediate 80b (9.81 g, 45.3 mmol) in anhydrous CH₂Cl₂ (190 mL) at 0° C. under nitrogen atmosphere were added Et₃N (12.6 mL, 90.7 mmol) and methanesulfonyl chloride (4.2 mL, 54.4 mmol). The reaction mixture was stirred at 0° C. for 2 h. The reaction was quenched with water and the mixture was extracted with CH₂Cl₂. The combined organic extracts were dried over Na₂SO₄, filtered and concentrated in vacuo to afford (2-(((tert-butyldimethylsilyl)oxy)methyl)cyclopropyl)methyl methanesulfonate (intermediate 80c, 13.06 g).

Synthesis of Intermediate 80d:

To a solution of intermediate 80c (13.0 g, 44.4 mmol) in anhydrous DMF (160 mL) was added NaN₃ (5.77 g, 88.7 mmol). The reaction mixture was stirred at 60° C. for 1.5 h. The reaction mixture was diluted with water and extracted with Et₂O. The combined organic extracts were dried over Na₂SO₄, filtered and concentrated in vacuo to afford ((2-(azidomethyl)cyclopropyl)methoxy)(tert-butyl)dimethylsilane (intermediate 80d, 10.7 g).

Synthesis of Intermediate 80e:

To a solution of intermediate 80d (10.7 g, 44.4 mmol) in THE (90 mL) and H₂O (20 mL) was added PPh₃ (23.3 g, 88.7 mmol). The reaction mixture was stirred at rt overnight. The reaction mixture was partitioned between Et₂O and water. The organic phase was washed with water and brine, dried over Na₂SO₄, filtered and concentrated in vacuo. Purification was carried out by flash chromatography over silica gel (220 g, CH₂Cl₂/MeOH from 95/5 to 70/30) and afforded (2-(((tert-butyldimethylsilyl)oxy)methyl)cyclopropyl)methanamine (intermediate 80e, 6.83 g).

Synthesis of Intermediate 80f:

3-(benzyloxy)-N-((2-(((tert-butyldimethylsilyl)oxy)methyl)cyclopropyl)methyl)-4-oxo-1,4-dihydropyridine-2-carboxamide (intermediate 80f, 7.66 g) was obtained using the procedure described for intermediate 5b.

Synthesis of Intermediate 80g:

1-amino-3-(benzyloxy)-N-((2-(((tert-butyldimethylsilyl)oxy)methyl)cyclopropyl)methyl)-4-oxo-1,4-dihydropyridine-2-carboxamide (intermediate 80g, 4.75 g) was obtained using the procedure described for intermediate 5c.

Synthesis of Intermediate 80h:

5-(benzyloxy)-3-((2-(((tert-butyldimethylsilyl)oxy)methyl)cyclopropyl)methyl)-2,3-dihydro-1H-pyrido[2,1-f][1,2,4]triazine-4,6-dione (intermediate 80h) was obtained using the procedure described for intermediate 5d. Crude intermediate 80h was combined with two other fractions (1.00 g, 2.19 mmol and 2.00 g, 4.37 mmol) and the mixture was purified by flash chromatography over silica gel (220 g, CH₂Cl₂/MeOH from 100/0 to 90/10) to afford intermediate 80h (3.58 g).

Synthesis of Intermediate 80i:

1-((2-(allyloxy)phenyl)(phenyl)methyl)-5-(benzyloxy)-3-((2-(((tert-butyldimethylsilyl)oxy)methyl)cyclopropyl)methyl)-2,3-dihydro-1H-pyrido[2,1-f][1,2,4]triazine-4,6-dione (intermediate 80i, 2.02 g) was obtained using the procedure described for intermediate 2d.

Synthesis of Intermediate 80j:

Intermediate 80i (2.02 g, 2.93 mmol) was dissolved in MeOH (33 mL) under nitrogen atmosphere. Pd(PPh₃)₄ (338 mg, 293 μmol) was added. The mixture was stirred for 10 min at rt and K₂CO₃ (1.21 g, 8.78 mmol) was added. The reaction mixture was stirred at rt for 22 h. The reaction mixture was concentrated in vacuo. The residue was taken up in CH₂Cl₂ and washed with water and brine, dried over Na₂SO₄, filtered and concentrated in vacuo. Purification was carried out by flash column chromatography (80 g, CH₂Cl₂/MeOH from 100/0 to 96/4) to afford 5-(benzyloxy)-3-((2-(((tert-butyldimethylsilyl)oxy)methyl)cyclopropyl)methyl)-1-((2-hydroxyphenyl)(phenyl)methyl)-2,3-dihydro-1H-pyrido[2,1-f][1,2,4]triazine-4,6-dione (intermediate 80j, 1.54 g).

Synthesis of Intermediate 80k:

Intermediate 80j (1.55 g, 2.37 mmol) was dissolved in anhydrous THF (25 mL) under nitrogen atmosphere. TBAF (1.0 M in THF, 2.84 mL, 2.84 mmol) was added and the reaction mixture was stirred at rt for 15 h. The reaction mixture was diluted with MeOH and concentrated in vacuo. Purification was carried out by flash column chromatography (40 g, CH₂Cl₂/MeOH from 100/0 to 94/6) to afford 5-(benzyloxy)-3-((2-(hydroxymethyl)cyclopropyl)methyl)-1-((2-hydroxyphenyl)(phenyl)methyl)-2,3-dihydro-1H-pyrido[2,1-f][1,2,4]triazine-4,6-dione (intermediate 80k, 1.1 g).

Synthesis of Intermediate 80l:

Intermediate 80k (501 mg, 932 μmol) was dissolved in anhydrous CH₂Cl₂ (15 mL) under nitrogen atmosphere. The solution was cooled to 0° C. and PPh₃ (407 mg, 1.86 mmol) was added. The mixture was stirred for 15 min and CBr₄ (618 mg, 1.86 mmol) was added. The reaction mixture was stirred at rt for 15 h. The reaction mixture was concentrated in vacuo. Purification was carried out by flash column chromatography (80 g, CH₂Cl₂/MeOH from 100/0 to 96/4) to afford 5-(benzyloxy)-3-((2-(bromomethyl)cyclopropyl)methyl)-1-((2-hydroxyphenyl)(phenyl)methyl)-2,3-dihydro-1H-pyrido[2,1-f][1,2,4]triazine-4,6-dione (intermediate 80l, 538 mg).

Synthesis of Intermediate 80m

Intermediate 80l (538 mg, 896 μmol) was dissolved in anhydrous CH₃CN (20 mL) under nitrogen atmosphere. K₂CO₃ (248 mg, 1.79 mmol) was added and the reaction mixture was stirred at 120° C. under microwave irradiation for 30 min. The reaction mixture was diluted with EtOAc and washed with water and brine. The organic phase was dried over Na₂SO₄, filtered and concentrated in vacuo. Purification was carried out by flash column chromatography (40 g, CH₂Cl₂/MeOH from 100/0 to 96/4). The residue was triturated with Et₂O to afford 14-(benzyloxy)-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (intermediate 80m, 260 mg) as a mixture of diastereoisomers.

The diastereoisomers were separated via chiral SFC (Stationary phase: CHIRALPAK AS-H 5 μm 250*20 mm, Mobile phase: 75% CO₂, 25% MeOH) to afford two fractions: fraction A (intermediates 80mb and 80mc, 62 mg) and fraction B (intermediates 80ma and 80 md, 37 mg). Fraction A was purified via chiral SFC (Stationary phase: Whelk-O1 (S,S) 5 μm 250*21.2 mm, Mobile phase: 75% CO₂, 25% MeOH) to afford intermediate 80mb (29 mg) and intermediate 80mc (17 mg). Fraction B was purified via chiral SFC (Stationary phase: Whelk-O1 (S,S) 5 μm 250*21.2 mm, Mobile phase: 70% CO₂, 30% MeOH) to afford intermediate 80md (20 mg) and intermediate 80ma (13 mg).

Synthesis of Compound 80AA:

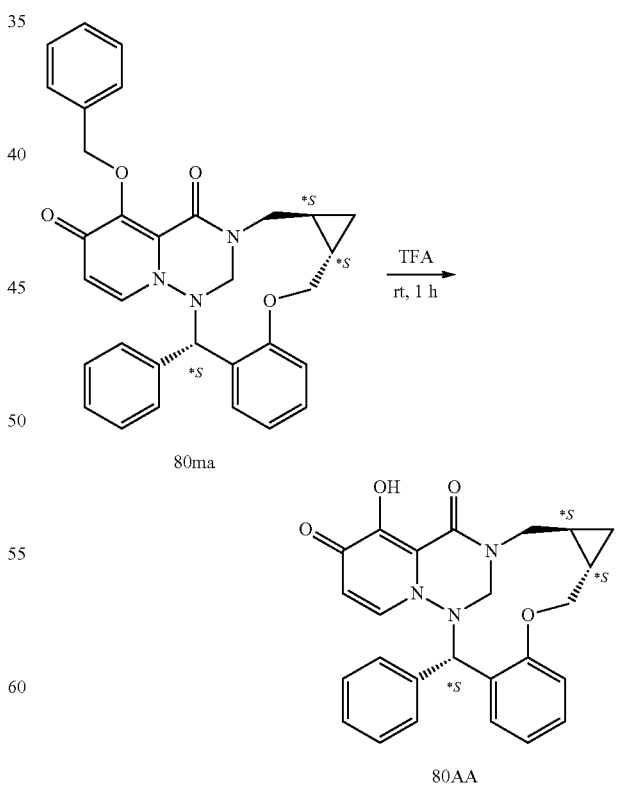

(1a*S,8*S,17a*S)-14-hydroxy-8-phenyl-1a,2,17,17a-tetrahydro-1H,8H-9,16-methanobenzo[b]cyclopropa[k]pyrido

[1,2-f][1]oxa[5,6,9]triazacyclotridecine-13,15-dione (compound 80AA, 4 mg) was obtained using the procedure described for compound 1.

Compound 80AA:

¹H NMR (500 MHz, DMSO-d₆) δ ppm 8.21 (dd, J=7.9, 1.6 Hz, 1H), 7.38-7.43 (m, 2H), 7.33-7.36 (m, 1H), 7.29 (t, J=7.4 Hz, 1H), 7.21-7.26 (m, 2H), 7.16-7.20 (m, 3H), 6.08 (s, 1H), 5.49 (d, J=7.9 Hz, 1H), 5.10 (d, J=13.6 Hz, 1H), 4.76 (dd, J=12.3, 3.5 Hz, 1H), 4.36 (dd, J=13.9, 2.5 Hz, 1H), 4.29 (d, J=13.2 Hz, 1H), 2.16 (dd, J=13.9, 11.0 Hz, 1H), 1.27-1.35 (m, 1H), 0.98-1.06 (m, 1H), 0.55 (dt, J=9.0, 4.7 Hz, 1H), 0.35 (dt, J=9.1, 4.8 Hz, 1H).

LC/MS (method LC-C): Rt 2.62 min, MH⁺430

Chiral HPLC (method HPLC-B): Rt 5.73 min. chiral purity 98%

Synthesis of Compound 80BB:

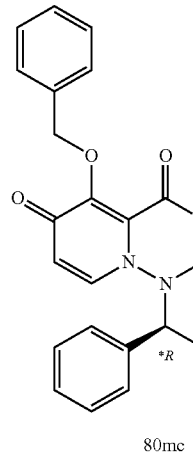

80mc

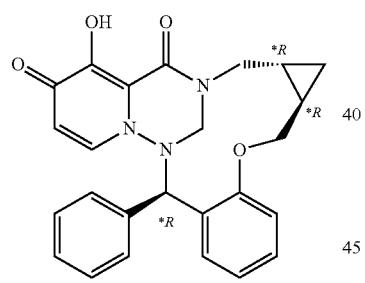

80BB (1a*R, 8*R,17a*R)-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (compound 80BB, 9 mg) was obtained using the procedure described for compound 1.

Compound 80BB:

¹H NMR (500 MHz, DMSO-d₆) δ ppm 8.21 (dd, J=7.9, 1.3 Hz, 1H), 7.38-7.43 (m, 2H), 7.33-7.36 (m, 1H), 7.29 (t, J=7.4 Hz, 1H), 7.21-7.25 (m, 2H), 7.17-7.21 (m, 3H), 6.08 (s, 1H), 5.50 (d, J=7.6 Hz, 1H), 5.10 (d, J=13.6 Hz, 1H), 4.76 (dd, J=12.3, 3.5 Hz, 1H), 4.36 (dd, J=14.0, 2.4 Hz, 1H), 4.29 (d, J=13.6 Hz, 1H), 2.16 (dd, J=13.9, 11.3 Hz, 1H), 1.27-1.35 (m, 1H), 0.98-1.06 (m, 1H), 0.55 (dt, J=8.9, 4.5 Hz, 1H), 0.35 (dt, J=9.1, 4.8 Hz, 1H) (mixture of isomers 65/35)

LC/MS (method LC-C): Rt 2.60 min, MH⁺430 (presence of an isomer)

Chiral HPLC (method HPLC-B): Rt 5.18 min, chiral purity 100%

Synthesis of Compound 80AB:

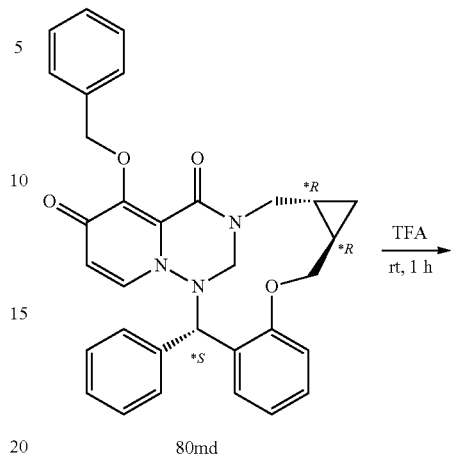

80md

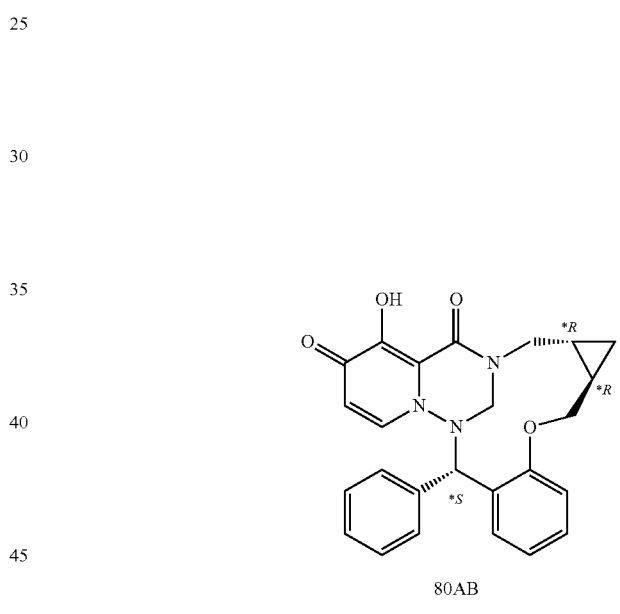

80AB (1a*R, 8*S,17a*R)-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (compound 80AB, 10 mg) was obtained using the procedure described for compound 1.

Compound 80AB:

¹H NMR (500 MHz, DMSO-d₆) δ ppm 8.03 (dd, J=7.7, 1.4 Hz, 1H), 7.20-7.37 (m, 8H), 7.07 (d, J=8.2 Hz, 1H), 5.99 (s, 1H), 5.51 (d, J=7.6 Hz, 1H), 5.05 (d, J=13.6 Hz, 1H), 4.84 (dd, J=12.8, 4.6 Hz, 1H), 4.47 (d, J=13.6 Hz, 1H), 3.52 (br dd, J=14.3, 10.2 Hz, 1H), 3.39 (br s, 1H), 3.18 (br dd, J=14.7, 4.9 Hz, 1H), 1.32-1.40 (m, 1H), 0.64-0.73 (m, 2H), 0.50-0.56 (m, 1H).

LC/MS (method LC-C): Rt 2.63 min, MH⁺430

$[\alpha]_D^{20}$: −302.75° (c 0.109, DMF)

Chiral HPLC (method HPLC-B): Rt 7.10 min, chiral purity 100%

Synthesis of Compound 80BA:

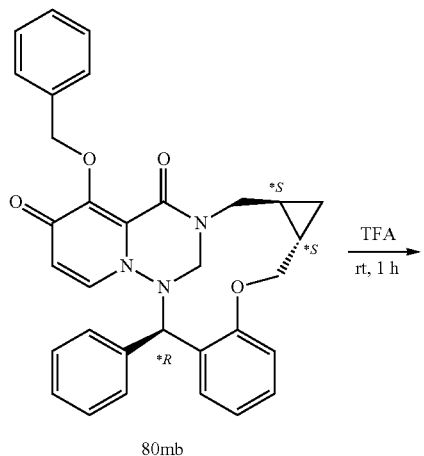

80mb

Example 81: Synthesis of (((2R,E)-14,16-dioxo-2-phenyl-12,13,14,16-tetrahydro-11H-4-oxa-1(1,3)-pyrido[2,1-f][1,2,4]triazina-3(1,2)-benzenacyclononaphan-6-en-15-yl)oxy)methyl methyl Carbonate (Compound 81)

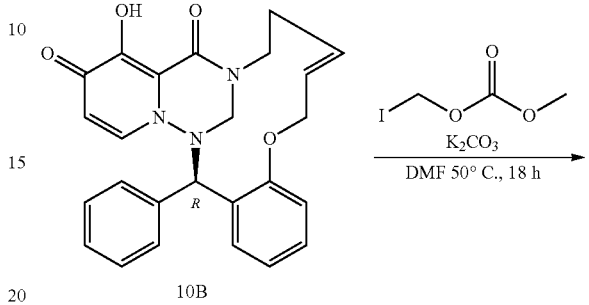

10B

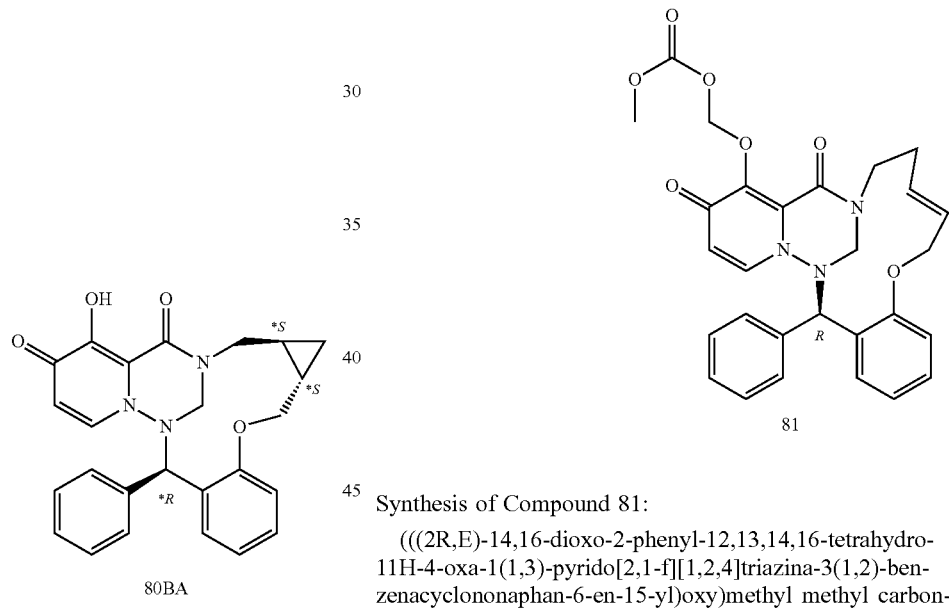

81

(1a*S,8*R,17a*S)-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (compound 80BA, 16 mg) was obtained using the procedure described for compound 1.

Compound 80BA:

$^1$H NMR (500 MHz, DMSO-d$_6$) δ ppm 8.03 (dd, J=7.6, 1.6 Hz, 1H), 7.20-7.44 (m, 8H), 7.07 (d, J=8.2 Hz, 1H), 5.99 (s, 1H), 5.51 (d, J=7.9 Hz, 1H), 5.05 (d, J=13.2 Hz, 1H), 4.84 (dd, J=12.9, 4.7 Hz, 1H), 4.47 (d, J=13.6 Hz, 1H), 3.52 (br dd, J=14.3, 10.2 Hz, 1H), 3.39 (br s, 1H), 3.18 (br dd, J=14.7, 4.9 Hz, 1H), 1.31-1.40 (m, 1H), 0.64-0.74 (m, 2H), 0.49-0.57 (m, 1H).

LC/MS (method LC-C): R$_t$ 2.63 min, MH$^+$430

[α]$_D^{20}$: +260.00° (c 0.14, DMF)

Chiral HPLC (method HPLC-B): R$_t$ 5.41 min, chiral purity 100%

Synthesis of Compound 81:

(((2R,E)-14,16-dioxo-2-phenyl-12,13,14,16-tetrahydro-11H-4-oxa-1(1,3)-pyrido[2,1-f][1,2,4]triazina-3(1,2)-benzenacyclononaphan-6-en-15-yl)oxy)methyl methyl carbonate (compound 81, 332 mg) was obtained using the procedure described for compound 62. After purification by flash chromatography the residue was triturated in Et$_2$O.

Compound 81:

$^1$H NMR (500 MHz, DMSO-d$_6$) δ ppm 8.01 (dd, J=7.7, 1.4 Hz, 1H), 7.41 (td, J=7.7, 1.6 Hz, 1H), 7.32 (t, J=7.3 Hz, 1H), 7.22 (d, J=7.6 Hz, 1H), 7.12-7.20 (m, 4H), 7.08 (br s, 1H), 6.01 (s, 1H), 5.89 (ddd, J=15.3, 9.9, 4.7 Hz, 1H), 5.64 (d, J=6.6 Hz, 1H), 5.59 (d, J=3.8 Hz, 1H), 5.57 (d, J=4.7 Hz, 1H), 5.49 (br ddd, J=15.2, 10.3, 4.4 Hz, 1H), 5.03 (d, J=12.9 Hz, 1H), 4.72 (dd, J=11.8, 5.2 Hz, 1H), 4.21 (d, J=12.9 Hz, 1H), 4.16 (dd, J=11.8, 10.3 Hz, 1H), 3.79 (s, 3H), 3.69 (br dt, J=13.5, 3.5 Hz, 1H), 2.89-3.00 (m, 1H), 2.78-2.86 (m, 1H), 2.17 (br d, J=12.3 Hz, 1H).

LC/MS (method LC-C): Rt 2.73 min, MH$^+$518

[α]$_D^{20}$: −406.33° (c 0.156, DMF)

Example 82: Synthesis of (17aS,E)-12-hydroxy-2,6, 9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione 1,1-dioxide (Compound 82)

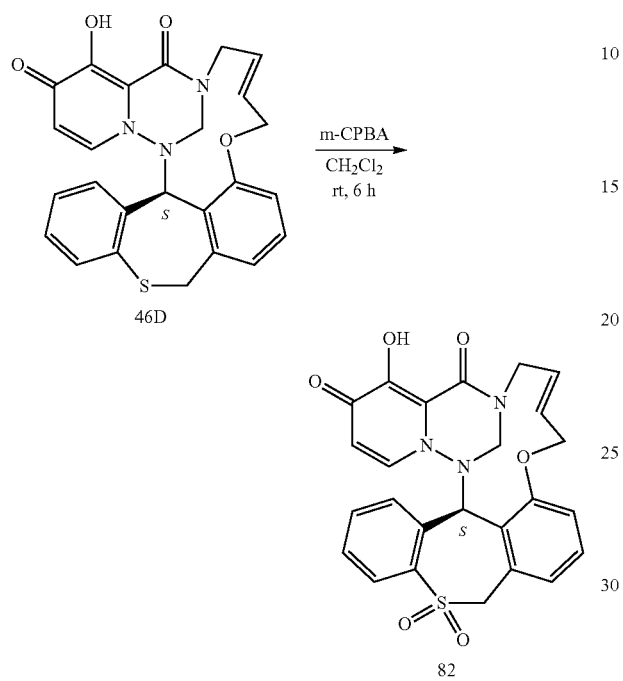

Synthesis of Compound 82:

At 0° C., m-CPBA (26.4 mg, 153 µmol) was added to a solution of intermediate 46D (32.0 mg, 69.6 µmol) in $CH_2Cl_2$ (1 mL). The reaction mixture was stirred at rt for 6 h. The reaction mixture was diluted with $CH_2Cl_2$ and washed with water. The organic phase was dried over $MgSO_4$, filtered and the solvent was evaporated in vacuo. Purification was carried out by flash chromatography over silica gel (30 µm, 24 g, $CH_2Cl_2$/MeOH from 99/1 to 97/3) The pure fractions were collected and evaporated to dryness. The product was freeze-dried (water/$CH_3CN$, 4/1) to give (17aS,E)-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione 1,1-dioxide (compound 82, 13 mg).

Compound 82:

$^1$H NMR (500 MHz, DMSO-$d_6$) δ ppm 11.40 (br s, 1H), 7.85 (dd, J=7.9, 0.9 Hz, 1H), 7.57-7.63 (m, 1H), 7.49 (t, J=7.9 Hz, 1H), 7.41 (td, J=7.6, 1.3 Hz, 1H), 7.36 (dd, J=12.1, 7.7 Hz, 2H), 7.13 (d, J=7.9 Hz, 1H), 7.10 (d, J=7.3 Hz, 1H), 6.57 (d, J=14.5 Hz, 1H), 6.29 (dt, J=15.6, 7.6 Hz, 1H), 5.83-5.93 (m, 1H), 5.51-5.56 (m, 2H), 5.19 (d, J=13.9 Hz, 1H), 4.98 (d, J=14.5 Hz, 1H), 4.85 (dd, J=11.0, 6.3 Hz, 1H), 4.75 (dd, J=14.2, 4.1 Hz, 1H), 4.47 (br t, J=10.1 Hz, 1H), 4.20 (d, J=13.9 Hz, 1H), 3.15 (dd, J=14.3, 7.7 Hz, 1H).

LC/MS (method LC-C): Rt 2.12 min, MH$^+$492

$[α]_D^{20}$: -445.5° (c 0.200, DMF)

Example 83: Synthesis of (13Z,23b*R)-6-hydroxy-9,10,12,18,19,23b-hexahydro-1,8-methanobenzo[4,5]cyclohepta[1,2,3-qr]pyrido[1,2-c][9,2,3,6]benzoxatriazacyclotetradecine-5,7-dione (Compound 83A), (13Z,23b*S)-6-hydroxy-9,10,12,18,19,23b-hexahydro-1,8-methanobenzo[4,5]cyclohepta[1,2,3-qr]pyrido[1,2-c][9,2,3,6]benzoxatriazacyclotetradecine-5,7-dione (Compound 83B)

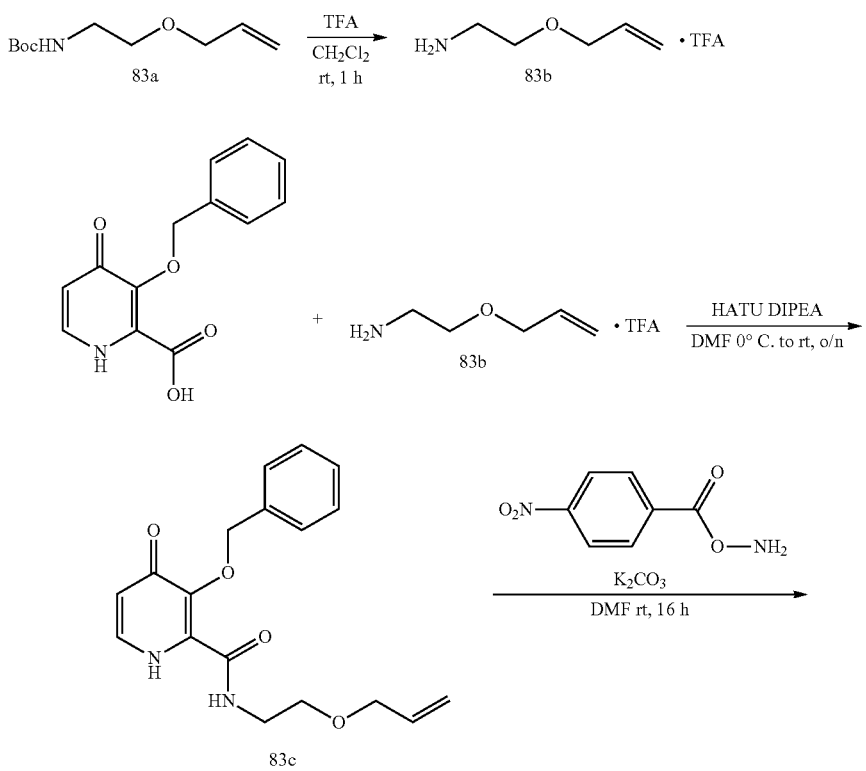

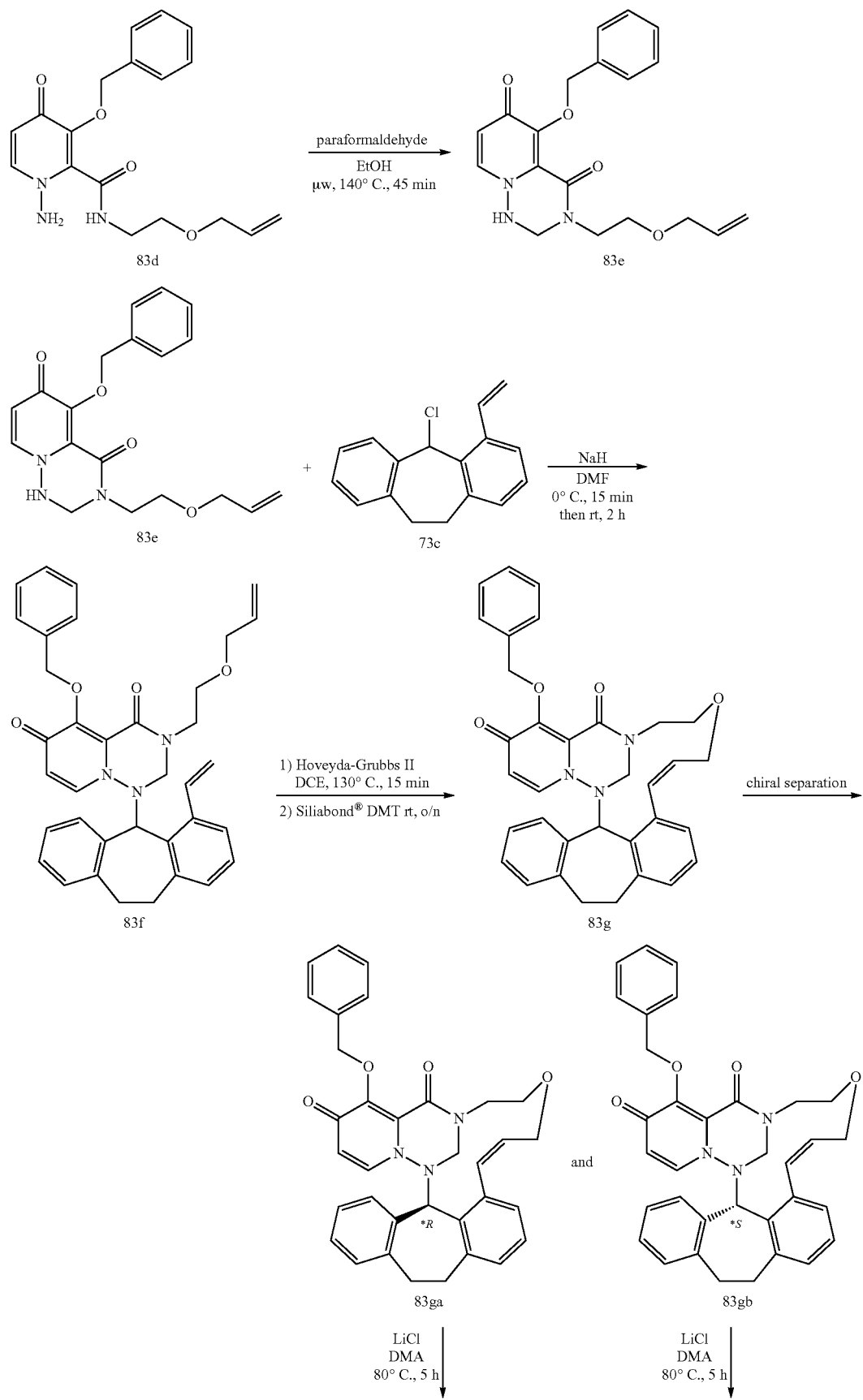

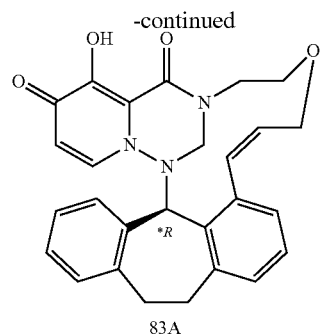
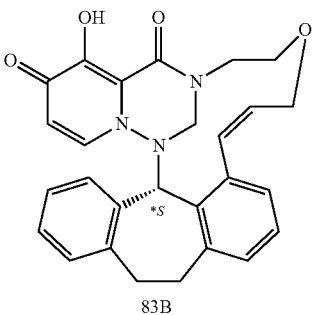

83A and 83B

Synthesis of Intermediate 83b:

To a solution of intermediate 83a [CAS 441752-75-6] (29.6 g, 147 mmol) in $CH_2Cl_2$ (75 mL) was added TFA (75 mL) portionwise. The reaction mixture was stirred at rt for 1 h. The mixture was concentrated in vacuo and co-evaporated with toluene. Purification was carried out by flash column chromatography on silica gel (220 g, $CH_2Cl_2$/ ($CH_2Cl_2$/MeOH/$NH_4OH$ 70/29/1) from 100/0 to 0/100) to afford 2-(prop-2-en-1-yloxy)ethan-1-amine, trifluoroacetic acid (intermediate 83b, 29.6 g).

Synthesis of Intermediate 83c:

N-(2-(allyloxy)ethyl)-3-(benzyloxy)-4-oxo-1,4-dihydropyridine-2-carboxamide (intermediate 83c, 5.3 g) was obtained using the procedure described for intermediate 5b.

Synthesis of Intermediate 83d:

N-(2-(allyloxy)ethyl)-1-amino-3-(benzyloxy)-4-oxo-1,4-dihydropyridine-2-carboxamide (intermediate 83d, 3.1 g) was obtained using the procedure described for intermediate 1b.

Synthesis of Intermediate 83e:

3-(2-(allyloxy)ethyl)-5-(benzyloxy)-2,3-dihydro-1H-pyrido[2,1-f][1,2,4]triazine-4,6-dione (intermediate 83e, 290 mg) was obtained using the procedure described for intermediate 73f.

Synthesis of Intermediate 83f:

3-(2-(allyloxy)ethyl)-5-(benzyloxy)-1-(4-vinyl-10,11-dihydro-5H-dibenzo[a,d][7]annulen-5-yl)-2,3-dihydro-1H-pyrido[2,1-f][1,2,4]triazine-4,6-dione (intermediate 83f, 170 mg) was obtained using the procedure described for intermediate 2d.

Synthesis of Intermediate 83g:

(13Z)-6-(benzyloxy)-9,10,12,18,19,23b-hexahydro-1,8-methanobenzo[4,5]cyclohepta[1,2,3-qr]pyrido[1,2-c][9,2,3,6]benzoxatriazacyclotetradecine-5,7-dione (crude intermediate 83g) was obtained using the procedure described for intermediate 59d.

Crude intermediate 83g was purified by flash chromatography over silica gel (40 g, $CH_2Cl_2$/MeOH from 100/0 to 98/2). A second purification was performed by flash chromatography C18 (40 μm, 45 g, $H_2O$/MeOH from 70/30 to 0/100). The residue was finally purified via achiral SFC (Stationary phase: AMINO 5 μm 150*30 mm, Mobile phase: 80% $CO_2$, 20% MeOH) to afford intermediate 83g (105 mg).

The enantiomers were separated via chiral SFC (Stationary phase: Whelk-O1 (S,S) 5 μm 250*21.2 mm, Mobile phase: 45% $CO_2$, 55% MeOH) to afford the first eluted enantiomer 83ga (44 mg) and the second eluted enantiomer 83gb (46 mg).

Synthesis of Compound 83A:

(((13Z,23b*R)-6-hydroxy-9,10,12,18,19,23b-hexahydro-1,8-methanobenzo[4,5]cyclohepta[1,2,3-qr]pyrido[1,2-c][9,2,3,6]benzoxatriazacyclotetradecine-5,7-dione (compound 83A, 19 mg) was obtained using the procedure described for compound 28A.

Compound 83A:

$^1$H NMR (500 MHz, DMSO-$d_6$) δ ppm 11.67 (br s, 1H), 7.24-7.31 (m, 2H), 7.16-7.22 (m, 1H), 7.08-7.13 (m, 2H), 7.06 (d, J=7.6 Hz, 1H), 6.90 (t, J=7.3 Hz, 1H), 6.63-6.74 (m, 2H), 6.37 (dt, J=11.3, 6.4 Hz, 1H), 5.38-5.43 (m, 2H), 4.94 (d, J=12.7 Hz, 1H), 4.58 (td, J=14.0, 5.3 Hz, 1H), 4.47 (ddd, J=13.0, 7.2, 1.5 Hz, 1H), 4.30 (d, J=12.7 Hz, 1H), 3.89 (br d, J=13.6 Hz, 1H), 3.62-3.74 (m, 3H), 3.55 (br d, J=17.4 Hz, 1H), 2.88-2.98 (m, 1H), 2.71-2.80 (m, 2H).

LC/MS (method LC-C): Rt 2.88 min, MH$^+$456

[α]$D^{20}$: +227.12° (c 0.236, DMF)

Synthesis of compound 83B:

(((13Z,23b*S)-6-hydroxy-9,10,12,18,19,23b-hexahydro-1,8-methanobenzo[4,5]cyclohepta[1,2,3-qr]pyrido[1,2-c][9,2,3,6]benzoxatriazacyclotetradecine-5,7-dione (compound 83B, 23 mg) was obtained using the procedure described for compound 28A.

Compound 83B:

$^1$H NMR (500 MHz, DMSO-$d_6$) δ ppm 11.67 (br s, 1H), 7.25-7.31 (m, 2H), 7.17-7.22 (m, 1H), 7.08-7.12 (m, 2H), 7.06 (d, J=7.6 Hz, 1H), 6.90 (t, J=7.6 Hz, 1H), 6.64-6.72 (m, 2H), 6.37 (dt, J=10.9, 6.5 Hz, 1H), 5.38-5.44 (m, 2H), 4.94 (d, J=12.6 Hz, 1H), 4.58 (br td, J=13.9, 5.0 Hz, 1H), 4.47 (ddd, J=13.0, 7.3, 1.1 Hz, 1H), 4.30 (d, J=12.6 Hz, 1H), 3.89 (br d, J=14.8 Hz, 1H), 3.62-3.75 (m, 3H), 3.55 (br d, J=17.0 Hz, 1H), 2.88-2.98 (m, 1H), 2.71-2.80 (m, 2H).

LC/MS (method LC-C): Rt 2.88 min, MH$^+$456

[α]$_D^{20}$: −220.43° (c 0.230, DMF)

Example 84: Synthesis of (19*R, E/Z)-4-fluoro-13-hydroxy-19-phenyl-9,10-dihydro-6H,19H-11,18-methanopyrido[2,1-i][1,7,10,11]benzoxatriazacyclo-tetradecine-12,14-dione (Compound 84A), (19*S, E/Z)-4-fluoro-13-hydroxy-19-phenyl-9,10-dihydro-6H,19H-11,18-methanopyrido[2,1-i][1,7,10,11]benzoxatriazacyclotetradecine-12,14-dione (Compound 84B)
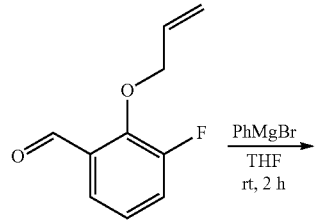
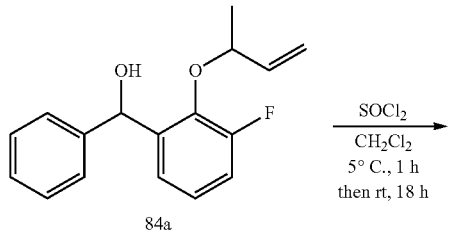
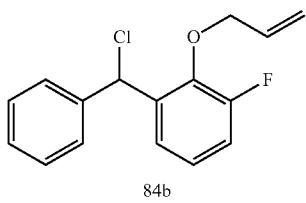
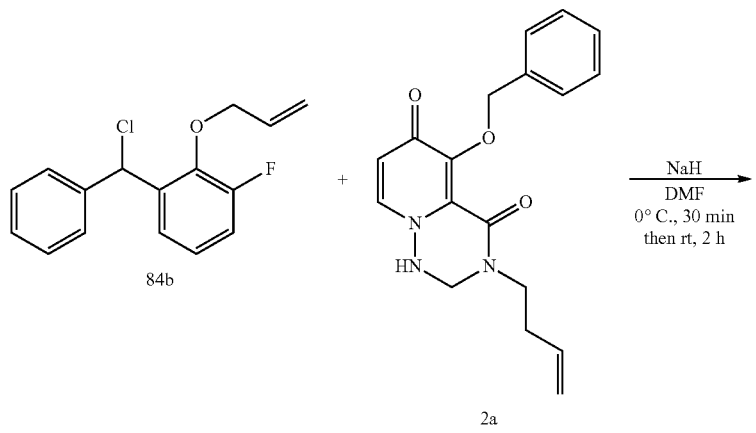

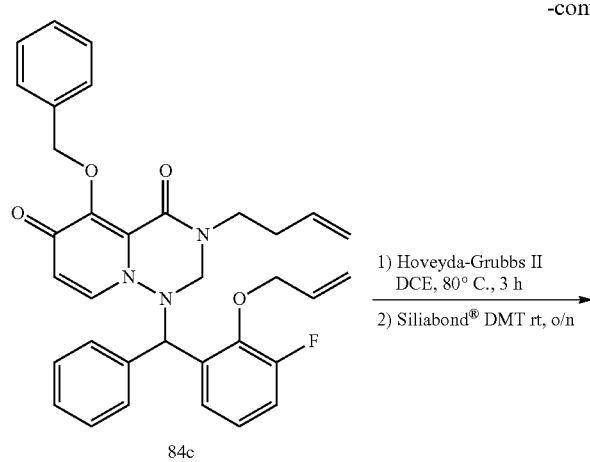

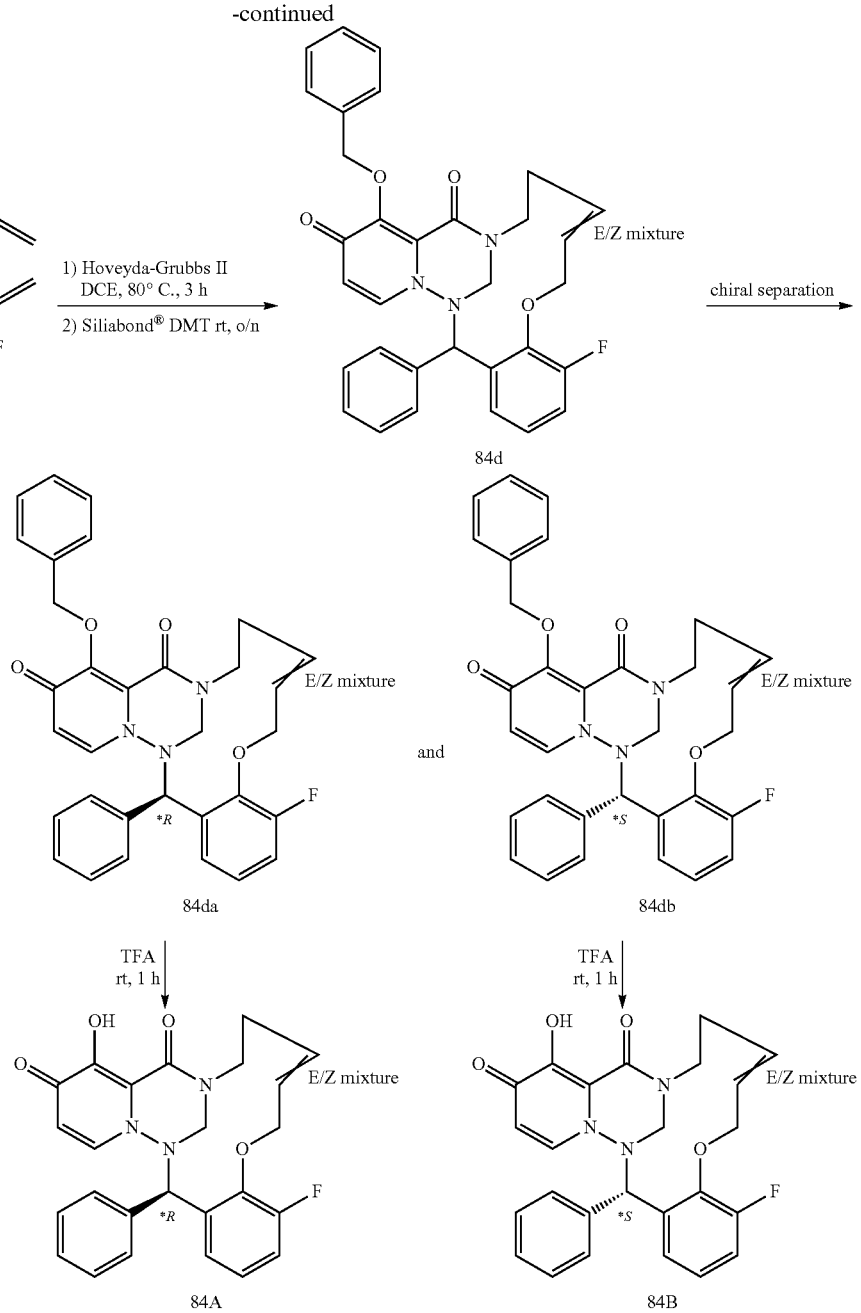

Synthesis of Intermediate 84a:
(2-(allyloxy)-3-fluorophenyl)(phenyl)methanol (intermediate 84a, 2.8 g) was obtained using the procedure described for intermediate 2b. Crude intermediate 84a was purified by flash chromatography over silica gel (30 μm, 80 g, heptane/EtOAc 90/10).

Synthesis of Intermediate 84b:
2-(allyloxy)-1-(chloro(phenyl)methyl)-3-fluorobenzene (intermediate 84b, 3.0 g) was obtained using the procedure described for intermediate 5a.

Synthesis of Intermediate 84c:
1-((2-(allyloxy)-3-fluorophenyl)(phenyl)methyl)-5-(benzyloxy)-3-(but-3-en-1-yl)-2,3-dihydro-1H-pyrido[2,1-f][1,2,4]triazine-4,6-dione (intermediate 84c, 3.3 g) was obtained using the procedure described for intermediate 2d.

Synthesis of Intermediate 84d:
(E/Z)13-(benzyloxy)-4-fluoro-19-phenyl-9,10-dihydro-6H,19H-11,18-methanopyrido[2,1-i][1,7,10,11]benzoxatriazacyclotetradecine-12,14-dione (intermediate 84d, mixture of Z and E isomers, 2.4 g) was obtained using the procedure described for intermediate 1f.

The isomers were separated via chiral SFC (Stationary phase: Whelk-O1 (S,S) 5 μm 250*21.2 mm, Mobile phase: 53% $CO_2$, 47% (MeOH/$CH_2Cl_2$ 90/10)) to afford the first eluted enantiomer 84da (1.05 g) and the second eluted enantiomer 84db (1.03 g).

Synthesis of Compound 84A:
(19*R, E/Z)-4-fluoro-13-hydroxy-19-phenyl-9,10-dihydro-6H,19H-11,18-methanopyrido[2,1-i][1,7,10,11]benzoxatriazacyclotetradecine-12,14-dione (compound 84A, mixture of Z and E isomers 9/91, 530 mg) was obtained using the procedure described for compound 1.

Compound 84A:

¹H NMR (500 MHz, DMSO-d₆) δ ppm 11.73 (br s, 1H), 7.87 (d, J=7.9 Hz, 1H), 7.30-7.41 (m, 2H), 6.92-7.22 (m, 6H), 6.07 (br ddd, J=15.3, 10.2, 4.7 Hz, 1H), 5.98 (s, 1H), 5.63 (br ddd, J=15.1, 10.3, 4.3 Hz, 1H), 5.41 (d, J=7.6 Hz, 1H), 5.09 (d, J=12.9 Hz, 1H), 4.73 (dd, J=12.0, 5.0 Hz, 1H), 4.33 (d, J=12.9 Hz, 1H), 4.04 (t, J=10.9 Hz, 1H), 3.81 (dt, J=13.2, 3.3 Hz, 1H), 2.79-2.97 (m, 2H), 2.26 (br d, J=12.3 Hz, 1H).

LC/MS (method LC-C): Rt 2.69 min, MH⁺448

$[\alpha]_D^{20}$: +425.62° (c 0.121, DMF)

Chiral HPLC (method HPLC-B): Rt 4.94 min, chiral purity 100%

Synthesis of Compound 84B:

(19*S, E/Z)-4-fluoro-13-hydroxy-19-phenyl-9,10-dihydro-6H,19H-11,18-methanopyrido[2,1-i][1,7,10,11]benzoxatriazacyclotetradecine-12,14-dione (compound 84B, mixture of Z and E isomers 8/92, 560 mg) was obtained using the procedure described for compound 1.

Compound 84B:

¹H NMR (500 MHz, DMSO-d₆) δ ppm 11.70 (br s, 1H), 7.87 (br d, J=7.9 Hz, 1H), 7.30-7.41 (m, 2H), 6.93-7.23 (m, 6H), 6.07 (br ddd, J=15.0, 10.1, 4.9 Hz, 1H), 5.98 (s, 1H), 5.63 (ddd, J=15.1, 10.2, 4.3 Hz, 1H), 5.41 (d, J=7.9 Hz, 1H), 5.09 (d, J=13.2 Hz, 1H), 4.73 (br dd, J=12.0, 5.0 Hz, 1H), 4.33 (d, J=12.9 Hz, 1H), 4.04 (br t, J=11.0 Hz, 1H), 3.81 (br d, J=13.6 Hz, 1H), 2.87-2.97 (m, 1H), 2.79-2.88 (m, 1H), 2.26 (br d, J=13.2 Hz, 1H).

LC/MS (method LC-C): Rt 2.69 min, MH⁺448

$[\alpha]D^{20}$: −422.5° (c 0.160, DMF)

Chiral HPLC (method HPLC-B): Rt 6.06 min, chiral purity 93.6%

Example 85: Synthesis of (9*S,18*R,E)-9-ethyl-4-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 85AA), (9*R,18*S,E)-9-ethyl-4-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 85BB), (9*R,18*R,E)-9-ethyl-4-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 85AB) and (9*S,18*S,E)-9-ethyl-4-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 85BA)

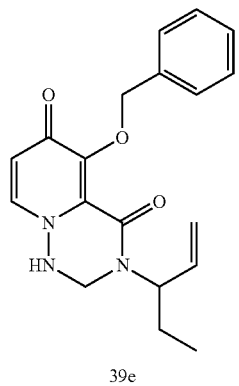

39e

+

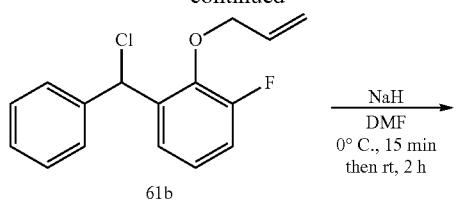

61b

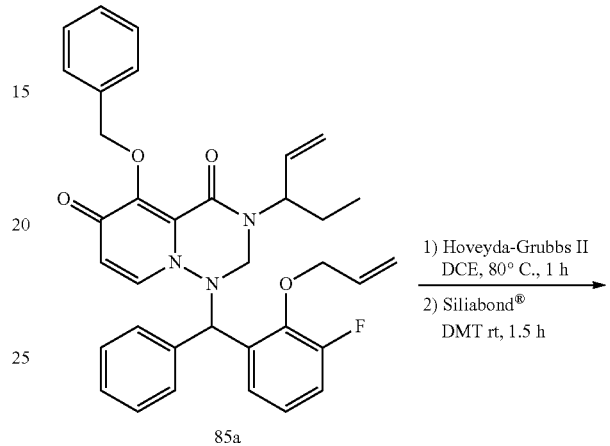

85a

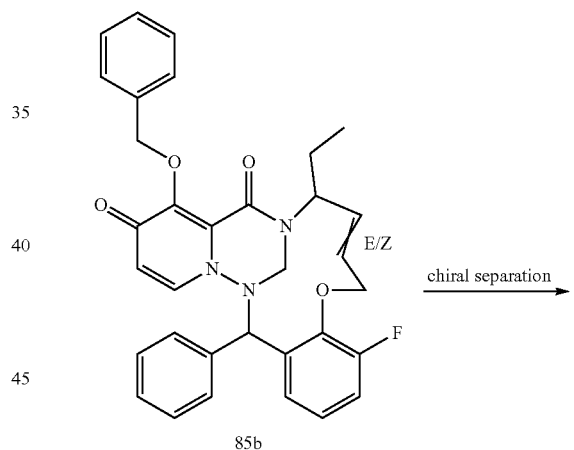

85b

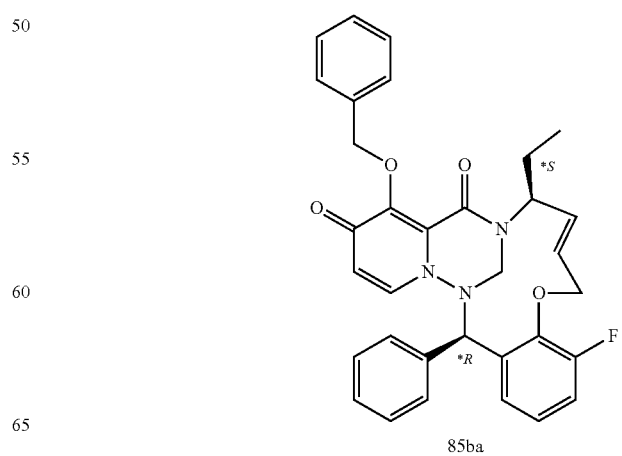

85ba

-continued

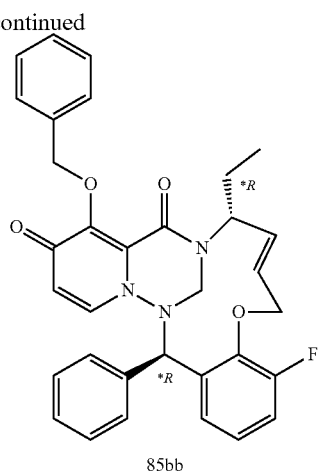

85bb

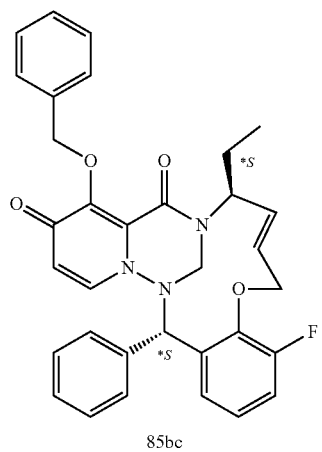

85bc

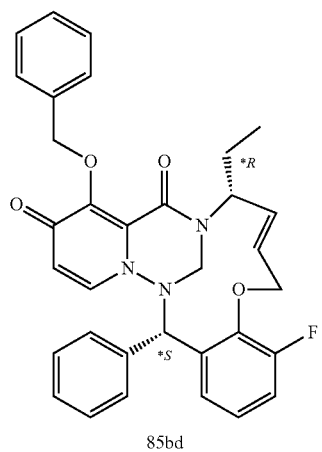 [SMILES: CC[C@@H]1/C=C/COc2c(F)cccc2[C@H](c2ccccc2)N2CN1C(=O)c1c(OCc3ccccc3)c(=O)ccn12]

85bd

Synthesis of Intermediate 85a:

Under nitrogen atmosphere, to solution of intermediate 39e (844 mg, 2.49 mmol) in anhydrous DMF (20 mL) at −20° C. was added NaH (60% dispersion in mineral oil, 169 mg, 4.23 mmol). The mixture was stirred for 5 min at this temperature and a solution of intermediate 61b (1.03 g, 3.72 mmol) in anhydrous DMF (20 mL) was added dropwise. The reaction mixture was allowed to warm to 0° C. and stirred for 7 h. The reaction mixture was diluted with EtOAc and the reaction was quenched by the careful addition of a saturated aqueous solution of $NH_4Cl$. The layers were separated and the aqueous phase was extracted with EtOAc (twice). The combined organic extracts were washed with a saturated aqueous solution of $NH_4Cl$ and brine, dried over $Na_2SO_4$, filtered and concentrated in vacuo. Purification was carried out by flash chromatography over silica gel (40 g, $CH_2Cl_2$/MeOH from 100/0 to 95/5). A second purification was performed over silica gel (40 g, petroleum ether/EtOAc from 100/0 to 0/100) to afford 1-((2-(allyloxy)-3-fluorophenyl)(phenyl)methyl)-5-(benzyloxy)-3-(pent-1-en-3-yl)-2,3-dihydro-1H-pyrido[2,1-f][1,2,4]triazine-4,6-dione (intermediate 85a, 815 mg).

Synthesis of Intermediate 85b:

$(E/Z)_{12}$-(benzyloxy)-9-ethyl-4-fluoro-18-phenyl-6,9-dihydro-18H-10,17-methanobenzo[b]pyrido[1,2-f][1]oxa[5,6,9]triazacyclotridecine-11,13-dione (crude intermediate 85b) was obtained using the procedure described for intermediate 1f. Crude intermediate 85b was purified by flash chromatography over silica gel (80 g, $CH_2Cl_2$/MeOH from 100/0 to 95/5). A second purification was performed by reverse flash chromatography on silica C18 (30 g, $H_2O$/MeOH from 70/30 to 0/100) to afford intermediate 85b (358 mg). The product was combined with another fraction (352 mg) and the mixture was purified again by flash chromatography over silica gel (80 g, toluene/i-PrOH from 100/0 to 90/10) to afford intermediate 85b (518 mg).

Purification by chiral SFC (Stationary phase: CHIRALPAK IC 5 μm 250*30 mm, Mobile phase: 50% $CO_2$, 50% MeOH) to afford intermediate 85b (2 fractions of 77 mg and 194 mg) and intermediate 85ba (127 mg).

The fraction 85b (194 mg) was purified via chiral SFC (Stationary phase: CHIRALPAK IC 5 μm 250*30 mm, Mobile phase: 50% $CO_2$, 50% MeOH) to afford intermediate 85bd (111 mg) and intermediate 85bb (58 mg).

The second fraction 85b (77 mg) was purified via chiral SFC (Stationary phase: CHIRACEL OJ-H 5 μm 250*30 mm, Mobile phase: 80% $CO_2$, 20% MeOH) to afford intermediate 85bc (64 mg).

Synthesis of Compound 85AA:

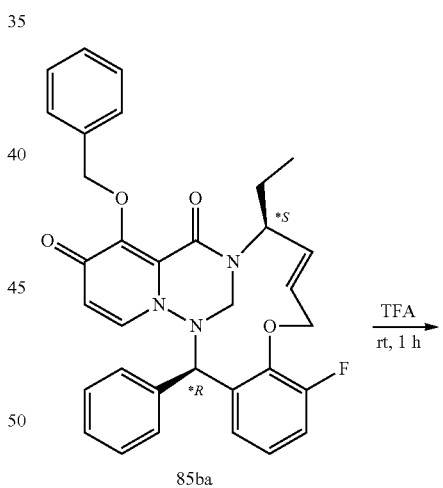

85ba

TFA
rt, 1 h

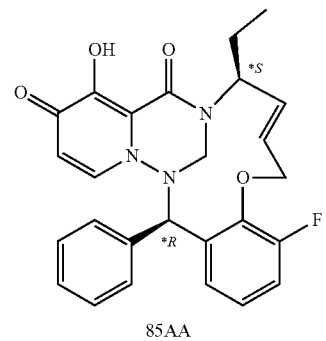

85AA (9*S,18*R,E)-9-ethyl-4-fluoro-12-hydroxy-18-phenyl-6,9-dihydro-18H-10,17-methanobenzo[b]pyrido[1,2-f][1]oxa[5,6,9]triazacyclotridecine-11,13-dione (compound 85AA, 50 mg) was obtained using the procedure described for compound 1.

Compound 85AA:

$^1$H NMR (500 MHz, DMSO-d$_6$) δ ppm 7.92 (br d, J=7.9 Hz, 1H), 7.32-7.45 (m, 2H), 7.04-7.26 (m, 6H), 6.37 (br ddd, J=15.3, 10.2, 5.0 Hz, 1H), 5.53 (dd, J=15.1, 5.0 Hz, 1H), 5.48 (d, J=7.6 Hz, 1H), 5.21 (s, 1H), 5.18 (q, J=7.6 Hz, 1H), 5.06 (d, J=13.6 Hz, 1H), 4.88 (br dd, J=11.3, 5.4 Hz, 1H), 4.22 (d, J=13.6 Hz, 1H), 3.99 (br t, J=10.7 Hz, 1H), 1.53 (dq, J=14.3, 7.0 Hz, 1H), 1.39-1.49 (m, 1H), 0.83 (t, J=7.3 Hz, 3H).

LC/MS (method LC-C): Rt 2.89 min, MH$^+$462

$[α]_D^{20}$: −562.24° (c 0.241, DMF)

Synthesis of Compound 85AB:

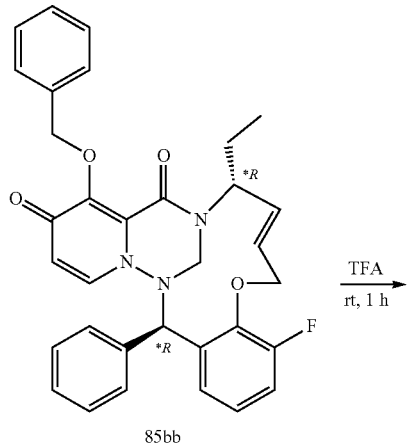

85bb

→ TFA, rt, 1 h (9*R,18*R,E)-9-ethyl-4-fluoro-12-hydroxy-18-phenyl-6,9-dihydro-18H-10,17-methanobenzo[b]pyrido[1,2-f][1]oxa[5,6,9]triazacyclotridecine-11,13-dione (compound 85AB, 24 mg) was obtained using the procedure described for compound 1.

Compound 85AB:

$^1$H NMR (500 MHz, DMSO-d$_6$) δ ppm 7.97 (br d, J=7.6 Hz, 1H), 7.36-7.43 (m, 1H), 7.30-7.36 (m, 2H), 7.14-7.21 (m, 3H), 7.10 (br s, 1H), 6.44 (br s, 1H), 5.89 (br s, 1H), 5.49 (d, J=7.6 Hz, 1H), 5.44 (s, 1H), 5.21 (d, J=13.9 Hz, 1H), 4.64 (br t, J=10.4 Hz, 1H), 4.54 (br s, 1H), 4.22 (d, J=14.2 Hz, 1H), 3.43-3.50 (m, 2H), 2.27-2.35 (m, 1H), 2.10-2.19 (m, 1H), 0.86 (t, J=7.4 Hz, 3H).

LC/MS (method LC-C): Rt 2.95 min, MH$^+$462

$[α]_D^{20}$: −559.07° (c 0.281, DMF)

Chiral HPLC (method HPLC-B): Rt 8.45 min, chiral purity 100%

Synthesis of Compound 85BB:

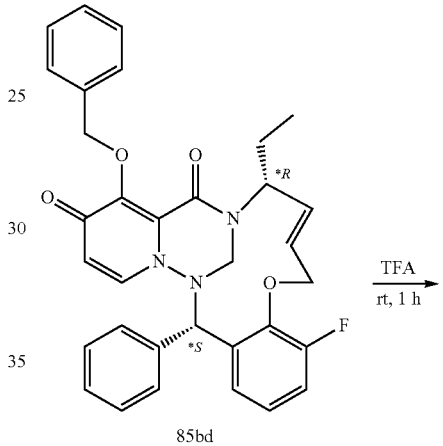

85bd

→ TFA, rt, 1 h

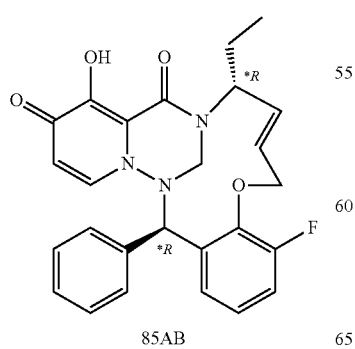

85AB

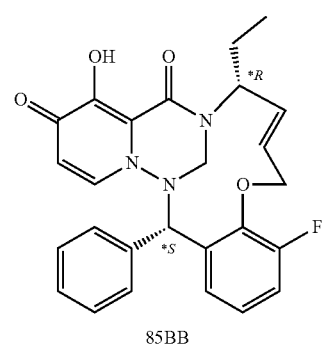

85BB

275

(9*R,18*S,E)-9-ethyl-4-fluoro-12-hydroxy-18-phenyl-6,9-dihydro-18H-10,17-methanobenzo[b]pyrido[1,2-f][1]oxa[5,6,9]triazacyclotridecine-11,13-dione (compound 85BB, 55 mg) was obtained using the procedure described for compound 1.

Compound 85BB:

$^1$H NMR (500 MHz, DMSO-$d_6$) δ ppm 7.92 (d, J=7.9 Hz, 1H), 7.41 (td, J=8.0, 5.5 Hz, 1H), 7.33-7.38 (m, 1H), 7.23 (d, J=7.6 Hz, 1H), 7.05-7.21 (m, 5H), 6.37 (br ddd, J=15.4, 10.2, 5.2 Hz, 1H), 5.52 (br dd, J=15.8, 6.3 Hz, 1H), 5.48 (d, J=7.6 Hz, 1H), 5.21 (s, 1H), 5.18 (q, J=7.5 Hz, 1H), 5.06 (d, J=13.6 Hz, 1H), 4.88 (dd, J=11.3, 5.4 Hz, 1H), 4.22 (d, J=13.2 Hz, 1H), 3.99 (br t, J=10.9 Hz, 1H), 1.49-1.58 (m, 1H), 1.39-1.49 (m, 1H), 0.83 (t, J=7.4 Hz, 3H).

LC/MS (method LC-C): Rt 2.89 min, MH$^+$462

[α]$_D^{20}$: +600.42° (c 0.237, DMF)

Synthesis of Compound 85BA:

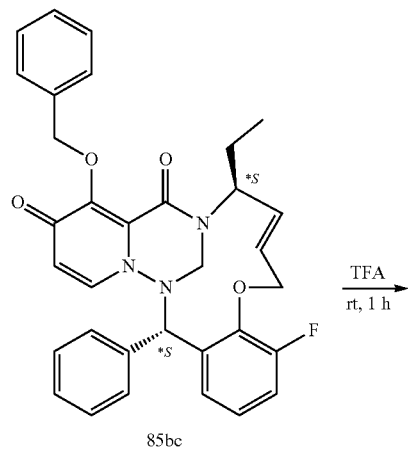

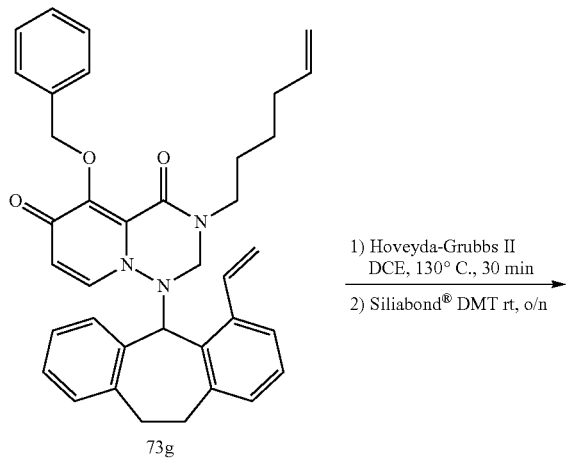 [SMILES: C=CCCCCN1CN(C2c3ccccc3CCc3cccc(C=C)c32)n2ccc(=O)c(OCc3ccccc3)c2C1=O]

276

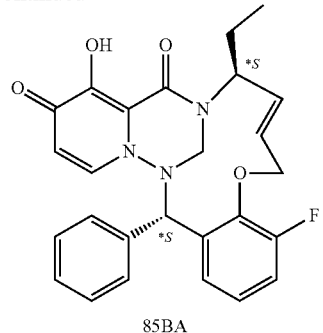

85BA (9*S,18*S,E)-9-ethyl-4-fluoro-12-hydroxy-18-phenyl-6,9-dihydro-18H-10,17-methanobenzo[b]pyrido[1,2-f][1]oxa[5,6,9]triazacyclotridecine-11,13-dione (compound 85BA, 22 mg) was obtained using the procedure described for compound 1.

Compound 85BA:

$^1$H NMR (500 MHz, DMSO-$d_6$) δ ppm 7.97 (br d, J=7.9 Hz, 1H), 7.36-7.42 (m, 1H), 7.29-7.36 (m, 2H), 7.14-7.20 (m, 3H), 7.09 (br s, 1H), 6.44 (br s, 1H), 5.88 (br s, 1H), 5.49 (d, J=7.6 Hz, 1H), 5.44 (s, 1H), 5.21 (d, J=13.9 Hz, 1H), 4.64 (br t, J=10.4 Hz, 1H), 4.54 (br s, 1H), 4.22 (d, J=14.2 Hz, 1H), 3.43-3.49 (m, 2H), 2.28-2.35 (m, 1H), 2.11-2.20 (m, 1H), 0.86 (t, J=7.3 Hz, 3H).

LC/MS (method LC-C): Rt 2.94 min, MH$^+$462

[α]D2°: +648.56° (c 0.243, DMF)

Chiral HPLC (method HPLC-B): Rt 5.74 min, chiral purity 100%

Example 86: Synthesis of (13*Z,23b*R)-6-hydroxy-10,11,12,18,19,23b-hexahydro-9H-1,8-methanobenzo[4,5]cyclohepta[1,2,3-qr]pyrido[1,2-c][2,3,6]benzotriazacyclotetradecine-5,7-dione (Compound 86A), (13*Z,23b*R)-6-hydroxy-10,11,12,18,19,23b-hexahydro-9H-1,8-methanobenzo[4,5]cyclohepta[1,2,3-qr]pyrido[1,2-c][2,3,6]benzotriazacyclotetradecine-5,7-dione (Compound 86B)

1) Hoveyda-Grubbs II DCE, 130° C., 30 min
2) Siliabond® DMT rt, o/n

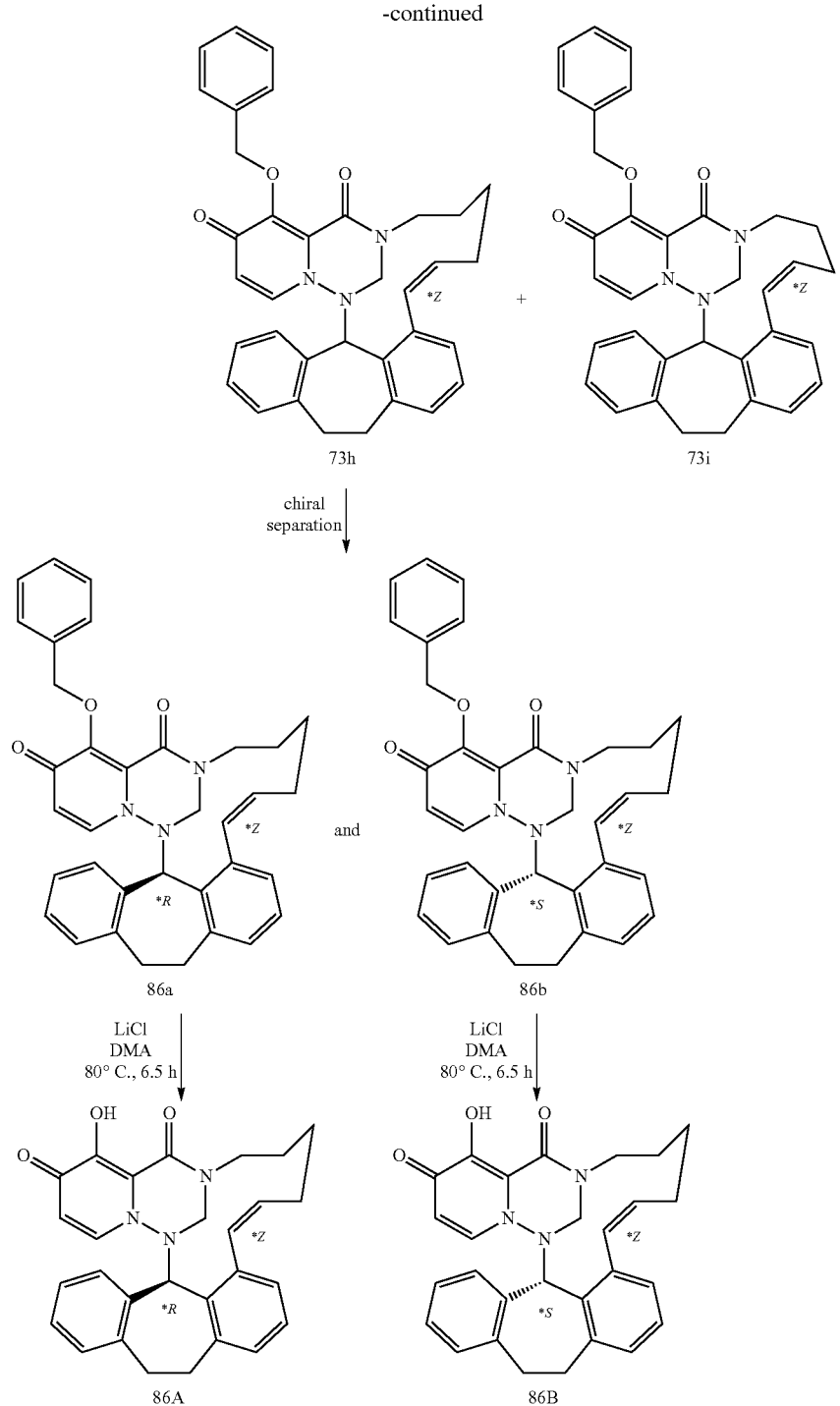

Synthesis of Intermediates 73h and 73i:

A mixture of (13*Z)-6-(benzyloxy)-10,11,12,18,19,23b-hexahydro-9H-1,8-methanobenzo[4,5]cyclohepta[1,2,3-qr]pyrido[1,2-c][2,3,6]benzotriazacyclotetradecine-5,7-dione (intermediate 73h), (12*Z)-6-(benzyloxy)-9,10,11,17,18,22b-hexahydro-1,8-methanobenzo[4,5]cyclohepta[1,2,3-pq]pyrido[1,2-c][2,3,6]benzotriazacyclotridecine-5,7-dione (intermediate 73i) was obtained using the procedure described for intermediate 59d.

The crude mixture was purified by flash chromatography over silica gel (40 g, CH$_2$Cl$_2$/MeOH from 100/0 to 98/2) to afford intermediate 73h and intermediate 73i. The two products were independently purified by flash chromatography C18 (40 µm, 45 g, H$_2$O/MeOH from 70/30 to 0/100) to give intermediate 73h (510 mg) and intermediate 73i (103 mg).

Intermediate 73h was purified by flash chromatography over silica gel (15 µm, 24 g, toluene/i-PrOH 94/6). The residue was purified via reverse phase (Stationary phase:

YMC-actus Triart C18 10 μm 30*150 mm, mobile phase gradient: 0.2% aq.NH₄HCO₃/MeCN from 45/55 to 25/75) to afford intermediate 73h (80 mg).

The enantiomers were separated via chiral SFC (Stationary phase: CHIRALPAK AS-H 5 μm 250*20 mm, Mobile phase: 60% CO$_2$, 40% MeOH) to afford the first eluted enantiomer 86 (27 mg) and the second eluted enantiomer 86 (27 mg).

Synthesis of Compound 86A:

(13*Z,23b*R)-6-hydroxy-10,11,12,18,19,23b-hexahydro-9H-1,8-methanobenzo[4,5]cyclohepta[1,2,3-qr]pyrido[1,2-c][2,3,6]benzotriazacyclotetradecine-5,7-dione (compound 86A, 9 mg) was obtained using the procedure described for compound 28A.

Compound 86A:

¹H NMR (500 MHz, DMSO-d₆) δ ppm 11.91 (br s, 1H), 7.25-7.32 (m, 2H), 7.18-7.22 (m, 1H), 7.13 (d, J=7.6 Hz, 1H), 7.05 (dd, J=6.9, 1.9 Hz, 1H), 6.96 (d, J=7.6 Hz, 1H), 6.91 (t, J=7.3 Hz, 1H), 6.69 (d, J=7.3 Hz, 1H), 6.39 (d, J=11.3 Hz, 1H), 5.88 (br ddd, J=11.0, 9.5, 4.4 Hz, 1H), 5.48 (s, 1H), 5.41 (d, J=7.6 Hz, 1H), 4.93 (d, J=13.2 Hz, 1H), 4.54 (br td, J=14.0, 5.2 Hz, 1H), 4.11 (d, J=13.2 Hz, 1H), 3.64 (br ddd, J=13.6, 8.8, 2.5 Hz, 1H), 3.54 (br d, J=18.0 Hz, 1H), 2.94 (br ddd, J=18.5, 13.8, 4.9 Hz, 1H), 2.74-2.80 (m, 1H), 2.39-2.46 (m, 2H), 2.06-2.14 (m, 1H), 1.86-1.96 (m, 1H), 1.70-1.79 (m, 1H), 1.49-1.59 (m, 1H), 1.26-1.37 (m, 1H).

LC/MS (method LC-C): Rt 3.35 min, MH⁺454

$[α]_D^{20}$: +86.54° (c 0.104, DMF)

Chiral HPLC (method HPLC-B): Rt 5.74 min, chiral purity 100%

Synthesis of Compound 86B:

(13*Z,23b*R)-6-hydroxy-10,11,12,18,19,23b-hexahydro-9H-1,8-methanobenzo[4,5]cyclohepta[1,2,3-qr]pyrido[1,2-c][2,3,6]benzotriazacyclotetradecine-5,7-dione (compound 86B, 6 mg) was obtained using the procedure described for compound 28A.

Compound 86B:

¹H NMR (500 MHz, DMSO-d₆) δ ppm 11.88 (br s, 1H), 7.26-7.33 (m, 2H), 7.17-7.23 (m, 1H), 7.11-7.15 (m, 1H), 7.05 (dd, J=6.9, 1.6 Hz, 1H), 6.96 (d, J=7.6 Hz, 1H), 6.91 (t, J=7.4 Hz, 1H), 6.69 (d, J=6.9 Hz, 1H), 6.39 (d, J=11.3 Hz, 1H), 5.85-5.91 (m, 1H), 5.49 (s, 1H), 5.41 (d, J=7.6 Hz, 1H), 4.93 (d, J=12.9 Hz, 1H), 4.54 (br td, J=13.9, 5.0 Hz, 1H), 4.11 (d, J=12.9 Hz, 1H), 3.60-3.67 (m, 1H), 3.54 (br d, J=17.7 Hz, 1H), 2.94 (br ddd, J=18.4, 13.8, 4.7 Hz, 1H), 2.74-2.81 (m, 1H), 2.40-2.45 (m, 2H), 2.06-2.14 (m, 1H), 1.87-1.96 (m, 1H), 1.70-1.80 (m, 1H), 1.50-1.59 (m, 1H), 1.27-1.37 (m, 1H).

LC/MS (method LC-C): Rt 3.35 min, MH⁺454

$[α]_D^{20}$: −135.29° (c 0.102, DMF)

Chiral HPLC (method HPLC-B): Rt 7.11 min, chiral purity 100%

Example 87: Synthesis of (1aS,11bR,20aS)-17-hydroxy-1a,2,6,11b,20,20a-hexahydro-1H-5,4-(epiprop[1]en[1]yl[3]ylidene)-12,19-methanobenzo[6,7]thiepino[4,5-c]cyclopropa[k]pyrido[1,2-f][1]oxa[5,6,9]triazacyclotridecine-16,18-dione (Compound 87AA), (1aR,11bS,20aR)-17-hydroxy-1a,2,6,11b,20,20a-hexahydro-1H-5,4-(epiprop[1]en[1]yl[3]ylidene)-12,19-methanobenzo[6,7]thiepino[4,5-c]cyclopropa[k]pyrido[1,2-f][1]oxa[5,6,9]triazacyclotridecine-16,18-dione (Compound 87BB), (1aR,11bR,20aR)-17-hydroxy-1a,2,6,11b,20,20a-hexahydro-1H-5,4-(epiprop[1]en[1]yl[3]ylidene)-12,19-methanobenzo[6,7]thiepino[4,5-c]cyclopropa[k]pyrido[1,2-f][1]oxa[5,6,9]triazacyclotridecine-16,18-dione (Compound 87AB) and (1aS,11bS,20aS)-17-hydroxy-1a,2,6,11b,20,20a-hexahydro-1H-5,4-(epiprop[1]en[1]yl[3]ylidene)-12,19-methanobenzo[6,7]thiepino[4,5-c]cyclopropa[k]pyrido[1,2-f][1]oxa[5,6,9]triazacyclotridecine-16,18-dione (Compound 87BA)

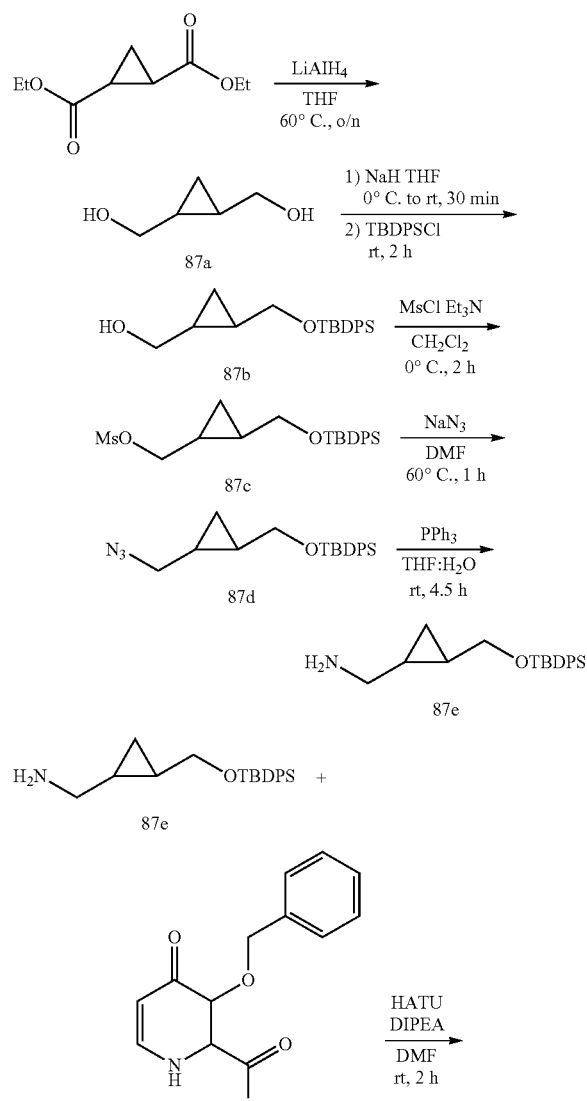

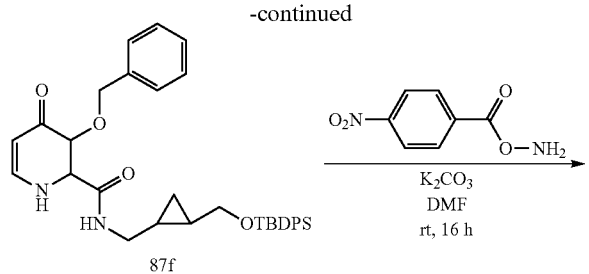
87f
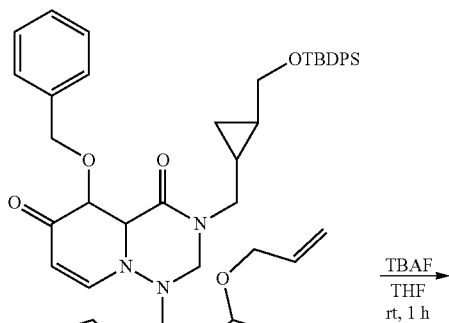
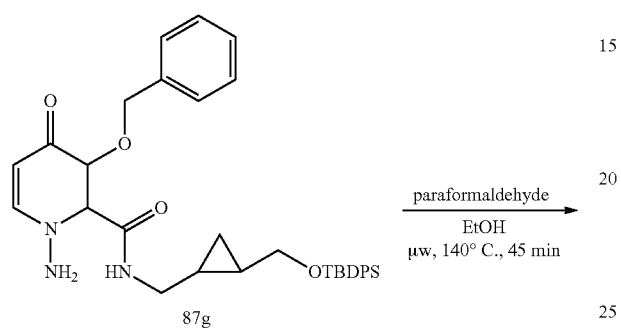
87g
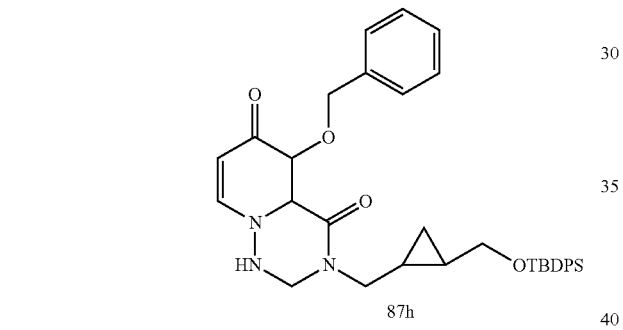
87h
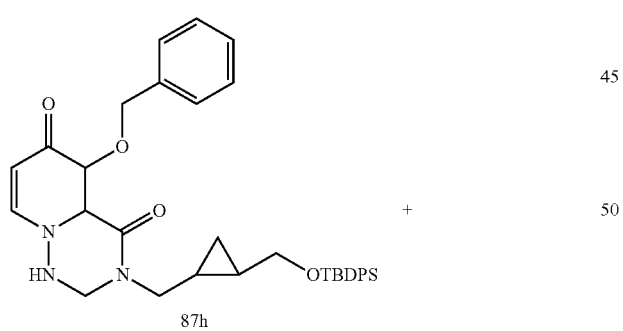
87h +
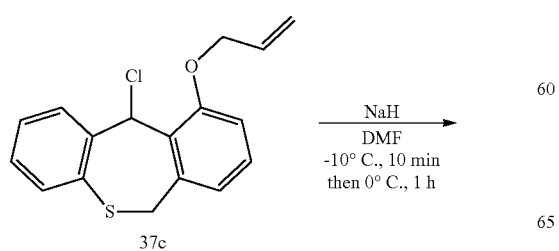
37c
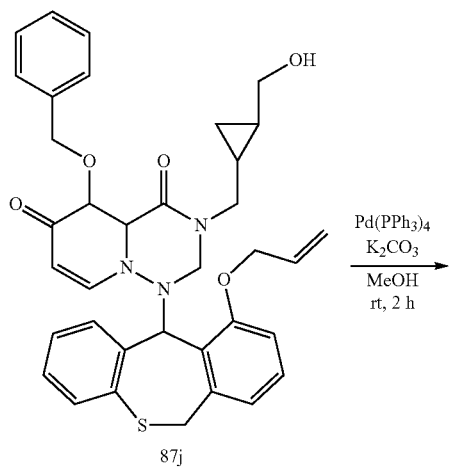
87i
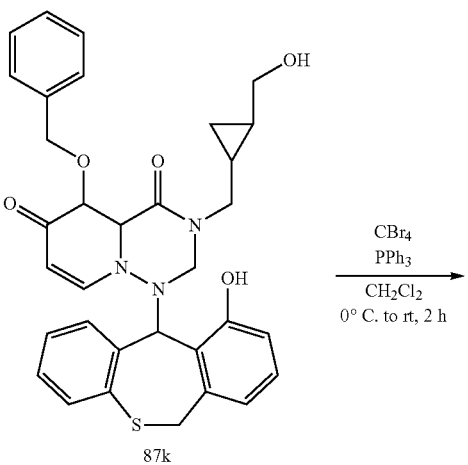
87j
87k 283
-continued
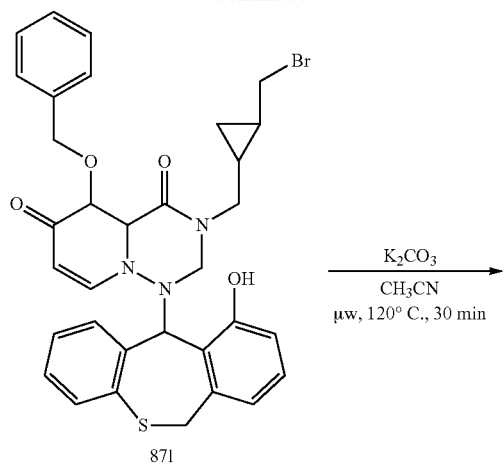
87l
K₂CO₃
CH₃CN
μw, 120° C., 30 min
284
-continued
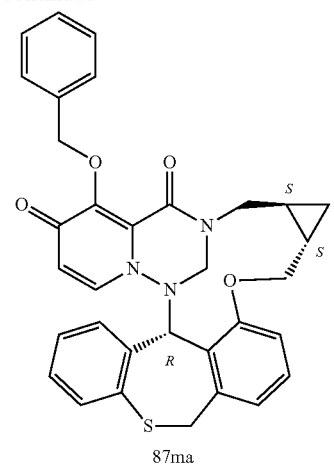
87ma
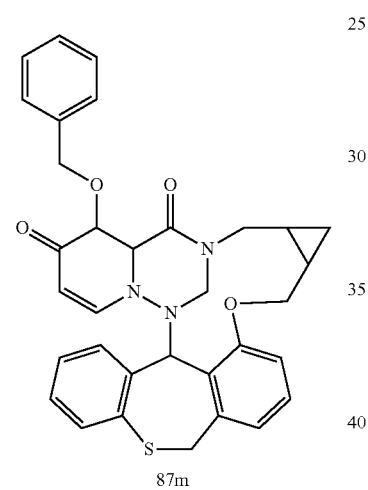
87m
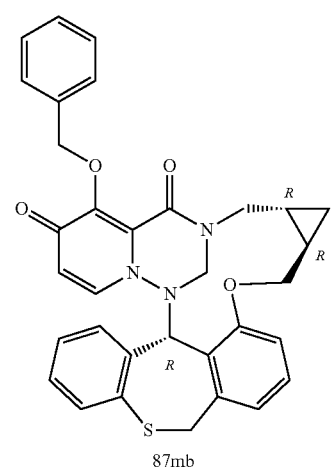
87mb
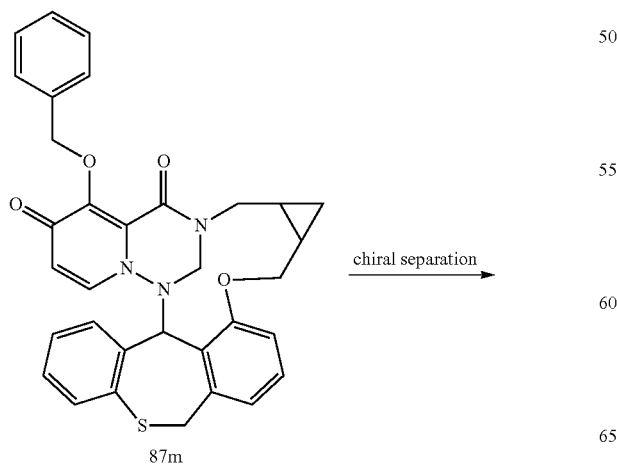
87m
chiral separation
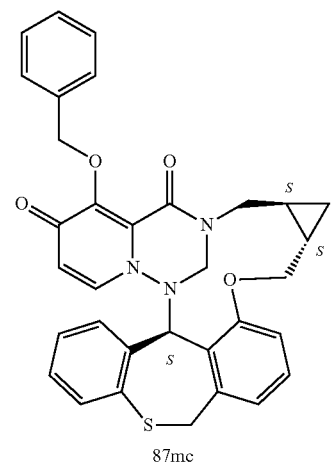
87mc

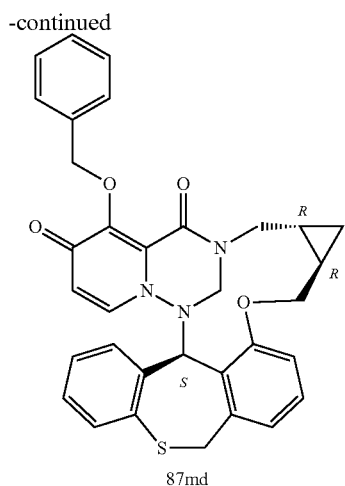

87md

Synthesis of Intermediate 87a:

To a solution of diethyl trans-1,2-cyclopropanedicarboxylate [CAS 3999-55-1] (9.85 g, 52.9 mmol) in anhydrous THF (150 mL) under nitrogen atmosphere at 0° C. was added LiAlH₄ (1.0 M in THF, 80 mL, 80 mmol) dropwise. The reaction mixture was stirred at 60° C. overnight. The reaction was quenched by the addition of water followed by a 15% aqueous solution of NaOH and water again. The mixture was filtered over a pad of Celite® and washed with EtOAc. The filtrate was partially concentrated in vacuo, dried over Na₂SO₄, filtered and concentrated in vacuo to afford [2 cyclopropane-1,2-diyldimethanol (intermediate 87a, 4.9 g).

Synthesis of Intermediate 87b:

To a solution of intermediate 87a (4.90 g, 48.0 mmol) in anhydrous THF (200 mL) at 0° C. under nitrogen atmosphere was added NaH (60% dispersion in mineral oil, 2.30 g, 57.6 mmol) portionwise. The mixture was stirred at rt for 30 minutes and TBDPSCl (12.5 mL, 48.8 mmol) was added. The reaction mixture was stirred at rt for 2 h. The reaction mixture was diluted with Et₂O and washed with a saturated aqueous solution of NH₄Cl and brine. The aqueous phase was extracted with Et₂O. The combined organic extracts were dried over Na₂SO₄, filtered and concentrated in vacuo. Purification was carried out by flash column chromatography over silica gel (220 g, petroleum ether/EtOAc from 100/0 to 75/25) to afford (2-(((tert-butyldiphenylsilyl)oxy)methyl)cyclopropyl)methanol (intermediate 87b, 11.95 g).

Synthesis of Intermediate 87c:

(2-(((tert-butyldiphenylsilyl)oxy)methyl)cyclopropyl)methyl methanesulfonate (intermediate 87c, 14.7 g) was obtained using the procedure described for intermediate 80c.

Synthesis of Intermediate 87d:

To a solution of intermediate 87c (14.7 g, 35.1 mmol) in anhydrous DMF (70 mL) under nitrogen atmosphere was added NaN₃ (4.56 g, 70.2 mmol). The reaction mixture was stirred at 60° C. for 1 h. The reaction mixture was diluted with EtOAc and washed with a saturated aqueous solution of NH₄Cl (twice), water and brine. The organic phase was dried over Na₂SO₄, filtered and concentrated in vacuo to afford ((2-(azidomethyl)cyclopropyl)methoxy)(tert-butyl)diphenylsilane (intermediate 87d, 12.8 g).

Synthesis of Intermediate 87e:

(2-(((tert-butyldiphenylsilyl)oxy)methyl)cyclopropyl)methanamine (intermediate 87e, 9.74 g) was obtained using the procedure described for intermediate 80e. Crude intermediate 87e was purified by flash chromatography over silica gel (220 g, CH₂Cl₂/(CH₂Cl₂/MeOH/Et₃N 90/9/1) from 100/0 to 90/10).

Synthesis of Intermediate 87f:

3-(benzyloxy)-N-((2-(((tert-butyldiphenylsilyl)oxy)methyl)cyclopropyl)methyl)-4-oxo-1,2,3,4-tetrahydropyridine-2-carboxamide (intermediate 87f, 8.87 g) was obtained using the procedure described for intermediate 5b.

Synthesis of Intermediate 87g:

To a solution of intermediate 87f (8.87 g, 15.7 mmol) in anhydrous DMF (80 mL) under nitrogen atmosphere was suspended K₂CO₃ (6.45 g, 46.7 mmol). After 5 min o-(4-nitrobenzoyl)hydroxylamine [CAS35657-36-3] (4.28 g, 23.5 mmol) was added. The reaction mixture was stirred at rt for 16 h, then at 35° C. for 24 h. The reaction mixture was diluted with EtOAc and washed with a saturated aqueous solution of NH₄Cl (twice), water and brine. The organic phase was dried over Na₂SO₄, filtered and concentrated in vacuo. Purification was carried out by flash column chromatography on silica gel (220 g, CH₂Cl₂/MeOH from 100/0 to 96/4) to afford 1-amino-3-(benzyloxy)-N-((2-(((tert-butyldiphenylsilyl)oxy)methyl)cyclopropyl)methyl)-4-oxo-1,2,3,4-tetrahydropyridine-2-carboxamide (intermediate 87g, 6.51 g).

Synthesis of Intermediate 87h:

5-(benzyloxy)-3-((2-(((tert-butyldiphenylsilyl)oxy)methyl)cyclopropyl)methyl)-2,3,4a,5-tetrahydro-1H-pyrido[2,1-f][1,2,4]triazine-4,6-dione (intermediate 87h, 4.48 g) was obtained using the procedure described for intermediate 5d. Crude intermediate 87h was purified by flash column chromatography over silica gel (220 g, CH₂Cl₂/MeOH from 100:0 to 94:6).

Synthesis of Intermediate 87i:

Intermediate 87h (2.00 g, 3.37 mmol) was dissolved under nitrogen atmosphere in anhydrous DMF (25 mL). The solution was cooled to −10° C. and NaH (60% dispersion in mineral oil, 162 mg, 4.04 mmol) was added. After stirring for 10 min a solution of intermediate 37c (1.53 g, 5.05 mmol) in anhydrous DMF (5 mL) was added dropwise. The reaction mixture was stirred between −10 and 0° C. for 1 h. The reaction mixture was diluted with EtOAc and washed with a saturated aqueous solution of NH₄Cl (4 times). The combined organic extracts were dried over Na₂SO₄, filtered and concentrated in vacuo. Purification was carried out by flash column chromatography over silica gel (120 g, CH₂Cl₂/MeOH from 100/0 to 97/3) to afford 1-(10-(allyloxy)-6,11-dihydrodibenzo[b,e]thiepin-11-yl)-5-(benzyloxy)-3-((2-(((tert-butyldiphenylsilyl)oxy)methyl)cyclopropyl)methyl)-2,3,4a,5-tetrahydro-1H-pyrido[2,1-f][1,2,4]triazine-4,6-dione (intermediate 87i, 2.5 g).

Synthesis of Intermediate 87j:

To a solution of intermediate 87i (2.50 g, 2.91 mmol) in anhydrous THF (30 mL) under nitrogen atmosphere was added TBAF (1.0 M in THF, 3.2 mL, 3.20 mmol) dropwise. The reaction mixture was stirred at rt for 1 h and concentrated in vacuo. Purification was carried out by flash column chromatography over silica gel (120 g, CH₂Cl₂/MeOH from 100/0 to 96/4) to afford 1-(10-(allyloxy)-6,11-dihydrodibenzo[b,e]thiepin-11-yl)-5-(benzyloxy)-3-((2-(hydroxymethyl)cyclopropyl)methyl)-2,3,4a,5-tetrahydro-1H-pyrido[2,1-f][1,2,4]triazine-4,6-dione (intermediate 87j, 1.5 g).

Synthesis of Intermediate 87k:

Intermediate 87j (1.50 g, 2.41 mmol) was dissolved in MeOH (50 mL) under nitrogen atmosphere. Pd(PPh₃)₄(279 mg, 241 μmol) was added and the mixture was stirred for 10 min. K₂CO₃ (1.00 g, 7.24 mmol) was added and the reaction mixture was stirred at rt for 2 h. The mixture was filtered over a pad of Celite®. The filtrate was diluted with CH₂Cl₂ and washed with water and brine, dried over Na₂SO₄, filtered and concentrated in vacuo. Purification was carried out by flash column chromatography over silica gel (80 g, CH₂Cl₂/MeOH/aq.NH₃ from 100/0 to 90/10) to afford 5-(benzyloxy)-1-(10-hydroxy-6,11-dihydrodibenzo[b,e]thiepin-11-yl)-3-((2-(hydroxymethyl)cyclopropyl)methyl)-2,3,4a,5-tetrahydro-1H-pyrido[2,1-f][1,2,4]triazine-4,6-dione (intermediate 87k, 1.3 g).

Synthesis of Intermediate 87l:

Intermediate 87k (900 mg, 1.55 mmol) was dissolved in anhydrous CH₂Cl₂ (30 mL) under nitrogen atmosphere. The solution was cooled to 0° C. and PPh₃ (675 mg, 3.09 mmol) was added. After stirring for 15 min, CBr₄ (1.03 g, 3.09 mmol) was added. The reaction mixture was stirred at rt for 2 h and concentrated in vacuo. Purification was carried out by flash column chromatography over silica gel (40 g, CH₂Cl₂/MeOH from 100/0 to 98/2) to afford 5-(benzyloxy)-3-((2-(bromomethyl)cyclopropyl)methyl)-1-(10-hydroxy-6,11-dihydrodibenzo[b,e]thiepin-11-yl)-2,3,4a,5-tetrahydro-1H-pyrido[2,1-f][1,2,4]triazine-4,6-dione (intermediate 87l, 850 mg).

Synthesis of Intermediate 87m:

17-(benzyloxy)-1a,2,6,11b,17,17a,20,20a-octahydro-1H-5,4-(epiprop[1]en[1]yl[3]ylidene)-12,19-methanobenzo[6,7]thiepino[4,5-c]cyclopropa[k]pyrido[1,2-f][1]oxa[5,6,9]triazacyclotridecine-16,18-dione (intermediate 87m) was obtained using the procedure described for intermediate 80m. Crude intermediate 87m was purified by flash column chromatography over silica gel (40 g, CH₂Cl₂/MeOH from 100/0 to 97/3). A second purification was performed by flash column chromatography C18 (40 μm, 45 g, H₂O/MeOH from 70/30 to 0/100) to afford intermediate 87m (508 mg) as a mixture of diastereoisomers.

The isomers were separated via chiral SFC (Stationary phase: CHIRALPAK AS-H 5 μm 250*20 mm, Mobile phase: 60% CO₂, 40% MeOH) to afford two fractions: fraction A (intermediates 87ma and 87mb, 192 mg) and fraction B (intermediates 87mc and 87md, 195 mg).

The diastereoisomers 87ma and 87mb were separated via chiral SFC (Stationary phase: CHIRALPAK AD-H 5 μm 250*30 mm, Mobile phase: 55% CO₂, 45% EtOH) to afford intermediate 87ma (85 mg) and intermediate 87mb (72 mg).

The diastereoisomers 87mc and 87md were separated via chiral SFC (Stationary phase: Whelk-O1 (S,S) 5 μm 250*21.2 mm, Mobile phase: 50% CO₂, 50% (EtOH+10% CH₂Cl₂) to afford intermediate 87md (79 mg) and intermediate 87mc (75 mg).

Synthesis of Compound 87AA:

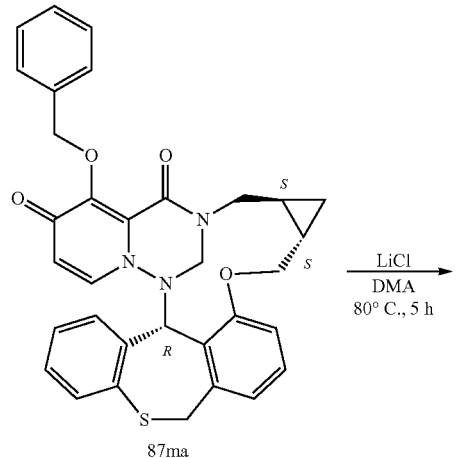
87ma

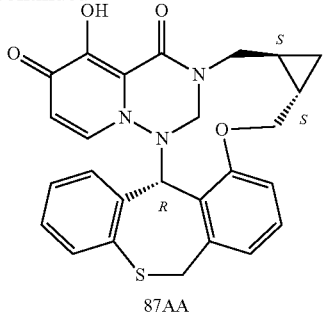
87AA (1aS,11bR,20aS)-17-hydroxy-1a,2,6,11b,20,20a-hexahydro-1H-5,4-(epiprop[1]en[1]yl[3]ylidene)-12,19-methanobenzo[6,7]thiepino[4,5-c]cyclopropa[k]pyrido[1,2-f][1]oxa[5,6,9]triazacyclotridecine-16,18-dione (compound 87AA, 44 mg) was obtained using the procedure described for compound 28A.

Compound 87AA:

¹H NMR (500 MHz, DMSO-d₆) δ ppm 7.34 (t, J=7.9 Hz, 1H), 7.20 (d, J=7.6 Hz, 1H), 7.03-7.15 (m, 4H), 6.85 (td, J=7.6, 1.2 Hz, 1H), 6.73-6.79 (m, 1H), 6.09 (s, 1H), 5.75 (d, J=13.6 Hz, 1H), 5.61 (d, J=7.9 Hz, 1H), 5.06 (d, J=13.2 Hz, 1H), 4.83 (dd, J=12.6, 4.7 Hz, 1H), 4.49 (d, J=13.6 Hz, 1H), 3.86 (d, J=13.2 Hz, 1H), 3.51 (dd, J=14.0, 10.9 Hz, 2H), 3.17 (dd, J=14.5, 5.0 Hz, 1H), 1.31-1.39 (m, 1H), 0.80-0.88 (m, 1H), 0.74-0.79 (m, 1H), 0.65 (dt, J=8.4, 5.0 Hz, 1H).

LC/MS (method LC-C): Rt 2.72 min, MH⁺474

[α]$_D^{20}$: +170.77° (c 0.284, DMF)

Chiral HPLC (method HPLC-B): Rt 6.89 min, chiral purity 100%

Synthesis of Compound 87AB:

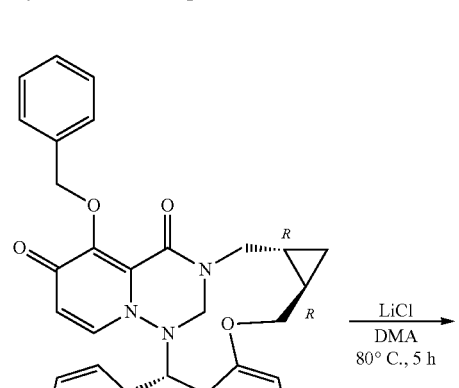
87mb

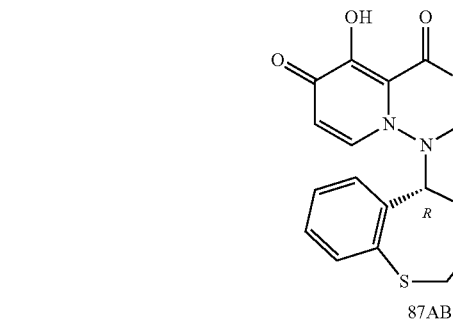
87AB (1aR,11bR,20aR)-17-hydroxy-1a,2,6,11b,20,20a-hexahydro-1H-5,4-(epiprop[1]en[1]yl[3]ylidene)-12,19-methanobenzo[6,7]thiepino[4,5-c]cyclopropa[k]pyrido[1,2-f][1]oxa[5,6,9]triazacyclotridecine-16,18-dione (compound 87AB, 28 mg) was obtained using the procedure described for compound 28A.

Compound 87AB:

$^1$H NMR (500 MHz, DMSO-d$_6$) δ ppm 11.58 (br s, 1H), 7.45 (d, J=7.9 Hz, 1H), 7.35-7.43 (m, 2H), 7.07-7.15 (m, 2H), 7.02-7.05 (m, 1H), 6.85 (br td, J=7.4, 1.3 Hz, 1H), 6.76 (dd, J=7.7, 1.1 Hz, 1H), 6.18 (s, 1H), 5.93 (d, J=13.6 Hz, 1H), 5.61 (d, J=7.6 Hz, 1H), 5.11 (d, J=13.2 Hz, 1H), 4.91 (dd, J=12.3, 3.5 Hz, 1H), 4.38 (d, J=13.2 Hz, 1H), 4.30 (dd, J=13.6, 2.5 Hz, 1H), 3.85 (d, J=13.6 Hz, 1H), 3.29-3.37 (m, 1H), 2.17 (dd, J=13.7, 11.2 Hz, 1H), 1.24-1.32 (m, 1H), 1.08-1.15 (m, 1H), 0.61 (dt, J=8.9, 4.7 Hz, 1H), 0.42 (dt, J=8.8, 5.2 Hz, 1H).

LC/MS (method LC-C): Rt 2.69 min, MH$^+$474

$[α]_D^{20}$: +283.46° (c 0.254, DMF)

Chiral HPLC (method HPLC-B): Rt 6.85 min, chiral purity 100%

Synthesis of Compound 87BB:

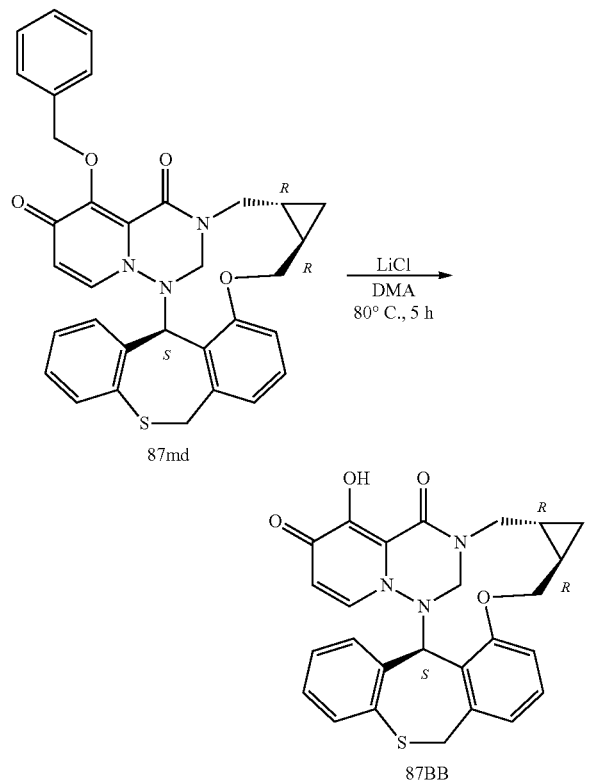

87md

87BB (1aR,11bS,20aR)-17-hydroxy-1a,2,6,11b,20,20a-hexahydro-1H-5,4-(epiprop[1]en[1]yl[3]ylidene)-12,19-methanobenzo[6,7]thiepino[4,5-c]cyclopropa[k]pyrido[1,2-f][1]oxa[5,6,9]triazacyclotridecine-16,18-dione (compound 87BB, 32 mg) was obtained using the procedure described for compound 28A.

Compound 87BB:

$^1$H NMR (500 MHz, DMSO-d$_6$) δ ppm 7.27 (t, J=7.9 Hz, 1H), 7.13 (d, J=7.6 Hz, 1H), 6.95-7.09 (m, 4H), 6.74-6.84 (m, 1H), 6.69 (d, J=7.6 Hz, 1H), 6.02 (s, 1H), 5.68 (d, J=13.6 Hz, 1H), 5.54 (d, J=7.6 Hz, 1H), 4.99 (d, J=13.2 Hz, 1H), 4.76 (dd, J=12.6, 4.7 Hz, 1H), 4.42 (d, J=13.6 Hz, 1H), 3.79 (d, J=13.2 Hz, 1H), 3.40-3.48 (m, 2H), 3.10 (br dd, J=14.3, 5.2 Hz, 1H), 1.24-1.33 (m, 1H), 0.73-0.81 (m, 1H), 0.70 (dt, J=8.4, 4.5 Hz, 1H), 0.58 (dt, J=8.2, 4.7 Hz, 1H).

LC/MS (method LC-C): Rt 2.72 min, MH$^+$474

$[α]_D^{20}$: −162.80° (c 0.250, DMF)

Chiral HPLC (method HPLC-B): Rt 9.48 min, chiral purity 100%

Synthesis of Compound 87BA:

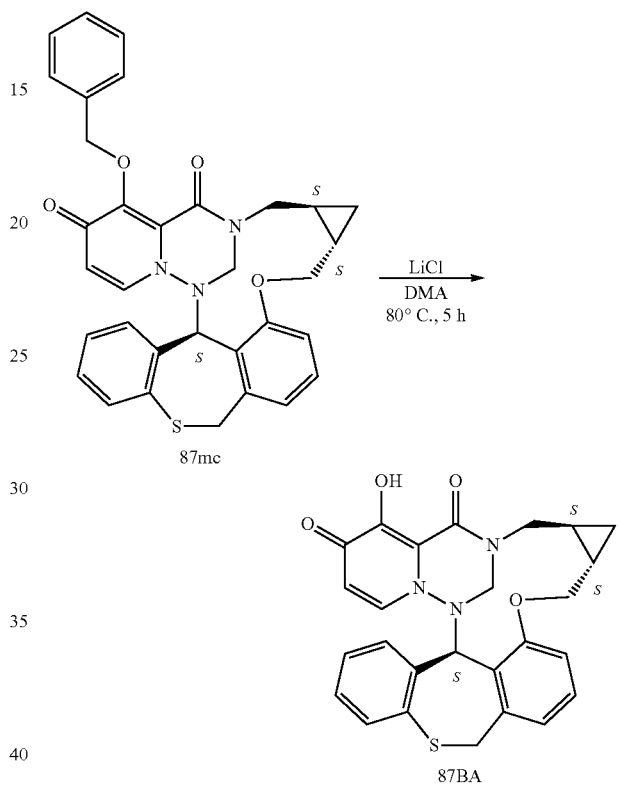

87mc

87BA (1aS,11bS,20aS)-17-hydroxy-1a,2,6,11b,20,20a-hexahydro-1H-5,4-(epiprop[1]en[1]yl[3]ylidene)-12,19-methanobenzo[6,7]thiepino[4,5-c]cyclopropa[k]pyrido[1,2-f][1]oxa[5,6,9]triazacyclotridecine-16,18-dione (compound 87BA, 23 mg) was obtained using the procedure described for compound 28A.

Compound 87BA:

$^1$H NMR (500 MHz, DMSO-d$_6$) δ ppm 11.53 (br s, 1H), 7.45 (d, J=7.9 Hz, 1H), 7.35-7.43 (m, 2H), 7.08-7.17 (m, 2H), 7.01-7.07 (m, 1H), 6.85 (t, J=7.4 Hz, 1H), 6.76 (d, J=7.3 Hz, 1H), 6.18 (s, 1H), 5.93 (d, J=13.2 Hz, 1H), 5.61 (d, J=7.6 Hz, 1H), 5.11 (d, J=13.6 Hz, 1H), 4.91 (dd, J=12.0, 3.2 Hz, 1H), 4.38 (d, J=13.6 Hz, 1H), 4.30 (dd, J=13.6, 2.2 Hz, 1H), 3.85 (d, J=13.6 Hz, 1H), 3.36 (br s, 1H), 2.17 (dd, J=13.6, 11.3 Hz, 1H), 1.24-1.33 (m, 1H), 1.07-1.16 (m, 1H), 0.61 (dt, J=9.1, 4.8 Hz, 1H), 0.42 (dt, J=9.2, 4.7 Hz, 1H).

LC/MS (method LC-C): Rt 2.69 min, MH$^+$474

$[α]_D^{20}$: −315.35° (c 0.241, DMF)

Chiral HPLC (method HPLC-B): Rt 10.12 min, chiral purity 100%

Example 88: Synthesis of (23b*R, Z)-16,17-difluoro-6-hydroxy-10,13,18,23b-tetrahydro-9H-1,8-methano[1]benzothiepino[5,4,3-lm]pyrido[2,1-i][1,7,10,11]benzoxatriazacyclotetradecine-5,7-dione (Compound 88A), (23b*S, Z)-16,17-difluoro-6-hydroxy-10,13,18,23b-tetrahydro-9H-1,8-methano[1]benzothiepino[5,4,3-lm]pyrido[2,1-i][1,7,10,11]benzoxatriazacyclotetradecine-5,7-dione (Compound 88B), (23b*R, E)-16,17-difluoro-6-hydroxy-10,13,18,23b-tetrahydro-9H-1,8-methano[1]benzothiepino[5,4,3-lm]pyrido[2,1-i][1,7,10,11]benzoxatriazacyclotetradecine-5,7-dione (Compound 88C) and (23b*S, E)-16,17-difluoro-6-hydroxy-10,13,18,23b-tetrahydro-9H-1,8-methano[1]benzothiepino[5,4,3-lm]pyrido[2,1-i][1,7,10,11]benzoxatriazacyclotetradecine-5,7-dione (Compound 88D)

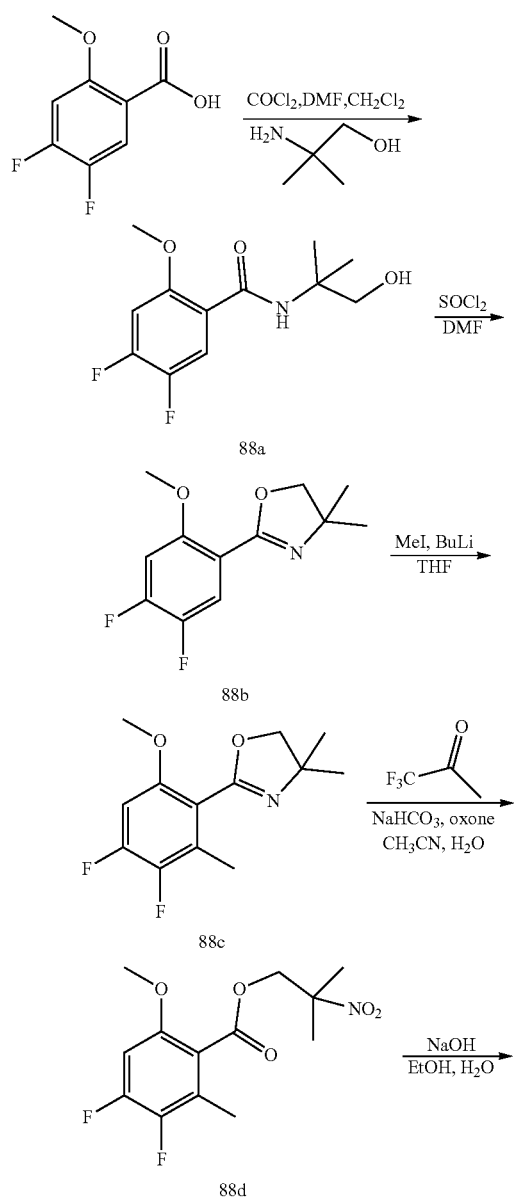

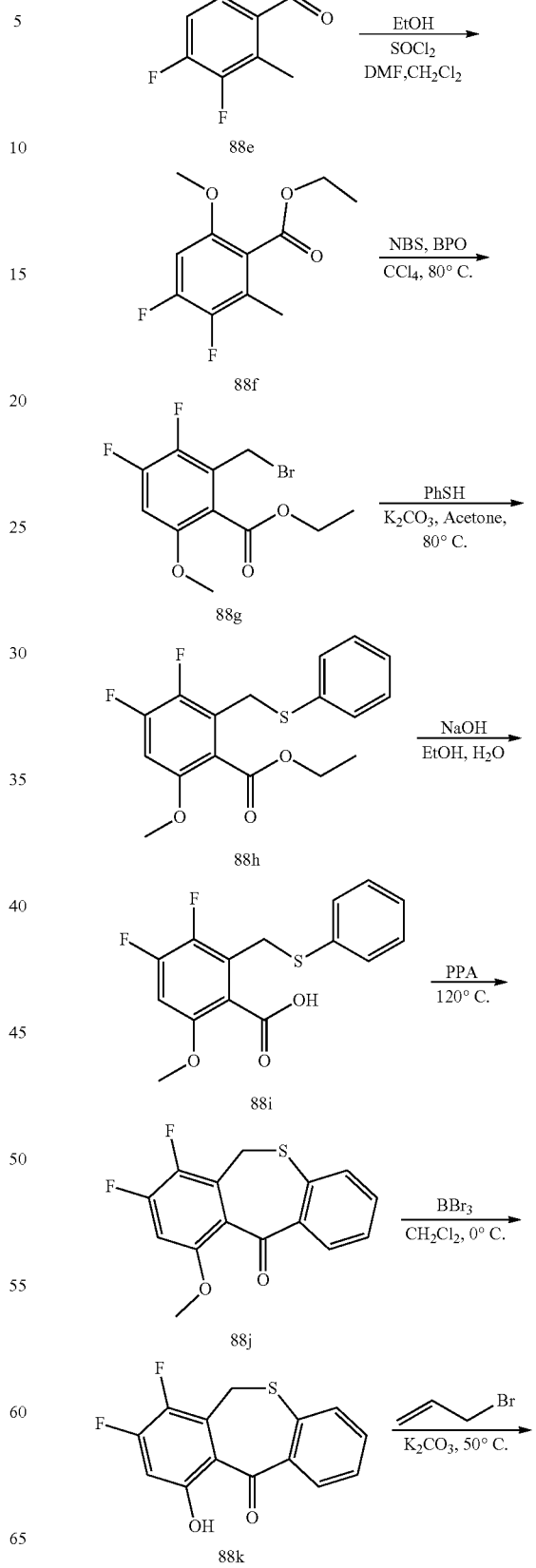

-continued
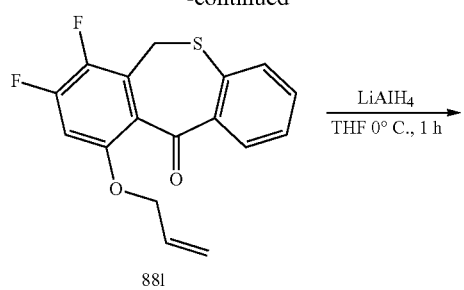
88l
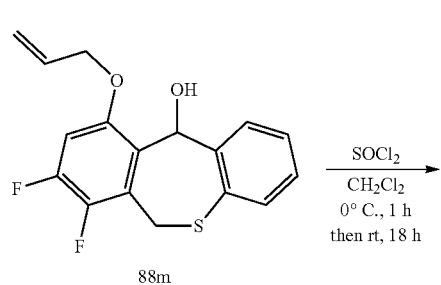
88m
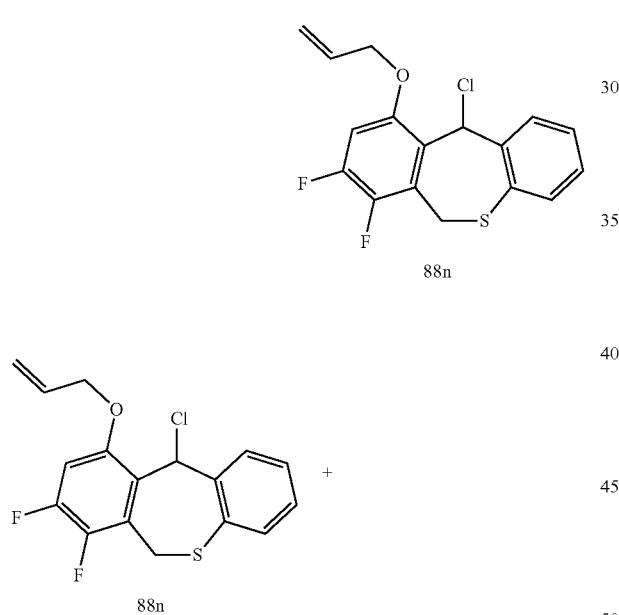
88n
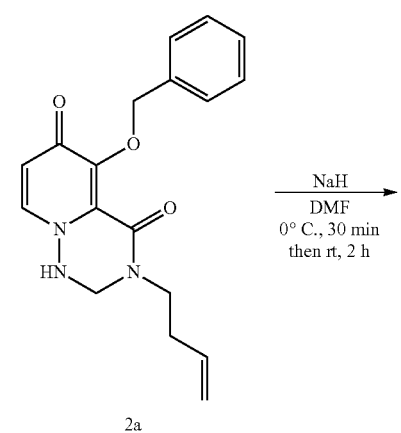
2a
-continued
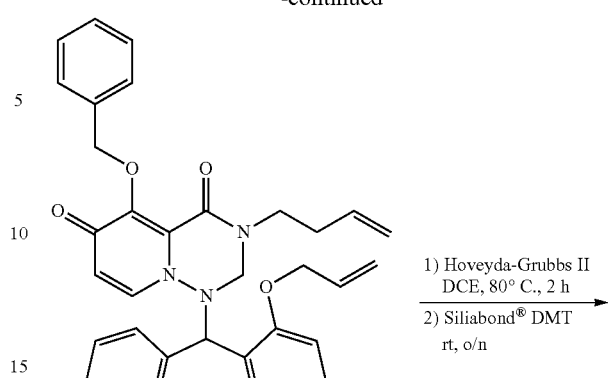
88o
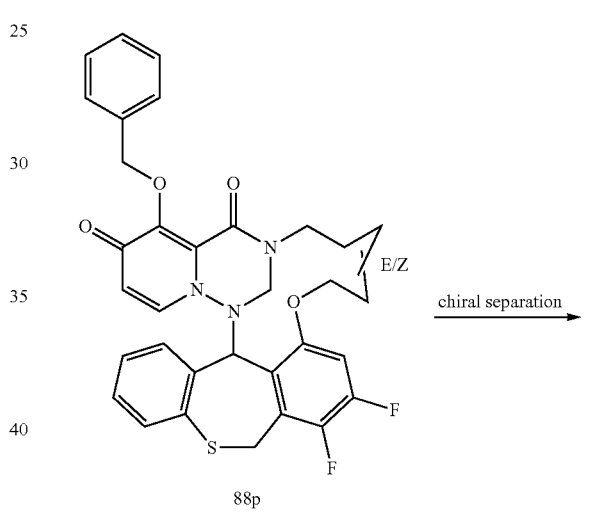
88p
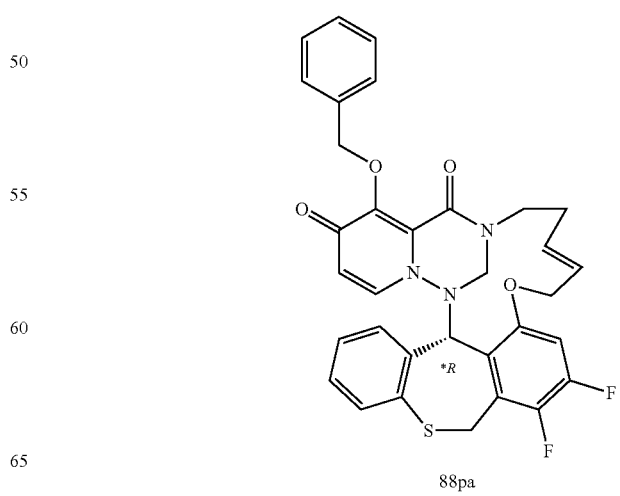
88pa

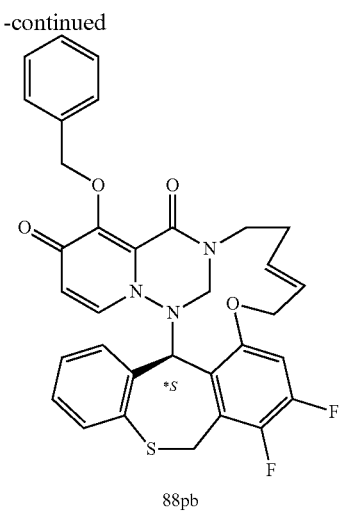

88pb

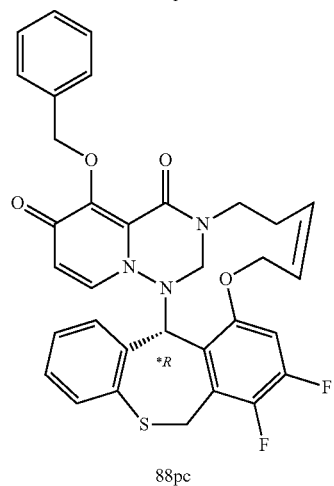

88pc

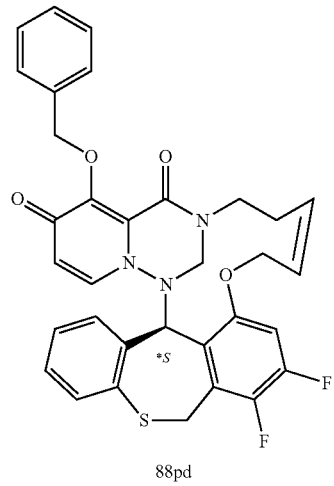

88pd

Synthesis of Intermediate 88a:
To a solution of 4,5-difluoro-2-methoxybenzoic acid [CAS 425702-18-7] (32.05 g, 170.37 mmol) in CH$_2$Cl$_2$ (300 mL) was added DMF (660 µL, 8.52 mmol) and oxalyl chloride (17.6 mL, 204.44 mmol) dropwise at 0° C. The light yellow mixture was stirred at rt for 2h. Then the mixture was concentrated in vacuo. The solution of the residue in CH$_2$Cl$_2$ (150 mL) was added dropwise into a solution of 2-amino-2-methylpropan-1-ol (27.6 mL, 289.6 mmol) in CH$_2$Cl$_2$ (200 mL) at 0° C. The mixture was stirred at rt for 12h. The solids were filtered and the filtrate was washed with water (300 mL), 5% NaHCO$_3$ in H2O (300 mL) and 1M HCl (300 mL). The organic layer was dried over Na$_2$SO$_4$, filtered and concentrated in vacuo to afford 42.7 g of 4,5-difluoro-N-(1-hydroxy-2-methylpropan-2-yl)-2-methoxybenzamide (intermediate 88a) as a white solid, which was used as such in the next step.

Synthesis of Intermediate 88b:
To a solution of intermediate 88a (42.7 g, 164.71 mmol) in CH$_2$Cl$_2$ (500 mL) was added DMF (640 µL, 8.24 mmol) and thionyl chloride (35.8 mL, 494.12 mmol) dropwise at 0° C. The yellow mixture was stirred at rt for 3h. The reaction was concentrated in vacuo and quenched with water (500 mL). pH was adjusted to 8 with 5N aq solution of NaOH and the solution was extracted with CH$_2$Cl$_2$ (3×500 mL). The combined organic layer were washed with brine (300 mL), dried over Na$_2$SO$_4$, filtered and concentrated. The residue was purified by flash chromatography (330 g, eluent petroleum ether/EtOAc (100:0 to 30:70)) to give 2-(4,5-difluoro-2-methoxyphenyl)-4,4-dimethyl-4,5-dihydrooxazole (intermediate 88b, 21 g) as a white solid.

Synthesis of Intermediate 88c:
To a solution of intermediate 88b (10.0 g, 41.5 mmol) in THE (300 mL) was added n-BuLi (19.9 mL, 49.7 mmol) at −78° C. over 15 min under N$_2$. The yellow mixture was stirred at −78° C. for 30 min, then MeI (7.8 mL, 125.1 mmol) was added dropwise at −78° C. over 15 min. The mixture was stirred at −78° C. for 30 min and then warmed-up to rt for 30 min. The reaction mixture was quenched by addition of a saturated solution of NH$_4$Cl in water (300 mL), and extracted with EtOAc twice. The combined organic phase was washed with brine, dried over Na$_2$SO$_4$, filtered and concentrated in vacuo. The residue was purified by flash chromatography (Grace 120 g, eluent petroleum ether/EtOAc (100:0 to 60:40) to give 4.4 g of 2-(3,4-difluoro-6-methoxy-2-methylphenyl)-4,4-dimethyl-4,5-dihydrooxazole (intermediate 88c).

Synthesis of Intermediate 88d:
To a solution of intermediate 88c (14.0 g, 54.85 mmmol) in CH$_3$CN (300 mL) was added 1,1,1-trifluoropropan-2-one (49.2 g, 438.8 mmol) at rt. Then a mixture of NaHCO$_3$ (110.6 g, 1.316 mol) and oxone (134.9 g, 439 mmol) in water (60 mL) was added over 10 min at 0° C. The yellow mixture was stirred at rt for 16h. The reaction mixture was filtered and washed with CH$_2$Cl$_2$ and the organic layer was concentrated in vacuum. The residue was purified by flash chromatography (Grace 220 g, eluent petroleum ether/EtOAc (100:0 to 80:20)) to give 2-methyl-2-nitropropyl 3,4-difluoro-6-methoxy-2-methylbenzoate (intermediate 88d, 13 g).

Synthesis of Intermediate 88e:
To a solution of intermediate 88d (13 g, 42.9 mmol) in EtOH (80 mL) was added water (80 mL) and NaOH (8.6 g, 214.3 mmol) at 0° C. The yellow mixture was stirred at 60° C. for 2h. The reaction mixture was concentrated in vacuo. Water was added to the residue (200 mL) and the solution was extracted with methyl tert-butyl ether (2×100 mL). The aqueous layer was acidified with 6N HCl, extracted with CH$_2$Cl$_2$ (3×20 mL), dried over Na$_2$SO$_4$, filtered and concentrated in vacuo to afford 3,4-difluoro-6-methoxy-2-methylbenzoic acid (intermediate 88e, 8.2 g).

Synthesis of Intermediate 88f:
To a solution of intermediate 88e (7.5 g, 37.10 mmol) in CH$_2$Cl$_2$ (100 mL) was added DMF (144 µL, 1.86 mmol) and SOCl$_2$ (3.2 mL, 44.52 mmol) dropwise at 0° C. The yellow mixture was stirred at rt for 2h. The reaction mixture was concentrated in vacuo. EtOH (30 mL) was added to the residue at 0° C. and and the reaction was stirred for 30 min at rt. The reaction mixture was concentrated and the residue was purified by flash chromatography (Grace 120 g, eluent petroleum ether/EtOAc (100:0 to 90:10) to give ethyl 3,4-difluoro-6-methoxy-2-methylbenzoate (intermediate 88f, 6.9 g) as a colorless oil.

Synthesis of Intermediate 88g:

Benzoyl peroxide (3.16 g, 13.03 mmol) was added to a stirred solution of intermediate 88f (60.0 g, 260.63 mmol) and NBS (51.0 g, 286.70 mmol) in $CCl_4$ (1440 mL) at 25° C. Then the mixture was heated to 80° C. and stirred at reflux for 4 h. A brownish solution was formed. The mixture was poured into water (1000 mL) and extracted with $CH_2Cl_2$ (800 mL×3). The combined organic layer was washed with brine (1000 mL×3), dried with anhydrous $Na_2SO_4$, filtered and concentrated in vacuum to afford ethyl 2-(bromomethyl)-3,4-difluoro-6-methoxybenzoate (intermediate 88g, 60.0 g, crude) as a yellow oil. The compound was used as such in the next step.

Synthesis of Intermediate 88h:

Intermediate 88g (60.0 g, 194.11 mmol) was dissolved in acetone (840 mL). $K_2CO_3$ (40.24 g, 291.16 mmol) and benzenethiol (32.5 g, 294.98 mmol, 30.09 mL, 1.52 eq) was added and the mixture was stirred at 80° C. for 4 hours. A brownish mixture was formed. The mixture was filtered and concentrated in vacuum to give a brown solid. Crude product was triturated with MTBE (150 mL) and filtered. The residue was dried in vacuum to give ethyl 3,4-difluoro-6-methoxy-2-((phenylthio)methyl)benzoate (intermediate 88h, 60.0 g, 163.14 mmol) as a brown solid.

Synthesis of Intermediate 88i:

To a solution of intermediate 88h (55.0 g, 162.54 mmol) in EtOH (1050 mL) was added NaOH (2 M, 406.36 mL) at 25° C. The solution was heated at 80° C. and stirred at reflux for 4 hours. A brown solution was formed. The solution was concentrated in vacuum, then water (300 mL) was added and the mixture was made acidic (pH=2) with diluted 2N hydrochloric acid and extracted with ethyl acetate (300 mL×3). The combined organic phase was washed with brine (300 mL×3), dried with anhydrous $Na_2SO_4$, filtered and concentrated in vacuum to afford 3,4-difluoro-6-methoxy-2-((phenylthio)methyl)benzoic acid (intermediate 88i, 50.0 g, crude) as a brown oil.

Synthesis of Intermediate 88j:

Intermediate 88i (10.0 g, 32.23 mmol, 1 eq) was added in polyphosphoric acid (150.0 g, 443.88 mmol, 13.77 eq) at 25° C. The mixture was stirred for 4 hours at 120° C. A dark red solution was formed. The residue was poured into ice-water (500 mL) and stirred. The aqueous phase was extracted with ethyl acetate (500 mL×3). The combined organic phase was washed with brine (500 mL×3), dried over anhydrous $Na_2SO_4$, filtered and concentrated in vacuum. The crude product was triturated with MTBE (150 mL) and filtered. The residue was dried in vacuum to afford 7,8-difluoro-10-methoxydibenzo[b,e]thiepin-11(6H)-one (intermediate 88j, 30.0 g) as a brown solid.

Synthesis of Intermediate 88k:

To a mixture of intermediate 88j (13.1 g, 44.82 mmol, 1 eq) in $CH_2Cl_2$ (180 mL), a solution of $BBr_3$ (1 M, 95.27 mL, 2.13 eq) in $CH_2Cl_2$ (100 mL) was added dropwise at 0° C. The mixture was stirred at 25° C. for 2 hours. A brown solution was formed. An aqueous saturated sodium chloride solution was added, and the mixture was extracted with $CH_2Cl_2$ (200 mL×3). Organic layer was washed with brine (200 mL×3), dried over anhydrous $Na_2SO_4$, filtered and concentrated in vacuum to afford 7,8-difluoro-10-hydroxydibenzo[b,e]thiepin-11(6H)-one (intermediate 88k, 11.4 g) as a brown solid.

Synthesis of Intermediate 88l:

10-(allyloxy)-7,8-difluorodibenzo[b,e]thiepin-11(6H)-one (intermediate 88l, 11.8 g) was obtained using the procedure described for intermediate 37a.

Synthesis of Intermediate 88m:

10-(allyloxy)-7,8-difluoro-6,11-dihydrodibenzo[b,e]thiepin-11-ol (intermediate 88m, 11.2 g) was obtained using the procedure described for intermediate 37b. Crude intermediate 88m was purified by flash chromatography over silica gel (Petroleum ether/Ethyl acetate 20/1 to 5:1).

Synthesis of Intermediate 88n:

10-(allyloxy)-11-chloro-7,8-difluoro-6,11-dihydrodibenzo[b,e]thiepine (intermediate 88n, 680 mg) was obtained using the procedure described for intermediate 37c.

Synthesis of Intermediate 88o:

1-(10-(allyloxy)-7,8-difluoro-6,11-dihydrodibenzo[b,e]thiepin-11-yl)-5-(benzyloxy)-3-(but-3-en-1-yl)-2,3-dihydro-1H-pyrido[2,1-f][1,2,4]triazine-4,6-dione (intermediate 88o, 304 mg) was obtained using the procedure described for intermediate 37d.

Synthesis of Intermediate 88p:

(Z/E)-6-(benzyloxy)-16,17-difluoro-10,13,18,23b-tetrahydro-9H-1,8-methano[1]benzothiepino[5,4,3-lm]pyrido[2,1-i][1,7,10,11]benzoxatriazacyclotetradecine-5,7-dione (intermediate 88p, mixture of Z and E isomers, 144 mg) was obtained using the procedure described for intermediates 37e and 37f.

The isomers were separated via reverse phase (Stationary phase: YMC-actus Triart C18 10 μm 30*300 mm, mobile phase gradient: 0.2% aq.$NH_4HCO_3$/MeCN from 50/50 to 30/70) to afford a fraction containing the E isomers (intermediates 88pa and 88pb, 33 mg) and a second fractions of Z isomers (intermediates 88pc and 88pd, 89 mg).

The enantiomers 88pa and 88pb were separated via chiral SFC (Stationary phase: Whelk-O1 (S,S) 5 μm 250*21.2 mm, Mobile phase: 50% $CO_2$, 50% MeOH) to give the first eluted enantiomer 88pa (24 mg) and the second eluted enantiomer 88pb (29 mg).

The enantiomers 88pc and 88pd were separated via chiral SFC (Stationary phase: CHIRALPAK AS-H 5 μm 250*20 mm, Mobile phase: 45% $CO_2$, 55% MeOH) to give the first eluted enantiomer 88pc (62 mg) and the second eluted enantiomer 88pd (63 mg).

Synthesis of Compound 88A:

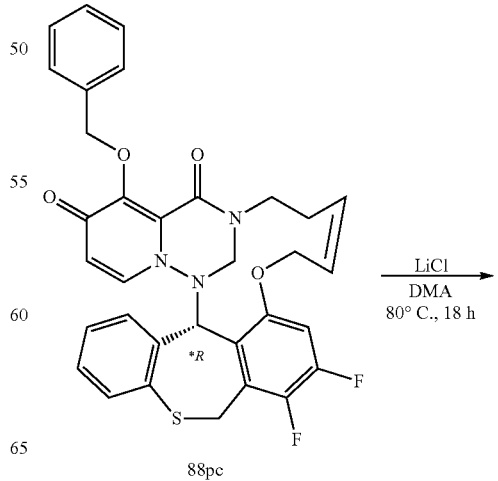

88pc

299

-continued

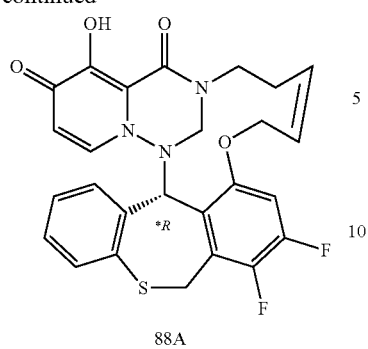

88A (23b*R, Z)-16,17-difluoro-6-hydroxy-10,13,18,23b-tetrahydro-9H-1,8-methano[1]benzothiepino[5,4,3-lm]pyrido[2,1-i][1,7,10,11]benzoxatriazacyclotetradecine-5,7-dione (compound 88A, 32 mg) was obtained using the procedure described for compound 37A.

Compound 88A:

$^1$H NMR (500 MHz, DMSO-d$_6$) δ ppm 11.70 (br s, 1H), 7.23 (br dd, J=12.1, 6.8 Hz, 1H), 7.14 (d, J=7.6 Hz, 1H), 6.99-7.10 (m, 2H), 6.77 (t, J=7.3 Hz, 1H), 6.51 (d, J=7.6 Hz, 1H), 5.96-6.03 (m, 1H), 5.88-5.95 (m, 2H), 5.54 (dd, J=14.3, 1.4 Hz, 1H), 5.49 (d, J=7.9 Hz, 1H), 4.86 (br d, J=13.6 Hz, 1H), 4.41-4.49 (m, 2H), 4.37 (d, J=13.2 Hz, 1H), 4.18 (br t, J=12.5 Hz, 1H), 4.00 (d, J=14.2 Hz, 1H), 2.74 (br d, J=14.2 Hz, 1H), 2.20-2.27 (m, 1H), 2.11 (br d, J=14.8 Hz, 1H).

LC/MS (method LC-C): Rt 2.96 min, MH$^+$510

$[α]_D^{20}$: +180.18° (c 0.111, DMF)

Chiral HPLC (method HPLC-B): Rt 5.72 min, chiral purity 100%

Synthesis of Compound 88B:

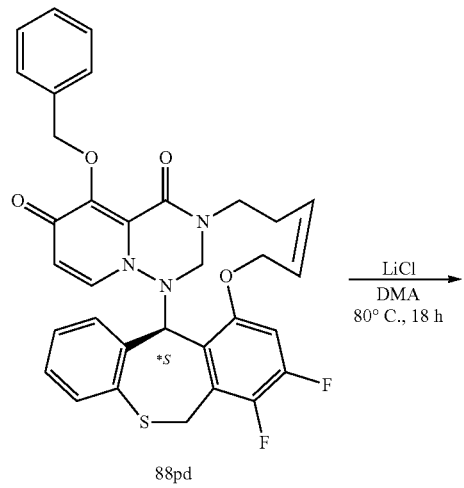

88pd

300

-continued

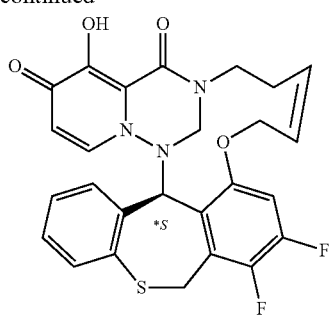

88B (23b*S, Z)-16,17-difluoro-6-hydroxy-10,13,18,23b-tetrahydro-9H-1,8-methano[1]benzothiepino[5,4,3-/m]pyrido[2,1-i][1,7,10,11]benzoxatriazacyclotetradecine-5,7-dione (compound 88B, 30 mg) was obtained using the procedure described for compound 37A.

Compound 88B:

$^1$H NMR (500 MHz, DMSO-d$_6$) δ ppm 11.75 (br s, 1H), 7.30 (dd, J=12.1, 6.8 Hz, 1H), 7.20 (d, J=7.6 Hz, 1H), 7.07-7.17 (m, 2H), 6.84 (td, J=7.6, 1.0 Hz, 1H), 6.58 (d, J=7.3 Hz, 1H), 6.03-6.09 (m, 1H), 5.95-6.02 (m, 2H), 5.61 (dd, J=14.2, 1.9 Hz, 1H), 5.56 (d, J=7.6 Hz, 1H), 4.93 (d, J=13.2 Hz, 1H), 4.48-4.56 (m, 2H), 4.44 (d, J=13.2 Hz, 1H), 4.25 (br t, J=13.1 Hz, 1H), 4.06 (d, J=13.9 Hz, 1H), 2.81 (br d, J=14.2 Hz, 1H), 2.26-2.34 (m, 1H), 2.14-2.22 (m, 1H).

LC/MS (method LC-C): Rt 2.96 min, MH$^+$510

$[α]_D^{20}$: −176.99° (c 0.113, DMF)

Chiral HPLC (method HPLC-B): Rt 11.47 min. chiral purity 100%

Synthesis of Compound 88C:

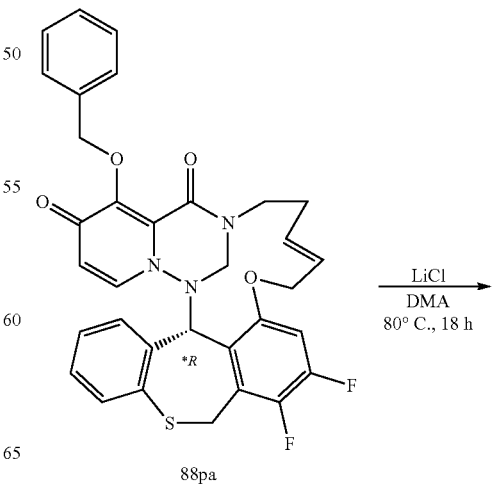

88pa

-continued

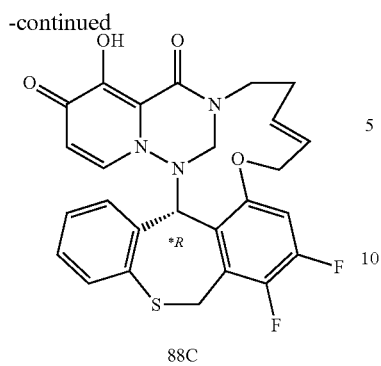

88C (23b*R, E)-16,17-difluoro-6-hydroxy-10,13,18,23b-tetrahydro-9H-1,8-methano[1]benzothiepino[5,4,3-/m]pyrido[2,1-i][1,7,10,11]benzoxatriazacyclotetradecine-5,7-dione (compound 88C, 9 mg) was obtained using the procedure described for compound 37A.

Compound 88C:

$^1$H NMR (500 MHz, DMSO-d$_6$) δ ppm 11.92 (br s, 1H), 7.48 (dd, J=12.0, 7.3 Hz, 1H), 7.17 (d, J=7.6 Hz, 1H), 7.12-7.15 (m, 1H), 7.06-7.09 (m, 1H), 6.86-6.91 (m, 1H), 6.82-6.85 (m, 1H), 5.91 (br ddd, J=15.1, 9.6, 5.5 Hz, 1H), 5.79 (s, 1H), 5.58-5.65 (m, 1H), 5.50-5.56 (m, 2H), 4.98 (d, J=13.2 Hz, 1H), 4.72 (dd, J=11.8, 5.5 Hz, 1H), 4.48 (dd, J=11.5, 9.9 Hz, 1H), 4.28 (d, J=13.2 Hz, 1H), 4.10 (d, J=13.9 Hz, 1H), 3.80 (br dd, J=8.8, 3.8 Hz, 1H), 2.78-2.85 (m, 2H), 2.18-2.25 (m, 1H).

LC/MS (method LC-C): Rt 2.94 min, MH$^+$510

$[α]_D^{20}$: +295.05° (c 0.101, DMF)

Chiral HPLC (method HPLC-B): Rt 5.78 min, chiral purity 100%

Synthesis of Compound 88D:

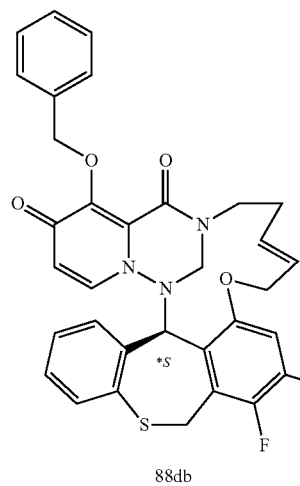

88db

-continued

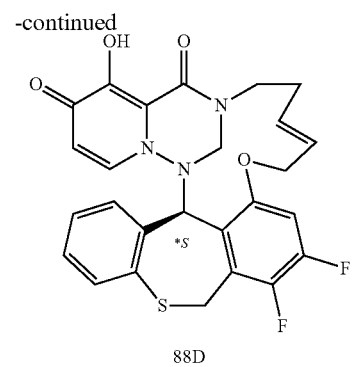

88D (23b*S, E)-16,17-difluoro-6-hydroxy-10,13,18,23b-tetrahydro-9H-1,8-methano[1]benzothiepino[5,4,3-/m]pyrido[2,1-i][1,7,10,11]benzoxatriazacyclotetradecine-5,7-dione (compound 88D, 9 mg) was obtained using the procedure described for compound 37A.

Compound 88D:

$^1$H NMR (500 MHz, DMSO-d$_6$) δ ppm 11.92 (br s, 1H), 7.48 (dd, J=12.1, 7.1 Hz, 1H), 7.12-7.19 (m, 2H), 7.05-7.10 (m, 1H), 6.86-6.91 (m, 1H), 6.82-6.86 (m, 1H), 5.91 (br ddd, J=15.3, 9.6, 5.7 Hz, 1H), 5.79 (s, 1H), 5.58-5.66 (m, 1H), 5.50-5.56 (m, 2H), 4.97 (d, J=12.9 Hz, 1H), 4.72 (dd, J=11.8, 5.5 Hz, 1H), 4.48 (dd, J=11.7, 10.1 Hz, 1H), 4.28 (d, J=13.2 Hz, 1H), 4.10 (d, J=13.9 Hz, 1H), 3.80 (br dd, J=9.0, 3.9 Hz, 1H), 2.75-2.86 (m, 2H), 2.18-2.26 (m, 1H).

LC/MS (method LC-C): Rt 2.94 min, MH$^+$510

$[α]_D^{20}$: −285.45° (c 0.110, DMF)

Chiral HPLC (method HPLC-B): Rt 8.21 min, chiral purity 100%

Example 89: Synthesis of (9*S,18*R,E)-9-ethyl-3-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 89AA), (9*R,18*S,E)-9-ethyl-3-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 89BB)

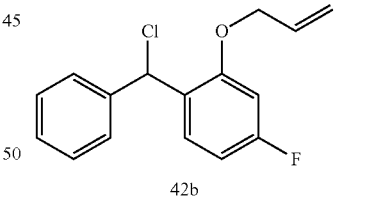

42b

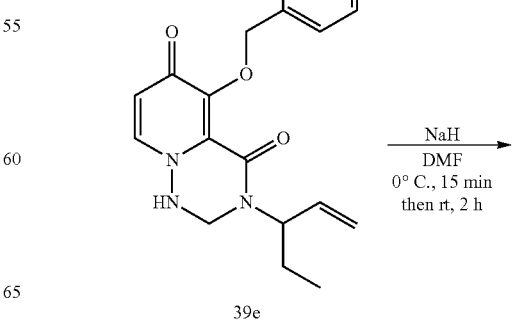

39e

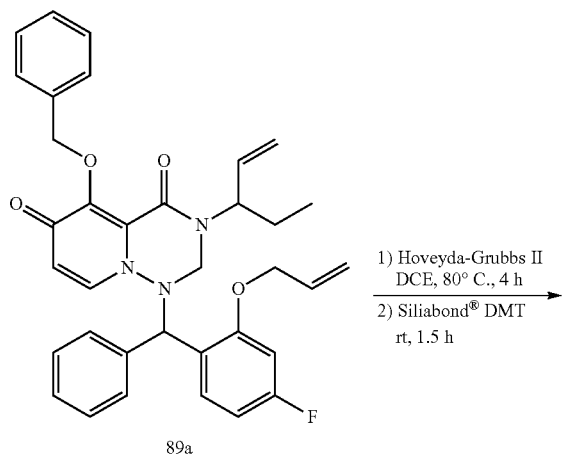

89a

1) Hoveyda-Grubbs II
DCE, 80° C., 4 h
2) Siliabond® DMT
rt, 1.5 h

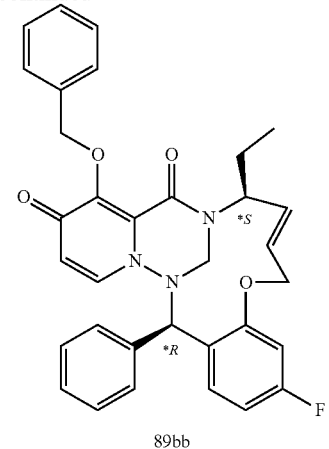 [SMILES: CC[C@H]1/C=C/COc2cc(F)ccc2[C@H](c2ccccc2)N2CN1C(=O)c1c(OCc3ccccc3)c(=O)ccn12]

89bb

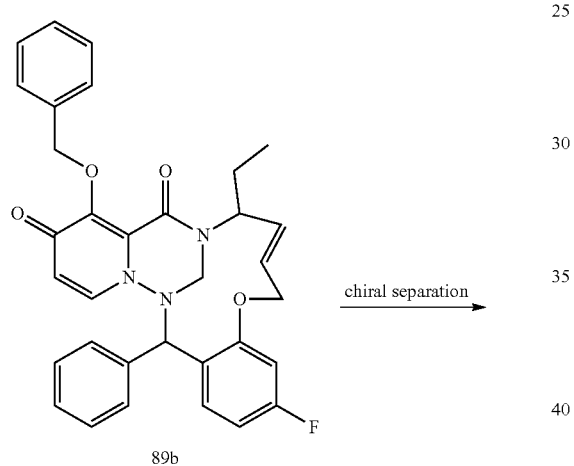

89b chiral separation

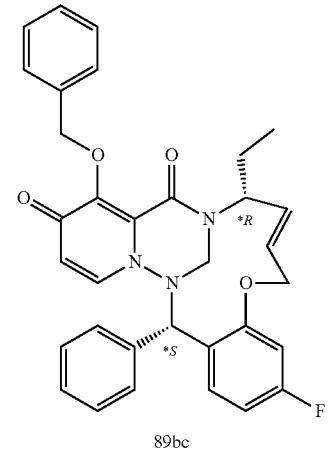

89bc

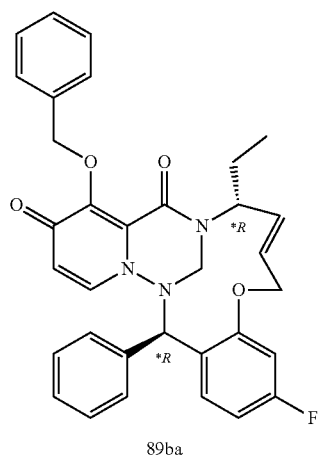

89ba

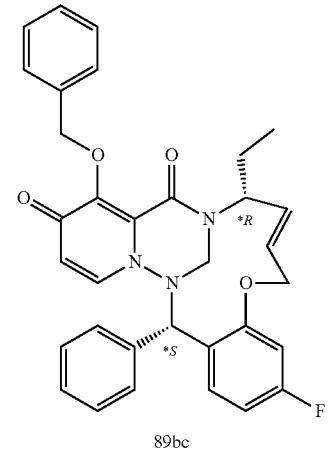

89bd

Synthesis of Intermediate 89a 1-((2-(allyloxy)-4-fluorophenyl)(phenyl)methyl)-5-(benzyloxy)-3-(pent-1-en-3-yl)-2,3-dihydro-1H-pyrido[2,1-f][1,2,4]triazine-4,6-dione (intermediate 89a, 1.08 mg) was obtained using the procedure described for intermediate 85a. Purification was carried out by flash chromatography over silica gel (80 g, $CH_2Cl_2$/MeOH from 100/0 to 95/5). A second purification was performed by flash chromatography over silica gel (40 g, petroleum ether/EtOAc from 100/0 to 0/100).

Synthesis of Intermediate 89b (E)-12-(benzyloxy)-9-ethyl-3-fluoro-18-phenyl-6,9-dihydro-18H-10,17-methanobenzo[b]pyrido[1,2-f][1]oxa[5,6, 9]triazacyclotridecine-11,13-dione (intermediate 89b, 380 mg) was obtained using the procedure described for intermediate 1f.

The residue was purified via achiral SFC (Stationary phase: AMINO 5 μm 150*30 mm, Mobile phase: 85% $CO_2$, 15% MeOH) to afford two fractions of intermediate 89b (fraction a: intermediates 89bb and 89bc, 247 mg; fraction b: intermediates 89ba and 89bd, 111 mg).

The enantiomers 89bb and 89bc were separated via chiral SFC (Stationary phase: CHIRALPAK IC 5 μm 250*30 mm, Mobile phase: 50% $CO_2$, 50% MeOH) to afford 89bb (90 mg) and 89bc (95 mg). The enantiomers 89ba and 89bd were separated via chiral SFC (Stationary phase: Chiralpak IC 5 μm 250*21.2 mm, Mobile phase: 50% $CO_2$, 50% MeOH) to afford 89ba (22 mg) and 89bd (34 mg).

Synthesis of Compound 89AA:

Synthesis of Compound 89BB:

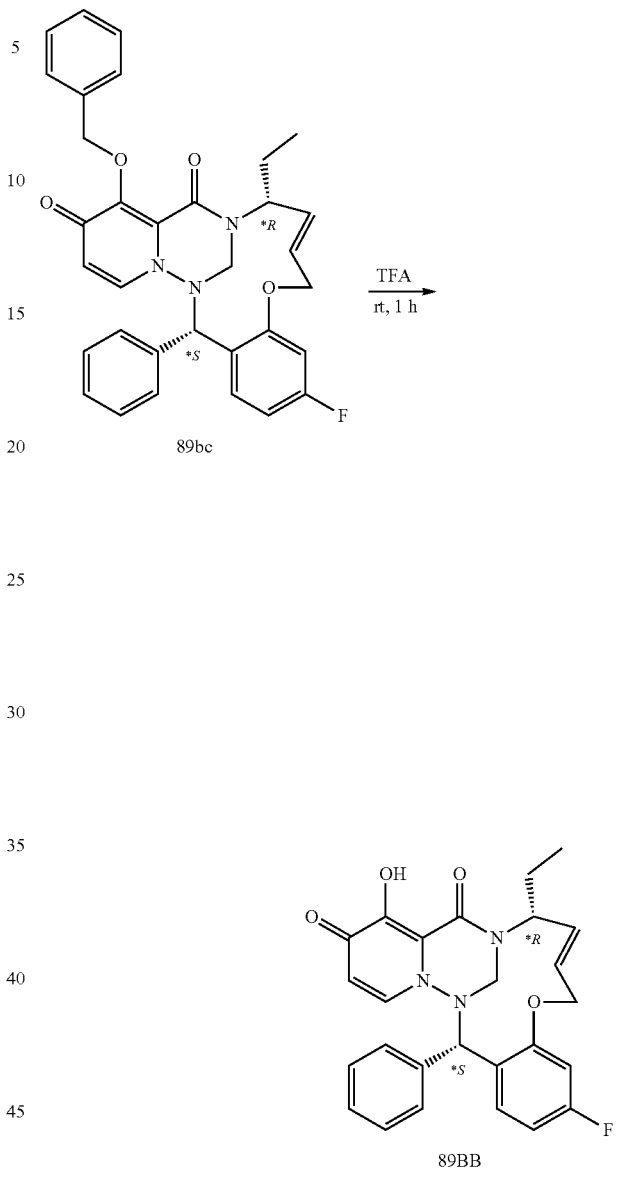

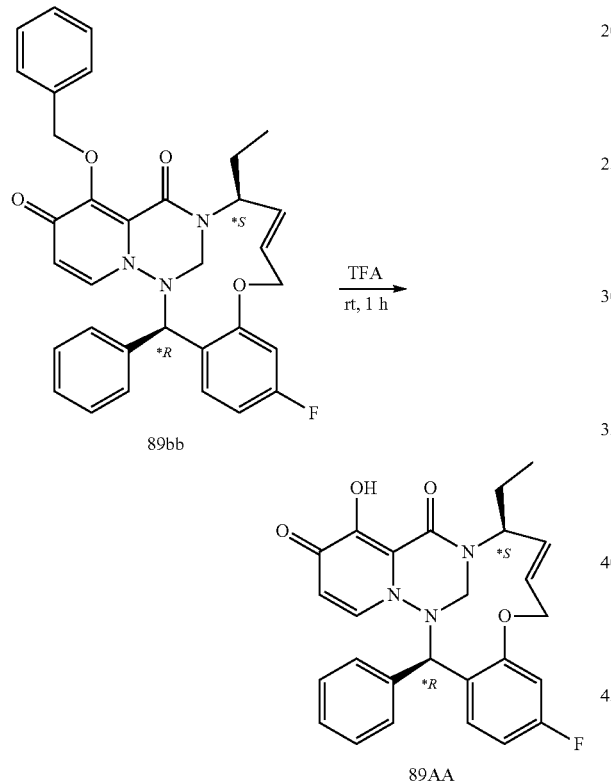

(9*S,18*R,E)-9-ethyl-3-fluoro-12-hydroxy-18-phenyl-6,9-dihydro-18H-10,17-methanobenzo[b]pyrido[1,2-f][1]oxa[5,6,9]triazacyclotridecine-11,13-dione (compound 89AA, 42 mg) was obtained using the procedure described for compound 1.

Compound 89AA:

$^1$H NMR (500 MHz, DMSO-$d_6$) δ ppm 8.05 (dd, J=8.5, 6.9 Hz, 1H), 7.00-7.19 (m, 8H), 6.23 (br ddd, J=15.7, 9.9, 5.4 Hz, 1H), 5.38-5.46 (m, 1H), 5.40 (d, J=7.6 Hz, 1H), 5.10 (s, 1H), 5.05-5.12 (m, 1H), 4.94 (d, J=13.6 Hz, 1H), 4.79 (dd, J=11.5, 5.5 Hz, 1H), 4.06-4.15 (m, 2H), 1.42-1.51 (m, 1H), 1.32-1.42 (m, 1H), 0.75 (t, J=7.4 Hz, 3H).

LC/MS (method LC-C): Rt 2.89 min, MH$^+$462

$[α]_D^{20}$: +553.46° (c 0.260, DMF)

Chiral HPLC (method HPLC-B): Rt 5.32 min. chiral purity 100%

(9*R,18*S E)-9-ethyl-3-fluoro-12-hydroxy-18-phenyl-6,9-dihydro-18H-10,17-methanobenzo[b]pyrido[1,2-f][1]oxa[5,6,9]triazacyclotridecine-11,13-dione (compound 89BB, 38 mg) was obtained using the procedure described for compound 1.

Compound 89BB:

$^1$H NMR (500 MHz, DMSO-$d_6$) δ ppm 8.05 (dd, J=8.5, 6.9 Hz, 1H), 6.99-7.21 (m, 8H), 6.23 (br ddd, J=15.5, 9.9, 5.5 Hz, 1H), 5.40 (d, J=7.6 Hz, 1H), 5.36-5.46 (m, 1H), 5.10 (s, 1H), 5.04-5.13 (m, 1H), 4.94 (d, J=13.6 Hz, 1H), 4.79 (dd, J=11.5, 5.5 Hz, 1H), 4.05-4.16 (m, 2H), 1.42-1.51 (m, 1H), 1.32-1.41 (m, 1H), 0.75 (t, J=7.3 Hz, 3H).

LC/MS (method LC-C): Rt 2.89 min, MH$^+$462

$[α]_D^{20}$: −532.62° (c 0.282, DMF)

Chiral HPLC (method HPLC-B): Rt 6.95 min, chiral purity 100%

Example 91: Synthesis of (18R,19R,E)-4-fluoro-12-hydroxy-19-methyl-18-phenyl-6,9-dihydro-18H-10,17-methanobenzo[b]pyrido[1,2-f][1]oxa[5,6,9]triazacyclotridecine-11,13-dione (Compound 91A), (18S,19S,E)-4-fluoro-12-hydroxy-19-methyl-18-phenyl-6,9-dihydro-18H-10,17-methanobenzo[b]pyrido[1,2-f][1]oxa[5,6,9]triazacyclotridecine-11,13-dione (Compound 91B)
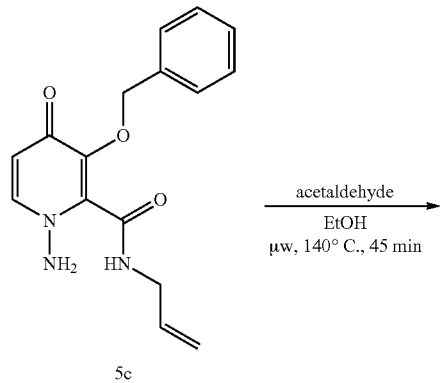
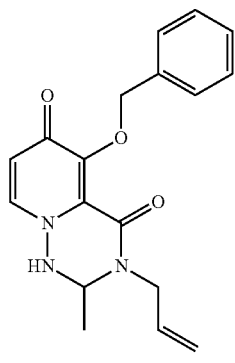
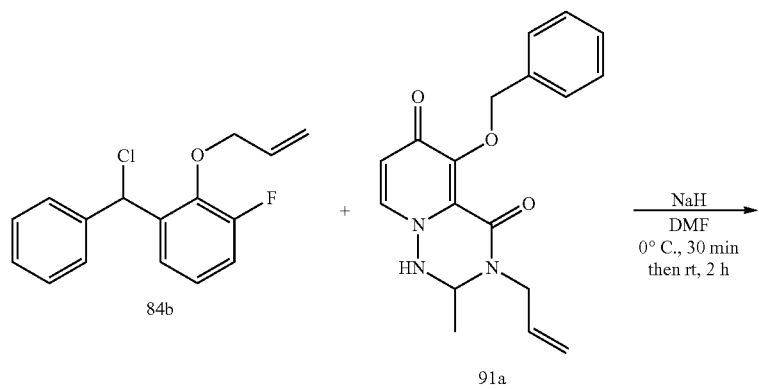

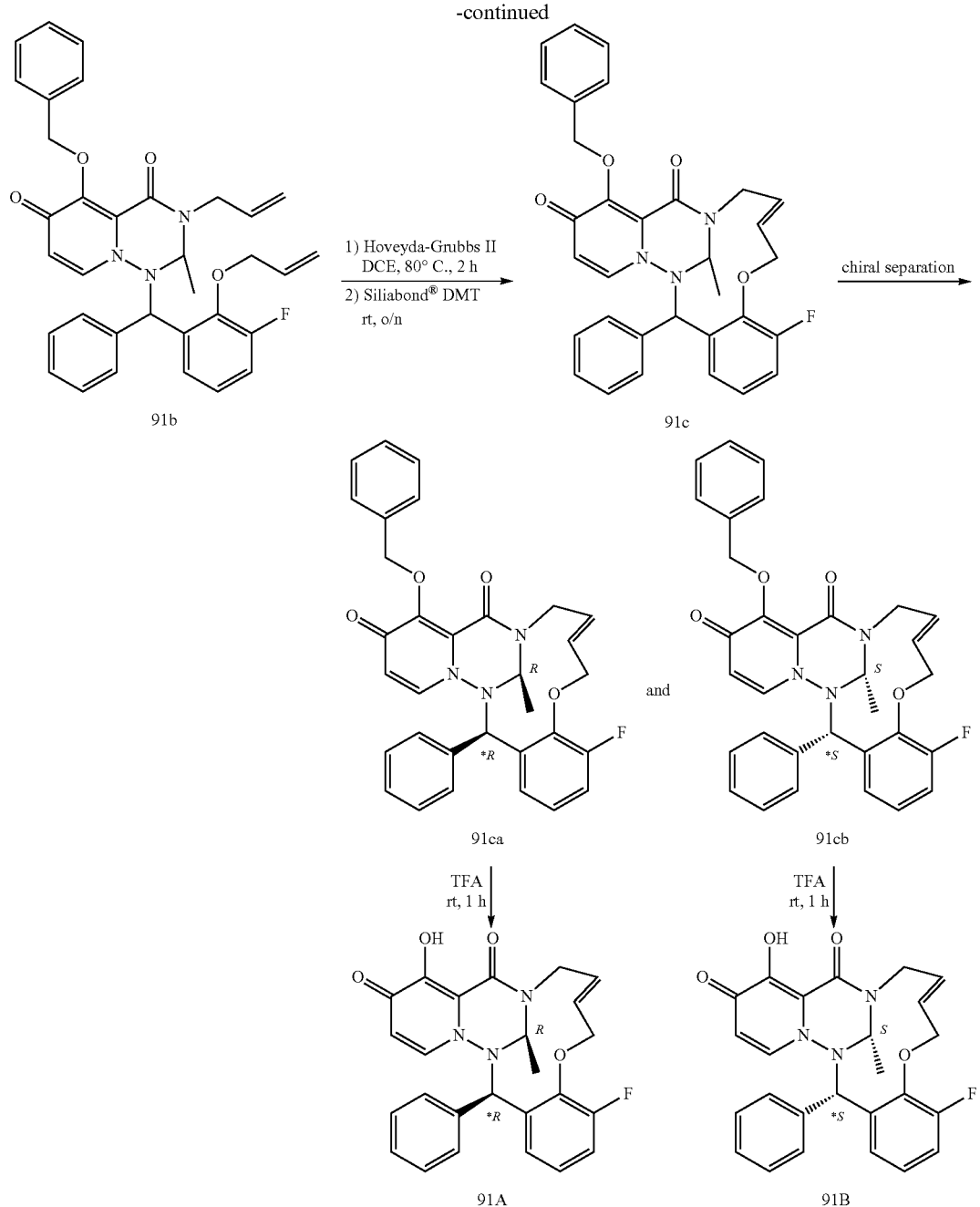

Synthesis of Intermediate 91a:

In a microwave a mixture of intermediate 5c (1.00 g, 3.34 mmol) and acetaldehyde [CAS 75-07-0] (200 µL, 3.56 mmol) in EtOH (15 mL) was stirred at 140° C. using a single mode microwave (Biotage® Initiator EXP 60) with a power output ranging from 0 to 400 W for 45 min. The mixture was concentrated under vacuum. Purification was carried out by flash chromatography over silica gel (30 µm, 24 g, $CH_2Cl_2$/MeOH 97/3 to 94/6) to give 3-allyl-5-(benzyloxy)-2-methyl-2,3-dihydro-1H-pyrido[2,1-f][1,2,4]triazine-4,6-dione (intermediate 91a, 935 mg).

Synthesis of Intermediate 91b:

3-allyl-1-((2-(allyloxy)-3-fluorophenyl)(phenyl)methyl)-5-(benzyloxy)-2-methyl-2,3-dihydro-1H-pyrido[2,1-f][1,2,4]triazine-4,6-dione (intermediate 91b, 1.20 g) was obtained using the procedure described for intermediate 2d.

Synthesis of Intermediate 91c:

(E)-12-(benzyloxy)-4-fluoro-19-methyl-18-phenyl-6,9-dihydro-18H-10,17-methanobenzo[b]pyrido[1,2-f][1]oxa[5,6,9]triazacyclotridecine-11,13-dione (intermediate 91c, 1.22 g) was obtained using the procedure described for intermediate 1f. Crude intermediate 91c was purified by flash chromatography over silica gel (30 µm, 40 g, $CH_2Cl_2$/MeOH from 97/3 to 95/5). A second purification was performed via reverse phase (Stationary phase: YMC-actus Triart C18 10 µm 30*150 mm, mobile phase gradient: 0.2% aq. $NH_4HCO_3$/$CH_3CN$ from 50/50 to 30/70) to afford intermediate 91c (344 mg).

The enantiomers were separated via chiral SFC (Stationary phase: CHIRALPAK AD-H 5 μm 250*30 mm, Mobile phase: 60% CO$_2$, 40% EtOH) to give the first eluted enantiomer 91ca (154 mg) and the second eluted enantiomer 91cb (159 mg).

Synthesis of Compound 91A:
(18*R,19*R,E)-4-fluoro-12-hydroxy-19-methyl-18-phenyl-6,9-dihydro-18H-10,17-methanobenzo[b]pyrido[1,2-f][1]oxa[5,6,9]triazacyclotridecine-11,13-dione (compound 91A, 81 mg) was obtained using the procedure described for compound 1.
Compound 91A:
$^1$H NMR (500 MHz, DMSO-d$_6$, 77° C.) δ ppm 7.87 (d, J=7.9 Hz, 1H), 7.37 (td, J=8.0, 5.5 Hz, 1H), 7.25-7.32 (m, 1H), 7.10-7.21 (m, 6H), 6.23 (dt, J=15.6, 7.6 Hz, 1H), 5.92-6.00 (m, 1H), 5.51 (d, J=7.6 Hz, 1H), 5.25 (s, 1H), 4.75-4.86 (m, 2H), 4.52 (q, J=6.3 Hz, 1H), 4.24 (br dd, J=10.7, 9.1 Hz, 1H), 3.25 (dd, J=13.9, 8.2 Hz, 1H), 1.34 (d, J=6.3 Hz, 3H).
LC/MS (method LC-C): Rt 2.66 min, MH$^+$448
$[α]_D^{20}$: -643.42° (c 0.152, DMF)

Synthesis of compound 91B:
(18*S,19*S,E)-4-fluoro-12-hydroxy-19-methyl-18-phenyl-6,9-dihydro-18H-10,17-methanobenzo[b]pyrido[1,2-f][1]oxa[5,6,9]triazacyclotridecine-11,13-dione (compound 91B, 16 mg) was obtained using the procedure described for compound 1.
Compound 91B:
$^1$H NMR (500 MHz, DMSO-d$_6$) δ ppm 7.90 (br d, J=7.6 Hz, 1H), 7.40 (br td, J=8.0, 5.4 Hz, 1H), 7.31-7.37 (m, 1H), 7.26 (br d, J=7.6 Hz, 1H), 7.07-7.22 (m, 5H), 6.22 (br s, 1H), 5.98 (br s, 1H), 5.53 (d, J=7.6 Hz, 1H), 5.21 (br s, 1H), 4.79 (br dd, J=13.7, 4.3 Hz, 2H), 4.52 (q, J=6.3 Hz, 1H), 4.24 (br s, 1H), 3.24-3.30 (m, 1H), 1.33 (d, J=6.3 Hz, 3H).
LC/MS (method LC-C): Rt 2.66 min, MH$^+$448
$[α]_D^{20}$: +626.43° (c 0.140, DMF)

Example 92: Synthesis of (13S,21aR,Z)-13-ethyl-16-hydroxy-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (Compound 92AA), (13R,21aS,Z)-13-ethyl-16-hydroxy-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (Compound 92BB), (9R,17aR,E)-9-ethyl-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 92AB) and (9S,17aS,E)-9-ethyl-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 92BA)

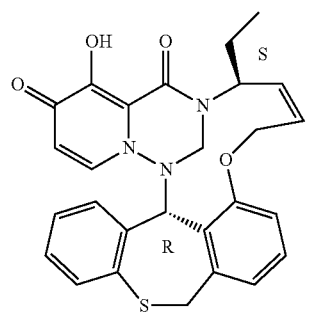
92AA

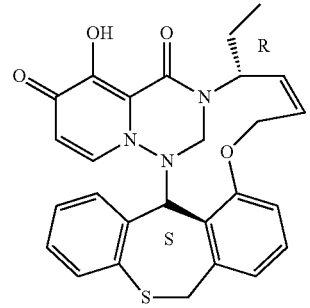
92BB

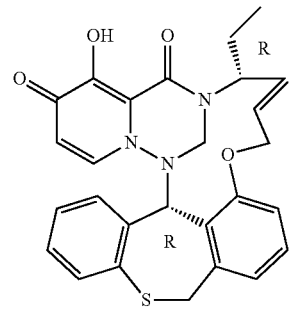
92AB

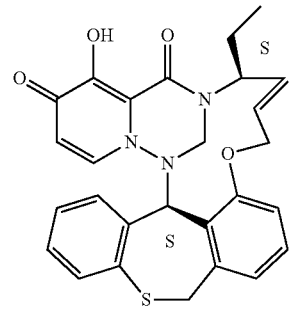
92BA

Compounds 92AA, 92BB, 92AB and 92BA were synthesized according to the procedures described in example 89 starting from intermediates 37c and 39e.

Compound 92AA:
LC/MS (method LC-C): Rt 3.01 min, MH$^+$488.3
$[α]_D^{20}$: +148.4° (c 0.128, DMF)
Chiral HPLC (method HPLC-B): Rt 3.83 min, chiral purity 100%

Compound 92BB:
$^1$H NMR (500 MHz, DMSO-d$_6$) δ ppm 10.88-12.18 (m, 1H) 7.41 (t, J=7.9 Hz, 1H) 7.20 (d, J=7.9 Hz, 1H) 7.04-7.16 (m, 4H) 6.74-6.85 (m, 1H) 6.53 (d, J=7.3 Hz, 1H) 6.42-6.51 (m, 1H) 6.24 (dt, J=10.6, 7.0 Hz, 1H) 6.07 (s, 1H) 5.71 (d, J=13.6 Hz, 1H) 5.60 (d, J=7.6 Hz, 1H) 5.17 (d, J=13.2 Hz, 1H) 4.79 (dd, J=10.1, 6.6 Hz, 1H) 4.38-4.46 (m, 1H) 4.36 (d, J=13.2 Hz, 1H) 3.74-3.90 (m, 2H) 1.90 (br dd, J=13.9, 6.6 Hz, 1H) 1.73-1.84 (m, 1H) 0.82 (t, J=7.4 Hz, 3H)
LC/MS (method LC-C): Rt 3.00 min, MH$^+$488
$[α]_D^{20}$: -144.92° (c 0.118, DMF)
Chiral HPLC (method HPLC-B): Rt 5.13 min, chiral purity 99.6%

Compound 92AB:
LC/MS (method LC-C): Rt 2.88 min, MH$^+$488
$[α]_D^{20}$: +488.89° (c 0.108, DMF)
Chiral HPLC (method HPLC-B): Rt 6.55 min, chiral purity 100%

Compound 92BA:

$^1$H NMR (500 MHz, DMSO-d$_6$) δ ppm 7.42 (t, J=7.9 Hz, 1H) 7.34 (d, J=7.9 Hz, 1H) 7.19 (dd, J=13.1, 7.7 Hz, 2H) 7.08-7.14 (m, 1H) 7.01-7.07 (m, 1H) 6.79-6.91 (m, 2H) 6.29-6.42 (m, 1H) 5.81 (d, J=13.2 Hz, 1H) 5.62 (d, J=7.9 Hz, 1H) 5.50-5.59 (m, 1H) 5.34 (s, 1H) 5.18 (q, J=7.1 Hz, 1H) 5.06 (d, J=13.6 Hz, 1H) 4.89 (dd, J=11.2, 5.5 Hz, 1H) 4.20-4.36 (m, 2H) 3.87 (d, J=13.6 Hz, 1H) 1.39-1.62 (m, 2H) 0.82 (t, J=7.3 Hz, 3H)

LC/MS (method LC-C): Rt 2.88 min, MH$^+$488

[α]$_D^{20}$: −510.78° (c 0.102, DMF)

Chiral HPLC (method HPLC-B): Rt 10.1 min, chiral purity 100%

Example 93: Synthesis of (1*R,13Z)-20-fluoro-7-hydroxy-16-oxa-23-thia-2,3,10-triazahexacyclo[15.12.1.1$^{2,10}$.0$^{3,8}$.0$^{21,30}$.0$^{24,29}$]hentriaconta-4,7,13,17,19,21(30),24(29),25,27-nonaene-6 (Compound 93A) and (1*SR,13Z)-20-fluoro-7-hydroxy-16-oxa-23-thia-2,3,10-triazahexacyclo[15.12.1.1$^{2,10}$.0$^{3,8}$.0$^{21,30}$.0$^{24,29}$]hentriaconta-4,7,13,17,19,21(30),24(29),25,27-nonaene-6 (Compound 93B)

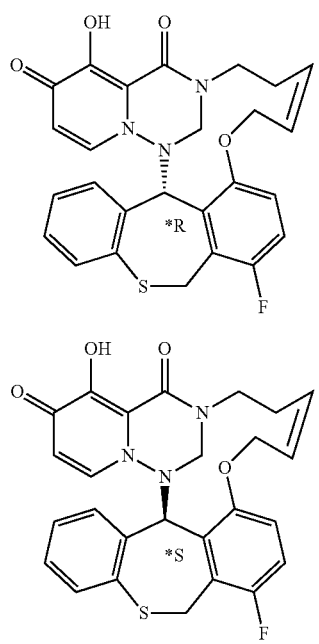

Compounds 93A and 93B were synthesized according to the procedures described in example 37 starting from intermediate 10-(allyloxy)-11-chloro-7-fluoro-6,11-dihydrodibenzo[b,e]thiepine.

Compound 93A:

LC/MS (method LC-C): Rt 2.85 min, MH$^+$492

[α]$_D^{20}$: +197.09° (c 0.103, DMF)

Chiral HPLC (method HPLC-B): Rt 4.41 min, chiral purity 100%

Compound 93B:

$^1$H NMR (500 MHz, DMSO-d$_6$) δ ppm 7.25 (t, J=9.1 Hz, 1H) 7.16 (d, J=7.6 Hz, 1H) 7.04-7.09 (m, 1H) 6.98-7.04 (m, 2H) 6.77 (t, J=7.3 Hz, 1H) 6.53 (d, J=7.3 Hz, 1H) 5.96-6.04 (m, 2H) 5.86-5.93 (m, 1H) 5.44-5.56 (m, 2H) 4.89 (d, J=13.2 Hz, 1H) 4.38-4.52 (m, 2H) 4.33 (d, J=13.2 Hz, 1H) 4.14-4.22 (m, 1H) 3.94 (d, J=13.9 Hz, 1H) 2.77 (br d, J=14.2 Hz, 1H) 2.15-2.26 (m, 1H) 2.04-2.15 (m, 1H)

LC/MS (method LC-C): Rt 2.85 min, MH$^+$492

[α]$_D^{20}$: −185.38° (c 0.13, DMF)

Chiral HPLC (method HPLC-B): Rt 6.28 min, chiral purity 100%

Example 94: Synthesis of (18*S,Z)-3-(difluoromethyl)-12-hydroxy-18-phenyl-6,9-dihydro-18H-10,17-methanobenzo[b]pyrido[1,2-f][1]oxa[5,6,9]triazacyclotridecine-11,13-dione (Compound 94A) and (18*R,Z)-3-(difluoromethyl)-12-hydroxy-18-phenyl-6,9-dihydro-18H-10,17-methanobenzo[b]pyrido[1,2-f][1]oxa[5,6,9]triazacyclotridecine-11,13-dione (Compound 94B)

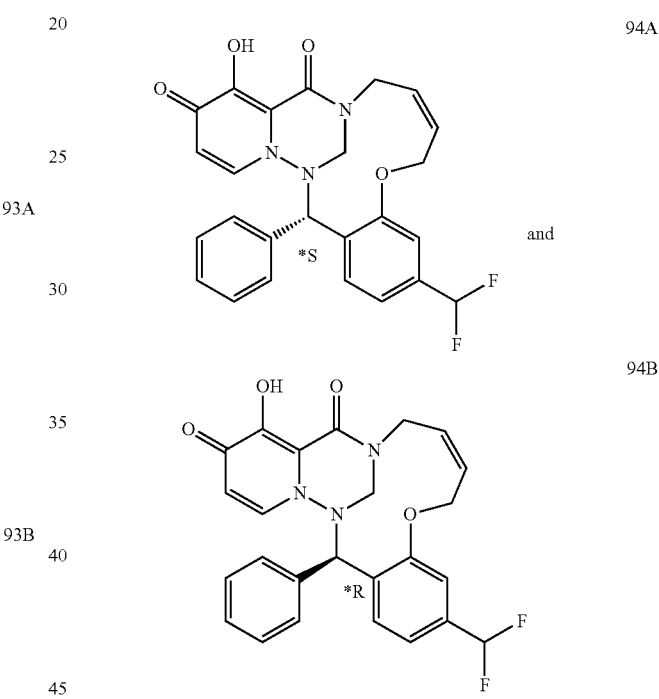

Compounds 94A and 94B were synthesized according to the procedures described in example 5 starting from intermediate 2-(allyloxy)-1-(chloro(phenyl)methyl)-4-(difluoromethyl)benzene.

Compound 94A:

$^1$H NMR (500 MHz, DMSO-d$_6$) δ ppm 8.26 (d, J=7.9 Hz, 1H) 7.56 (d, J=7.9 Hz, 1H) 7.46 (s, 1H) 7.26 (br d, J=7.9 Hz, 1H) 6.92-7.22 (m, 6H) 6.06-6.24 (m, 1H) 5.85-6.04 (m, 1H) 5.49 (d, J=7.9 Hz, 1H) 5.35 (s, 1H) 5.12 (d, J=13.9 Hz, 1H) 4.71-4.89 (m, 2H) 4.31-4.41 (m, 1H) 4.24 (d, J=13.9 Hz, 1H) 3.16-3.24 (m, 1H)

LC/MS (method LC-C): Rt 2.59 min, MH$^+$466

[α]$_D^{20}$: −609.86° (c 0.142, DMF)

Chiral HPLC (method HPLC-B): Rt 4.79 min, chiral purity 100%

Compound 94B:

LC/MS (method LC-C): Rt 2.59 min, MH$^+$466

[α]$_D^{20}$: +569.83° (c 0.179, DMF)

Chiral HPLC (method HPLC-B): Rt 4.14 min, chiral purity 100%

Example 95: Synthesis of (18'*S,E)-4'-fluoro-12'-hydroxy-18'-phenyl-6'H,18'H-spiro[cyclopropane-1,9'-[10,17]methanobenzo[b]pyrido[1,2-f][1]oxa[5,6,9]triazacyclotridecine]-11',13'-dione (Compound 95A) and (18'*R,E)-4'-fluoro-12'-hydroxy-18'-phenyl-6'H,18'H-spiro[cyclopropane-1,9'-[10,17]methanobenzo[b]pyrido[1,2-f][1]oxa[5,6,9]triazacyclotridecine]-11',13'-dione (Compound 95B)

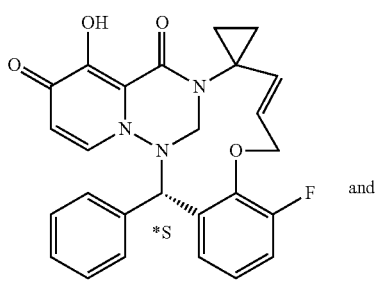

and

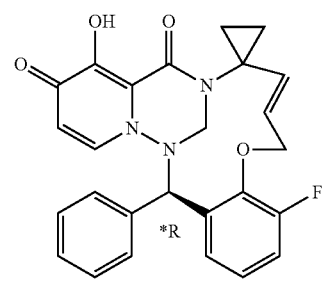

Compounds 95A and 95B were synthesized according to the procedures described in example 79 starting from intermediate 2-(allyloxy)-1-(chloro(phenyl)methyl)-3-fluorobenzene 61b Compound 95A:

LC/MS (method LC-C): Rt 2.76 min, MH⁺460

$[\alpha]_D^{20}$: +543.93° (c 0.107, DMF)

Chiral HPLC (method HPLC-A): Rt 6.25 min. chiral purity 100%

Compound 95B:

¹H NMR (500 MHz, DMSO-$d_6$) δ ppm 7.88 (br d, J=7.9 Hz, 1H) 7.37-7.43 (m, 1H) 7.30-7.37 (m, 1H) 7.13-7.30 (m, 6H) 6.30-6.41 (m, 1H) 5.80 (br d, J=15.1 Hz, 1H) 5.51 (d, J=7.6 Hz, 1H) 5.37 (s, 1H) 5.13 (d, J=13.6 Hz, 1H) 4.86 (br dd, J=10.7, 6.0 Hz, 1H) 4.22 (d, J=13.6 Hz, 1H) 4.16 (br t, J=10.1 Hz, 1H) 1.53 (dt, J=9.8, 6.8 Hz, 1H) 1.18 (dt, J=9.6, 6.5 Hz, 1H) 0.84-0.93 (m, 1H) 0.69-0.78 (m, 1H)

LC/MS (method LC-C): Rt 2.76 min, MH⁺460

$[\alpha]_D^{20}$: −576.12° (c 0134, DMF)

Chiral HPLC (method HPLC-A): Rt 7.93 min, chiral purity 100%

Example 96: Synthesis of (18'*R,E)-4'-chloro-12'-hydroxy-18'-phenyl-6'H,18'H-spiro[cyclopropane-1,9'-[10,17]methanobenzo[b]pyrido[1,2-f][1]oxa[5,6,9]triazacyclotridecine]-11',13'-dione (Compound 96A) and (18'*S,E)-4'-fluoro-12'-hydroxy-18'-phenyl-6'H,18'H-spiro[cyclopropane-1,9'-[10,17]methanobenzo[b]pyrido[1,2-f][1]oxa[5,6,9]triazacyclotridecine]-11',13'-dione (Compound 96B)

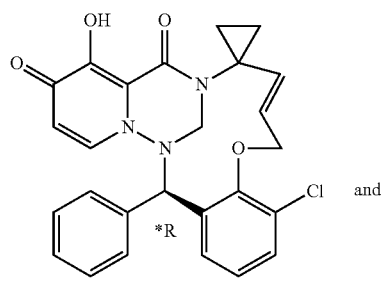

and

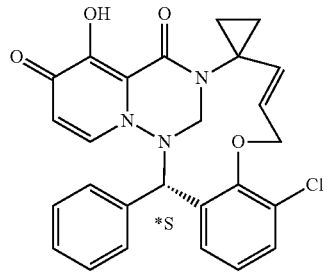

Compounds 96A and 96B were synthesized according to the procedures described in example 79 starting from intermediate 2-(allyloxy)-1-(chloro(phenyl)methyl)-3-chlorobenzene 75b Compound 96A:

¹H NMR (500 MHz, DMSO-$d_6$) δ ppm 8.04 (d, J=7.6 Hz, 1H) 7.55 (dd, J=7.9, 1.3 Hz, 1H) 7.41 (t, J=8.0 Hz, 1H) 7.14-7.27 (m, 6H) 6.42 (ddd, J=14.9, 9.2, 6.1 Hz, 1H) 5.71 (br d, J=15.1 Hz, 1H) 5.50 (d, J=7.9 Hz, 1H) 5.40 (s, 1H) 5.16 (d, J=13.9 Hz, 1H) 4.86 (dd, J=11.0, 5.7 Hz, 1H) 4.22-4.36 (m, 2H) 1.51-1.61 (m, 1H) 1.19 (dt, J=9.5, 6.5 Hz, 1H) 0.86-0.94 (m, 1H) 0.71-0.79 (m, 1H)

LC/MS (method LC-C): Rt 2.95 min, MH⁺476

$[\alpha]_D^{20}$: −549.22° (c 0.128, DMF)

Chiral HPLC (method HPLC-A and B): No separation observed

Compound 96B:

LC/MS (method LC-C): Rt 2.95 min, MH⁺476

$[\alpha]D^{20}$: +530.4° (c 0.125, DMF)

Chiral HPLC (method HPLC-A and B): No separation observed

Example 97: Synthesis of (9R,18R,E)-3-chloro-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 97AA) and (9S,18S,E)-3-chloro-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 97BB) and (9R,18S,E)-3-chloro-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 97BA) and (9S,18R,E)-3-chloro-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 97AB)

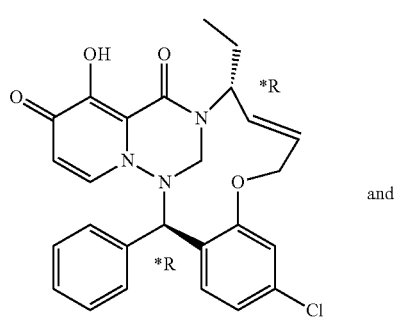

97AA and

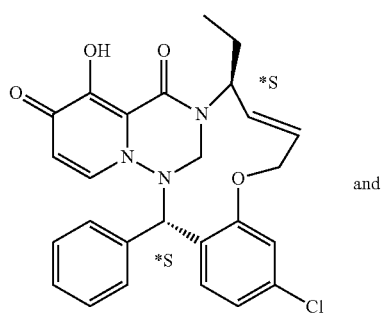

97BB and

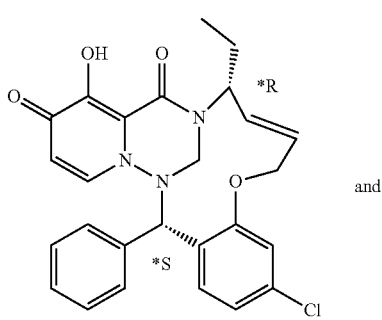

97BA and

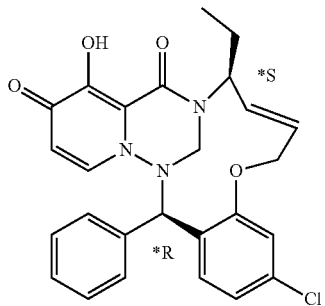

97AB

Compounds 97AA, 97BB, 97BA and 97AB were synthesized according to the procedures described in example 39 starting from intermediate 2-(allyloxy)-4-chloro-1-(chloro(phenyl)methyl)benzene 72b.

Compound 97AA:

$^1$H NMR (500 MHz, DMSO-d$_6$) δ ppm 8.04 (d, J=8.5 Hz, 1H) 7.37 (dd, J=8.4, 2.0 Hz, 1H) 7.26 (d, J=1.9 Hz, 1H) 6.96-7.21 (m, 6H) 6.22 (ddd, J=15.6, 9.9, 5.4 Hz, 1H) 5.37-5.51 (m, 2H) 5.04-5.16 (m, 2H) 4.95 (d, J=13.6 Hz, 1H) 4.80 (dd, J=11.5, 5.5 Hz, 1H) 4.14 (d, J=13.9 Hz, 1H) 4.09 (br t, J=10.9 Hz, 1H) 1.33-1.52 (m, 2H) 0.75 (t, J=7.3 Hz, 3H)

LC/MS (method LC-C): Rt 3.12 min, MH$^+$478

$[α]_D^{20}$: −677.24° (c 0.123, DMF)

Chiral HPLC (method HPLC-B): Rt 7.21 min. chiral purity 100%

Compound 97BB:

LC/MS (method LC-C): Rt 3.12 min, MH$^+$478

$[α]_D^{20}$: +631.94° (c 0.144, DMF)

Chiral HPLC (method HPLC-B): Rt 5.37 min, chiral purity 100%

Compound 97BA:

LC/MS (method LC-C): Rt 3.14 min, MH$^+$478

$[α]_D^{20}$: +704.50° (c 0.111, DMF)

Chiral HPLC (method HPLC-A): Rt 4.41 min, chiral purity 100%

Compound 97AB:

$^1$H NMR (500 MHz, DMSO-d$_6$) δ ppm 8.09 (d, J=8.5 Hz, 1H) 7.38 (d, J=1.9 Hz, 1H) 7.34 (dd, J=8.5, 1.9 Hz, 1H) 7.26 (d, J=7.6 Hz, 1H) 6.95-7.21 (m, 5H) 6.33 (br dd, J=15.1, 10.1 Hz, 1H) 5.80 (dt, J=15.3, 7.5 Hz, 1H) 5.42 (d, J=7.6 Hz, 1H) 5.33 (s, 1H) 5.09 (d, J=13.9 Hz, 1H) 4.55 (br d, J=7.9 Hz, 2H) 4.12 (d, J=14.2 Hz, 1H) 2.18-2.28 (m, 1H) 1.99-2.13 (m, 1H) 0.78 (t, J=7.3 Hz, 3H)

LC/MS (method LC-C): Rt 3.14 min, MH$^+$478

$[α]_D^{20}$: −718.25° (c 0.137, DMF)

Chiral HPLC (method HPLC-A): Rt 5.39 min, chiral purity 100%

Example 98: Synthesis of (9*S,18*S,E)-4-chloro-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 98AA) and (9*R,18*R,E)-4-chloro-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 98BB) and (9*S,18*R,E)-4-chloro-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 98BA) and (9*R,18*S,E)-4-chloro-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 98AB)

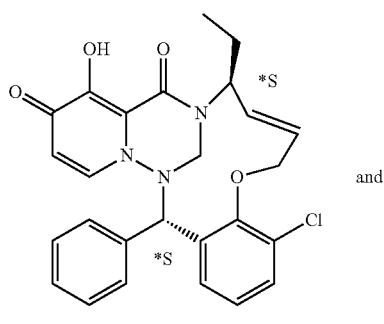

98AA and

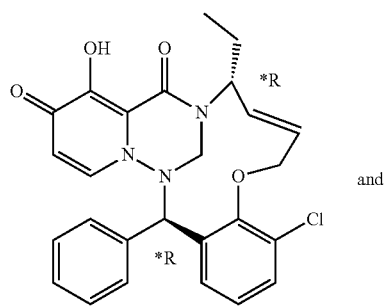

98BB and

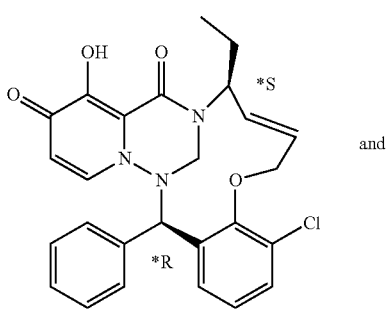

98BA and

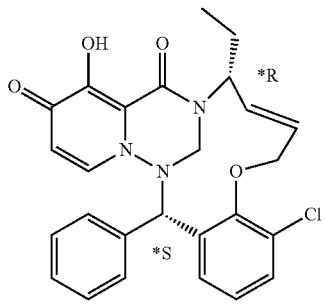

98AB

Compounds 98AA, 98BB, 98BA and 98AB were synthesized according to the procedures described in example 39 starting from intermediate 2-(allyloxy)-1-chloro-3-(chloro (phenyl)methyl)benzene 75b.

Compound 98AA:

LC/MS (method LC-C): Rt 3.10 min, MH$^+$478.2

$[\alpha]_D^{20}$: +585.32° (c 0.218, DMF)

Chiral HPLC (method HPLC-A): Rt 7.57 min, chiral purity 100%

Compound 98BB:

$^1$H NMR (500 MHz, DMSO-d$_6$) δ ppm 8.10 (dd, J=7.9, 1.3 Hz, 1H) 7.58 (dd, J=7.9, 1.6 Hz, 1H) 7.42 (t, J=7.9 Hz, 1H) 7.25 (d, J=7.9 Hz, 1H) 6.99-7.21 (m, 5H) 6.40 (ddd, J=15.4, 10.4, 5.0 Hz, 1H) 5.50-5.56 (m, 1H) 5.48 (d, J=7.6 Hz, 1H) 5.26 (s, 1H) 5.18 (q, J=7.6 Hz, 1H) 5.08 (d, J=13.6 Hz, 1H) 4.87 (dd, J=11.7, 5.0 Hz, 1H) 4.26 (d, J=13.6 Hz, 1H) 4.08 (br t, J=11.0 Hz, 1H) 1.40-1.60 (m, 2H) 0.83 (t, J=7.3 Hz, 3H)

LC/MS (method LC-C): Rt 3.10 min, MH$^+$478

$[\alpha]_D^{20}$: −587.58° (c 0.161, DMF)

Chiral HPLC (method HPLC-A): Rt 6.78 min, chiral purity 100%

Compound 98BA:

LC/MS (method LC-C): Rt 3.13 min, MH$^+$478

$[\alpha]_D^{20}$: +620.73° (c 0.164, DMF)

Chiral HPLC (method HPLC-A): Rt 5.81 min, chiral purity 100%

Compound 98AB:

$^1$H NMR (500 MHz, DMSO-d$_6$) δ ppm 8.13 (br d, J=7.6 Hz, 1H) 7.53 (dd, J=7.9, 1.3 Hz, 1H) 7.37-7.45 (m, 1H) 7.32 (d, J=7.6 Hz, 1H) 7.16 (br d, J=2.8 Hz, 5H) 6.44 (br s, 1H) 5.84 (br s, 1H) 5.49 (d, J=7.6 Hz, 1H) 5.47 (s, 1H) 5.23 (d, J=13.9 Hz, 1H) 4.75-4.86 (m, 1H) 4.60-4.68 (m, 1H) 4.27 (d, J=13.9 Hz, 1H) 3.44-3.51 (m, 1H) 2.29-2.37 (m, 1H) 2.10-2.20 (m, 1H) 0.87 (t, J=7.4 Hz, 3H)

LC/MS (method LC-C): Rt 3.13 min, MH$^+$478

$[\alpha]_D^{20}$: −680.36° (c 0.168, DMF)

Chiral HPLC (method HPLC-A): Rt 6.59 min, chiral purity 100%

Example 99: Synthesis of (2*R)-18-hydroxy-2-phenyl-9,12-dioxa-1,15,22-triazatetracyclo[13.7.1.03,8.017,22]tricosa-3,5,7,17,20-pentaene-16,19-dione (Compound 99A) and (2*S)-18-hydroxy-2-phenyl-9,12-dioxa-1,15,22-triazatetracyclo[13.7.1.03,8.017,22]tricosa-3,5,7,17,20-pentaene-16,19-dione (Compound 99B)

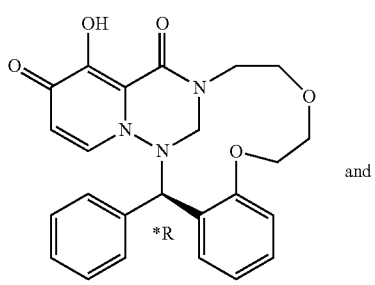

99A and

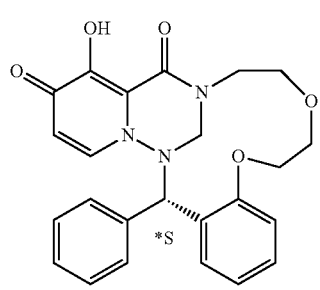

Compounds 99A and 99B were synthesized according to the procedures described in example 80 starting from intermediates 5-(benzyloxy)-3-(2-(2-((tert-butyldiphenylsilyl)oxy)ethoxy)ethyl)-2,3-dihydro-1H-pyrido[2,1-f][1,2,4]triazine-4,6-dione and 5a.

Compound 99A:

LC/MS (method LC-C): Rt 2.43 min, MH+434

$[\alpha]_D^{20}$: +262.6° (c 0.123, DMF)

Chiral HPLC (method HPLC-A): Rt 5.30 min, chiral purity 89.24%

Compound 99B:

$^1$H NMR (500 MHz, DMSO-d$_6$) δ ppm 8.12 (dd, J=7.7, 1.1 Hz, 1H) 7.29-7.39 (m, 2H) 7.21 (t, J=7.6 Hz, 1H) 7.05-7.18 (m, 6H) 6.14 (s, 1H) 5.45 (d, J=7.9 Hz, 1H) 5.08 (d, J=12.9 Hz, 1H) 4.33-4.42 (m, 1H) 4.26 (d, J=12.9 Hz, 1H) 4.16-4.23 (m, 1H) 4.06-4.14 (m, 1H) 3.82 (td, J=9.5, 2.2 Hz, 1H) 3.68-3.76 (m, 1H) 3.52-3.63 (m, 2H) 3.02 (ddd, J=14.3, 9.1, 2.4 Hz, 1H)

LC/MS (method LC-C): Rt 2.43 min, MH+434

$[\alpha]_D^{20}$: −202.86° (c 0.140, DMF)

Chiral HPLC (method HPLC-A): Rt 5.01 min, chiral purity 76.75%

Example 100: Synthesis of (2*R,9*S,*E)-33-fluoro-15-hydroxy-9-methyl-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (Compound 100AA), (2*R,9*R,*E)-33-fluoro-15-hydroxy-9-methyl-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (Compound 100AB), (2*S,9*S,*E)-33-fluoro-15-hydroxy-9-methyl-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (Compound 100BA) and (2*S,9*R,*E)-33-fluoro-15-hydroxy-9-methyl-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (Compound 100BB)

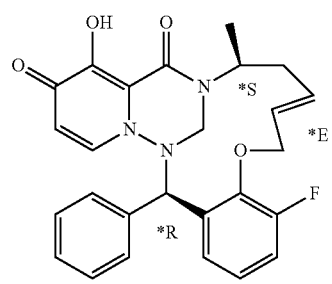

100AA and

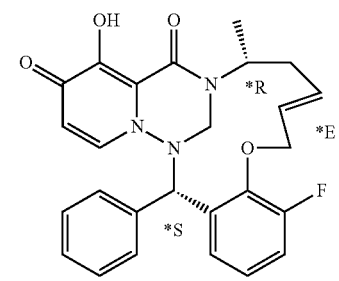

100BB and

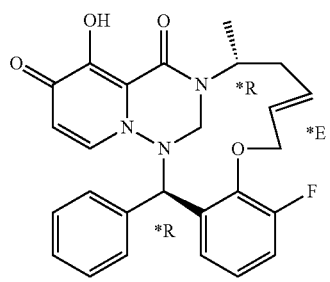

100AB and

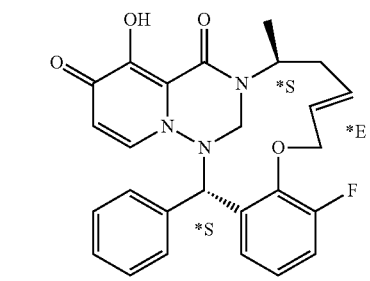

100BA

Compounds 100AA, 100BB, 100BA and 100AB were synthesized according to the procedures described in example 29 starting from intermediates 5-(benzyloxy)-3-(pent-4-en-2-yl)-2,3-dihydro-1H-pyrido[2,1-f][1,2,4]triazine-4,6-dione 29c and 2-(allyloxy)-1-(chloro(phenyl)methyl)-3-fluorobenzene 61b.

Compound 100AA:
$^1$H NMR (500 MHz, DMSO-$d_6$) δ ppm 7.77 (d, J=7.6 Hz, 1H) 7.28-7.40 (m, 2H) 7.09-7.27 (m, 4H) 7.06 (d, J=7.6 Hz, 1H) 6.84-7.02 (m, 1H) 6.03 (ddd, J=15.2, 9.7, 5.7 Hz, 1H) 5.86 (s, 1H) 5.61-5.71 (m, 1H) 5.39 (d, J=7.6 Hz, 1H) 5.21 (d, J=13.2 Hz, 1H) 4.73 (dd, J=12.0, 5.7 Hz, 1H) 4.30 (d, J=13.2 Hz, 1H) 4.11 (t, J=10.9 Hz, 1H) 3.18-3.26 (m, 2H) 2.07-2.15 (m, 1H) 1.40 (d, J=6.0 Hz, 3H)
LC/MS (method LC-C): Rt 2.90 min, MH$^+$462
$[α]_D^{20}$: −393.65° (c 0.126, DMF)
Chiral HPLC (method HPLC-A and B): No separation observed Compound 100AB:
$^1$H NMR (500 MHz, DMSO-$d_6$) δ ppm 7.91 (d, J=7.6 Hz, 1H) 7.37 (td, J=8.0, 5.4 Hz, 1H) 7.29-7.33 (m, 1H) 7.27 (d, J=7.6 Hz, 1H) 6.92-7.25 (m, 5H) 5.78 (dt, J=15.6, 7.6 Hz, 1H) 5.68 (s, 1H) 5.48-5.58 (m, 1H) 5.40 (d, J=7.9 Hz, 1H) 5.00 (d, J=12.9 Hz, 1H) 4.86 (ddd, J=10.8, 6.5, 4.4 Hz, 1H) 4.69 (dd, J=11.2, 6.8 Hz, 1H) 4.15-4.26 (m, 2H) 2.21 (ddd, J=17.6, 10.6, 7.1 Hz, 1H) 1.11 (d, J=6.9 Hz, 3H)
LC/MS (method LC-C): Rt 2.84 min, MH$^+$462
$[α]_D^{20}$: −402.94° (c 0.102, DMF)
Chiral HPLC (method HPLC-A): Rt 5.89 min. chiral purity 100%

Compound 100BA:
LC/MS (method LC-C): Rt 2.84 min, MH$^+$462
$[α]_D^{20}$: +374.15° (c 0.147, DMF)
Chiral HPLC (method HPLC-A): Rt 8.28 min, chiral purity 100%

Compound 100BB:
LC/MS (method LC-C): Rt 2.90 min, MH$^+$462
$[α]_D^{20}$: +385.04° (c 0.127, DMF)
Chiral HPLC (method HPLC-A and B): No separation observed Example 101: Synthesis of (9S,18R,E)-9-ethyl-3,4-difluoro-12-hydroxy-18-phenyl-6,9-dihydro-18H-10,17-methanobenzo[b]pyrido[1,2-f][1]oxa[5,6,9]triazacyclotridecine-11,13-dione (Compound 101AA) and (9R,18S,E)-9-ethyl-3,4-difluoro-12-hydroxy-18-phenyl-6,9-dihydro-18H-10,17-methanobenzo[b]pyrido[1,2-f][1]oxa[5,6,9]triazacyclotridecine-11,13-dione (Compound 101BB) and (9R,18R,E)-9-ethyl-3,4-difluoro-12-hydroxy-18-phenyl-6,9-dihydro-18H-10,17-methanobenzo[b]pyrido[1,2-f][1]oxa[5,6,9]triazacyclotridecine-11,13-dione (Compound 101AB) and (9S,18S,E)-9-ethyl-3,4-difluoro-12-hydroxy-18-phenyl-6,9-dihydro-18H-10,17-methanobenzo[b]pyrido[1,2-f][1]oxa[5,6,9]triazacyclotridecine-11,13-dione (Compound 101BA)

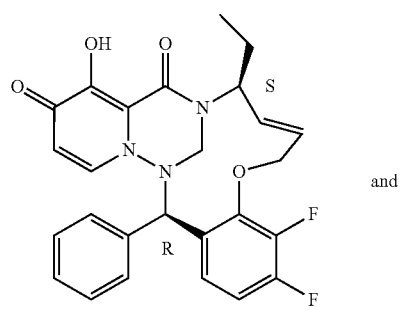

101AA and

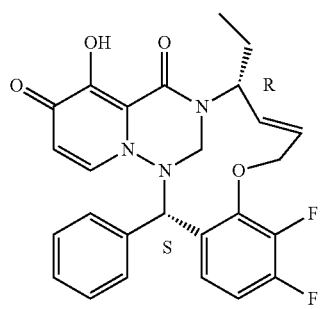

101BB and

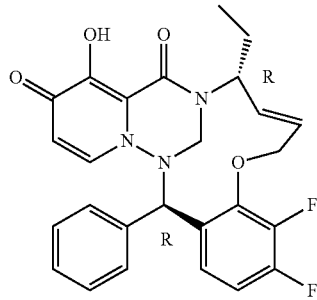

101AB and

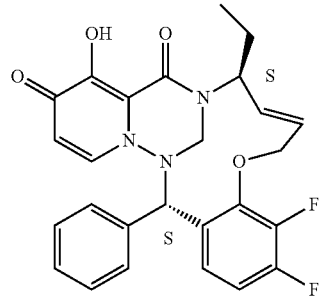

101BA

Compounds 101AA, 101BB, 101BA and 101AB were synthesized according to the procedures described in example 39 starting from intermediate 2-(allyloxy)-1-(chloro(phenyl)methyl)-3,4-difluorobenzene 74c.

Compound 101AA:
$^1$H NMR (500 MHz, DMSO-$d_6$) δ ppm 10.70-11.53 (m, 1H) 7.94 (br t, J=6.8 Hz, 1H) 7.45-7.54 (m, 1H) 7.01-7.30 (m, 6H) 6.37 (ddd, J=15.4, 10.1, 5.4 Hz, 1H) 5.67 (br dd, J=15.4, 6.3 Hz, 1H) 5.48 (d, J=7.6 Hz, 1H) 5.12-5.25 (m, 2H) 5.05 (d, J=13.6 Hz, 1H) 4.92 (dd, J=11.3, 5.4 Hz, 1H) 4.23 (d, J=13.6 Hz, 1H) 4.08 (br t, J=10.9 Hz, 1H) 1.39-1.64 (m, 2H) 0.83 (t, J=7.3 Hz, 3H)
LC/MS (method LC-C): Rt 2.98 min, MH$^+$480
$[α]_D^{20}$: −545.62° (c 0.217, DMF)
Chiral HPLC (method HPLC-B): Rt 5.88 min, chiral purity 100%

Compound 101AB:
$^1$H NMR (500 MHz, DMSO-$d_6$) δ ppm 9.89-11.09 (m, 1H) 7.99 (br t, J=6.8 Hz, 1H) 7.41-7.57 (m, 1H) 7.32 (d, J=7.6 Hz, 1H) 6.91-7.26 (m, 5H) 6.39-6.58 (m, 1H) 5.87-6.03 (m, 1H) 5.49 (d, J=7.6 Hz, 1H) 5.37 (s, 1H) 5.20 (d, J=13.9 Hz, 1H) 4.70 (br t, J=10.2 Hz, 1H) 4.58 (br dd, J=10.2, 5.2 Hz, 1H) 4.22 (d, J=13.9 Hz, 1H) 3.40-3.48 (m, 1H) 2.27-2.38 (m, 1H) 2.08-2.24 (m, 1H) 0.87 (t, J=7.4 Hz, 3H)
LC/MS (method LC-C): Rt 3.04 min, MH$^+$480
$[α]_D^{20}$: −683.61° (c 0.244, DMF)

Chiral HPLC (method HPLC-A): Rt 7.01 min, chiral purity 100%

Compound 101BA:
LC/MS (method LC-C): Rt 3.05 min, MH$^+$480
$[\alpha]_D^{20}$: +623.44° (c 0.209, DMF)
Chiral HPLC (method HPLC-A): Rt 4.42 min, chiral purity 100%

Compound 101BB:
LC/MS (method LC-C): Rt 2.99 min, MH$^+$480
$[\alpha]_D^{20}$: +568.75° (c 0.112, DMF)
Chiral HPLC (method HPLC-B): Rt 4.41 min, chiral purity 100%

Example 102: Synthesis of (18'R,E)-3',4'-difluoro-12'-hydroxy-18'-phenyl-6'H,18'H-spiro[cyclopropane-1,9'-[10,17]methanobenzo[b]pyrido[1,2-f][1]oxa[5,6,9]triazacyclotridecine]-11',13'-dione (Compound 102A), (18'S,E)-3',4'-difluoro-12'-hydroxy-18'-phenyl-6'H,18'H-spiro[cyclopropane-1,9'-[10,17]methanobenzo[b]pyrido[1,2-f][1]oxa[5,6,9]triazacyclotridecine]-11',13'-dione (Compound 102B)

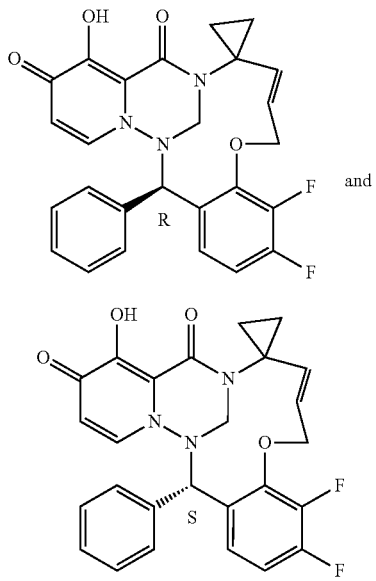

Compounds 102A and 102B were synthesized according to the procedures described in example 79 starting from intermediate 2-(allyloxy)-1-(chloro(phenyl)methyl)-3,4-difluorobenzene 74c.

Compound 102A:
$^1$H NMR (500 MHz, DMSO-d$_6$) δ ppm 7.90 (br t, J=7.1 Hz, 1H) 7.47 (br d, J=8.2 Hz, 1H) 6.99-7.37 (m, 6H) 6.37 (dt, J=14.5, 7.6 Hz, 1H) 5.94 (br d, J=14.8 Hz, 1H) 5.50 (d, J=7.6 Hz, 1H) 5.32 (s, 1H) 5.11 (br d, J=13.9 Hz, 1H) 4.90 (br dd, J=10.9, 6.1 Hz, 1H) 4.16-4.35 (m, 2H) 1.52 (br dd, J=5.8, 2.7 Hz, 1H) 1.13-1.28 (m, 1H) 0.82-0.97 (m, 1H) 0.69-0.78 (m, 1H)
LC/MS (method LC-C): Rt 2.90 min, MH$^+$478
$[\alpha]_D^{20}$: −575.36° (c 0.138, DMF)
Chiral HPLC (method HPLC-B): Rt 5.70 min, chiral purity 100%

Compound 102B:
LC/MS (method LC-C): Rt 2.87 min, MH$^+$478
$[\alpha]_D^{20}$: +563.28° (c 0.128, DMF)
Chiral HPLC (method HPLC-B): Rt 4.64 min, chiral purity 100%

Example 103: Synthesis of (18*R,Z)-3,4-dichloro-12-hydroxy-18-phenyl-6,9-dihydro-18H-10,17-methanobenzo[b]pyrido[1,2-f][1]oxa[5,6,9]triazacyclotridecine-11,13-dione (Compound 103A) and (18*S,Z)-3,4-dichloro-12-hydroxy-18-phenyl-6,9-dihydro-18H-10,17-methanobenzo[b]pyrido[1,2-f][1]oxa[5,6,9]triazacyclotridecine-11,13-dione (Compound 103B)

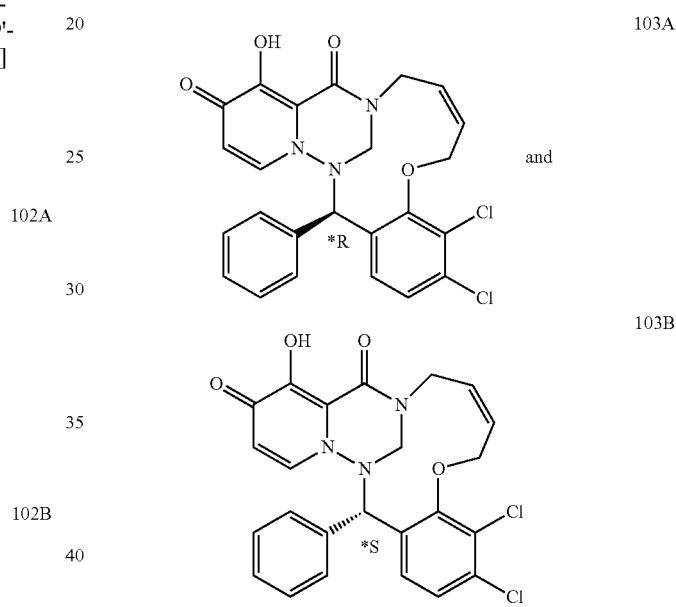

Compounds 103A and 103B were synthesized according to the procedures described in example 5 starting from intermediate 2-(allyloxy)-3,4-dichloro-1-(chloro(phenyl)methyl) benzene (synthesized as 74c from 3,4-dichloro-2-hydroxybenzaldehyde [CAS 23602-61-1]).

Compound 103A:
LC/MS (method LC-C): Rt 3.01 min, MH$^+$484
$[\alpha]_D^{20}$: +709.83° (c 0.173, DMF)
Chiral HPLC (method HPLC-B): Rt 5.22 min, chiral purity 100%

Compound 103B:
$^1$H NMR (500 MHz, DMSO-d$_6$) δ ppm 8.11 (br d, J=8.5 Hz, 1H) 7.71 (d, J=8.5 Hz, 1H) 6.98-7.32 (m, 6H) 6.28 (br s, 1H) 5.97 (br s, 1H) 5.49 (d, J=7.6 Hz, 1H) 5.27 (br s, 1H) 5.16 (d, J=13.6 Hz, 1H) 4.83 (br dd, J=13.6, 4.4 Hz, 2H) 4.26-4.51 (m, 2H) 3.20 (br dd, J=14.0, 7.7 Hz, 1H)
LC/MS (method LC-C): Rt 3.01 min, MH$^+$484
$[\alpha]_D^{20}$: −666.42° (c 0.134, DMF)
Chiral HPLC (method HPLC-B): Rt 5.79 min, chiral purity 99.31%

Example 104: Synthesis of (18*R,*Z)-4-fluoro-18-(6-fluoropyridin-2-yl)-12-hydroxy-6,9-dihydro-18H-10,17-methanobenzo[b]pyrido[1,2-f][1]oxa[5,6,9]triazacyclotridecine-11,13-dione (Compound 104A) and (18*S,*Z)-4-fluoro-18-(6-fluoropyridin-2-yl)-12-hydroxy-6,9-dihydro-18H-10,17-methanobenzo[b]pyrido[1,2-f][1]oxa[5,6,9]triazacyclotridecine-11,13-dione (Compound 104B)

Example 105: Synthesis of (2*R,9*S,*E)-9-ethyl-33-fluoro-15-hydroxy-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (Compound 105AA), (2*R,9*R,*E)-9-ethyl-33-fluoro-15-hydroxy-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (Compound 105AB), (2*S,9*S,*E)-9-ethyl-33-fluoro-15-hydroxy-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (Compound 105BA) and (2*S,9*R,*E)-9-ethyl-33-fluoro-15-hydroxy-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (Compound 105BB)

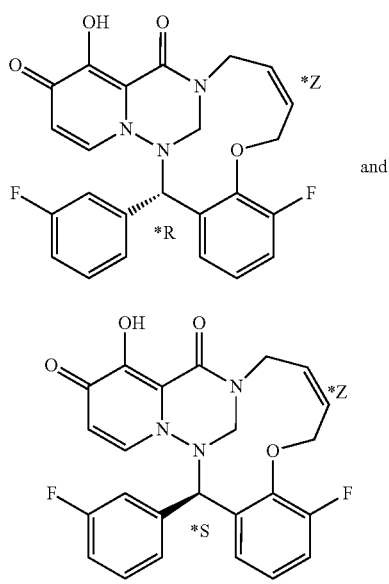

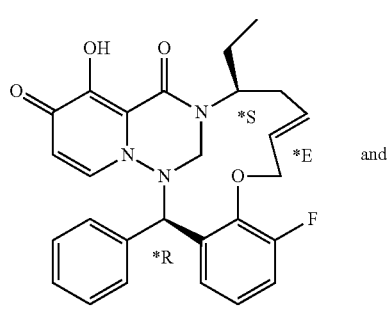

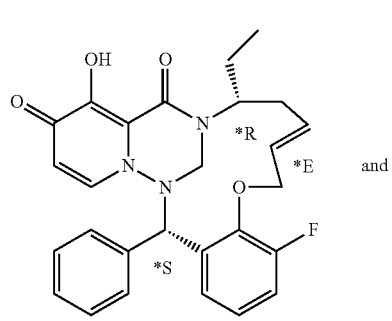

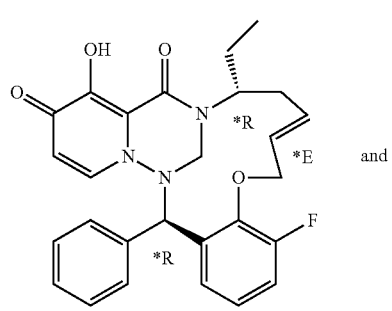

Compounds 104A and 104B were synthesized according to the procedures described in example 5 starting from intermediate 2-((2-(allyloxy)-3-fluorophenyl)chloromethyl)-6-fluoropyridine (synthesized as 76c from 1-bromo-3-fluoro-2-(2-propen-1-yloxy)-benzene [CAS 1010422-27-1]).

Compound 104A:

$^1$H NMR (500 MHz, DMSO-d$_6$) δ ppm 7.90 (br d, J=7.3 Hz, 1H) 7.85 (q, J=8.2 Hz, 1H) 7.33-7.46 (m, 2H) 7.21-7.28 (m, 1H) 7.15 (d, J=7.6 Hz, 1H) 7.06 (dd, J=8.2, 2.2 Hz, 1H) 6.16-6.33 (m, 1H) 5.96 (br s, 1H) 5.59 (d, J=7.9 Hz, 1H) 5.41 (s, 1H) 5.14 (d, J=13.9 Hz, 1H) 4.81 (br dd, J=13.6, 4.7 Hz, 2H) 4.25 (d, J=13.9 Hz, 2H) 3.21 (br dd, J=14.0, 8.0 Hz, 1H)

LC/MS (method LC-C): Rt 2.46 min, MH$^+$453

[α]$_D^{20}$: −622.99° (c 0.087, DMF)

Chiral HPLC (method HPLC-A): Rt 6.78 min, chiral purity 100%

Compound 104B:

LC/MS (method LC-C): Rt 2.46 min, MH$^+$453

[α]$_D^{20}$: +637.18° (c 0.078, DMF)

Chiral HPLC (method HPLC-A): Rt 5.41 min, chiral purity 100%

329
-continued

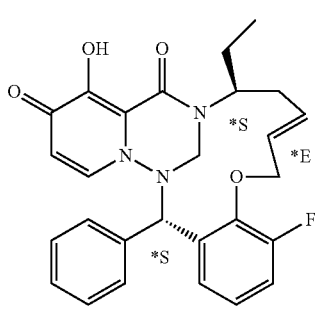

105BA

Compounds 105AA, 105BB, 105BA and 105AB were synthesized according to the procedures described in example 39 starting from intermediates 5-(benzyloxy)-3-(hex-5-en-3-yl)-2,3-dihydro-1H-pyrido[2,1-f][1,2,4]triazine-4,6-dione (synthesized as 39e from 5-hexen-3-amine [CAS 239126-98-8]) and 2-(allyloxy)-1-(chloro(phenyl)methyl)-3-fluorobenzene 61b.

Compound 105AA:

$^{1}$H NMR (500 MHz, DMSO-d$_{6}$) δ ppm 7.77 (d, J=7.6 Hz, 1H) 7.29-7.44 (m, 2H) 7.19 (br s, 4H) 7.06 (d, J=7.6 Hz, 1H) 6.84-7.01 (m, 1H) 6.05 (ddd, J=15.2, 9.9, 5.5 Hz, 1H) 5.88 (s, 1H) 5.64 (ddd, J=15.4, 10.5, 4.7 Hz, 1H) 5.39 (d, J=7.6 Hz, 1H) 5.13 (d, J=13.2 Hz, 1H) 4.72 (dd, J=12.0, 5.4 Hz, 1H) 4.37 (d, J=13.2 Hz, 1H) 4.10 (br t, J=10.9 Hz, 1H) 3.13-3.22 (m, 1H) 2.99-3.09 (m, 1H) 2.15-2.25 (m, 1H) 2.08 (dt, J=14.1, 7.8 Hz, 1H) 1.64 (dt, J=14.0, 6.7 Hz, 1H) 0.81 (t, J=7.4 Hz, 3H)

LC/MS (method LC-C): Rt 3.04 min, MH$^{+}$476

$[α]_{D}^{20}$: −322.46° (c 0.138, DMF)

Chiral HPLC (method HPLC-A and B): No separation observed

Compound 105AB:

$^{1}$H NMR (500 MHz, DMSO-d$_{6}$) δ ppm 7.90 (d, J=7.6 Hz, 1H) 7.34-7.42 (m, 1H) 7.27-7.33 (m, 2H) 6.90-7.26 (m, 5H) 5.67-5.75 (m, 1H) 5.65 (s, 1H) 5.54-5.62 (m, 1H) 5.41 (d, J=7.6 Hz, 1H) 4.96 (d, J=12.9 Hz, 1H) 4.78 (br dd, J=11.5, 4.6 Hz, 1H) 4.67 (dd, J=11.0, 7.3 Hz, 1H) 4.20-4.30 (m, 2H) 2.53-2.58 (m, 1H) 2.14-2.27 (m, 1H) 1.45-1.53 (m, 2H) 0.81 (t, J=7.4 Hz, 3H)

LC/MS (method LC-C): Rt 2.98 min, MH$^{+}$476

$[α]_{D}^{20}$: −386.61° (c 0.127, DMF)

Chiral HPLC (method HPLC-A): Rt 5.89 min, chiral purity 100%

Compound 105BA:

LC/MS (method LC-C): Rt 2.98 min, MH$^{+}$476

$[α]_{D}^{20}$: +418.47 (c 0.112, DMF)

Chiral HPLC (method HPLC-A): Rt 8.00 min, chiral purity 100%

Compound 105BB:

LC/MS (method LC-C): Rt 3.04 min, MH$^{+}$476

$[α]_{D}^{20}$: +350.00° (c 0.150, DMF)

Chiral HPLC (method HPLC-A and B): No separation observed

Example 106: Synthesis of (18'*R,E)-12'-hydroxy-18'-phenyl-6'H,18'H-spiro[cyclobutane-1,9'-[10,17]methanobenzo[b]pyrido[1,2-f][1]oxa[5,6,9]triazacyclotridecine]-11',13'-dione (Compound 106A), ((18'*S,E)-12'-hydroxy-18'-phenyl-6'H,18'H-spiro[cyclobutane-1,9'-[10,17]methanobenzo[b]pyrido[1,2-f][1]oxa[5,6,9]triazacyclotridecine]-11',13'-dione (Compound 106B)

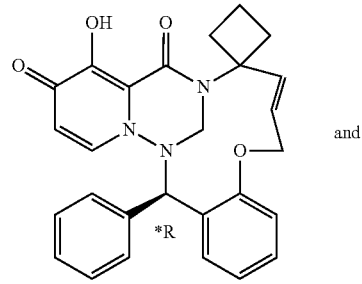

106A and

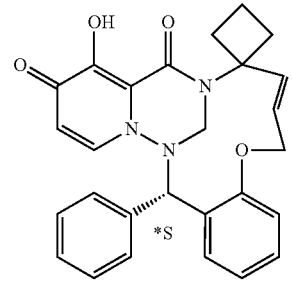

106B

Compounds 106A and 106B were synthesized according to the procedures described in example 79 starting from intermediate 5-(benzyloxy)-3-(1-vinylcyclobutyl)-2,3-dihydro-1H-pyrido[2,1-f][1,2,4]triazine-4,6-dione 146f.

Compound 106A:

$^{1}$H NMR (500 MHz, DMSO-d$_{6}$) δ ppm 8.09 (dd, J=7.7, 1.1 Hz, 1H) 7.40 (br dd, J=7.9, 1.3 Hz, 1H) 7.29-7.36 (m, 2H) 7.26 (d, J=7.9 Hz, 1H) 7.04-7.22 (m, 5H) 6.40 (br d, J=15.8 Hz, 1H) 5.91-6.05 (m, 1H) 5.49 (d, J=7.6 Hz, 1H) 5.32 (s, 1H) 5.09 (d, J=13.6 Hz, 1H) 4.70-4.79 (m, 1H) 4.53 (br dd, J=10.7, 6.3 Hz, 1H) 3.79 (d, J=13.6 Hz, 1H) 2.77-2.87 (m, 1H) 2.41-2.48 (m, 1H) 2.01-2.10 (m, 1H) 1.93-2.00 (m, 1H) 1.68-1.80 (m, 1H) 1.52-1.65 (m, 1H)

LC/MS (method LC-C): Rt 2.90 min, MH$^{+}$456

$[α]_{D}^{20}$: −666.91° (c 0.139, DMF)

Chiral HPLC (method HPLC-A and B): No separation observed

Compound 106B:

LC/MS (method LC-C): Rt 2.90 min, MH$^{+}$456

$[α]_{D}^{20}$: +686.26° (c 0.182, DMF)

Chiral HPLC (method HPLC-A and B): No separation observed

Example 107: Synthesis of (17a'*R,*E)-12'-hydroxy-2',17a'-dihydro-6'H-spiro[cyclopropane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 107A), (17a'*S,*E)-12'-hydroxy-2',17a'-dihydro-6'H-spiro[cyclopropane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 107B)

Example 108: Synthesis of (17a'*R,*E)-24',25'-difluoro-12'-hydroxy-2',17a'-dihydro-6'H-spiro[cyclopropane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 108A), (17a'*S,*E)-24',25'-difluoro-12'-hydroxy-2',17a'-dihydro-6'H-spiro[cyclopropane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 108B)

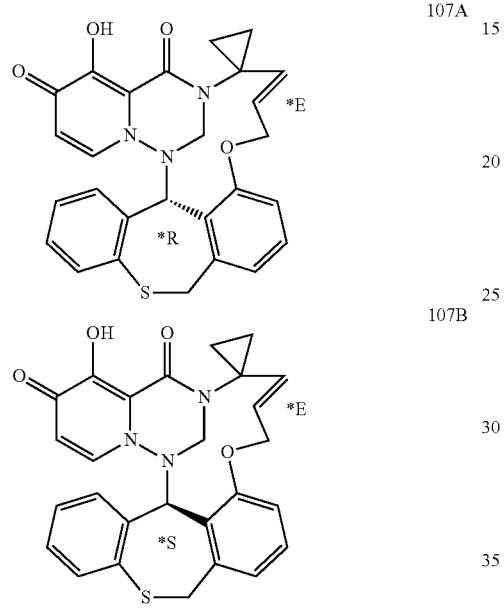

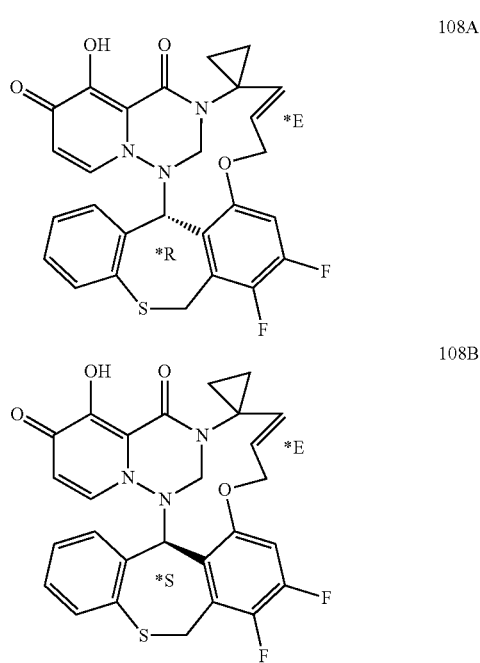

Compounds 107A and 107B were synthesized according to the procedures described in example 46 starting from intermediate 79c.

Compound 107A:

LC/MS (method LC-C): Rt 2.73 min, MH⁺486

$[\alpha]_D^{20}$: +405.74° (c 0.122, DMF)

Chiral HPLC (method HPLC-B): Rt 6.89 min, chiral purity 100%

Compound 107B:

¹H NMR (500 MHz, DMSO-d₆) δ ppm 7.35-7.45 (m, 1H) 7.23 (d, J=7.6 Hz, 1H) 7.19 (d, J=8.2 Hz, 2H) 7.09-7.14 (m, 1H) 7.03-7.08 (m, 1H) 6.83-6.90 (m, 2H) 6.33 (ddd, J=15.4, 9.5, 5.7 Hz, 1H) 5.68-5.77 (m, 2H) 5.62 (d, J=7.6 Hz, 1H) 5.49 (s, 1H) 5.13 (d, J=13.6 Hz, 1H) 4.88 (dd, J=11.0, 5.7 Hz, 1H) 4.35 (t, J=10.2 Hz, 1H) 4.16 (d, J=13.6 Hz, 1H) 3.87 (d, J=13.6 Hz, 1H) 1.51 (ddd, J=10.4, 7.3, 6.0 Hz, 1H) 1.11-1.20 (m, 1H) 0.87-0.96 (m, 1H) 0.73 (ddd, J=9.5, 7.5, 5.0 Hz, 1H)

LC/MS (method LC-C): Rt 2.73 min, MH⁺486

$[\alpha]_D^{20}$: -426.40° (c 0.125, DMF)

Chiral HPLC (method HPLC-B): Rt 9.05 min, chiral purity 100%

Compounds 108A and 108B were synthesized according to the procedures described in example 88 starting from intermediate 79c.

Compound 108A:

LC/MS (method LC-C): Rt 2.96 min, MH⁺522

$[\alpha]_D^{20}$: +391.8° (c 0.122, DMF)

Chiral HPLC (method HPLC-B): Rt 7.44 min, chiral purity 100%

Compound 108B:

¹H NMR (500 MHz, DMSO-d₆) δ ppm 7.46 (dd, J=11.7, 7.3 Hz, 1H) 7.20 (d, J=7.6 Hz, 1H) 7.12-7.17 (m, 1H) 7.06-7.11 (m, 1H) 6.83-6.95 (m, 2H) 6.33 (ddd, J=15.4, 9.1, 6.0 Hz, 1H) 5.86 (br d, J=15.4 Hz, 1H) 5.58-5.67 (m, 2H) 5.44 (s, 1H) 5.09 (d, J=13.9 Hz, 1H) 4.85 (dd, J=11.0, 6.0 Hz, 1H) 4.39 (dd, J=10.9, 9.6 Hz, 1H) 4.33 (d, J=13.9 Hz, 1H) 4.10 (d, J=14.2 Hz, 1H) 1.46-1.55 (m, 1H) 1.13-1.21 (m, 1H) 0.87-0.95 (m, 1H) 0.76 (ddd, J=9.5, 7.6, 5.2 Hz, 1H)

LC/MS (method LC-C): Rt 2.96 min, MH⁺522

$[\alpha]_D^{20}$: -410.85° (c 0.129, DMF)

Chiral HPLC (method HPLC-B): Rt 7.63 min, chiral purity 100%

Example 109: Synthesis of (18*R,19*R,*Z)-12-hydroxy-19-(methoxymethyl)-18-phenyl-6,9-dihydro-18H-10,17-methanobenzo[b]pyrido[1,2-f][1]oxa[5,6,9]triazacyclotridecine-11,13-dione (Compound 109A), (18*S,19*S,*Z)-12-hydroxy-19-(methoxymethyl)-18-phenyl-6,9-dihydro-18H-10,17-methanobenzo[b]pyrido[1,2-f][1]oxa[5,6,9]triazacyclotridecine-11,13-dione (Compound 109B)

Example 110: Synthesis of (18*S,Z)-12-hydroxy-4-methyl-18-phenyl-6,9-dihydro-18H-10,17-methanobenzo[b]pyrido[1,2-f][1]oxa[5,6,9]triazacyclotridecine-11,13-dione (Compound 110A) and (18*R,Z)-12-hydroxy-4-methyl-18-phenyl-6,9-dihydro-18H-10,17-methanobenzo[b]pyrido[1,2-f][1]oxa[5,6,9]triazacyclotridecine-11,13-dione (Compound 110B)

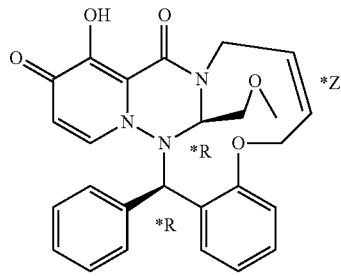

109A

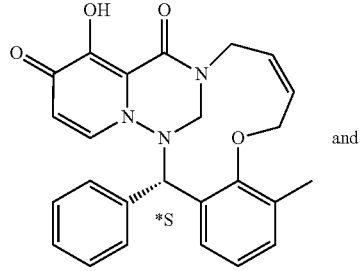

110A and

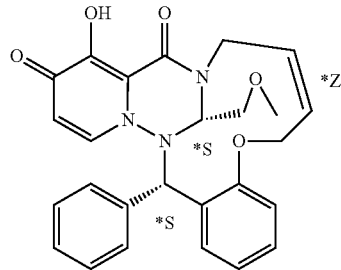

109B

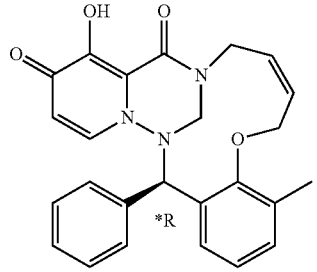

110B

Compounds 109A and 109B were synthesized according to the procedures described in example 91 starting from intermediate 5a and using methoxyacetaldehyde dimethyl acetal [CAS 10312-83-1] instead of acetaldehyde.

Compound 109A:

$^1$H NMR (500 MHz, DMSO-$d_6$) δ ppm 8.08 (br d, J=7.3 Hz, 1H) 7.38-7.49 (m, 1H) 7.31-7.37 (m, 1H) 7.02-7.29 (m, 7H) 6.05-6.22 (m, 1H) 5.82-6.03 (m, 1H) 5.51 (d, J=7.6 Hz, 1H) 5.29 (s, 1H) 4.67-4.88 (m, 2H) 4.45 (t, J=6.1 Hz, 1H) 4.21-4.39 (m, 1H) 3.45-3.55 (m, 2H) 3.22-3.27 (m, 4H)

LC/MS (method LC-C): Rt 2.61 min, MH$^+$460

$[α]_D^{20}$: −602.82° (c 0.142, DMF)

Chiral HPLC (method HPLC-B): Rt 5.88 min, chiral purity 100%

Compound 109B:

LC/MS (method LC-C): Rt 2.61 min, MH$^+$460

$[α]_D^{20}$: +584.94° (c 0.166, DMF)

Chiral HPLC (method HPLC-B): Rt 4.62 min, chiral purity 100%

Compounds 110A and 110B were synthesized according to the procedures described in example 5 starting from intermediate 2-(allyloxy)-1-(chloro(phenyl)methyl)-3-methylbenzene (synthesized as 74c from 3-methyl-2-(2-propen-1-yloxy)-benzaldehyde [CAS 153034-23-2]).

Compound 110A:

LC/MS (method LC-C): Rt 2.65 min. MH$^+$430

$[α]_D^{20}$: +730.43° (c 0.138, DMF)

Chiral HPLC (method HPLC-B): Rt 4.93 min, chiral purity 99.38%

Compound 110B:

$^1$H NMR (400 MHz, DMSO-$d_6$) δ ppm 10.51-11.37 (m, 1H) 7.89 (t, J=4.7 Hz, 1H) 7.27 (d, J=4.9 Hz, 2H) 6.90-7.23 (m, 6H) 6.13-6.40 (m, 1H) 5.67-5.92 (m, 1H) 5.46 (d, J=7.6 Hz, 1H) 5.30 (s, 1H) 5.15 (d, J=13.8 Hz, 1H) 4.83 (br dd, J=13.8, 4.8 Hz, 1H) 4.74 (br dd, J=10.6, 5.9 Hz, 1H) 4.33 (d, J=13.6 Hz, 1H) 3.97-4.17 (m, 1H) 3.21 (br dd, J=13.9, 7.5 Hz, 1H) 2.21 (s, 3H)

LC/MS (method LC-C): Rt 2.65 min, MH$^+$430

$[α]_D^{20}$: −724.07° (c 0.108, DMF)

Chiral HPLC (method HPLC-B): Rt 3.26 min, chiral purity 100%

Example 111: Synthesis of (2*S,*E)-33,34-dichloro-15-hydroxy-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (Enantiomer 111A)

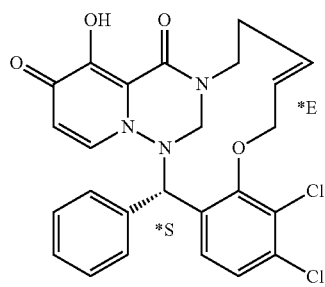

Compounds 111A was synthesized according to the procedures described in example 10 starting from intermediate 2-(allyloxy)-3,4-dichloro-1-(chloro(phenyl)methyl)benzene (see example 103).

Compound 111A:

$^1$H NMR (400 MHz, DMSO-d$_6$) δ ppm 11.39-12.00 (m, 1H) 8.10 (d, J=8.7 Hz, 1H) 7.68 (d, J=8.7 Hz, 1H) 7.11-7.26 (m, 4H) 7.03 (br s, 2H) 6.08-6.18 (m, 1H) 6.07 (s, 1H) 5.73 (ddd, J=14.6, 10.2, 4.2 Hz, 1H) 5.38 (d, J=7.6 Hz, 1H) 5.10 (d, J=13.0 Hz, 1H) 4.76 (dd, J=12.0, 4.4 Hz, 1H) 4.38 (d, J=13.3 Hz, 1H) 4.14 (t, J=11.3 Hz, 1H) 3.82 (br d, J=13.2 Hz, 1H) 2.78-3.00 (m, 2H) 2.27 (br d, J=13.3 Hz, 1H)

LC/MS (method LC-C): Rt 3.12 min, MH$^+$498

[α]$_D^{20}$: −531.15° (c 0.122, DMF)

Example 112: Synthesis of (2*S,E)-33,34-difluoro-15-hydroxy-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (enantiomer 112A)

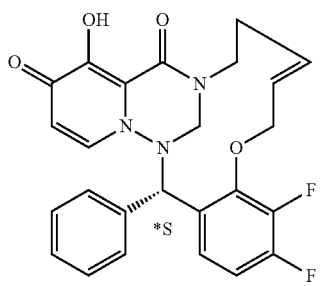

Compounds 112A was synthesized according to the procedures described in example 10 starting from intermediates 2a and 74c.

Compound 112A:

$^1$H NMR (500 MHz, DMSO-d$_6$) δ ppm 7.89 (br t, J=6.8 Hz, 1H) 7.41-7.53 (m, 1H) 6.81-7.39 (m, 6H) 6.01-6.18 (m, 1H) 5.92 (s, 1H) 5.71 (ddd, J=15.1, 10.3, 4.6 Hz, 1H) 5.38 (d, J=7.6 Hz, 1H) 5.07 (d, J=12.9 Hz, 1H) 4.78 (dd, J=11.8, 5.2 Hz, 1H) 4.32 (d, J=13.2 Hz, 1H) 4.11 (t, J=11.0 Hz, 1H) 3.76-3.88 (m, 1H) 2.78-2.99 (m, 2H) 2.27 (br d, J=12.3 Hz, 1H)

LC/MS (method LC-C): Rt 2.79 min, MH$^+$466

[α]$_D^{20}$: −429.09° (c 0.11, DMF)

Example 113: Synthesis of (18'*R,*E)-3',4'-dichloro-12'-hydroxy-18'-phenyl-6'H,18'H-spiro[cyclopropane-1,9'-[10,17]methanobenzo[b]pyrido[1,2-f][1]oxa[5,6,9]triazacyclotridecine]-11',13'-dione (Compound 113A), (18'*S,*E)-3',4'-dichloro-12'-hydroxy-18'-phenyl-6'H,18'H-spiro[cyclopropane-1,9'-[10,17]methanobenzo[b]pyrido[1,2-f][1]oxa[5,6,9]triazacyclotridecine]-11',13'-dione (Compound 113B)

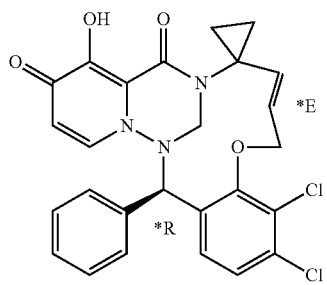

and

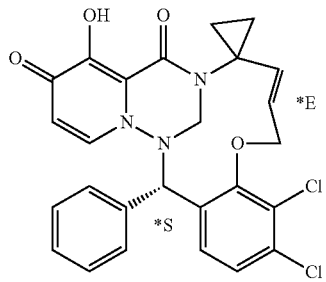

Compounds 113A and 113B were synthesized according to the procedures described in example 79 starting from intermediate 2-(allyloxy)-3,4-dichloro-1-(chloro(phenyl)methyl) benzene (see example 103).

Compound 113A:

LC/MS (method LC-C): Rt 3.21 min, MH$^+$510

[α]$_D^{20}$: +635.27° (c 0.207, DMF)

Chiral HPLC (method HPLC-B): Rt 6.39 min, chiral purity 100%

Compound 113B:

$^1$H NMR (500 MHz, DMSO-d$_6$) δ ppm 8.07 (d, J=8.5 Hz, 1H) 7.70 (d, J=8.5 Hz, 1H) 6.97-7.44 (m, 6H) 6.31-6.55 (m, 1H) 5.83 (br d, J=13.2 Hz, 1H) 5.50 (d, J=7.6 Hz, 1H) 5.38 (s, 1H) 5.15 (d, J=13.9 Hz, 1H) 4.89 (br dd, J=10.9, 5.8 Hz, 1H) 4.35 (br t, J=10.2 Hz, 1H) 4.28 (d, J=13.6 Hz, 1H) 1.55 (dt, J=9.8, 6.8 Hz, 1H) 1.19 (dt, J=9.5, 6.4 Hz, 1H) 0.85-0.97 (m, 1H) 0.71-0.80 (m, 1H)

LC/MS (method LC-C): Rt 3.21 min, MH$^+$510

[α]$_D^{20}$: −663.91° (c 0.169, DMF)

Chiral HPLC (method HPLC-B): Rt 7.11 min, chiral purity 100%

Example 114: (18*R)-4-fluoro-12-hydroxy-18-phenyl-6,7,8,9-tetrahydro-18H-10,17-methanobenzo[b]pyrido[1,2-f][1]oxa[5,6,9]triazacyclotridecine-11,13-dione (Compound 114A) and (18*S)-4-fluoro-12-hydroxy-18-phenyl-6,7,8,9-tetrahydro-18H-10,17-methanobenzo[b]pyrido[1,2-f][1]oxa[5,6,9]triazacyclotridecine-11,13-dione (Compound 114B)

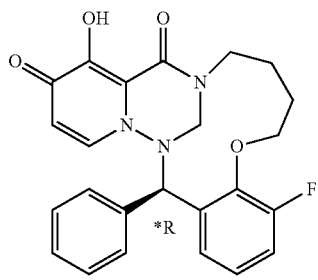

114A and

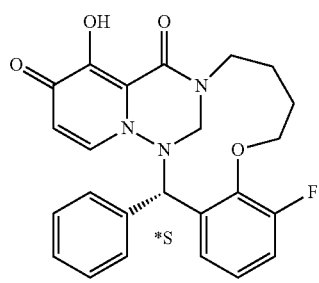

114B

Compounds 114A and 114B were synthesized according to the procedures described in example 8 starting from intermediates 61da and 61db.

Compound 114A:

$^1$H NMR (500 MHz, DMSO-d$_6$) δ ppm 10.26-12.37 (m, 1H) 7.72-7.83 (m, 1H) 7.19-7.35 (m, 4H) 7.13-7.19 (m, 3H) 7.10 (d, J=7.9 Hz, 1H) 5.77 (s, 1H) 5.44 (d, J=7.9 Hz, 1H) 5.01 (d, J=13.6 Hz, 1H) 4.38 (br d, J=12.3 Hz, 1H) 4.30 (d, J=13.6 Hz, 1H) 3.92-4.12 (m, 2H) 2.63 (br d, J=13.9 Hz, 1H) 1.74-1.97 (m, 2H) 1.49-1.66 (m, 1H) 0.91-1.08 (m, 1H)

LC/MS (method LC-C): Rt 2.64 min, MH$^+$436

[α]$_D^{20}$: −336.88° (c 0.141, DMF)

Chiral HPLC (method HPLC-B): Rt 6.03 min, chiral purity 100%

Compound 114B:

LC/MS (method LC-C): Rt 2.64 min, MH$^+$436

[α]$_D^{20}$: +331.55° (c 0.168, DMF)

Chiral HPLC (method HPLC-B): Rt 4.71 min, chiral purity 100%

Example 115: (18*R)-3,4-difluoro-12-hydroxy-18-phenyl-6,7,8,9-tetrahydro-18H-10,17-methanobenzo[b]pyrido[1,2-f][1]oxa[5,6,9]triazacyclotridecine-11,13-dione (Compound 115A) and (18*S)-3,4-difluoro-12-hydroxy-18-phenyl-6,7,8,9-tetrahydro-18H-10,17-methanobenzo[b]pyrido[1,2-f][1]oxa[5,6,9]triazacyclotridecine-11,13-dione (Compound 115B)

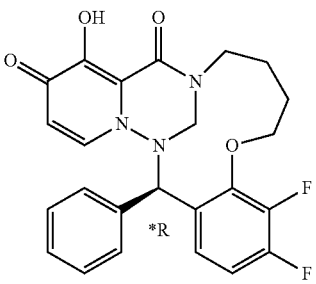

115A and

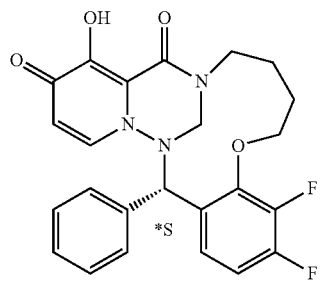

115B

Compounds 115A and 115B were synthesized according to the procedures described in example 8 starting from intermediates 74ea and 74eb.

Compound 115A:

LC/MS (method LC-C): Rt 2.74 min, MH$^+$454

[α]$_D^{20}$: +320.41° (c 0.098, DMF)

Chiral HPLC (method HPLC-A and B): No separation observed

Compound 115B:

$^1$H NMR (500 MHz, DMSO-d$_6$) δ ppm 10.42-12.05 (m, 1H) 7.79 (br t, J=6.8 Hz, 1H) 7.30-7.42 (m, 1H) 7.00-7.28 (m, 6H) 5.70 (s, 1H) 5.44 (d, J=7.6 Hz, 1H) 5.00 (d, J=13.9 Hz, 1H) 4.44 (br d, J=12.3 Hz, 1H) 4.32 (d, J=13.9 Hz, 1H) 3.95-4.16 (m, 2H) 2.62 (br d, J=13.9 Hz, 1H) 1.75-1.97 (m, 2H) 1.55-1.72 (m, 1H) 0.94-1.11 (m, 1H)

LC/MS (method LC-C): Rt 2.74 min, MH$^+$454

[α]$_D^{20}$: −308.21° (c 0.207, DMF)

Chiral HPLC (method HPLC-A and B): No separation observed

339

Example 116: Synthesis of (2*S,Z)-33,34-difluoro-15-hydroxy-2-phenyl-12,13,14,16-tetrahydro-11H-4-oxa-1(1,3)-pyrido[2,1-f][1,2,4]triazina-3(1,2)-benzenacyclononaphan-6-ene-14,16-dione (Enantiomer 116A)

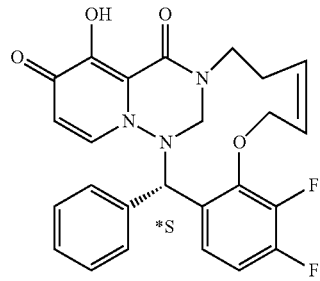 [SMILES: O=C1c2c(O)c(=O)ccn2N2CN1CC/C=C\COc1c(ccc(F)c1F)[C@@H]2c1ccccc1]

Compounds 116A was synthesized according to the procedures described in example 10 starting from intermediate 74c.

Compound 116A:

$^1$H NMR (500 MHz, DMSO-d$_6$) δ ppm 10.71-12.27 (m, 1H) 7.84 (br t, J=6.8 Hz, 1H) 7.30-7.40 (m, 1H) 7.23 (d, J=7.6 Hz, 1H) 6.80-7.18 (m, 5H) 5.96-6.05 (m, 1H) 5.88-5.95 (m, 1H) 5.69 (s, 1H) 5.37 (d, J=7.9 Hz, 1H) 4.97 (d, J=13.2 Hz, 1H) 4.70 (dd, J=11.3, 6.0 Hz, 1H) 4.43 (br t, J=10.2 Hz, 1H) 4.27-4.35 (m, 2H) 2.79 (br d, J=13.9 Hz, 1H) 2.48-2.54 (m, 1H) 2.12 (br d, J=15.8 Hz, 1H)

LC/MS (method LC-C): Rt 2.81 min, MH$^+$466

[α]$_D^{20}$: −316.03° (c 0.156, DMF)

Example 117: Synthesis of (18*R,*Z)-4-fluoro-12-hydroxy-18-(2-methoxyphenyl)-6,9-dihydro-18H-10,17-methanobenzo[b]pyrido[1,2-f][1]oxa[5,6,9]triazacyclotridecine-11,13-dione (Compound 117A) and ((18*S,*Z)-4-fluoro-12-hydroxy-18-(2-methoxyphenyl)-6,9-dihydro-18H-10,17-methanobenzo[b]pyrido[1,2-f][1]oxa[5,6,9]triazacyclotridecine-11,13-dione (compound 117B)

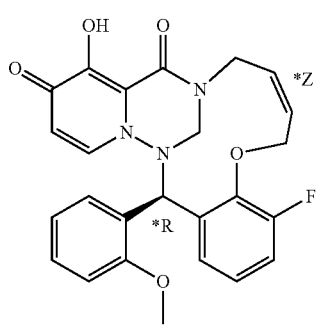

and

340

-continued

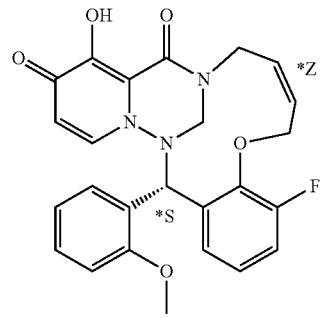

Compounds 117A and 117B were synthesized according to the procedures described in example 5 starting from intermediate 2-(allyloxy)-1-(chloro(2-methoxyphenyl)methyl)-3-fluorobenzene (synthesized as 23a from 2-bromoanisole [CAS 578-57-4] and 3-fluoro-2-(2-propen-1-yloxy)benzaldehyde [CAS 1006304-54-4]).

Compound 117A:

$^1$H NMR (400 MHz, DMSO-d$_6$) δ ppm 10.34-11.38 (m, 1H) 7.92 (br d, J=7.1 Hz, 1H) 7.29-7.47 (m, 2H) 7.04-7.22 (m, 3H) 6.70-6.88 (m, 2H) 6.09-6.28 (m, 2H) 5.85-6.08 (m, 1H) 5.47 (d, J=7.6 Hz, 1H) 5.08 (d, J=13.6 Hz, 1H) 4.87 (br dd, J=13.8, 4.0 Hz, 1H) 4.62-4.79 (m, 1H) 4.11-4.38 (m, 2H) 3.53 (s, 3H) 3.25 (br dd, J=13.7, 8.4 Hz, 1H)

LC/MS (method LC-C): Rt 2.59 min, MH$^+$464

[α]$_D^{20}$: −653.6° (c 0.222, DMF)

Chiral HPLC (method HPLC-B): Rt 4.48 min, chiral purity 100%

Compound 117B:

LC/MS (method LC-C): Rt 2.59 min, MH$^+$464

[α]$_D^{20}$: +674.02° (c 0.204, DMF)

Chiral HPLC (method HPLC-B): Rt 4.21 min, chiral purity 100%

Example 118: Synthesis of (1a*R,11b*S,20a*S)-17-hydroxy-1a,2,6,11 b,17,17a,20,20a-octahydro-1H-5,4-(epiprop[1]en[1]yl[3]ylidene)-12,19-methanobenzo[6,7]thiepino[4,5-c]cyclopropa[k]pyrido[1,2-f][1]oxa[5,6,9]triazacyclotridecine-16,18-dione (Compound 118AA), (1a*S,11b*S,20a*R)-17-hydroxy-1a,2,6,11b,17,17a,20,20a-octahydro-1H-5,4-(epiprop[1]en[1]yl[3]ylidene)-12,19-methanobenzo[6,7]thiepino[4,5-c]cyclopropa[k]pyrido[1,2-f][1]oxa[5,6,9]triazacyclotridecine-16,18-dione (Compound 118AB)

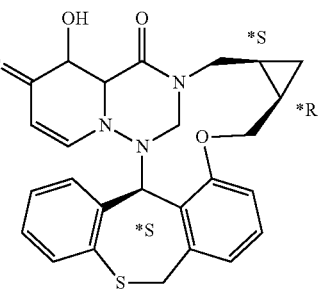

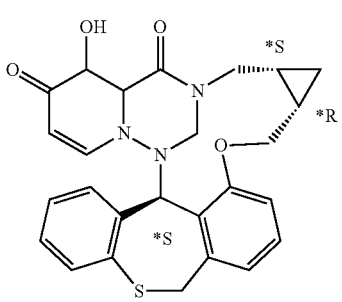

118AB

Compounds 118AA and 118AB were synthesized according to the procedures described in example 87 starting from intermediate cis-((1RS,2RS)-2-(((tert-butyldiphenylsilyl)oxy)methyl)cyclopropyl)methanamine.

Compound 118AA:

$^1$H NMR (500 MHz, DMSO-d$_6$) δ ppm 11.36-11.81 (m, 1H) 7.37-7.43 (m, 1H) 7.33 (t, J=8.0 Hz, 2H) 7.04-7.20 (m, 3H) 6.76-6.84 (m, 1H) 6.61 (d, J=7.6 Hz, 1H) 6.16 (s, 1H) 5.75 (d, J=13.6 Hz, 1H) 5.62 (d, J=7.6 Hz, 1H) 5.06 (br dd, J=13.2, 4.7 Hz, 1H) 4.95 (d, J=12.9 Hz, 1H) 4.70 (d, J=13.2 Hz, 1H) 3.82-3.95 (m, 2H) 3.79 (d, J=13.6 Hz, 1H) 3.56-3.67 (m, 1H) 1.29-1.37 (m, 1H) 0.99-1.07 (m, 1H) 0.88 (td, J=8.5, 4.1 Hz, 1H) 0.58 (q, J=4.7 Hz, 1H)

LC/MS (method LC-C): Rt 2.74 min, MH$^+$474

[α]$_D^{20}$: −211.69° (c 0.154, DMF)

Chiral HPLC (method HPLC-B): Rt 8.50 min, chiral purity 100%

Compound 118AB:

$^1$H NMR (500 MHz, DMSO-d$_6$) δ ppm 11.77-12.15 (m, 1H) 7.38 (t, J=7.9 Hz, 1H) 7.28 (d, J=7.9 Hz, 1H) 7.11-7.17 (m, 2H) 7.08 (br d, J=3.5 Hz, 2H) 6.82-6.89 (m, 1H) 6.70 (d, J=7.6 Hz, 1H) 6.46 (s, 1H) 5.70 (d, J=14.2 Hz, 1H) 5.61 (d, J=7.6 Hz, 1H) 4.94-5.05 (m, 2H) 4.03-4.14 (m, 2H) 3.77 (d, J=13.9 Hz, 1H) 3.35-3.41 (m, 1H) 2.66-2.75 (m, 1H) 2.06-2.19 (m, 1H) 1.50-1.65 (m, 1H) 0.85-0.94 (m, 1H) 0.16 (q, J=5.4 Hz, 1H)

LC/MS (method LC-C): Rt 2.74 min, MH$^+$474

[α]$_D^{20}$: −209.03° (c 0.144, DMF)

Chiral HPLC (method HPLC-B): Rt 7.63 min, chiral purity 100%

Example 119: Synthesis of (18*R,*Z)-4-fluoro-12-hydroxy-18-(2-(methylthio)phenyl)-6,9-dihydro-18H-10,17-methanobenzo[b]pyrido[1,2-f][1]oxa[5,6,9]triazacyclotridecine-11,13-dione (Compound 119A) and (18*S,*Z)-4-fluoro-12-hydroxy-18-(2-(methylthio)phenyl)-6,9-dihydro-18H-10,17-methanobenzo[b]pyrido[1,2-f][1]oxa[5,6,9]triazacyclotridecine-11,13-dione (Compound 119B)

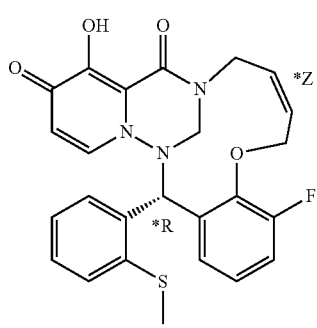

119A and

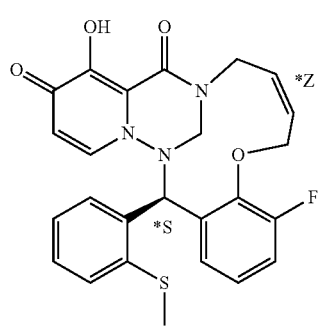

119B

Compounds 119A and 119B were synthesized according to the procedures described in example 5 starting from intermediate (2-((2-(allyloxy)-3-fluorophenyl)chloromethyl)phenyl)(methyl)sulfane (synthesized as 23a from 1-bromo-2-methylthiobenzene [CAS 19614-16-5] and 3-fluoro-2-(2-propen-1-yloxy)benzaldehyde [CAS 1106304-54-4]).

Compound 119A:

[α]$_D^{20}$: +670.86° (c 0.175, DMF)

Chiral HPLC (method HPLC-A): Rt 7.54 min, chiral purity 98.93%

Compound 119B:

$^1$H NMR (500 MHz, DMSO-d$_6$) δ ppm 9.72-12.25 (m, 1H) 7.92 (br d, J=7.6 Hz, 1H) 7.49 (d, J=7.3 Hz, 1H) 7.40 (td, J=8.0, 5.5 Hz, 1H) 7.26-7.36 (m, 2H) 7.17-7.23 (m, 1H) 7.09-7.16 (m, 2H) 6.23-6.47 (m, 2H) 5.82-6.11 (m, 1H) 5.46 (d, J=7.9 Hz, 1H) 5.13 (d, J=13.9 Hz, 1H) 4.86 (br dd, J=14.2, 4.7 Hz, 1H) 4.73-4.82 (m, 1H) 4.13-4.33 (m, 2H) 3.20-3.25 (m, 1H) 2.28 (s, 3H)

[α]$_D^{20}$: −701.36° (c 0.22, DMF)

Chiral HPLC (method HPLC-A): Rt 5.95 min, chiral purity 100%

Example 120: Synthesis of (((18'*R,E)-4'-fluoro-11',13'-dioxo-18'-phenyl-11',13'-dihydro-6'H,18'H-spiro[cyclopropane-1,9'-[10,17]methanobenzo[b]pyrido[1,2-f][1]oxa[5,6,9]triazacyclotridecin]-12'-yl)oxy)methyl methyl carbonate (Compound 120)

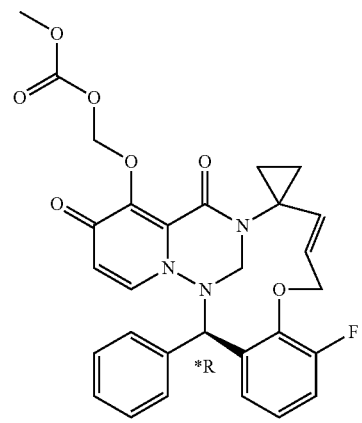

120

Compounds 120 was synthesized according to the procedure described in example 62 starting from compound 95B and using 1,8diazabicyclo[5.4.0]undec-7-ene (DBU) and CH$_3$CN.

Compound 120:

¹H NMR (400 MHz, DMSO-d₆) δ ppm 7.90 (d, J=7.7 Hz, 1H) 7.32-7.47 (m, 2H) 7.06-7.31 (m, 6H) 6.25-6.46 (m, 1H) 5.82-5.99 (m, 1H) 5.74-5.80 (m, 1H) 5.71 (d, J=7.8 Hz, 1H) 5.53 (d, J=6.6 Hz, 1H) 5.33 (s, 1H) 5.12 (d, J=13.8 Hz, 1H) 4.83 (br dd, J=10.9, 6.4 Hz, 1H) 4.11-4.26 (m, 2H) 3.78 (s, 3H) 1.26-1.37 (m, 1H) 1.16 (dt, J=9.6, 6.5 Hz, 1H) 0.78-0.91 (m, 1H) 0.68-0.77 (m, 1H)

LC/MS (method LC-B): Rt 2.57 min, MH⁺548

[α]$_D^{20}$: −480.51° (c 0.195, DMF)

Chiral HPLC (method HPLC-B): Rt 7.85 min, chiral purity 100%

Example 121: Synthesis of (9*R,18*R,*E)-3,4-dichloro-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 121AA) and (9*S,18*R,*E)-3,4-dichloro-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 121AB) and (9*R,18*S,*E)-3,4-dichloro-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 121BA) and (9*S,18*S,*E)-3,4-dichloro-9-ethyl-12-hydroxy-18-phenyl-6,9-dihydro-18H-10,17-methanobenzo[b]pyrido[1,2-f][1]oxa[5,6,9]triazacyclotridecine-11,13-dione (Compound 121BB)

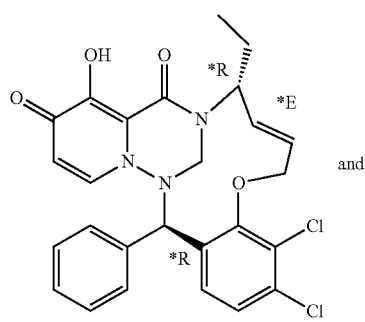

121AA

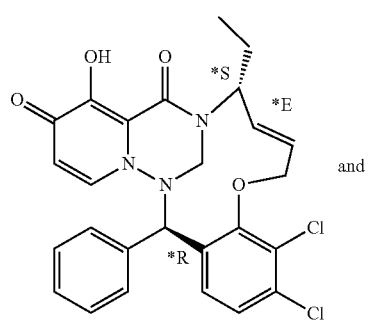

121AB

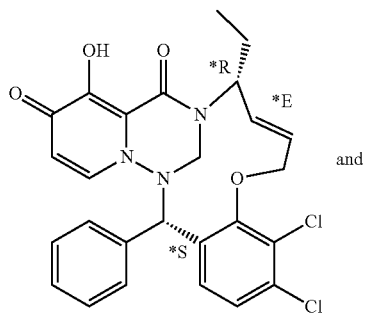

121BA

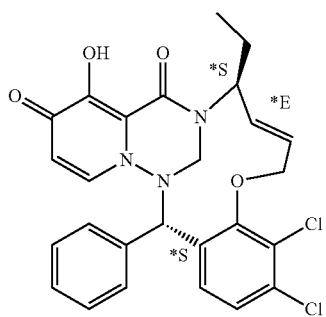

121BB

Compounds 121AA, 121AB, 121BA and 121BB were synthesized according to the procedures described in example 39 starting from intermediate 2-(allyloxy)-3,4-dichloro-1-(chloro(phenyl)methyl)benzene (see example 103).

Compound 121AA:

¹H NMR (500 MHz, DMSO-d₆) δ ppm 8.13 (d, J=8.5 Hz, 1H) 7.70 (d, J=8.8 Hz, 1H) 6.99-7.39 (m, 6H) 6.41 (ddd, J=15.4, 10.4, 5.0 Hz, 1H) 5.66 (br dd, J=15.6, 6.5 Hz, 1H) 5.48 (d, J=7.6 Hz, 1H) 5.24 (s, 1H) 5.18 (q, J=7.6 Hz, 1H) 5.07 (d, J=13.6 Hz, 1H) 4.89 (br dd, J=11.7, 5.0 Hz, 1H) 4.29 (d, J=13.6 Hz, 1H) 4.12 (br t, J=11.0 Hz, 1H) 1.41-1.66 (m, 2H) 0.84 (br t, J=7.3 Hz, 3H)

LC/MS (method LC-C): Rt 3.34 min, MH⁺512

[α]$_D^{20}$: −564.94° (c 0.154, DMF)

Chiral HPLC (method HPLC-B): Rt 7.11 min, chiral purity 100%

Compound 121AB:

LC/MS (method LC-C): Rt 3.37 min, MH⁺512

[α]D²⁰: +755.34° (c 0.103, DMF)

Chiral HPLC (method HPLC-B): Rt 4.80 min, chiral purity 100%

Compound 121BA:

¹H NMR (500 MHz, DMSO-d₆) δ ppm 8.09 (d, J=8.5 Hz, 1H) 7.63 (d, J=8.8 Hz, 1H) 7.26 (br d, J=7.6 Hz, 1H) 6.82-7.20 (m, 5H) 6.28-6.57 (m, 1H) 5.67-5.97 (m, 1H) 5.42 (d, J=7.6 Hz, 1H) 5.36 (s, 1H) 5.16 (d, J=13.9 Hz, 1H) 4.72-4.88 (m, 1H) 4.55-4.68 (m, 1H) 4.22 (br d, J=14.2 Hz, 1H) 3.35-3.43 (m, 1H) 2.20-2.28 (m, 1H) 2.03-2.15 (m, 1H) 0.80 (t, J=7.4 Hz, 3H)

LC/MS (method LC-C): Rt 3.37 min, MH⁺512

[α]$_D^{20}$: −732.23° (c 0.121, DMF)

Chiral HPLC (method HPLC-B): Rt 4.83 min, chiral purity 100%

Compound 121BB:

LC/MS (method LC-C): Rt 3.34 min. MH⁺512

[α]$_D^{20}$: +606.32° (c 0.190, DMF)

Chiral HPLC (method HPLC-B): Rt 5.55 min, chiral purity 100%

Example 122: Synthesis of (18*S,*Z)-4-fluoro-12-hydroxy-18-(2-(methylsulfonyl)phenyl)-6,9-dihydro-18H-10,17-methanobenzo[b]pyrido[1,2-f][1]oxa[5,6,9]triazacyclotridecine-11,13-dione (Compound 122)

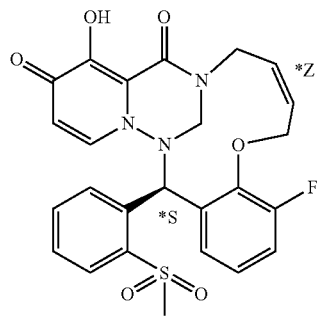

122

Compound 122 was synthesized according to the procedures described in example 82 starting from the O-benzyl protected 119A.

Compound 122:

$^1$H NMR (500 MHz, DMSO-d$_6$) δ ppm 11.26-11.67 (m, 1H) 8.11 (d, J=7.6 Hz, 1H) 8.02 (br d, J=7.6 Hz, 1H) 7.84 (dd, J=8.2, 1.3 Hz, 1H) 7.62-7.73 (m, 1H) 7.50-7.58 (m, 1H) 7.42-7.48 (m, 1H) 7.34-7.41 (m, 1H) 7.06 (br d, J=7.3 Hz, 1H) 6.89 (s, 1H) 6.20-6.47 (m, 1H) 5.73-6.01 (m, 1H) 5.43 (d, J=7.9 Hz, 1H) 5.12 (d, J=13.9 Hz, 1H) 4.83-4.94 (m, 1H) 4.79 (dd, J=14.0, 4.3 Hz, 1H) 4.18-4.37 (m, 2H) 3.25 (s, 3H) 3.18 (dd, J=14.2, 7.6 Hz, 1H)

LC/MS (method LC-C): Rt 2.31 min, MH$^+$512

[α]$_D^{20}$: −570.59° (c 0.102, DMF)

Chiral HPLC (method HPLC-A and B): No separation observed

Example 123: synthesis (18R,E)-18-(2-cyclopropylphenyl)-4-fluoro-12-hydroxy-6,9-dihydro-18H-10,17-methanobenzo[b]pyrido[1,2-f][1]oxa[5,6,9]triazacyclotridecine-11,13-dione (Compound 123A) and (18S,E)-18-(2-cyclopropylphenyl)-4-fluoro-12-hydroxy-6,9-dihydro-18H-10,17-methanobenzo[b]pyrido[1,2-f][1]oxa[5,6,9]triazacyclotridecine-11,13-dione (compound 123B)

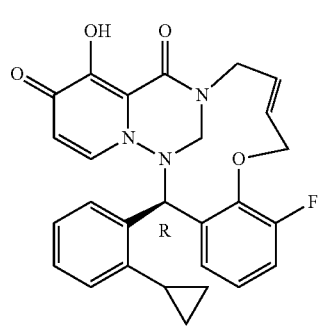

123A and

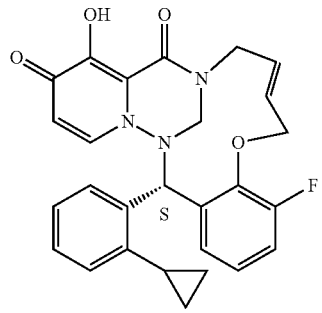

123B

Compounds 123A and 123B were synthesized according to the procedures described in example 5 starting from intermediate 2-(allyloxy)-1-(chloro(2-cyclopropylphenyl)methyl)-3-fluorobenzene (synthesized as 23a from 1-bromo-2-cyclopropylbenzene [CAS 57807-28-0] and 3-fluoro-2-(2-propen-1-yloxy)benzaldehyde [CAS 1106304-54-4]).

Compound 123A:

$^1$H NMR (500 MHz, DMSO-d$_6$) δ ppm 7.96 (br d, J=7.9 Hz, 1H) 7.57-7.67 (m, 1H) 7.40 (td, J=8.0, 5.4 Hz, 1H) 7.29-7.36 (m, 1H) 7.26 (br d, J=7.6 Hz, 1H) 7.03-7.14 (m, 2H) 6.77-6.87 (m, 1H) 6.10-6.24 (m, 1H) 6.06 (br s, 1H) 5.84-5.98 (m, 1H) 5.51 (d, J=7.9 Hz, 1H) 5.18 (d, J=13.9 Hz, 1H) 4.76-4.88 (m, 2H) 4.37 (d, J=13.9 Hz, 1H) 4.24 (br s, 1H) 3.25 (br dd, J=13.9, 7.9 Hz, 1H) 2.01-2.10 (m, 1H) 0.85-0.99 (m, 2H) 0.76-0.84 (m, 1H) 0.00-0.05 (m, 1H)

LC/MS (method LC-C): Rt 2.78 min, MH$^+$474

[α]$_D^{20}$: −700.56° (c 0.177, DMF)

Chiral HPLC (method HPLC-A): Rt 5.42 min, chiral purity 100%

Compound 123B:

LC/MS (method LC-C): Rt 2.78 min, MH$^+$474

[α]$_D^{20}$: +721.21° (c 0.165, DMF)

Chiral HPLC (method HPLC-A): Rt 5.90 min, chiral purity 100%

Example 124: Synthesis of (9*S,18*R,*E)-4-fluoro-12-hydroxy-9-isopropyl-18-phenyl-6,9-dihydro-18H-10,17-methanobenzo[b]pyrido[1,2-f][1]oxa[5,6,9]triazacyclotridecine-11,13-dione (Compound 124AA) and (9*R,18*S,*E)-4-fluoro-12-hydroxy-9-isopropyl-18-phenyl-6,9-dihydro-18H-10,17-methanobenzo[b]pyrido[1,2-f][1]oxa[5,6,9]triazacyclotridecine-11,13-dione (Compound 124BB)

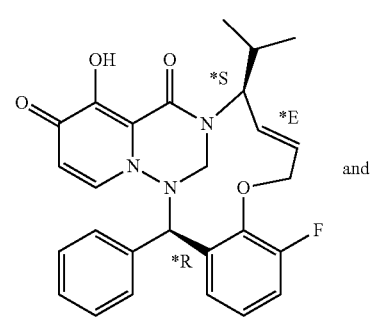

124AA and

-continued

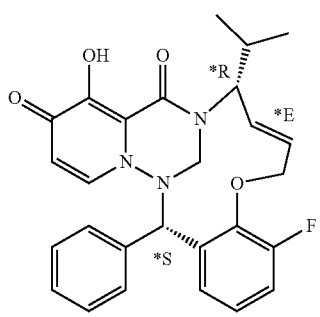

124BB

Compounds 124AA and 124BB were synthesized according to the procedures described in example 39 starting from intermediates 5-hydroxy-3-(4-methylpent-1-en-3-yl)-2,3-dihydro-1H-pyrido[2,1-f][1,2,4]triazine-4,6-dione (synthesized as 39e from 4-methylpent-1-en-3-amine [CAS 127209-34-1] and 2-(allyloxy)-1-(chloro(phenyl)methyl)-3-fluorobenzene 61b).

Compound 124AA:
LC/MS (method LC-C): Rt 3.03 min, MH⁺476
$[\alpha]_D^{20}$: +522.41° (c 0.116, DMF)
Chiral HPLC (method HPLC-B): Rt 5.90 min, chiral purity 100%

Compound 124BB:
¹H NMR (500 MHz, DMSO-d₆) δ ppm 7.93 (br d, J=7.6 Hz, 1H) 7.39-7.45 (m, 1H) 7.33-7.39 (m, 1H) 7.02-7.31 (m, 6H) 6.38 (ddd, J=15.4, 10.1, 5.4 Hz, 1H) 5.60 (br dd, J=15.8, 6.9 Hz, 1H) 5.48 (d, J=7.6 Hz, 1H) 5.22 (s, 1H) 5.10 (br d, J=13.6 Hz, 1H) 4.87 (br dd, J=11.3, 6.0 Hz, 2H) 4.24 (br d, J=13.6 Hz, 1H) 4.01 (br t, J=10.9 Hz, 1H) 1.60-1.79 (m, 1H) 0.85 (br d, J=4.4 Hz, 6H)
LC/MS (method LC-C): Rt 3.03 min, MH⁺476
$[\alpha]_D^{20}$: −638.98° (c 0.118, DMF)
Chiral HPLC (method HPLC-B): Rt 5.61 min, chiral purity 100%

Example 125: Synthesis of (1a*R,8*R,17a*R)-4-fluoro-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (Compound 125AA), (1a*R,8*S,17a*R)-4-fluoro-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (Compound 125AB), (1a*S,8*R,17a*S)-4-fluoro-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (Compound 125BA) and (1a*S,8*S,17a*S)-4-fluoro-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (Compound 125BB)

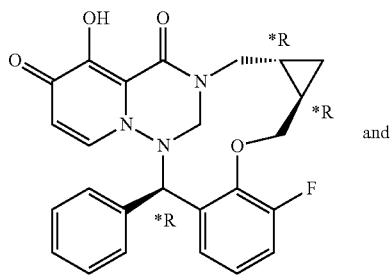

125AA

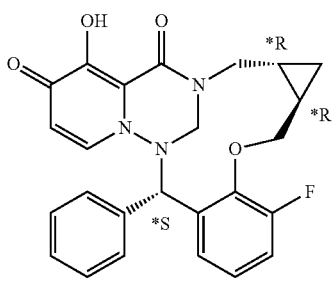

125BA

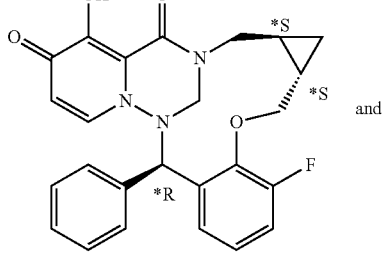

125AB

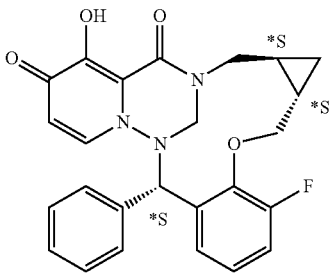

125BB

Compounds 125AA, 125AB, 125BA and 125BB were synthesized according to the procedures described in example 80 starting from intermediate 2-(allyloxy)-1-(chloro(phenyl)methyl)-3-fluorobenzene 61b.

Compound 125AA:
¹H NMR (500 MHz, DMSO-d₆) δ ppm 7.99 (br d, J=7.6 Hz, 1H) 7.21-7.40 (m, 3H) 7.12 (br s, 5H) 5.98 (s, 1H) 5.43 (d, J=7.6 Hz, 1H) 5.09 (br d, J=13.6 Hz, 1H) 4.66 (br dd, J=12.1, 2.7 Hz, 1H) 4.32 (br d, J=13.6 Hz, 2H) 3.29-3.37 (m, 1H) 2.11 (br dd, J=13.6, 11.7 Hz, 1H) 1.34 (br s, 1H) 0.93-1.10 (m, 1H) 0.48 (dt, J=8.8, 4.4 Hz, 1H) 0.31 (dt, J=8.9, 4.5 Hz, 1H)
LC/MS (method LC-C): Rt 2.69 min, MH⁺448
$[\alpha]_D^{20}$: −483.78° (c 0.148, DMF)
Chiral HPLC (method HPLC-B): Rt 4.33 min, chiral purity 100%

Compound 125BA:
LC/MS (method LC-C): Rt 2.71 min, MH⁺448
$[\alpha]_D^{20}$: +282.00° (c 0.100, DMF)
Chiral HPLC (method HPLC-B): Rt 4.71 min, chiral purity 100%

Compound 125BB:
LC/MS (method LC-C): Rt 2.69 min, MH⁺448
$[\alpha]_D^{20}$: +458.06° (c 0.155, DMF)
Chiral HPLC (method HPLC-B): Rt 4.33 min, chiral purity 100%

Compound 125AB:
¹H NMR (500 MHz, DMSO-d₆) δ ppm 7.89 (d, J=7.6 Hz, 1H) 7.30-7.37 (m, 1H) 7.17-7.30 (m, 7H) 5.98 (s, 1H) 5.50 (d, J=7.6 Hz, 1H) 5.10 (d, J=13.6 Hz, 1H) 4.84 (dd, J=12.9, 4.1 Hz, 1H) 4.56 (d, J=13.6 Hz, 1H) 3.58 (br dd, J=14.5, 10.7

Hz, 1H) 3.12-3.25 (m, 2H) 1.34-1.47 (m, 1H) 0.88 (td, J=9.2, 4.9 Hz, 1H) 0.70 (dt, J=8.7, 4.5 Hz, 1H) 0.50-0.59 (m, 1H)

LC/MS (method LC-C): Rt 2.71 min, MH$^+$448

$[\alpha]_D^{20}$: −299.14 (c 0.116, DMF)

Chiral HPLC (method HPLC-B): Rt 5.55 min, chiral purity 100%

Example 126: Synthesis of (13*S,21a*R,Z)-13-ethyl-24,25-difluoro-16-hydroxy-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (Compound 126AA), (9*R,17a*R,E)-9-ethyl-24,25-difluoro-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 126AB), (9*S,17a*S,E)-9-ethyl-24,25-difluoro-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 126BA), (13*R,21a*S,Z)-13-ethyl-24,25-difluoro-16-hydroxy-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (Compound 126BB)

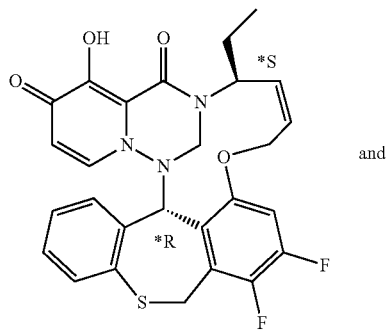

126AA and

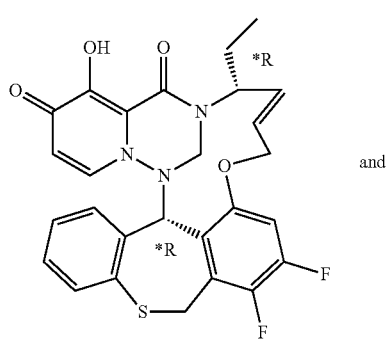

126AB and

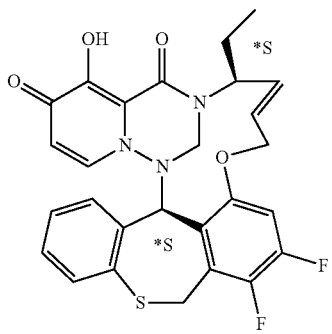

126BA and

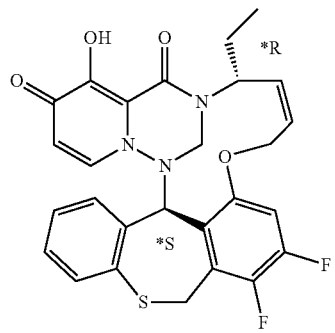

126BB

Compounds 126AA, 126AB, 126BA and 126BB were synthesized according to the procedures described in example 88 starting from intermediate 39e.

Compound 126AA:
LC/MS (method LC-C): Rt 3.17 min, MH$^+$524
$[\alpha]_D^{20}$: +115.09° (c 0.212, DMF)
Chiral HPLC (method HPLC-B): Rt 4.29 min, chiral purity 100%

Compound 126AB:
LC/MS (method LC-C): Rt 3.08 min, MH$^+$524
$[\alpha]_D^{20}$: +423.19° (c 0.138, DMF)
Chiral HPLC (method HPLC-B): Rt 5.57 min, chiral purity 100%

Compound 126BA:
$^1$H NMR (500 MHz, DMSO-d$_6$) δ ppm 11.06-11.91 (m, 1H) 7.43 (br dd, J=11.5, 7.4 Hz, 1H) 7.26 (d, J=7.6 Hz, 1H) 7.11-7.18 (m, 1H) 7.04-7.11 (m, 1H) 6.86-6.92 (m, 1H) 6.79-6.85 (m, 1H) 6.33 (ddd, J=15.4, 9.8, 5.7 Hz, 1H) 5.58-5.74 (m, 3H) 5.27 (s, 1H) 5.16 (q, J=7.6 Hz, 1H) 5.02 (d, J=13.9 Hz, 1H) 4.85 (br dd, J=11.5, 5.5 Hz, 1H) 4.43 (d, J=13.6 Hz, 1H) 4.31 (br t, J=10.7 Hz, 1H) 4.12 (br d, J=14.2 Hz, 1H) 1.42-1.69 (m, 2H) 0.83 (br t, J=7.3 Hz, 3H)
LC/MS (method LC-C): Rt 3.08 min, MH$^+$524
$[\alpha]D^{20}$: −436.7° (c 0.109, DMF)
Chiral HPLC (method HPLC-A and B): No separation observed Compound 126BB:
$^1$H NMR (500 MHz, DMSO-d$_6$) δ ppm 10.86-12.40 (m, 1H) 7.36 (dd, J=11.8, 6.8 Hz, 1H) 7.07-7.25 (m, 3H) 6.78-6.92 (m, 1H) 6.53 (d, J=7.6 Hz, 1H) 6.48 (t, J=9.9 Hz, 1H) 6.22 (dt, J=10.6, 7.0 Hz, 1H) 5.98 (s, 1H) 5.54-5.68 (m, 2H) 5.17 (d, J=13.2 Hz, 1H) 4.79 (dd, J=10.2, 6.8 Hz, 1H) 4.49 (d, J=13.6 Hz, 1H) 4.43 (br t, J=8.8 Hz, 1H) 4.04 (d, J=14.2 Hz, 1H) 3.84 (q, J=7.6 Hz, 1H) 1.89 (br dd, J=13.9, 6.9 Hz, 1H) 1.72-1.83 (m, 1H) 0.83 (t, J=7.4 Hz, 3H)
LC/MS (method LC-C): Rt 3.19 min, MH$^+$524
$[\alpha]_D^{20}$: −118.70° (c 0.123, DMF)

Chiral HPLC (method HPLC-A and B): No separation observed

Example 127: Synthesis of (1a*S,11b*S,20a*S)-22,23-difluoro-17-hydroxy-1a,2,6,11b,20,20a-hexahydro-1H-5,4-(epiprop[1]en[1]yl[3]ylidene)-12,19-methanobenzo[6,7]thiepino[4,5-c]cyclopropa[k]pyrido[1,2-f][1]oxa[5,6,9]triazacyclotridecine-16,18-dione (Compound 127AA), (1a*S,11b*R,20a*S)-22,23-difluoro-17-hydroxy-1a,2,6,11b,20,20a-hexahydro-1H-5,4-(epiprop[1]en[1]yl[3]ylidene)-12,19-methanobenzo[6,7]thiepino[4,5-c]cyclopropa[k]pyrido[1,2-f][1]oxa[5,6,9]triazacyclotridecine-16,18-dione (Compound 127BA)

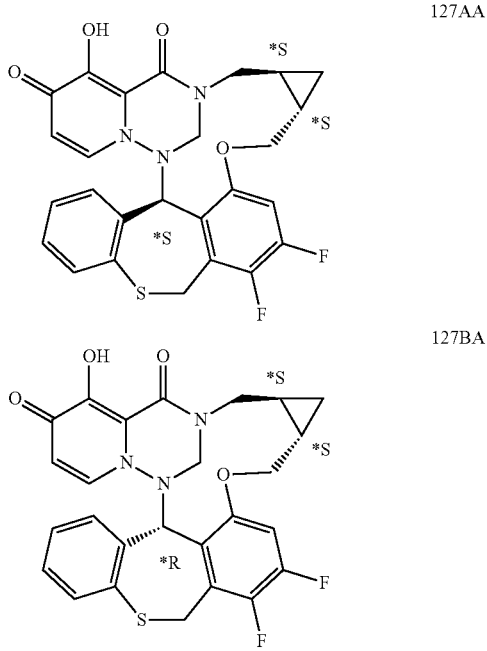

Compounds 127AA and 127BA were synthesized according to the procedures described in example 87 starting from intermediate 88n.

Compound 127AA:
$^1$H NMR (400 MHz, DMSO-d$_6$) δ ppm 10.78-12.30 (m, 1H) 7.28 (br dd, J=12.3, 7.0 Hz, 1H) 7.06-7.21 (m, 3H) 6.88 (t, J=7.3 Hz, 1H) 6.76 (d, J=7.6 Hz, 1H) 6.01 (s, 1H) 5.56-5.70 (m, 2H) 5.04 (br d, J=13.7 Hz, 1H) 4.82 (dd, J=12.7, 5.0 Hz, 1H) 4.65 (d, J=13.7 Hz, 1H) 4.10 (d, J=14.1 Hz, 1H) 3.46-3.57 (m, 2H) 3.12 (br dd, J=14.3, 5.1 Hz, 1H) 1.28-1.41 (m, 1H) 1.00 (td, J=9.1, 4.7 Hz, 1H) 0.79 (dt, J=8.5, 4.4 Hz, 1H) 0.66 (dt, J=8.4, 4.4 Hz, 1H)

LC/MS (method LC-C): Rt 2.92 min, MH$^+$510

[α]$_D^{20}$: −152.03° (c 0.148, DMF)

Chiral HPLC (method HPLC-B): Rt 8.81 min, chiral purity 97.46%

Compound 127BA:
$^1$H NMR (400 MHz, DMSO-d$_6$) δ ppm 11.18-11.92 (m, 1H) 7.66 (br dd, J=12.5, 7.3 Hz, 1H) 7.39 (d, J=7.7 Hz, 1H) 7.04-7.20 (m, 2H) 6.88 (t, J=7.2 Hz, 1H) 6.77 (br d, J=7.6 Hz, 1H) 6.12 (s, 1H) 5.81 (br d, J=15.0 Hz, 1H) 5.62 (d, J=7.6 Hz, 1H) 5.10 (br d, J=13.7 Hz, 1H) 4.89 (br dd, J=12.2, 2.6 Hz, 1H) 4.49 (br d, J=13.6 Hz, 1H) 4.31 (br d, J=12.5 Hz, 1H) 4.10 (br d, J=14.1 Hz, 1H) 3.36-3.42 (m, 1H) 2.02-2.15 (m, 1H) 1.13-1.40 (m, 2H) 0.63 (dt, J=8.8, 4.6 Hz, 1H) 0.37-0.52 (m, 1H)

LC/MS (method LC-C): Rt 2.89 min, MH$^+$510

[α]$_D^{20}$: −280.13° (c 0.156, DMF)

Chiral HPLC (method HPLC-B): Rt 6.54 min, chiral purity 97.58%

Example 128: Synthesis of (9*R,18*R,*E)-3,4-difluoro-12-hydroxy-9-isopropyl-18-phenyl-6,9-dihydro-18H-10,17-methanobenzo[b]pyrido[1,2-f][1]oxa[5,6,9]triazacyclotridecine-11,13-dione (Compound 128AA) (9*S,18*R,*E)-3,4-difluoro-12-hydroxy-9-isopropyl-18-phenyl-6,9-dihydro-18H-10,17-methanobenzo[b]pyrido[1,2-f][1]oxa[5,6,9]triazacyclotridecine-11,13-dione (Compound 128AB) and (9*R,18*S,*E)-3,4-difluoro-12-hydroxy-9-isopropyl-18-phenyl-6,9-dihydro-18H-10,17-methanobenzo[b]pyrido[1,2-f][1]oxa[5,6,9]triazacyclotridecine-11,13-dione (Compound 128BA) and (9*S,18*S,*E)-9-ethyl-3,4-difluoro-12-hydroxy-18-phenyl-6,9-dihydro-18H-10,17-methanobenzo[b]pyrido[1,2-f][1]oxa[5,6,9]triazacyclotridecine-11,13-dione (Compound 128BB)

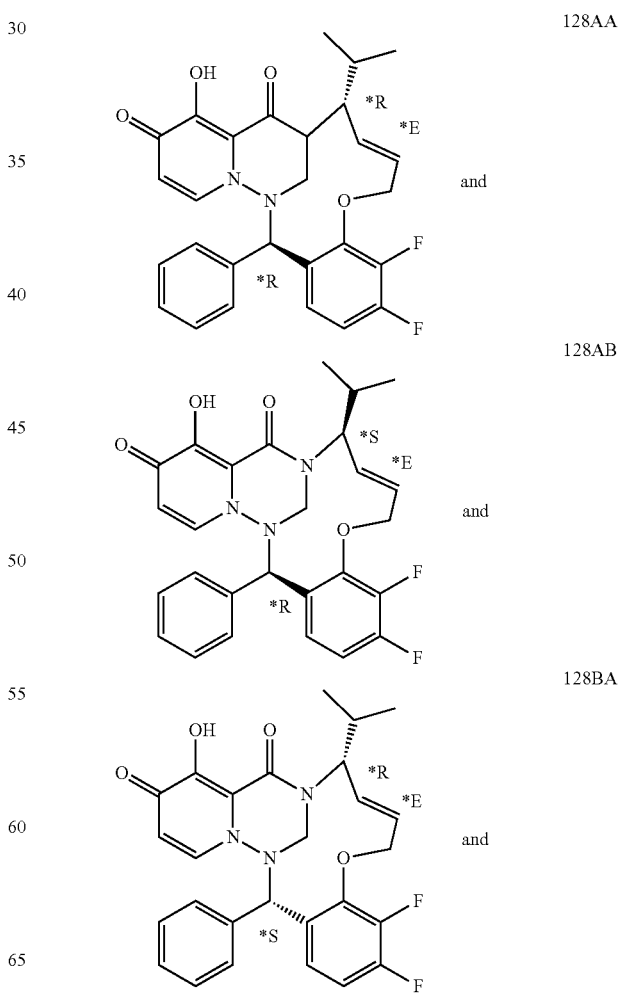

353
-continued

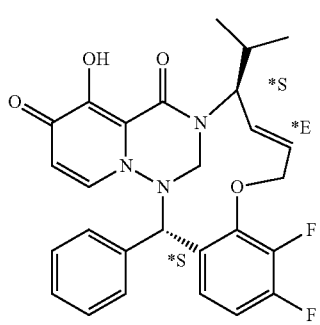

128BB

Compounds 128AA, 128AB, 128BA and 128BB were synthesized according to the procedures described in example 39 starting from intermediates 5-hydroxy-3-(4-methylpent-1-en-3-yl)-2,3-dihydro-1H-pyrido[2,1-f][1,2,4]triazine-4,6-dione (see example 124) and 2-(allyloxy)-1-(chloro(phenyl)methyl)-3,4-difluorobenzene 74c.

Compound 128AA:

LC/MS (method LC-C): Rt 3.12 min, MH+494

$[\alpha]_D^{20}$: +564.63° (c 0.147, DMF)

Chiral HPLC (method HPLC-B): Rt 4.18 min, chiral purity 100%

Compound 128AB:

LC/MS (method LC-C): Rt 3.29 min, MH+494

$[\alpha]_D^{20}$: +306.67° (c 0.135, DMF)

Chiral HPLC (method HPLC-A): Rt 4.93 min, chiral purity 100%

Compound 128BA:

$^1$H NMR (500 MHz, DMSO-d$_6$) δ ppm 10.01-11.61 (m, 1H) 7.52 (br d, J=7.6 Hz, 1H) 7.25-7.45 (m, 5H) 6.92 (q, J=8.4 Hz, 1H) 6.27-6.43 (m, 1H) 5.98-6.10 (m, 2H) 5.82-5.98 (m, 2H) 5.15 (br d, J=13.2 Hz, 1H) 4.96-5.10 (m, 2H) 4.81-4.92 (m, 1H) 4.30 (br t, J=10.4 Hz, 1H) 1.76-2.00 (m, 1H) 0.92 (br d, J=6.3 Hz, 3H) 0.75 (br d, J=6.3 Hz, 3H)

LC/MS (method LC-C): Rt 3.29 min, MH+494

$[\alpha]_D^{20}$: −311.32° (c 0.106, DMF)

Chiral HPLC (method HPLC-A): Rt 4.56 min. chiral purity 100%

Compound 128BB:

$^1$H NMR (500 MHz, DMSO-d$_6$) δ ppm 7.94 (br t, J=6.9 Hz, 1H) 7.43-7.58 (m, 1H) 7.03-7.35 (m, 6H) 6.37 (ddd, J=15.4, 10.1, 5.4 Hz, 1H) 5.75 (br dd, J=15.6, 7.1 Hz, 1H) 5.47 (d, J=7.6 Hz, 1H) 5.15 (s, 1H) 5.08 (d, J=13.6 Hz, 1H) 4.91 (dd, J=11.3, 5.4 Hz, 1H) 4.85 (dd, J=11.0, 6.9 Hz, 1H) 4.24 (d, J=13.6 Hz, 1H) 4.08 (br t, J=10.9 Hz, 1H) 1.63-1.81 (m, 1H) 0.85 (d, J=6.3 Hz, 6H)

LC/MS (method LC-C): Rt 3.12 min, MH+494

$[\alpha]_D^{20}$: −555.17° (c 0.174, DMF)

Chiral HPLC (method HPLC-B): Rt 5.87 min, chiral purity 100%

Example 129: Synthesis of (((18'R,E)-3',4'-difluoro-11',13'-dioxo-18'-phenyl-11',13'-dihydro-6'H,18'H-spiro[cyclopropane-1,9'-[10,17]methanobenzo[b]pyrido[1,2-f][1]oxa[5,6,9]triazacyclotridecin]-12'-yl)oxy)methyl methyl carbonate (Compound 129)

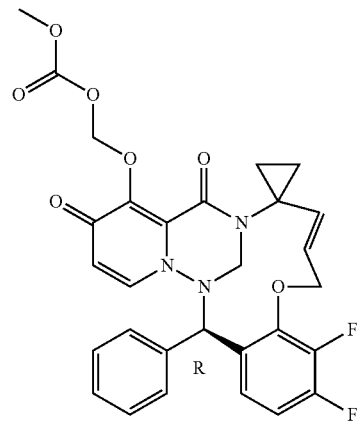

129

Compounds 120 was synthesized according to the procedure described in example 120

Compound 129:

$^1$H NMR (500 MHz, DMSO-d$_6$) δ ppm 7.92 (br t, J=6.9 Hz, 1H) 7.44-7.57 (m, 1H) 7.29 (d, J=7.6 Hz, 1H) 7.02-7.26 (m, 5H) 6.29-6.46 (m, 1H) 5.93-6.14 (m, 1H) 5.74-5.78 (m, 1H) 5.70 (d, J=7.9 Hz, 1H) 5.53 (d, J=6.3 Hz, 1H) 5.28 (s, 1H) 5.10 (d, J=13.9 Hz, 1H) 4.87 (br dd, J=11.0, 6.6 Hz, 1H) 4.25 (br t, J=9.6 Hz, 1H) 4.19 (d, J=13.9 Hz, 1H) 3.78 (s, 3H) 1.25-1.34 (m, 1H) 1.16 (dt, J=9.7, 6.3 Hz, 1H) 0.79-0.87 (m, 1H) 0.73 (dq, J=7.6, 4.9 Hz, 1H)

LC/MS (method LC-A): Rt 2.76 min, MH+566

$[\alpha]_D^{20}$: −491.18° (c 0.170, DMF)

Chiral HPLC (method HPLC-A and B): One peak observed

Example 130: Synthesis of (18*R,Z)-12-hydroxy-18-phenyl-4-(trifluoromethyl)-6,9-dihydro-18H-10,17-methanobenzo[b]pyrido[1,2-f][1]oxa[5,6,9]triazacyclotridecine-11,13-dione (Compound 130A) and (18*S,Z)-12-hydroxy-18-phenyl-4-(trifluoromethyl)-6,9-dihydro-18H-10,17-methanobenzo[b]pyrido[1,2-f][1]oxa[5,6,9]triazacyclotridecine-11,13-dione (compound 130B)

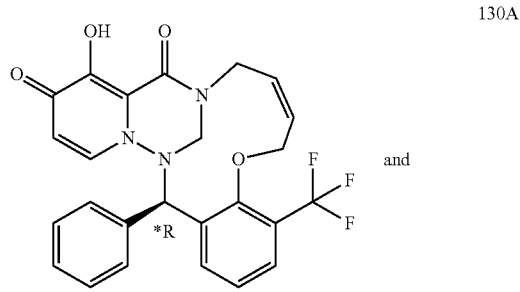

130A and

-continued

130B

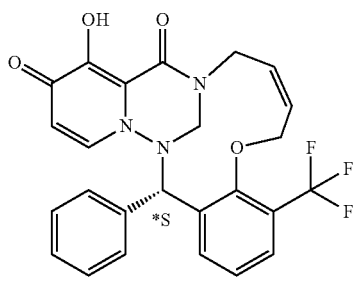

Compounds 130A and 130B were synthesized according to the procedures described in example 5 starting from intermediate 2-(allyloxy)-1-(chloro(phenyl)methyl)-3-(trifluoromethyl)benzene (synthesized as 74c from 2-hydroxy-3-(trifluoromethyl)-benzaldehyde [CAS 336628-67-2).

Compound 130A:
¹H NMR (500 MHz, DMSO-d₆) δ ppm 10.33-11.48 (m, 1H) 8.44 (br d, J=7.6 Hz, 1H) 7.79 (br d, J=7.6 Hz, 1H) 7.61 (brt, J=7.9 Hz, 1H) 6.94-7.31 (m, 6H) 6.17-6.44 (m, 1H) 5.86-6.11 (m, 1H) 5.48 (d, J=7.6 Hz, 1H) 5.40 (s, 1H) 5.19 (br d, J=13.9 Hz, 1H) 4.97 (br dd, J=10.6, 6.5 Hz, 1H) 4.85 (br dd, J=14.0, 4.3 Hz, 1H) 4.36 (br d, J=13.9 Hz, 1H) 4.07-4.27 (m, 1H) 3.23 (br dd, J=14.2, 7.6 Hz, 1H)

LC/MS (method LC-C): Rt 2.78 min, MH⁺484

[α]$_D^{20}$: −600.00° (c 0.205, DMF)

Chiral HPLC (method HPLC-A): Rt 4.31 min, chiral purity 100%

Compound 130B:
LC/MS (method LC-C): Rt 2.78 min, MH⁺484

[α]$_D^{20}$: +600.80° (c 0.25, DMF)

Chiral HPLC (method HPLC-A): Rt 4.80 min, chiral purity 100%

Example 131: Synthesis of (1*R,13*S,15*R)-7-hydroxy-17-oxa-24-thia-2,3,10-triazaheptacyclo[16.12.1.1².¹⁰.0³,⁸.0¹³,¹⁵.0²²,³¹.0²⁵,³⁰]dotriaconta-4,18,20,22(31),25(30),26,28-heptaene-6,9-dione (Compound 131AA), (1*R,13*R,15*S)-7-hydroxy-17-oxa-24-thia-2,3,10-triazaheptacyclo [16.12.1.1².¹⁰.0³,⁸.0¹³,¹⁵.0²²,³¹.0²⁵,³⁰]dotriaconta-4,18,20,22(31),25(30),26,28-heptaene-6,9-dione (Compound 131AB), (1*S,13*R,15*S)-7-hydroxy-17-oxa-24-thia-2,3,10-triazaheptacyclo [16.12.1.1².¹⁰.0³,⁸.0¹³,¹⁵.0²²,³¹.0²⁵,³⁰] dotriaconta-4,18,20,22(31),25(30),26,28-heptaene-6,9-dione (Compound 131BB) and (1*S,13*S,15*R)-7-hydroxy-17-oxa-24-thia-2,3,10-triazaheptacyclo [16.12.1.1².¹⁰.0³,⁸.0¹³,¹⁵.0²²,³¹.0²⁵,³⁰] dotriaconta-4,18,20,22(31),25(30),26,28-heptaene-6,9-dione (Compound 131BA)

131AA

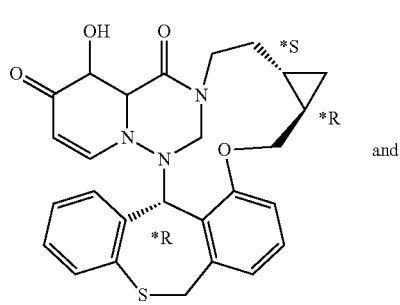
and

-continued

131AB

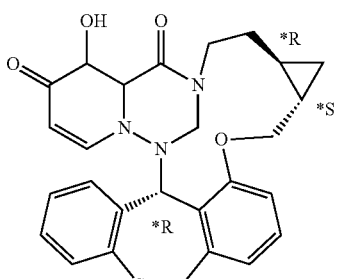
and

131BB

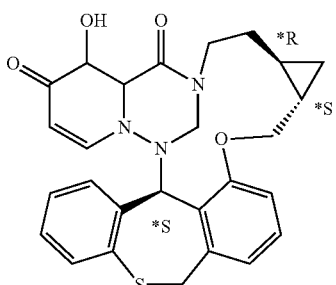
and

131BA

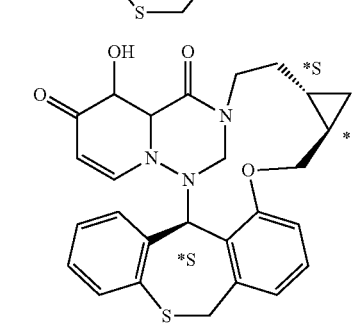

Compounds 131AA, 131AB, 131BB and 131BA were synthesized according to the procedures described in example 87 starting from aminoethyl-cyclopropane-methanol [CAS 2086269-44-3].

Compound 131AA:
¹H NMR (500 MHz, DMSO-d₆) δ ppm 11.48-12.44 (m, 1H) 7.31 (t, J=7.9 Hz, 1H) 7.10-7.17 (m, 2H) 7.05-7.09 (m, 1H) 7.02 (dd, J=7.9, 3.5 Hz, 2H) 6.82-6.89 (m, 1H) 6.76-6.81 (m, 1H) 6.21 (s, 1H) 5.63 (d, J=13.2 Hz, 1H) 5.56 (br d, J=7.6 Hz, 1H) 5.00 (br d, J=12.9 Hz, 1H) 4.65 (dd, J=12.0, 3.5 Hz, 1H) 4.34 (d, J=12.9 Hz, 1H) 3.83 (d, J=13.6 Hz, 1H) 3.63-3.72 (m, 1H) 3.55 (br t, J=11.5 Hz, 1H) 2.79 (br t, J=12.1 Hz, 1H) 1.91 (br d, J=14.8 Hz, 1H) 1.65-1.80 (m, 1H) 1.16-1.29 (m, 1H) 0.41-0.52 (m, 1H) 0.37 (dt, J=8.7, 4.5 Hz, 1H) 0.25 (dt, J=8.7, 4.5 Hz, 1H)

LC/MS (method LC-C): Rt 2.93 min, MH⁺488

[α]$_D^{20}$: −83.75° (c 0.16, DMF)

Chiral HPLC (method HPLC-B): Rt 6.68 min, chiral purity 100%

Compound 131AB:
¹H NMR (500 MHz, DMSO-d₆) δ ppm 11.32-12.35 (m, 1H) 7.26-7.31 (m, 1H) 7.20 (d, J=8.2 Hz, 1H) 7.04-7.10 (m, 1H) 7.00-7.03 (m, 1H) 6.98 (d, J=7.6 Hz, 1H) 6.95 (d, J=7.6 Hz, 1H) 6.77 (t, J=6.9 Hz, 1H) 6.68 (d, J=7.3 Hz, 1H) 6.03 (s, 1H) 5.56 (d, J=13.6 Hz, 1H) 5.52 (d, J=7.6 Hz, 1H) 4.88-5.00 (m, 2H) 4.05 (d, J=13.2 Hz, 1H) 3.74 (d, J=13.6 Hz, 1H) 3.66-3.72 (m, 1H) 3.11-3.18 (m, 1H) 2.45-2.55 (m, 2H) 0.97-1.07 (m, 1H) 0.89-0.96 (m, 1H) 0.81-0.88 (m, 1H) 0.65 (dt, J=8.3, 4.2 Hz, 1H) 0.42-0.51 (m, 1H)

LC/MS (method LC-C): Rt 2.94 min. MH⁺488
[α]$_D^{20}$: −251.11° (c 0.135, DMF)
Chiral HPLC (method HPLC-B): Rt 6.60 min, chiral purity 100%
Compound 131BB:
LC/MS (method LC-C): Rt 2.93 min, MH⁺488
[α]$_D^{20}$: +149.22° (c 0.128, DMF)
Chiral HPLC (method HPLC-B): Rt 5.21 min, chiral purity 100%
Compound 131BA:
LC/MS (method LC-C): Rt 2.94 min, MH⁺488
[α]$_D^{20}$: +249.52° (c 0.105, DMF)
Chiral HPLC (method HPLC-B): Rt 5.60 min, chiral purity 100%

Example 132: Synthesis of (9*R,18*R,*E)-12-hydroxy-9-isopropyl-18-phenyl-9,10-dihydro-6H,18H-10,17-methanobenzo[b]pyrido[1,2-f][1]oxa[5,6]diazacyclotridecine-11,13-dione (Compound 132A) and (9*S,18*S,*E)-12-hydroxy-9-isopropyl-18-phenyl-6,9-dihydro-18H-10,17-methanobenzo[b]pyrido[1,2-f][1]oxa[5,6,9]triazacyclotridecine-11,13-dione (Compound 132B)

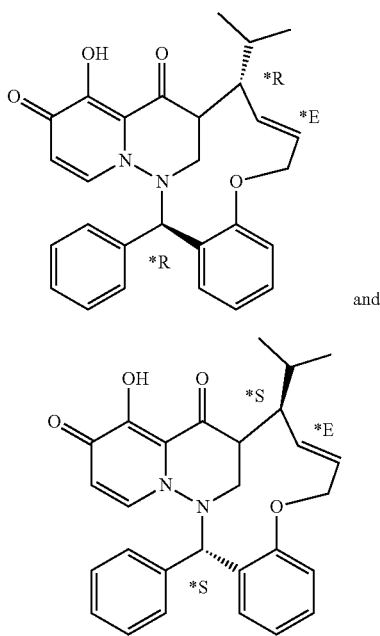

Compounds 132A and 132B were synthesized according to the procedures described in example 39 starting from intermediate 5-hydroxy-3-(4-methylpent-1-en-3-yl)-2,3-dihydro-1H-pyrido[2,1-f][1,2,4]triazine-4,6-dione (see example 124).
Compound 132A:
LC/MS (method LC-C): Rt 2.99 min, MH⁺458
[α]$_D^{20}$: +649.62° (c 0.133, DMF)
Chiral HPLC (method HPLC-B): Rt 4.95 min, chiral purity 100%
Compound 132B:
¹H NMR (500 MHz, DMSO-d₆) δ ppm 10.47-11.84 (m, 1H) 8.08 (dd, J=7.7, 1.4 Hz, 1H) 7.44 (td, J=7.7, 1.6 Hz, 1H) 7.31-7.39 (m, 1H) 7.07-7.28 (m, 7H) 6.31 (ddd, J=15.7, 10.0, 5.5 Hz, 1H) 5.47 (d, J=7.9 Hz, 1H) 5.40 (dd, J=15.8, 7.3 Hz, 1H) 5.21 (s, 1H) 5.06 (d, J=13.6 Hz, 1H) 4.80-4.92 (m, 2H) 4.21 (d, J=13.6 Hz, 1H) 4.10 (t, J=10.9 Hz, 1H) 1.58-1.77 (m, 1H) 0.83 (t, J=6.1 Hz, 6H)
LC/MS (method LC-C): Rt 2.98 min, MH⁺458
[α]D$^{20}$: 610.17° (c 0.118, DMF)
Chiral HPLC (method HPLC-B): Rt 6.17 min, chiral purity 100%

Example 133: Synthesis of (18*R,Z)-3-fluoro-12-hydroxy-4-methyl-18-phenyl-6,9-dihydro-18H-10,17-methanobenzo[b]pyrido[1,2-f][1]oxa[5,6,9]triazacyclotridecine-11,13-dione (Compound 133A) and (18*S,Z)-3-fluoro-12-hydroxy-4-methyl-18-phenyl-6,9-dihydro-18H-10,17-methanobenzo[b]pyrido[1,2-f][1]oxa[5,6,9]triazacyclotridecine-11,13-dione (compound 133B)

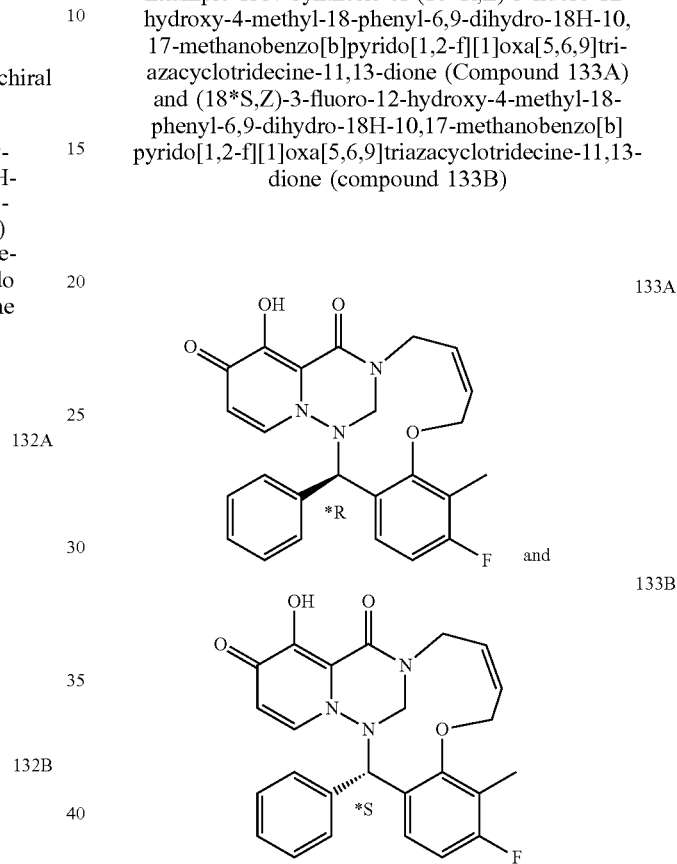

Compounds 133A and 133B were synthesized according to the procedures described in example 5 starting from intermediate 2-(allyloxy)-1-(chloro(phenyl)methyl)-4-fluoro-3-methylbenzene (synthesized as 74c from 4-fluoro-2-hydroxy-3-methyl-benzaldehyde [CAS 775337-99-0]).
Compound 133A:
¹H NMR (500 MHz, DMSO-d₆) δ ppm 7.93 (br t, J=7.7 Hz, 1H) 6.99-7.28 (m, 7H) 6.12-6.37 (m, 1H) 5.78-5.94 (m, 1H) 5.47 (d, J=7.6 Hz, 1H) 5.25 (s, 1H) 5.13 (d, J=13.9 Hz, 1H) 4.73-4.91 (m, 2H) 4.32 (d, J=13.9 Hz, 1H) 4.08 (br t, J=8.4 Hz, 1H) 3.21 (br dd, J=14.2, 7.6 Hz, 1H) 2.12 (d, J=1.6 Hz, 3H)
LC/MS (method LC-C): Rt 2.74 min, MH⁺448
[α]$_D^{20}$: −624.63° (c 0.134, DMF)
Chiral HPLC (method HPLC-B): Rt 5.38 min, chiral purity 100%
Compound 133B:
LC/MS (method LC-C): Rt 2.74 min, MH⁺448
[α]$_D^{20}$: +674.22° (c 0.128, DMF)
Chiral HPLC (method HPLC-B): Rt 4.80 min. chiral purity 100%

Example 134: Synthesis of (18*R,Z)-12-hydroxy-18-phenyl-4-(trifluoromethoxy)-6,9-dihydro-18H-10,17-methanobenzo[b]pyrido[1,2-f][1]oxa[5,6,9]triazacyclotridecine-11,13-dione (Compound 134A) and (18*S,Z)-12-hydroxy-18-phenyl-4-(trifluoromethoxy)-6,9-dihydro-18H-10,17-methanobenzo[b]pyrido[1,2-f][1]oxa[5,6,9]triazacyclotridecine-11,13-dione (compound 134B)

Example 135: Synthesis of (18*R,Z)-4-fluoro-12-hydroxy-3-methyl-18-phenyl-6,9-dihydro-18H-10,17-methanobenzo[b]pyrido[1,2-f][1]oxa[5,6,9]triazacyclotridecine-11,13-dione (Compound 135A) and (18*S,Z)-4-fluoro-12-hydroxy-3-methyl-18-phenyl-6,9-dihydro-18H-10,17-methanobenzo[b]pyrido[1,2-f][1]oxa[5,6,9]triazacyclotridecine-11,13-dione (compound 135B)

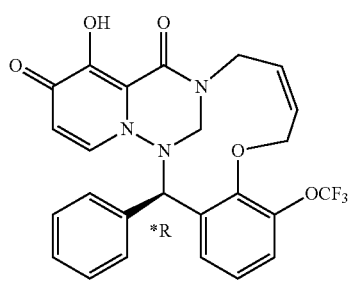

134A

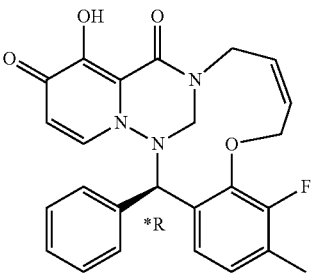

135A and

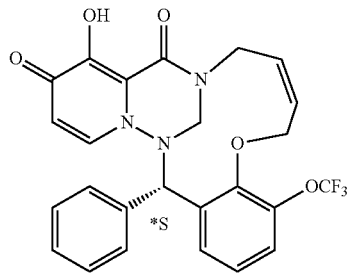

134B

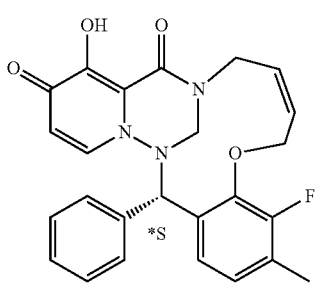

135B

Compounds 134A and 134B were synthesized according to the procedures described in example 5 starting from intermediate 2-(allyloxy)-1-(chloro(phenyl)methyl)-3-(trifluoromethoxy)benzene (synthesized as 74c from 2-hydroxy-3-(trifluoromethoxy)-benzaldehyde [CAS 497959-31-9]).

Compound 134A:

$^1$H NMR (500 MHz, DMSO-d$_6$) δ ppm 8.14 (br d, J=3.8 Hz, 1H) 7.43-7.59 (m, 2H) 6.97-7.36 (m, 6H) 6.13-6.34 (m, 1H) 5.80-6.10 (m, 1H) 5.48 (d, J=7.9 Hz, 1H) 5.31 (br s, 1H) 5.14 (d, J=13.6 Hz, 1H) 4.68-4.93 (m, 2H) 4.26 (br d, J=13.9 Hz, 2H) 3.21 (br dd, J=14.0, 8.0 Hz, 1H)

LC/MS (method LC-C): Rt 2.86 min, MH$^+$500

$[α]_D^{20}$: −644.53° (c 0.137, DMF)

Chiral HPLC (method HPLC-A): Rt 4.19 min, chiral purity 100%

Compound 134B:

LC/MS (method LC-C): Rt 2.86 min, MH$^+$500

$[α]_D^{20}$: +618.18° (c 0.154, DMF)

Chiral HPLC (method HPLC-A): Rt 4.61 min, chiral purity 100%

Compounds 135A and 135B were synthesized according to the procedures described in example 5 starting from intermediate 2-(allyloxy)-1-(chloro(phenyl)methyl)-3-fluoro-4-methylbenzene (synthesized as 74c from 3-fluoro-2-hydroxy-4-methyl-benzaldehyde [CAS 1287718-64-8]).

Compound 135A:

$^1$H NMR (500 MHz, DMSO-d$_6$) δ ppm 10.44-11.39 (m, 1H) 7.78 (br d, J=7.9 Hz, 1H) 7.28 (t, J=7.6 Hz, 1H) 6.97-7.24 (m, 6H) 6.14-6.32 (m, 1H) 5.83-6.07 (m, 1H) 5.48 (d, J=7.6 Hz, 1H) 5.23 (s, 1H) 5.12 (d, J=13.9 Hz, 1H) 4.71-4.89 (m, 2H) 4.29 (d, J=13.9 Hz, 1H) 4.15-4.25 (m, 1H) 3.21 (dd, J=13.9, 7.9 Hz, 1H) 2.27 (s, 3H)

LC/MS (method LC-C): Rt 2.76 min, MH$^+$448

$[α]_D^{20}$: −659.18° (c 0.245, DMF)

Compound 135B:

LC/MS (method LC-C): Rt 2.76 min, MH$^+$448

$[α]_D^{20}$: +578.38° (c 0.185, DMF)

Example 136: synthesis (18*R,*Z)-18-(2-cyclopropylphenyl)-3,4-difluoro-12-hydroxy-6,9-dihydro-18H-10,17-methanobenzo[b]pyrido[1,2-f][1]oxa[5,6,9]triazacyclotridecine-11,13-dione (Compound 136A) and (18*S,*Z)-18-(2-cyclopropylphenyl)-3,4-difluoro-12-hydroxy-6,9-dihydro-18H-10,17-methanobenzo[b]pyrido[1,2-f][1]oxa[5,6,9]triazacyclotridecine-11,13-dione (compound 136B)

Example 137: Synthesis of (1*R,13*E)-25-fluoro-7-hydroxy-16-oxa-23-thia-2,3,10-triazahexacyclo[15.12.1.1²,¹⁰.0³,⁸.0²¹,³⁰.0²⁴,²⁹]hentriaconta-4,7,13,17,19,21(30),24(29),25,27-nonaene-6,9-dione (Compound 137A) and (1*S,13*E)-25-fluoro-7-hydroxy-16-oxa-23-thia-2,3,10-triazahexacyclo[15.12.1.1²,¹⁰.0³,⁸.0²¹,³⁰.0²⁴,²⁹]hentriaconta-4,7,13,17,19,21(30),24(29),25,27-nonaene-6,9-dione (Compound 137B)

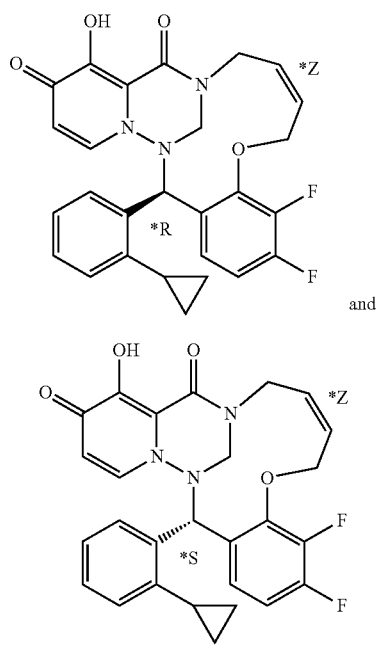

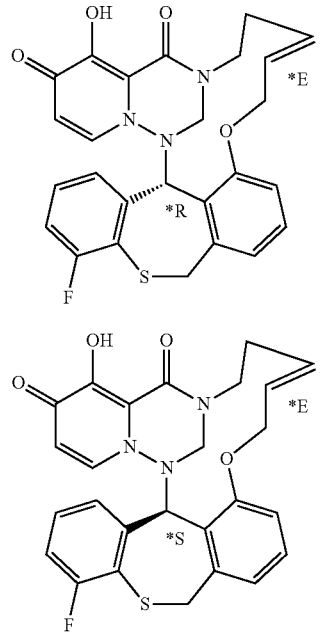

Compounds 136A and 136B were synthesized according to the procedures described in example 5 starting from intermediate 2-(allyloxy)-1-(chloro(2-cyclopropylphenyl)methyl)-3,4-difluorobenzene (synthesized as in example 123 from 74a).

Compound 136A:

$^1$H NMR (500 MHz, DMSO-d$_6$) δ ppm 10.52-11.22 (m, 1H) 7.87-8.08 (m, 1H) 7.56-7.64 (m, 1H) 7.44-7.54 (m, 1H) 7.27 (br d, J=7.6 Hz, 1H) 7.03-7.18 (m, 2H) 6.75-6.84 (m, 1H) 6.12-6.28 (m, 1H) 5.88-6.10 (m, 2H) 5.51 (d, J=7.6 Hz, 1H) 5.17 (d, J=13.9 Hz, 1H) 4.85-4.92 (m, 1H) 4.81 (br dd, J=13.9, 4.4 Hz, 1H) 4.27-4.42 (m, 2H) 3.23 (dd, J=14.0, 8.0 Hz, 1H) 1.97-2.06 (m, 1H) 0.85-1.00 (m, 2H) 0.74-0.82 (m, 1H) 0.01-0.08 (m, 1H)

LC/MS (method LC-C): Rt 2.89 min, MH$^+$492

$[α]_D^{20}$: −648.00° (c 0.125, DMF)

Chiral HPLC (method HPLC-A and B): No separation observed

Compound 136B:

LC/MS (method LC-C): Rt 2.89 min, MH$^+$492

$[α]_D^{20}$: +610.49° (c 0.143, DMF)

Chiral HPLC (method HPLC-A and B): No separation observed

Compounds 137A and 137B were synthesized according to the procedures described in example 37 starting from intermediate 10-(allyloxy)-11-chloro-4-fluoro-6,11-dihydrodibenzo[b,e]thiepine (synthesized as 88n from 2-methoxy-methyl ester-benzoic acid [CAS 606-45-1] and 2-fluoro-benzenethiol [CAS 2557-78-0]).

Compound 137A:

LC/MS (method LC-C): Rt 2.80 min, MH$^+$492

$[α]_D^{20}$: +62.81° (c 0.121, DMF)

Chiral HPLC (method HPLC-B): Rt 5.38 min, chiral purity 100%

Compound 137B:

$^1$H NMR (500 MHz, DMSO-d$_6$) δ ppm 11.75 (br s, 1H) 7.39 (t, J=7.9 Hz, 1H) 7.24 (d, J=7.6 Hz, 1H) 7.03-7.13 (m, 3H) 6.84-6.92 (m, 1H) 6.48 (d, J=7.9 Hz, 1H) 6.16 (s, 1H) 6.03-6.12 (m, 1H) 5.96 (td, J=10.6, 4.1 Hz, 1H) 5.75 (d, J=13.6 Hz, 1H) 5.62 (d, J=7.9 Hz, 1H) 4.95 (d, J=13.2 Hz, 1H) 4.47-4.59 (m, 2H) 4.20-4.34 (m, 2H) 3.95 (d, J=13.2 Hz, 1H) 2.85 (br d, J=14.2 Hz, 1H) 2.12-2.32 (m, 2H)

LC/MS (method LC-C): Rt 2.81 min, MH$^+$492

$[α]_D^{20}$: −161.05° (c 0.172, DMF)

Chiral HPLC (method HPLC-B): Rt 7.55 min, chiral purity 100%

Example 138: Synthesis of (13*S,21a*S,Z)-16-hydroxy-13-methyl-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (Compound 138AA), (13*R,21a*R,Z)-16-hydroxy-13-methyl-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (Compound 138BB), (9*R,17a*R,E)-12-hydroxy-9-methyl-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 138C) and (9*S,17a*S,E)-12-hydroxy-9-methyl-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 138D) and (13*R,21a*S,Z)-16-hydroxy-13-methyl-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (Compound 138AB) and (13*S,21a*R,Z)-16-hydroxy-13-methyl-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (Compound 138BA)

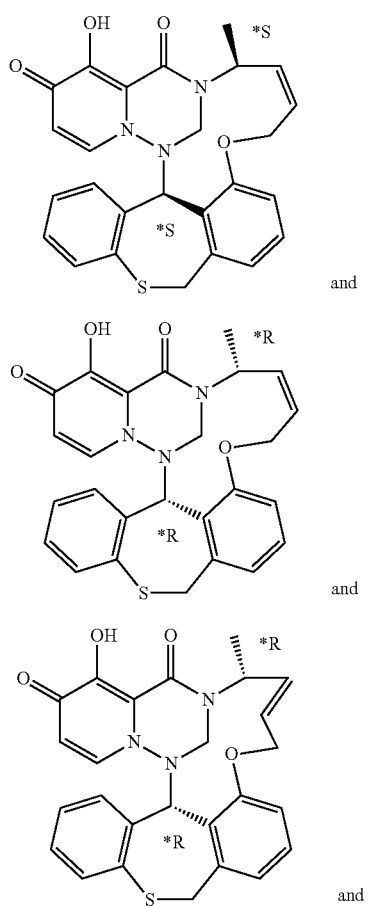

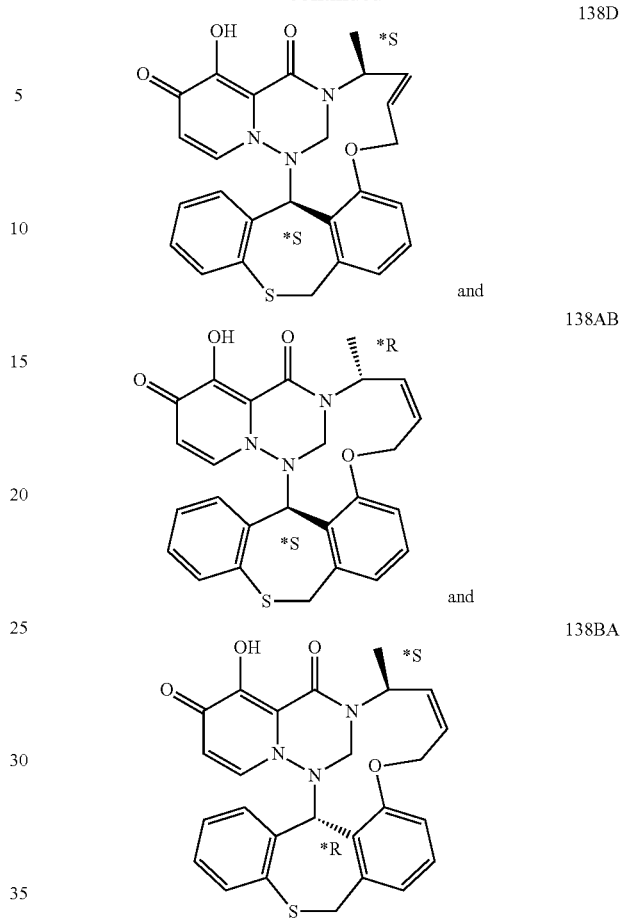

Compounds 138AA, 138BB, 138C, 138D, 138AB and 138BA were synthesized according to the procedures described in example 46 starting from 29c and 37c.

Compound 138AA:
$^1$H NMR (500 MHz, DMSO-d$_6$) δ ppm 7.41 (t, J=7.9 Hz, 1H) 7.19 (d, J=7.6 Hz, 1H) 7.02-7.15 (m, 4H) 6.75-6.87 (m, 1H) 6.53 (d, J=7.6 Hz, 1H) 6.47 (br t, J=9.8 Hz, 1H) 6.18 (dt, J=10.3, 6.8 Hz, 1H) 6.07 (s, 1H) 5.70 (d, J=13.9 Hz, 1H) 5.60 (d, J=7.6 Hz, 1H) 5.17 (d, J=13.2 Hz, 1H) 4.77 (dd, J=10.4, 6.9 Hz, 1H) 4.37-4.49 (m, 1H) 4.30 (d, J=13.2 Hz, 1H) 3.96-4.09 (m, 1H) 3.79 (d, J=13.9 Hz, 1H) 1.37 (d, J=6.3 Hz, 3H)

LC/MS (method LC-C): Rt 2.84 min, MH$^+$474
$[α]_D^{20}$: −170.83° (c 0.096, DMF)
Chiral HPLC (method HPLC-B): Rt 7.91 min, chiral purity 100%

Compound 138BB:
LC/MS (method LC-C): Rt 2.84 min, MH$^+$474
$[α]_D^{20}$: +160.82° (c 0.097, DMF)
Chiral HPLC (method HPLC-B): Rt 4.75 min, chiral purity 100%

Compound 138C:
LC/MS (method LC-C): Rt 2.72 min, MH$^+$474
$[α]_D^{20}$: +498.95° (c 0.191, DMF)
Chiral HPLC (method HPLC-B): Rt 6.61 min. chiral purity 100%

Compound 138D:
$^1$H NMR (500 MHz, DMSO-d$_6$) δ ppm 10.83-12.19 (m, 1H) 7.41 (t, J=7.9 Hz, 1H) 7.33 (d, J=7.6 Hz, 1H) 7.19 (dd, J=11.0, 7.9 Hz, 2H) 7.07-7.13 (m, 1H) 7.01-7.06 (m, 1H)

6.78-6.89 (m, 2H) 6.31 (ddd, J=15.7, 9.7, 5.5 Hz, 1H) 5.82 (d, J=13.2 Hz, 1H) 5.54-5.66 (m, 2H) 5.43 (quin, J=6.8 Hz, 1H) 5.33 (s, 1H) 5.06 (d, J=13.2 Hz, 1H) 4.88 (dd, J=11.2, 5.5 Hz, 1H) 4.23-4.35 (m, 2H) 3.87 (d, J=13.2 Hz, 1H) 1.14 (d, J=7.3 Hz, 3H)

LC/MS (method LC-C): Rt 2.72 min, MH+474

[α]$_D^{20}$: −500.00° (c 0.107, DMF)

Chiral HPLC (method HPLC-B): Rt 8.81 min, chiral purity 100%

Compound 138AB:

¹H NMR (500 MHz, DMSO-d$_6$) δ ppm 7.34-7.45 (m, 2H) 7.31 (br d, J=7.6 Hz, 1H) 7.09-7.22 (m, 3H) 6.86 (br t, J=7.1 Hz, 1H) 6.70 (br d, J=7.6 Hz, 1H) 6.08-6.18 (m, 1H) 6.02 (s, 1H) 5.64-5.77 (m, 3H) 5.32-5.42 (m, 1H) 4.88-5.07 (m, 3H) 4.28 (br d, J=13.2 Hz, 1H) 3.83 (br d, J=13.6 Hz, 1H) 1.39 (br d, J=6.0 Hz, 3H)

LC/MS (method LC-C): Rt 2.77 min, MH+474

[α]$_D^{20}$: −258.59° (c, DMF)

Chiral HPLC (method HPLC-A): Rt 7.38 min, chiral purity 100%

Compound 138BA:

LC/MS (method LC-C): Rt 2.77 min, MH+474

[α]$_D^{20}$: +277.53° (c 0.089, DMF)

Chiral HPLC (method HPLC-A): Rt 6.36 min, chiral purity 100%

Example 139: Synthesis of (1a*S,8*S,17a*S)-4,5-difluoro-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (Compound 139AA), (1a*R,8*R,17a*R)-4,5-difluoro-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (Compound 139BB), (1a*R,8*S,17a*R)-4,5-difluoro-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (Compound 139AB) and (1a*S,8*R,17a*S)-4,5-difluoro-14-hydroxy-8-phenyl-1a,2,17,17a-tetrahydro-1H,8H-9,16-methanobenzo[b]cyclopropa[k]pyrido[1,2-f][1]oxa[5,6,9]triazacyclotridecine-13,15-dione (Compound 139BA)

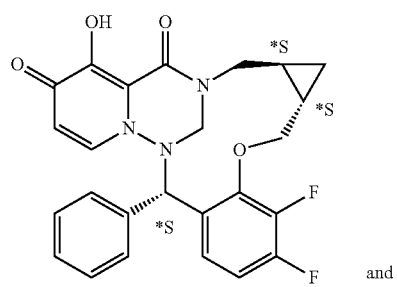
139AA

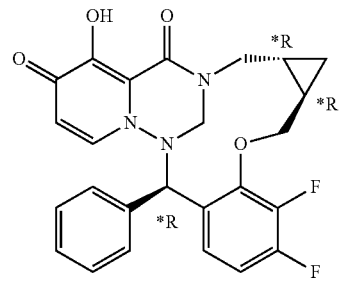
139BB

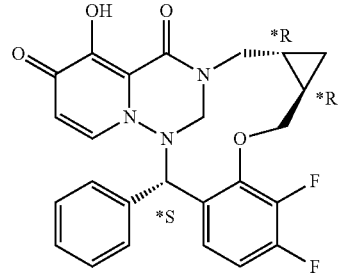
139AB

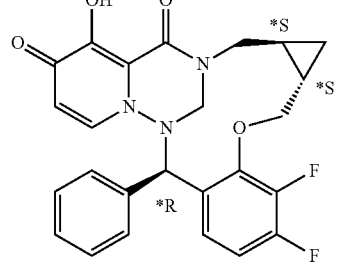
139BA

Compounds 139AA, 139BB, 139AB and 139BA were synthesized according to the procedures described in example 80 starting from intermediate 2-(allyloxy)-1-(chloro(phenyl)methyl)-3,4-difluorobenzene 74c.

Compound 139AA:

LC/MS (method LC-C): Rt 2.81 min, MH+466

[α]$_D^{20}$: +265.85° (c 0.164, DMF)

Chiral HPLC (method HPLC-B): Rt 4.43 min, chiral purity 100%

Compound 139BB:

¹H NMR (500 MHz, DMSO-d$_6$) δ ppm 10.64-11.63 (m, 1H) 7.87-7.95 (m, 1H) 7.36-7.50 (m, 1H) 7.04-7.35 (m, 6H) 5.92 (s, 1H) 5.50 (d, J=7.6 Hz, 1H) 5.09 (d, J=13.6 Hz, 1H) 4.89 (dd, J=12.8, 4.3 Hz, 1H) 4.57 (d, J=13.6 Hz, 1H) 3.58 (dd, J=14.5, 10.7 Hz, 1H) 3.18-3.27 (m, 2H) 1.29-1.53 (m, 1H) 1.01 (ddt, J=14.0, 9.5, 4.5, 4.5 Hz, 1H) 0.71 (dt, J=8.7, 4.5 Hz, 1H) 0.54-0.64 (m, 1H)

LC/MS (method LC-C): Rt 2.81 min, MH+466

[α]D$^{20}$: −260.99° (c 0.182, DMF)

Chiral HPLC (method HPLC-B): Rt 5.78 min, chiral purity 99.07%

Compound 139AB:

LC/MS (method LC-C): Rt 2.80 min, MH+466

[α]$_D^{20}$: +441.9° (c 0.253, DMF)

Chiral HPLC (method HPLC-A): Rt 8.62 min, chiral purity 100%

Compound 139BA:

¹H NMR (400 MHz, DMSO-d$_6$) δ ppm 10.64-11.62 (m, 1H) 8.04-8.15 (m, 1H) 7.40-7.52 (m, 2H) 7.19 (br s, 5H) 5.97 (s, 1H) 5.50 (d, J=7.7 Hz, 1H) 5.14 (d, J=13.6 Hz, 1H)

4.75 (dd, J=12.5, 3.2 Hz, 1H) 4.34-4.46 (m, 2H) 3.47 (t, J=12.0 Hz, 1H) 2.14 (dd, J=13.9, 11.2 Hz, 1H) 1.36-1.52 (m, 1H) 1.20 (td, J=8.0, 4.5 Hz, 1H) 0.57 (dt, J=8.9, 4.5 Hz, 1H) 0.40 (dt, J=9.2, 4.7 Hz, 1H)

LC/MS (method LC-C): Rt 2.80 min. MH+466

$[\alpha]_D^{20}$: −424.27° (c 0.206, DMF)

Chiral HPLC (method HPLC-A): Rt 4.81 min, chiral purity 100%

Example 140: Synthesis of (17a*R,*E)-24,25-difluoro-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 140A), (17a*S,*E)-24,25-difluoro-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (compound 140B), (21a*R,*Z)-24,25-difluoro-16-hydroxy-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (compound 140C) and (21a*S,*Z)-24,25-difluoro-16-hydroxy-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (Compound 140D)

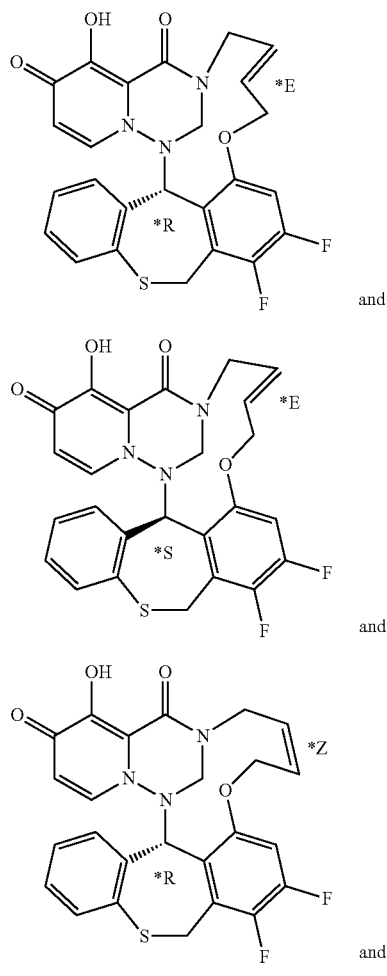

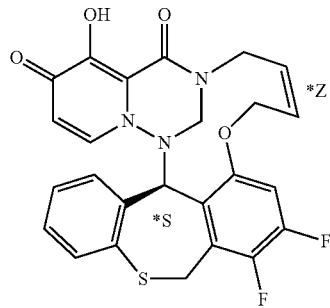

Compounds 140A, 140B, 140C and 140D were synthesized according to the procedures described in example 88 starting from intermediate 5d.

Compound 140A:

LC/MS (method LC-C): Rt 2.79 min, MH+496

$[\alpha]_D^{20}$: +476.06° (c 0.071, DMF)

Chiral HPLC (method HPLC-B): Rt 5.58 min, chiral purity 100%

Compound 140B:

$^1$H NMR (500 MHz, DMSO-$d_6$) δ ppm 7.50 (br dd, J=11.7, 7.3 Hz, 1H) 7.28 (d, J=7.6 Hz, 1H) 7.11-7.19 (m, 1H) 7.05-7.10 (m, 1H) 6.89 (t, J=7.3 Hz, 1H) 6.77-6.85 (m, 1H) 6.23 (dt, J=15.5, 7.5 Hz, 1H) 5.96-6.12 (m, 1H) 5.70 (br d, J=14.2 Hz, 1H) 5.62 (d, J=7.6 Hz, 1H) 5.36 (s, 1H) 5.14 (d, J=13.9 Hz, 1H) 4.71-4.83 (m, 2H) 4.49 (br t, J=9.5 Hz, 1H) 4.37 (d, J=13.9 Hz, 1H) 4.11 (d, J=13.9 Hz, 1H) 3.12 (br dd, J=13.9, 8.5 Hz, 1H)

LC/MS (method LC-C): Rt 2.78 min, MH+496

$[\alpha]_D^{20}$: −528.75° (c 0.08, DMF)

Chiral HPLC (method HPLC-B): Rt 8.09 min, chiral purity 100%

Compound 140C:

LC/MS (method LC-C): Rt 2.87 min, MH+496

$[\alpha]_D^{20}$: +306.67° (c 0.060, DMF)

Chiral HPLC (method HPLC-B): Rt 5.07 min, chiral purity 100%

Compound 140D:

$^1$H NMR (400 MHz, DMSO-$d_6$) δ ppm 10.78-12.11 (m, 1H) 7.47 (dd, J=12.0, 7.1 Hz, 1H) 7.24 (d, J=7.7 Hz, 1H) 7.07-7.19 (m, 2H) 6.80-6.90 (m, 1H) 6.57 (d, J=7.6 Hz, 1H) 6.37-6.49 (m, 1H) 6.29 (dt, J=10.4, 7.4 Hz, 1H) 6.01 (s, 1H) 5.55-5.68 (m, 2H) 5.02 (d, J=13.4 Hz, 1H) 4.86 (dd, J=10.6, 6.8 Hz, 1H) 4.57 (dd, J=10.4, 7.9 Hz, 1H) 4.41 (d, J=13.4 Hz, 1H) 4.18 (dd, J=13.5, 7.5 Hz, 1H) 4.03 (d, J=14.4 Hz, 1H) 3.81 (dd, J=13.4, 8.6 Hz, 1H)

LC/MS (method LC-C): Rt 2.88 min, MH+496

$[\alpha]_D^{20}$: −265.79° (c 0.076, DMF)

Chiral HPLC (method HPLC-B): Rt 9.82 min, chiral purity 100%

Example 141: synthesis (9*R,18*R,E)-4-fluoro-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 141AA), (9*S,18*S,E)-4-fluoro-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 141BB), (9*S,18*R,E)-4-fluoro-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 141AB) and (9*R,18*S,E)-4-fluoro-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 141BA)

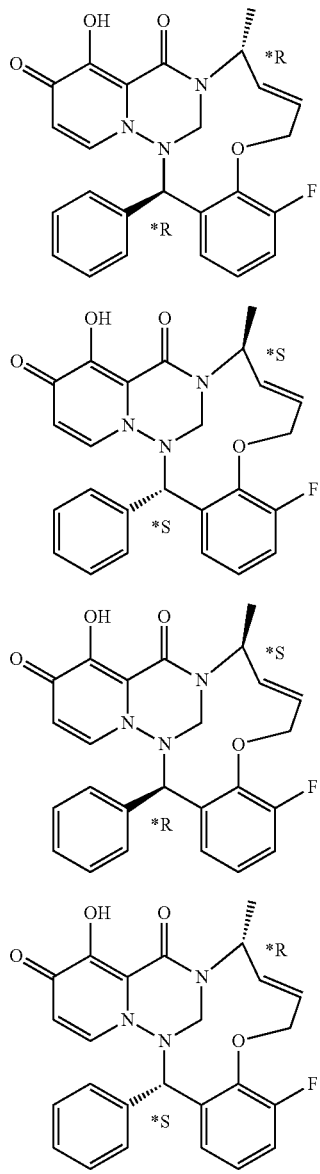

141AA

141BB

141AB

141BA

Compounds 141AA, 141BB, 141AB and 141BA were synthesized according to the procedures described in example 29 starting from intermediate 61b.

Compound 141AA:
$^1$H NMR (400 MHz, DMSO-$d_6$) δ ppm 10.54-11.62 (m, 1H) 7.93 (d, J=7.7 Hz, 1H) 7.31-7.50 (m, 2H) 7.04-7.28 (m, 6H) 6.35 (ddd, J=15.4, 10.1, 5.5 Hz, 1H) 5.37-5.62 (m, 3H) 5.20 (s, 1H) 5.06 (d, J=13.6 Hz, 1H) 4.88 (dd, J=11.3, 5.3 Hz, 1H) 4.26 (d, J=13.7 Hz, 1H) 4.00 (br t, J=10.8 Hz, 1H) 1.15 (d, J=7.1 Hz, 3H)
LC/MS (method LC-C): Rt 2.72 min, MH$^+$448
$[α]_D^{20}$: −602.86° (c 0.175, DMF)
Chiral HPLC (method HPLC-A): Rt 8.25 min, chiral purity 100%

Compound 141BB:
LC/MS (method LC-C): Rt 2.72 min, MH$^+$448
$[α]_D^{20}$: +613.41° (c 0.179, DMF)
Chiral HPLC (method HPLC-A): Rt 5.97 min, chiral purity 100%

Compound 141AB:
$^1$H NMR (400 MHz, DMSO-$d_6$) δ ppm 9.83-11.25 (m, 1H) 7.97 (d, J=7.7 Hz, 1H) 7.28-7.46 (m, 3H) 7.00-7.25 (m, 5H) 6.39-6.58 (m, 1H) 5.81-6.02 (m, 1H) 5.50 (d, J=7.7 Hz, 1H) 5.42 (s, 1H) 5.19 (d, J=13.9 Hz, 1H) 4.59-4.71 (m, 1H) 4.46-4.58 (m, 1H) 4.22 (d, J=13.9 Hz, 1H) 3.65-3.86 (m, 1H) 1.75 (d, J=7.0 Hz, 3H)
LC/MS (method LC-C): Rt 2.75 min, MH$^+$448
$[α]_D^{20}$: −710.91° (c 0.220, DMF)

Compound 141BA:
LC/MS (method LC-C): Rt 2.75 min, MH$^+$448
$[α]_D^{20}$: +717.45° (c 0.212, DMF)

Example 142: Synthesis of (((9S,18R,E)-9-ethyl-3,4-difluoro-11,13-dioxo-18-phenyl-6,9,11,13-tetrahydro-18H-10,17-methanobenzo[b]pyrido[1,2-f][1]oxa[5,6,9]triazacyclotridecin-12-yl)oxy)methyl methyl carbonate (Compound 142)

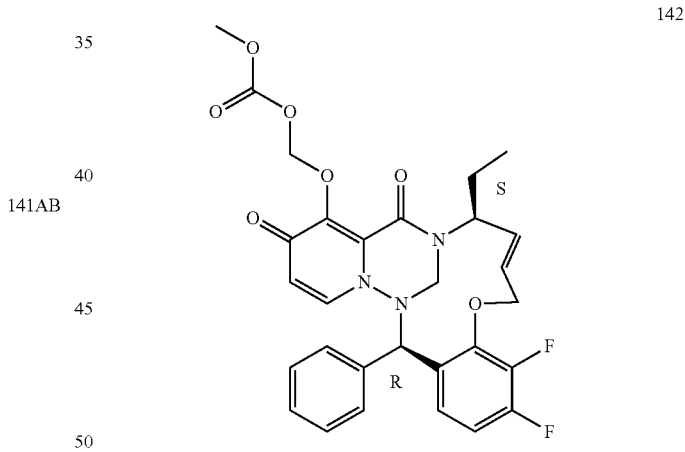

142

Compounds 142 was synthesized according to the procedure described in example 120 starting from compound 101AA.

Compound 142:
$^1$H NMR (400 MHz, DMSO-$d_6$) δ ppm 7.93 (br t, J=6.9 Hz, 1H) 7.44-7.59 (m, 1H) 7.31 (d, J=7.7 Hz, 1H) 6.94-7.26 (m, 5H) 6.30 (ddd, J=15.6, 10.1, 5.3 Hz, 1H) 5.74 (d, J=6.6 Hz, 1H) 5.69 (d, J=7.8 Hz, 1H) 5.59-5.67 (m, 1H) 5.56 (d, J=6.5 Hz, 1H) 5.16 (q, J=7.4 Hz, 1H) 5.10 (s, 1H) 5.01 (d, J=13.8 Hz, 1H) 4.92 (dd, J=11.2, 5.4 Hz, 1H) 4.17 (d, J=13.8 Hz, 1H) 4.07 (br t, J=10.9 Hz, 1H) 3.77 (s, 3H) 1.35-1.60 (m, 2H) 0.81 (t, J=7.3 Hz, 3H)
LC/MS (method LC-A): Rt 2.84 min, MH$^+$568
$[α]_D^{20}$: −500.62° (c 0.161, DMF)
Chiral HPLC (method HPLC-B): Rt 7.66 min, chiral purity 99.43%

Example 143: Synthesis of (((9R,18R,E)-9-ethyl-3, 4-difluoro-11,13-dioxo-18-phenyl-6,9,11,13-tetra-hydro-18H-10,17-methanobenzo[b]pyrido[1,2-f][1]oxa[5,6,9]triazacyclotridecin-12-yl)oxy)methyl methyl carbonate (Compound 143)

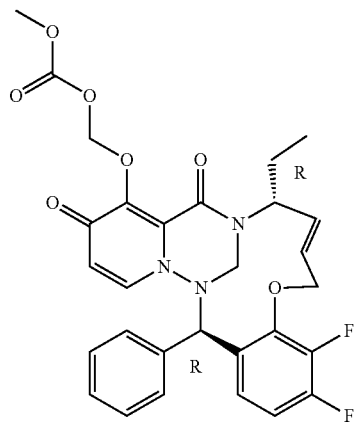

Compounds 143 was synthesized according to the procedure described in example 120 starting from compound 101AB.

Compound 143:
$^1$H NMR (400 MHz, DMSO-d$_6$) δ ppm 8.00 (br t, J=7.0 Hz, 1H) 7.44-7.57 (m, 1H) 7.40 (d, J=7.8 Hz, 1H) 7.13-7.25 (m, 3H) 6.91-7.12 (m, 2H) 6.42-6.59 (m, 1H) 5.87-6.08 (m, 1H) 5.74 (d, J=6.5 Hz, 1H) 5.68 (d, J=7.7 Hz, 1H) 5.57 (d, J=6.5 Hz, 1H) 5.38 (s, 1H) 5.15 (d, J=14.1 Hz, 1H) 4.63-4.73 (m, 1H) 4.52-4.62 (m, 1H) 4.17 (d, J=14.2 Hz, 1H) 3.77 (s, 3H) 3.35-3.42 (m, 1H) 2.05-2.27 (m, 2H) 0.84 (t, J=7.4 Hz, 3H)

LC/MS (method LC-A): Rt 2.89 min, MH$^+$568
[α]$_D^{20}$: −596.53° (c 0.173, DMF)
Chiral HPLC (method HPLC-B): Rt 5.44 min, chiral purity 98.79%

Example 144: Synthesis of (1*R,13*S,15*S)-7-hydroxy-17-oxa-24-thia-2,3,10-triazaheptacyclo[16.12.1.1$^{2,10}$.0$^{3,8}$.0$^{13,15}$.0$^{22,31}$.0$^{25,30}$]dotriaconta-4,18,20,22(31),25(30),26,28-heptaene-6,9-dione (Compound 144AA), (1*R,13*R,15*R)-7-hydroxy-17-oxa-24-thia-2,3,10-triazaheptacyclo[16.12.1.1$^{2,10}$.0$^{3,8}$.0$^{13,15}$.0$^{22,31}$.0$^{25,30}$]dotriaconta-4,18,20,22(31),25(30),26,28-heptaene-6,9-dione (Compound 144AB), (1*S,13*R,15*R)-7-hydroxy-17-oxa-24-thia-2,3,10-triazaheptacyclo[16.12.1.1$^{2,10}$.0$^{3,8}$.0$^{13,15}$.0$^{22,31}$.0$^{25,30}$]dotriaconta-4,18,20,22(31),25(30),26,28-heptaene-6,9-dione (Compound 144BB) and (1*S,13*S,15*S)-7-hydroxy-17-oxa-24-thia-2,3,10-triazaheptacyclo[16.12.1.1$^{2,10}$.0$^{3,8}$.0$^{13,15}$.0$^{22,31}$.0$^{25,30}$]dotriaconta-4,18,20,22(31),25(30),26,28-heptaene-6,9-dione (Compound 144BA)

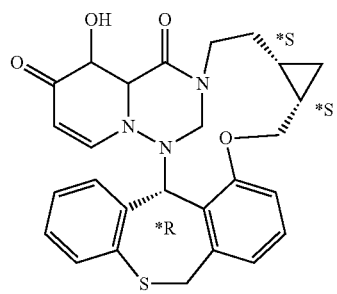

and

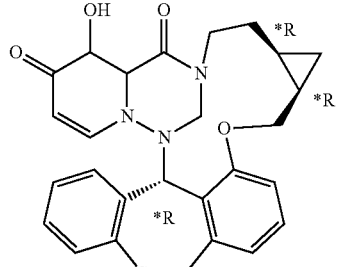

and

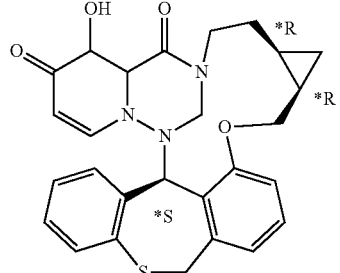

and

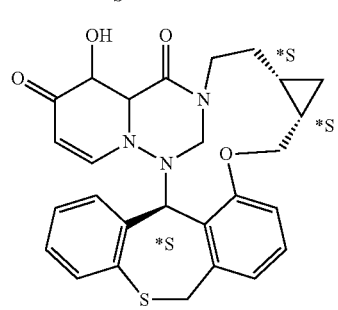

Compounds 144AA, 144AB, 144BB and 144BA were synthesized according to the procedures described in example 87 starting from intermediate trans-2-((1RS,2RS)-2-(((tert-butyldiphenylsilyl)oxy)methyl)cyclopropyl)ethan-1-amine (synthesized as 87e from trans-(1RS,2RS)cyclopropaneethanol, 2-[[[(1,1-dimethylethyl)diphenylsilyl]oxy]methyl] [CAS 2243217-26-5]).

Compound 144AA:
LC/MS (method LC-C): Rt 3.00 min, MH$^+$488
[α]$_D^{20}$: +122.22° (c 0.063, DMF)
Chiral HPLC (method HPLC-B): Rt 5.87 min, chiral purity 100%

Compound 144AB:
LC/MS (method LC-C): Rt 2.91 min, MH$^+$488
[α]$_D^{20}$: +220.59° (c 0.068, DMF)
Chiral HPLC (method HPLC-B): Rt 6.48 min, chiral purity 100%

Compound 144BB:
$^1$H NMR (500 MHz, DMSO-d$_6$) δ ppm 11.23-12.74 (m, 1H) 7.34 (t, J=7.9 Hz, 1H) 7.25 (d, J=7.6 Hz, 1H) 7.10-7.16 (m, 1H) 7.05-7.10 (m, 1H) 7.02 (d, J=7.6 Hz, 1H) 6.93 (d, J=8.2 Hz, 1H) 6.80-6.88 (m, 1H) 6.69 (d, J=6.9 Hz, 1H) 6.23 (s, 1H) 5.71 (d, J=13.6 Hz, 1H) 5.58 (d, J=7.9 Hz, 1H) 4.93 (d, J=13.2 Hz, 1H) 4.69 (dd, J=10.6, 4.3 Hz, 1H) 4.14-4.35 (m, 2H) 3.80 (d, J=13.2 Hz, 1H) 3.25 (br d, J=11.0 Hz, 1H) 2.80 (br d, J=14.2 Hz, 1H) 1.66 (br d, J=15.4 Hz, 1H) 1.43-1.58 (m, 1H) 1.24-1.37 (m, 1H) 1.05-1.19 (m, 1H) 0.86 (td, J=8.7, 4.7 Hz, 1H) 0.11 (q, J=5.4 Hz, 1H)

LC/MS (method LC-C): Rt 3.00 min, MH$^+$488
[α]$_D^{20}$: −143.33° (c 0.06, DMF)

Chiral HPLC (method HPLC-B): Rt 8.67 min, chiral purity 100%

Compound 144BA:

$^1$H NMR (500 MHz, DMSO-d$_6$) δ ppm 7.36 (t, J=7.9 Hz, 1H) 7.30 (d, J=7.6 Hz, 1H) 7.09-7.16 (m, 1H) 6.99-7.09 (m, 3H) 6.84 (t, J=7.1 Hz, 1H) 6.67 (d, J=7.3 Hz, 1H) 5.99 (s, 1H) 5.76 (d, J=13.6 Hz, 1H) 5.59 (d, J=7.6 Hz, 1H) 5.00 (d, J=12.9 Hz, 1H) 4.38 (br d, J=11.0 Hz, 1H) 4.15-4.32 (m, 3H) 3.81 (d, J=13.6 Hz, 1H) 2.75 (br dd, J=13.9, 3.2 Hz, 1H) 1.77 (br dd, J=14.2, 6.6 Hz, 1H) 1.28-1.43 (m, 2H) 0.92-1.03 (m, 1H) 0.71-0.90 (m, 2H)

LC/MS (method LC-C): Rt 2.91 min, MH$^+$488

$[α]_D^{20}$: −233.87° (c 0.062, DMF)

Chiral HPLC (method HPLC-B): Rt 11.08 min, chiral purity 100%

Example 145: Synthesis of (18'*R,E)-4'-fluoro-12'-hydroxy-18'-phenyl-6'H,18'H-spiro[cyclobutane-1, 9'-[10,17]methanobenzo[b]pyrido[1,2-f][1]oxa[5,6, 9]triazacyclotridecine]-11',13'-dione (Compound 145A), (18'*S,E)-4'-fluoro-12'-hydroxy-18'-phenyl-6'H,18'H-spiro[cyclobutane-1,9'-[10,17]methanobenzo[b]pyrido[1,2-f][1]oxa[5,6,9]triazacyclotridecine]-11',13'-dionene (Compound 145B)

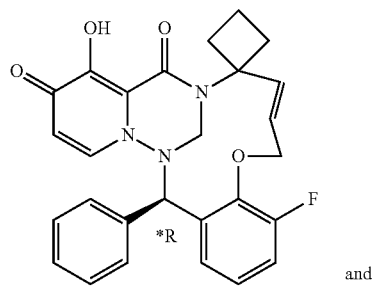

145A and

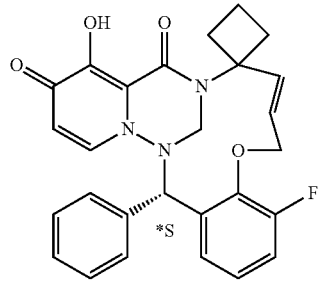

145B

Compounds 145A and 145B were synthesized according to the procedures described in example 146 starting from intermediates 146f and 61b.

Compound 145A:

$^1$H NMR (400 MHz, DMSO-d$_6$) δ ppm 7.93 (br d, J=7.6 Hz, 1H) 7.27-7.43 (m, 3H) 7.01-7.22 (m, 5H) 6.46 (br d, J=15.2 Hz, 1H) 6.01-6.21 (m, 1H) 5.49 (d, J=7.6 Hz, 1H) 5.29 (s, 1H) 5.13 (d, J=13.7 Hz, 1H) 4.72-4.85 (m, 1H) 4.42-4.56 (m, 1H) 3.84 (d, J=13.7 Hz, 1H) 2.80-2.92 (m, 1H) 2.40-2.47 (m, 1H) 1.98-2.15 (m, 2H) 1.75 (q, J=8.8 Hz, 1H) 1.52-1.67 (m, 1H)

LC/MS (method LC-C): Rt 2.99 min, MH$^+$474

$[α]D^{20}$: −664.47° (c 0.197, DMF)

Chiral HPLC (method HPLC-A): Rt 10.57 min, chiral purity 100%

Compound 145B:

LC/MS (method LC-C): Rt 2.99 min, MH$^+$474

$[α]D^{20}$: +640.63° (c 0.224, DMF)

Chiral HPLC (method HPLC-A): Rt 7.62 min, chiral purity 100%

Example 146: Synthesis of (18'R,E)-3',4'-difluoro-12'-hydroxy-18'-phenyl-6'H,18'H-spiro[cyclobutane-1,9'-[10,17]methanobenzo[b]pyrido[1,2-f][1]oxa[5,6, 9]triazacyclotridecine]-11',13'-dione (Compound 146A), (18'S,E)-3',4'-difluoro-12'-hydroxy-18'-phenyl-6'H,18'H-spiro[cyclobutane-1,9'-[10,17]methanobenzo[b]pyrido[1,2-f][1]oxa[5,6,9]triazacyclotridecine]-11',13'-dione (Compound 146B)

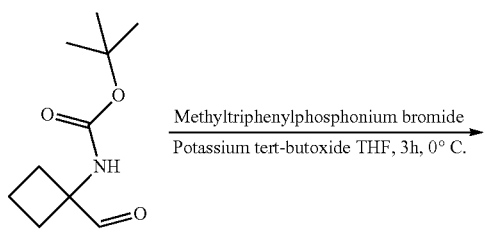

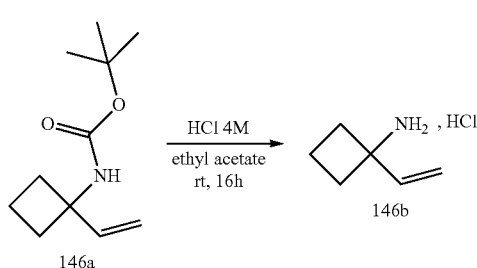

-continued
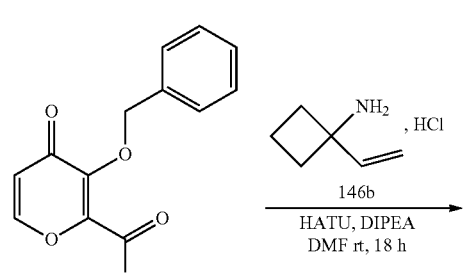 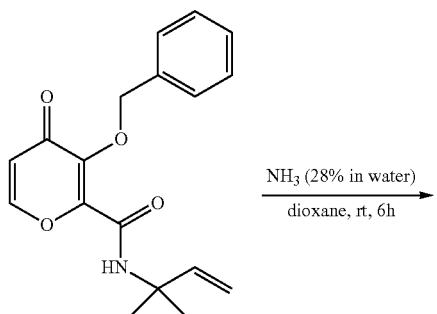
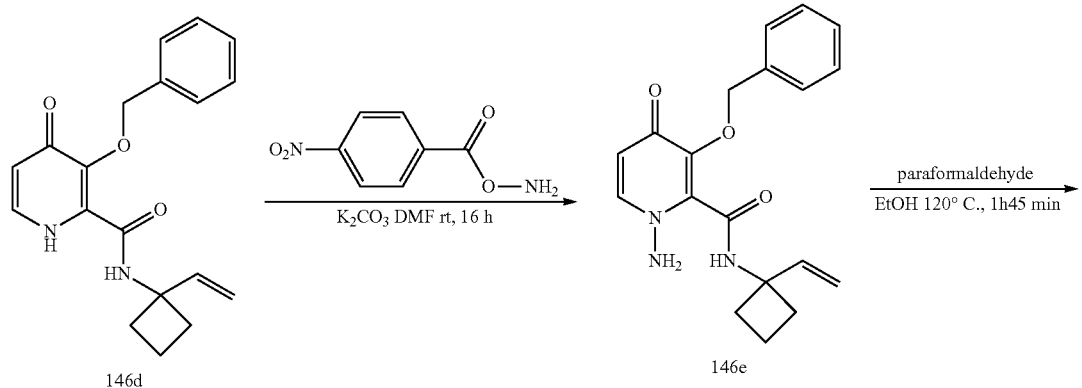
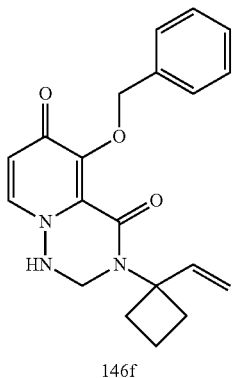
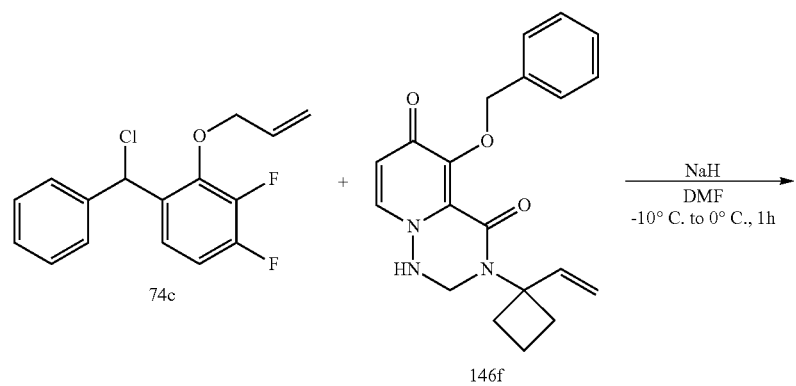

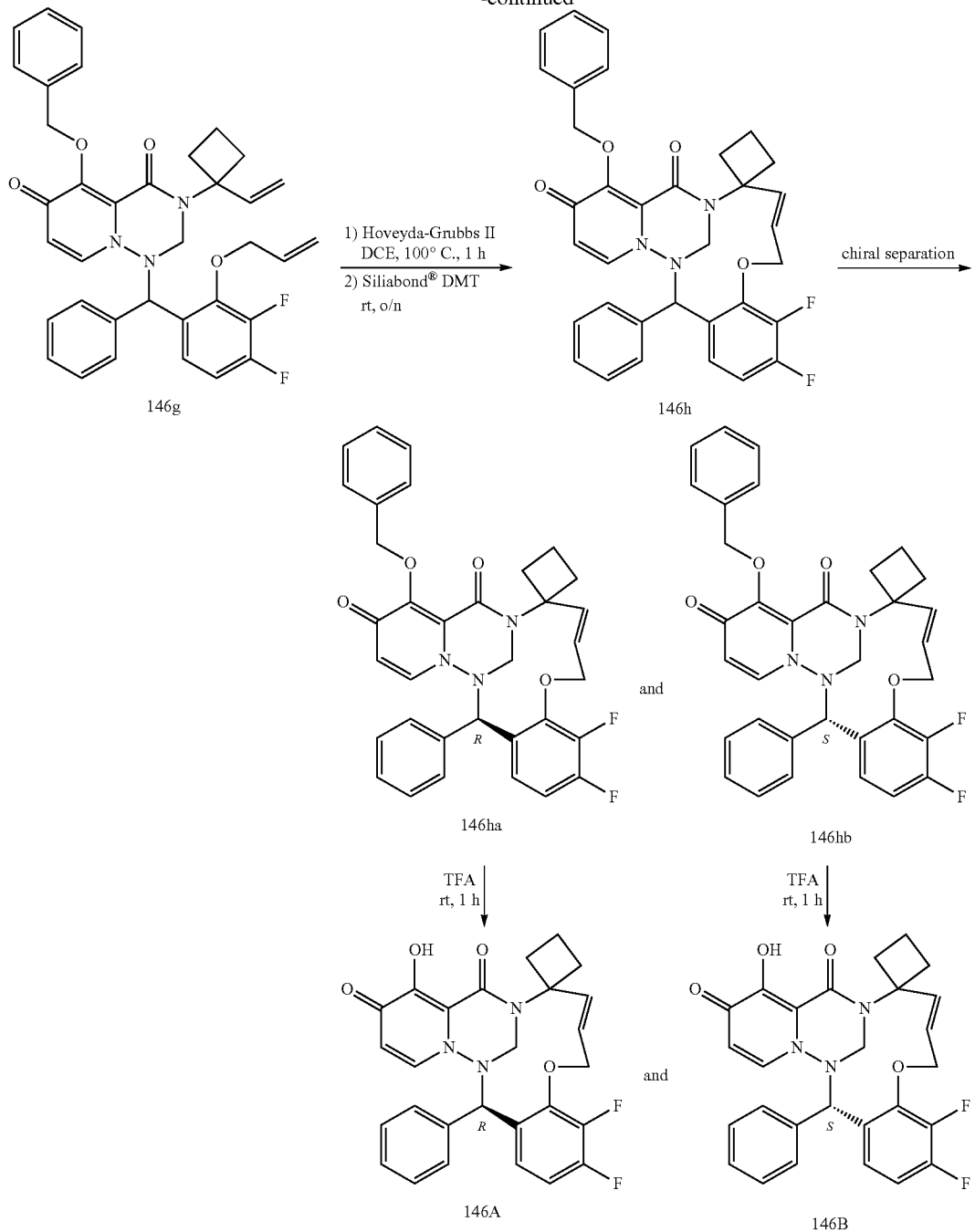

Synthesis of Intermediate 146a:

To a solution of Methyltriphenylphosphonium bromide (499.135 g, 1397.261 mmol) in THF (3000 ml) was added Potassium tert-butoxide (146.990 g, 1309.932 mmol) at 0° C. under $N_2$. The reaction was stirred for 30 min at 0° C. To the reaction was added tert-butyl 1-formylcyclobutylcarbamate (174 g, 873.288 mmol) in THF (500 mL). The reaction was stirred for 3 hours at 0° C. Sat. NaCl (1000 mL) was added and the reaction mixture was extracted with EtOAc (3×1000 mL). The organic layer was dried over $Na_2SO_4$, filtered and concentrated. The residue was purified by silica gel chromatography (0-10% EtOAc/Petroleum Ether) to afford tert-butyl 1-vinylcyclobutylcarbamate (intermediate 146a, 160 g) as white solid.

Synthesis of Intermediate 146b:

To a solution of tert-butyl 1-vinylcyclobutylcarbamate 146a (160 g, 811.055 mmol) in ethyl acetate (300 ml) was added hydrogen chloride (4 M in ethyl acetate, 811.077 ml) at 0° C. The reaction was stirred overnight at rt. To the stirred reaction was added n-hexane (1.5 L), and the resulting mixture was filtered to afford intermediate 1-vinylcyclobutanamine hydrochloride (intermediate 146b, 100 g) as white solid.

Synthesis of Intermediate 146c:

Under $N_2$, a mixture of 3-(benzyloxy)-4-oxo-4H-pyran-2-carboxylic acid [CAS 119736-16-2] (20 g, 81 mmol), 1-vinylcyclobutan-1-amine (intermediate 146b, 11.97 g, 90 mmol), HATU (46.6 g, 123 mmol) and N,N-diisopropylethylamine (49 mL, 284 mmol) in DMF (150 mL) was stirred at rt for 18 h. The mixture was diluted with EtOAc, washed 2 times with water and 2 times with 10% $K_2CO_3$ in water. The organic layer was dried over $MgSO_4$, filtered and concentrated under reduced pressure to give 3-(benzyloxy)-4-oxo-N-(1-vinylcyclobutyl)-4H-pyran-2-carboxamide (intermediate 146c, 25.6 g), used as such in the next step.

Synthesis of Intermediate 146d:

A mixture of 3-(benzyloxy)-4-oxo-N-(1-vinylcyclobutyl)-4H-pyran-2-carboxamide (intermediate 146c, 25.6 g, 78.681 mmol) in $NH_3$ (28% in water) (133 mL) and dioxane (250 mL) was stirred at rt for 6 h. The mixture was diluted with water and acidified with HCl 3N. The mixture was extracted with EtOAc. The organic layer was dried over $MgSO_4$, filtered and the solvent was evaporated. Purification was carried out by flash chromatography over silica gel (irregular 20-45 µm, 330 g, $CH_2Cl_2/CH_3OH$ 99/1 to 93/7) to give 3-(benzyloxy)-4-oxo-N-(1-vinylcyclobutyl)-1,4-dihydropyridine-2-carboxamide (intermediate 146d, 20 g).

Synthesis of Intermediate 146e:

1-amino-3-(benzyloxy)-4-oxo-N-(1-vinylcyclobutyl)-1,4-dihydropyridine-2-carboxamide (intermediate 146e, 14.9 g) was obtained using the procedure described for intermediate 1b. It was purified by trituration in EtOAc and washed with diisopropylether.

Synthesis of Intermediate 146f:

1-amino-3-(benzyloxy)-4-oxo-N-(1-vinylcyclobutyl)-1,4-dihydropyridine-2-carboxamide (intermediate 146e, 9.5 g, 27.991 mmol) was suspended in EtOH (133 mL). The mixture was heated at 100° C., then paraformaldehyde (0.84 g, 27.991 mmol) was added. The reaction mixture was heated at 120° C. for 1h45 min. The solvent was concentrated under reduced pressure, a few mL of EtOH were added and white solid was was filtered and dried under vacuum pressure to give a first batch of 5-(benzyloxy)-3-(1-vinylcyclobutyl)-2,3-dihydro-1H-pyrido[2,1-f][1,2,4]triazine-4,6-dione (intermediate 146f, 6.2g). Mother layers (5.6 g) were evaporated and then purified by flash column chromatography on silica gel (120 g, eluent DCM/MeOH 94:6 to 90:10) to give, after solidification in EtOH/diisopropylether, a second batch of intermediate 146f (1.3 g).

Synthesis of Intermediate 146g:

5-(benzyloxy)-3-(1-vinylcyclobutyl)-2,3-dihydro-1H-pyrido[2,1-f][1,2,4]triazine-4,6-dione (intermediate 146f, 20 g, 56.914 mmol) was dissolved under $N_2$ atmosphere in dry DMF (200 mL). The reaction mixture was cooled down to −10° C., then NaH (60% in oil) (2.5 g, 62.606 mmol) was added. After stirring 10 min at −10° C., a solution of 2-(allyloxy)-1-(chloro(phenyl)methyl)-3,4-difluorobenzene (intermediate 74c, 20.2 g, 68.297 mmol) in dry DMF (100 mL) was added dropwise and the reaction mixture was stirred between −10 and 0° C. during 1h. The solution was diluted with EtOAc (1000 mL) and washed twice with a saturated aqueous solution of $NH_4Cl$ (2×500 mL), once with water (500 mL) and once with brine (500 mL). The combined organic layers were dried over $Na_2SO_4$, filtered and concentrated under reduced pressure. Purification was carried out by flash column chromatography on silica gel (220 g, eluent DCM/MeOH 100:0-98:2-90:10) to give 1-((2-(allyloxy)-3,4-difluorophenyl)(phenyl)methyl)-5-(benzyloxy)-3-(1-vinylcyclobutyl)-2,3-dihydro-1H-pyrido[2,1-f][1,2,4]triazine-4,6-dione (intermediate 146g, 17.6 g).

Synthesis of Intermediate 146h:

In a 2 L flask, a solution of 1-((2-(allyloxy)-3,4-difluorophenyl)(phenyl)methyl)-5-(benzyloxy)-3-(1-vinylcyclobutyl)-2,3-dihydro-1H-pyrido[2,1-f][1,2,4]triazine-4,6-dione (intermediate 146g, 8.45 g, 13.86 mmol) in dry dichloroethane (1100 mL) was degassed under $N_2$ for 1 h. Hoveyda-Grubbs II catalyst (1.74 g, 2.772 mmol) in solution in 50 mL of dichloroethane was added dropwise over 4 h (12.5 mL/hour) at 100° C. The reaction was then stirred at 100° C. for 2 h under nitrogen atmosphere. The reaction medium was allowed to cool to room temperature and 18 g of SiliaMetS® DMT were added and the mixture was stirred overnight. A few MeOH was added to the mixture, which was then filtered over a pad of Celite® and washed with solution of $CH_2Cl_2$/MeOH (90/10). Solvent was concentrated in vacuo. The resulting crude brown oil was purified by flash chromatography on silica gel (120 g, eluent $CH_2Cl_2$/MeOH 99.5:0.5/98:2/90:10) to give, after crystallization in $CH_3CN$/diisopropylether, (E)-12'-(benzyloxy)-3',4'-difluoro-18'-phenyl-6'H,18'H-spiro[cyclobutane-1,9'-[10,17]methanobenzo[b]pyrido[1,2-f][1]oxa[5,6,9]triazacyclotridecine]-11',13'-dione (intermediate 146h, 3.28 g).

Different batches of 146h were combined (13.5 g). A purification was performed via achiral SFC (Stationary phase: AMINO 5 µm 150*30 mm, Mobile phase: 87% $CO_2$, 13% MeOH) yielding 11.99 g.

The enantiomers were separated via chiral SFC (Stationary phase: Chiralpak IG 5 µm 250*30 mm, Mobile phase: 55% $CO_2$, 45% of a mixture of MeOH/$CH_2Cl_2$ 90/10) to afford the first eluted enantiomer 146ha (5.18 g) and the second eluted enantiomer 146hb (5.22 g).

Synthesis of Compound 146A:

TFA (33.2 mL, 438.352 mmol) was added to enantiomer 146ha (5.05 g; 8.769 mmol). The mixture was stirred at rt for 1 h and then concentrated under reduced pressure. The residue was purified by preparative LC (regular SiOH 30 µm, 120 g, $CH_2Cl_2$/MeOH from 99:1 to 97:3) to give, after crystallization in $Et_2O$, (18'R,E)-3',4'-difluoro-12'-hydroxy-18'-phenyl-6'H,18'H-spiro[cyclobutane-1,9'-[10,17]methanobenzo[b]pyrido[1,2-f][1]oxa[5,6,9]triazacyclotridecine]-11',13'-dione (compound 146A, 3.27 g).

Compound 146A:

$^1$H NMR (500 MHz, DMSO-$d_6$) δ ppm 7.95 (br t, J=6.5 Hz, 1H) 7.40-7.50 (m, 1H) 7.33 (br d, J=7.3 Hz, 1H) 7.13-7.24 (m, 3H) 7.09 (br s, 2H) 6.52 (br d, J=14.8 Hz, 1H) 6.09-6.27 (m, 1H) 5.49 (d, J=7.9 Hz, 1H) 5.24 (s, 1H) 5.11 (br d, J=13.6 Hz, 1H) 4.82 (br t, J=9.5 Hz, 1H) 4.47-4.62 (m, 1H) 3.84 (br d, J=13.6 Hz, 1H) 2.86 (q, J=10.3 Hz, 1H) 2.43-2.46 (m, 1H) 2.01-2.16 (m, 2H) 1.71-1.81 (m, 1H) 1.54-1.67 (m, 1H)

LC/MS (method LC-C): Rt 3.06 min, MH$^+$492

$[α]_D^{20}$: −688.89° (c 0.099, DMF)

Chiral HPLC (method HPLC-A): Rt 11.11 min, chiral purity 100%

Synthesis of Compound 146B:

(18'S,E)-3',4'-difluoro-12'-hydroxy-18'-phenyl-6'H,18'H-spiro[cyclobutane-1,9'-[10,17]methanobenzo[b]pyrido[1,2-f][1]oxa[5,6,9]triazacyclotridecine]-11',13'-dione (compound 146B) was obtained using the procedure described for compound 146A.

Compound 146B:

$^1$H NMR (400 MHz, DMSO-$d_6$) δ ppm 7.95 (br t, J=6.8 Hz, 1H) 7.40-7.52 (m, 1H) 7.35 (br d, J=7.5 Hz, 1H) 7.14-7.20 (m, 3H) 7.09 (br s, 2H) 6.53 (br d, J=15.3 Hz, 1H) 6.11-6.26 (m, 1H) 5.49 (d, J=7.6 Hz, 1H) 5.24 (s, 1H) 5.11 (d, J=13.7 Hz, 1H) 4.82 (br t, J=9.7 Hz, 1H) 4.48-4.61 (m, 1H) 3.84 (d, J=13.7 Hz, 1H) 2.80-2.90 (m, 1H) 2.41-2.46 (m, 1H) 2.01-2.17 (m, 2H) 1.75 (q, J=9.2 Hz, 1H) 1.52-1.67 (m, 1H)

LC/MS (method LC-C): Rt 3.02 min, MH+492

[α]$_D^{20}$: +651.10° (c 0.182, DMF)

Chiral HPLC (method HPLC-A): Rt 6.07 min, chiral purity 100%

Example 147: Synthesis of (17a'*R,*E)-12'-hydroxy-2',17a'-dihydro-6'H-spiro[cyclobutane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 147A), (17a'*S,*E)-12'-hydroxy-2',17a'-dihydro-6'H-spiro[cyclobutane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 147B)

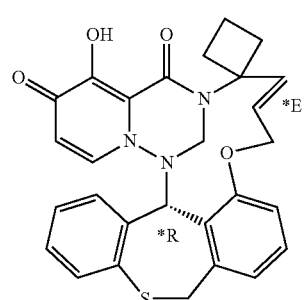

147A

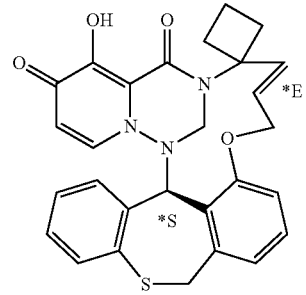

147B

Compounds 147A and 147B were synthesized according to the procedures described in example 46 starting from intermediate 146f and 37c.

Compound 147A:

LC/MS (method LC-C): Rt 2.98 min, MH+500

[α]$_D^{20}$: +500.53° (c 0.188, DMF)

Chiral HPLC (method HPLC-B): Rt 6.47 min, chiral purity 100%

Compound 147B:

¹H NMR (400 MHz, DMSO-d$_6$) δ ppm 10.12-11.64 (m, 1H) 7.43 (d, J=7.6 Hz, 1H) 7.37-7.42 (m, 1H) 7.28 (d, J=7.8 Hz, 1H) 7.16 (d, J=7.2 Hz, 1H) 7.05-7.11 (m, 1H) 6.98-7.03 (m, 1H) 6.80-6.87 (m, 1H) 6.70 (d, J=7.2 Hz, 1H) 6.43 (d, J=15.7 Hz, 1H) 6.13 (dt, J=15.3, 7.5 Hz, 1H) 5.86 (d, J=13.4 Hz, 1H) 5.61 (d, J=7.7 Hz, 1H) 5.42 (s, 1H) 5.14 (d, J=13.6 Hz, 1H) 4.73-4.80 (m, 1H) 4.64-4.72 (m, 1H) 3.86 (t, J=12.7 Hz, 2H) 2.76-2.87 (m, 1H) 2.41-2.47 (m, 1H) 1.97-2.16 (m, 2H) 1.74 (q, J=9.7 Hz, 1H) 1.53-1.68 (m, 1H)

LC/MS (method LC-C): Rt 2.98 min, MH+500

[α]D$_{20}$: −511.54° (c 0.13, DMF)

Chiral HPLC (method HPLC-B): Rt 7.31 min, chiral purity 100%

Example 148: Synthesis of (9*R,18*R,*E)-3,4-difluoro-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 148AA) and (9*S,18*S,*E)-3,4-difluoro-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 148BB) and (9*R,18*S,*E)-3,4-difluoro-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 148BA) and (9*S,18*R,*E)-3,4-difluoro-12-hydroxy-9-methyl-18-phenyl-6,9-dihydro-18H-10,17-methanobenzo[b]pyrido[1,2-f][1]oxa[5,6,9]triazacyclotridecine-11,13-dione (Compound 148AB)

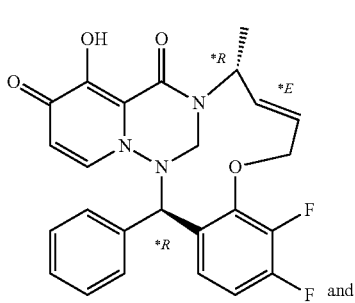

148AA and

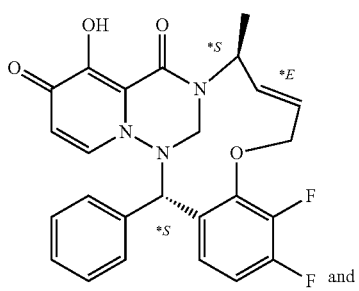

148BB and

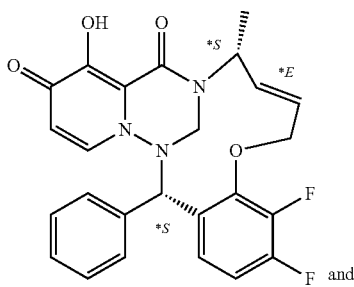

148BA and

-continued

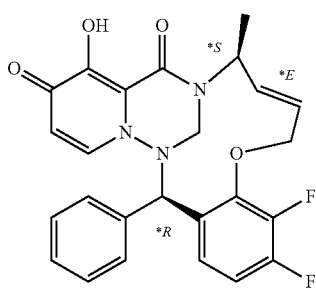

148AB

Compounds 148AA, 148BB, 148BA and 148AB were synthesized according to the procedures described in example 29 starting from intermediate 74c.

Compound 148AA:

$^1$H NMR (500 MHz, DMSO-d$_6$) δ ppm 7.95 (br t, J=6.9 Hz, 1H) 7.45-7.55 (m, 1H) 7.03-7.29 (m, 6H) 6.35 (ddd, J=15.5, 10.0, 5.0 Hz, 1H) 5.68 (br d, J=10.1 Hz, 1H) 5.48 (d, J=7.6 Hz, 1H) 5.40-5.46 (m, 1H) 5.15 (s, 1H) 5.04 (d, J=13.6 Hz, 1H) 4.92 (br dd, J=11.3, 5.4 Hz, 1H) 4.26 (d, J=13.6 Hz, 1H) 4.09 (br t, J=10.6 Hz, 1H) 1.16 (d, J=6.9 Hz, 3H)

LC/MS (method LC-C): Rt 2.83 min, MH$^+$466

$[α]_D^{20}$: −570.00° (c 0.07, DMF)

Chiral HPLC (method HPLC-B): Rt 4.60 min, chiral purity 100%

Compound 148AB:

$^1$H NMR (500 MHz, DMSO-d$_6$) δ ppm 8.00 (br t, J=7.1 Hz, 1H) 7.44-7.53 (m, 1H) 7.34 (d, J=7.6 Hz, 1H) 7.17 (br d, J=3.2 Hz, 3H) 7.08 (br s, 2H) 6.43-6.61 (m, 1H) 5.88-6.06 (m, 1H) 5.49 (d, J=7.6 Hz, 1H) 5.35 (s, 1H) 5.18 (d, J=14.2 Hz, 1H) 4.70 (br t, J=10.2 Hz, 1H) 4.57 (br dd, J=9.8, 5.0 Hz, 1H) 4.22 (d, J=14.2 Hz, 1H) 3.70 (br dd, J=9.6, 7.1 Hz, 1H) 1.76 (d, J=6.9 Hz, 3H)

LC/MS (method LC-C): Rt 2.87 min, MH$^+$466

$[α]_D^{20}$: −713.25° (c 0.083, DMF)

Chiral HPLC (method HPLC-A): Rt 8.38 min, chiral purity 100%

Compound 148BA:

LC/MS (method LC-C): Rt 2.87 min, MH$^+$466

$[α]_D^{20}$: +700.00° (c 0.068, DMF)

Chiral HPLC (method HPLC-A): Rt 4.31 min, chiral purity 100%

Compound 148BB:

LC/MS (method LC-C): Rt 2.83 min, MH$^+$466

$[α]D^{20}$: +560.2° (c 0.098, DMF)

Chiral HPLC (method HPLC-B): Rt 4.42 min, chiral purity 99.59%

Example 150: Synthesis of (9*R,18*R,*E)-12-hydroxy-9-(methoxymethyl)-18-phenyl-6,9-dihydro-18H-10,17-methanobenzo[b]pyrido[1,2-f][1]oxa[5,6,9]triazacyclotridecine-11,13-dione (Compound 150A), (9*S,18*S,*E)-12-hydroxy-9-(methoxymethyl)-18-phenyl-6,9-dihydro-18H-10,17-methanobenzo[b]pyrido[1,2-f][1]oxa[5,6,9]triazacyclotridecine-11,13-dione (Compound 150B)

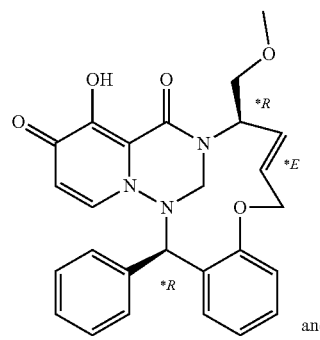

150A and

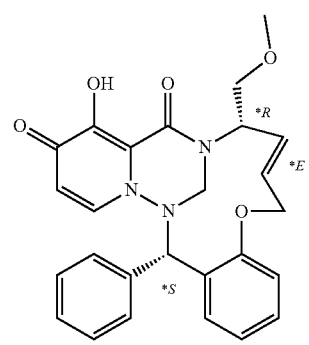

150B

Compounds 150A and 150B were synthesized according to the procedures described in example 39 starting from intermediate 5-(benzyloxy)-3-(1-methoxybut-3-en-2-yl)-2,3-dihydro-1H-pyrido[2,1-f][1,2,4]triazine-4,6-dione (synthesized as 39e from 1-methoxy-3-buten-2-amine [CAS 1391253-55-6]).

Compound 150A:

$^1$H NMR (500 MHz, DMSO-d$_6$) δ ppm 8.01 (dd, J=7.9, 1.3 Hz, 1H) 7.33-7.41 (m, 1H) 7.27-7.32 (m, 1H) 7.03-7.19 (m, 7H) 6.29 (ddd, J=15.4, 10.1, 5.0 Hz, 1H) 5.32-5.45 (m, 3H) 5.16 (s, 1H) 4.91 (d, J=13.9 Hz, 1H) 4.82 (dd, J=11.3, 5.4 Hz, 1H) 4.22 (d, J=13.6 Hz, 1H) 4.02 (t, J=10.9 Hz, 1H) 3.35-3.39 (m, 2H) 3.14 (s, 3H)

LC/MS (method LC-C): Rt 2.66 min, MH$^+$460

$[α]_D^{20}$: −555.23° (c 0.172, DMF)

Chiral HPLC (method HPLC-B): Rt 6.14 min, chiral purity 100%

Compound 150B:

LC/MS (method LC-C): Rt 2.66 min, MH$^+$460

$[α]_D^{20}$: +526.29° (c 0.194, DMF)

Chiral HPLC (method HPLC-B): Rt 11.76 min, chiral purity 100%

Example 151: Synthesis of (1*R,13*Z)-20,25-difluoro-7-hydroxy-16-oxa-23-thia-2,3,10-triazahexacyclo[15.12.1.1²,¹⁰.0³,⁸.0²¹,³⁰.0²⁴,²⁹]hentriaconta-4,7,13,17,19,21(30),24(29),25,27-nonaene-6,9-dione (Compound 151A) and (1*S,13*Z)-20,25-difluoro-7-hydroxy-16-oxa-23-thia-2,3,10-triazahexacyclo[15.12.1.1²,¹⁰.0³,⁸.0²¹,³⁰.0²⁴,²⁹]hentriaconta-4,7,13,17,19,21(30),24(29),25,27-nonaene-6,9-dione (Compound 151B)

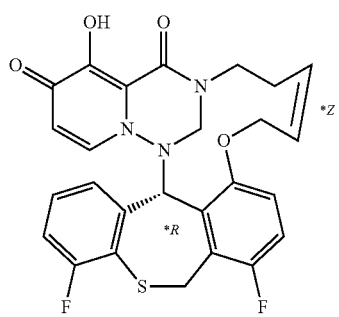

151A

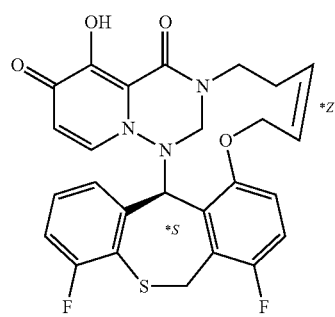

151B

Compounds 151A and 151B were synthesized according to the procedures described in example 88 starting from intermediate 10-(allyloxy)-11-chloro-4,7-difluoro-6,11-dihydrodibenzo[b,e]thiepine (synthesized as 88n from 5-fluoro-2-hydroxy-benzoic acid [CAS 345-16-4] and 2-fluoro-benzenethiol [CAS 2557-78-0]).

Compound 151A:

LC/MS (method LC-C): Rt 2.89 min, MH⁺510

[α]$_D^{20}$: +150.50° (c 0.200, DMF)

Compound 151B:

¹H NMR (400 MHz, DMSO-d₆) δ ppm 11.28-12.22 (m, 1H) 7.35 (t, J=9.1 Hz, 1H) 7.23 (d, J=7.7 Hz, 1H) 7.07-7.18 (m, 2H) 6.91 (td, J=7.9, 5.9 Hz, 1H) 6.49 (d, J=7.7 Hz, 1H) 6.13 (s, 1H) 6.02-6.11 (m, 1H) 5.91-6.01 (m, 1H) 5.57-5.67 (m, 2H) 4.96 (d, J=13.4 Hz, 1H) 4.46-4.59 (m, 2H) 4.40 (d, J=13.4 Hz, 1H) 4.19-4.30 (m, 1H) 4.14 (d, J=14.1 Hz, 1H) 2.78-2.89 (m, 1H) 2.11-2.31 (m, 2H)

LC/MS (method LC-C): Rt 2.89 min, MH⁺510

[α]$_D^{20}$: −155.8° (c 0.181, DMF)

Example 152: Synthesis of (9*S,18*S,*E)-9-cyclopropyl-3,4-difluoro-12-hydroxy-18-phenyl-6,9-dihydro-18H-10,17-methanobenzo[b]pyrido[1,2-f][1]oxa[5,6,9]triazacyclotridecine-11,13-dione (Compound 152AA) and (9*R,18*R,*E)-9-cyclopropyl-3,4-difluoro-12-hydroxy-18-phenyl-6,9-dihydro-18H-10,17-methanobenzo[b]pyrido[1,2-f][1]oxa[5,6,9]triazacyclotridecine-11,13-dione (Compound 152BB) and (9*S,18*R,*E)-9-cyclopropyl-3,4-difluoro-12-hydroxy-18-phenyl-6,9-dihydro-18H-10,17-methanobenzo[b]pyrido[1,2-f][1]oxa[5,6,9]triazacyclotridecine-11,13-dione (Compound 152BA) and (9*R,18*S,*E)-9-cyclopropyl-3,4-difluoro-12-hydroxy-18-phenyl-6,9-dihydro-18H-10,17-methanobenzo[b]pyrido[1,2-f][1]oxa[5,6,9]triazacyclotridecine-11,13-dione (Compound 152AB)

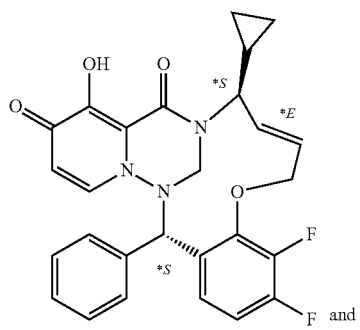

152AA and

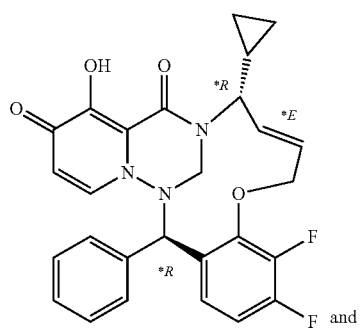

152BB and

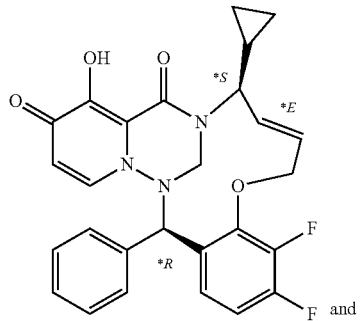

152BA and

387
-continued

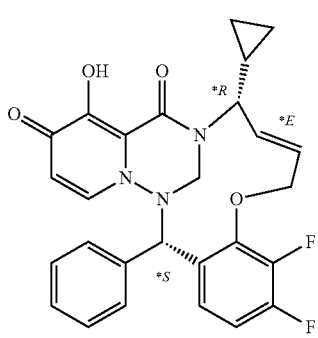

152AB

Compounds 152AA, 152BB, 152BA and 152AB were synthesized according to the procedures described in example 39 starting from intermediates 3-(1-cyclopropylallyl)-5-(benzyloxy)-3-(1-cyclopropylallyl)-2,3-dihydro-1H-pyrido[2,1-f][1,2,4]triazine-4,6-dione (synthesized from cyclopropane-methane-amine [CAS 1160786-80-8] and 74c.

Compound 152AA:

LC/MS (method LC-C): Rt 3.04 min, MH⁺492

$[\alpha]_D^{20}$: +575.71° (c 0.07, DMF)

Chiral HPLC (method HPLC-A): Rt 5.15 min, chiral purity 100%

Compound 152AB:

LC/MS (method LC-C): Rt 3.03 min, MH⁺492

$[\alpha]_D^{20}$: +575.00° (c 0.056, DMF)

Chiral HPLC (method HPLC-B): Rt 4.57 min. chiral purity 100%

Compound 152BA:

¹H NMR (500 MHz, DMSO-d₆) δ ppm 7.95 (br t, J=6.8 Hz, 1H) 7.43-7.55 (m, 1H) 7.03-7.32 (m, 6H) 6.32 (ddd, J=15.6, 10.1, 5.5 Hz, 1H) 5.82 (br dd, J=15.8, 6.6 Hz, 1H) 5.48 (d, J=7.6 Hz, 1H) 5.11-5.19 (m, 2H) 4.91 (dd, J=11.3, 5.4 Hz, 1H) 4.60 (dd, J=9.5, 6.6 Hz, 1H) 4.40 (d, J=13.6 Hz, 1H) 4.12 (br t, J=10.7 Hz, 1H) 1.05-1.14 (m, 1H) 0.49-0.57 (m, 1H) 0.45 (tt, J=8.6, 4.5 Hz, 1H) 0.33 (dq, J=9.3, 4.7 Hz, 1H) 0.23 (dq, J=9.5, 4.9 Hz, 1H)

LC/MS (method LC-C): Rt 3.03 min, MH⁺492

$[\alpha]_D^{20}$: −544.44° (c 0.072, DMF)

Chiral HPLC (method HPLC-B): Rt 7.57 min, chiral purity 100%

Compound 152BB:

¹H NMR (500 MHz, DMSO-d₆) δ ppm 7.96 (br t, J=6.9 Hz, 1H) 7.40-7.53 (m, 1H) 7.31 (d, J=7.6 Hz, 1H) 6.95-7.27 (m, 5H) 6.61 (br dd, J=13.6, 10.4 Hz, 1H) 5.77-5.96 (m, 1H) 5.49 (d, J=7.6 Hz, 1H) 5.35 (s, 1H) 5.20 (d, J=13.9 Hz, 1H) 4.71 (br t, J=10.4 Hz, 1H) 4.58 (br dd, J=10.4, 5.4 Hz, 1H) 4.12 (d, J=13.9 Hz, 1H) 2.73 (t, J=9.8 Hz, 1H) 2.04-2.17 (m, 1H) 0.50-0.66 (m, 2H) 0.28 (br dd, J=9.1, 4.1 Hz, 1H) 0.10 (br dd, J=9.0, 3.9 Hz, 1H)

LC/MS (method LC-C): Rt 3.04 min, MH⁺492

$[\alpha]_D^{20}$: −543.48° (c 0.069, DMF)

Chiral HPLC (method HPLC-A): Rt 6.68 min, chiral purity 100%

Example 153: Synthesis of (9*S,18*S,*E)-3,4-difluoro-12-hydroxy-9-(methoxymethyl)-18-phenyl-6,9-dihydro-18H-10,17-methanobenzo[b]pyrido[1,2-f][1]oxa[5,6,9]triazacyclotridecine-11,13-dione (Compound 153AA) and (9*R,18*R,*E)-3,4-difluoro-12-hydroxy-9-(methoxymethyl)-18-phenyl-6,9-dihydro-18H-10,17-methanobenzo[b]pyrido[1,2-f][1]oxa[5,6,9]triazacyclotridecine-11,13-dione (Compound 153BB) and (9*S,18*R,*E)-3,4-difluoro-12-hydroxy-9-(methoxymethyl)-18-phenyl-6,9-dihydro-18H-10,17-methanobenzo[b]pyrido[1,2-f][1]oxa[5,6,9]triazacyclotridecine-11,13-dione (Compound 153BA) and (9*R,18*S,*E)-3,4-difluoro-12-hydroxy-9-(methoxymethyl)-18-phenyl-6,9-dihydro-18H-10,17-methanobenzo[b]pyrido[1,2-f][1]oxa[5,6,9]triazacyclotridecine-11,13-dione (Compound 153AB)

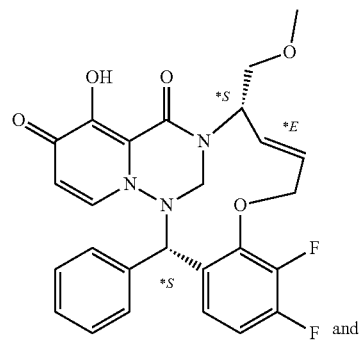

153AA and

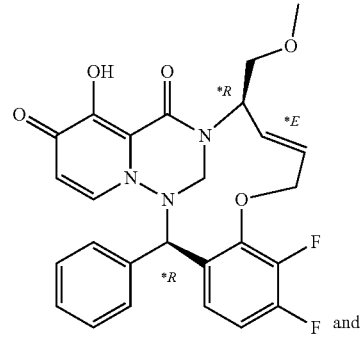

153BB and

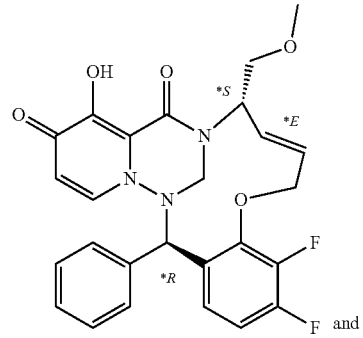

153BA and

-continued

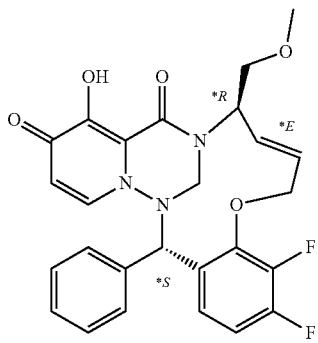

153AB

Compounds 153AA, 153BB, 153BA and 153AB were synthesized according to the procedures described in example 150 starting from 74c.

Compound 153AA:

LC/MS (method LC-C): Rt 2.83 min, MH$^+$496

$[\alpha]_D^{20}$: +515.79° (c 0.076, DMF)

Chiral HPLC (method HPLC-B): Rt 11.97 min, chiral purity 100%

Compound 153AB:

LC/MS (method LC-C): Rt 2.77 min, MH$^+$496

$[\alpha]_D^{20}$: +551.56° (c 0.064, DMF)

Chiral HPLC (method HPLC-A and B): No separation observed

Compound 153BA:

$^1$H NMR (500 MHz, DMSO-d$_6$) δ ppm 7.98 (br t, J=7.3 Hz, 1H) 7.42-7.54 (m, 1H) 7.33 (d, J=7.6 Hz, 1H) 6.92-7.28 (m, 5H) 6.35-6.56 (m, 1H) 5.96-6.17 (m, 1H) 5.50 (d, J=7.6 Hz, 1H) 5.35 (s, 1H) 5.19 (d, J=13.9 Hz, 1H) 4.71 (br t, J=10.2 Hz, 1H) 4.56 (br dd, J=10.2, 5.2 Hz, 1H) 4.30 (d, J=13.9 Hz, 1H) 4.11-4.19 (m, 1H) 4.03-4.10 (m, 1H) 3.77 (dt, J=9.1, 6.9 Hz, 1H) 3.27 (s, 3H)

LC/MS (method LC-C): Rt 2.77 min, MH$^+$496

$[\alpha]_D^{20}$: −698.25° (c 0.057, DMF)

Chiral HPLC (method HPLC-A and B): No separation observed

Compound 153BB:

$^1$H NMR (500 MHz, DMSO-d$_6$) δ ppm 7.94 (br t, J=6.9 Hz, 1H) 7.44-7.54 (m, 1H) 7.02-7.34 (m, 6H) 6.44 (ddd, J=15.4, 10.4, 5.0 Hz, 1H) 5.72 (dd, J=15.8, 6.6 Hz, 1H) 5.44-5.55 (m, 2H) 5.17 (s, 1H) 5.00 (d, J=13.6 Hz, 1H) 4.94 (dd, J=11.2, 5.2 Hz, 1H) 4.31 (d, J=13.6 Hz, 1H) 4.09 (br t, J=10.9 Hz, 1H) 3.42-3.50 (m, 2H) 3.23 (s, 3H)

LC/MS (method LC-C): Rt 2.83 min. MH$^+$496

$[\alpha]_D^{20}$: −526.15° (c 0.065, DMF)

Chiral HPLC (method HPLC-B): Rt 6.44 min, chiral purity 100%

Example 154: Synthesis of (9*R,18*S,*E)-9-ethyl-4-fluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (Compound 154AA) and (9*S,18*R,*E)-9-ethyl-4-fluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (Compound 154BB) and (9*R,18*R,*E)-9-ethyl-4-fluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (Compound 154BA) and (9*S,18*S,*E)-9-ethyl-4-fluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (Compound 154AB)

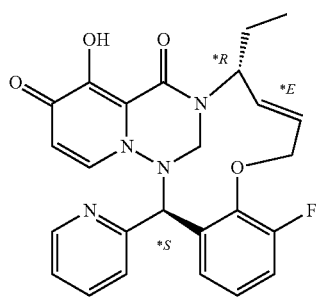

154AA and

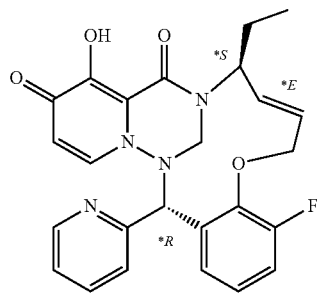

154BB and

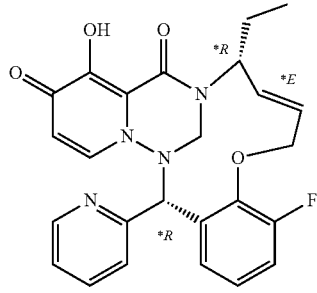

154BA and

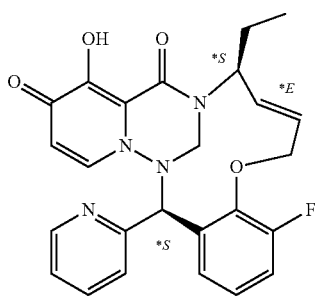

154AB

Compounds 154AA, 154BB, 154BA and 154AB were synthesized according to the procedures described in example 39 starting from intermediate 2-(2-(allyloxy)-3-fluorophenyl)(chloromethyl-pyridine) (synthesized as 41b from 2-bromopyridine [CAS 109-04-6] and 3-fluoro-2-(2-propen-1-yloxy)benzaldehyde [CAS 1106304-54-4]).

Compound 154AA:

LC/MS (method LC-C): Rt 2.63 min, MH⁺463

$[\alpha]_D^{20}$: +651.32° (c 0.076, DMF)

Chiral HPLC (method HPLC-A): Rt 5.32 min, chiral purity 100%

Compound 154AB:

LC/MS (method LC-C): Rt 2.57 min, MH⁺463

$[\alpha]_D^{20}$: +627.16° (c 0.081, DMF)

Chiral HPLC (method HPLC-A and B): No separation observed

Compound 154BA:

¹H NMR (400 MHz, DMSO-d₆) δ ppm 8.38 (d, J=4.2 Hz, 1H) 7.95 (br d, J=7.3 Hz, 1H) 7.64 (td, J=7.6, 1.2 Hz, 1H) 7.32-7.44 (m, 2H) 7.28 (d, J=7.7 Hz, 1H) 7.22 (dd, J=7.2, 5.0 Hz, 1H) 7.11 (d, J=7.7 Hz, 1H) 6.35 (ddd, J=15.5, 10.3, 5.1 Hz, 1H) 5.56 (br dd, J=15.7, 6.4 Hz, 1H) 5.50 (d, J=7.7 Hz, 1H) 5.41 (s, 1H) 5.17 (q, J=7.3 Hz, 1H) 5.07 (d, J=13.6 Hz, 1H) 4.88 (dd, J=11.4, 5.3 Hz, 1H) 4.23 (d, J=13.6 Hz, 1H) 4.02 (br t, J=10.9 Hz, 1H) 1.38-1.63 (m, 2H) 0.83 (t, J=7.3 Hz, 3H)

LC/MS (method LC-C): Rt 2.57 min, MH⁺463

$[\alpha]_D^{20}$: −596.92° (c 0.13, DMF)

Chiral HPLC (method HPLC-A and B): No separation observed

Compound 154BB:

¹H NMR (400 MHz, DMSO-d₆) δ ppm 8.31-8.39 (m, 1H) 7.98 (d, J=7.3 Hz, 1H) 7.62 (td, J=7.7, 1.7 Hz, 1H) 7.28-7.44 (m, 2H) 7.14-7.23 (m, 3H) 6.41 (br dd, J=15.0, 10.0 Hz, 1H) 5.78-6.00 (m, 1H) 5.62 (s, 1H) 5.50 (d, J=7.6 Hz, 1H) 5.21 (d, J=13.9 Hz, 1H) 4.60-4.69 (m, 1H) 4.49-4.59 (m, 1H) 4.23 (d, J=14.1 Hz, 1H) 3.41-3.53 (m, 1H) 2.26-2.41 (m, 1H) 2.08-2.23 (m, 1H) 0.87 (t, J=7.4 Hz, 3H)

LC/MS (method LC-C): Rt 2.63 min, MH⁺463

$[\alpha]_D^{20}$: −681.25° (c 0.08, DMF)

Chiral HPLC (method HPLC-A): Rt 6.25 min, chiral purity 100%

Example 155: synthesis (18*R,*Z)-3,4-difluoro-12-hydroxy-18-(o-tolyl)-6,9-dihydro-18H-10,17-methanobenzo[b]pyrido[1,2-f][1]oxa[5,6,9]triazacyclotridecine-11,13-dione (Compound 155A) and (18*S,*Z)-3,4-difluoro-12-hydroxy-18-(o-tolyl)-6,9-dihydro-18H-10,17-methanobenzo[b]pyrido[1,2-f][1]oxa[5,6,9]triazacyclotridecine-11,13-dione (Compound 155B)

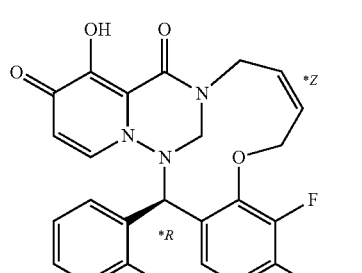

155A and

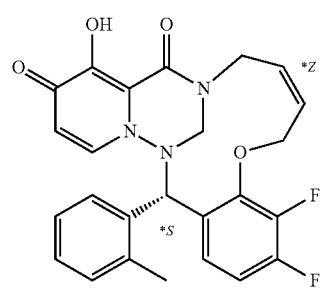

155B

Compounds 155A and 155B were synthesized according to the procedures described in example 5 starting from intermediate 2-(allyloxy)-1-(chloro(o-tolyl)methyl)-3,4-difluorobenzene (synthesized as 74c from 1-bromo-2-methylbenzene [CAS 95-46-5]).

Compound 155A:

¹H NMR (500 MHz, DMSO-d₆) δ ppm 7.96 (br t, J=6.3 Hz, 1H) 7.41-7.55 (m, 2H) 7.30 (br d, J=6.6 Hz, 1H) 7.03-7.14 (m, 2H) 6.95-7.02 (m, 1H) 6.16-6.32 (m, 1H) 5.93-6.13 (m, 1H) 5.64 (br s, 1H) 5.52 (d, J=7.9 Hz, 1H) 5.16 (d, J=13.9 Hz, 1H) 4.88-4.95 (m, 1H) 4.84 (br dd, J=13.7, 4.6 Hz, 1H) 4.27-4.38 (m, 2H) 3.24 (br dd, J=13.9, 8.2 Hz, 1H) 2.23 (s, 3H)

LC/MS (method LC-C): Rt 2.79 min, MH⁺466

$[\alpha]_D^{20}$: −670.33° (c 0.091, DMF)

Chiral HPLC (method HPLC-A): Rt 5.03 min, chiral purity 100%

Compound 155B:

LC/MS (method LC-C): Rt 2.79 min, MH⁺466

$[\alpha]_D^{20}$: +682.89° (c 0.076, DMF)

Chiral HPLC (method HPLC-A): Rt 5.75 min, chiral purity 100%

Example 156: Synthesis of (17a'*S,*E)-12'-hydroxy-2',17a'-dihydro-6'H-spiro[cyclopentane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 156A)

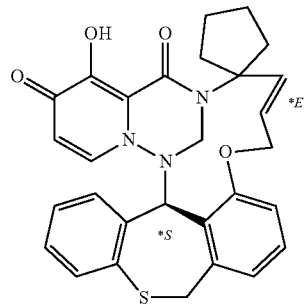

156A

Compound 156A was synthesized according to the procedures described in example 46 starting from intermediate 5-(benzyloxy)-3-(1-vinylcyclopentyl)-2,3-dihydro-1H-pyrido[2,1-f][1,2,4]triazine-4,6-dione (synthesized as 146f from 1-ethenyl-cyclopentanamine [CAS 1391303-96-0]).

Compound 156A:
$^1$H NMR (500 MHz, DMSO-d$_6$) δ ppm 7.36-7.43 (m, 2H) 7.23 (d, J=7.6 Hz, 1H) 7.18 (d, J=7.3 Hz, 1H) 7.06-7.11 (m, 1H) 6.99-7.03 (m, 1H) 6.84 (td, J=7.5, 1.1 Hz, 1H) 6.71-6.76 (m, 1H) 6.22 (dt, J=15.5, 7.5 Hz, 1H) 6.04-6.14 (m, 1H) 5.84 (d, J=13.2 Hz, 1H) 5.61 (d, J=7.6 Hz, 1H) 5.44 (s, 1H) 5.13 (d, J=13.6 Hz, 1H) 4.79 (dd, J=11.0, 7.3 Hz, 1H) 4.53 (dd, J=11.2, 7.4 Hz, 1H) 4.20 (d, J=13.6 Hz, 1H) 3.85 (d, J=13.2 Hz, 1H) 2.74-2.81 (m, 1H) 2.34-2.38 (m, 1H) 1.76-1.84 (m, 1H) 1.68-1.75 (m, 1H) 1.52-1.67 (m, 2H) 1.32-1.52 (m, 2H)

LC/MS (method LC-C): Rt 3.14 min, MH$^+$514

[α]$_D^{20}$: −473.93° (c 0.171, DMF)

Chiral HPLC (method HPLC-B): Rt 7.41 min, chiral purity 100%

Example 157: Synthesis of (9*R,17a*S,*E)-9-(tert-butyl)-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 157A), (9*S,17a*R,*E)-9-(tert-butyl)-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 157B)

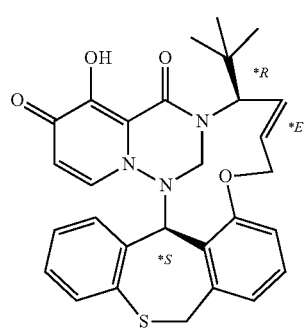

157A

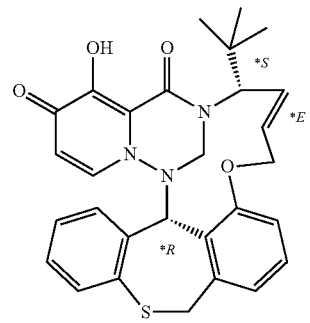

157B

Compounds 157A and 157B were synthesized according to the procedures described in example 46 starting from intermediate 5-(benzyloxy)-3-(4,4-dimethylpent-1-en-3-yl)-2,3-dihydro-1H-pyrido[2,1-f][1,2,4]triazine-4,6-dione (synthesized as 29c from 4,4-dimethyl-1-penten-3-amine [CAS 36024-39-2]).

Compound 157A:
$^1$H NMR (500 MHz, DMSO-d$_6$) δ ppm 7.44 (d, J=7.6 Hz, 1H) 7.35-7.42 (m, 1H) 7.28 (d, J=8.2 Hz, 1H) 7.16 (d, J=7.3 Hz, 1H) 7.04-7.11 (m, 1H) 6.97-7.03 (m, 1H) 6.79-6.86 (m, 1H) 6.67 (d, J=7.3 Hz, 1H) 6.53 (dd, J=15.3, 10.2 Hz, 1H) 5.82-5.94 (m, 2H) 5.61 (d, J=7.6 Hz, 1H) 5.51 (s, 1H) 5.25 (d, J=13.9 Hz, 1H) 4.74 (dd, J=10.7, 5.0 Hz, 1H) 4.58-4.67 (m, 1H) 4.34 (d, J=13.9 Hz, 1H) 3.88 (d, J=13.2 Hz, 1H) 3.34 (br d, J=10.4 Hz, 3H) 1.07 (s, 9H)

LC/MS (method LC-C): Rt 3.26 min, MH$^+$516

[α]$_D^{20}$: −405.23° (c 0.153, DMF)

Chiral HPLC (method HPLC-B): Rt 4.60 min, chiral purity 100%

Compound 157B:
LC/MS (method LC-C): Rt 3.26 min. MH$^+$516

[α]D$^{20}$: +418.3° (c 0.153, DMF)

Chiral HPLC (method HPLC-B): Rt 5.39 min, chiral purity 100%

Example 158: synthesis (18*S,*Z)-3,4-difluoro-12-hydroxy-18-(2-isopropylphenyl)-6,9-dihydro-18H-10,17-methanobenzo[b]pyrido[1,2-f][1]oxa[5,6,9]triazacyclotridecine-11,13-dione (Compound 158A) and (18*R,*Z)-3,4-difluoro-12-hydroxy-18-(2-isopropylphenyl)-6,9-dihydro-18H-10,17-methanobenzo[b]pyrido[1,2-f][1]oxa[5,6,9]triazacyclotridecine-11,13-dione (Compound 158B)

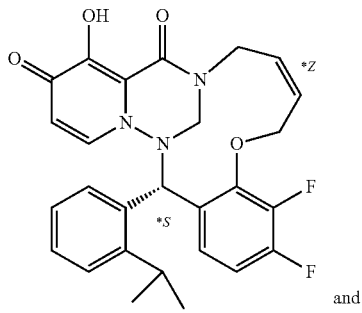

158A and

-continued

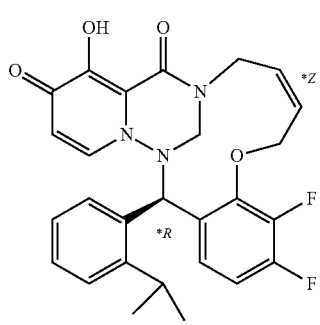

158B

Compounds 158A and 158B were synthesized according to the procedures described in example 5 starting from intermediate 2-(allyloxy)-1-(chloro(2-isopropylphenyl)methyl)-3,4-difluorobenzene (synthesized as 74c from 1-bromo-)-isopropyl-benzene [CAS 7073-94-1]).

Compound 158A:

LC/MS (method LC-C): Rt 3.01 min, MH+494

$[\alpha]_D^{20}$: +627.1° (c 0.214, DMF)

Chiral HPLC (method HPLC-B): Rt 4.10 min. chiral purity 100%

Compound 158B:

¹H NMR (500 MHz, DMSO-$d_6$) δ ppm 9.86-11.64 (m, 1H) 7.99 (br t, J=6.1 Hz, 1H) 7.42-7.55 (m, 2H) 7.22 (br d, J=7.6 Hz, 1H) 7.12-7.19 (m, 2H) 7.05-7.11 (m, 1H) 6.18 (dt, J=15.1, 7.4 Hz, 1H) 5.94-6.10 (m, 1H) 5.84 (br s, 1H) 5.49 (d, J=7.9 Hz, 1H) 5.15 (d, J=13.6 Hz, 1H) 4.84 (br dd, J=13.9, 4.7 Hz, 1H) 4.73-4.81 (m, 1H) 4.34-4.45 (m, 1H) 4.31 (d, J=13.9 Hz, 1H) 3.25 (br dd, J=13.9, 8.2 Hz, 1H) 3.01 (dt, J=13.3, 6.7 Hz, 1H) 1.18 (d, J=6.9 Hz, 3H) 0.93 (d, J=6.6 Hz, 3H)

LC/MS (method LC-C): Rt 3.01 min MH+494

$[\alpha\sim]_D^{20}$: −623.63° (c 0.182, DMF)

Chiral HPLC (method HPLC-B): Rt 4.49 min chiral purity 10000

Example 159: Synthesis of (17a'*R,*E)-24',25'-difluoro-12'-hydroxy-2',17a'-dihydro-6'H-spiro[cyclobutane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 159A), (17a'*S,*E)-24',25'-difluoro-12'-hydroxy-2',17a'-dihydro-6'H-spiro[cyclobutane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 159B)

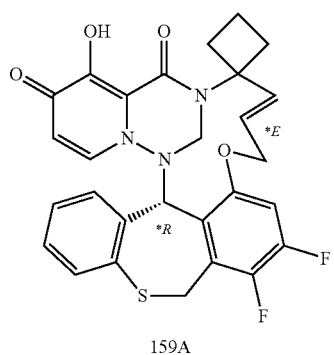

159A

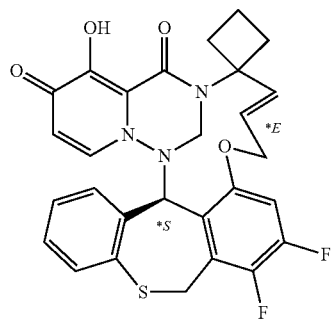

159B

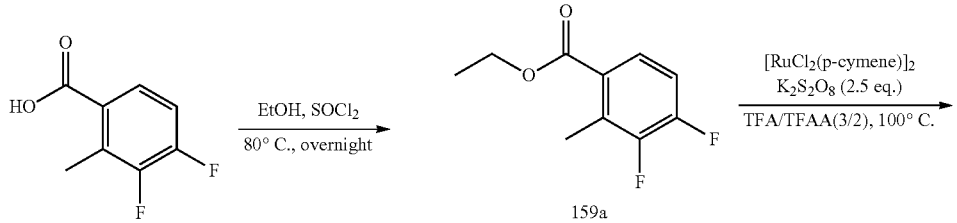

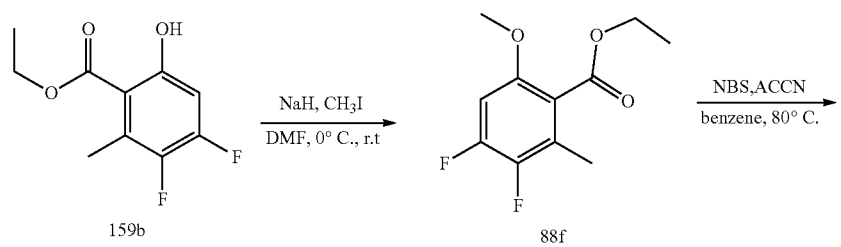

-continued
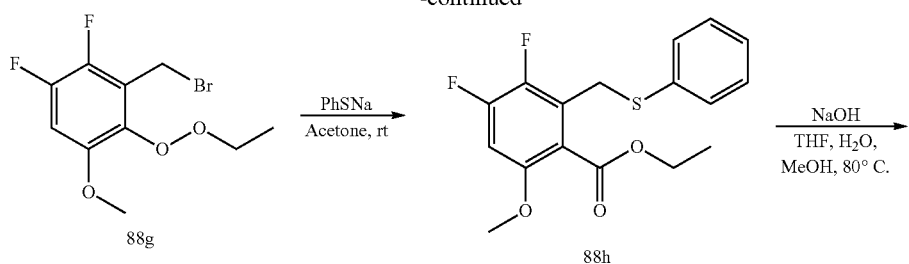
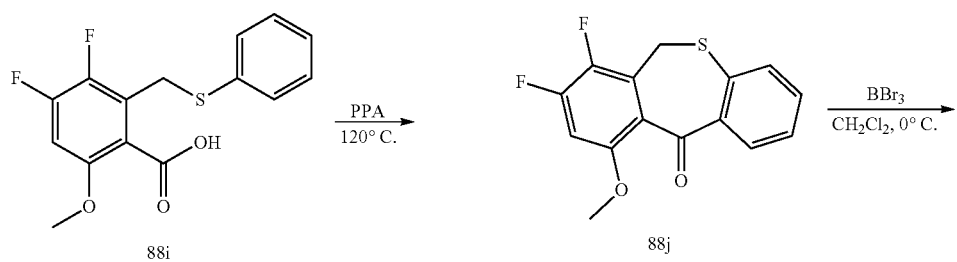
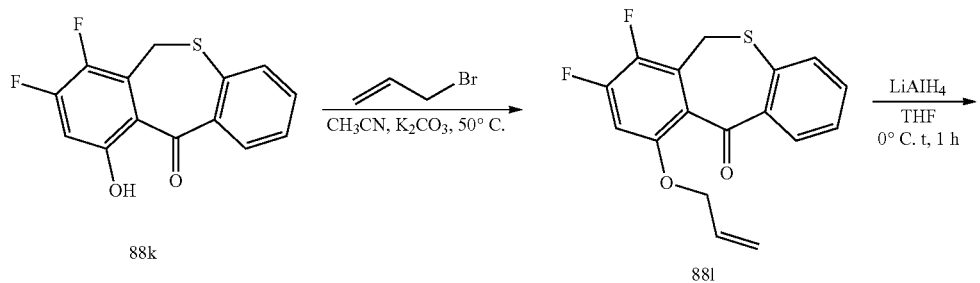
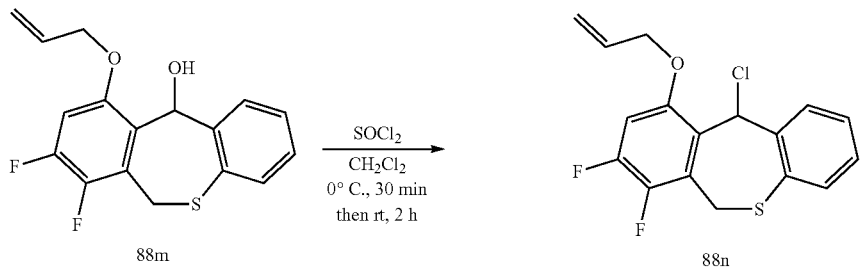
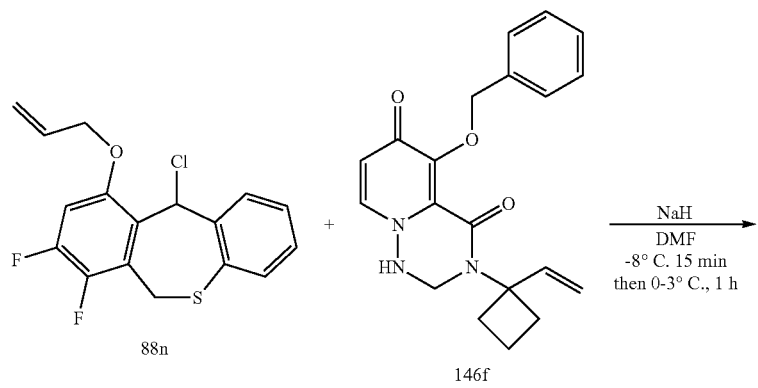

-continued

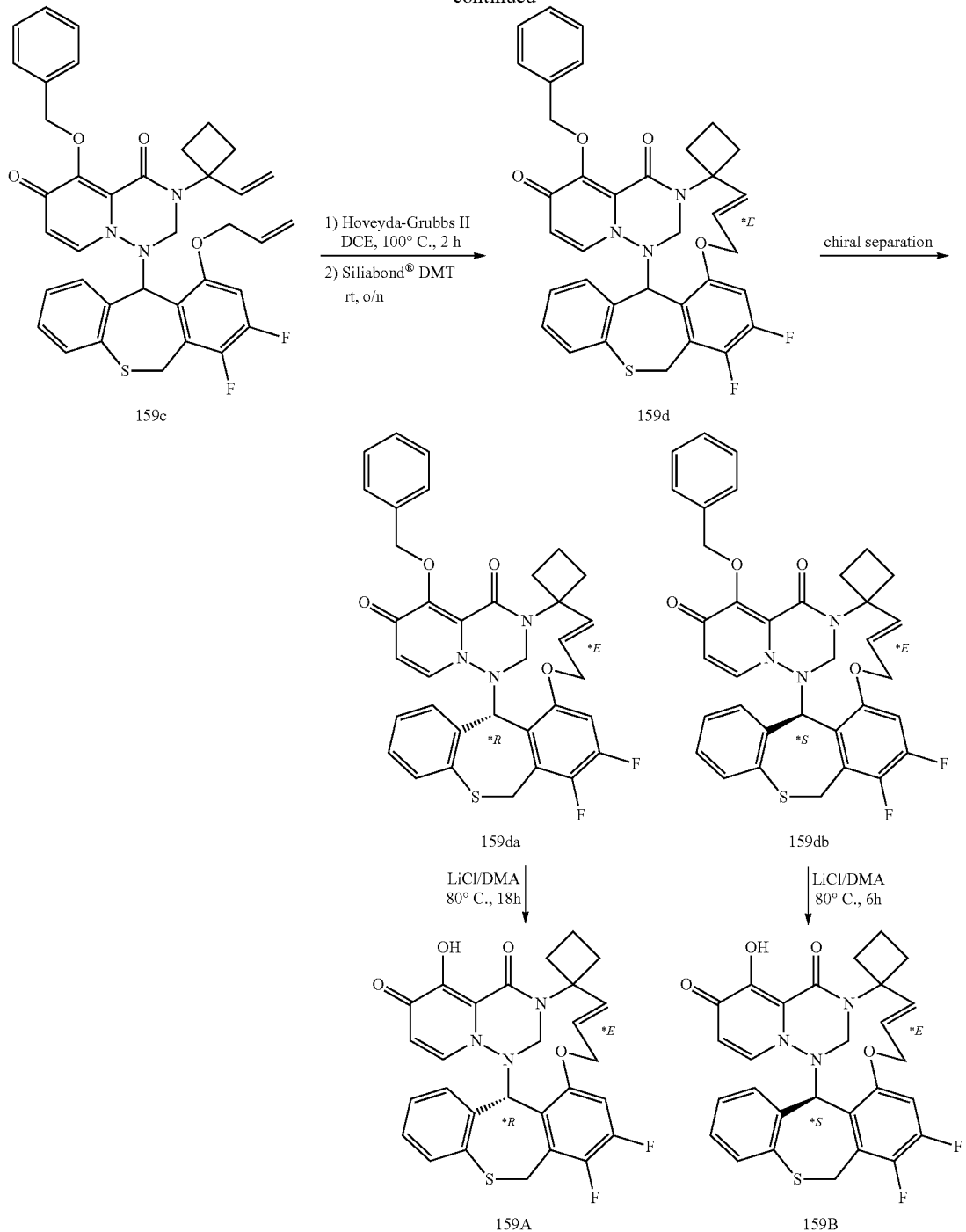

Synthesis of Intermediate 159a:

SOCl$_2$ (311.025 g, 2614.318 mmol) was slowly added into EtOH (1.5 L) at 0° C. Then 3,4-difluoro-2-methylbenzoic acid [CAS 157652-31-8] (150 g, 871.439 mmol) was added. The resulting mixture was heated at 80° C. for 12 h. The reaction mixture was concentrated under vacuum. The residue obtained was adjusted to pH 8 with a saturated sodium bicarbonate solution in water and extracted by EtOAc. Then the organic layer was washed with brine and dried over Na$_2$SO$_4$. The solution was concentrated under vacuum to afford ethyl 3,4-difluoro-2-methylbenzoate (intermediate 159a, 160 g) as a yellow oil.

Synthesis of Intermediate 159b:

Into a 2000 ml three round bottom flask, ethyl 3,4-difluoro-2-methylbenzoate (160 g, 799.273 mmol) was dissolved in TFA (600 ml) and TFAA (400 ml). Then K$_2$S$_2$O$_8$ (539.509 g, 1998.182 mmol) and [RuCl$_2$(p-cymene)]$_2$ (48.915 g, 79.927 mmol) were added. The resulting solution was stirred 4 days at 100° C. When the reaction was completed, it was concentrated under vacuum and the residue was diluted with ETOAc, washed with H$_2$O and brine.

Then the organic phase was concentrated under reduced pressure. The residue was purified by gel chromatography (0-5% EtOAc/petroleum ether) to afford ethyl 3,4-difluoro-6-hydroxy-2-methylbenzoate (intermediate 159b, 100 g) as a white solid.

Synthesis of Intermediate 88f:

Into a 2000 ml round bottom flask, ethyl 3,4-difluoro-6-hydroxy-2-methylbenzoate (100 g, 462.575 mmol) was dissolved in DMF (1.5 L). Then NaH (22.204 g, 555.090 mmol) was added and the solution was stirred 0.5 h at 0° C. Iodomethane (78.789 g, 555.090 mmol) was added and the reaction was stirred 1 h. When the reaction was completed, it was quenched with $H_2O$ (1.5 L) and a solid was formed. The solution was filtrated and the solid was dissolved by EtOAc. The organic layer was washed with brine and dried over $Na_2SO_4$, and then concentrated under reduced pressure. 100 g of ethyl 3,4-difluoro-6-methoxy-2-methylbenzoate (intermediate 88f) was obtained as a yellow solid.

Synthesis of Intermediate 88g:

To a solution of ethyl 3,4-difluoro-6-methoxy-2-methylbenzoate (50 g, 217.195 mmol) in benzene (1 L) was added 1-bromopyrrolidine-2,5-dione (96.643 g, 542.987 mmol), ACCN [CAS 2094-98-6] (2.65 g, 10.860 mmol). The resulting solution was stirred at 80° C. for 48 h. The resulting mixture was quenched with water and concentrated under vacuum. Water was added, and the solution was extracted with EtOAc. The combined organic layers were washed with brine, dried and concentrated under vacuum. The residue was purified by gel chromatography (0-10% EtOAc/petroleum ether) to afford ethyl 2-(bromomethyl)-3,4-difluoro-6-methoxybenzoate (intermediate 88g, 50 g) as a yellow solid.

Synthesis of Intermediate 88h:

To a solution of ethyl 2-(bromomethyl)-3,4-difluoro-6-methoxybenzoate (250 g, 808.789 mmol) in acetone (1.5 L) was added sodium benzenethiolate (117.578 g, 889.668 mmol). The resulting mixture was stirred at r.t. for 3 h, then filtered and the solid was washed with acetone three times. The filtrate was dried over anhydrous sodium sulfate and concentrated under reduced pressure. The residue was purified by gel chromatography (0-15% EtOAc/petroleum ether) to afford ethyl 3,4-difluoro-6-methoxy-2-((phenylthio)methyl)benzoate (intermediate 88h, 200 g) as a yellow solid.

Synthesis of Intermediate 88i:

To a solution of ethyl 3,4-difluoro-6-methoxy-2-((phenylthio)methyl)benzoate (100 g, 295.535 mmol) in EtOH/$H_2O$ (2:1) at 0° C. was added sodium hydroxide (59.107 g, 1477.677 mmol). The resulting mixture was stirred at 80° C. for overnight, then concentrated under reduced pressure. Water was added to the reaction solution. The pH value of the water layer was adjusted to pH~3, then extracted with EtOAc. The organic layers were combined, washed with $H_2O$, brine, dried over anhydrous sodium sulfate, filtered and concentrated to afford the 3,4-difluoro-6-methoxy-2-((phenylthio)methyl)benzoic acid an yellow solid (intermediate 88i, 160g).

Synthesis of Intermediate 88j:

3,4-difluoro-6-methoxy-2-((phenylthio)methyl)benzoic acid (43 g, 138.568 mmol) was added to the solution of polyphosphoric acid (PPA) at 80° C., then the reaction was warmed up to 120° C. and stirred for 1 h. The resulting reaction mixture was cooled to 0° C., then ice-cold water was added to the reaction mixture and stirred for another 2 h. The precipitate was filtrated off, washed with water and dried to obtain 7,8-difluoro-10-methoxydibenzo[b,e]thiepin-11(6H)-one (intermediate 88j, 30 g) as a brown solid.

Synthesis of Intermediate 88k:

To a solution of 7,8-difluoro-10-methoxydibenzo[b,e]thiepin-11(6H)-one (25 g, 85.529 mmol) in $CH_2Cl_2$ (0.5 L) was added dropwise tribromoborane over 1 h (170 mL, 1.0 M in $CH_2Cl_2$) at 0° C. The mixture was stirred for another 2 h at 0° C., and was quenched with aq. sat. $NaHCO_3$ solution at 0° C. The resulting mixture was extracted with $CH_2Cl_2$ and the organic layers were combined, washed with $H_2O$ and brine, dried over anhydrous sodium sulfate, filtered and concentrated to afford 7,8-difluoro-10-hydroxydibenzo[b,e]thiepin-11(6H)-one (intermediate 88k, 20 g) as a yellow solid.

Synthesis of Intermediate 88l:

To a solution of 7,8-difluoro-10-hydroxydibenzo[b,e]thiepin-11(6H)-one (22 g, 71.872 mmol) in $CH_3CN$ (0.5 L) was added potassium carbonate (29.755 g, 215.615 mmol) and 3-bromoprop-1-ene (9.564 g, 79.059 mmol). The resulting mixture was heated at 50° C. for 3 h. The reaction mixture was filtered, the solid was washed with EtOAc three times, then the filtrate was dried over anhydrous sodium sulfate and concentrated. The residue was washed with EtOAc/hexane to afford 10-(allyloxy)-7,8-difluorodibenzo[b,e]thiepin-11(6H)-one as an yellow solid (intermediate 88l, 22g).

Synthesis of Intermediate 88m:

To a solution of 10-(allyloxy)-7,8-difluorodibenzo[b,e]thiepin-11(6H)-one (26 g, 81.674 mmol) in THE (500 mL) was added $LiAlH_4$ (3.104 g, 81.674 mmol) at 0° C. under $N_2$.

After 1 h at 0° C., the resulting mixture was quenched with water (4 mL), then aqueous NaOH solution (15%, 4 mL) and water (12 mL) were added. The resulting mixture was filtered on Celite® and the solid was washed with EtOAc three times. The filtrate was washed with $H_2O$, dried over anhydrous sodium sulfate and concentrated. The residue was washed with EtOAc/hexane (10/1).Then the resulting solution was filtered to afford 10-(allyloxy)-7,8-difluoro-6,11-dihydrodibenzo[b,e]thiepin-11-ol (intermediate 88m, 20 g) as an off-white solid.

Synthesis of Intermediate 88n:

At 0° C., $SOCl_2$ (5.2 mL, 71.303 mmol) was added dropwise to a solution of 10-(allyloxy)-7,8-difluoro-6,11-dihydrodibenzo[b,e]thiepin-11-ol (19.12 g, 59.419 mmol) in $CH_2Cl_2$ (285 mL). The mixture was stirred at 0° C. for 30 min then at rt for 2 h. The mixture was evaporated until dryness, taken up with toluene and evaporated again to give 10-(allyloxy)-11-chloro-7,8-difluoro-6,11-dihydrodibenzo[b,e]thiepine (intermediate 88n), used as such in the next step.

Synthesis of Intermediate 159c:

5-(benzyloxy)-3-(1-vinylcyclobutyl)-2,3-dihydro-1H-pyrido[2,1-f][1,2,4]triazine-4,6-dione (20 g, 49.516 mmol) was dissolved in dry DMF (280 mL) under $N_2$ atmosphere, and the solution was cooled to −9° C. NaH (60% in oil) (2.38 g, 59.419 mmol) was added and the reaction mixture was stirred at −8° C. for 15 min. 10-(allyloxy)-11-chloro-7,8-difluoro-6,11-dihydrodibenzo[b,e]thiepine (20.13 g, 59.419 mmol) in DMF (100 mL) was added dropwise (over 30 mins) at −8° C. The brine/ice cooling bath was changed for an ice bath and the reaction was stirred at 0-3° C. for 1 h. The reaction was quenched with cold water (300 mL) and EtOAc was added (500 mL). The reaction mixture was stirred at rt for 1 h and the precipitate was filtered off, washed with EtOAc (200 mL) and dried to give a first batch of 1-(10-(allyloxy)-7,8-difluoro-6,11-dihydrodibenzo[b,e]thiepin-11-yl)-5-(benzyloxy)-3-(1-vinylcyclobutyl)-2,3-dihydro-1H-pyrido[2,1-f][1,2,4]triazine-4,6-dione (intermediate 159c, 25.7 g). The filtrate was extracted with EtOAc. The organic layer was washed with water and brine, dried over MgSO$_4$, filtered and the solvent was evaporated. The residue was purified via preparative LC (Stationary phase: irregular SiOH 40 μm, Mobile phase: 99% CH$_2$Cl$_2$, 1% MeOH) to give a second batch of intermediate 159c (5.8 g).

Synthesis of Intermediate 159d:

The solvent was degassed by bubbling N$_2$ through for 1 h.

Using a syringe pump, a solution of Hoveyda-Grubbs II catalyst (1.21 g, 1.927 mmol) in dichloroethane (30 mL) was added dropwise over 2 h to a solution of 1-(10-(allyloxy)-7,8-difluoro-6,11-dihydrodibenzo[b,e]thiepin-11-yl)-5-(benzyloxy)-3-(1-vinylcyclobutyl)-2,3-dihydro-1H-pyrido[2,1-f][1,2,4]triazine-4,6-dione (12.6 g, 19.27 mmol) in dichloroethane (1230 mL) under N$_2$ bubbling through the mixture at 100° C. The reaction was monitored 15 min after the end of the addition (LC/MS showed the reaction was completed). The mixture was cooled to rt and SiliaMetS® DMT (12.6 g, 7.71 mmol) was added and the reaction mixture was stirred at rt overnight. The mixture was filtered through a pad of Celite®. The Celite® was washed with CH$_2$Cl$_2$/CH$_3$OH 95/5 (200 mL) and the filtrate was concentrated under reduced pressure (m=11.8 g). This batch was combined with other batches before purification (total amount 34 g). The combined batch was taken up with 150 mL of CH$_3$CN and stirred for 30 min at rt. The precipitate was filtered off and dried (m=24.1 g). This batch was combined with another one to afford 30.8 g of (*E)-12'-(benzyloxy)-24',25'-difluoro-2',17a'-dihydro-6'H-spiro[cyclobutane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (intermediate 159d).

The enantiomers were separated via chiral SFC (Stationary phase: CHIRACEL OJ-H 5 μm 250×30 mm, Mobile phase: 70% CO$_2$, 30% MeOH (0.3% iPrNH$_2$)) to afford the first eluted enantiomer 159da (16.5 g) and the second eluted enantiomer 159db (15.1 g).

Synthesis of Compound 159A:

LiCl (257 mg, 6.057 mmol) was added to a solution of enantiomer 159da (379 mg, 0.606 mmol) in DMA (5.6 mL) and the mixture was stirred at 80° C. for 18 h. The mixture was cooled to rt and ice with HCl 0.5N was added. The mixture was extracted with CH$_2$Cl$_2$. The organic layer was washed with HCl 0.5N (3 times), dried over MgSO$_4$, filtered and the solvent was evaporated under reduced pressure. CH$_2$Cl$_2$ was added, the white solid was filtered and dried under vacuum pressure at 60° C. overnight to give enantiomer 159A (197 mg).

Synthesis of Compound 159B:

Enantiomer 159db (19.5 g, 31.16 mmol) and LiCl (13.2 g, 311.65 mmol) in DMA (246 mL) was stirred at 80° C. for 6 h. The mixture was cooled to rt and diluted with water. The mixture was extracted with CH$_2$Cl$_2$ (2 times). The organic layer was washed with water, dried over MgSO$_4$, filtered and the solvent was evaporated. Purification was carried out by flash chromatography over silica gel (330 g SiO$_2$ 30 μm (CH$_2$Cl$_2$/CH$_3$OH/AcOH 99/I/O to 90/10/0.5)) The pure fractions were collected and evaporated to dryness to give compound 159B (16.5 g). This batch was combined with another one to afford 19.6 g. 50 mL of CH$_3$CN was added. The mixture was stirred at rt for 2 h. The precipitate was filtered off and dried (m=11.8 g).

Compound 159A:
LC/MS (method LC-C): Rt 3.16 min, MH+536
$[\alpha]_D^{20}$: +489.23° (c 0.13, DMF)
Chiral HPLC (method HPLC-B): Rt 5.99 min, chiral purity 100%

Compound 159B:
$^1$H NMR (400 MHz, DMSO-d$_6$) δ ppm 11.00 (br d, J=2.4 Hz, 1H) 7.55 (dd, J=11.9, 7.5 Hz, 1H) 7.40 (d, J=7.6 Hz, 1H) 7.07-7.18 (m, 1H) 7.00-7.06 (m, 1H) 6.86 (td, J=7.4, 1.2 Hz, 1H) 6.65-6.74 (m, 1H) 6.48 (d, J=15.6 Hz, 1H) 6.11-6.26 (m, 1H) 5.75 (dd, J=14.0, 2.3 Hz, 1H) 5.61 (d, J=7.7 Hz, 1H) 5.37 (s, 1H) 5.11 (d, J=13.8 Hz, 1H) 4.63-4.85 (m, 2H) 3.89-4.19 (m, 2H) 2.71-2.87 (m, 1H) 2.40-2.46 (m, 1H) 2.01-2.22 (m, 2H) 1.69-1.81 (m, 1H) 1.52-1.68 (m, 1H)

LC/MS (method LC-C): Rt 3.16 min, MH+536
$[\alpha]_D^{20}$: −502.15° (c 0.093, DMF)
Chiral HPLC (method HPLC-B): Rt 6.70 min, chiral purity 100%

Example 160: Synthesis of (9*S,18*S,*E)-9-ethyl-3,4-difluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (Compound 160AA) and (9*R,18*R,*E)-9-ethyl-3,4-difluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (Compound 160BB) and (9*S,18*R,*E)-9-ethyl-3,4-difluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (Compound 160BA) and (9*R,18*S,*E)-9-ethyl-3,4-difluoro-12-hydroxy-18-(pyridin-2-yl)-6,9-dihydro-18H-10,17-methanobenzo[b]pyrido[1,2-f][1]oxa[5,6,9]triazacyclotridecine-11,13-dione (Compound 160AB)

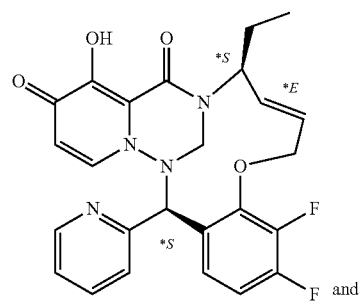

160AA

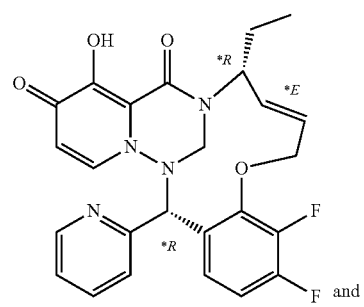

160BB

-continued

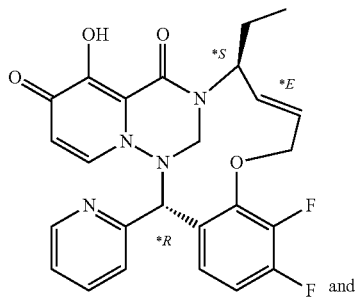

160BA and

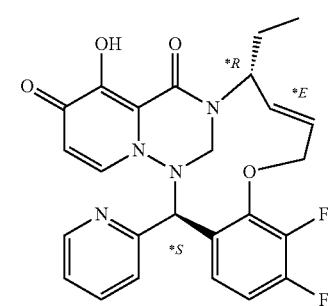

160AB

Compounds 160AA, 160BB, 160BA and 160AB were synthesized according to the procedures described in example 39 starting from intermediate 2-((2-(allyloxy)-3,4-difluorophenyl)chloromethyl)pyridine (synthesized as 45b from 2-bromopyridine [CAS 109-04-6] and 74a).

Compound 160AA:

$^1$H NMR (400 MHz, DMSO-d$_6$) δ ppm 8.39 (d, J=3.8 Hz, 1H) 7.89-8.01 (m, 1H) 7.64 (td, J=7.7, 1.7 Hz, 1H) 7.41-7.55 (m, 1H) 7.18-7.33 (m, 2H) 7.09 (d, J=7.7 Hz, 1H) 6.36 (ddd, J=15.6, 10.1, 5.2 Hz, 1H) 5.71 (br dd, J=15.7, 6.5 Hz, 1H) 5.49 (d, J=7.6 Hz, 1H) 5.36 (s, 1H) 5.16 (q, J=7.6 Hz, 1H) 5.05 (d, J=13.6 Hz, 1H) 4.93 (dd, J=11.4, 5.4 Hz, 1H) 4.24 (d, J=13.6 Hz, 1H) 4.10 (br t, J=10.8 Hz, 1H) 1.38-1.64 (m, 2H) 0.83 (t, J=7.3 Hz, 3H)

LC/MS (method LC-C): Rt 2.71 min, MH$^+$481

$[α]_D^{20}$: −476.71° (c 0.146, DMF)

Chiral HPLC (method HPLC-A and B): No separation observed

Compound 160AB:

$^1$H NMR (500 MHz, DMSO-d$_6$) δ ppm 8.36 (d, J=3.8 Hz, 1H) 7.99 (br t, J=6.8 Hz, 1H) 7.62 (td, J=7.6, 1.7 Hz, 1H) 7.41-7.51 (m, 1H) 7.18-7.22 (m, 1H) 7.16 (dd, J=7.9, 3.2 Hz, 2H) 6.44 (br dd, J=15.3, 9.9 Hz, 1H) 5.97 (ddd, J=15.1, 9.4, 5.8 Hz, 1H) 5.54 (s, 1H) 5.49 (d, J=7.9 Hz, 1H) 5.20 (d, J=13.9 Hz, 1H) 4.66-4.76 (m, 1H) 4.60 (br dd, J=10.6, 5.5 Hz, 1H) 4.23 (d, J=13.9 Hz, 1H) 3.39-3.48 (m, 1H) 2.28-2.35 (m, 1H) 2.10-2.22 (m, 1H) 0.87 (t, J=7.4 Hz, 3H)

LC/MS (method LC-C): Rt 2.77 min, MH$^+$481

$[α]_D^{20}$: −548.99° (c 0.149, DMF)

Chiral HPLC (method HPLC-A): Rt 5.93 min, chiral purity 100%

Compound 160BA:

LC/MS (method LC-C): Rt 2.77 min, MH$^+$481

$[α]_D^{20}$: +524.41° (c 0.127, DMF)

Chiral HPLC (method HPLC-A): Rt 4.75 min, chiral purity 100%

Compound 160BB:

LC/MS (method LC-C): Rt 2.71 min, MH$^+$481

$[α]_D^{20}$: +512.18° (c 0.156, DMF)

Chiral HPLC (method HPLC-A and B): No separation observed

Example 161: Synthesis of Compound 161A and Compound 161B

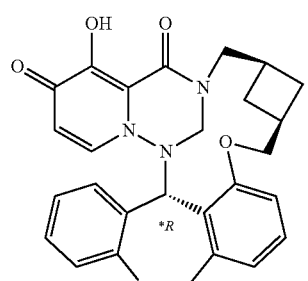

161A and

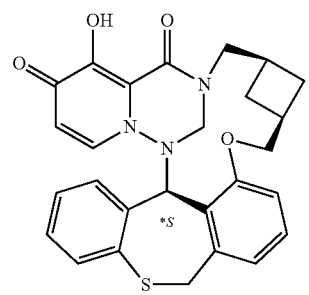

161B

Compounds 161A and 161B were synthesized according to the procedures described in example 87 starting from intermediate (3-(((tert-butyldiphenylsilyl)oxy)methyl)cyclobutyl)methanamine (synthesized as 87e from cis-1,3-cyclobutane-dimethanol [CAS 2453-47-6]).

Compound 161A:

LC/MS (method LC-C): Rt 2.92 min, MH$^+$488

$[α]_D^{20}$: +214.62° (c 0.171, DMF)

Chiral HPLC (method HPLC-B): Rt 5.67 min, chiral purity 100%

Compound 161B:

$^1$H NMR (500 MHz, DMSO-d$_6$) δ ppm 10.93-12.40 (m, 1H) 7.31 (d, J=7.6 Hz, 1H) 7.25 (t, J=8.0 Hz, 1H) 7.02-7.10 (m, 2H) 6.97-7.01 (m, 1H) 6.94 (d, J=7.6 Hz, 1H) 6.76-6.83 (m, 1H) 6.70-6.75 (m, 1H) 6.37 (s, 1H) 5.76 (d, J=13.2 Hz, 1H) 5.51 (d, J=7.9 Hz, 1H) 5.08 (d, J=13.2 Hz, 1H) 4.53 (br d, J=12.9 Hz, 1H) 4.37 (d, J=13.2 Hz, 1H) 3.72-3.90 (m, 3H) 2.60 (br d, J=14.5 Hz, 1H) 2.45-2.54 (m, 2H) 2.26-2.36 (m, 1H) 1.93-2.05 (m, 1H) 1.61-1.73 (m, 1H) 1.42 (q, J=10.6 Hz, 1H)

LC/MS (method LC-C): Rt 2.92 min, MH$^+$488

$[α]_D^{20}$: −217.5° (c 0.200, DMF)

Chiral HPLC (method HPLC-B): Rt 8.86 min, chiral purity 100%

407

Example 162: Synthesis of (9*R,17a*R,*E)-24,25-difluoro-12-hydroxy-9-methyl-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 162A) and (9*S,17a*S,*E)-24,25-difluoro-12-hydroxy-9-methyl-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 162B) and (13*R,21a*R,*Z)-24,25-difluoro-16-hydroxy-13-methyl-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (Compound 162C) and (13*S,21a*S,*Z)-24,25-difluoro-16-hydroxy-13-methyl-6,10,13,21a-tetrahydro-7,8-(epiprop[1]en[1]yl[3]ylidene)-14,21-methanobenzo[6,7]thiepino[4,5-c]pyrido[1,2-f][1]oxa[5,6,9]triazacyclotridecine-15,17-dione (Compound 162D)

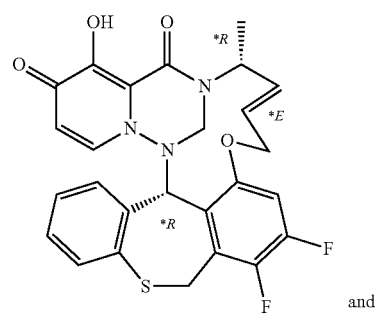

162A and

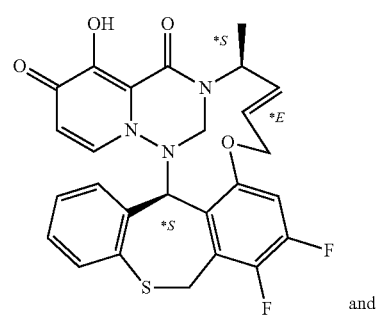

162B and

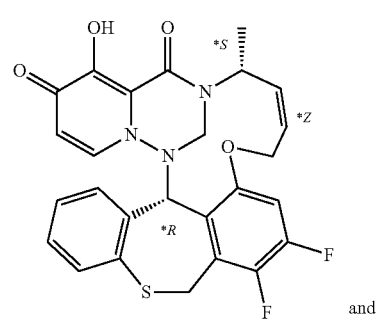

162C and

408

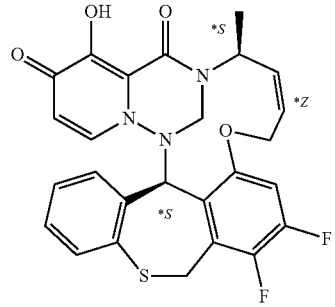

162D

Compounds 162A, 162B, 16C and 162D were synthesized according to the procedures described in example 159 starting from intermediate 29c and 88n.

Compound 162A:

LC/MS (method LC-C): Rt 2.98 min, MH+ 510

$[\alpha]_D^{20}$: +459.62° (c 0.104, DMF)

Chiral HPLC (method HPLC-B): Rt 5.57 min, chiral purity 100%

Compound 162B:

$^1$H NMR (500 MHz, DMSO-$d_6$) δ ppm 7.42 (dd, J=11.7, 7.3 Hz, 1H) 7.27 (d, J=7.9 Hz, 1H) 7.11-7.18 (m, 1H) 7.04-7.10 (m, 1H) 6.85-6.91 (m, 1H) 6.78-6.84 (m, 1H) 6.30 (ddd, J=15.5, 9.7, 6.0 Hz, 1H) 5.65-5.76 (m, 2H) 5.60 (d, J=7.9 Hz, 1H) 5.42 (quin, J=6.9 Hz, 1H) 5.27 (s, 1H) 5.02 (d, J=13.9 Hz, 1H) 4.85 (dd, J=11.3, 5.7 Hz, 1H) 4.44 (d, J=13.9 Hz, 1H) 4.32 (t, J=10.7 Hz, 1H) 4.11 (d, J=13.9 Hz, 1H) 1.18 (d, J=7.3 Hz, 3H)

LC/MS (method LC-C): Rt 2.98 min, MH⁺510

$[\alpha]_D^{20}$: −460.71° (c 0.084, DMF)

Chiral HPLC (method HPLC-B): Rt 8.26 min, chiral purity 100%

Compound 162C:

LC/MS (method LC-C): Rt 3.07 min, MH⁺510

$[\alpha]_D^{20}$: +130.69° (c 0.101, DMF)

Chiral HPLC (method HPLC-B): Rt 4.32 min. chiral purity 100%

Compound 162D:

$^1$H NMR (500 MHz, DMSO-$d_6$) δ ppm 7.39 (br dd, J=11.7, 6.9 Hz, 1H) 7.14-7.27 (m, 3H) 6.89 (br t, J=7.1 Hz, 1H) 6.49-6.65 (m, 2H) 6.21 (dt, J=10.3, 6.7 Hz, 1H) 6.05 (s, 1H) 5.59-5.75 (m, 2H) 5.22 (br d, J=13.2 Hz, 1H) 4.83 (br dd, J=10.2, 7.1 Hz, 1H) 4.41-4.59 (m, 2H) 4.04-4.20 (m, 2H) 1.44 (br d, J=6.3 Hz, 3H)

LC/MS (method LC-C): Rt 3.07 min, MH+ 510

$[\alpha]_D^{20}$: −131.07° (c 0.103, DMF)

Chiral HPLC (method HPLC-B): Rt 8.10 min, chiral purity 99.28%

Example 163: Synthesis of (9*R,17a*S,*E)-9-(difluoromethyl)-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 163AA) and (9*S,17a*R,*E)-9-(difluoromethyl)-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 163BB) and (9*R,17a*R,*E)-9-(difluoromethyl)-12-hydroxy-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 163BA)

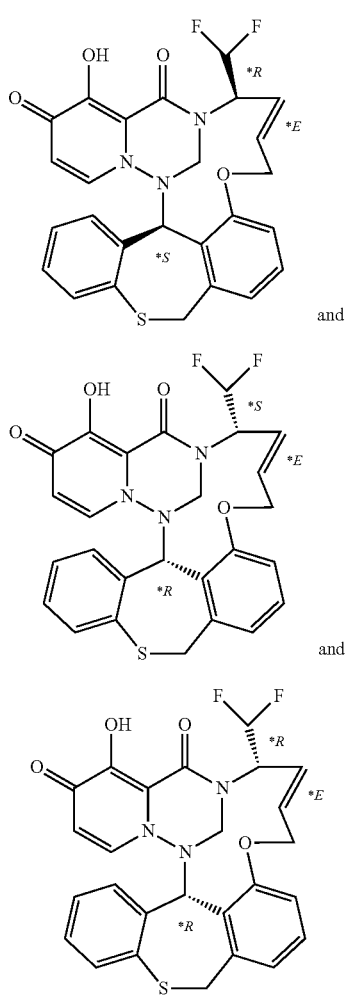

Compounds 163AA, 163BB and 163BA were synthesized according to the procedures described in example 37 starting from intermediate 3-(1,1-difluorobut-3-en-2-yl)-5-benzyloxy-2,3-dihydro-1H-pyrido[2,1-f][1,2,4]triazine-4,6-dione (synthesized as 39e from 1,1-difluoro-3-buten-2-amine, HCl [CAS 2061940-62-1]).

Compound 163AA:
$^1$H NMR (400 MHz, DMSO-d$_6$) δ ppm 7.48 (br t, J=7.6 Hz, 1H) 7.30 (br d, J=7.5 Hz, 1H) 7.17 (br s, 4H) 6.86 (br t, J=6.5 Hz, 1H) 6.24-6.74 (m, 4H) 6.11 (s, 1H) 5.61-5.83 (m, 2H) 5.20 (br d, J=13.2 Hz, 1H) 4.81-4.97 (m, 1H) 4.58 (br d, J=12.7 Hz, 3H) 3.86 (br d, J=13.4 Hz, 1H)
LC/MS (method LC-C): Rt 2.90 min. MH$^+$510
$[α]_D^{20}$: −179.52° (c 0.083, DMF)
Chiral HPLC (method HPLC-B): Rt 7.69 min, chiral purity 100%

Compound 163BB:
LC/MS (method LC-C): Rt 2.82 min, MH$^+$510
$[α]_D^{20}$: +433.33° (c 0.090, DMF)
Chiral HPLC (method HPLC-B): Rt 5.27 min, chiral purity 100%

Compound 163BA:
LC/MS (method LC-C): Rt 2.89 min, MH$^+$510
$[α]_D^{20}$: +230.56° (c 0.108, DMF)
Chiral HPLC: No chiral HPLC performed.

Example 164: Synthesis of (9*S,18*R)-9-ethyl-3,4-difluoro-12-hydroxy-18-phenyl-6,7,8,9-tetrahydro-18H-10,17-methanobenzo[b]pyrido[1,2-f][1]oxa[5,6,9]triazacyclotridecine-11,13-dione (Compound 164A) and (9*R,18*S)-9-ethyl-3,4-difluoro-12-hydroxy-18-phenyl-6,7,8,9-tetrahydro-18H-10,17-methanobenzo[b]pyrido[1,2-f][1]oxa[5,6,9]triazacyclotridecine-11,13-dione (Compound 164B)

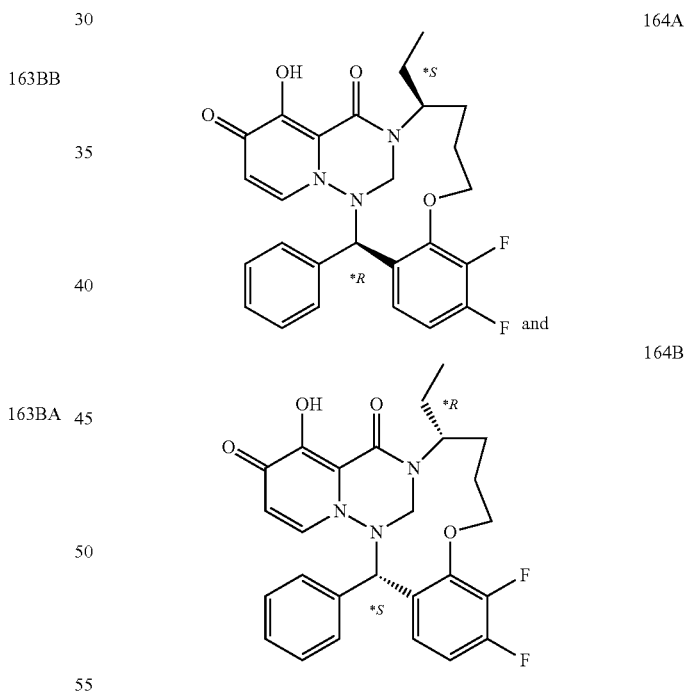

Compounds 164A and 164B were synthesized according to the procedures described in example 80 starting from intermediates 6-((tert-butyldiphenylsilyl)oxy)hexan-3-amine and 2-(allyloxy)-1-(chloro(phenyl)methyl)-3,4-difluorobenzene (synthesized as 80h from 1,4-hexanediol [CAS 16432-53-4]).

Compound 164A:
LC/MS (method LC-C): Rt 3.07 min, MH+ 482
$[α]_D^{20}$: +263.82° (c 0.152, DMF)
Chiral HPLC (method HPLC-B): Rt 4.22 min. chiral purity 100%

Compound 164B:

¹H NMR (500 MHz, DMSO-d₆) δ ppm 10.41-12.26 (m, 1H) 7.87 (br t, J=6.8 Hz, 1H) 7.36-7.46 (m, 1H) 7.11-7.35 (m, 6H) 5.78 (s, 1H) 5.51 (d, J=7.6 Hz, 1H) 4.97 (d, J=13.6 Hz, 1H) 4.50 (br dd, J=12.1, 2.7 Hz, 1H) 4.29-4.44 (m, 2H) 4.05 (br t, J=11.5 Hz, 1H) 1.99-2.12 (m, 1H) 1.83-1.95 (m, 1H) 1.65 (dt, J=14.3, 10.2 Hz, 1H) 1.26-1.42 (m, 2H) 0.89-1.03 (m, 1H) 0.77 (t, J=7.3 Hz, 3H)

LC/MS (method LC-C): Rt 3.07 min, MH+ 482

$[\alpha]_D^{20}$: −233.73° (c 0.166, DMF)

Chiral HPLC (method HPLC-B): Rt 6.85 min, chiral purity 96.00%

Example 165: Synthesis of (18*R,Z)-18-(2-(difluoromethyl)phenyl)-3,4-difluoro-12-hydroxy-6,9-dihydro-18H-10,17-methanobenzo[b]pyrido[1,2-f][1]oxa[5,6,9]triazacyclotridecine-11,13-dione (Compound 165A) and (18*S,*Z)-18-(2-(difluoromethyl)phenyl)-3,4-difluoro-12-hydroxy-6,9-dihydro-18H-10,17-methanobenzo[b]pyrido[1,2-f][1]oxa[5,6,9]triazacyclotridecine-11,13-dione (Compound 165B)

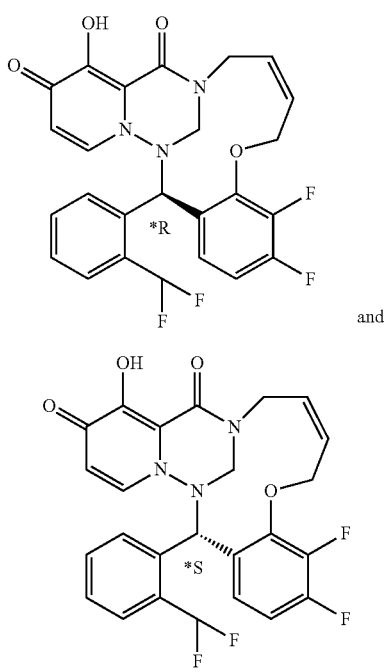

Compounds 165A and 165B were synthesized according to the procedures described in example 5 starting from intermediate 2-(allyloxy)-1-(chloro(2-(difluoromethyl)phenyl)methyl)-3,4-difluorobenzene (synthesized as 70a from 1-bromo-2-(difluoromethyl)benzene [CAS 845866-82-2]).

Compound 165A:

¹H NMR (500 MHz, DMSO-d₆) δ ppm 7.98-8.07 (m, 1H) 7.95 (br d, J=7.9 Hz, 1H) 7.46-7.57 (m, 2H) 7.34-7.45 (m, 3H) 6.96-7.27 (m, 1H) 6.14-6.31 (m, 1H) 5.95-6.10 (m, 1H) 5.44-5.64 (m, 2H) 5.20 (d, J=13.9 Hz, 1H) 4.95-5.06 (m, 1H) 4.82 (br dd, J=13.9, 4.1 Hz, 1H) 4.36 (br d, J=13.9 Hz, 2H) 3.22 (br dd, J=13.9, 7.9 Hz, 1H)

LC/MS (method LC-C): Rt 2.77 min, MH⁺502

$[\alpha]_D^{20}$: −570.37° (c 0.270, DMF)

Chiral HPLC (method HPLC-A): Rt 4.49 min. chiral purity 100%

Compound 165B:

LC/MS (method LC-C): Rt 2.77 min, MH⁺502

$[\alpha]_D^{20}$: +576.14° (c 0.197, DMF)

Chiral HPLC (method HPLC-A): Rt 5.23 min, chiral purity 100%

Example 166: Synthesis of cis-(11a*RS,12a*RS, 13S,20a*R)-15-hydroxy-6,11,11a,12,12a,20a-hexahydro-10H-7,8-(epiprop[1]en[1]yl[3]ylidene)-13,20-methanobenzo[6,7]thiepino[4,5-c]cyclopropa[j]pyrido[1,2-f][1]oxa[5,6,9]triazacyclotridecine-14,16-dione (Compound 166A) and cis-(11a*RS,12a*RS, 13S,20a*S)-15-hydroxy-6,11,11a,12,12a,20a-hexahydro-10H-7,8-(epiprop[1]en[1]yl[3]ylidene)-13,20-methanobenzo[6,7]thiepino[4,5-c]cyclopropa[j]pyrido[1,2-f][1]oxa[5,6,9]triazacyclotridecine-14,16-dione (Compound 166B)

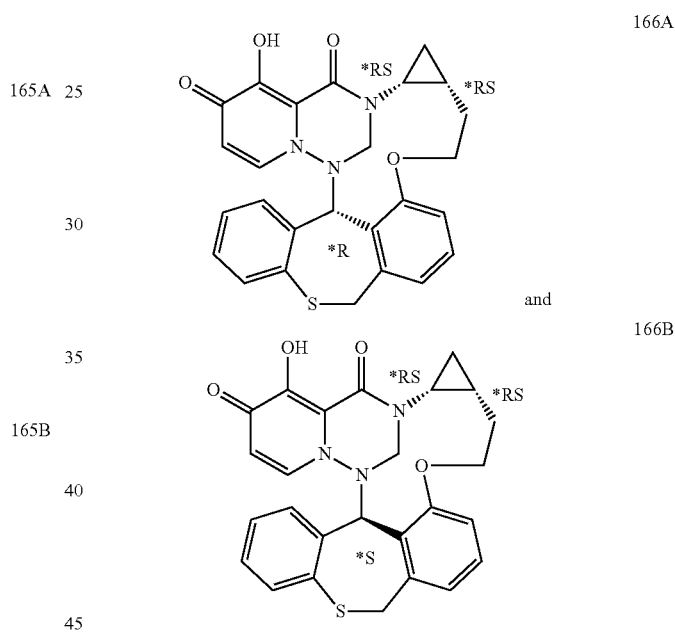

Compounds 166A and 166B were synthesized according to the procedures described in example 87 starting from intermediate cis-(1*RS,2*RS)-2-(2-((tert-butyldiphenylsilyl)oxy)ethyl)cyclopropan-1-amine (synthesized as described for 2-[2-[[(1,1-dimethylethyl)dimethylsilyl]oxy]ethyl]-cyclopropanamine [CAS 134716-76-0] but using tert-butyl-diphenylchlorosilane as a protecting group), Compound 166A:

LC/MS (method LC-C): Rt 2.82 min, MH⁺474

$[\alpha]_D^{20}$: +188.70° (c 0.177, DMF)

Chiral HPLC (method HPLC-B): Rt 7.28 min, chiral purity 100%

Compound 166B:

¹H NMR (400 MHz, DMSO-d₆) δ ppm 7.64 (t, J=7.9 Hz, 1H) 7.33-7.44 (m, 2H) 7.29 (d, J=7.5 Hz, 2H) 7.23 (d, J=7.6 Hz, 1H) 7.01-7.10 (m, 1H) 6.85 (d, J=7.3 Hz, 1H) 6.34 (s, 1H) 5.86 (d, J=7.6 Hz, 1H) 5.78 (d, J=13.6 Hz, 1H) 5.31 (d, J=12.8 Hz, 1H) 4.63 (br dd, J=11.1, 3.9 Hz, 1H) 4.27-4.42 (m, 2H) 4.02 (d, J=13.6 Hz, 1H) 2.83-2.97 (m, 1H) 2.51-2.63

(m, 1H) 2.30-2.46 (m, 1H) 1.71-1.85 (m, 1H) 0.83-0.96 (m, 1H) −0.02 (q, J=6.0 Hz, 1H)

LC/MS (method LC-C): Rt 2.82 min, MH⁺474

$[\alpha]_D^{20}$: −190.23° (c 0.133, DMF)

Chiral HPLC (method HPLC-B): Rt 11.85 min, chiral purity 100%

Example 167: Synthesis of (9*S,18*R,E)-9-ethyl-3,4-difluoro-12-hydroxy-18-(o-tolyl)-6,9-dihydro-18H-10,17-methanobenzo[b]pyrido[1,2-f][1]oxa[5,6,9]triazacyclotridecine-11,13-dione (Compound 167AA) and (9*R,18*S,E)-9-ethyl-3,4-difluoro-12-hydroxy-18-(o-tolyl)-6,9-dihydro-18H-10,17-methanobenzo[b]pyrido[1,2-f][1]oxa[5,6,9]triazacyclotridecine-11,13-dione (Compound 167BB) and (9*R,18*R,E)-9-ethyl-3,4-difluoro-12-hydroxy-18-(o-tolyl)-6,9-dihydro-18H-10,17-methanobenzo[b]pyrido[1,2-f][1]oxa[5,6,9]triazacyclotridecine-11,13-dione (Compound 167AB) and (9*S,18*S,E)-9-ethyl-3,4-difluoro-12-hydroxy-18-(o-tolyl)-6,9-dihydro-18H-10,17-methanobenzo[b]pyrido[1,2-f][1]oxa[5,6,9]triazacyclotridecine-11,13-dione (Compound 167BA)

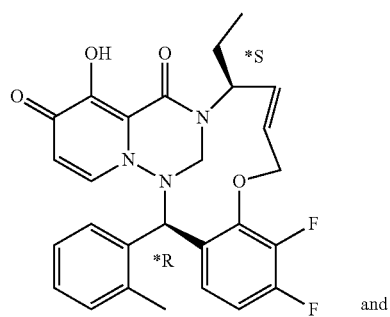
167AA and

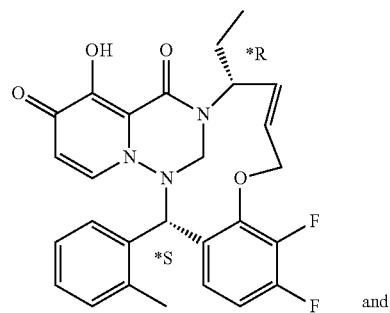
167BB and

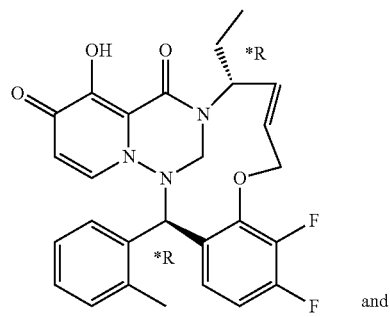
and

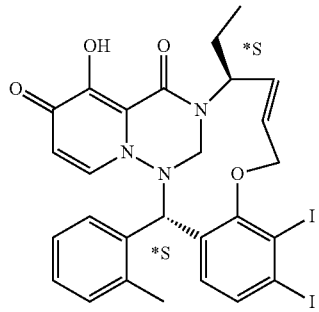
167BA

Compounds 167AA, 167BB, 167AB and 167BA were synthesized according to the procedures described in example 39 starting from intermediate 2-(allyloxy)-1-(chloro(o-tolyl)methyl)-3,4-difluorobenzene (see example 155).

Compound 167AA:

¹H NMR (500 MHz, DMSO-d₆) δ ppm 7.96 (br t, J=7.1 Hz, 1H) 7.42-7.58 (m, 2H) 7.31 (d, J=7.6 Hz, 1H) 7.03-7.14 (m, 2H) 6.96-7.02 (m, 1H) 6.33 (ddd, J=15.6, 10.1, 5.5 Hz, 1H) 5.69 (br dd, J=15.6, 6.5 Hz, 1H) 5.57 (s, 1H) 5.51 (d, J=7.9 Hz, 1H) 5.20 (q, J=7.6 Hz, 1H) 5.07 (d, J=13.6 Hz, 1H) 4.99 (dd, J=11.3, 5.4 Hz, 1H) 4.28 (d, J=13.6 Hz, 1H) 4.11 (br t, J=10.9 Hz, 1H) 2.21 (s, 3H) 1.42-1.63 (m, 2H) 0.84 (t, J=7.3 Hz, 3H)

LC/MS (method LC-C): Rt 3.11 min. MH+ 494

$[\alpha]_D^{20}$: −621.77° (c 0.147, DMF)

Chiral HPLC (method HPLC-B): Rt 5.51 min, chiral purity 100%

Compound 167BB:

LC/MS (method LC-C): Rt 3.10 min, MH⁺494

$[\alpha]_D^{20}$: +568.49° (c 0.146, DMF)

Chiral HPLC (method HPLC-B): Rt 4.85 min, chiral purity 100%

Compound 167AB:

¹H NMR (500 MHz, DMSO-d₆) δ ppm 7.85-8.01 (m, 1H) 7.30-7.50 (m, 3H) 6.84-7.08 (m, 3H) 6.28-6.47 (m, 1H) 5.80-5.97 (m, 1H) 5.72 (br s, 1H) 5.45 (br d, J=7.6 Hz, 1H) 5.16 (br d, J=13.9 Hz, 1H) 4.68 (br t, J=10.1 Hz, 1H) 4.50-4.61 (m, 1H) 4.19 (br d, J=13.9 Hz, 1H) 3.36-3.46 (m, 1H) 2.17-2.33 (m, 4H) 2.03-2.12 (m, 1H) 0.80 (br t, J=7.3 Hz, 3H)

LC/MS (method LC-C): Rt 3.18 min, MH⁺494

$[\alpha]_D^{20}$: −604.35° (c 0.161, DMF)

Chiral HPLC (method HPLC-A): Rt 3.97 min, chiral purity 100%

Compound 167BA:

LC/MS (method LC-C): Rt 3.18 min, MH⁺494

$[\alpha]_D^{20}$: +641.61° (c 0.149, DMF)

Chiral HPLC (method HPLC-A): Rt 4.54 min, chiral purity 100%

Example 168: Synthesis of (21a'*R,*E)-24',25'-difluoro-16'-hydroxy-6',21a'-dihydro-10'H-spiro[cyclobutane-1,13'-[7,8](epiprop[1]en[1]yl[3]ylidene)[14,21]methanopyrido[1,2-f]pyrido[2',3':6,7]thiepino[4,5-c][1]oxa[5,6,9]triazacyclotridecine]-15',17'-dione (Compound 168A) and (21a'*S,*E)-24',25'-difluoro-16'-hydroxy-6',21a'-dihydro-10'H-spiro[cyclobutane-1,13'-[7,8](epiprop[1]en[1]yl[3]ylidene)[14,21]methanopyrido[1,2-f]pyrido[2',3':6,7]thiepino[4,5-c][1]oxa[5,6,9]triazacyclotridecine]-15',17'-dione (Compound 168B)

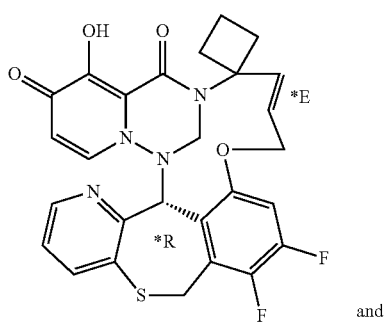

168A and

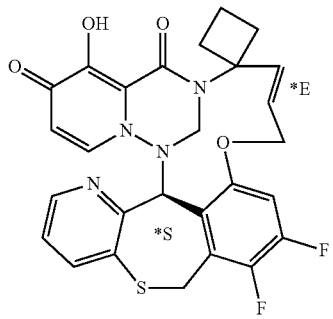

168B

Compounds 168A and 168B were synthesized according to the procedures described in example 159 starting from intermediate 10-(allyloxy)-11-chloro-7,8-difluoro-6,11-dihydrobenzo[5,6]thiepino[3,2-b]pyridine (synthesized as 88n from 3-pyridinethiol [CAS 16133-26-9]).

Compound 168A:

LC/MS (method LC-C): Rt 2.79 min, MH⁺537

$[\alpha]_D^{20}$: +482.67° (c 0.075, DMF)

Chiral HPLC (method HPLC-B): Rt 6.13 min, chiral purity 100%

Compound 168B:

¹H NMR (400 MHz, DMSO-$d_6$) δ ppm 7.99 (d, J=3.7 Hz, 1H) 7.58 (br dd, J=11.8, 7.4 Hz, 1H) 7.49 (d, J=7.6 Hz, 1H) 7.31 (d, J=7.7 Hz, 1H) 7.13 (dd, J=8.0, 4.6 Hz, 1H) 6.44 (d, J=15.7 Hz, 1H) 6.08-6.22 (m, 1H) 5.80 (br d, J=14.7 Hz, 1H) 5.70 (s, 1H) 5.60 (d, J=7.6 Hz, 1H) 5.10 (d, J=13.8 Hz, 1H) 4.74 (br d, J=7.2 Hz, 2H) 4.14 (d, J=14.2 Hz, 1H) 4.04 (br d, J=13.8 Hz, 1H) 2.79 (q, J=10.6 Hz, 1H) 2.41-2.47 (m, 1H) 2.06-2.19 (m, 2H) 1.69-1.83 (m, 1H) 1.52-1.67 (m, 1H)

LC/MS (method LC-C): Rt 2.80 min, MH⁺537

$[\alpha]_D^{20}$: −471.01° (c 0.069, DMF)

Chiral HPLC (method HPLC-B): Rt 7.34 min, chiral purity 100%

Example 169: Synthesis of (9*S,17a*S,*E)-24,25-difluoro-12-hydroxy-9-isopropyl-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 169AA) and (9*R,17a*R,*E)-24,25-difluoro-12-hydroxy-9-isopropyl-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 169BB) and (9*R,17a*S,*E)-24,25-difluoro-12-hydroxy-9-isopropyl-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 169AB) and (9*S,17a*R,*E)-24,25-difluoro-12-hydroxy-9-isopropyl-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 169BA)

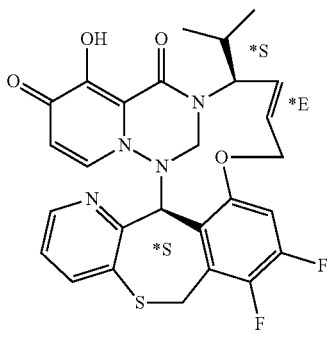

169AA and

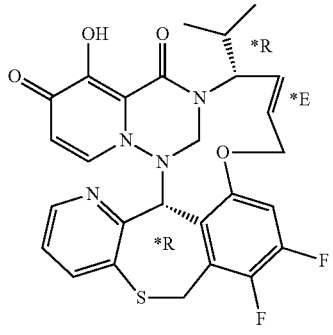

169BB and

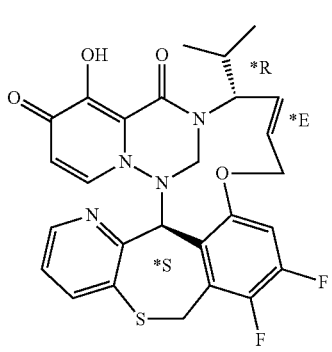

169AB and

-continued

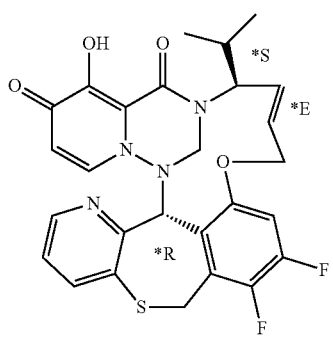

169BA

Compounds 169AA, 169BB, 169AB and 169BA were synthesized according to the procedures described in example 159 starting from intermediate 5-(benzyloxy)-3-(4-methylpent-1-en-3-yl)-2,3-dihydro-1H-pyrido[2,1-f][1,2,4]triazine-4,6-dione (see example 124).

Compound 169AA:

LC/MS (method LC-C): Rt 3.30 min, MH$^+$538

$[\alpha]_D^{20}$: +120.41° (c 0.196, DMF)

Chiral HPLC (method HPLC-B): Rt 4.46 min, chiral purity 100%

Compound 169BB:

$^1$H NMR (400 MHz, DMSO-d$_6$) δ ppm 10.33-12.74 (m, 1H) 7.38 (br dd, J=11.8, 6.9 Hz, 1H) 7.07-7.24 (m, 3H) 6.84 (br t, J=6.9 Hz, 1H) 6.46-6.63 (m, 2H) 6.17-6.34 (m, 1H) 5.95 (s, 1H) 5.56-5.71 (m, 2H) 5.13 (d, J=13.4 Hz, 1H) 4.80 (br dd, J=9.9, 6.8 Hz, 1H) 4.53 (br d, J=13.6 Hz, 1H) 4.40 (br t, J=9.0 Hz, 1H) 4.05 (d, J=14.3 Hz, 1H) 3.60 (br t, J=9.6 Hz, 1H) 2.31-2.43 (m, 1H) 0.76-0.95 (m, 6H)

LC/MS (method LC-C): Rt 3.30 min, MH$^+$538

$[\alpha]D^{20}$: −120.35° (c, DMF)

Chiral HPLC (method HPLC-B): Rt 8.09 min, chiral purity 100%

Compound 169AB:

LC/MS (method LC-C): Rt 3.18 min, MH$^+$538

$[\alpha]_D^{20}$: +420.13° (c 0.159, DMF)

Chiral HPLC (method HPLC-B): Rt 4.84 min. chiral purity 100%

Compound 169BA:

$^1$H NMR (500 MHz, DMSO-d$_6$) δ ppm 10.65-12.25 (m, 1H) 7.41 (br dd, J=11.7, 7.3 Hz, 1H) 7.26 (d, J=7.6 Hz, 1H) 7.11-7.17 (m, 1H) 7.03-7.10 (m, 1H) 6.84-6.93 (m, 1H) 6.81 (d, J=6.9 Hz, 1H) 6.35 (ddd, J=15.5, 9.7, 5.7 Hz, 1H) 5.75 (dd, J=15.8, 6.9 Hz, 1H) 5.66 (dd, J=14.0, 1.7 Hz, 1H) 5.61 (d, J=7.9 Hz, 1H) 5.26 (s, 1H) 5.05 (d, J=13.6 Hz, 1H) 4.85 (dt, J=10.9, 5.3 Hz, 2H) 4.47 (d, J=13.9 Hz, 1H) 4.31 (t, J=10.7 Hz, 1H) 4.12 (d, J=14.2 Hz, 1H) 1.80 (tt, J=12.3, 6.5 Hz, 1H) 0.85 (dd, J=10.6, 6.5 Hz, 6H)

LC/MS (method LC-C): Rt 3.19 min, MH$^+$538

$[\alpha]_D^{20}$: −387.50° (c 0.144, DMF)

Chiral HPLC (method HPLC-B): Rt 7.93 min, chiral purity 100%

Example 170: Synthesis of (9*S,18*S,E)-3-chloro-9-ethyl-4-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 170AA) and (9*R,18*R,E)-3-chloro-9-ethyl-4-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 170BB) and (9*R,18*S,E)-3-chloro-9-ethyl-4-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 170AB) and (9*S,18*R,E)-3-chloro-9-ethyl-4-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 170BA)

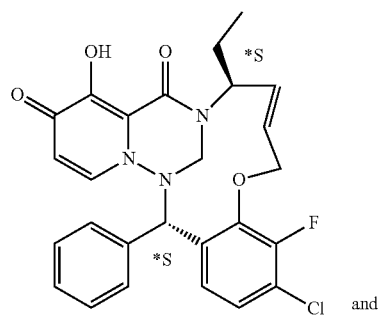

170AA and

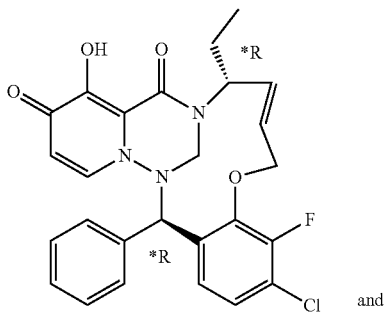

170BB and

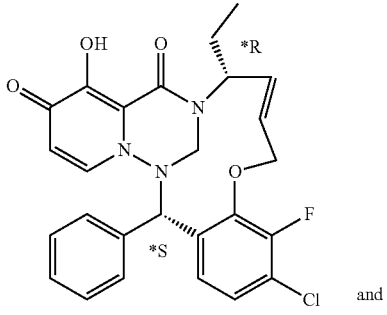

170AB and

419
-continued

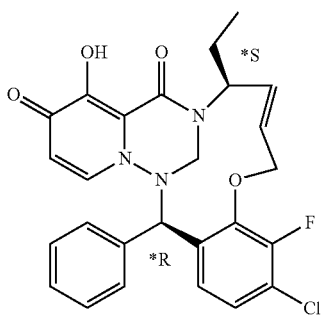

170BA

Compounds 170AA, 170BB, 170AB and 170BA were synthesized according to the procedures described in example 39 starting from intermediate 2-(allyloxy)-4-chloro-1-(chloro(phenyl)methyl)-3-fluorobenzene (synthesized as 74c from 4-chloro-3-fluoro-2-hydroxy-benzaldehyde [CAS 1427431-22-8]).

Compound 170AA:

LC/MS (method LC-C): Rt 3.14 min, MH+496

$[\alpha]_D^{20}$: +607.87° (c 0.178, DMF)

Chiral HPLC (method HPLC-B): Rt 4.64 min, chiral purity 100%

Compound 170BB:

$^1$H NMR (500 MHz, DMSO-d$_6$) δ ppm 10.61-11.48 (m, 1H) 7.96 (d, J=8.2 Hz, 1H) 7.61 (dd, J=8.5, 7.3 Hz, 1H) 7.02-7.28 (m, 6H) 6.37 (ddd, J=15.7, 10.3, 5.2 Hz, 1H) 5.68 (br dd, J=15.3, 6.1 Hz, 1H) 5.47 (d, J=7.6 Hz, 1H) 5.13-5.23 (m, 2H) 5.05 (d, J=13.6 Hz, 1H) 4.91 (dd, J=11.3, 5.0 Hz, 1H) 4.25 (d, J=13.6 Hz, 1H) 4.06 (br t, J=10.6 Hz, 1H) 1.40-1.63 (m, 2H) 0.83 (t, J=7.3 Hz, 3H)

LC/MS (method LC-C): Rt 3.14 min, MH+ 496

$[\alpha]_D^{20}$: −621.31° (c 0.183, DMF)

Chiral HPLC (method HPLC-B): Rt 7.09 min, chiral purity 100%

Compound 170AB:

LC/MS (method LC-C): Rt 3.19 min, MH+ 496

$[\alpha]_D^{20}$: +709.9° (c 0.192, DMF)

Chiral HPLC (method HPLC-A): Rt 4.57 min, chiral purity 100%

Compound 170BA:

$^1$H NMR (400 MHz, DMSO-d$_6$) δ ppm 8.01 (d, J=8.2 Hz, 1H) 7.61 (dd, J=8.6, 7.2 Hz, 1H) 7.35 (d, J=7.6 Hz, 1H) 7.00-7.25 (m, 5H) 6.39-6.55 (m, 1H) 5.84-6.08 (m, 1H) 5.49 (d, J=7.6 Hz, 1H) 5.39 (s, 1H) 5.20 (d, J=13.9 Hz, 1H) 4.64-4.75 (m, 1H) 4.58 (br dd, J=10.0, 4.5 Hz, 1H) 4.24 (d, J=14.1 Hz, 1H) 3.40-3.50 (m, 1H) 2.33 (br t, J=6.8 Hz, 1H) 2.07-2.22 (m, 1H) 0.86 (t, J=7.3 Hz, 3H)

LC/MS (method LC-C): Rt 3.19 min, MH+ 496

$[\alpha]_D^{20}$: −707.14° (c 0.252, DMF)

Chiral HPLC (method HPLC-A): Rt 6.67 min, chiral purity 100%

420

Example 171: Synthesis of (18'*S,*E)-3',4'-difluoro-12'-hydroxy-18'-(3-methylpyridin-2-yl)-6'H,18'H-spiro[cyclobutane-1,9'-[10,17]methanobenzo[b]pyrido[1,2-f][1]oxa[5,6,9]triazacyclotridecine]-11',13'-dione (Compound 171A) and (18'*R,*E)-3',4'-difluoro-12'-hydroxy-18'-(3-methylpyridin-2-yl)-6'H,18'H-spiro[cyclobutane-1,9'-[10,17]methanobenzo[b]pyrido[1,2-f][1]oxa[5,6,9]triazacyclotridecine]-11',13'-dione (Compound 171B)

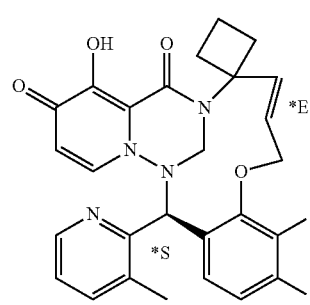

171A and

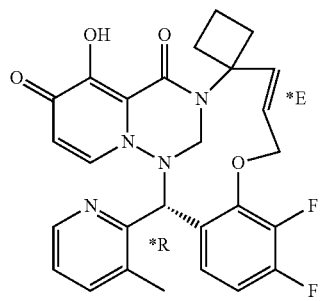

171B

Compounds 171A and 171B were synthesized according to the procedures described in example 146 starting from intermediate 2-((2-(allyloxy)-3,4-difluorophenyl)chloromethyl)-3-methylpyridine (synthesized as 45b from 2-bromo-3-methyl-pyridine [CAS 3430-17-9] and 74a).

Compound 171A:

$^1$H NMR (500 MHz, DMSO-d$_6$) δ ppm 8.34 (br d, J=4.1 Hz, 1H) 7.98 (br t, J=7.1 Hz, 1H) 7.42 (br d, J=7.6 Hz, 1H) 7.32-7.40 (m, 1H) 7.22 (br d, J=7.6 Hz, 1H) 7.07 (dd, J=7.6, 4.7 Hz, 1H) 6.55 (br d, J=15.4 Hz, 1H) 6.17-6.28 (m, 1H) 5.79 (s, 1H) 5.54 (d, J=7.9 Hz, 1H) 5.13 (d, J=13.6 Hz, 1H) 4.88 (br t, J=9.8 Hz, 1H) 4.59-4.69 (m, 1H) 3.89 (br d, J=13.9 Hz, 1H) 2.81-2.89 (m, 1H) 2.26 (s, 3H) 2.03-2.19 (m, 3H) 1.70-1.81 (m, 1H) 1.55-1.67 (m, 1H)

LC/MS (method LC-C): Rt 2.98 min, MH+507

$[\alpha]_D^{20}$: −650.65° (c 0.077, DMF)

Chiral HPLC (method HPLC-B): Rt 5.34 min, chiral purity 100%

Compound 171B:

LC/MS (method LC-C): Rt 2.98 min, MH+507

$[\alpha]_D^{20}$: +650.62° (c 0.081, DMF)

Chiral HPLC (method HPLC-B): Rt 7.22 min, chiral purity 100%

Example 172: Synthesis of (18'*S,*E)-3',4'-difluoro-12'-hydroxy-18'-(pyridin-2-yl)-6'H,18'H-spiro[cyclobutane-1,9'-[10,17]methanobenzo[b]pyrido[1,2-f][1]oxa[5,6,9]triazacyclotridecine]-11',13'-dione (Compound 172A) and (18'*R,*E)-3',4'-difluoro-12'-hydroxy-18'-(pyridin-2-yl)-6'H,18'H-spiro[cyclobutane-1,9'-[10,17]methanobenzo[b]pyrido[1,2-f][1]oxa[5,6,9]triazacyclotridecine]-11',13'-dione (Compound 172B)

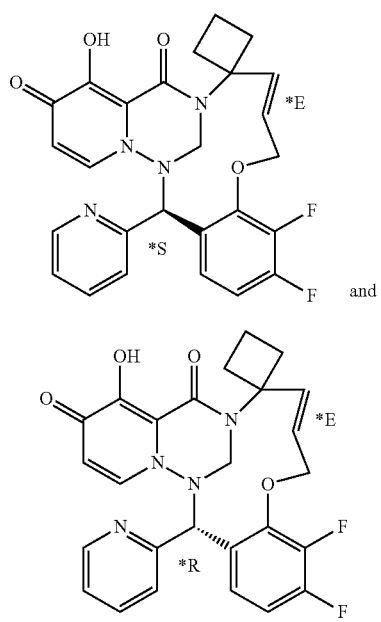

172A

172B

Compounds 172A and 172B were synthesized according to the procedures described in example 146 starting from intermediate 2-((2-(allyloxy)-3,4-difluorophenyl)chloromethyl)pyridine (synthesized as 45b from 2-bromo-pyridine [CAS 109-04-6] and 74a).

Compound 172A:

$^1$H NMR (500 MHz, DMSO-d$_6$) δ ppm 8.36 (br d, J=4.1 Hz, 1H) 7.95 (br t, J=7.1 Hz, 1H) 7.62 (td, J=7.6, 1.4 Hz, 1H) 7.38-7.49 (m, 1H) 7.13-7.25 (m, 3H) 6.51 (br d, J=15.8 Hz, 1H) 6.19 (dt, J=15.1, 7.3 Hz, 1H) 5.50 (d, J=7.6 Hz, 1H) 5.42 (s, 1H) 5.11 (d, J=13.6 Hz, 1H) 4.82 (br t, J=9.6 Hz, 1H) 4.52-4.65 (m, 1H) 3.86 (d, J=13.6 Hz, 1H) 2.83-2.92 (m, 1H) 2.42-2.47 (m, 1H) 2.02-2.17 (m, 2H) 1.75 (br d, J=8.5 Hz, 1H) 1.52-1.67 (m, 1H)

LC/MS (method LC-C): Rt 2.74 min, MH$^+$493

[α]$_D^{20}$: −589.04° (c 0.073, DMF)

Chiral HPLC (method HPLC-B): Rt 5.09 min, chiral purity 100%

Compound 172B:

LC/MS (method LC-C): Rt 2.73 min, MH$^+$493

[α]$_D^{20}$: +620.00° (c 0.080, DMF)

Chiral HPLC (method HPLC-B): Rt 5.57 min, chiral purity 100%

Example 173: Synthesis of (9*S,18*S,*E)-4-chloro-9-ethyl-3-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 173AA) and (9*R,18*R,*E)-4-chloro-9-ethyl-3-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 173BB) and (9*R,18*S,*E)-4-chloro-9-ethyl-3-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 173AB) and (9*S,18*R,*E)-4-chloro-9-ethyl-3-fluoro-12-hydroxy-18-phenyl-6,9-dihydro-18H-10,17-methanobenzo[b]pyrido[1,2-f][1]oxa[5,6,9]triazacyclotridecine-11,13-dione (Compound 173BA)

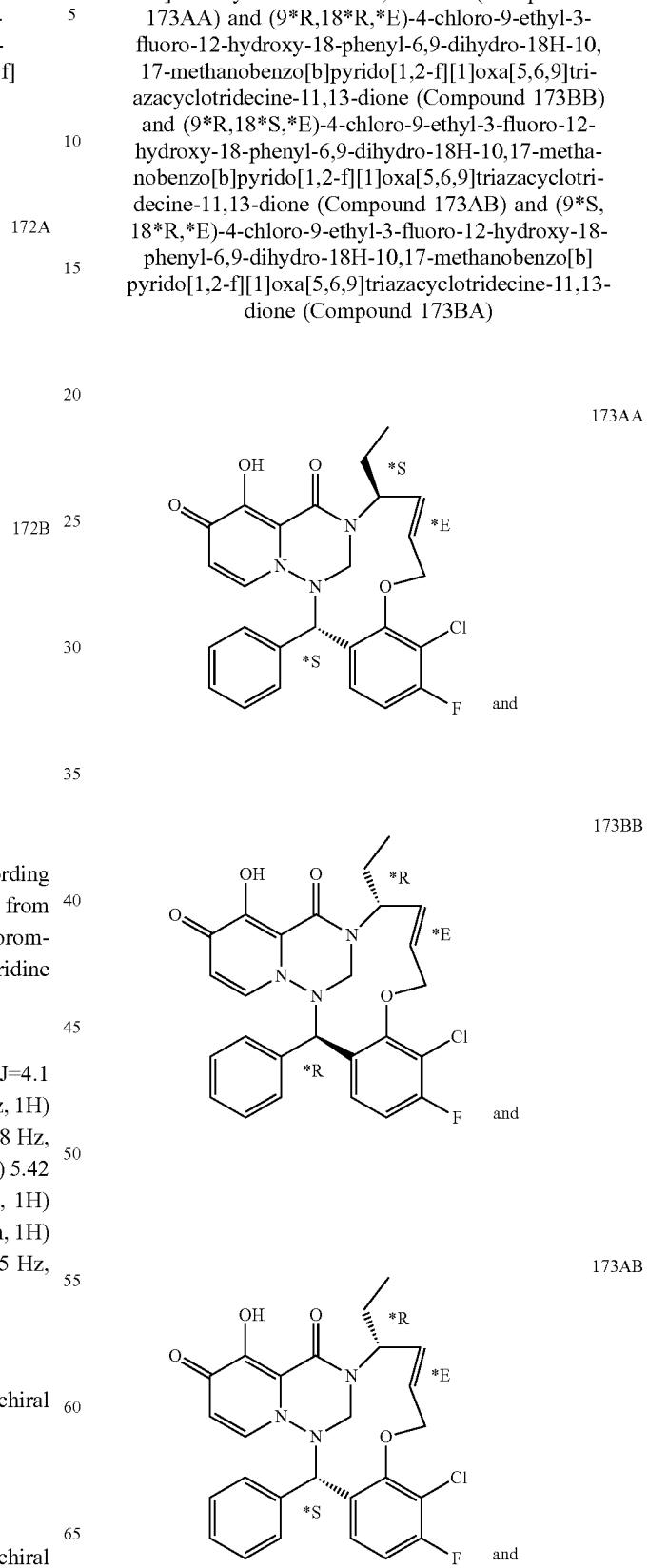

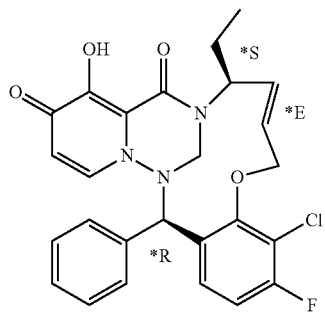

173BA

Compounds 173AA, 173BB, 173AB and 173BA were synthesized according to the procedures described in example 39 starting from intermediate 2-(allyloxy)-3-chloro-1-(chloro(phenyl)methyl)-4-fluorobenzene (synthesized as 74c from 3-chloro-4-fluoro-2-hydroxy-benzaldehyde [CAS 1260826-10-5]).

Compound 173AA:
LC/MS (method LC-C): Rt 3.13 min, MH+496
$[\alpha]_D^{20}$: +585.00° (c 0.120, DMF)

Compound 173BB:
$^1$H NMR (500 MHz, DMSO-d$_6$) δ ppm 9.90-11.04 (m, 1H) 8.18 (dd, J=8.5, 6.6 Hz, 1H) 7.49 (t, J=8.7 Hz, 1H) 7.32 (d, J=7.6 Hz, 1H) 6.93-7.26 (m, 5H) 6.36-6.58 (m, 1H) 5.79-6.00 (m, 1H) 5.49 (d, J=7.6 Hz, 1H) 5.41 (s, 1H) 5.22 (d, J=13.9 Hz, 1H) 4.79-4.94 (m, 1H) 4.64-4.76 (m, 1H) 4.27 (d, J=13.9 Hz, 1H) 3.40-3.49 (m, 1H) 2.28-2.38 (m, 1H) 2.06-2.24 (m, 1H) 0.87 (t, J=7.4 Hz, 3H)
LC/MS (method LC-C): Rt 3.13 min, MH+ 496
$[\alpha]_D^{20}$: -620.73° (c 0.164, DMF)

Compound 173AB:
LC/MS (method LC-C): Rt 3.09 min, MH+496
$[\alpha]_D^{20}$: +595.45° (c 0.088, DMF)
Chiral HPLC (method HPLC-B): Rt 4.68 min, chiral purity 100%

Compound 173BA:
$^1$H NMR (500 MHz, DMSO-d$_6$) δ ppm 8.09-8.22 (m, 1H) 7.50 (br t, J=8.7 Hz, 1H) 6.94-7.38 (m, 6H) 6.30-6.52 (m, 1H) 5.64 (br dd, J=14.7, 5.2 Hz, 1H) 5.48 (br d, J=7.9 Hz, 1H) 5.12-5.29 (m, 2H) 5.06 (br d, J=13.6 Hz, 1H) 4.91 (br dd, J=11.3, 4.7 Hz, 1H) 4.27 (br d, J=13.6 Hz, 1H) 4.13 (br t, J=10.9 Hz, 1H) 1.40-1.62 (m, 2H) 0.84 (br t, J=7.1 Hz, 3H)
LC/MS (method LC-C): Rt 3.09 min, MH+ 496
$[\alpha]_D^{20}$: -579.38° (c 0.097, DMF)
Chiral HPLC (method HPLC-B): Rt 5.50 min, chiral purity 100%

Example 174: Synthesis of (18'*R,*E)-3',4'-difluoro-12'-hydroxy-18'-(o-tolyl)-6'H,18'H-spiro[cyclobutane-1,9'-[10,17]methanobenzo[b]pyrido[1,2-f][1]oxa[5,6,9]triazacyclotridecine]-11',13'-dione (Compound 174A) and (18'*S,*E)-3',4'-difluoro-12'-hydroxy-18'-(o-tolyl)-6'H,18'H-spiro[cyclobutane-1,9'-[10,17]methanobenzo[b]pyrido[1,2-f][1]oxa[5,6,9]triazacyclotridecine]-11',13'-dione (Compound 174B)

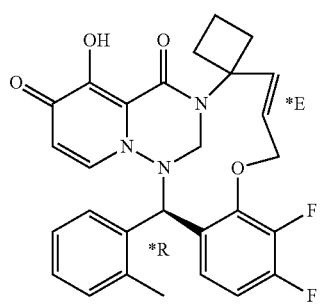

174A and

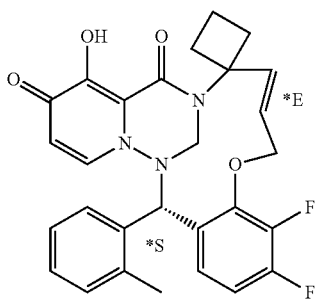

174B

Compounds 174A and 174B were synthesized according to the procedures described in example 146 starting from intermediate 2-(allyloxy)-1-(chloro(o-tolyl)methyl)-3,4-difluorobenzene (see example 155).

Compound 174A:
LC/MS (method LC-G): Rt 3.19 min, MH+ 506
$[\alpha]_D^{20}$: +637.58° (c 0.165, DMF)
Chiral HPLC (method HPLC-B): Rt 5.53 min, chiral purity 100%

Compound 174B:
$^1$H NMR (500 MHz, DMSO-d$_6$) δ ppm 9.67-11.20 (m, 1H) 7.97 (br t, J=6.9 Hz, 1H) 7.49 (d, J=7.6 Hz, 1H) 7.37-7.46 (m, 2H) 6.99-7.10 (m, 2H) 6.94-6.99 (m, 1H) 6.49 (br d, J=16.1 Hz, 1H) 6.11-6.24 (m, 1H) 5.65 (s, 1H) 5.52 (d, J=7.6 Hz, 1H) 5.14 (d, J=13.6 Hz, 1H) 4.87 (br t, J=9.6 Hz, 1H) 4.59 (br s, 1H) 3.87 (d, J=13.6 Hz, 1H) 2.79-2.92 (m, 1H) 2.42-2.47 (m, 1H) 2.26 (s, 3H) 2.00-2.17 (m, 2H) 1.76 (q, J=9.0 Hz, 1H) 1.53-1.68 (m, 1H)
LC/MS (method LC-G): Rt 3.19 min, MH+ 506
$[\alpha]_D^{20}$: -637.43° (c 0.179, DMF)
Chiral HPLC (method HPLC-B): Rt 4.84 min. chiral purity 100%

Example 175: Synthesis of (18*R,Z)-3,4-difluoro-18-(2-(fluoromethyl)phenyl)-12-hydroxy-6,9-dihydro-18H-10,17-methanobenzo[b]pyrido[1,2-f][1]oxa[5,6,9]triazacyclotridecine-11,13-dione (Compound 175A) and (18*S,Z)-3,4-difluoro-18-(2-(fluoromethyl)phenyl)-12-hydroxy-6,9-dihydro-18H-10,17-methanobenzo[b]pyrido[1,2-f][1]oxa[5,6,9]triazacyclotridecine-11,13-dione (Compound 175B)

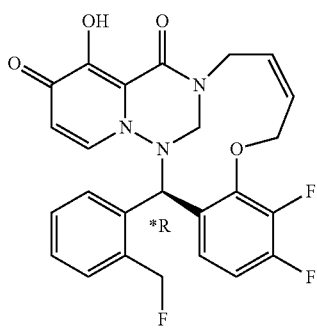

175A and

-continued

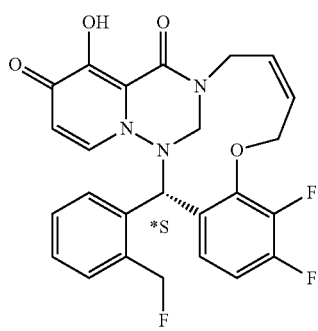
175B

Compounds 175A and 175B were synthesized according to the procedures described in example 5 starting from intermediate 2-(allyloxy)-1-(chloro(2-(fluoromethyl)phenyl)methyl)-3,4-difluorobenzene (synthesized as 74c from 1-bromo-2-(fluoromethyl)benzene [CAS 446-47-9]).

Compound 175A:
¹H NMR (500 MHz, DMSO-d₆) δ ppm 7.96-8.05 (m, 1H) 7.80 (br d, J=7.9 Hz, 1H) 7.48 (q, J=8.8 Hz, 1H) 7.30-7.43 (m, 2H) 7.19-7.28 (m, 2H) 6.12-6.28 (m, 1H) 5.90-6.10 (m, 1H) 5.48-5.70 (m, 3H) 5.22-5.40 (m, 1H) 5.17 (br d, J=13.9 Hz, 1H) 4.95 (br s, 1H) 4.82 (br dd, J=14.0, 4.6 Hz, 1H) 4.33 (br d, J=13.9 Hz, 2H) 3.17-3.22 (m, 1H)
LC/MS (method LC-G): Rt 2.67 min, MH+ 484
$[\alpha]_D^{20}$: −639.76° (c 0.083, DMF)
Chiral HPLC (method HPLC-A): Rt 4.88 min, chiral purity 100%

Compound 175B:
LC/MS (method LC-G): Rt 2.67 min, MH+ 484
$[\alpha]_D^{20}$: +658.67° (c 0.075, DMF)
Chiral HPLC (method HPLC-A): Rt 5.60 min, chiral purity 100%

Example 176: Synthesis of (3*R,17a'*R,*E)-24',25'-difluoro-12'-hydroxy-2',4,5,17a'-tetrahydro-2H,6'H-spiro[furan-3,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 176AA) and (3*S, 17a'*R, *E)-24',25'-difluoro-12'-hydroxy-2',4,5,17a'-tetrahydro-2H,6'H-spiro[furan-3,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 176AB) and (3*R, 17a'*S,*E)-24',25'-difluoro-12'-hydroxy-2',4,5,17a'-tetrahydro-2H,6'H-spiro[furan-3,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 176BA) and (3*S, 17a'*S,*E)-24',25'-difluoro-12'-hydroxy-2',4,5,17a'-tetrahydro-2H,6'H-spiro[furan-3,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 176BB)

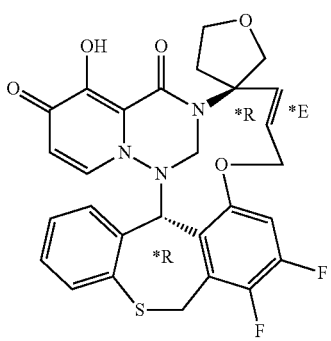
176AA and

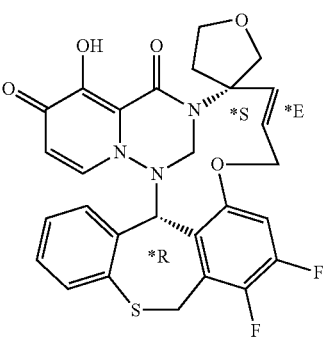
176AB and

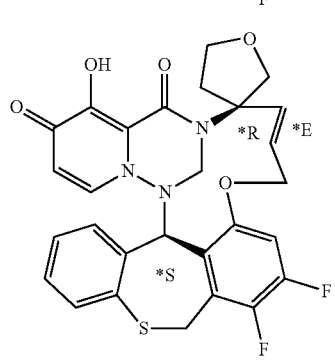
176BA and

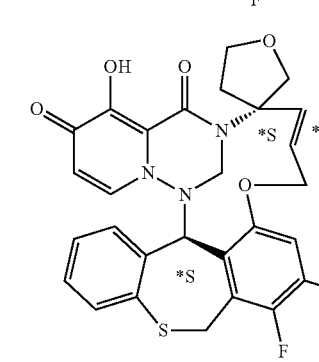
176BB

Compounds 176AA, 176AB, 176BA and 176BB were synthesized according to the procedures described in example 159 starting from intermediate 5-(benzyloxy)-3-(3-vinyltetrahydrofuran-3-yl)-2,3-dihydro-1H-pyrido[2,1-f][1,2,4]triazine-4,6-dione (synthesized as 146f from N-(3-formyltetrahydro-3-furanyl)carbamic acid-1,1-dimethyl ester [CAS 2170650-09-4]).

Compound 176AA:
LC/MS (method LC-D): Rt 2.31 min, MH+ 552
$[\alpha]_D^{20}$: +357.98° (c 0.238, DMF)

Compound 176AB:
LC/MS (method LC-D): Rt 1.34 min, MH+ 552
$[\alpha]_D^{20}$: +359.71° (c, DMF)

Compound 176BA:
¹H NMR (400 MHz, DMSO-d6) δ 7.48 (dd, J=11.9, 7.3 Hz, 1H), 7.38 (d, J=7.6 Hz, 1H), 7.16-7.01 (m, 2H), 6.88 (td, J=7.4, 1.4 Hz, 1H), 6.76 (dd, J=7.8, 1.5 Hz, 1H), 6.40 (dt, J=15.3, 7.4 Hz, 1H), 6.17 (d, J=15.9 Hz, 1H), 5.76-5.58 (m, 2H), 5.38 (s, 1H), 5.12 (d, J=13.7 Hz, 1H), 4.81 (dd, J=11.2, 7.1 Hz, 1H), 4.54 (dd, J=11.2, 7.9 Hz, 1H), 4.27 (d, J=13.7 Hz, 1H), 4.11 (d, J=14.1 Hz, 1H), 4.02 (d, J=8.5 Hz, 1H), 3.88 (td, J=8.0, 4.6 Hz, 1H), 3.68 (q, J=8.2 Hz, 1H), 3.55 (d, J=8.5 Hz, 1H), 2.98-2.75 (m, 2H).
LC/MS (method LC-D): Rt 2.31 min, MH+ 552
$[\alpha]_D^{20}$: −346.45° (c 0.211, DMF)

Compound 176BB:

1H NMR (400 MHz, DMSO-d6) δ 7.53 (dd, J=11.8, 7.3 Hz, 1H), 7.43 (d, J=7.6 Hz, 1H), 7.13 (ddd, J=8.5, 7.1, 1.4 Hz, 1H), 7.06 (dd, J=8.0, 1.4 Hz, 1H), 6.88 (td, J=7.4, 1.4 Hz, 1H), 6.75 (dd, J=7.8, 1.5 Hz, 1H), 6.41-6.23 (m, 2H), 5.77-5.67 (m, 2H), 5.39 (s, 1H), 5.21 (d, J=13.8 Hz, 1H), 4.79 (dd, J=11.2, 7.1 Hz, 1H), 4.68-4.54 (m, 2H), 4.38 (d, J=13.8 Hz, 1H), 4.19-4.00 (m, 2H), 3.78 (td, J=9.0, 2.5 Hz, 1H), 3.61 (td, J=8.8, 6.7 Hz, 1H), 2.38 (td, J=8.1, 6.9, 3.5 Hz, 1H), 2.16-1.92 (m, 1H).

LC/MS (method LC-D): Rt 1.32 min, MH+552

$[\alpha]_D^{20}$: −392.79° (c 0.208, DMF)

Example 177: Synthesis of (9*R,17a*R,*E)-24,25-difluoro-12-hydroxy-9-(methoxymethyl)-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 177AA) and (9*S,17a*R,*E)-24,25-difluoro-12-hydroxy-9-(methoxymethyl)-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 177AB) and (9*R,17a*S,*E)-24,25-difluoro-12-hydroxy-9-(methoxymethyl)-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 177BA) and (9*S,17a*S,*E)-24,25-difluoro-12-hydroxy-9-(methoxymethyl)-2,6,9,17a-tetrahydro-3,4-(epiprop[1]en[1]yl[3]ylidene)-10,17-methanobenzo[6,7]thiepino[4,5-c]pyrido[1,2-f][1]oxa[5,6,9]triazacyclotridecine-11,13-dione (Compound 177BB)

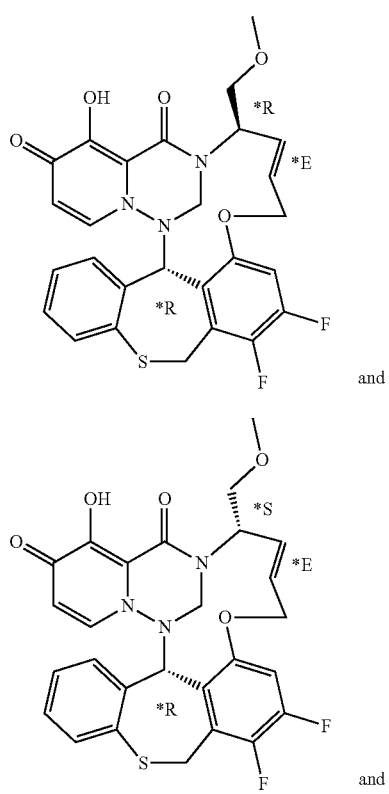

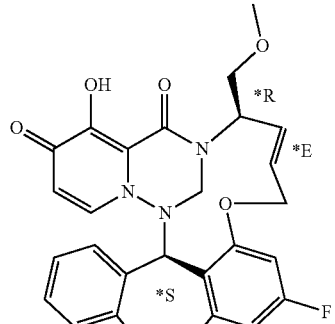

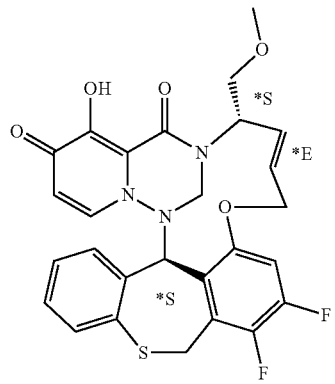

Compounds 177AA, 177AB, 177BA and 177BB were synthesized according to the procedures described in example 159 starting from intermediate 5-(benzyloxy)-3-(1-methoxybut-3-en-2-yl)-2,3-dihydro-1H-pyrido[2,1-f][1,2,4]triazine-4,6-dione (see example 150).

Compound 177AA:

LC/MS (method LC-D): Rt 1.37 min, MH+ 540

$[\alpha]_D^{20}$: +308.06° (c 0.211, DMF)

Compound 177AB:

1H NMR (400 MHz, DMSO-d6) δ 7.44 (dd, J=11.7, 7.2 Hz, 1H), 7.36-7.23 (m, 1H), 7.22-7.06 (m, 2H), 6.88 (q, J=5.7, 4.8 Hz, 2H), 6.40 (ddd, J=15.8, 10.4, 5.6 Hz, 1H), 5.81-5.59 (m, 3H), 5.50 (q, J=6.7 Hz, 1H), 5.30 (s, 1H), 5.01 (d, J=14.0 Hz, 1H), 4.89 (dd, J=11.3, 5.3 Hz, 1H), 4.49 (d, J=13.9 Hz, 1H), 4.31 (t, J=10.8 Hz, 1H), 4.13 (d, J=14.1 Hz, 1H), 3.58-3.41 (m, 2H), 3.24 (s, 3H).

LC/MS (method LC-D): Rt 1.37 min, MH+ 540

$[\alpha]_D^{20}$: −278.67° (c 0.211, DMF)

Compound 177BA:

1H NMR (400 MHz, DMSO-d6) δ 7.57 (dd, J=12.0, 7.0 Hz, 1H), 7.22 (d, J=7.5 Hz, 1H), 7.14 (dtd, J=16.2, 8.1, 1.5 Hz, 2H), 6.84 (td, J=7.4, 1.6 Hz, 1H), 6.66 (dd, J=7.9, 1.4 Hz, 1H), 6.26-6.14 (m, 1H), 5.94-5.78 (m, 2H), 5.65 (d, J=7.6 Hz, 1H), 5.55 (dd, J=14.2, 2.7 Hz, 1H), 5.45-5.35 (m, 1H), 4.98-4.82 (m, 3H), 4.27 (d, J=13.5 Hz, 1H), 4.01 (d, J=14.2 Hz, 1H), 3.64 (dd, J=9.6, 5.5 Hz, 1H), 3.49 (dd, J=9.6, 3.4 Hz, 1H), 3.27 (s, 3H).

LC/MS (method LC-D): Rt 1.42 min, MH+ 540

Compound 177BB:

LC/MS (method LC-D): Rt 1.40 min, MH+ 540

Example 178: Synthesis of (((17a'*S,*E)-24',25'-difluoro-11',13'-dioxo-2',11',13',17a'-tetrahydro-6'H-spiro[cyclobutane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecin]-12'-yl)oxy)methyl (2-(2-methoxyethoxy)ethyl) carbonate (Compound 178)

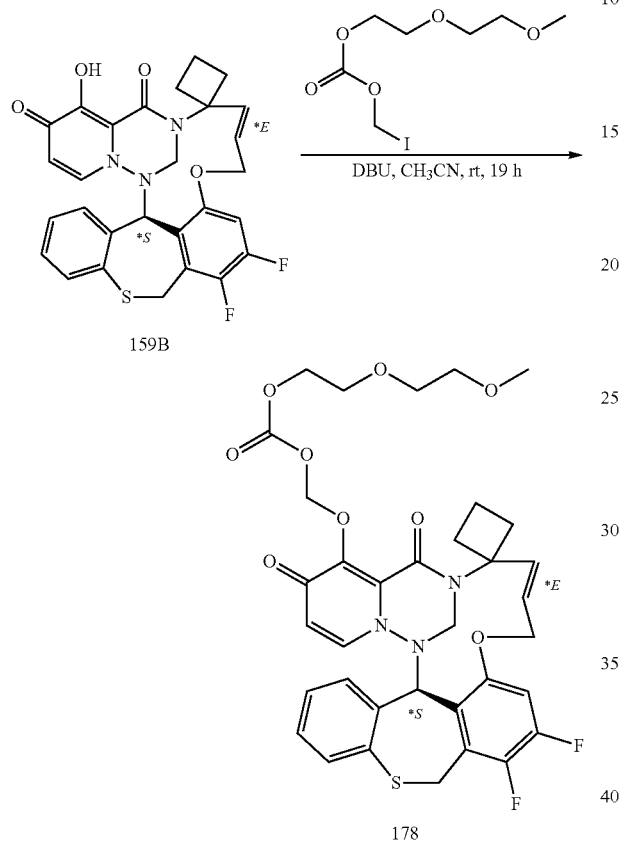

Synthesis of Compound 178:

To a solution of compound 159B (250 mg, 0.467 mmol) in dry CH$_3$CN (3 mL) was added a solution of iodomethyl (2-(2-methoxyethoxy)ethyl) carbonate [CAS 854924-77-9] (426 mg, 1.40 mmol) in dry CH$_3$CN (2 mL) and DBU (209 µL, 1.4 mmol). The reaction was stirred at rt for 19h and was then diluted with AcOEt and washed with H$_2$O, and brine. The organic layer was dried over Na$_2$SO4, filtered, and concentrated under reduced pressure. The residue was purified by flash column chromatography over silica gel (40 g, Eluent: CH$_2$Cl$_2$/MeOH 0 to 10%; 2 times) then over C18 (30 g, Eluent: H$_2$O/MeOH 0 to 100%) to compound 178 (184 mg) as a white solid.

Compound 178:

$^1$H NMR (400 MHz, DMSO-d6) δ 7.57-7.51 (m, 2H), 7.13-7.03 (m, 2H), 6.88 (t, J=7.3 Hz, 1H), 6.76 (d, J=7.4 Hz, 1H), 6.50 (d, J=15.8 Hz, 1H), 6.25-6.17 (m, 1H), 5.85 (d, J=7.8 Hz, 1H), 5.75-5.72 (m, 1H), 5.69 (d, J=6.5 Hz, 1H), 5.57 (d, J=6.5 Hz, 1H), 5.36 (s, 1H), 5.08 (d, J=14.0 Hz, 1H), 4.70 (d, J=7.2 Hz, 2H), 4.30-4.20 (m, 2H), 4.09 (d, J=14.2 Hz, 1H), 3.99 (d, J=14.0 Hz, 1H), 3.69 (t, J=4.6 Hz, 2H), 3.56-3.54 (m, 2H), 3.44-3.41 (m, 2H), 3.22 (s, 3H), 2.61-2.55 (m, 1H), 2.46-2.44 (m, 1H), 2.12 (brs, 1H), 2.01 (dd, J=20.7, 10.2 Hz, 1H), 1.78-1.73 (m, 1H), 1.65-1.56 (m, 1H).

LC/MS (method LC-F): Rt 4.91 min, MH$^+$712

Chiral SFC (method SFC-B): R$_t$ 1.25 min, chiral purity 99.87%.

Example 179: Synthesis of (((17a'S,E)-24',25'-difluoro-11',13'-dioxo-2',11',13',17a'-tetrahydro-6'H-spiro[cyclobutane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecin]-12'-yl)oxy)methyl methyl carbonate (Compound 179)

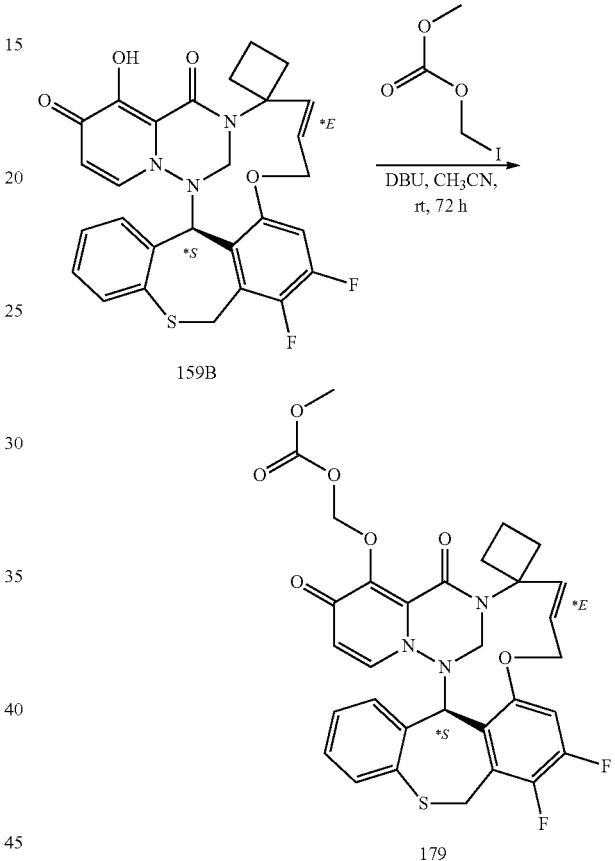

Synthesis of Compound 179:

A mixture of compound 159B (447 mg, 0.835 mmol), iodomethyl methyl carbonate [CAS 69862-08-4] (451 mg, 2.087 mmol) and DBU (311 µL, 2.087 mmol) in CH$_3$CN (7 mL) was stirred at rt for 72 h. The mixture was diluted with water and was extracted with EtOAc. The organic layer was washed with water then with brine. The organic layer was dried over MgSO$_4$, filtered and the solvent was evaporated under reduced pressure. Purification was carried out by flash chromatography over silica gel (24 g 30 µm (CH$_2$Cl$_2$/CH$_3$OH 99/1 to 97/3)). The pure fractions were collected and evaporated to dryness to give, after crystallisation from CH$_3$OH, 270 mg of compound 179.

Compound 179:

$^1$H NMR (500 MHz, DMSO-d$_6$) δ ppm 7.50-7.59 (m, 2H) 7.09-7.15 (m, 1H) 7.02-7.07 (m, 1H) 6.88 (td, J=7.4, 0.9 Hz, 1H) 6.72-6.77 (m, 1H) 6.49 (d, J=15.8 Hz, 1H) 6.21 (dt, J=15.3, 7.5 Hz, 1H) 5.85 (d, J=7.9 Hz, 1H) 5.74 (dd, J=14.5, 1.9 Hz, 1H) 5.67 (d, J=6.6 Hz, 1H) 5.54 (d, J=6.6 Hz, 1H) 5.36 (s, 1H) 5.08 (d, J=13.9 Hz, 1H) 4.66-4.77 (m, 2H) 4.09

(d, J=14.2 Hz, 1H) 4.00 (d, J=13.9 Hz, 1H) 3.77 (s, 3H) 2.54-2.62 (m, 1H) 2.41-2.47 (m, 1H) 2.09-2.18 (m, 1H) 2.01 (q, J=10.2 Hz, 1H) 1.70-1.80 (m, 1H) 1.54-1.67 (m, 1H)

LC/MS (method LC-A): Rt 2.99 min, MH+624

Chiral SFC (method SFC-B): R$_t$ 1.37 min, chiral purity 99.71%.

Example 180: Synthesis of (17a'*R,*E)-24'-fluoro-12'-hydroxy-2',17a'-dihydro-6'H-spiro[cyclobutane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 180A) and (17a'*S,*E)-24'-fluoro-12'-hydroxy-2',17a'-dihydro-6'H-spiro[cyclobutane-1,9'-[3,4](epiprop[1]en[1]yl[3]ylidene)[10,17]methanobenzo[6,7]thiepino[4,5-c]pyrido[1,2-f][1]oxa[5,6,9]triazacyclotridecine]-11',13'-dione (Compound 180B)

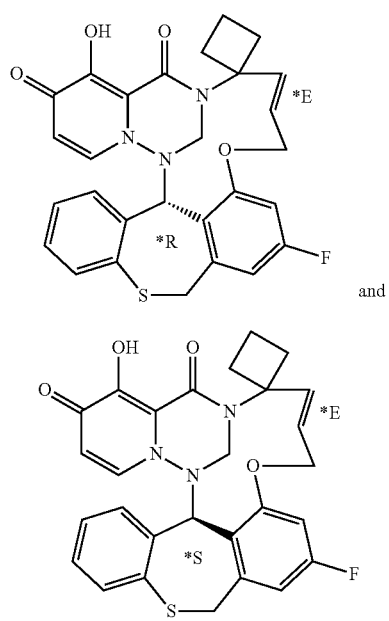

Compounds 180A and 180B were synthesized according to the procedures described in example 159 starting from intermediate 10-(allyloxy)-11-chloro-8-fluoro-6,11-dihydrodibenzo[b,e]thiepine (synthesized as 88n from 4-fluoro-2-methyl-benzoic acid [CAS 321-21-1]).

Compound 180A:

LC/MS (method LC-D): Rt 1.45 min, MH+ 518

Compound 180B:

$^1$H-NMR (400 MHz, DMSO-d6) δ (ppm): 7.47 (d, J=7.6 Hz, 1H), 7.26-7.29 (m, 1H), 7.07-7.13 (m, 2H), 7.02 (d, J=6.8 Hz, 1H), 6.83 (t, J=7.6 Hz, 1H), 6.68 (d, J=6.8 Hz, 1H), 6.47 (d, J=7.2 Hz, 1H), 6.14-6.22 (m, 1H), 5.87 (d, J=6.8 Hz, 1H), 5.73 (d, J=7.6 Hz, 1H), 5.37 (s, 1H), 5.12 (d, J=7.2 Hz, 1H), 4.75 (d, J=5.6 Hz, 2H), 3.85-3.94 (m, 2H), 2.76-2.82 (m, 1H), 2.45 (d, J=7.6 Hz, 1H), 2.10 (t, J=6.8 Hz, 2H), 1.72-1.76 (m, 1H), 1.59-1.64 (m, 1H)

LC/MS (method LC-D): Rt 1.45 min, MH+518

Example 181: Synthesis of ((((18'R,E)-3',4'-difluoro-11',13'-dioxo-18'-phenyl-11',13'-dihydro-6'H,18'H-spiro[cyclobutane-1,9'-[10,17]methanobenzo[b]pyrido[1,2-f][1]oxa[5,6,9]triazacyclotridecin]-12'-yl)oxy)methyl (2-(2-methoxyethoxy)ethyl) carbonate (Compound 181)

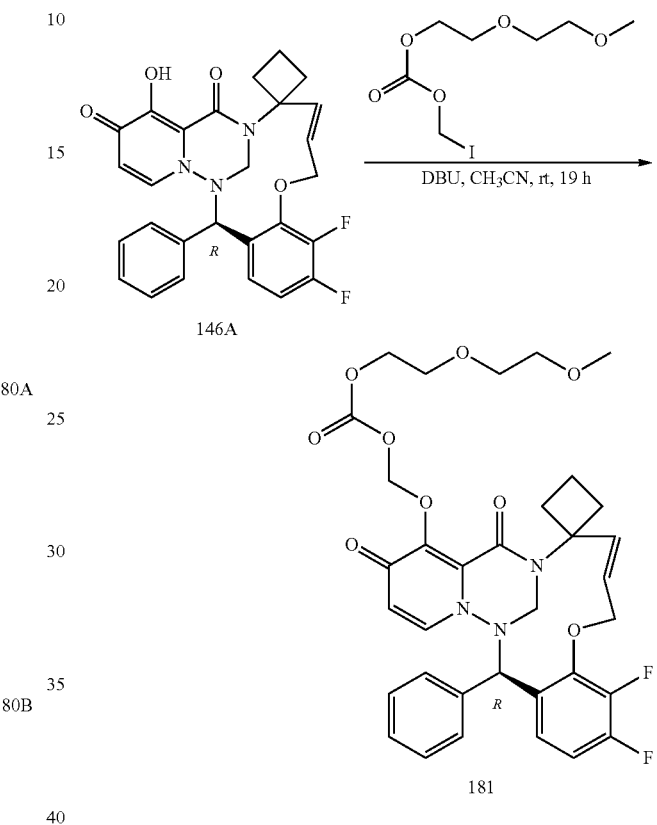

Synthesis of Compound 181:

To a solution of compound 146A (161 mg, 0.328 mmol) in dry CH$_3$CN (2.1 mL) were added a solution of iodomethyl (2-(2-methoxyethoxy)ethyl) carbonate [CAS 854924-77-9] (374 mg, 0.983 mmol) in dry CH$_3$CN (1.7 mL) and DBU (0.147 mL, 0.983 mmol). The reaction mixture was stirred for 19h at rt, was diluted with AcOEt and then washed with H$_2$O, and brine. The organic layer was dried over Na$_2$SO4, filtered, and concentrated under reduced pressure. The residue was purified by flash column chromatography over silica (40 g, Eluent: CH$_2$Cl$_2$/MeOH 0 to 10%). The compound was purified again over silica (C18 12 g (eluent H$_2$O/MeOH 50:50 to 0:100) to afford compound 181 (107 mg).

Compound 181:

$^1$H NMR (400 MHz, CDCl$_3$) δ 7.68-7.58 (m, 1H), 7.20-7.09 (m, 4H), 7.01 (d, J=3.7 Hz, 2H), 6.71 (d, J=7.8 Hz, 1H), 6.42 (brs, 1H), 6.07 (brs, 1H), 5.95 (d, J=6.3 Hz, 1H), 5.80 (d, J=6.3 Hz, 1H), 5.76 (d, J=7.8 Hz, 1H), 5.30 (s, 1H), 4.84 (d, J=13.6 Hz, 1H), 4.75-4.65 (m, 1H), 4.59 (brs, 1H), 4.48-4.30 (m, 2H), 3.88 (d, J=13.6 Hz, 1H), 3.79 (t, J=5.0 Hz, 2H), 3.66 (dd, J=5.6, 3.6 Hz, 2H), 3.51 (dd, J=5.6, 3.7 Hz, 2H), 3.34 (s, 3H), 2.87-2.80 (m, 1H), 2.67-2.51 (m, 1H), 2.01-1.95 (m, 2H), 1.89-1.77 (m, 1H), 1.76-1.63 (m, 1H).

LC/MS (method LC-E): Rt 3.36 min, MH+ 668

433

Chiral SFC (method SFC-C): Rt 1.12 min, chiral purity 100%.

Example 182: Synthesis of ((((18'R,E)-3',4'-difluoro-11',13'-dioxo-18'-phenyl-11',13'-dihydro-6'H,18'H-spiro[cyclobutane-1,9'-[10,17]methanobenzo[b]pyrido[1,2-f][1]oxa[5,6,9]triazacyclotridecin]-12'-yl)oxy)methyl methyl carbonate (Compound 182)

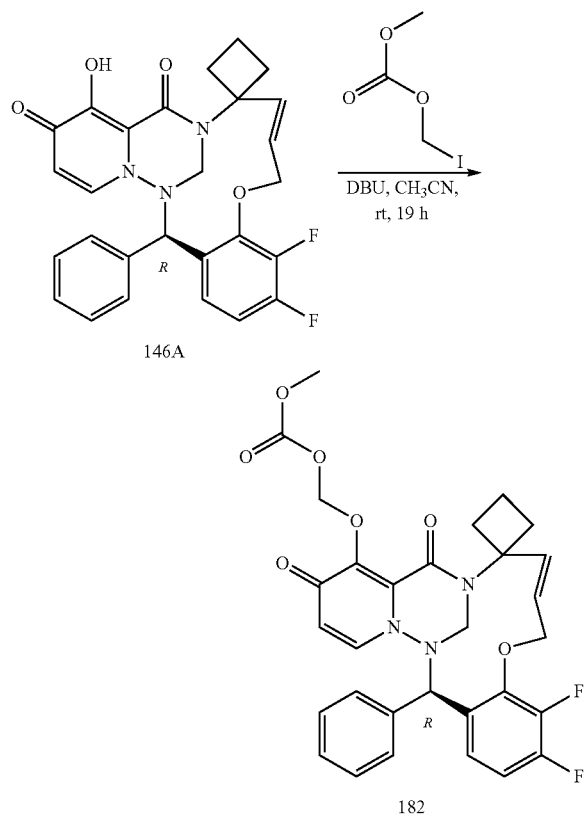

Synthesis of Compound 182:

To a solution of compound 146A (161 mg, 0.328 mmol) in dry $CH_3CN$ (2.1 mL) were added a solution of iodomethyl methyl carbonate [CAS 69862-08-4] (177 mg, 0.8 mmol) in dry $CH_3CN$ (1.4 mL) and DBU (0.122 mL, 0.82 mmol). The reaction mixture was stirred for 19h at rt, was diluted with AcOEt and then washed with $H_2O$, and brine. The organic layer was dried over $Na_2SO_4$, filtered, and concentrated under reduced pressure. The residue was purified by flash column chromatography over silica (40g, Eluent: $CH_2Cl_2$/MeOH 0 to 10%). The compound was purified again over silica (40g, Eluent: $CH_2Cl_2$/MeOH 0 to 10%). The compound was purified again over silica (C18 12 g (eluent $H_2O$/MeOH 50:50 to 0:100) to give compound 182 (98 mg).

Compound 182:

$^1$H NMR (400 MHz, $CDCl_3$) δ 7.67-7.59 (m, 1H), 7.20-7.09 (m, 4H), 7.01 (d, J=3.7 Hz, 2H), 6.72 (d, J=7.8 Hz, 1H), 6.41 (brs, 1H), 6.09 (brs, 1H), 5.96 (d, J=6.4 Hz, 1H), 5.76 (d, J=7.8 Hz, 1H), 5.75 (d, J=6.4 Hz, 1H), 5.28 (s, 1H), 4.85 (d, J=13.9 Hz, 1H), 4.76-4.66 (m, 1H), 4.59 (brs, 1H), 3.89 (d, J=13.9 Hz, 1H), 3.87 (s, 3H) 2.84 (dd, J=21.5, 10.7 Hz, 1H), 2.68-2.53 (m, 1H), 2.06-1.91 (m, 2H), 1.84 (dt, J=17.5, 5.9 Hz, 1H), 1.78-1.62 (m, 1H).

434

LC/MS (method LC-oxeltis standard): Rt 3.34 min, MH+ 580

Chiral SFC (method SFC-C): Rt 1.15 min, chiral purity 100%.

Antiviral Activity

Example A

Influenza Antiviral Assay

Human lung carcinoma A549 cells (ATCC, Manassas, Va.) were plated at a density of $5 \times 10^4$ cells/mL ($10 \times 10^3$ cells/well) in assay media (Ham's F12 media supplemented with 0.3% FBS, 1% penicillin/streptomycin, 1% L-Glutamine, and 1% non-essential amino acids (all Mediatech, Manassas, Va.) and 1% DMSO (Sigma-Aldrich, St Louis, Mo.)) in white 96-well plates. Cells were infected with 250 IU/well of Influenza strain A549 A/WSN/33 (H1N1) (Virapur, San Diego Calif.) and incubated for 20 hours at 37° C., 5% CO2. The cell culture supernatant was aspirated off and 50 μL of 25 μM 2'-(4-Methylumbelliferyl)-a-D-N-acetylneuraminic acid (Sigma-Aldrich) dissolved in 33 mM MES, pH 6.5 (Emerald Biosystems, Bainbridge Island, WA) was added to the cells. After incubation for 45 min at 37° C., reactions were stopped by addition of 150 μL stop solution (100 mM glycine, pH 10.5, 25% ethanol, all Sigma-Aldrich). Fluorescence was measured with excitation and emission filters of 355 and 460 nm, respectively, on a Victor X3 multi-label plate reader (Perkin Elmer, Waltham, Mass.). Cytotoxicity of uninfected parallel cultures was determined by addition of 100 μL of CellTiter-Glo® reagent (Promega, Madison, Wis.), and incubation for 10 min at RT. Luminescence was measured on a Victor X3 multi-label plate reader.

Example B

EN PA FRET Inhibition Assay

EN PA FRET inhibition assay was performed using a 19 nucleotide synthetic oligoribonucleotide substrate: 5'-FAM-AUUUUGUUUUUAAUAUUUC-BHQ-3' (Integrated DNA Technologies, Inc., Coralville, Iowa) (SEQ. ID. NO. 1). Upon RNA cleavage, the fluorescent FAM group is released from the BHQ quencher. The PA sequence used to produce active enzyme is derived from any one of multiple influenza A virus strains (e.g., A/goose/Nanchang/3-120/01 (H3N2), A/Victoria/3/1975 (H3N2), A/Brisbane/10/2007 (H3N2), A/WSN/33 (H1N1), A/CA/4/2009 (H1N1), A/CA/5/2009 (H1N1), A/Shanghai/1/2013 (H7N9), A/Guizhou/1/2009 (H5N1)). The full length recombinant protein was expressed from a baculovirus vector in insect cells. Full length EN PA was used in this assay at an effective concentration of 1 to 10 nM, together with 50 nM FRET probe with a final volume of 20 ml cleavage buffer (20 mM Tris Ph8, 100 mM NaCl, 5% Glycerol, 10 mM 3-ME, 0.0003% Tween-20, 5 mM $MgC_2$).

Compounds described herein were added to a 384-well black polypropylene plate. Fluorescence was measured in a continuous mode up to 120 minutes with a Wallac 1420 Victor$^3$V multilabel counter (PerkinElmer Life Sciences, Shelton, Conn.) (excitation 485 nm; emission 535 nm). Measured $IC_{50}$ is defined as the concentration at which fluorescence is 50% that of the uninhibited control (DMSO). $IC_{50}$ was calculated by fitting the data to the sigmoidal equation Y=% Min+(% Max−% Min)/(1+X/$IC_{50}$), where Y corresponds to the percent relative enzyme activity, Max is the maximum enzyme activity in the presence of DMSO, Min is the inhibited activity at saturating concentration of compound, and X corresponds to the compound concentration. The IC$_{50}$ values were derived from the mean of a minimum of two independent experiments.
Table 1A shows the antiviral data obtained against influenza A H1N1 strain and cellular toxicity.
TABLE 1A
| | Antiviral activity of selected compounds (cell based and enzymatic assays) | | |
|---|---|---|---|
| Compound number | A549_A(H1N1) EC$_{50}$ (uM) | CC$_{50}$ (μM) | FRET__IC$_{50}$ (uM |
| 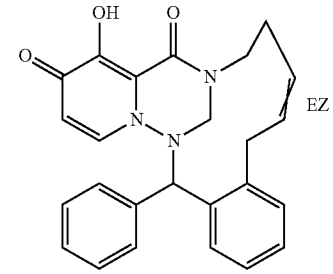 [SMILES: O=C1c2c(O)c(=O)ccn2N2CN1CCC=CCc1ccccc1C2c1ccccc1]<br>1 | 0.043 | >2 | 0.069 |
| 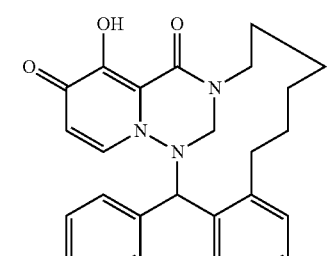<br>2 | 0.354 | >20 | 0.106 |
| 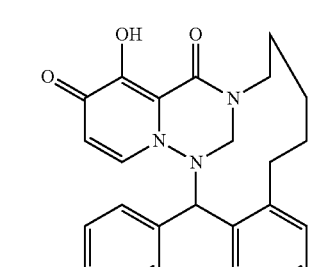<br>4 | 0.048 | >4 | 0.049 |
| 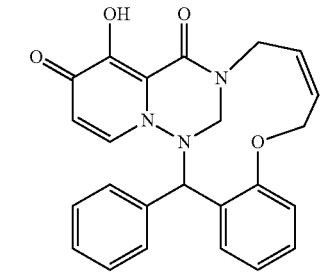 [SMILES: O=C1c2c(O)c(=O)ccn2N2CN1C/C=C\COc1ccccc1C2c1ccccc1]<br>5 | 0.026 | >2 | 0.114 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 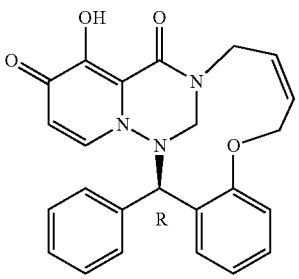 5A | 0.008 | >2 | 0.050 |
| 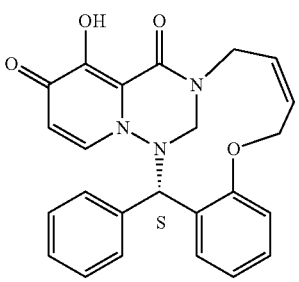 5B | >1 | >2 | 0.311 |
| 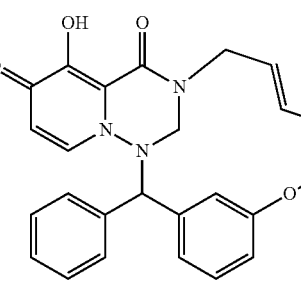 6 | 6.149 | >20 | 0.278 |
| 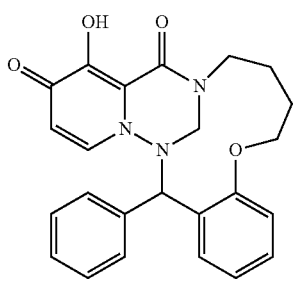 [SMILES: O=C1c2c(O)c(=O)ccn2N2CN1CCCCOc1ccccc1C2c1ccccc1] 8 | 0.059 | >2 | 0.048 |
| 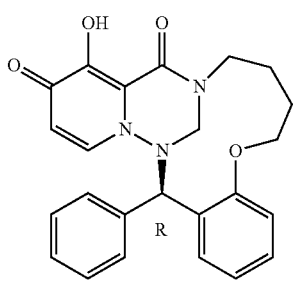 8A | 0.013 | >2 | 0.038 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 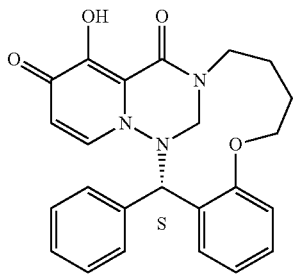 8B | 4.129 | >2 | 0.973 |
| 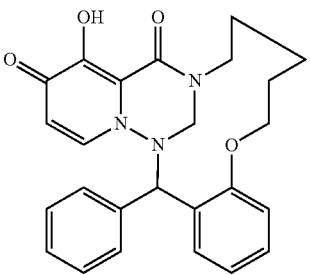 9 | 0.453 | >2 | 0.076 |
| 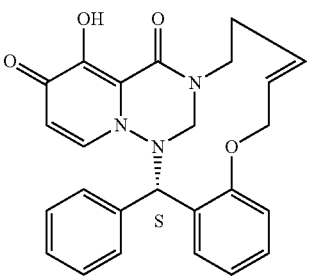 10A | >1 | >2 | 0.179 |
| 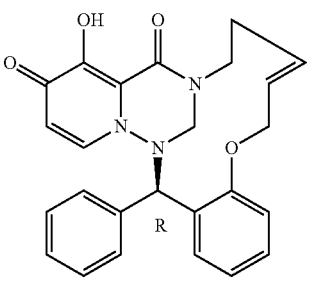 10B | 0.013 | >2 | 0.047 |
| 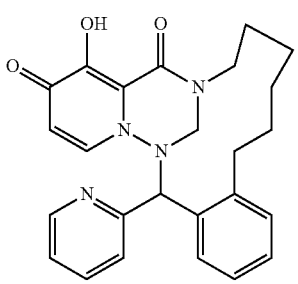 [SMILES: O=C1c2c(O)c(=O)ccn2N2CN1CCCCCCc1ccccc1C2c1ccccn1] 11 | 0.363 | >2 | 0.100 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 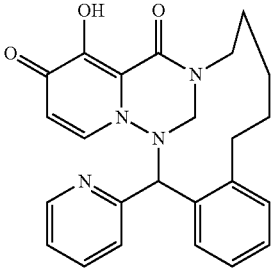 [SMILES: O=C1c2c(O)c(=O)ccn2N2CN1CCCCCc1ccccc1C2c1ccccn1] 12 | 0.086 | >2 | 0.049 |
| 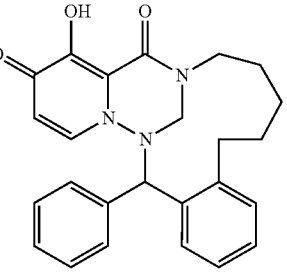 13 | 0.019 | >2 | 0.046 |
| 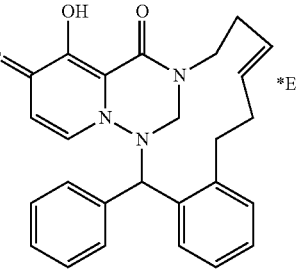 14 | 0.048 | >4 | 0.067 |
| 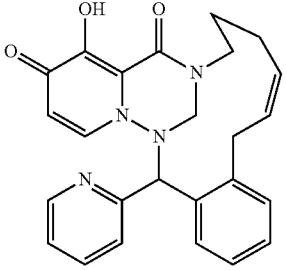 [SMILES: O=C1c2c(O)c(=O)ccn2N2CN1CCC/C=C\Cc1ccccc1C2c1ccccn1] 15 | 0.635 | >20 | 0.118 |
| 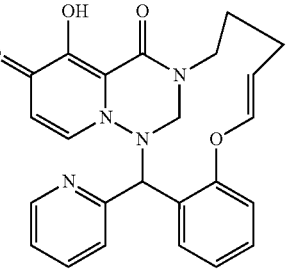 16 | 0.142 | >20 | 0.047 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 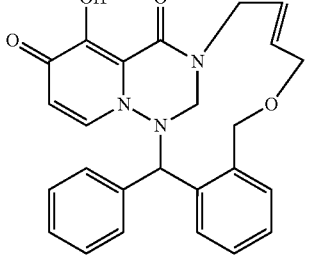 17 | 0.077 | >20 | 0.098 |
| 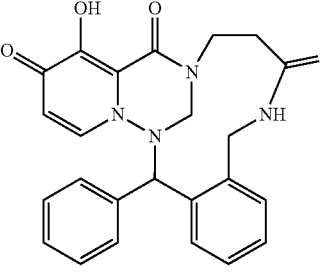 18 | 7.907 | >200 | 0.231 |
| 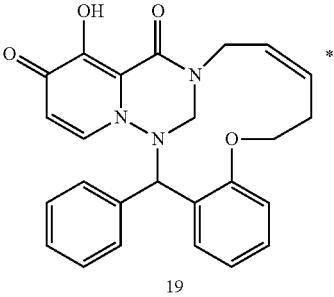 19 | 0.260 | >2 | 0.093 |
| 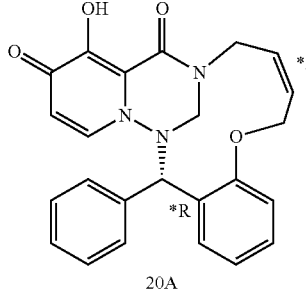 20A | 0.093 | >2 | 0.030 |
| 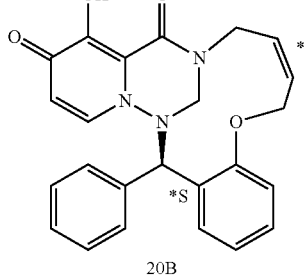 20B | 10.024 | >2 | 0.686 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 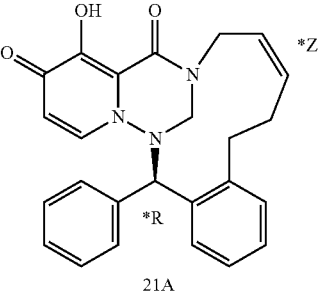 21A | 0.005 | >1 | 0.036 |
| 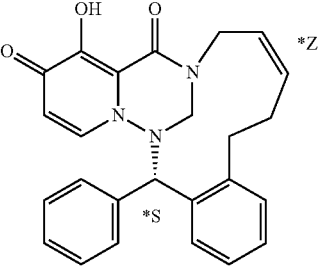 [SMILES: O=C1c2c(O)c(=O)ccn2N2CN1C/C=C\CCc1ccccc1[C@@H]2c1ccccc1] 21B | 0.815 | >1 | 0.128 |
| 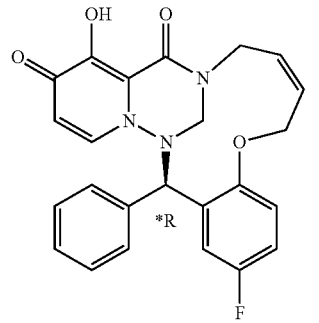 [SMILES: O=C1c2c(O)c(=O)ccn2N2CN1C/C=C\COc1ccc(F)cc1[C@H]2c1ccccc1] 22A | 9.540 | >1 | 0.322 |
| 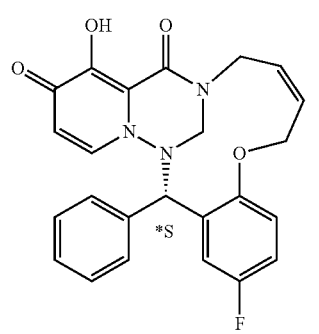 [SMILES: O=C1c2c(O)c(=O)ccn2N2CN1C/C=C\COc1ccc(F)cc1[C@@H]2c1ccccc1] 22B | 0.012 | >1 | 0.043 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 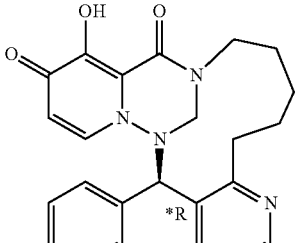 23A | 54.987 | >10 | 2.363 |
| 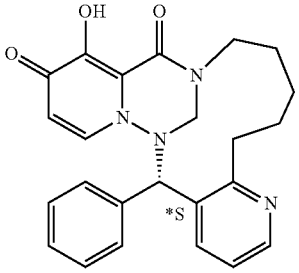 [SMILES: O=C1c2c(O)c(=O)ccn2N2CN1CCCCCc1ncccc1[C@@H]2c1ccccc1] 23B | 12.183 | >1 | 0.240 |
| 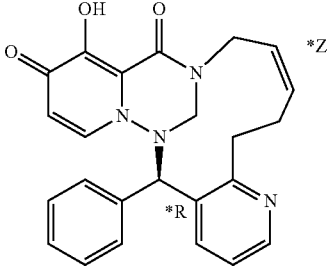 [SMILES: O=C1c2c(O)c(=O)ccn2N2CN1C/C=C\CCc1ncccc1[C@H]2c1ccccc1] 24A | 39.591 | >10 | 1.822 |
| 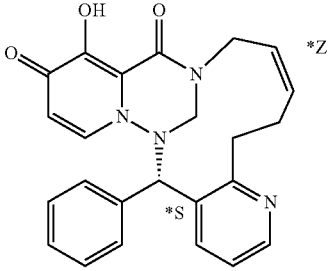 [SMILES: O=C1c2c(O)c(=O)ccn2N2CN1C/C=C\CCc1ncccc1[C@@H]2c1ccccc1] 24B | 1.526 | >1 | 0.233 |
| 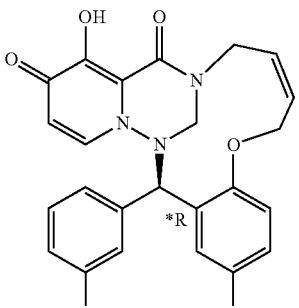 25A | 9.799 | >2 | 0.318 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 25B | 0.011 | >2 | 0.041 |
| 26A | 0.394 | >2 | 0.081 |
| 26B | 40.095 | >4 | 0.606 |
| 27A | 0.094 | >2 | 0.052 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM |
|---|---|---|---|
| 27B | 45.736 | >20 | 1.874 |
| 28A | 5.95 | >20 | 5.78 |
| 28B | 0.006 | >0.4 | 0.034 |
| 29AA | >3 | >2 | 1.437 |
| 29BB | 0.008 | >2 | 0.071 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 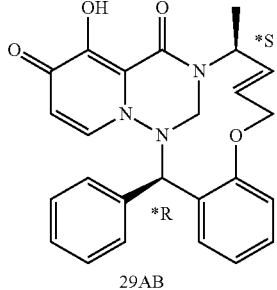 29AB | 0.0057 | >0.2 | 0.032 |
| 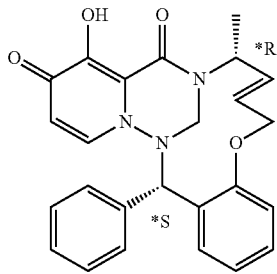 [SMILES: C[C@@H]1/C=C/COc2ccccc2[C@H](c2ccccc2)N2CN1C(=O)c1c(O)c(=O)ccn12] 29BA | 1.714 | 83.06 | 2.213 |
| 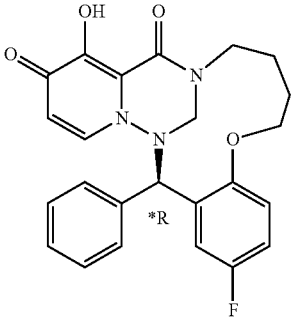 [SMILES: O=C1c2c(O)c(=O)ccn2N2CN1CCCCOc1ccc(F)cc1[C@H]2c1ccccc1] 30A | >1 | >2 | 3.114 |
| 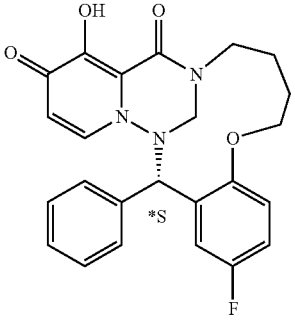 [SMILES: O=C1c2c(O)c(=O)ccn2N2CN1CCCCOc1ccc(F)cc1[C@@H]2c1ccccc1] 30B | 0.015 | >2 | 0.030 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 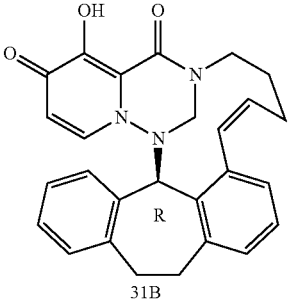 31B | 0.004 | >2 | 0.007 |
| 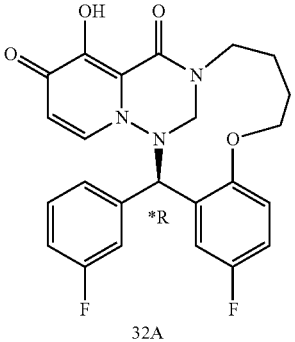 32A | >1 | >2 | 2.320 |
| 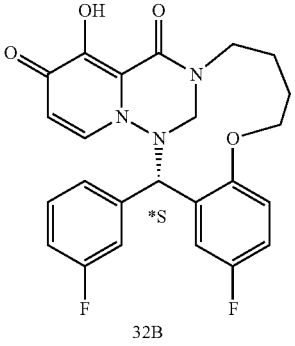 32B | 0.025 | >2 | 0.058 |
| 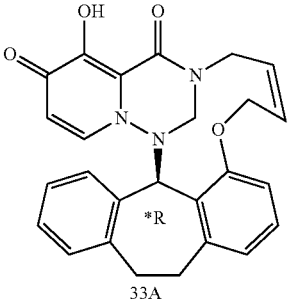 33A | >1 | >2 | 0.373 |

TABLE 1A-continued

Antiviral activity of selected compounds (cell based and enzymatic assays)

| Compound number | A549_A(H1N1) EC$_{50}$ (uM) | CC$_{50}$ (µM) | FRET__IC$_{50}$ (uM |
|---|---|---|---|
| 33B | 0.015 | >2 | 0.018 |
| 34A | 0.059 | >2 | 0.037 |
| 34B | >1 | >2 | 1.048 |
| 35A | 0.069 | >2 | 0.039 |
| 35B | >1 | >2 | 0.782 |

TABLE 1A-continued
Antiviral activity of selected compounds (cell based and enzymatic assays)
| Compound number | A549_A(H1N1) EC$_{50}$ (uM) | CC$_{50}$ (μM) | FRET_IC$_{50}$ (uM) |
|---|---|---|---|
| 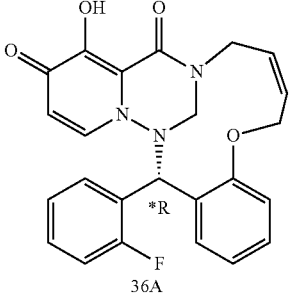 36A | 0.015 | >2 | 0.035 |
| 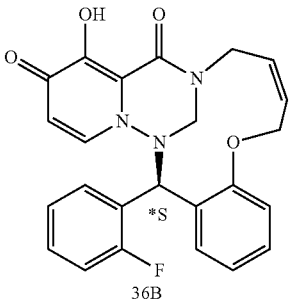 36B | 0.815 | >2 | 0.472 |
| 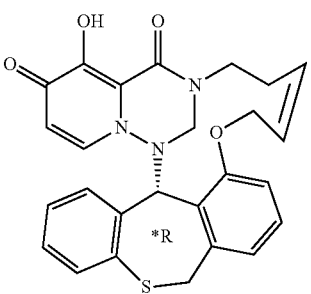 37A | 12.200 | >2 | 2.931 |
| 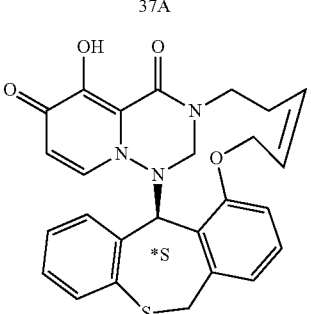 37B | 0.004 | >0.2 | 0.024 |
| 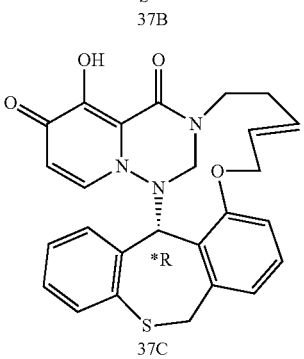 37C | >1 | >2 | ND |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 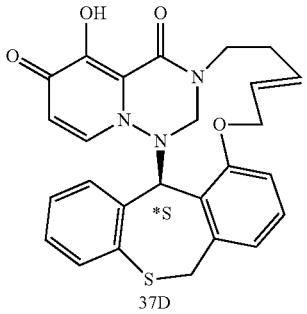 37D | 0.001 | >0.2 | ND |
| 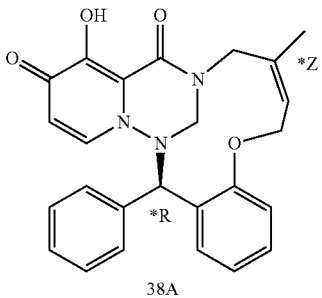 38A | >1 | >2 | 2.332 |
| 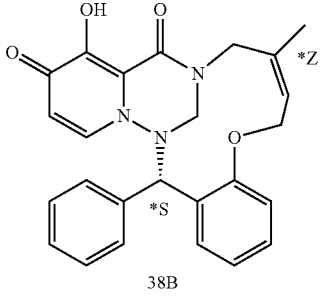 38B | 0.026 | >2 | 0.058 |
| 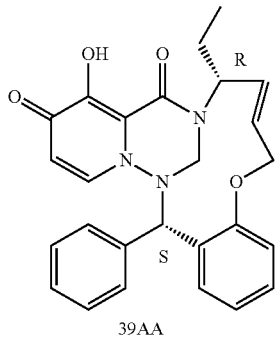 39AA | >1 | >2 | 37.432 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM |
| --- | --- | --- | --- |
| 39BB | 0.007 | >2 | 0.065 |
| 39BA | 0.006 | >0.2 | 0.049 |
| 39AB | >1 | >2 | 25.0 |
| 40A | 0.030 | >2 | 0.027 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 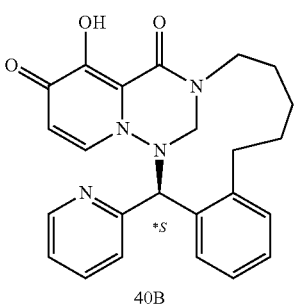 40B | >1 | >2 | 0.937 |
| 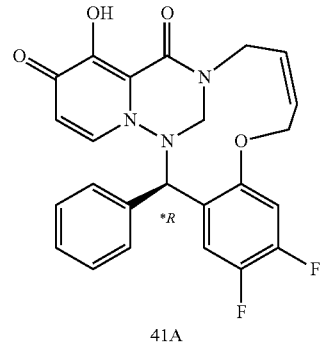 41A | 0.294 | >2 | 0.263 |
| 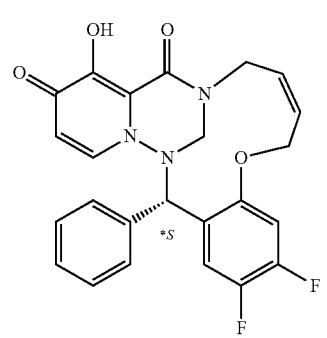 41B | 0.006 | >2 | 0.031 |
| 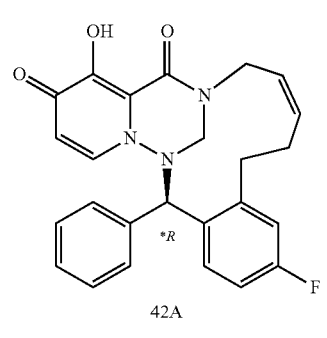 42A | >1 | >2 | 0.548 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 42B | 0.006 | >2 | 0.018 |
| 43A | 0.022 | >2 | 0.024 |
| 43B | >1 | >2 | 1.319 |
| 44A | >0.1 | >0.2 | 0.037 |
| 44B | >10 | >20 | 8.846 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 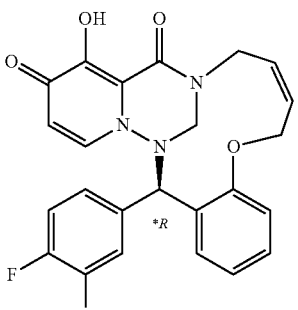 45A | >1 | >2 | 0.681 |
| 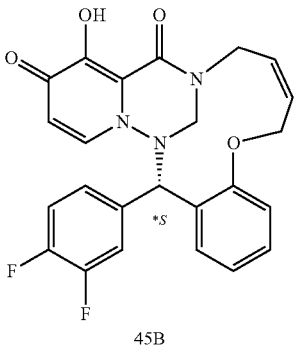 45B | 0.014 | >0.2 | 0.023 |
| 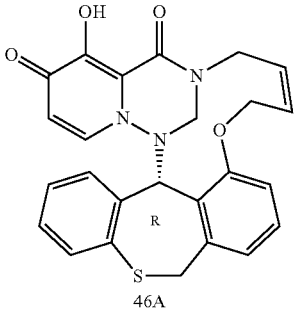 46A | 0.064 | >2 | 0.221 |
| 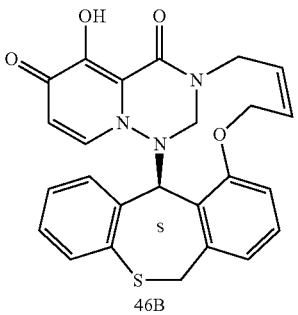 46B | 0.003 | >0.1 | 0.003 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 46C | 0.33 | >2 | 0.21 |
| 46D | 0.001 | >0.2 | 0.011 |
| 47A | >1 | >2 | 1.511 |
| 47B | 0.015 | >0.2 | 0.029 |
| 48 | 0.032 | >2 | 0.052 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 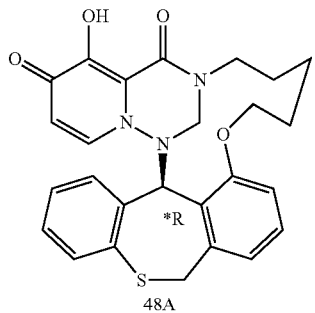 48A | >1 | >2 | 1.63 |
| 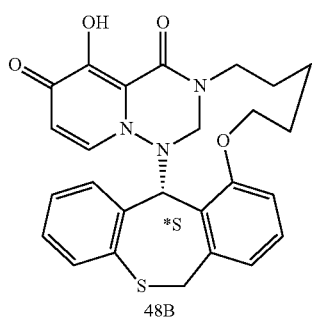 48B | 0.027 | >2 | 0.021 |
| 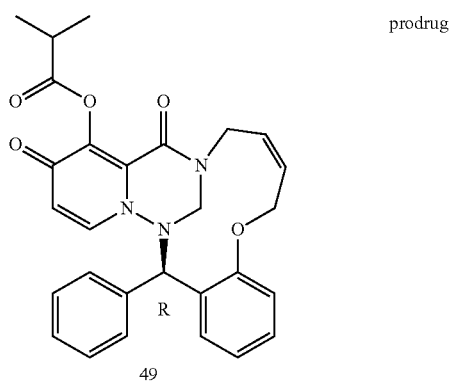 49 | prodrug | | |
| 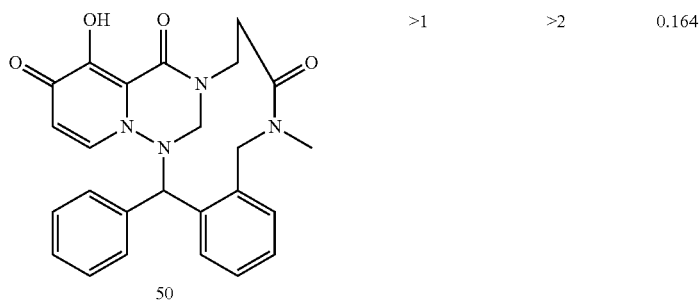 50 | >1 | >2 | 0.164 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 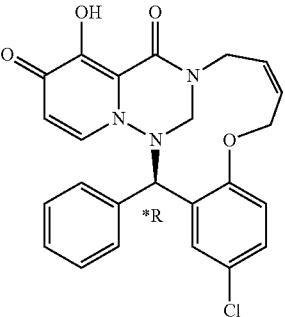 51A | >1 | >2 | 2.56 |
| 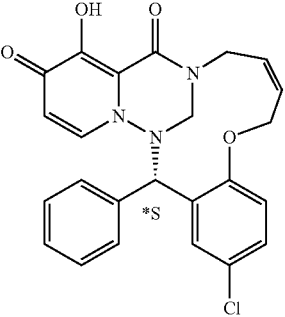 51B | 0.010 | >2 | 0.053 |
| 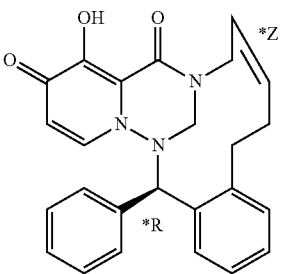 52A | >1 | >2 | 0.653 |
| 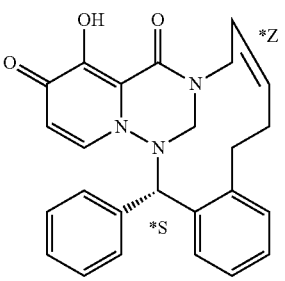 52B | 0.084 | >2 | 0.040 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 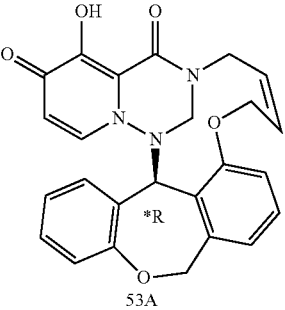 53A | 0.034 | >2 | 0.025 |
| 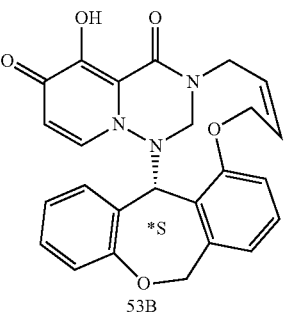 53B | >1 | >2 | 54.178 |
| 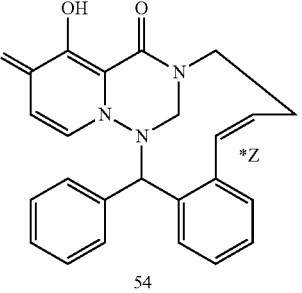 54 | 0.117 | >20 | 0.012 |
| 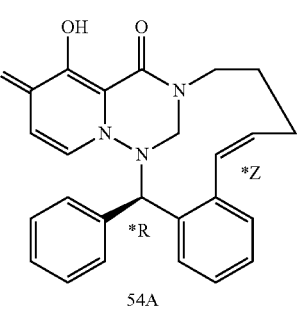 54A | >1 | >2 | 0.266 |
| 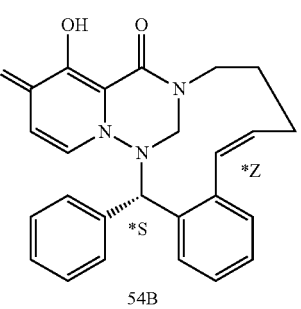 54B | 0.033 | >2 | 0.006 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 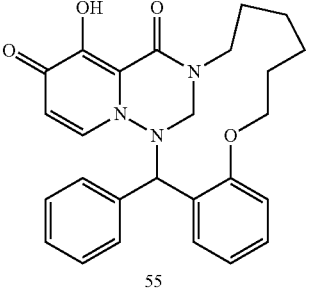 55 | 0.880 | >2 | 0.096 |
| 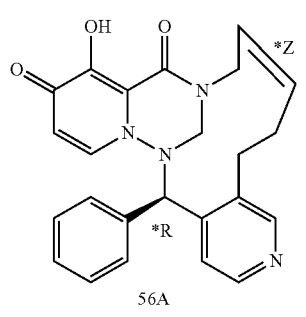 56A | >1 | >2 | 2.015 |
| 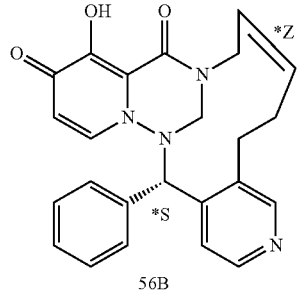 56B | 0.161 | >2 | 0.125 |
| 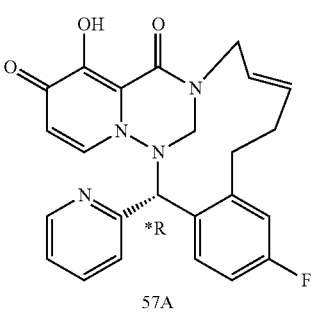 57A | 0.032 | >2 | 0.023 |
| 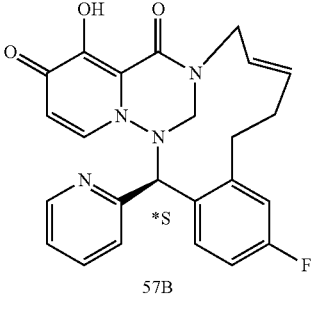 57B | >1 | >2 | 11.447 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 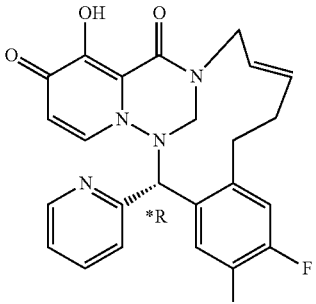 58A | 0.044 | >2 | 0.049 |
| 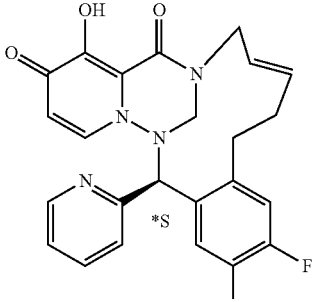 58B | >1 | >2 | 12.233 |
| 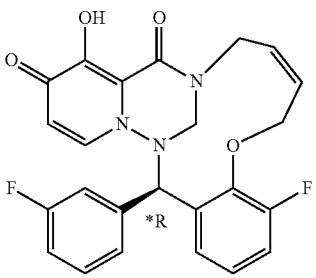 59A | 0.005 | | 0.007 |
| 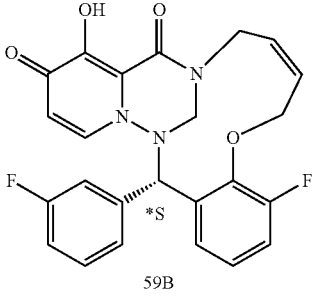 59B | 0.497 | >2 | 0.207 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 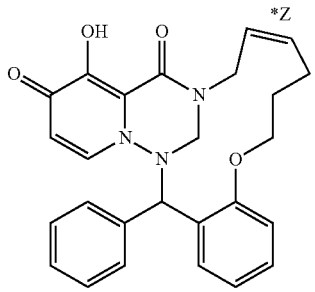 60 | >1 | >2 | 0.102 |
| 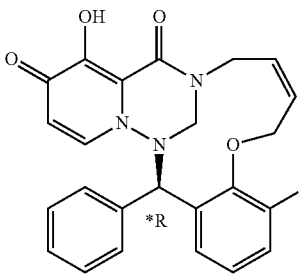 61A | 0.005 | >2 | 0.008 |
| 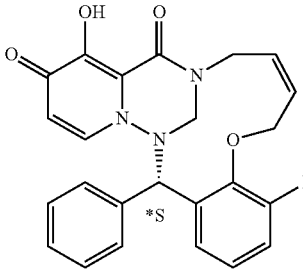 61B | 0.155 | >2 | 0.125 |
| 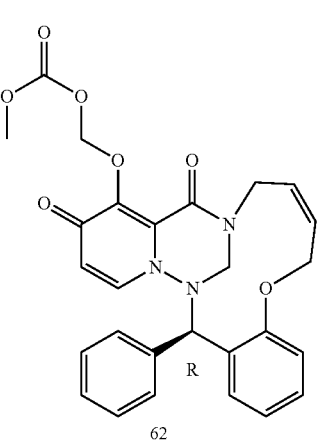 62 | prodrug | | |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 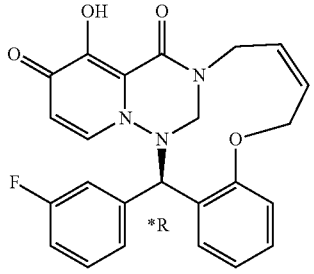 63A | >1 | >2 | 0.398 |
| 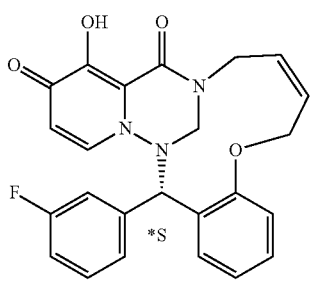 63B | 0.013 | >2 | 0.024 |
| 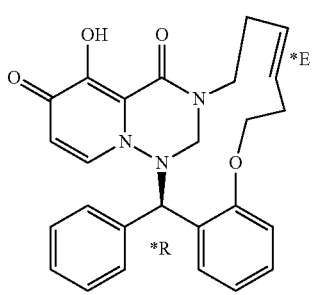 65A | >5 | >10 | 1.426 |
| 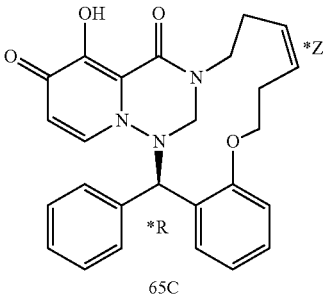 65C | 7.889 | >20 | 3.043 |
| 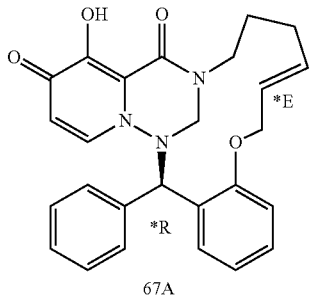 67A | >1 | >2 | 5.706 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 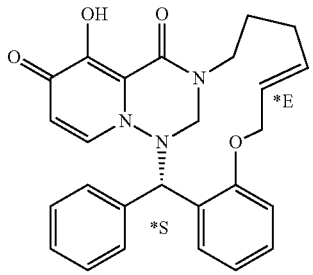 67B | >1 | >2 | 0.102 |
| 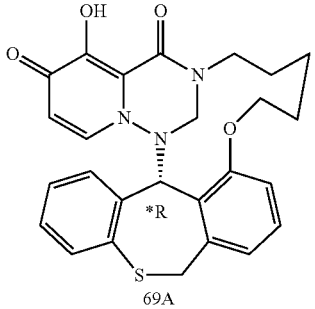 69A | >1 | >2 | 1.63 |
| 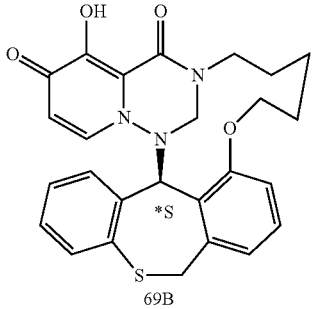 69B | 0.027 | >2 | 0.021 |
| 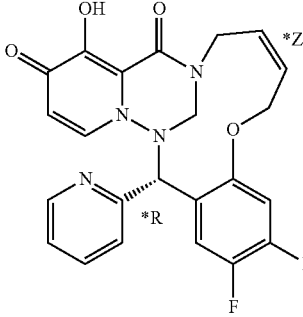 70A | >10 | >20 | 35.364 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM |
|---|---|---|---|
| 70B | 0.032 | >0.2 | 0.054 |
| 71A | 0.034 | >0.2 | 0.027 |
| 71B | 7.690 | >20 | 1.582 |
| 72A | >1 | >2 | 2.570 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 72B | 0.008 | >2 | 0.028 |
| 65B | 0.047 | >2 | 0.062 |
| 65D | 0.066 | >2 | 0.097 |
| 73 | 0.016 | >2 | 0.008 |
| 74A | >1 | >2 | 0.825 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 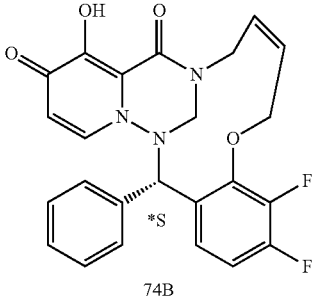 74B | 0.002 | >0.2 | 0.006 |
| 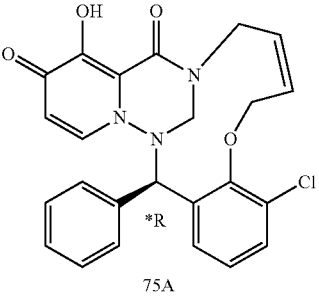 75A | 0.269 | >2 | 0.253 |
| 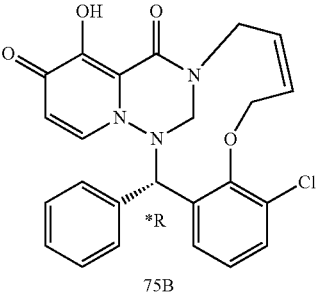 75B | 0.003 | >0.2 | 0.011 |
| 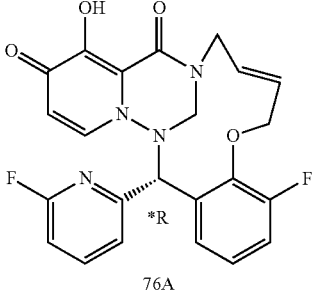 76A | 3.589 | 43.87 | 0.346 |
| 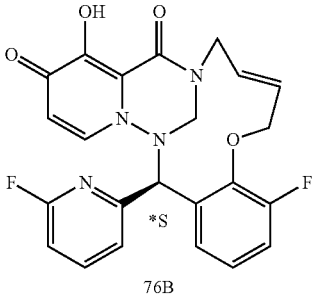 76B | 0.006 | >0.2 | 0.009 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 77A | 5.28 | 33.17 | 0.361 |
| 77B | 0.012 | >1 | 0.028 |
| 78A | 0.019 | >1 | 0.044 |
| 78B | 6.430 | 61.62 | 0.817 |
| 79A | >0.5 | >1 | 2.511 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 79B 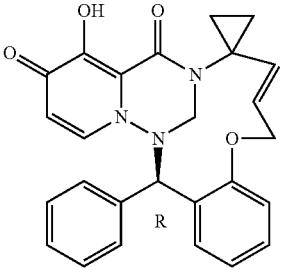 | 0.006 | >1 | 0.028 |
| 80AA 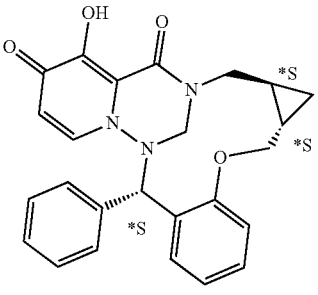 | 0.167 | >1 | 0.077 |
| 80BB 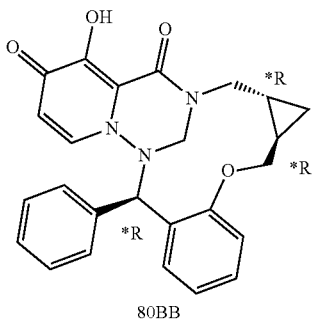 | >0.5 | >1 | 0.670 |
| 80AB 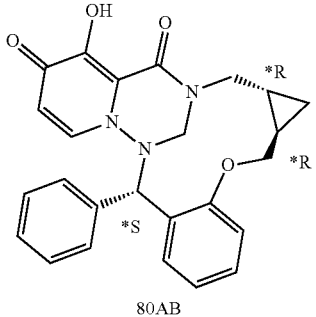 | 0.066 | >10 | 0.028 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 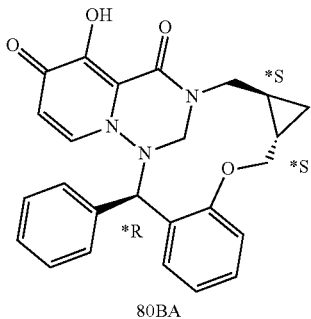 80BA | >0.5 | >1 | 0.367 |
| 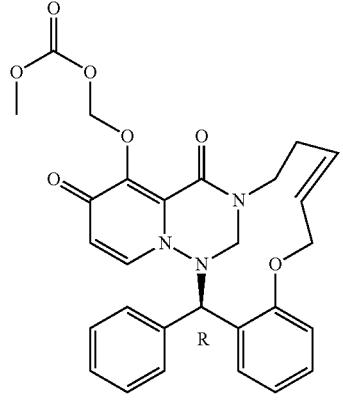 81 | prodrug | | |
| 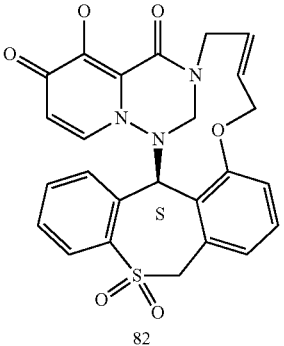 82 | 0.071 | >1 | 0.014 |
| 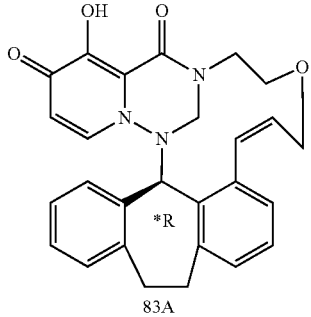 83A | >0.5 | >1 | 0.280 |

TABLE 1A-continued
| | Antiviral activity of selected compounds (cell based and enzymatic assays) | | |
|---|---|---|---|
| Compound number | A549_A(H1N1) EC$_{50}$ (uM) | CC$_{50}$ (μM) | FRET__IC$_{50}$ (uM |
| 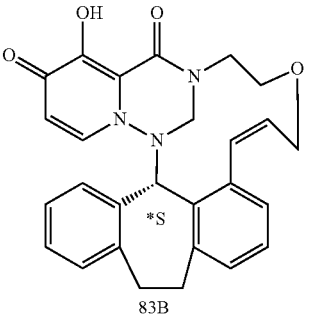 83B | 0.006 | >0.2 | 0.017 |
| 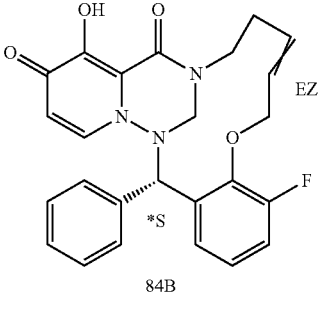 84B | 0.005 | >0.2 | 0.017 |
| 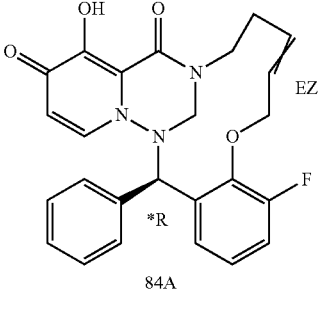 84A | ND | | 0.428 |
| 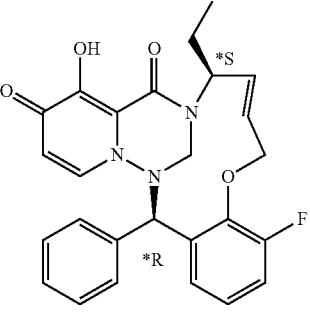 85AA | 0.003 | >0.2 | 0.017 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 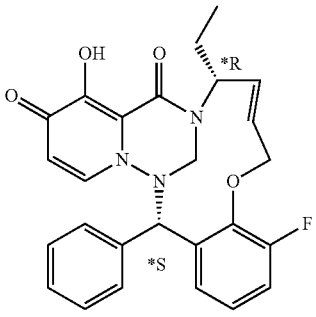 85BB | ND | ND | 0.902 |
| 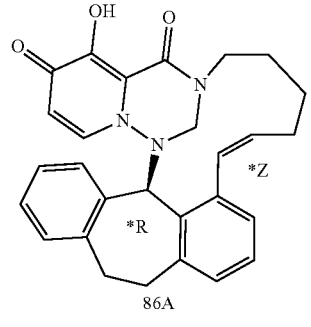 86A | ND | ND | 6.411 |
| 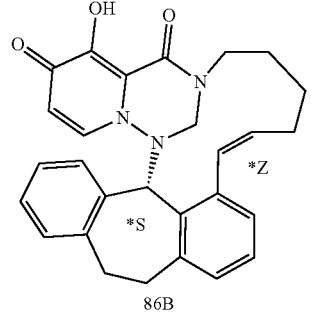 86B | 0.027 | >2 | 0.007 |
| 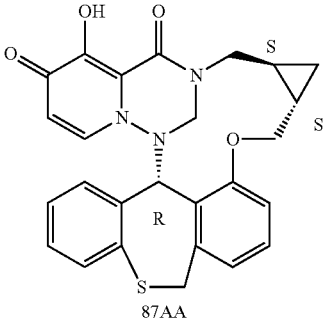 87AA | ND | ND | 2.375 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 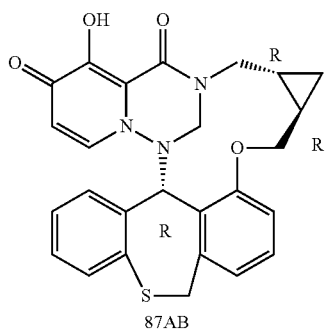 87AB | ND | ND | >100 |
| 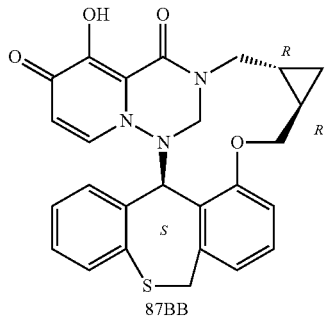 87BB | 0.004 | >0.2 | 0.014 |
| 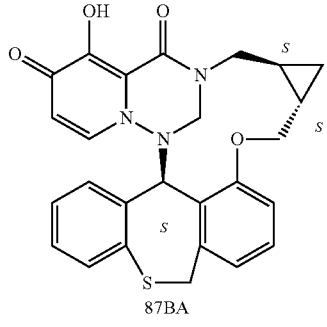 87BA | 0.004 | >0.2 | 0.017 |
| 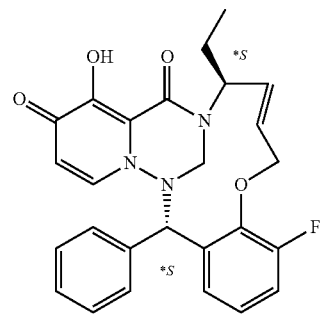 85BA | >0.5 | >1 | >100 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM |
|---|---|---|---|
| 88A | >0.5 | >1 | 2.423 |
| 88B | 0.001 | >0.2 | 0.006 |
| 85AB | 0.002 | >0.2 | 0.008 |
| 89AA | 10.820 | 39.28 | >100 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 89BB | 0.003 | >0.2 | 0.014 |
| 88C | >0.5 | >1 | 1.628 |
| 88D | 0.001 | >0.1 | 0.006 |
| 91A | 0.003 | >1 | 0.009 |

TABLE 1A-continued

Antiviral activity of selected compounds (cell based and enzymatic assays)

| Compound number | A549_A(H1N1) EC$_{50}$ (uM) | CC$_{50}$ (µM) | FRET__IC$_{50}$ (uM |
|---|---|---|---|
| 91B | >0.5 | >1 | 0.617 |
| 92AA | 0.108 | >1 | 0.340 |
| 92BB | 0.0015 | >0.1 | 0.008 |
| 93A | >0.5 | >1 | 79.912 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 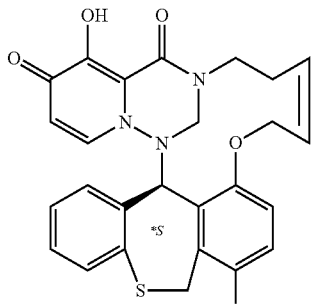 93B | 0.0022 | >0.2 | 0.022 |
| 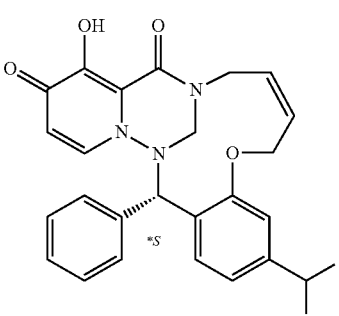 94A | 0.0257 | >1 | 0.031 |
| 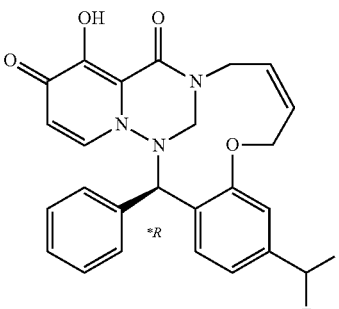 94B | >0.5 | >1 | 5.881 |
| 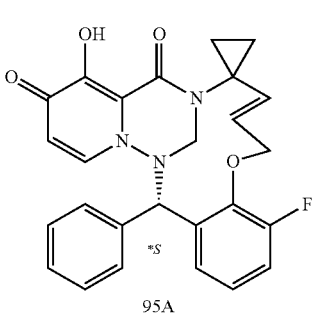 95A | >0.5 | >1 | 46.702 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 95B | 0.0017 | >1 | 0.010 |
| 96A | 0.0019 | >0.2 | 0.013 |
| 96B | >0.5 | >1 | 0.606 |
| 97AA | 0.0058 | >1 | 0.020 |
| 97BB | >0.5 | >1 | 1.726 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM |
|---|---|---|---|
| 97BA | >0.5 | >1 | 37.160 |
| 97AB | 0.0056 | >1 | 0.023 |
| 98AA | >0.5 | >1 | 66.379 |
| 98BB | 0.0021 | >1 | 0.017 |

TABLE 1A-continued
| Antiviral activity of selected compounds (cell based and enzymatic assays) | | | |
|---|---|---|---|
| Compound number | A549_A(H1N1) EC$_{50}$ (uM) | CC$_{50}$ (μM) | FRET__IC$_{50}$ (uM) |
| 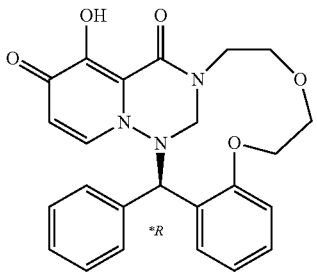 99A | >0.5 | >1 | 0.376 |
| 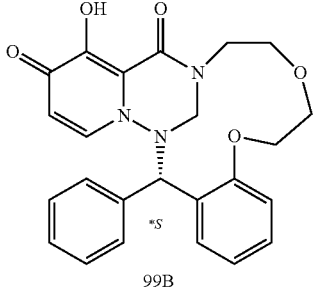 99B | 0.1673 | >1 | 0.102 |
| 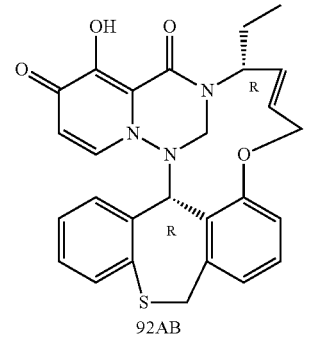 92AB | >0.5 | >1 | 5.779 |
| 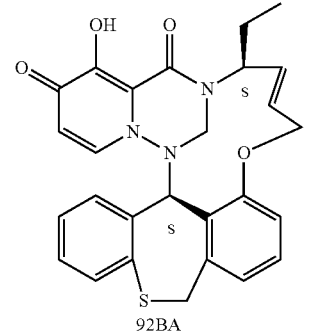 92BA | 0.0007 | ND | 0.011 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 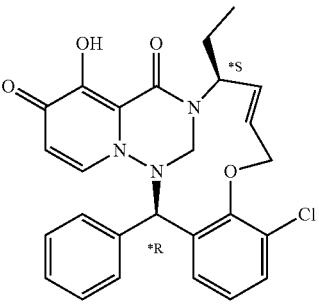 98BA | 0.830 | 26.45 | 9.782 |
| 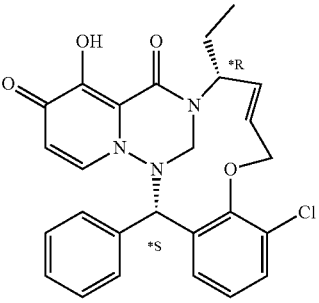 98AB | 0.0022 | >0.2 | 0.012 |
| 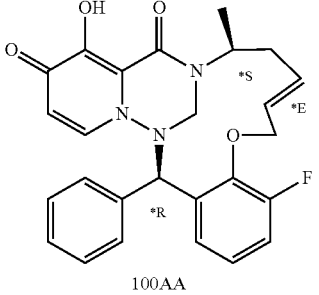 100AA | 0.0017 | >0.1 | 0.003 |
| 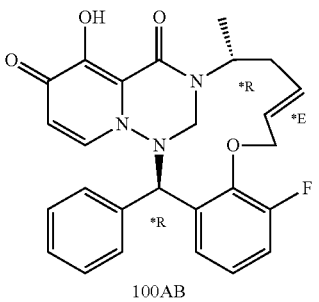 100AB | 0.0021 | >0.2 | 0.010 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 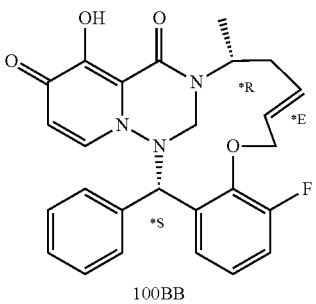 100BB | 1.156 | 32.52 | 2.0 |
| 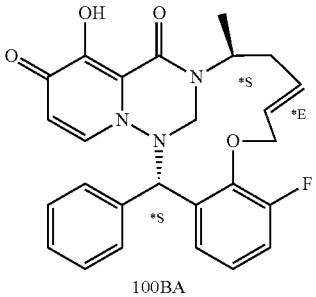 100BA | 5.214 | 40.21 | 10.267 |
| 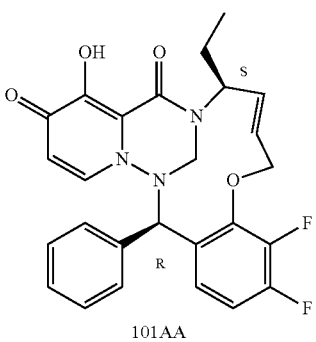 101AA | 0.0007 | >0.1 | 0.005 |
| 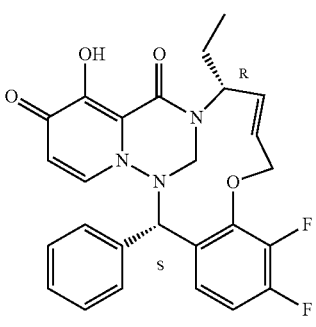 101BB | 5.031 | 29.89 | >100 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 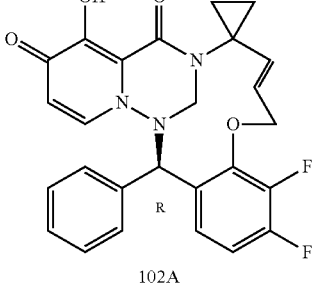 102A | 0.0009 | >0.1 | 0.004 |
| 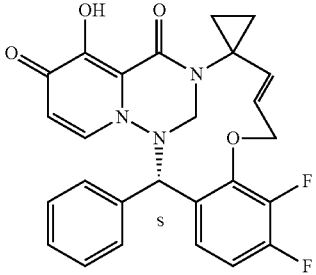 102B | 3.356 | 33.90 | >100 |
| 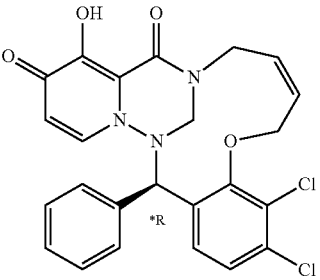 103A | >0.1 | >0.2 | 71.210 |
| 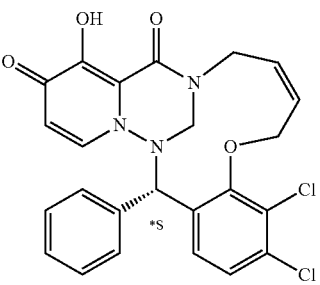 103B | 0.0031 | >0.2 | 0.009 |
| 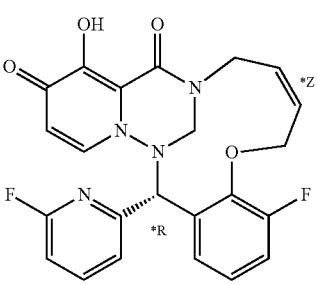 104A | 0.0107 | >0.2 | 0.012 |

TABLE 1A-continued
| Antiviral activity of selected compounds (cell based and enzymatic assays) | | | |
|---|---|---|---|
| Compound number | A549_A(H1N1) $EC_{50}$ (uM) | $CC_{50}$ (μM) | FRET__$IC_{50}$ (uM) |
| 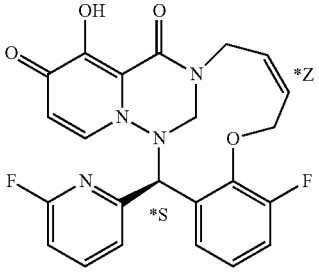 104B | >0.1 | >0.2 | 1.754 |
| 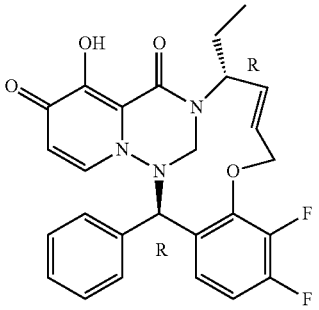 101AB | 0.0013 | >0.2 | 0.006 |
| 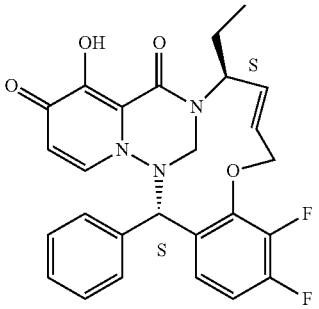 101BA | >0.1 | >0.2 | 0.671 |
| 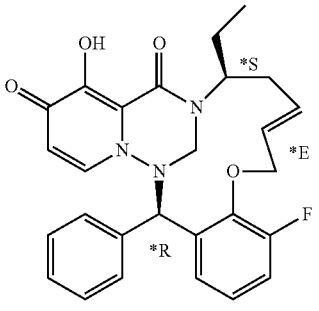 105AA | 0.0022 | >0.2 | 0.010 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 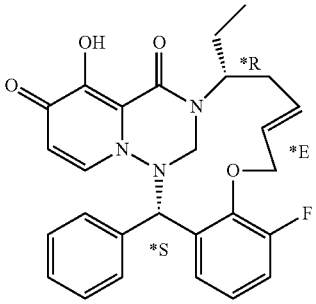 105BB | >0.1 | >0.2 | 1.724 |
| 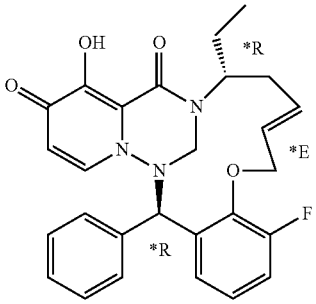 105AB | 0.0019 | >0.2 | 0.010 |
| 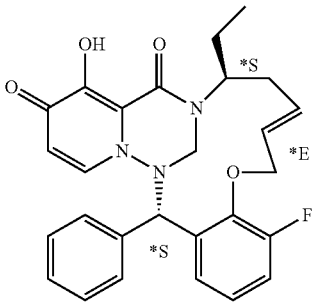 105BA | >0.1 | >0.2 | 0.984 |
| 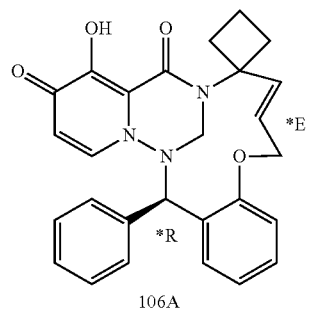 106A | 0.0035 | >0.2 | 0.032 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 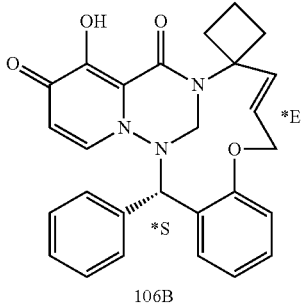 106B | >0.1 | >0.2 | >100 |
| 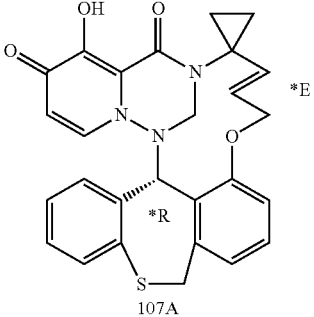 107A | >0.1 | >0.2 | 74.981 |
| 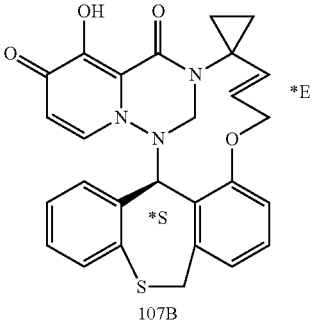 107B | 0.001 | >0.1 | 0.006 |
| 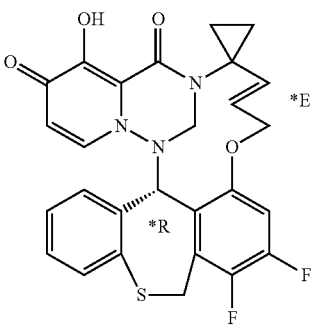 108A | 0.8395 | 22.60 | 3.733 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 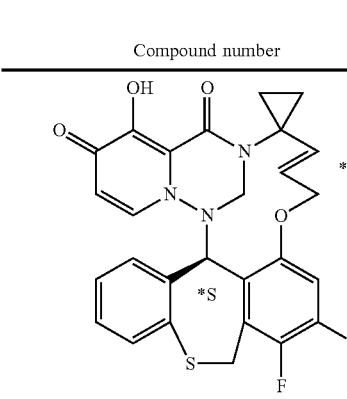 108B | 0.0002 | >0.05 | 0.002 |
| 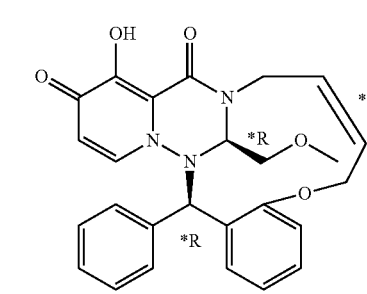 109A | 0.0066 | >0.2 | 0.033 |
| 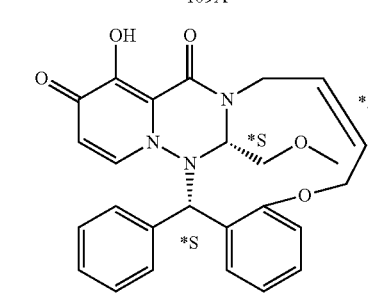 109B | >0.1 | >0.2 | 0.68 |
| 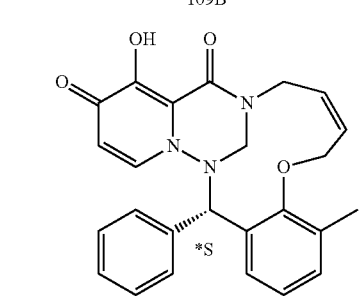 110A | 0.0064 | >0.2 | 0.024 |
| 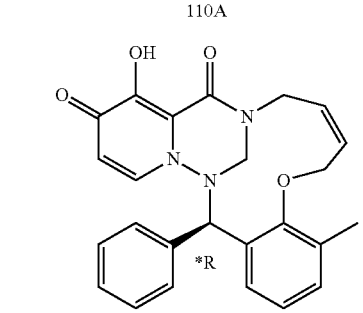 110B | >0.1 | >0.2 | 1.3 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 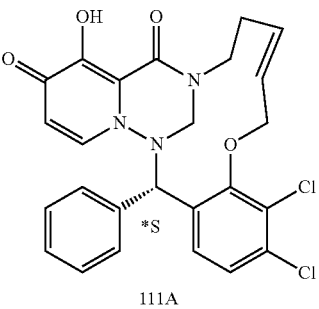 111A | 0.0043 | >0.2 | 0.01 |
| 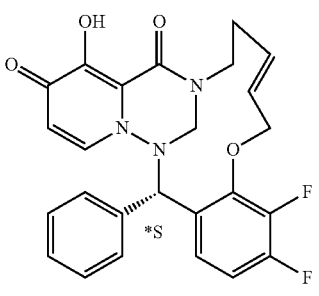 112A | 0.0038 | >0.2 | 0.009 |
| 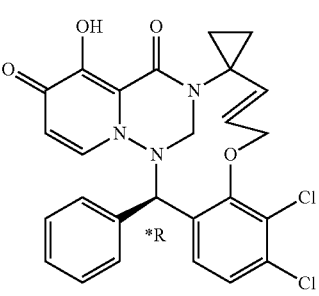 113A | >0.1 | >0.2 | 3.84 |
| 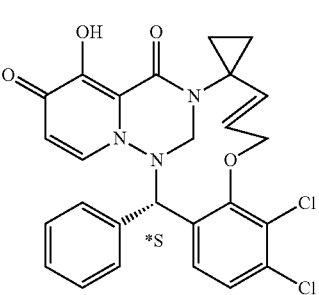 113B | 0.002 | >0.2 | 0.008 |
| 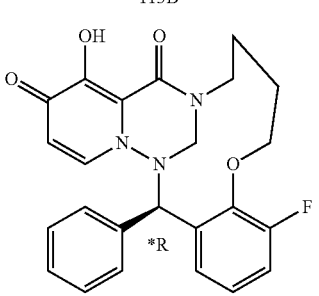 114A | 0.007 | >0.2 | 0.004 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 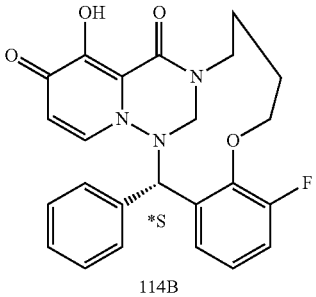 114B | >0.1 | >0.2 | 0.045 |
| 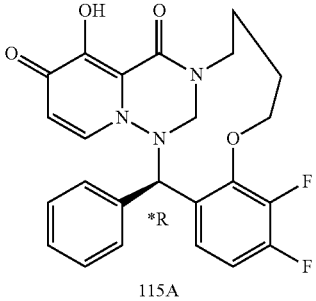 115A | >0.1 | >0.2 | 0.64 |
| 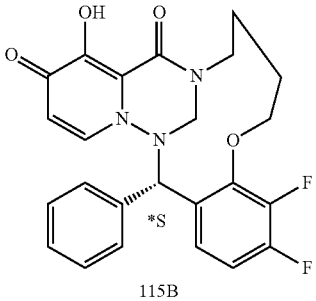 115B | 0.0044 | >0.2 | 0.083 |
| 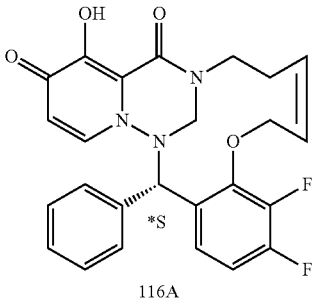 116A | 0.014 | >0.2 | 0.004 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 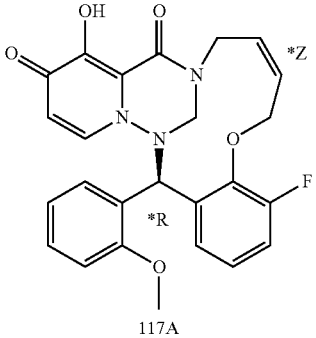 117A | 0.029 | >0.2 | 0.004 |
| 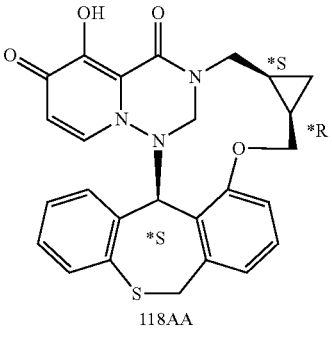 118AA | 0.0062 | >0.2 | 0.020 |
| 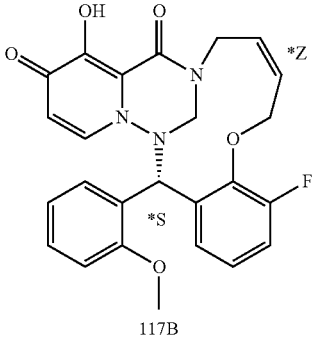 117B | >0.1 | >0.2 | 0.2 |
| 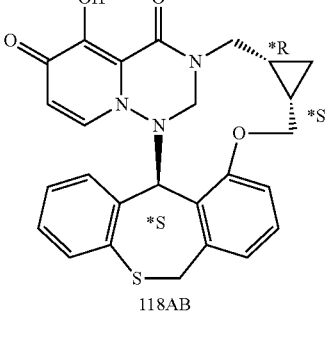 118AB | 0.010 | >0.2 | 0.012 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 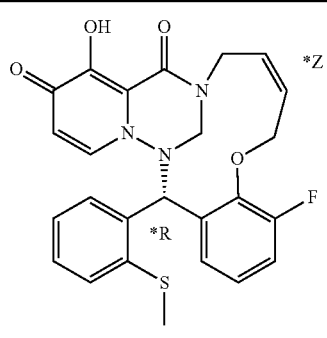 119A | >0.1 | >0.2 | 0.070 |
| 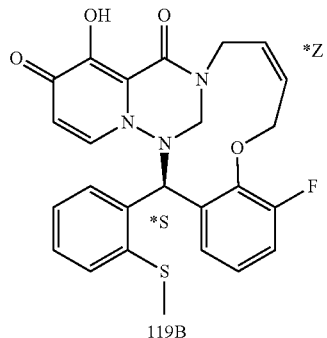 119B | 0.022 | >0.2 | 0.002 |
| 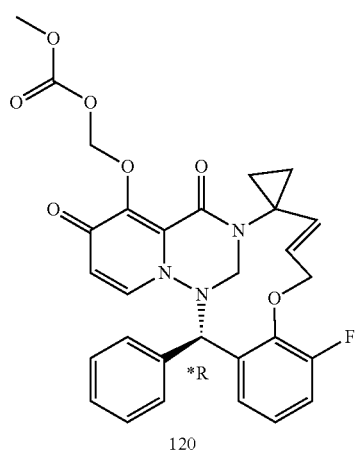 120 | prodrug | | |
| 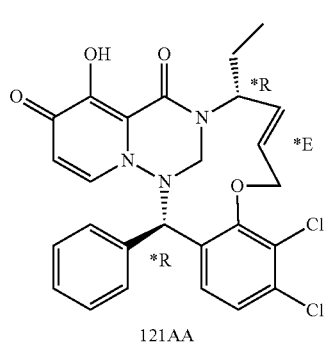 121AA | 0.0035 | >0.2 | 0.011 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM |
|---|---|---|---|
| 121AB | >0.1 | >0.2 | >100 |
| 121BA | 0.0028 | >0.2 | 0.011 |
| 121BB | 0.060 | >0.2 | 1.29 |
| 122 | >0.1 | >0.2 | 10 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 123A | 0.0029 | >0.2 | 0.0004 |
| 123B | >0.1 | >0.2 | >100 |
| 124AA | >0.1 | >0.2 | ND |
| 124BB | 0.0053 | >0.2 | 0.018 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 125AA | 0.051 | >0.2 | 0.016 |
| 125BA | >0.1 | >0.2 | 0.18 |
| 125BB | >0.1 | >0.2 | 3.41 |
| 125AB | 0.024 | >0.2 | 0.0096 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 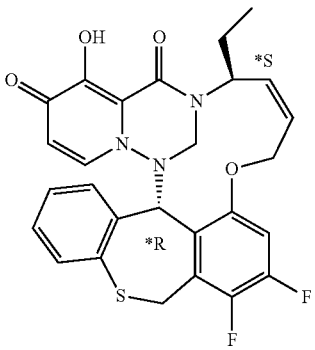 126AA | >0.1 | >0.2 | >50 |
| 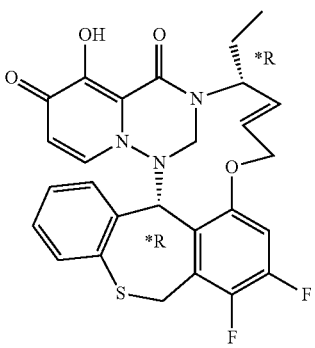 126AB | >0.1 | >0.2 | 3.15 |
| 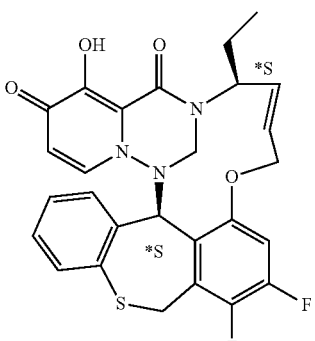 126BA | 0.00023 | >0.05 | 0.0034 |
| 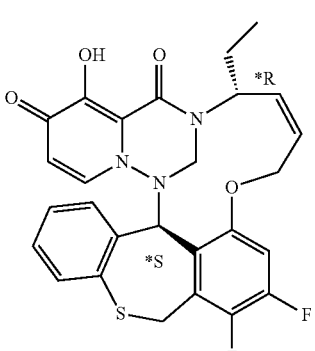 126BB | 0.001 | >0.2 | 0.0024 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 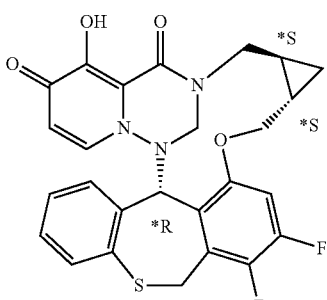 127AA | 0.0015 | >0.2 | 0.007 |
| 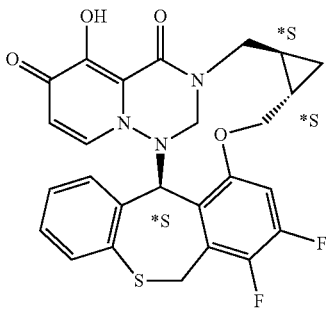 127BA | 0.0014 | >0.2 | 0.006 |
| 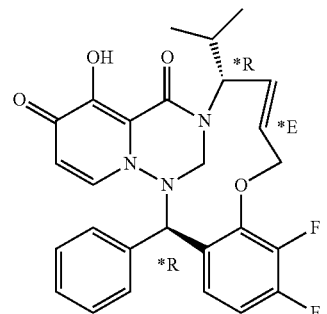 128AA | >0.1 | >0.2 | 46 |
| 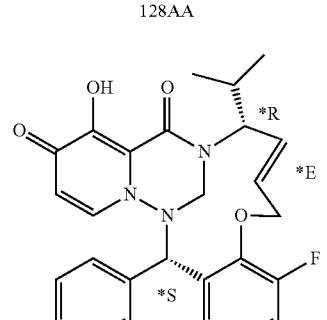 128BA | >0.1 | >0.2 | 0.043 |

TABLE 1A-continued

Antiviral activity of selected compounds (cell based and enzymatic assays)

| Compound number | A549_A(H1N1) EC₅₀ (uM) | CC₅₀ (μM) | FRET__IC₅₀ (uM) |
|---|---|---|---|
| 128BB | 0.0039 | >0.2 | 0.008 |
| 128AB | 0.065 | >0.2 | 0.093 |
| 129 | prodrug | | |
| 130A | 0.0048 | >0.2 | 0.012 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 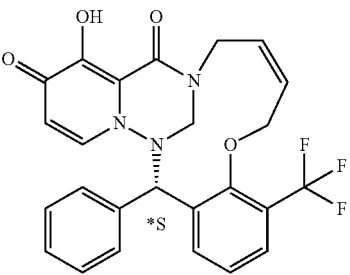 130B | >0.1 | >0.2 | >100 |
| 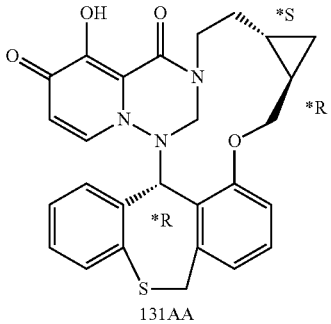 131AA | 0.0047 | >0.2 | 0.009 |
| 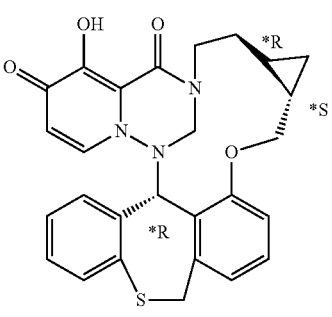 131AB | 0.017 | >0.2 | 0.006 |
| 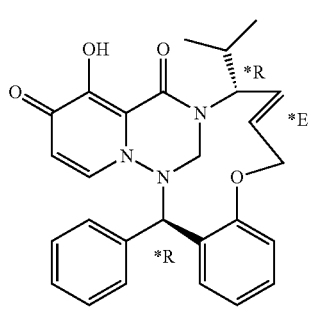 132A | >0.1 | >0.2 | >100 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM |
| --- | --- | --- | --- |
| 132B | 0.0093 | >0.2 | 0.064 |
| 133A | 0.0041 | >0.2 | 0.035 |
| 133B | >0.1 | >0.2 | 2.523 |
| 134A | 0.0693 | >0.2 | 0.059 |
| 134B | >0.1 | >0.2 | >100 |

TABLE 1A-continued
Antiviral activity of selected compounds (cell based and enzymatic assays)
| Compound number | A549_A(H1N1) EC$_{50}$ (uM) | CC$_{50}$ (µM) | FRET_IC$_{50}$ (uM |
|---|---|---|---|
| 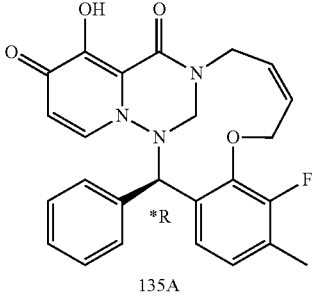 135A | 0.0073 | >0.2 | 0.011 |
| 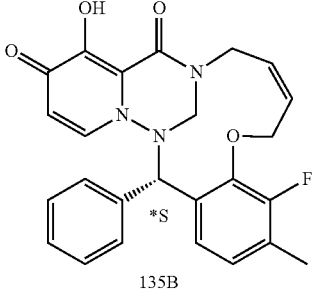 135B | >0.1 | >0.2 | 0.698 |
| 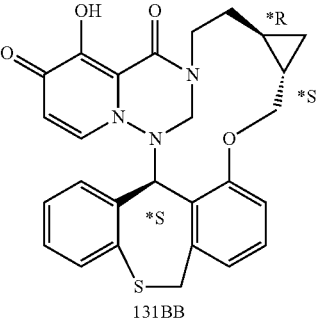 131BB | >0.1 | >0.2 | 0.851 |
| 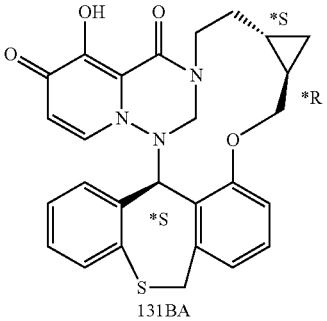 131BA | >0.1 | >0.2 | >100 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 108C | >0.1 | >0.2 | 2.388 |
| 108D | 0.0009 | >0.2 | 0.003 |
| 136A | 0.0063 | >0.2 | 0.001 |
| 136B | >0.1 | >0.2 | 0.200 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 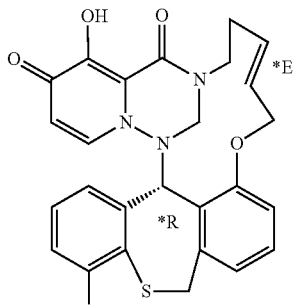 137A | >0.1 | >0.2 | 2.255 |
| 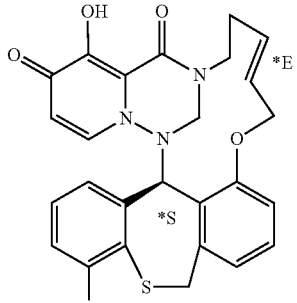 137B | 0.0053 | >0.2 | 0.010 |
| 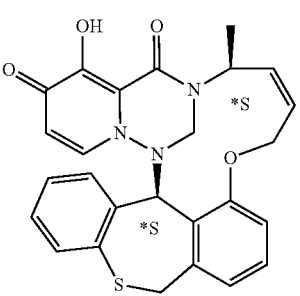 138AA | 0.0008 | >0.05 | 0.004 |
| 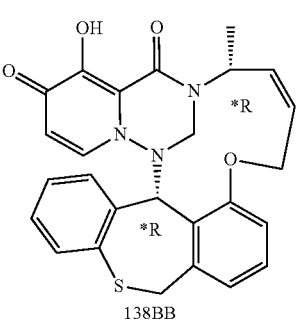 138BB | >0.1 | >0.2 | 0.298 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 138C 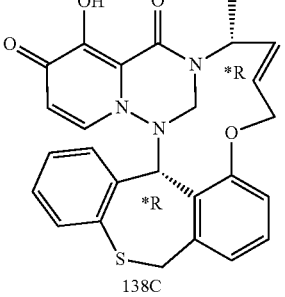 | >0.1 | >0.2 | 1.383 |
| 138D 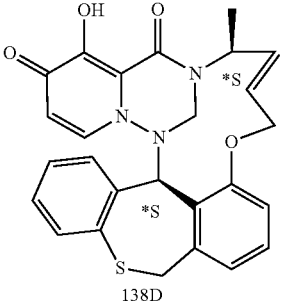 | 0.0009 | >0.2 | 0.003 |
| 139AA 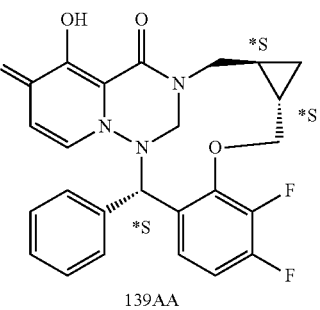 | 8.321 | 26.9 | 5.093 |
| 139BB 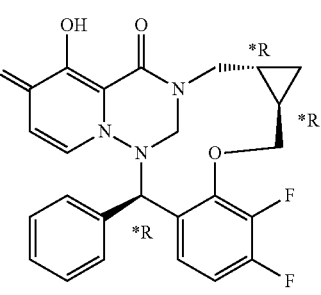 | >0.025 | >0.05 | 0.0071 |
| 139AB 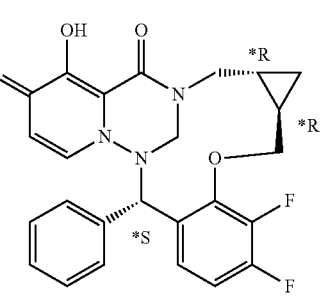 | 4.892 | 35.9 | 3.025 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 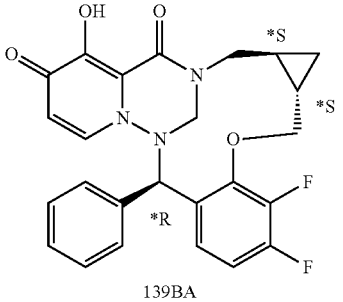 139BA | 0.0446 | >0.1 | 0.013 |
| 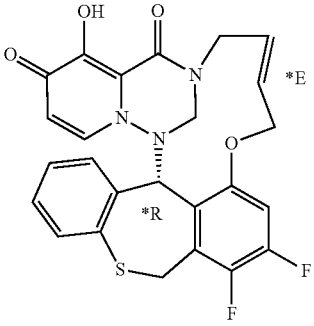 140A | 0.0963 | 9.96 | 0.606 |
| 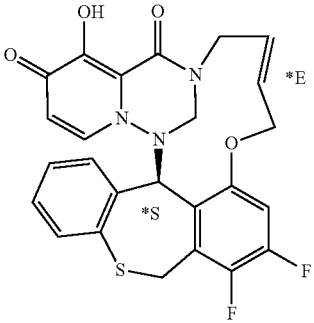 140B | 0.0003 | >0.05 | 0.003 |
| 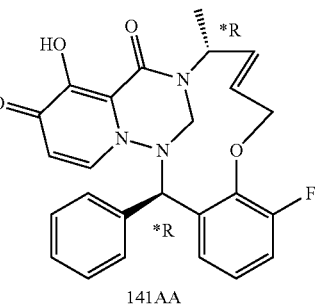 141AA | 0.0015 | >0.05 | 0.009 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 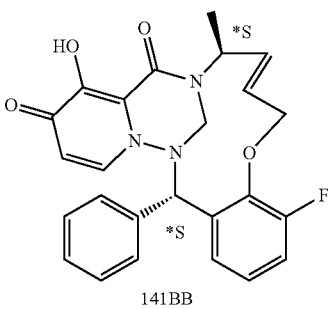 141BB | 0.6266 | >20 | 0.634 |
| 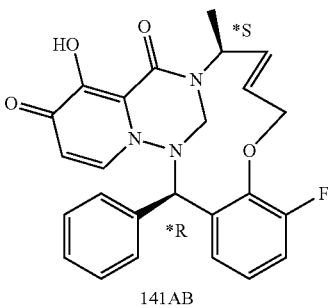 141AB | 0.0020 | >0.05 | 0.006 |
| 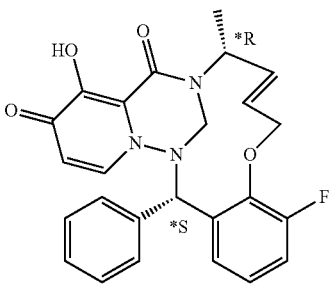 141BA | 0.3059 | >20 | 0.444 |
| 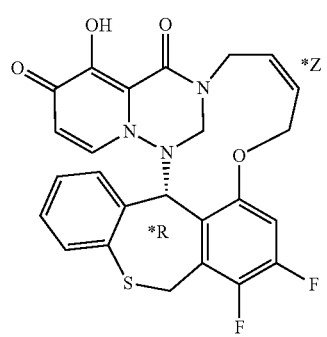 140C | 0.0374 | >10 | 0.165 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 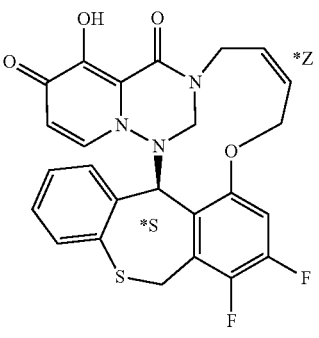 140D | 0.0012 | >0.05 | 0.001 |
| 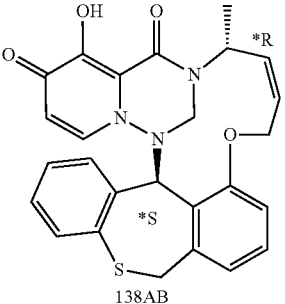 138AB | 0.0015 | >0.05 | 0.008 |
| 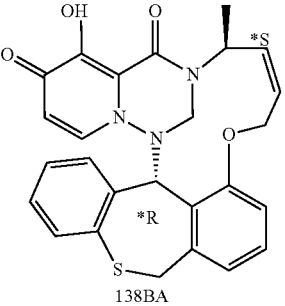 138BA | ND | ND | 3.887 |
| 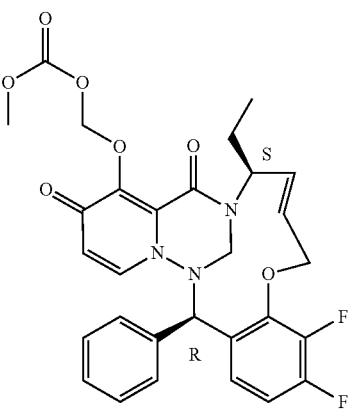 142 | prodrug | | |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM |
|---|---|---|---|
| 143 | prodrug | | |
| 144AA | >0.1 | >0.2 | |
| 144AB | >0.1 | >0.2 | |
| 144BB | 0.0513 | >4 | |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 144BA | 0.0729 | >0.2 | |
| 145A | 0.0031 | >0.1 | 0.0067 |
| 145B | 0.31 | >10 | >100 |
| 146A | 0.00065 | >0.1 | 0.0063 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 146B 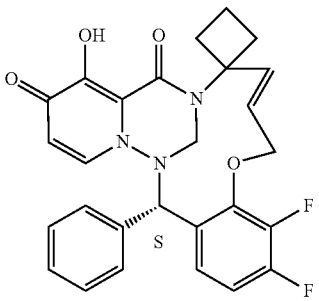 | 0.34 | >10 | >100 |
| 147A 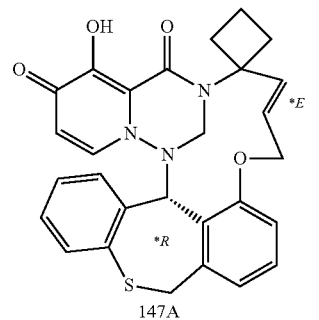 | >5 | >10 | >100 |
| 147B 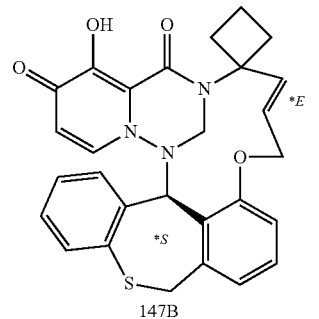 | 0.00033 | >0.1 | 0.010 |
| 148AA 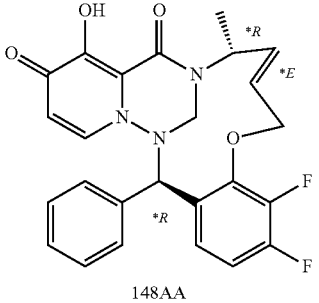 | 0.0016 | >0.05 | 0.0046 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM |
|---|---|---|---|
| 148BB | >5 | >10 | 0.47 |
| 148BA | 2.6 | >10 | >100 |
| 148BB | 0.0014 | >0.1 | 0.0062 |
| 150A | 0.009 | >0.1 | 0.033 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 150B 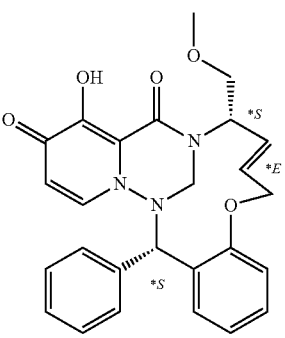 | 3.26 | >10 | 12.76 |
| 151B 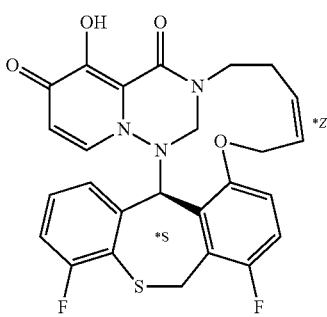 | 0.0044 | >0.1 | 0.0081 |
| 151A 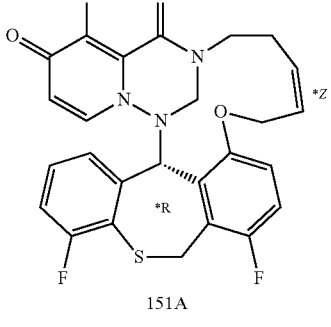 | >0.05 | >0.1 | 0.052 |
| 152AA 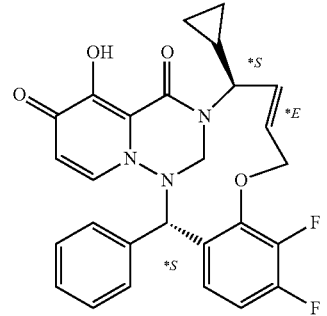 | >0.05 | >0.1 | 11.04 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM |
|---|---|---|---|
| 152BA | 0.0013 | >0.2 | 0.0012 |
| 152BB | 0.0018 | >0.2 | 0.0048 |
| 152AB | >0.05 | >0.1 | 21.69 |
| 153AA | >0.05 | >0.1 | 0.4 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 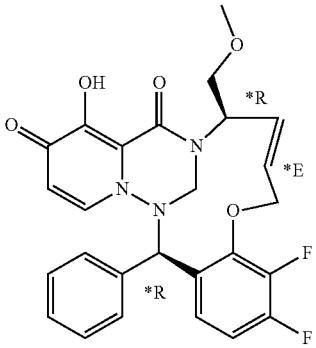 153BB | 0.0026 | >0.1 | 0.004 |
| 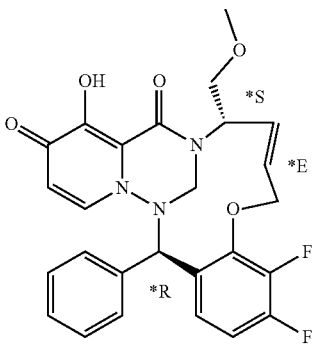 153BA | 0.0042 | >0.1 | 0.0091 |
| 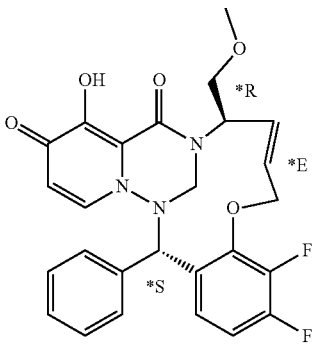 153AB | >0.05 | >0.1 | 0.52 |
| 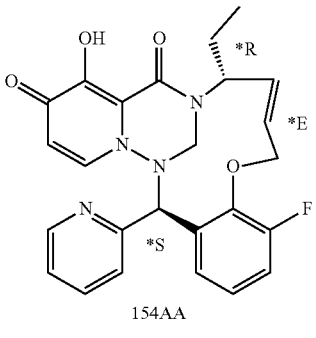 154AA | >0.05 | >0.1 | 2.98 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
|  154BB | 0.0034 | >0.1 | 0.0042 |
|  154AB | >0.05 | >0.1 | 5.15 |
|  154BA | 0.0068 | >0.1 | 0.011 |
|  155A | 0.0012 | >0.1 | 0.0028 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
|  155B | >0.05 | >0.1 | 0.61 |
|  156A | 0.00051 | >0.1 | 0.013 |
|  157A | 0.0013 | >0.1 | 0.029 |
|  157B | >0.05 | >0.1 | 13.54 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 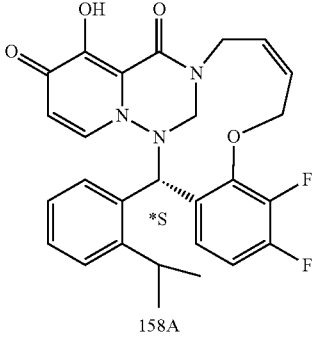 158A | >0.05 | >0.1 | >100 |
| 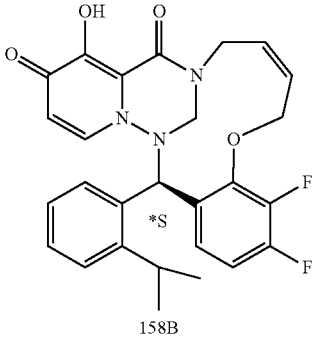 158B | >0.05 | >0.1 | 0.38 |
| 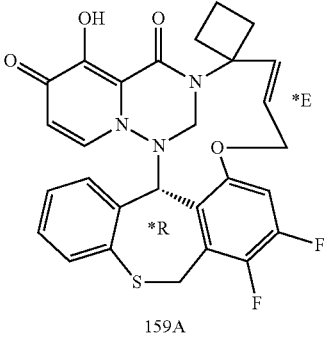 159A | >0.05 | >0.1 | >100 |
| 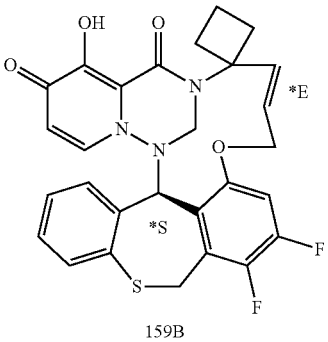 159B | 0.00019 | >0.1 | 0.03 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 160AA | 0.0052 | >0.1 | 0.011 |
| 160BB | >0.05 | >0.1 | 51.97 |
| 160BA | >0.05 | >0.1 | >100 |
| 160AB | 0.0028 | >0.1 | 0.0084 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
|  161A | >0.05 | >0.1 | Nd |
|  161B | 0.015 | >0.1 | 0.041 |
|  162A | >0.05 | >0.1 | 0.57 |
|  162B | 0.00023 | >0.1 | 0.0043 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 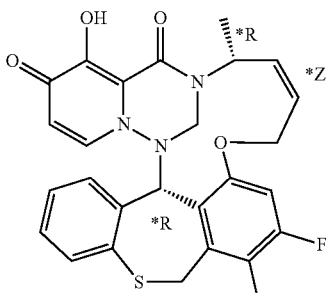 162C | 0.01 | >0.1 | 0.051 |
| 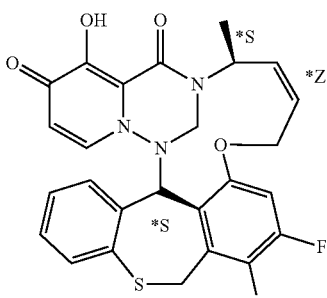 162D | 0.00051 | >0.1 | 0.002 |
| 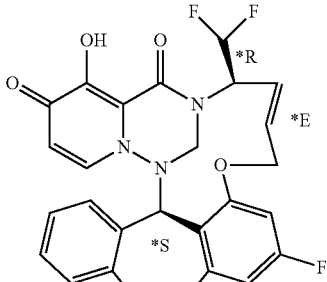 163AA | 0.0019 | >0.1 | 0.026 |
| 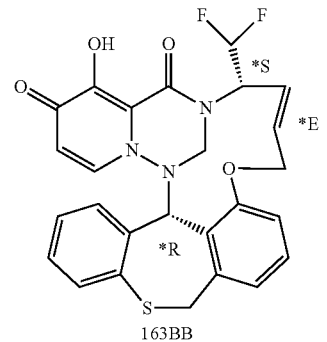 163BB | >0.05 | >0.1 | 69.43 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 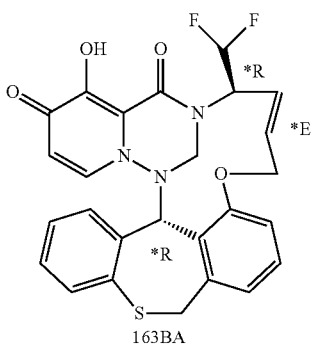 163BA | >0.05 | >0.1 | >100 |
| 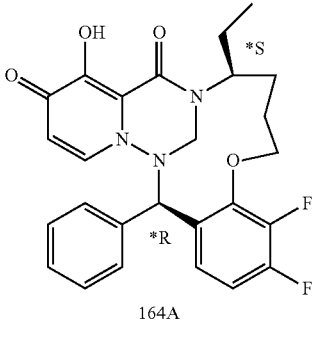 164A | >0.05 | >0.1 | 10.85 |
| 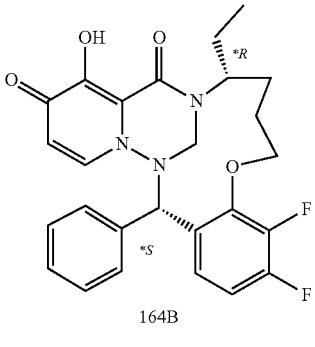 164B | 0.0024 | >0.1 | 0.018 |
| 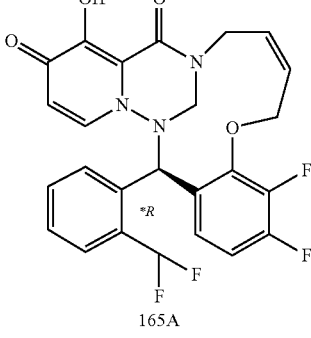 165A | 0.0072 | >0.1 | 0.003 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM |
|---|---|---|---|
| 165B | >0.05 | >0.1 | nd |
| 166A | >0.05 | >0.1 | 0.66 |
| 166B | 0.028 | nd | 0.011 |
| 167AA | 0.00091 | nd | 0.0053 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 167BB | >0.05 | nd | 2.02 |
| 167AB | 0.00096 | nd | 0.006 |
| 167BA | >0.05 | nd | 0.57 |
| 168A | >0.05 | >0.1 | 21.35 |
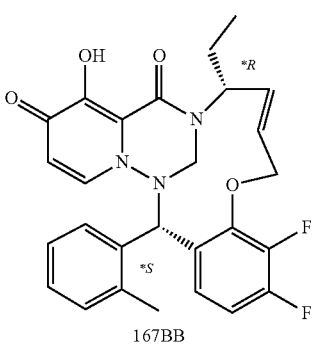
167BB
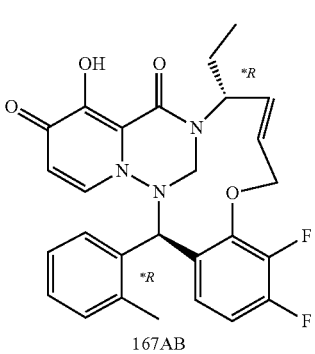
167AB
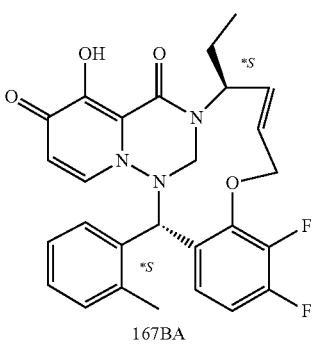
167BA
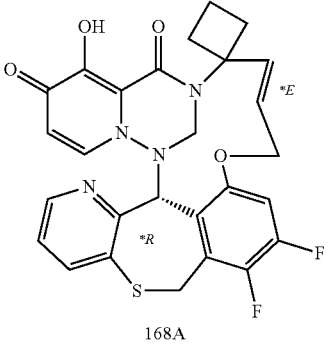
168A TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 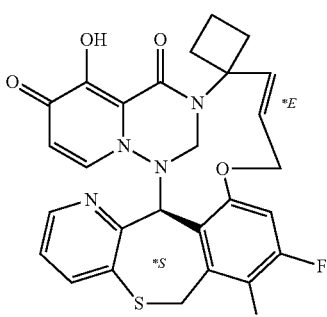 168B | 0.0006 | nd | 0.0052 |
| 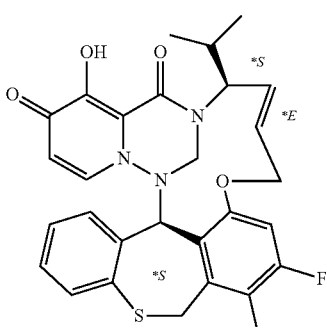 169AA | 0.048 | >0.1 | 1.76 |
| 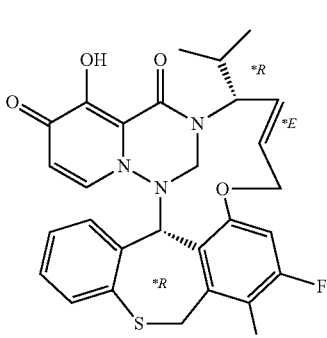 169BB | 0.0013 | >0.1 | 0.0054 |
| 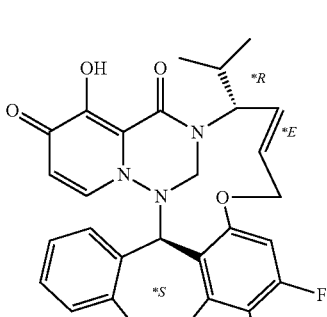 169AB | >0.05 | >0.1 | 4.64 |

TABLE 1A-continued
Antiviral activity of selected compounds (cell based and enzymatic assays)
| Compound number | A549_A(H1N1) EC$_{50}$ (uM) | CC$_{50}$ (µM) | FRET__IC$_{50}$ (uM |
|---|---|---|---|
| 169BA 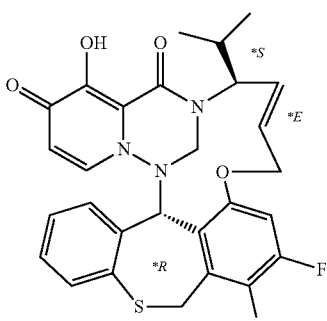 | 0.00083 | nd | 0.0093 |
| 170AA 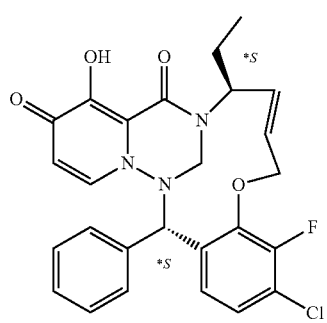 | >0.05 | >0.1 | 2.88 |
| 170BB 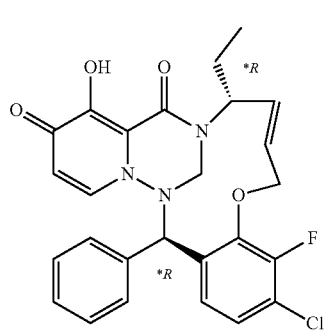 | 0.002 | nd | 0.0066 |
| 170AB 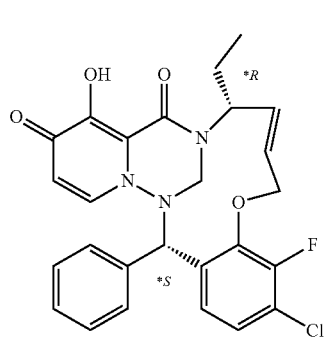 | >0.05 | >0.1 | 1.34 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM |
| --- | --- | --- | --- |
| 170BA | 0.024 | nd | 0.0081 |
| 171A | 0.0013 | >0.1 | 0.0083 |
| 171B | nd | nd | 11.27 |
| 172A | 0.0029 | >0.1 | 0.0077 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM) |
|---|---|---|---|
| 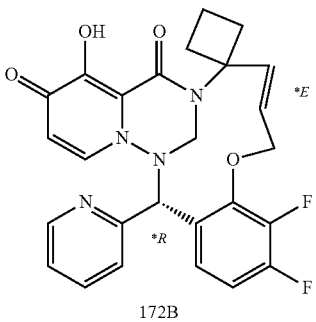<br>172B | >0.05 | >0.1 | 29.25 |
| 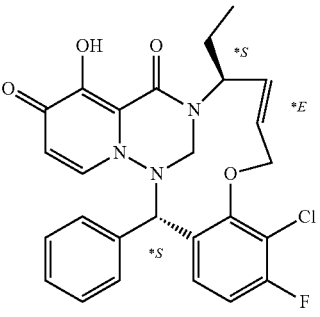<br>173AA | nd | nd | 3.4 |
| 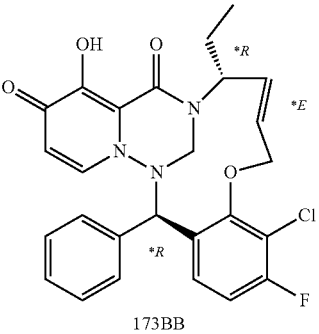<br>173BB | nd | nd | 0.011 |
| 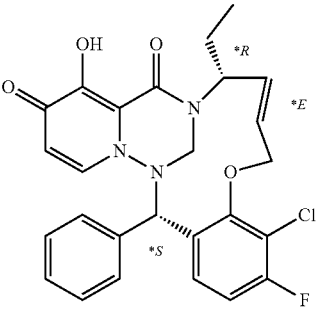<br>173AB | nd | nd | 4.15 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 173BA | 0.026 | nd | 0.0067 |
| 174A | nd | nd | 0.25 |
| 174B | 0.0012 | nd | 0.0038 |
| 175A | 0.0023 | nd | 0.0019 |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 175B | nd | nd | 0.29 |
| 176AA | nd | nd | 5.96 |
| 176AB | nd | nd | nd |
| 176BA | 0.0011 | nd | 0.0065 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 176BB 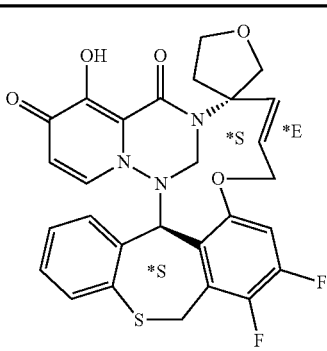 | 0.0014 | nd | 0.0051 |
| 177AA 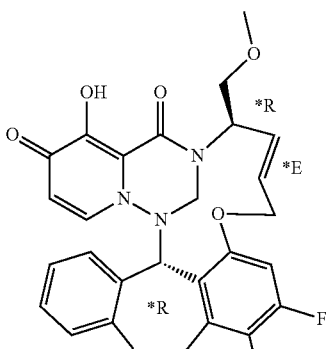 | 0.015 | nd | 0.41 |
| 177AB 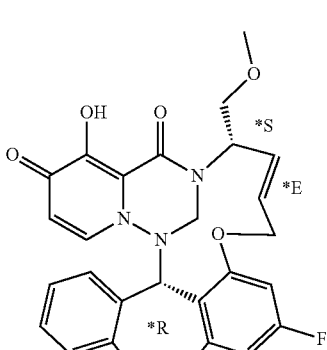 | 0.00067 | nd | 0.0052 |

TABLE 1A-continued
Antiviral activity of selected compounds (cell based and enzymatic assays)
| Compound number | A549_A(H1N1) EC$_{50}$ (uM) | CC$_{50}$ (μM) | FRET__IC$_{50}$ (uM |
|---|---|---|---|
| 177BA 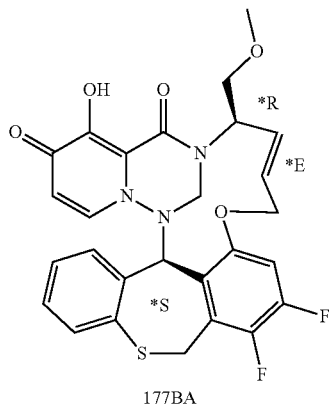 | nd | nd | nd |
| 177BB 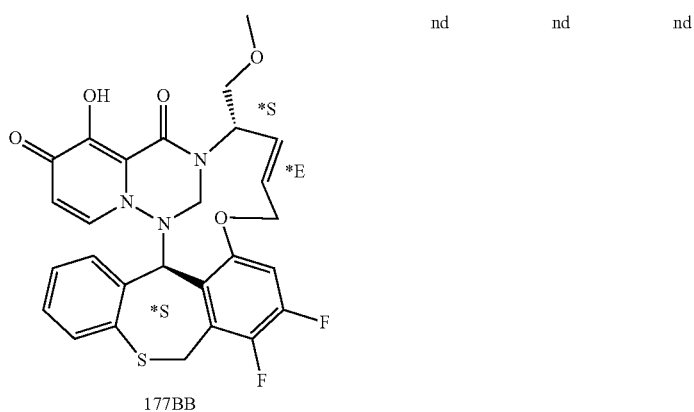 | nd | nd | nd |
| 178 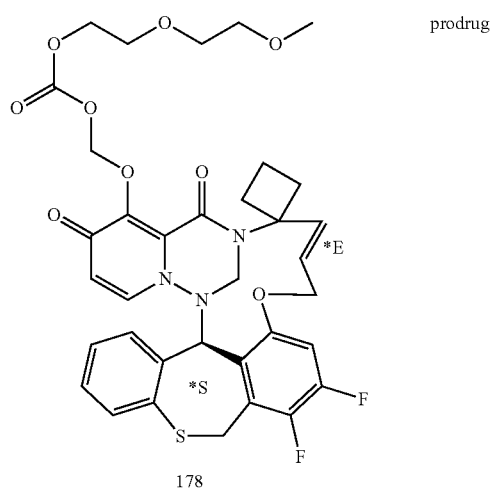 | prodrug | | |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM) |
|---|---|---|---|
| 179 | Prodrug | | |
| 180A | 0.029 | nd | nd |
| 180B | 0.00036 | nd | nd |

TABLE 1A-continued

Antiviral activity of selected compounds (cell based and enzymatic assays)

| Compound number | A549_A(H1N1) EC$_{50}$ (uM) | CC$_{50}$ (μM) | FRET__IC$_{50}$ (uM |
|---|---|---|---|
| 181 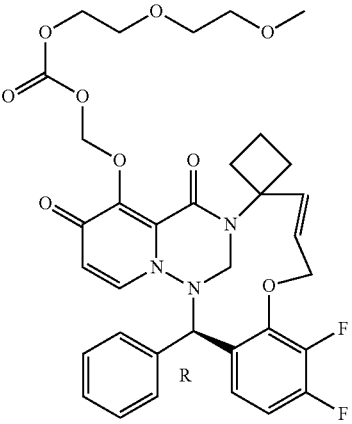 | Prodrug | | |
| 182 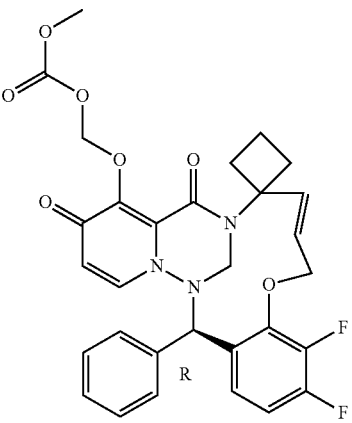 | Prodrug | | |

LIST OF ABBREVIATIONS

EDCI: 1-ethyl-3-(3-dimethylaminopropyl)carbodiimide
HOBt: 1-hydroxybenzotriazole
Rt: room temperature
DMF: dimethylformamide
DCE: dichloroethane
DMT: 2,4,6-trimercaptotriazine
TFA: trifluoro acetic acid
TFFA: trifluoroacetic anhydride
Rpm: rotations per minute
HATU: 1-[bis(dimethylamino)methylene]-1H-1,2,3-triazolo[4,5-b]pyridinium 3-oxide hexafluorophosphate
SFC: supercritical fluid chromatography
DBAD: di-tert-butyl azodicarboxylate
o/n: overnight
MTBE: methyl tert-butyl ether
ACCN: 1,1'-azobis(cyclohexanecarbonitrile)
PPA: polyphosphoric Acid

The invention claimed is:

1. A compound having Formula (I):

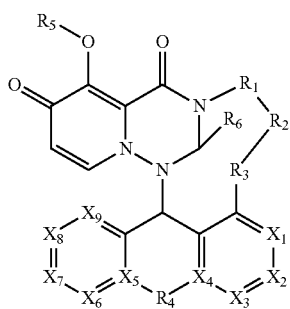

or any possible stereoisomeric form thereof,
wherein:
$R_1$ is $CH_2$, —$CH_2$—$CH_2$—O—, $C_{3-6}$cycloalkyl, oxetanyl, $C_{1-3}$alkyl-cyclopropyl, or $C_{1-3}$alkyl-cyclobutyl, each optionally substituted by one or more substituents independently selected from, halo, oxo, $CH_2$-methoxy, $C_{1-4}$alkyl, $C_{1-6}$cycloalkyl, and tetrahydrofuran;
$R_2$ is $C_{1-6}$alkyl, $C_{1-6}$alkyl-O—, $C_{1-6}$alkyl-N—, $C_{2-6}$alkenyl, $C_{2-6}$alkenyl-O—, or $C_{2-6}$alkenyl-N—, each optionally substituted by one or more substituents independently selected from halo, oxo, and $C_{1-4}$alkyl;
$R_3$ is $CH_2$ or O, wherein the $CH_2$ is optionally substituted by one or more substituents independently selected from halo, oxo, and methyl;
or, $R_2$ and $R_3$ together form $C_{2-8}$alkenyl optionally substituted by one or more substituents independently selected from halo, oxo, and methyl;
$X_1$, $X_2$, $X_3$, $X_4$, $X_5$, $X_6$, $X_7$, $X_8$ and $X_9$ are each independently N or CH and wherein any of $X_1$, $X_2$, $X_3$, $X_4$, $X_5$, $X_6$, $X_7$, $X_8$ and $X_9$ is CH, said CH is optionally substituted by one or more substituents independently selected from $C_{1-4}$alkyl, $C_{3-6}$cycloalkyl, $CHF_2$, $CH_2F$, $CF_3$, $OCF_3$, $SCF_3$, $OCH_3$, $SCH_3$, S—$(O)_2$—$CH_3$, and halogen;
the dotted lines are each an optional bond;
$R_4$ is absent, or is —$CH_2$—$CH_2$—, —O—$CH_2$—, —S—$CH_2$—, S—$(O)_2$—$CH_2$, or cyclopropyl, each optionally substituted by one or more substituents independently selected from halo, oxo, and methyl;
$R_5$ is H, —C(=O)Y, —($CH_2$)—O—(C=O)—Y, —($CH_2$)—O—(C=O)—O—Y, —(CHCH$_3$)—O—(C=O)—Y, —(CHCH$_3$)—O—(C=O)—O—Y, —($CH_2$)—O—(C=O)—NH—Y, or —($CH_2$)—O—(C=O)C($R_7$)—NH—($R_8$);

Y is $C_{1-6}$alkyl, $C_{3-6}$cycloalkyl, aryl, heteroaryl, heterocyclyl, $C_{1-4}$alkyl-(O—$R_7$), $C_{1-4}$alkyl-N—($R_7$)($R_8$), or $R_7$—O—$R_8$—O—$CH_2$;
wherein $R_7$ and $R_8$ are independently hydrogen or $C_{1-4}$alkyl; and
$R_6$ is H, methyl, or $CH_2$—O—$CH_3$;
or a pharmaceutically acceptable salt, polymorph, or solvate thereof.

2. The compound according to claim 1, wherein:
$R_1$ is $CH_2$, —$CH_2$—$CH_2$—O—, $C_{3-6}$cycloalkyl, $C_{1-3}$alkyl-cyclopropyl, or $C_{1-3}$alkyl-cyclobutyl, each optionally substituted by one or more substituents independently selected from, halo, oxo, $CH_2$-methoxy, $C_{1-4}$alkyl, and $C_{1-6}$cycloalkyl;
$R_2$ is $C_{1-6}$alkyl, $C_{2-6}$alkenyl, $C_{2-6}$alkenyl-O—, or $C_{2-6}$alkenyl-N—, each optionally substituted by one or more substituents independently selected from halo, oxo, and $C_{1-4}$alkyl;
$R_3$ is $CH_2$ or O, wherein the $CH_2$ is optionally substituted by one or more substituents independently selected from halo, oxo, and methyl;
or, $R_2$ and $R_3$ together form $C_{2-8}$alkenyl optionally substituted by one or more substituents independently selected from halo, oxo, and methyl;
$X_1$, $X_2$, $X_3$, $X_4$, $X_5$, $X_6$, $X_7$, $X_8$ and $X_9$ are each independently N or CH and wherein any of $X_1$, $X_2$, $X_3$, $X_4$, $X_5$, $X_6$, $X_7$, $X_8$ and $X_9$ is CH, said CH is optionally substituted by one or more substituents independently selected from $C_{1-4}$alkyl, $C_{3-6}$cycloalkyl, $CHF_2$, $CH_2F$, $CF_3$, $OCF_3$, $SCF_3$, $OCH_3$, $SCH_3$, S—$(O)_2$—$CH_3$ or halogen;
the dotted lines are each an optional bond;
$R_4$ is absent, or is —$CH_2$—$CH_2$—, —O—$CH_2$—, or —S—$CH_2$— each optionally substituted by one or more substituents independently selected from halo, oxo, and methyl;
$R_5$ is H, —C(=O)Y, —($CH_2$)—O—(C=O)—Y, —($CH_2$)—O—(C=O)—O—Y, —(CHCH$_3$)—O—(C=O)—Y, —(CHCH$_3$)—O—(C=O)—O—Y, —($CH_2$)—O—(C=O)—NH—Y, or —($CH_2$)—O—(C=O)C($R_7$)—NH—($R_8$);
Y is $C_{1-6}$alkyl, $C_{3-6}$cycloalkyl, aryl, heteroaryl, heterocyclyl, $C_{1-4}$alkyl-(O—$R_7$), $C_{1-4}$alkyl-N—($R_7$)($R_8$), or $R_7$—O—$R_8$—O—$CH_2$;
wherein $R_7$ and $R_8$ are independently hydrogen or $C_{1-4}$alkyl; and
$R_6$ is H or methyl.

3. The compound according to claim 1, wherein:
$R_1$ is $CH_2$, $C_{3-6}$cycloalkyl, $C_{1-3}$alkyl-cyclopropyl, or $C_{1-3}$alkyl-cyclobutyl, each optionally substituted by one or more substituents independently selected from, halo, and $C_{1-4}$alkyl;

R₂ is $C_{1-6}$alkyl or $C_{2-6}$alkenyl, each optionally substituted by one or more substituents independently selected from halo and $C_{1-4}$alkyl;

R₃ is $CH_2$ or O, wherein the $CH_2$ is optionally substituted by one or more substituents independently selected from halo and methyl;

or, R₂ and R₃ together form $C_{2-8}$alkenyl optionally substituted by one or more substituents independently selected from halo, oxo, and methyl;

$X_1$, $X_2$, $X_3$, $X_4$, $X_5$, $X_6$, $X_7$, $X_8$ and $X_9$ are each independently N or C and wherein any of $X_1$, $X_2$, $X_3$, $X_4$, $X_5$, $X_6$, $X_7$, $X_8$ and $X_9$ is CH, said CH is optionally substituted by one or more substituents independently selected from $C_{1-4}$alkyl, $C_{3-6}$cycloalkyl, $CHF_2$, $CH_2F$, $CF_3$, $OCF_3$, $SCF_3$, $OCH_3$, $SCH_3$, $S-(O)_2-CH_3$, and halogen;

the dotted lines are each an optional bond;

R₄ is absent or is —S—$CH_2$— optionally substituted by one or more substituents independently selected from halo and methyl;

R₅ is H; and

R₆ is H or methyl.

4. The compound according to claim 1, wherein:

R₁ is $CH_2$, $C_{3-6}$cycloalkyl, or $C_{1-3}$alkyl-cyclopropyl, each optionally substituted by one or more substituents independently selected from halo and $C_{1-4}$alkyl;

R₂ is $C_{1-6}$alkyl or $C_{2-6}$alkenyl, each optionally substituted by one or more substituents independently selected from halo and $C_{1-4}$alkyl;

R₃ is $CH_2$ or O, wherein the $CH_2$ is optionally substituted by one or more substituents independently selected from halo and methyl;

$X_1$, $X_2$, $X_3$, $X_4$, $X_5$, $X_6$, $X_7$, $X_8$ and $X_9$ are each independently N or CH and wherein any of $X_1$, $X_2$, $X_3$, $X_4$, $X_5$, $X_6$, $X_7$, $X_8$ and $X_9$ is CH, said CH is optionally substituted by one or more substituents independently selected from $C_{1-4}$alkyl, $C_{3-6}$cycloalkyl, $CHF_2$, $CH_2F$, $CF_3$, $OCF_3$, $SCF_3$, $OCH_3$, $SCH_3$, $S-(O)_2-CH_3$, and halogen;

the dotted lines are each an optional bond;

R₄ is absent or is —S—$CH_2$— optionally substituted by one or more substituents independently selected from halo and methyl;

R₅ is H; and

R₆ is H or methyl.

5. The compound according to claim 1, wherein:

R₁ is $CH_2$, $C_{3-6}$cycloalkyl, or $C_{1-3}$alkyl-cyclopropyl, each optionally substituted by one or more substituents independently selected from halo and $C_{1-4}$alkyl;

R₂ is $C_{1-6}$alkyl or $C_{2-6}$alkenyl, each optionally substituted by one or more substituents independently selected from halo and $C_{1-4}$alkyl;

R₃ is $CH_2$ or O, wherein the $CH_2$ is optionally substituted by one or more substituents independently selected from halo and methyl;

$X_1$, $X_2$, $X_3$, $X_4$, $X_5$, $X_6$, $X_7$, $X_8$ and $X_9$ are each CH which is optionally substituted by one or more substituents independently selected from $C_{1-4}$alkyl, $C_{3-6}$cycloalkyl, and halogen;

the dotted lines are each an optional bond;

R₄ is absent or is —S—$CH_2$— optionally substituted by one or more substituents independently selected from halo and methyl;

R₅ is H; and

R₆ is H.

6. A pharmaceutical composition comprising a compound according to claim 1 or a pharmaceutically acceptable salt, solvate or polymorph thereof and one or more pharmaceutically acceptable excipients, diluents, or carriers.

7. The compound according to claim 1, wherein R₁ is $CH_2$, $C_{3-6}$cycloalkyl, or $C_{1-3}$alkyl-cyclopropyl, each optionally substituted by one or more substituents independently selected from halo and $C_{1-4}$alkyl.

8. The compound according to claim 1, wherein R₂ is $C_{1-6}$alkyl or $C_{2-6}$alkenyl, each optionally substituted by one or more substituents independently selected from halo and $C_{1-4}$alkyl.

9. The compound according to claim 1, wherein R₃ is $CH_2$ or O, wherein the $CH_2$ is optionally substituted by one or more substituents independently selected from halo and methyl.

10. The compound according to claim 1, wherein $X_1$, $X_2$, $X_3$, $X_4$, $X_5$, $X_6$, $X_7$, $X_8$ and $X_9$ are each CH which is optionally substituted by one or more substituents independently selected from $C_{1-4}$alkyl, $C_{3-6}$cycloalkyl, and halogen.

11. The compound according to claim 1, wherein R₄ is absent or is —S—$CH_2$— optionally substituted by one or more substituents independently selected from halo and methyl.

12. The compound according to claim 1, wherein R₅ is H.

13. The compound according to claim 1, wherein R₆ is H.

14. A compound selected from the group consisting of:

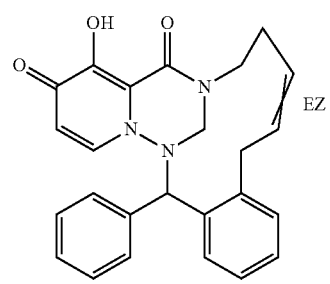

1

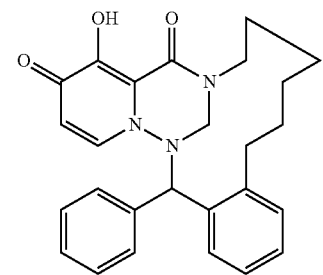

2

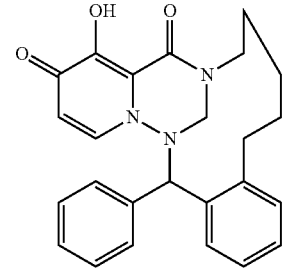

4

-continued
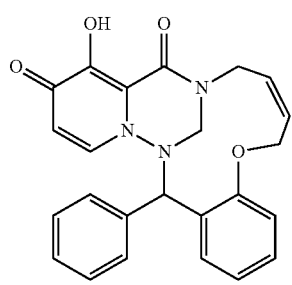
5
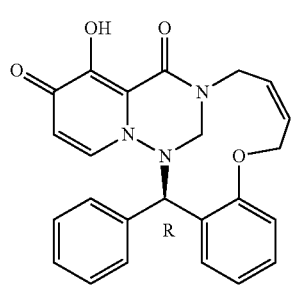
5A
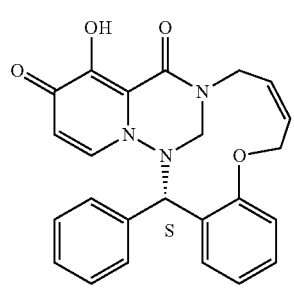
5B
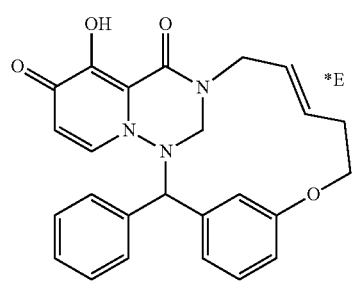
6
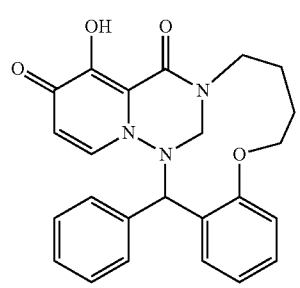
8
-continued
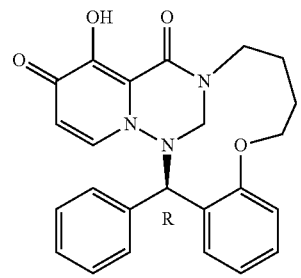
8A
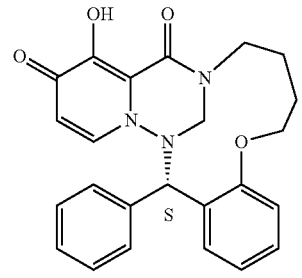
8B
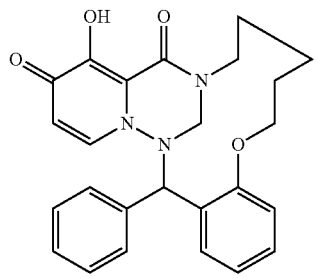
9
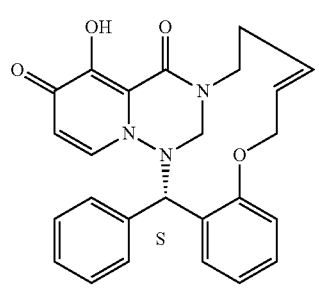
10A
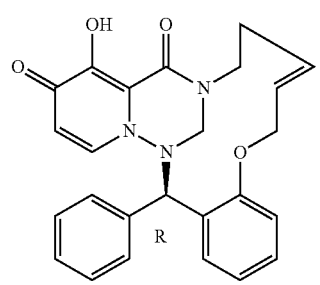
10B

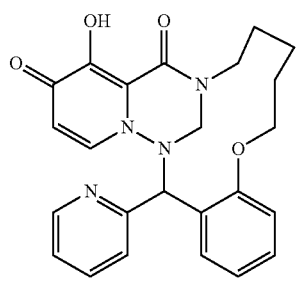
11
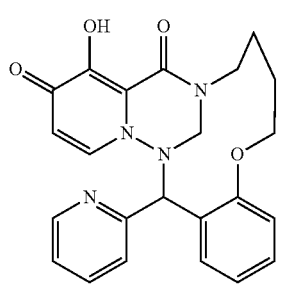
12
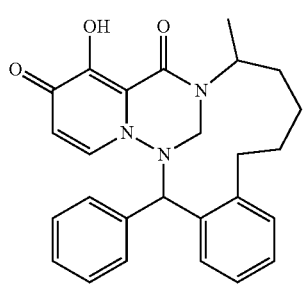
13
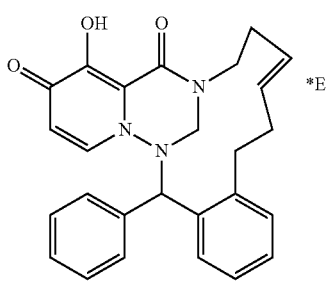
14
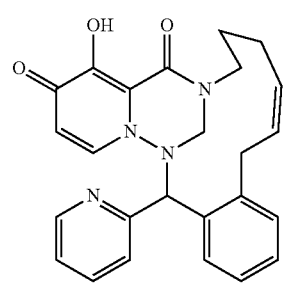
15
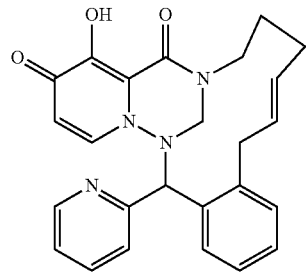
16
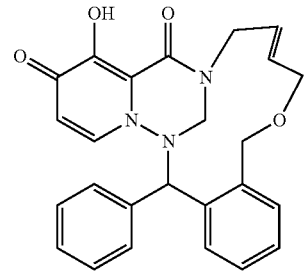
17
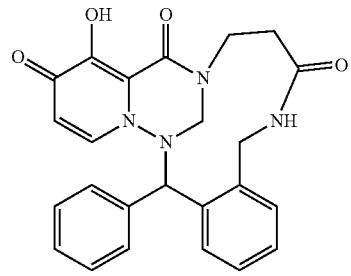
18
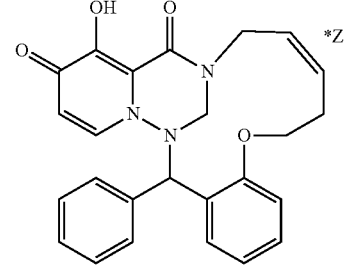
19
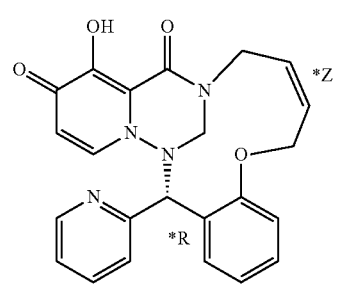
20A 20B
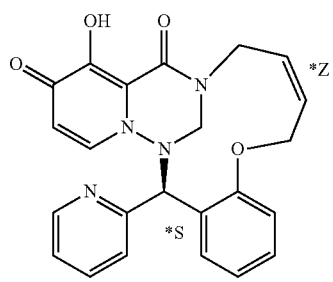
21A
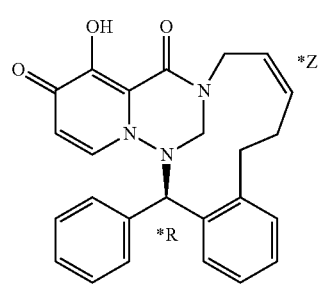
21B
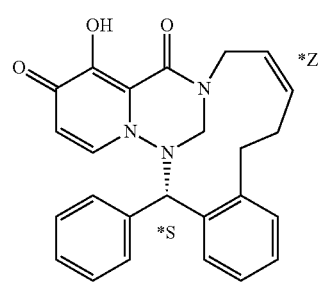
22A
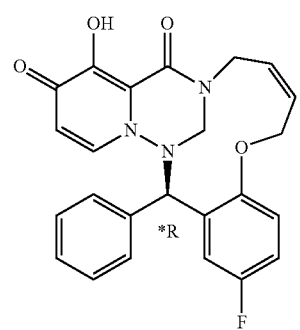
22B
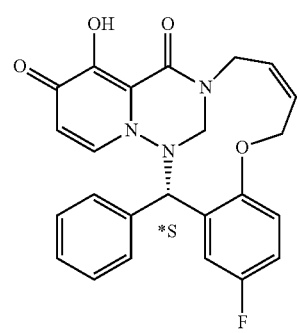
23A
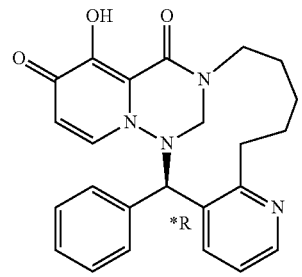
23B
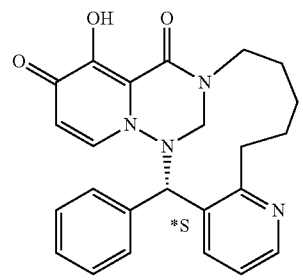
24A
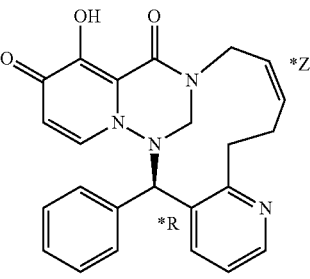
24B
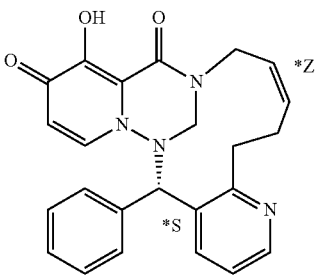
25A
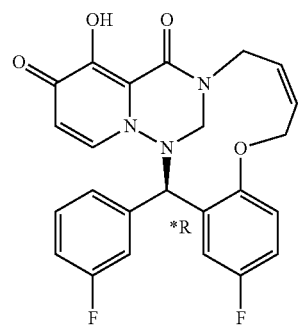 [SMILES: O=C1c2c(O)c(=O)ccn2N2CN1CCCCOc1ccc(F)cc1[C@H]2c1cccc(F)c1]

25B
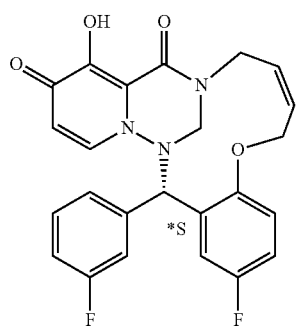 [SMILES: O=C1c2c(O)c(=O)ccn2N2CN1CCCCOc1ccc(F)cc1[C@@H]2c1cccc(F)c1]
26A
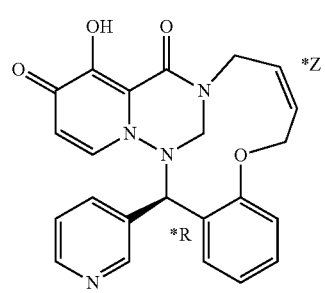
26B
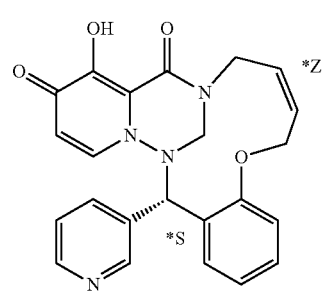
27A
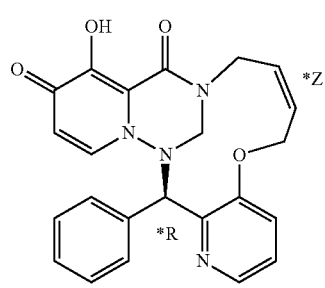
27B
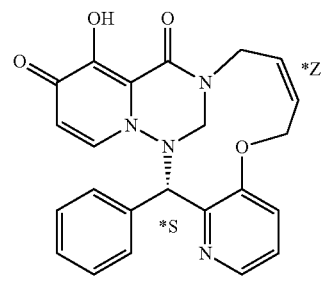
28A
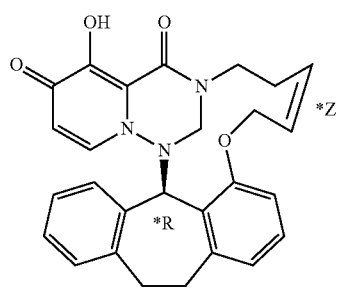
28B
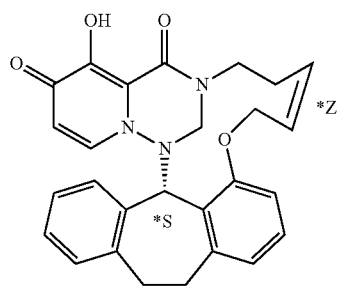
29AA
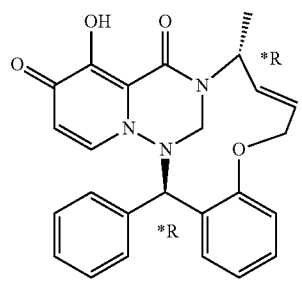
29AB
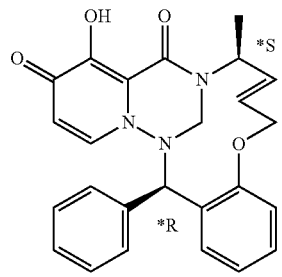
22BA
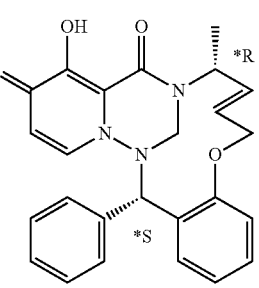

| | | |
|---|---|---|
| 29BB 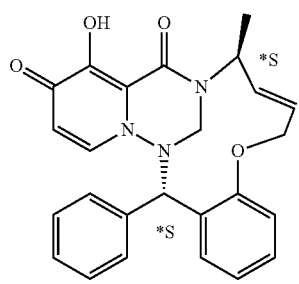 | 32B 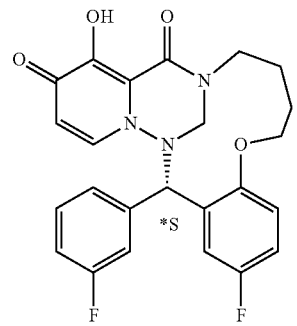 | |
| 30A 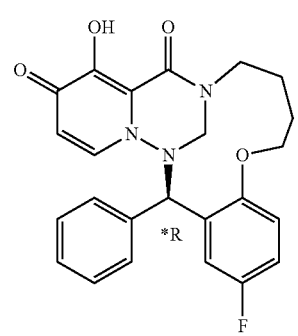 | 33A 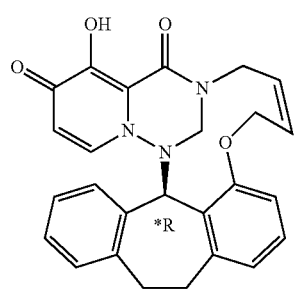 [SMILES: O=C1c2c(O)c(=O)ccn2N2CN1C/C=C\COc1cccc3c1[C@H]2c1ccccc1CC3] | |
| 30B 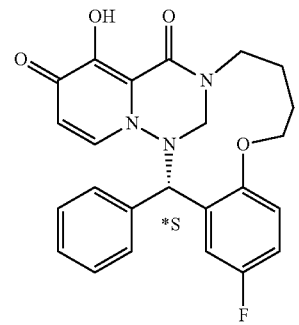 | 33B 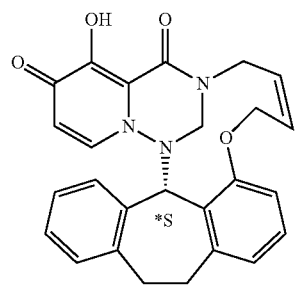 [SMILES: O=C1c2c(O)c(=O)ccn2N2CN1C/C=C\COc1cccc3c1[C@@H]2c1ccccc1CC3] | |
| 31B 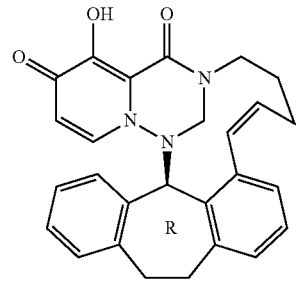 | 34A 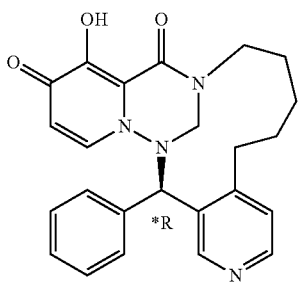 | |
| 32A 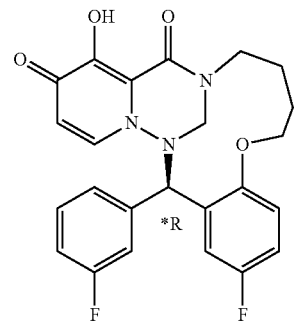 | 34B 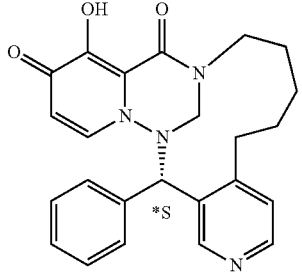 | |

| 639 -continued | 640 -continued |
|---|---|
| 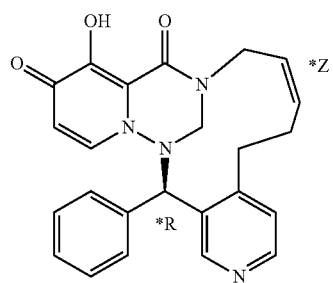 35A | 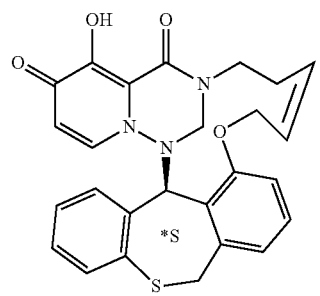 37B |
| 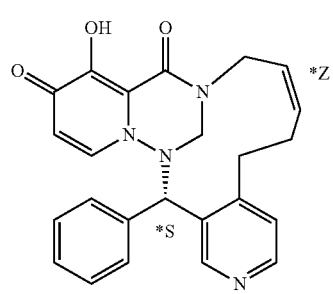 35B | 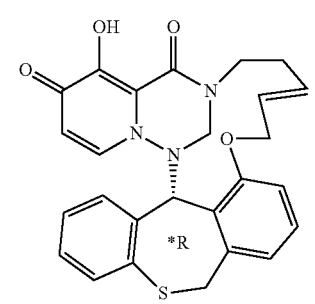 37C |
| 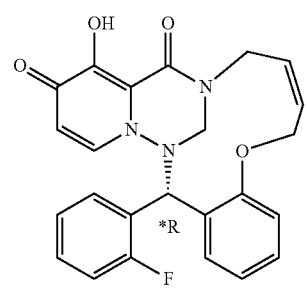 36A | 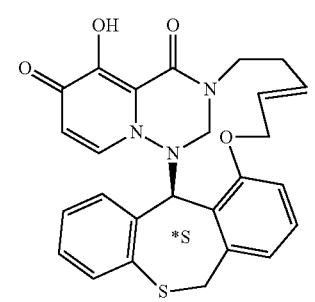 37D |
| 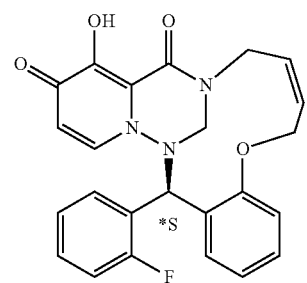 36B | 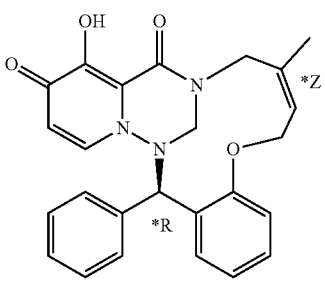 38A |
| 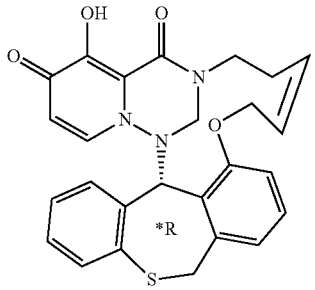 37A | 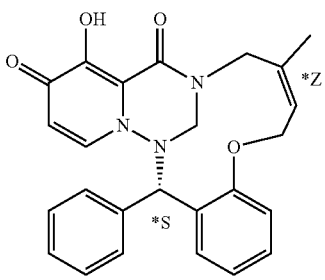 38B |

39AA
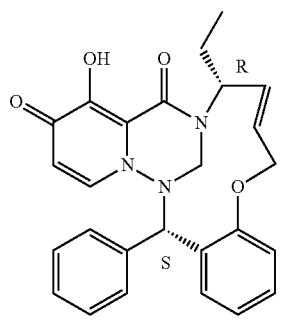
39AB
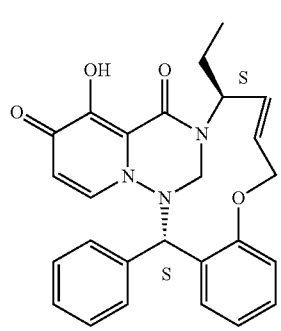
39BA
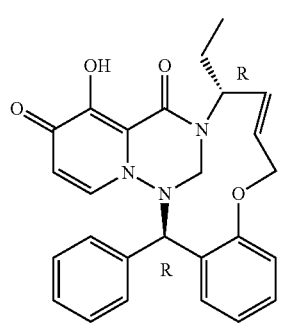
39BB
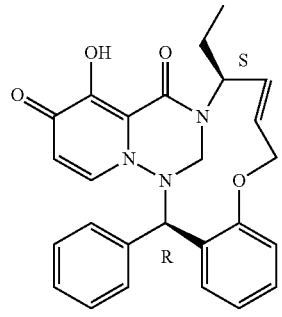
40A
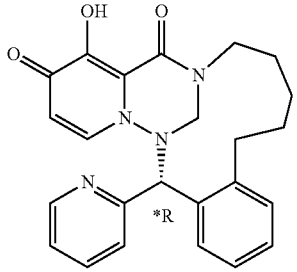 [SMILES: O=C1c2c(O)c(=O)ccn2N2CN1CCCCCc1ccccc1[C@@H]2c1ccccn1]
40B
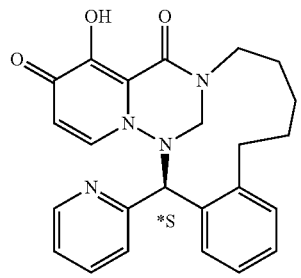 [SMILES: O=C1c2c(O)c(=O)ccn2N2CN1CCCCCc1ccccc1[C@H]2c1ccccn1]
41A
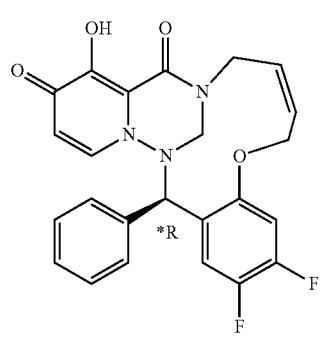 [SMILES: O=C1c2c(O)c(=O)ccn2N2CN1C/C=C\COc1cc(F)c(F)cc1[C@H]2c1ccccc1]
41B
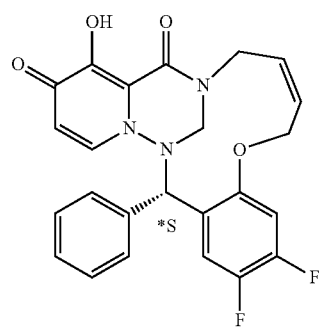
42A
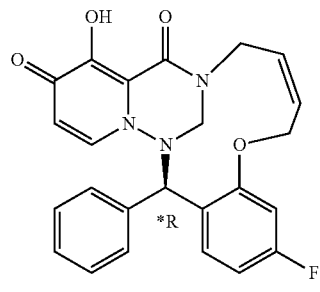 [SMILES: O=C1c2c(O)c(=O)ccn2N2CN1C/C=C\CCc1cc(F)ccc1[C@H]2c1ccccc1]
42B
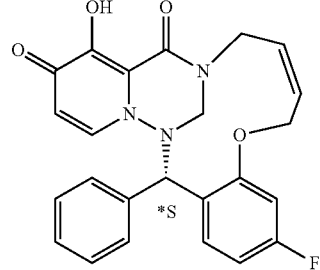 [SMILES: O=C1c2c(O)c(=O)ccn2N2CN1C/C=C\CCc1cc(F)ccc1[C@@H]2c1ccccc1]

-continued
| | |
|---|---|
| 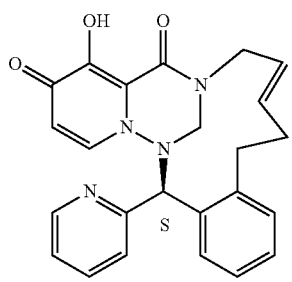 43A | 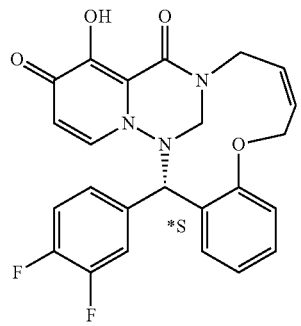 45B |
| 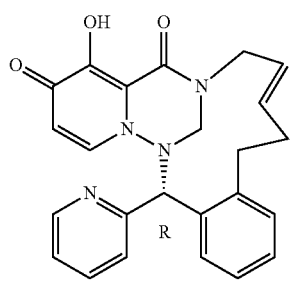 43B | 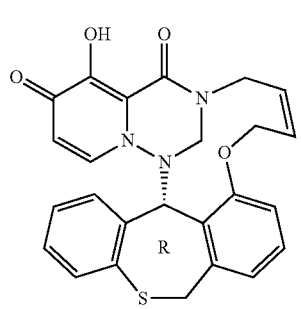 46A |
| 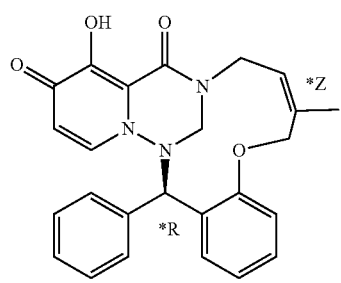 [SMILES: C/C1=C/CN2CN([C@H](c3ccccc3)c3ccccc3OC1)n1ccc(=O)c(O)c1C2=O] 44A | 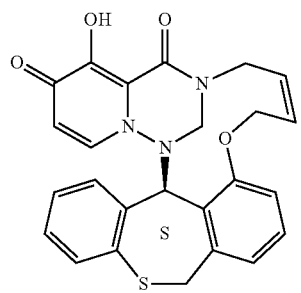 46B |
| 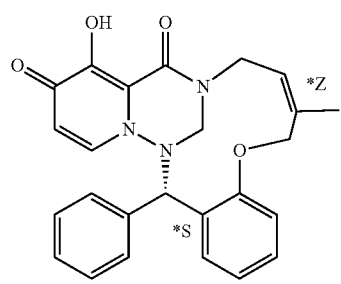 44B | 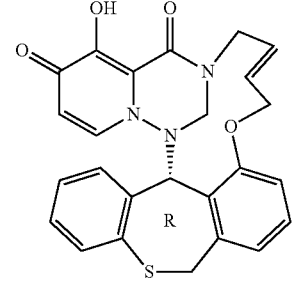 46C |
| 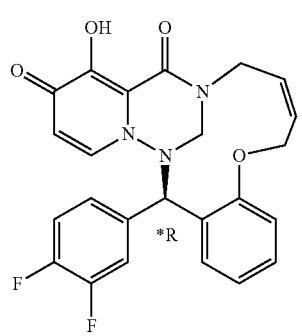 [SMILES: O=C1c2c(O)c(=O)ccn2N2CN1C/C=C\COc1ccccc1[C@H]2c1ccc(F)c(F)c1] 45A | 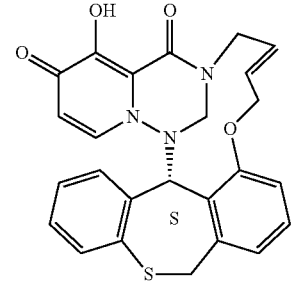 46D |

| | |
|---|---|
| 47A 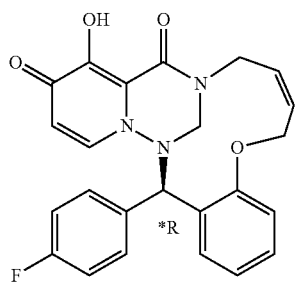 | 49 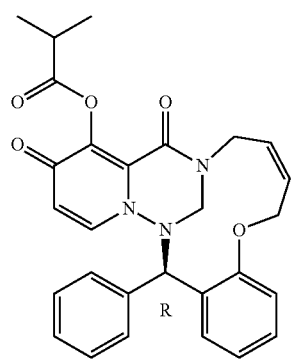 |
| 47B 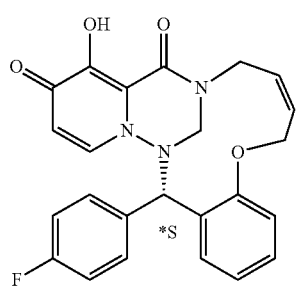 | 50 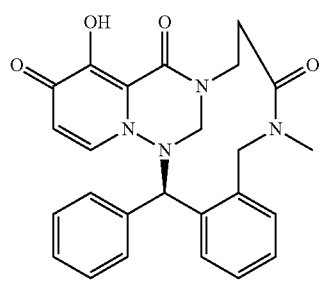 |
| 48 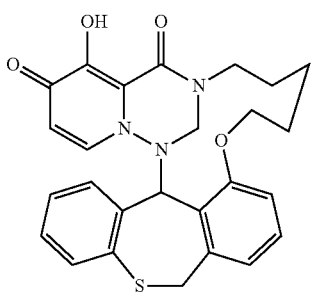 [SMILES: O=C1c2c(O)c(=O)ccn2N2CN1CCCCCOc1cccc3c1C2c1ccccc1SC3] | 51A 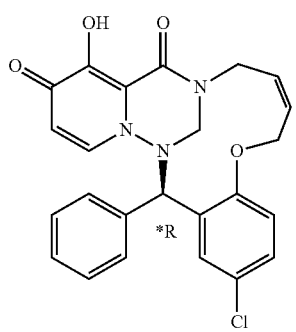 |
| 48A 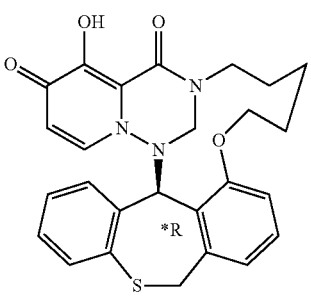 | 51B 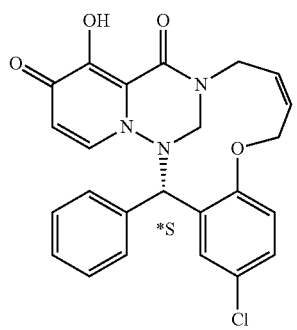 |
| 48B 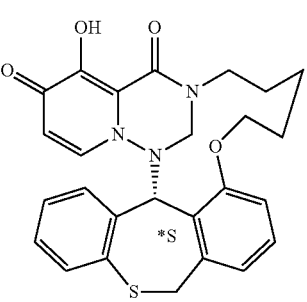 | 52A 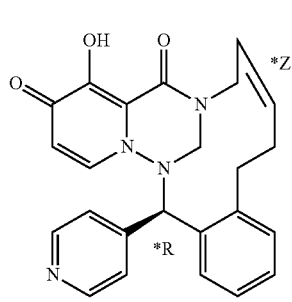 |

647
-continued
52B
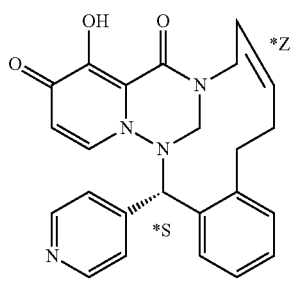
53A
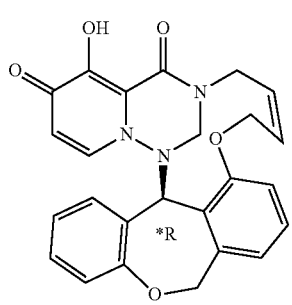
53B
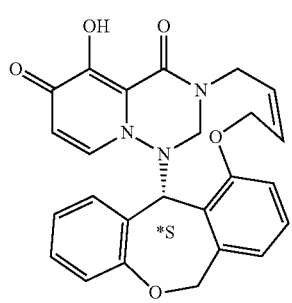
54
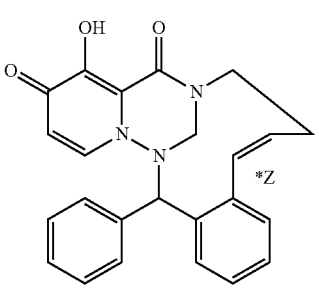 [SMILES: O=C1c2c(O)c(=O)ccn2N2CN1CC/C=C\c1ccccc1C2c1ccccc1]
54A
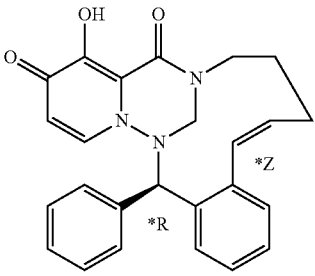 [SMILES: O=C1c2c(O)c(=O)ccn2N2CN1CCC/C=C\c1ccccc1[C@H]2c1ccccc1]
648
-continued
54B
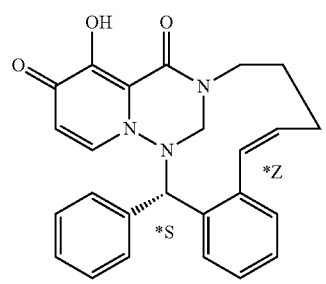 [SMILES: O=C1c2c(O)c(=O)ccn2N2CN1CCC/C=C\c1ccccc1[C@@H]2c1ccccc1]
55
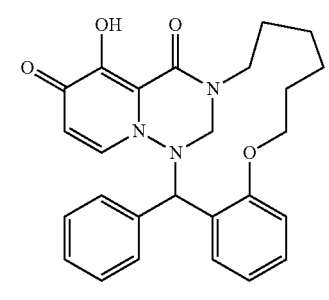 [SMILES: O=C1c2c(O)c(=O)ccn2N2CN1CCCCCCOc1ccccc1C2c1ccccc1]
56A
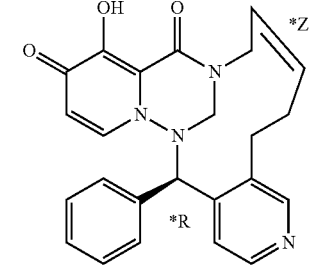 [SMILES: O=C1c2c(O)c(=O)ccn2N2CN1C/C=C\CCc1cnccc1[C@H]2c1ccccc1]
56B
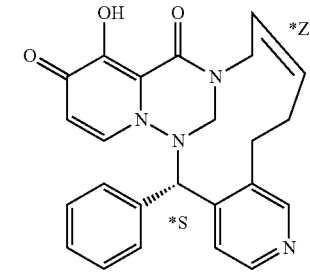 [SMILES: O=C1c2c(O)c(=O)ccn2N2CN1C/C=C\CCc1cnccc1[C@@H]2c1ccccc1]
57A
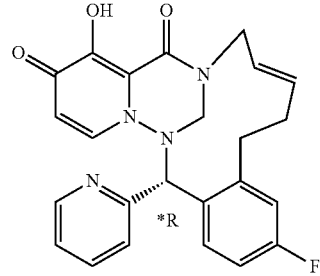

| | |
|---|---|
| 57B 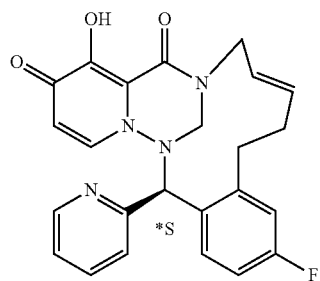 | 60 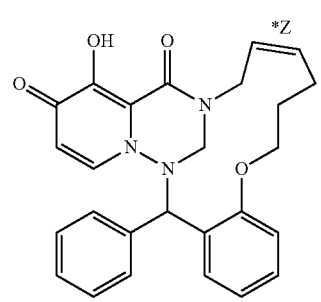 |
| 58A 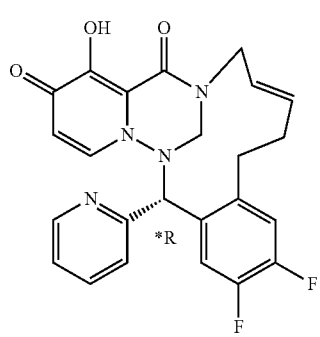 [SMILES: O=C1c2c(O)c(=O)ccn2N2CN1C/C=C/CCc1cc(F)c(F)cc1[C@@H]2c1ccccn1] | 61A 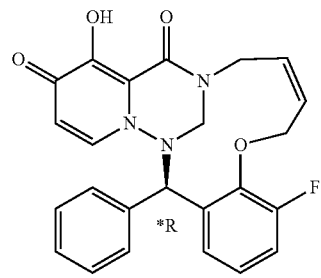 |
| 58B 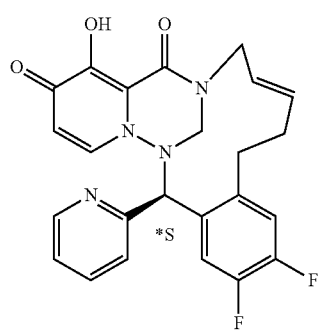 [SMILES: O=C1c2c(O)c(=O)ccn2N2CN1C/C=C/CCc1cc(F)c(F)cc1[C@H]2c1ccccn1] | 61B 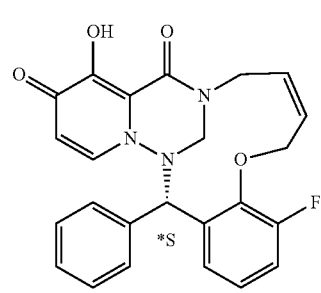 [SMILES: O=C1c2c(O)c(=O)ccn2N2CN1C/C=C\COc1c(F)cccc1[C@@H]2c1ccccc1] |
| 59A 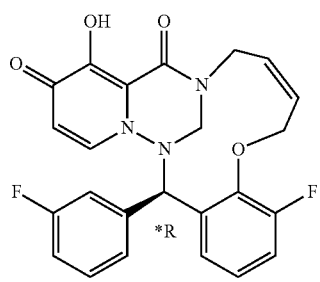 | 62 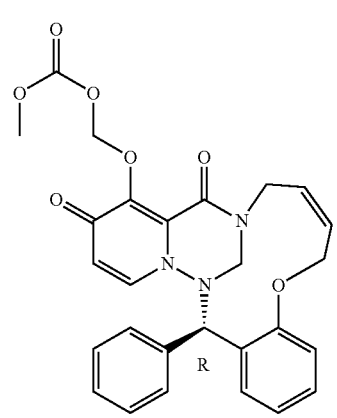 |
| 59B 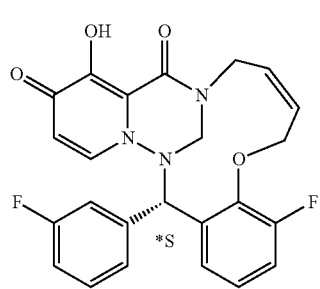 | 63A 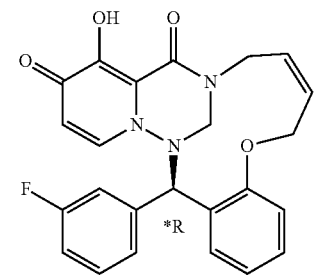 |

651
-continued
63B
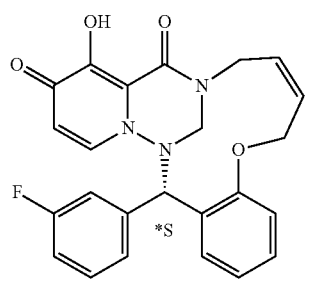
65A
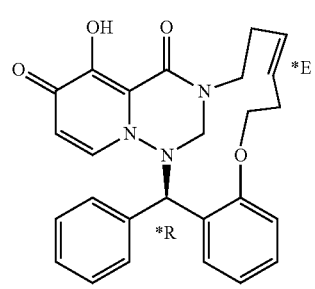
65B
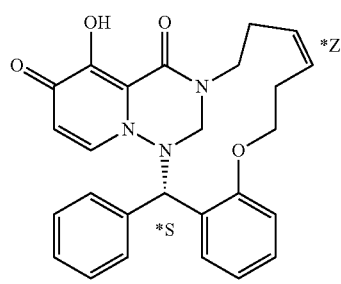
65C
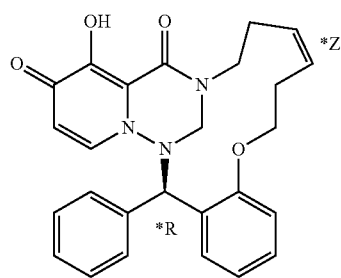
65D
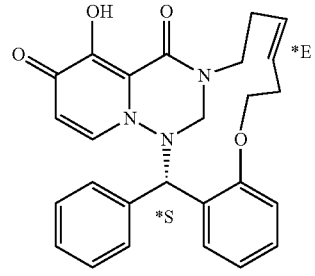
652
-continued
67A
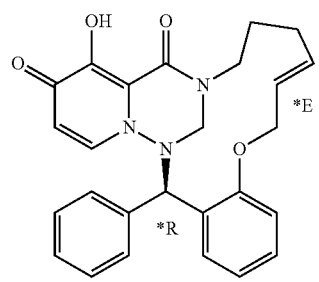
67B
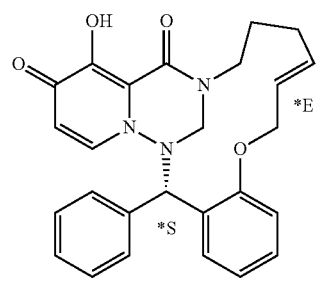
69A
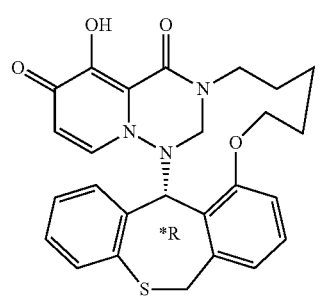 [SMILES: O=C1c2c(O)c(=O)ccn2N2CN1CCCCCOc1cccc3c1[C@@H]2c1ccccc1SC3]
69B
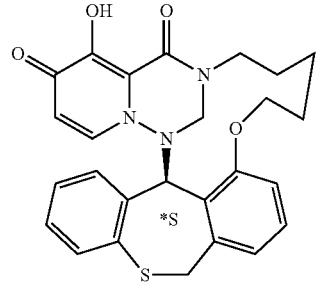 [SMILES: O=C1c2c(O)c(=O)ccn2N2CN1CCCCCOc1cccc3c1[C@H]2c1ccccc1SC3]
70A
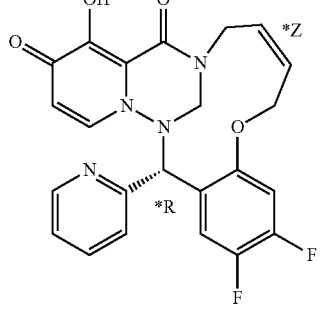

| 653 -continued | 654 -continued |
|---|---|
| 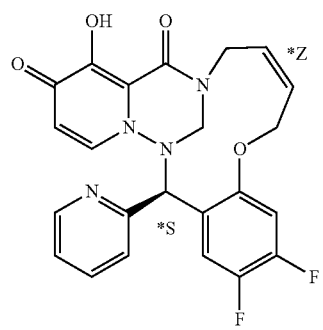 [SMILES: O=C1c2c(O)c(=O)ccn2N2CN1C/C=C\COc1cc(F)c(F)cc1[C@H]2c1ccccn1] 70B | 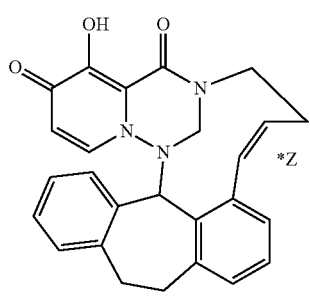 73 |
| 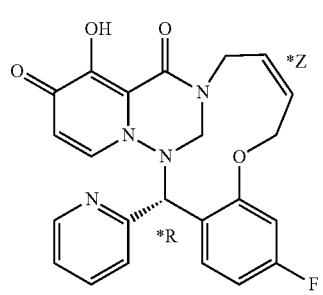 71A | 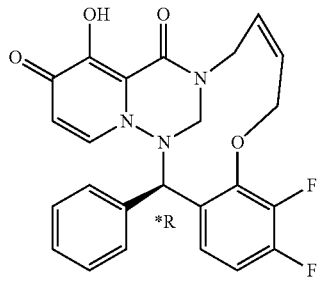 74A |
| 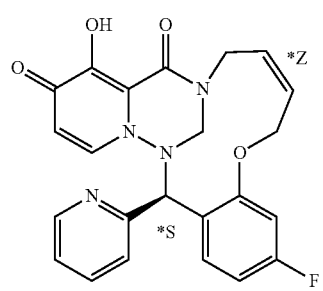 [SMILES: O=C1c2c(O)c(=O)ccn2N2CN1C/C=C\COc1cc(F)ccc1[C@H]2c1ccccn1] 71B | 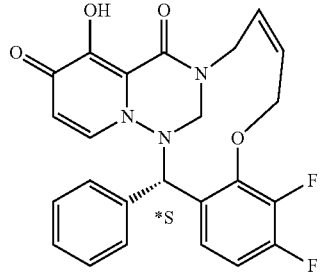 74B |
| 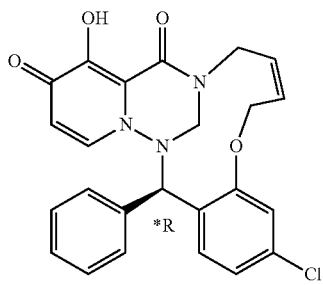 72A | 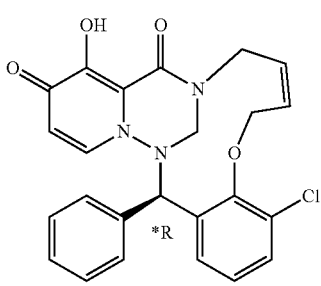 75A |
| 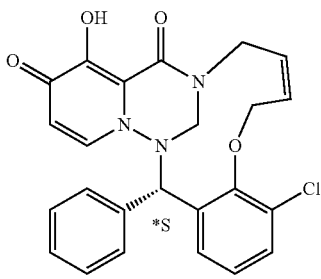 72B | 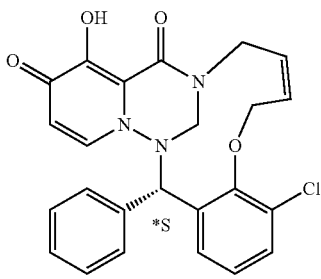 75B |

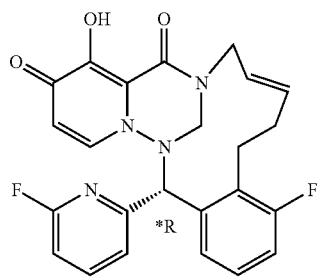
76A
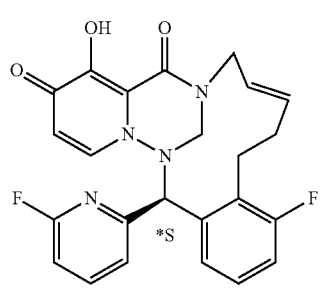
76B
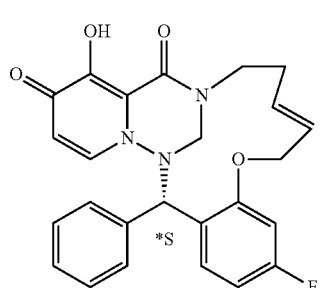
77A
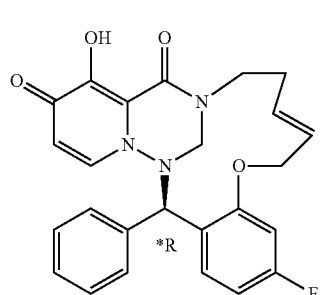
77B
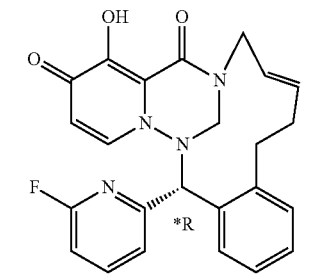
78A
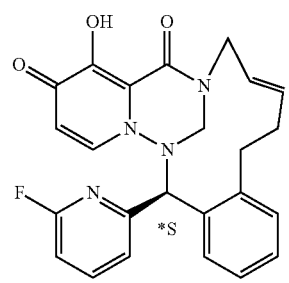
78B
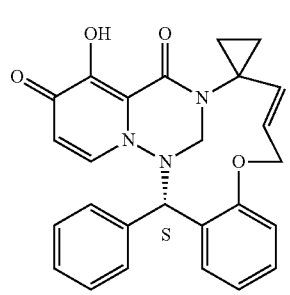
79A
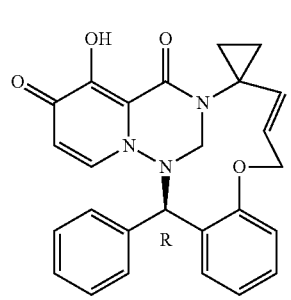
79B
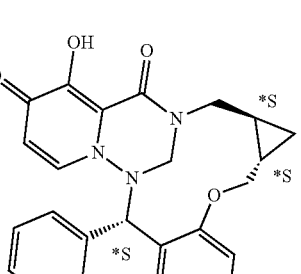
80AA
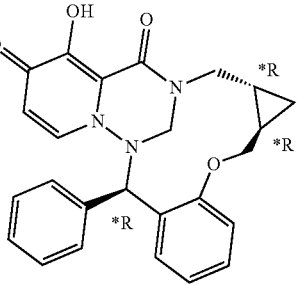
80AB 80BA
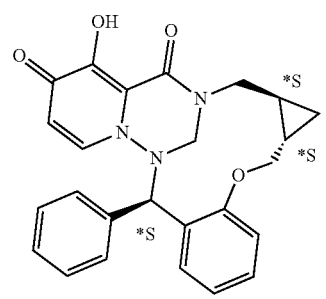
80BB
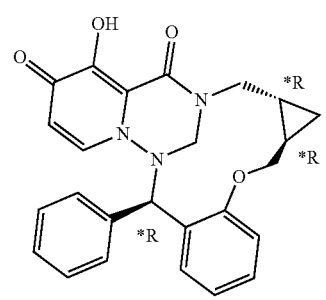
81
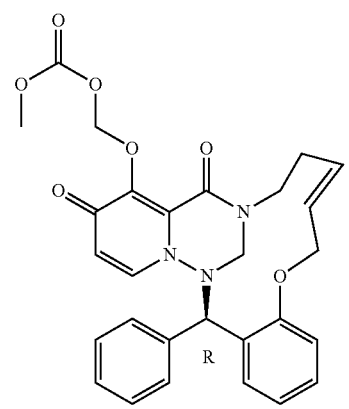
82
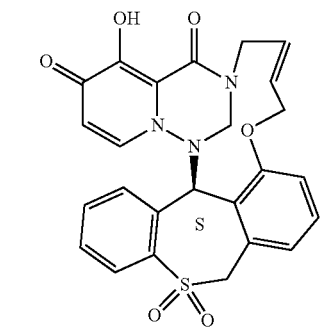
83A
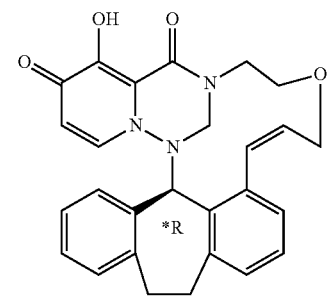
83B
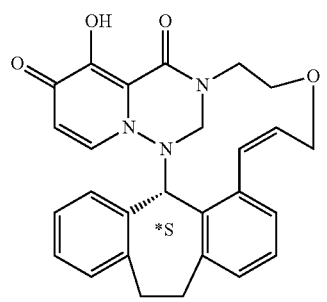
84A
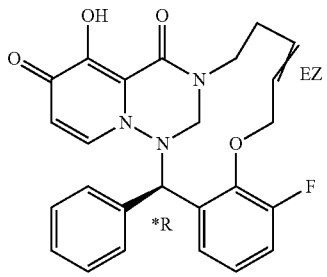
84B
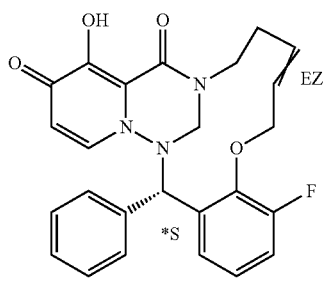
85AA
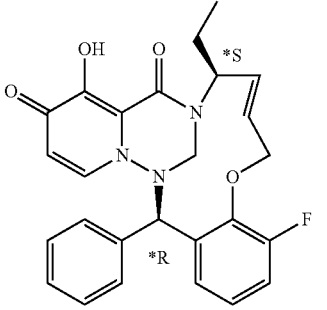
85AB
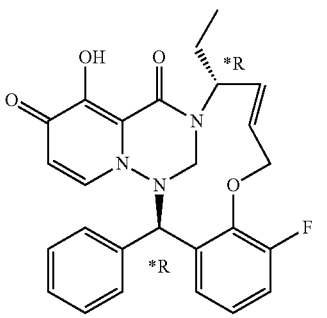

| 659 -continued | | 660 -continued | |
|---|---|---|---|
| 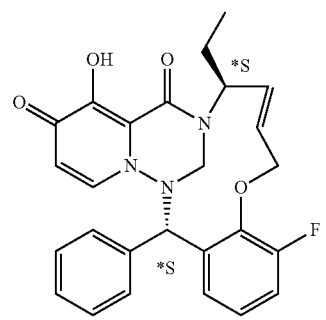 | 85BA | 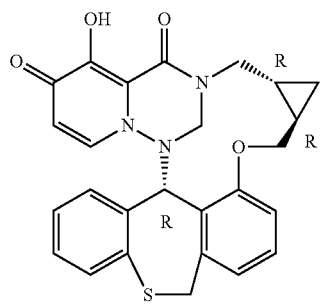 | 87AB |
| 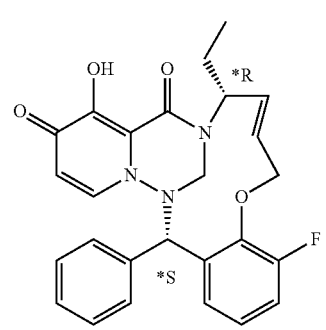 | 85BB | 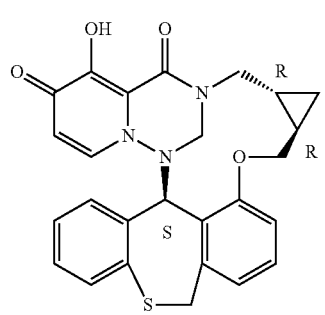 | 87BB |
| 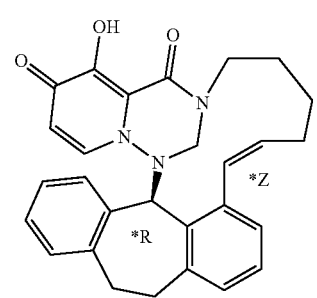 | 86A | 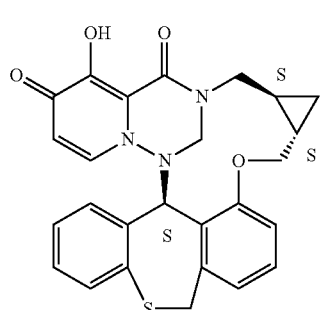 | 87BA |
| 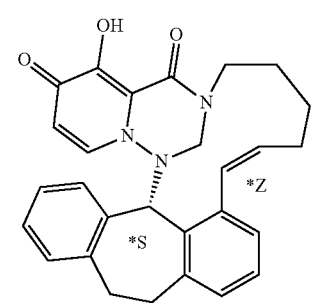 | 86B | 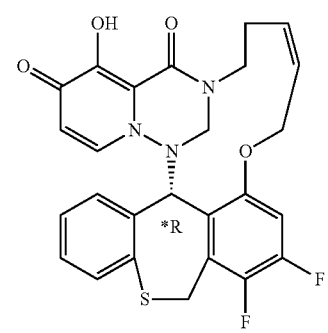 | 88A |
| 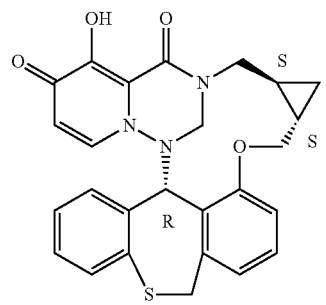 | 87AA | 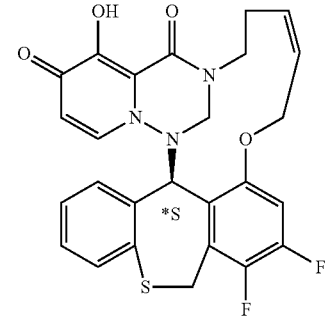 | 88B |

661
-continued
88C
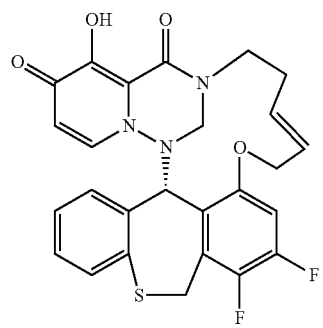
88D
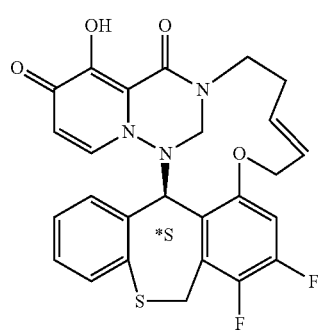
89AA
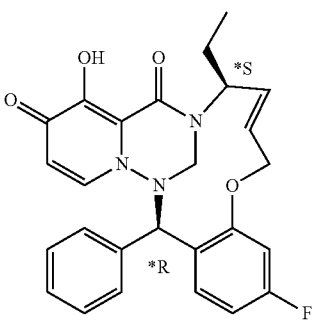
89BB
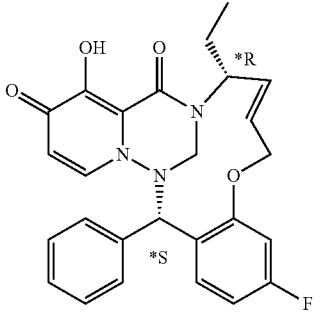
91A
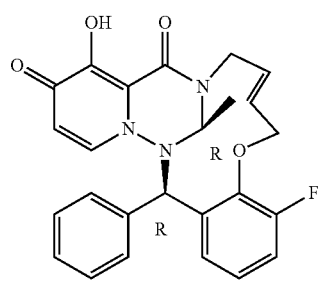
662
-continued
91B
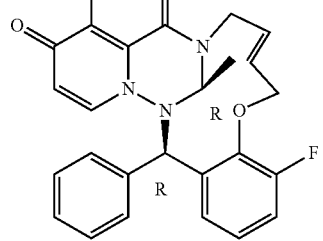
92AA
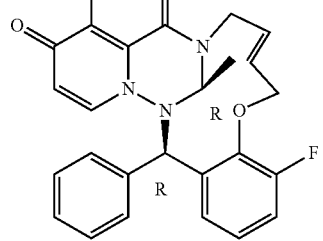
92AB
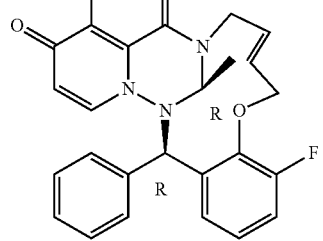
92BA
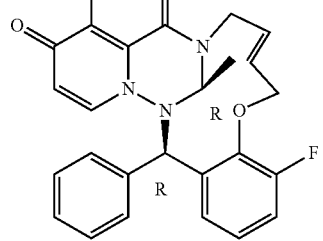
92BB
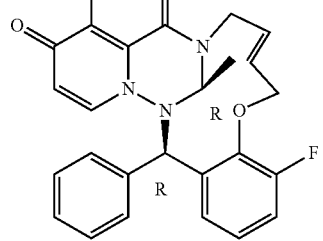

| | |
|---|---|
| 93B 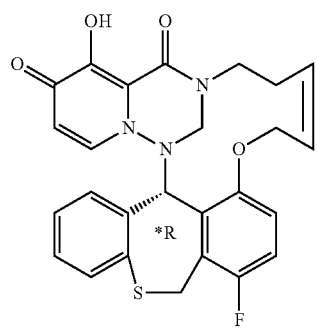 | 95B 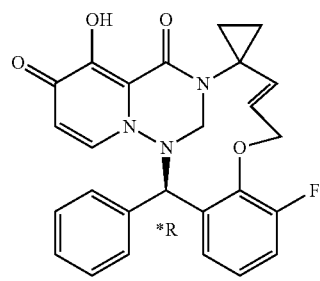 |
| 93B 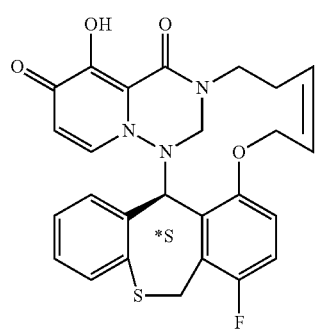 [SMILES: O=C1c2c(O)c(=O)ccn2N2CN1CC/C=C\COc1ccc(F)c3c1[C@H]2c1ccccc1SC3] | 96A 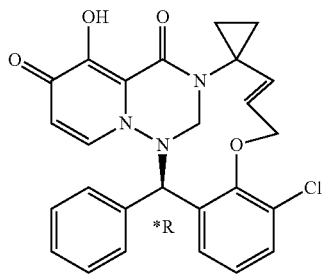 |
| 94A 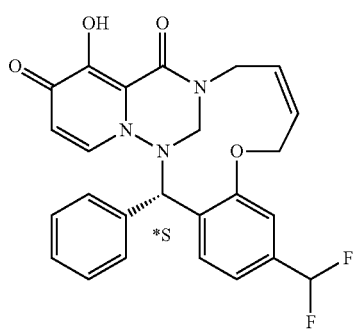 [SMILES: O=C1c2c(O)c(=O)ccn2N2CN1C/C=C\COc1cc(C(F)F)ccc1[C@@H]2c1ccccc1] | 96B 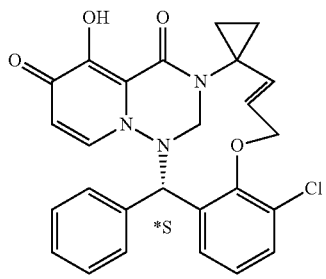 |
| 94B 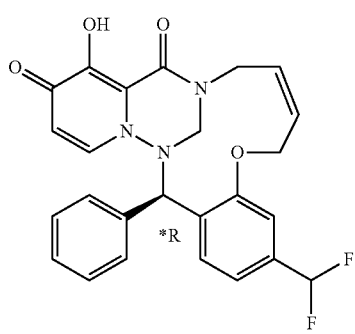 [SMILES: O=C1c2c(O)c(=O)ccn2N2CN1C/C=C\COc1cc(C(F)F)ccc1[C@H]2c1ccccc1] | 97AA 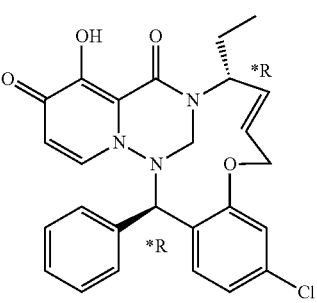 |
| 95A 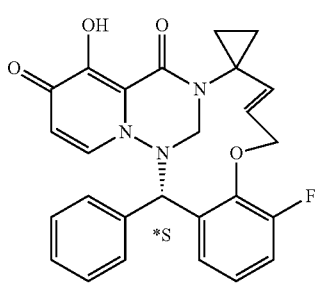 [SMILES: O=C1c2c(O)c(=O)ccn2N2CN1C1(/C=C/COc3c(F)cccc3[C@@H]2c2ccccc2)CC1] | 97AB 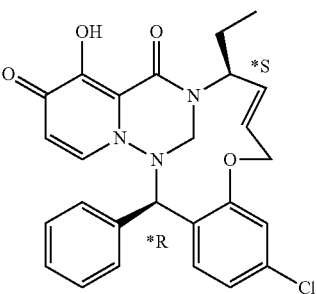 |

97BA
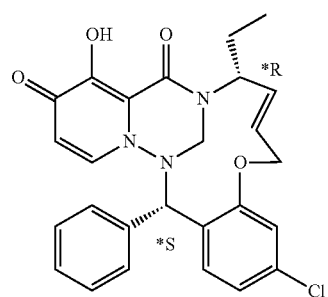
97BB
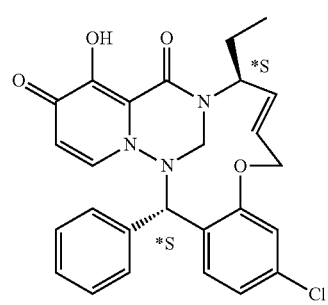
98AA
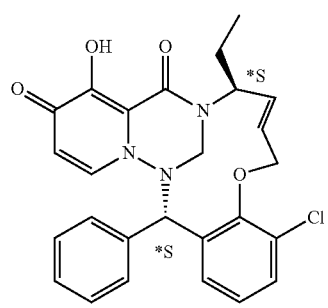
98AB
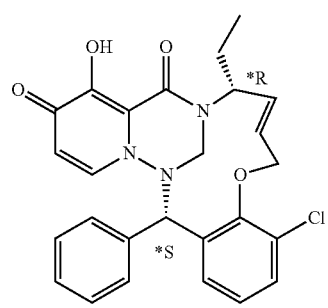
98BA
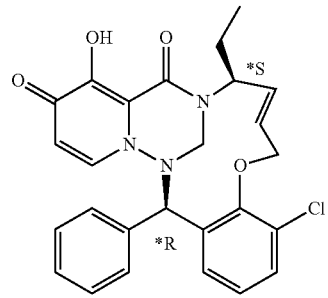
98BB
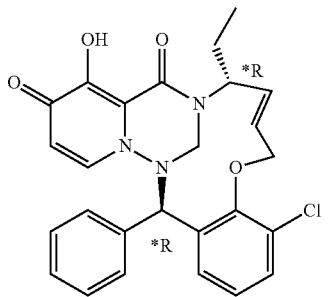
99A
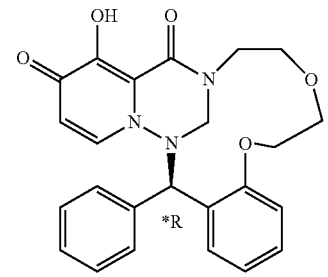
99B
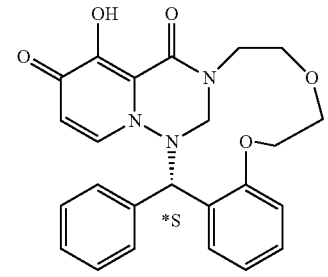 [SMILES: O=C1c2c(O)c(=O)ccn2N2CN1CCOCCOc1ccccc1[C@@H]2c1ccccc1]
100AA
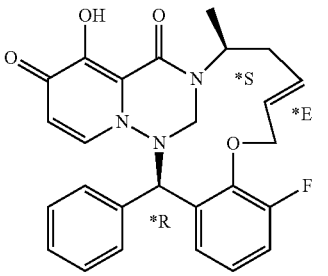
100AB
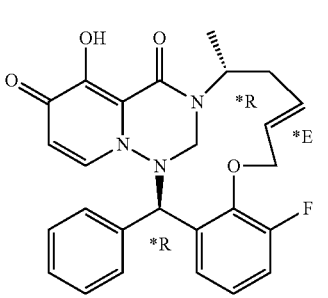

-continued
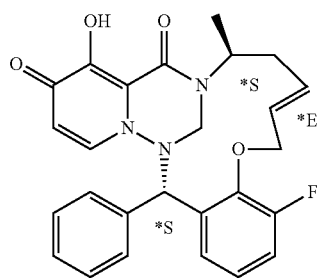
100BA
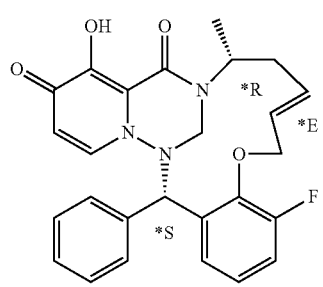
100BB
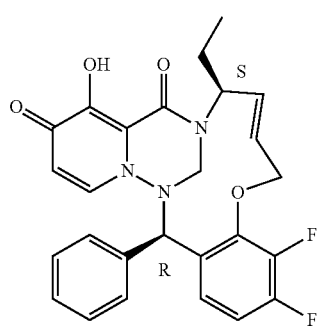
101AA
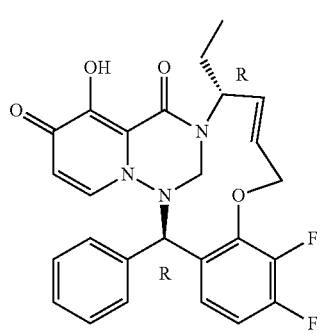
101AB
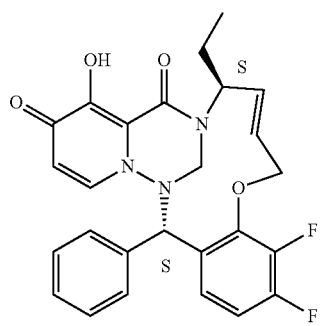
101BA
-continued
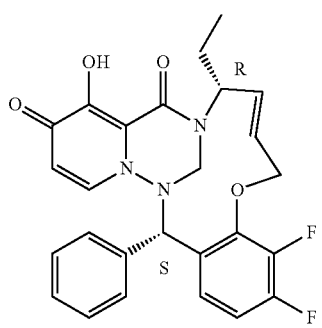
101BB
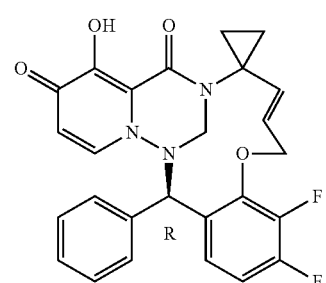
102A
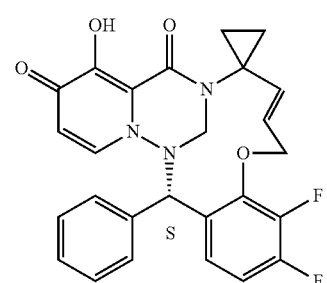
102B
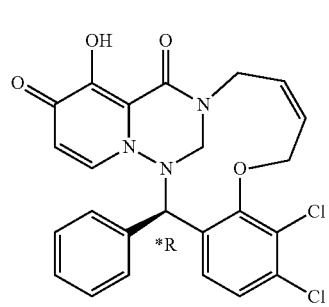
103A
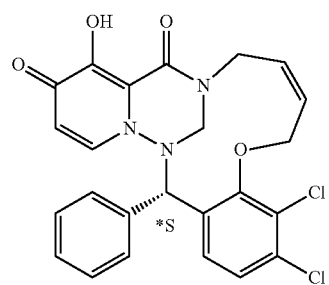
103B

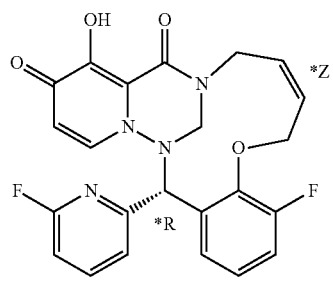
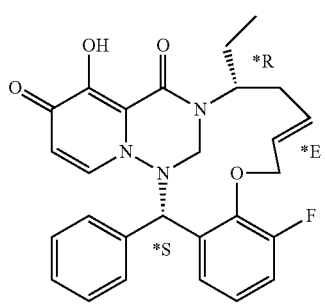
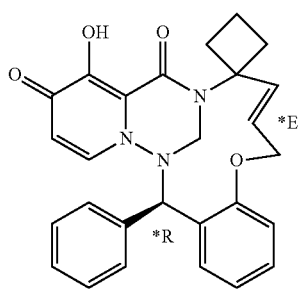
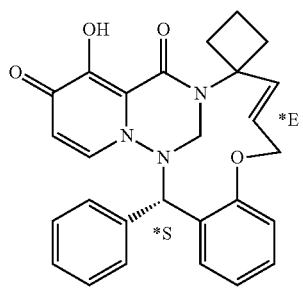
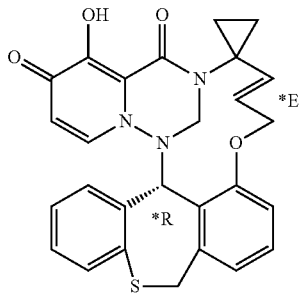
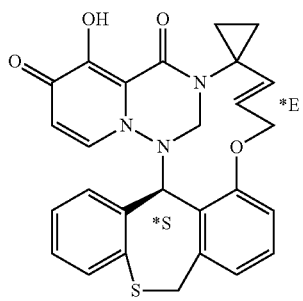

| | |
|---|---|
| 108A 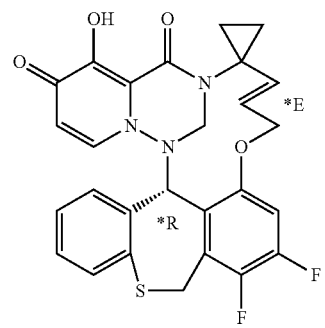 | 109B 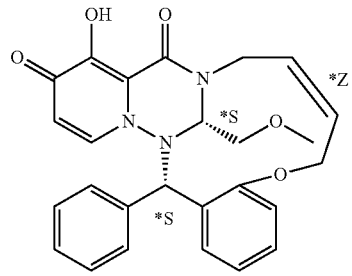 |
| 108B 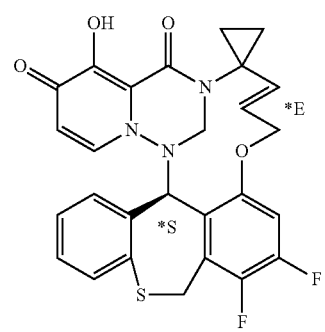 | 110A 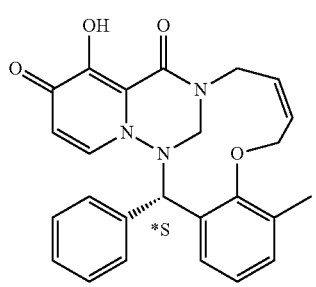 [SMILES: Cc1cccc2c1OC/C=C\CN1CN([C@H]2c2ccccc2)n2ccc(=O)c(O)c2C1=O] |
| 108C 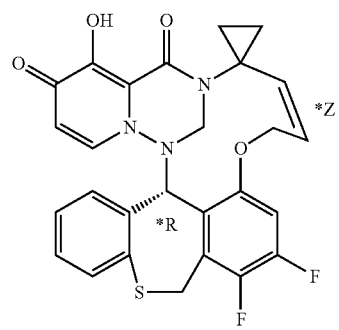 | 110B 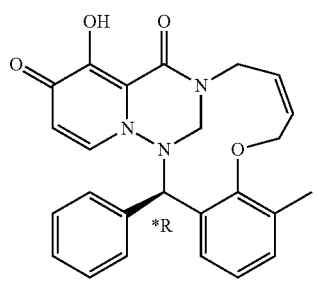 [SMILES: Cc1cccc2c1OC/C=C\CN1CN([C@@H]2c2ccccc2)n2ccc(=O)c(O)c2C1=O] |
| 108D 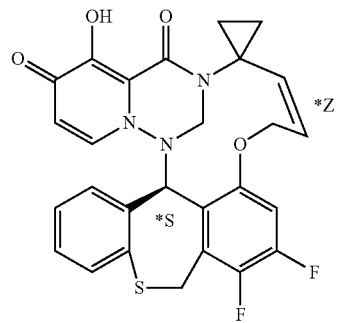 | 111A 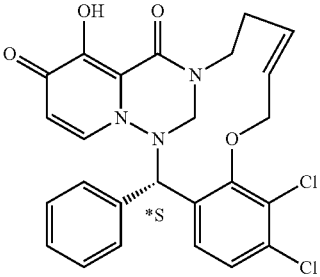 |
| 109A 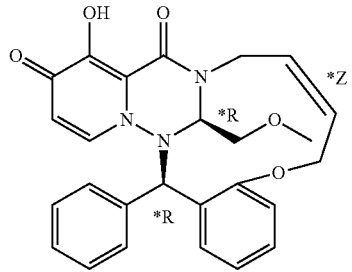 | 112A 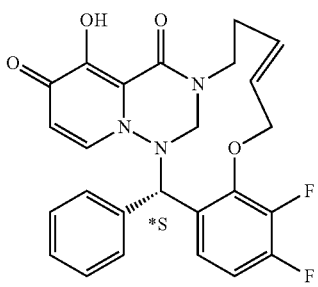 |

-continued
| | |
|---|---|
| 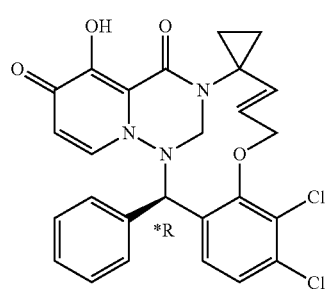 113A | 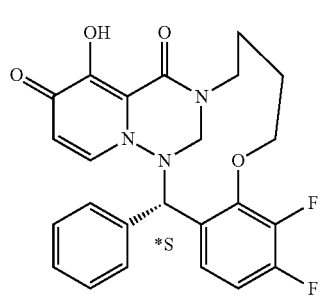 115B |
| 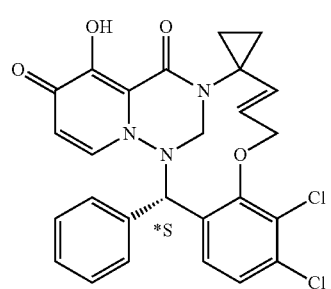 113B | 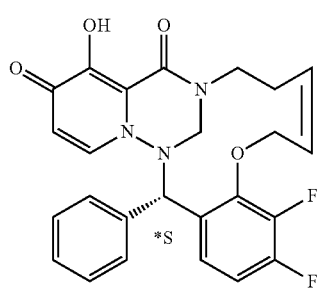 116A |
| 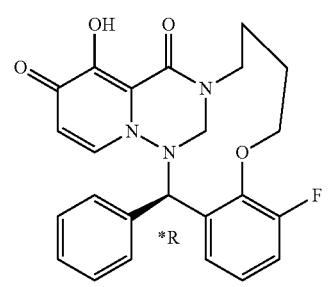 [SMILES: O=C1c2c(O)c(=O)ccn2N2CN1CCCCOc1c(F)cccc1[C@H]2c1ccccc1] 114A | 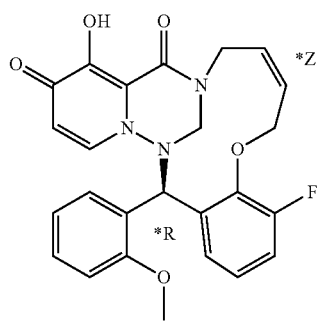 117A |
| 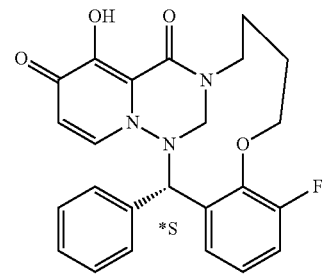 [SMILES: O=C1c2c(O)c(=O)ccn2N2CN1CCCCOc1c(F)cccc1[C@@H]2c1ccccc1] 114B | 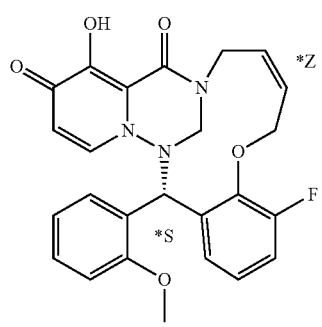 117B |
| 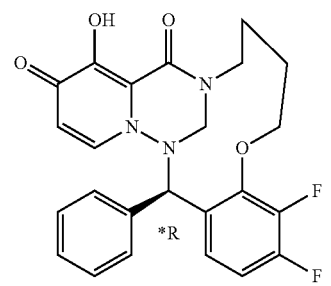 [SMILES: O=C1c2c(O)c(=O)ccn2N2CN1CCCCOc1c(ccc(F)c1F)[C@H]2c1ccccc1] 115A | 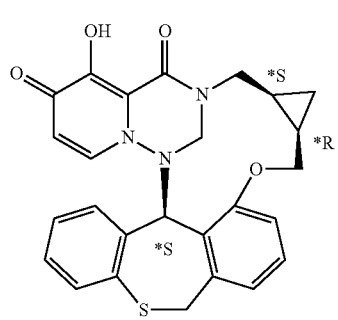 [SMILES: O=C1c2c(O)c(=O)ccn2N2CN1C[C@H]1C[C@H]1COc1cccc3c1[C@H]2c1ccccc1SC3] 118AA |

118AB
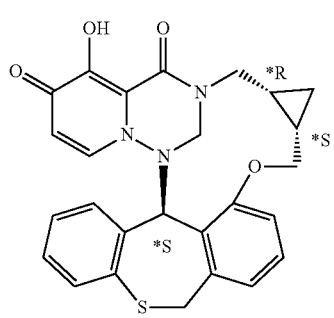 [SMILES: O=C1c2c(O)c(=O)ccn2N2CN1C[C@@H]1C[C@@H]1COc1cccc3c1[C@H]2c1ccccc1SC3]
119A
121AA
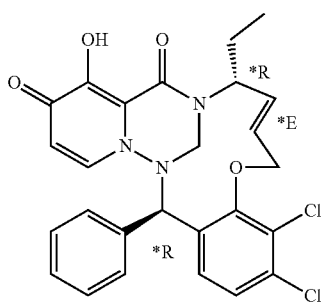
119B
121AB
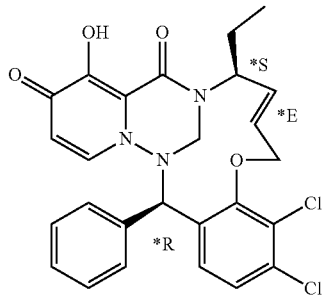
120
121BA
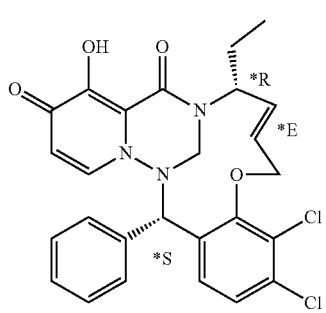
121BB
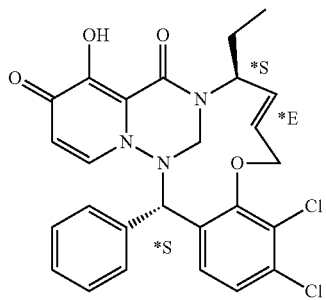
122
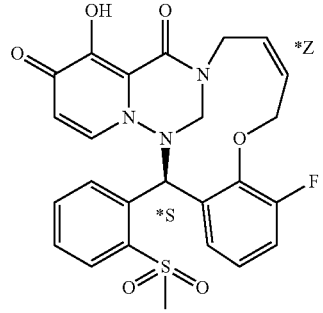 [SMILES: CS(=O)(=O)c1ccccc1[C@@H]1c2cccc(F)c2OC/C=C\CN2CN1n1ccc(=O)c(O)c1C2=O]

| | |
|---|---|
| 123A 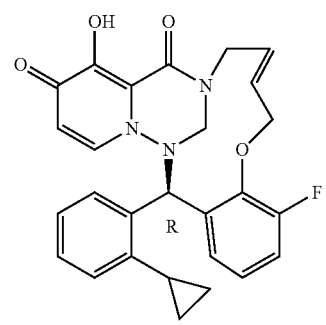 | 125AB 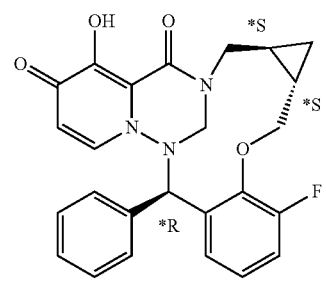 |
| 123B 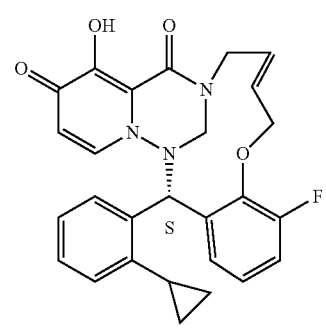 | 125BA 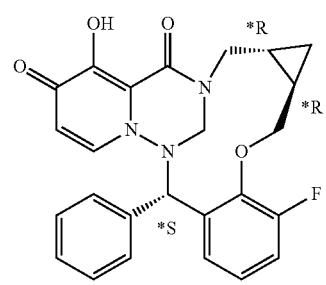 |
| 124AA 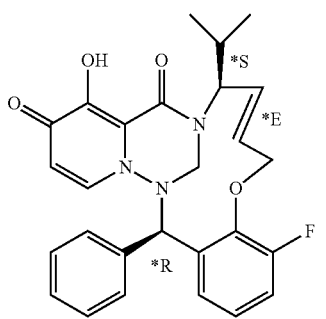 | 125BB 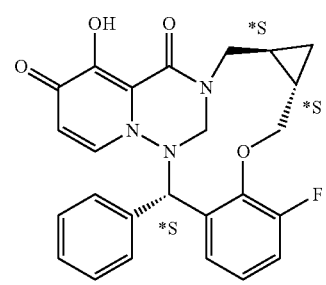 |
| 124BB 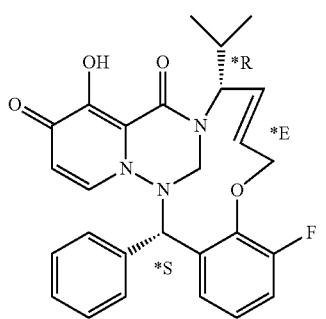 | 126AA 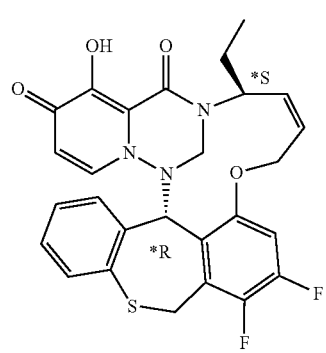 |
| 125AA 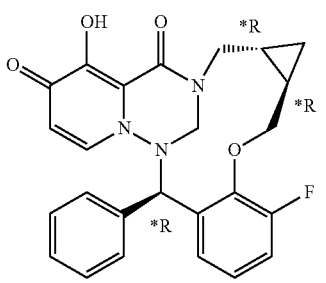 | 126AB 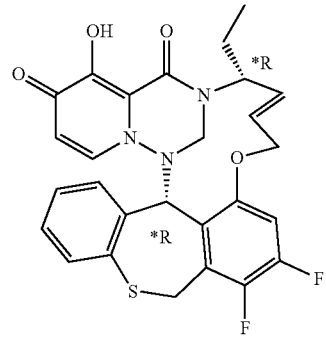 |

126BA
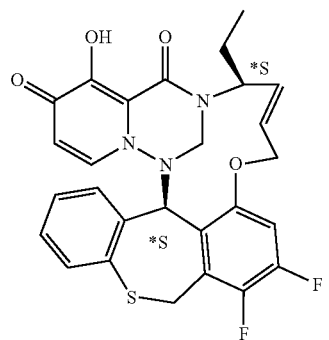
126BB
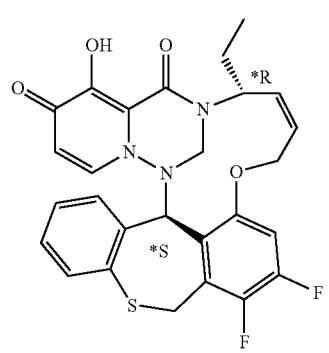
127AA
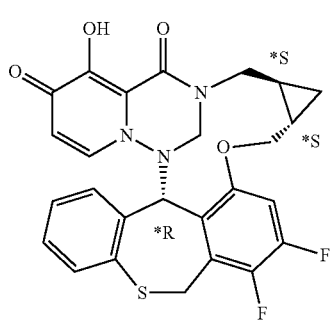
127BA
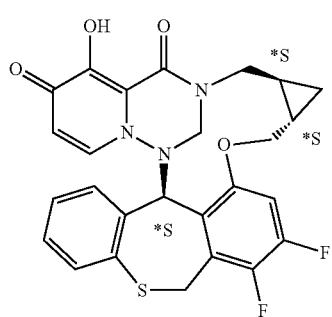
128AA
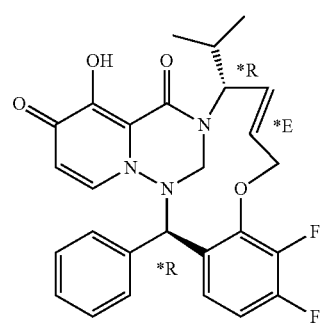
128AB
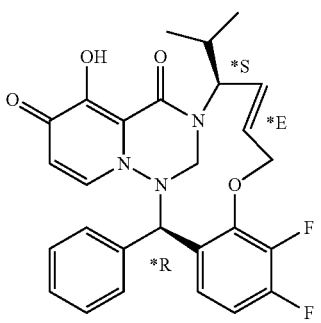
128BA
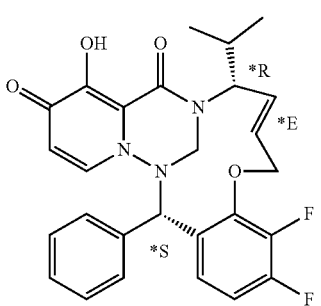
128BB
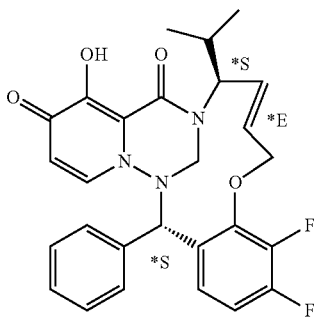
129
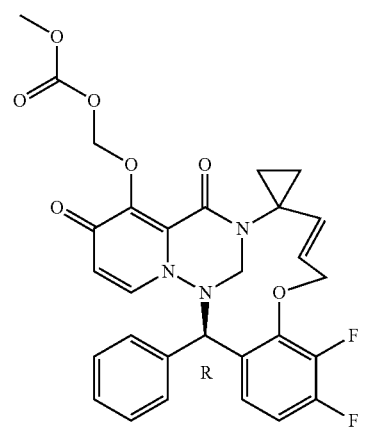
130A
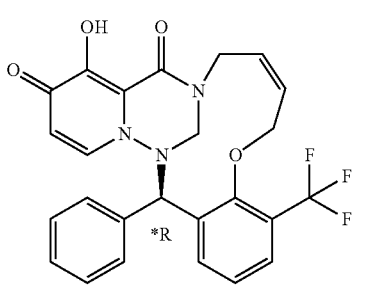 [SMILES: O=C1c2c(O)c(=O)ccn2N2CN1C/C=C\COc1c(cccc1C(F)(F)F)[C@H]2c1ccccc1]

130B
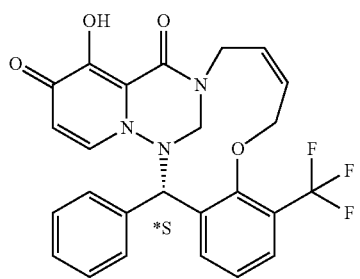
131AA
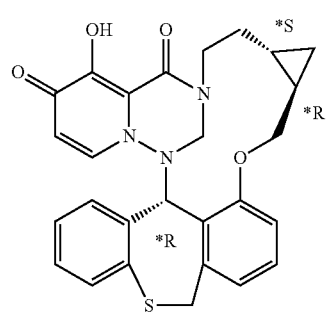
131AB
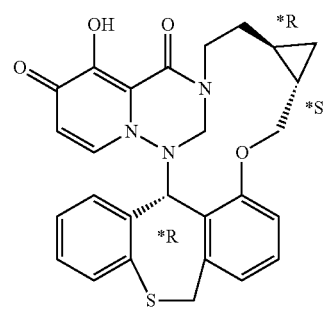
131BA
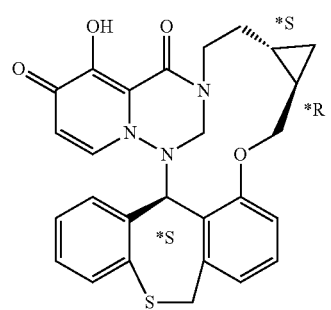
131BB
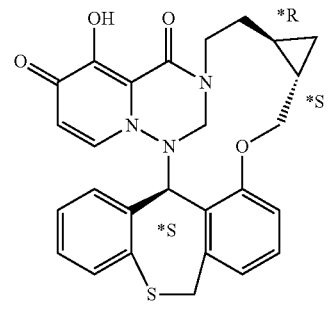
132A
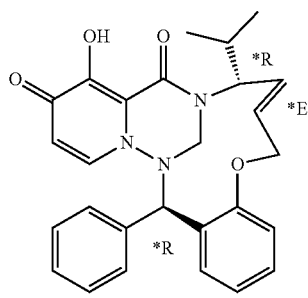
132B
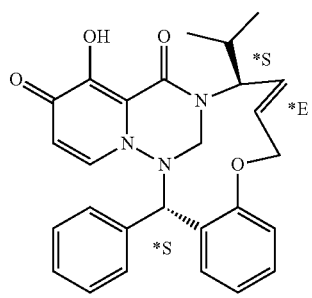
133A
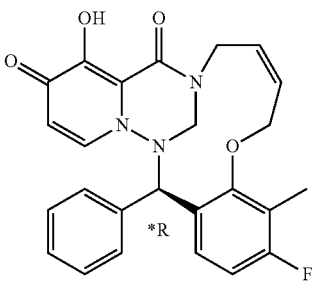 [SMILES: Cc1c(F)ccc2c1OC/C=C\CN1CN([C@@H]2c2ccccc2)n2ccc(=O)c(O)c2C1=O]
133B
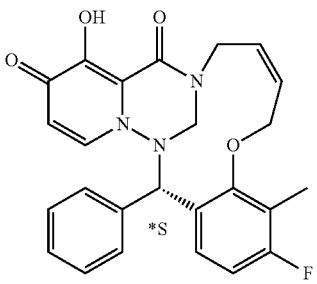 [SMILES: Cc1c(F)ccc2c1OC/C=C\CN1CN([C@H]2c2ccccc2)n2ccc(=O)c(O)c2C1=O]
134A
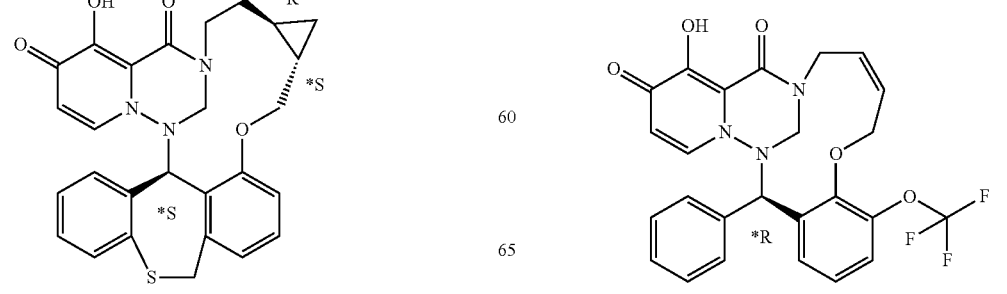

134B
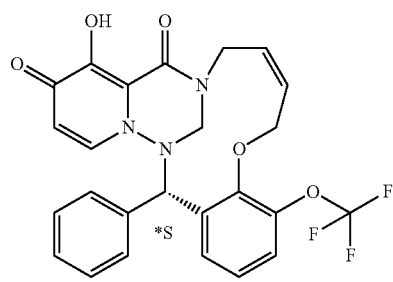 [SMILES: O=C1c2c(O)c(=O)ccn2N2CN1C/C=C\COc1c(OC(F)(F)F)cccc1[C@@H]2c1ccccc1]
135A
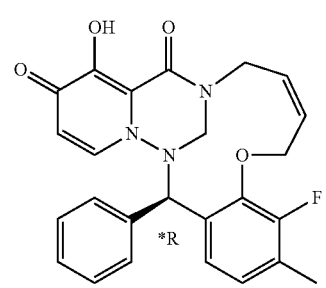 [SMILES: Cc1ccc2c(c1F)OC/C=C\CN1CN([C@@H]2c2ccccc2)n2ccc(=O)c(O)c2C1=O]
135B
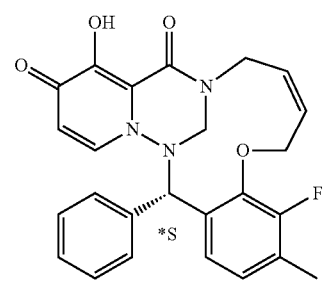
136A
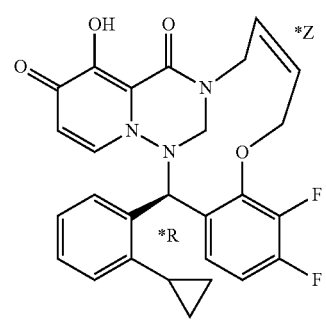 [SMILES: O=C1c2c(O)c(=O)ccn2N2CN1C/C=C\COc1c(ccc(F)c1F)[C@H]2c1ccccc1C1CC1]
136B
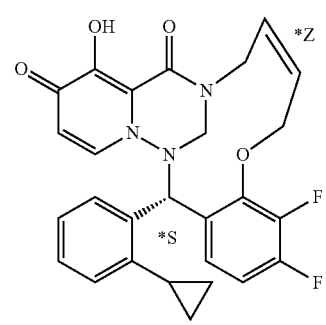
137A
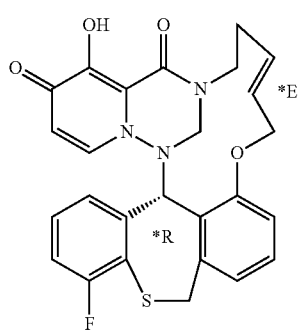
137B
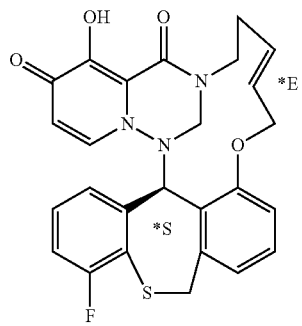
138C
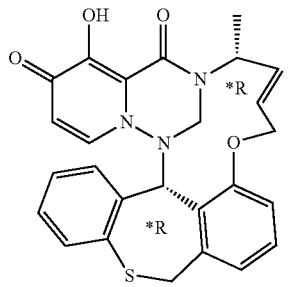
138D
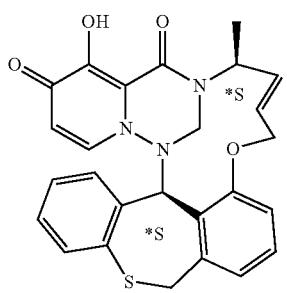
138AA
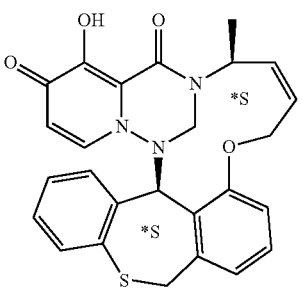

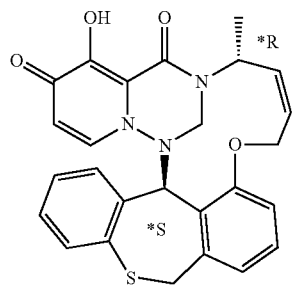 138AB
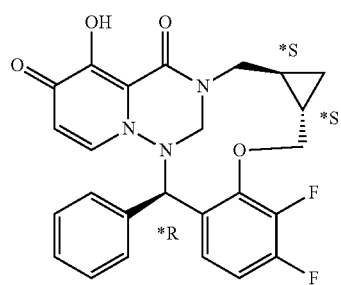 139BA
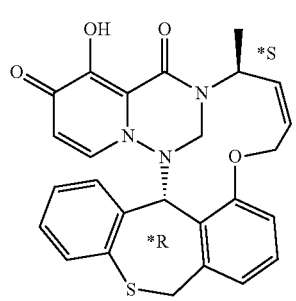 138BA
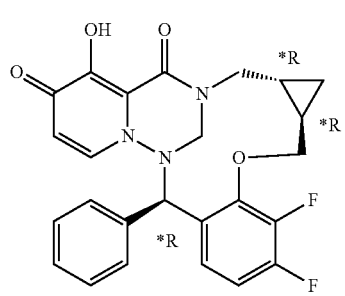 139BB
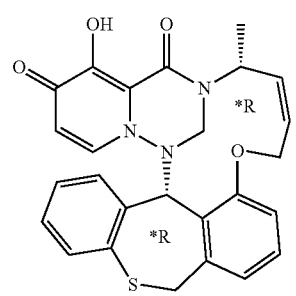 138BB
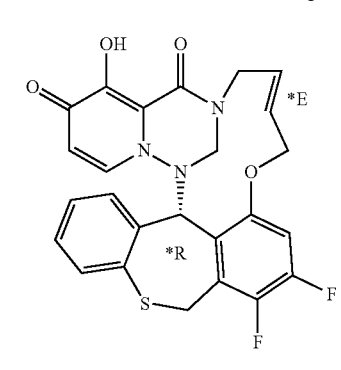 140A
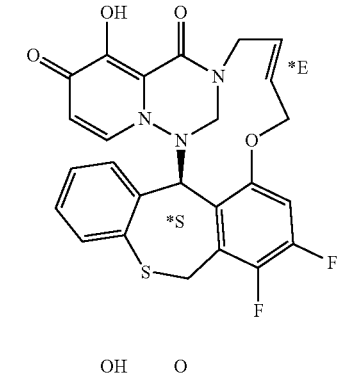 140B
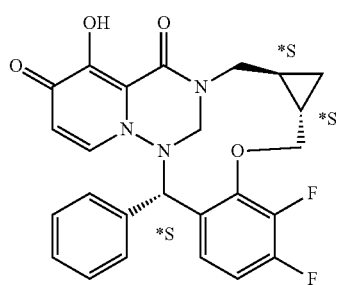 139AA
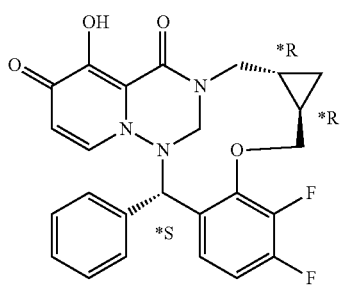 139AB
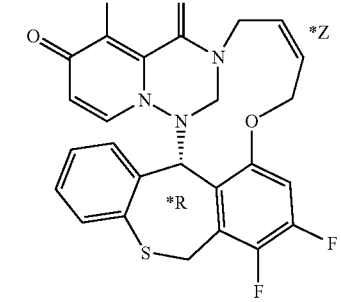 140C 140D
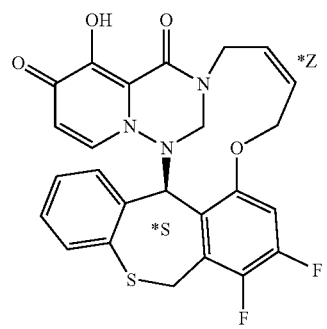
141AA
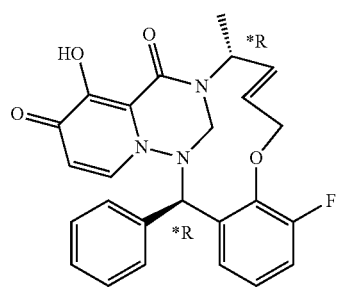
141AB
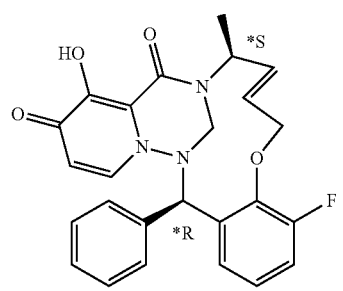
141BA
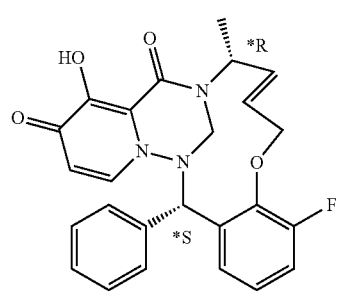
141BB
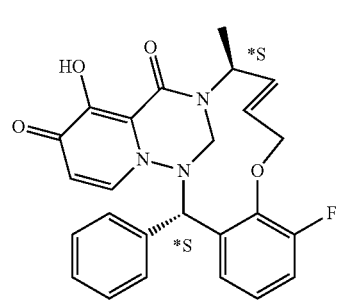
142
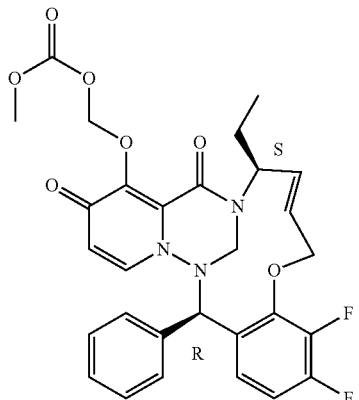
143
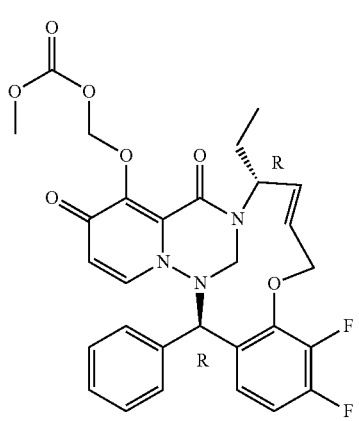
144AA
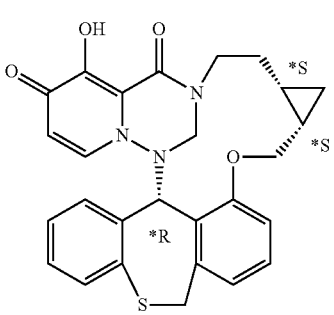
144AB
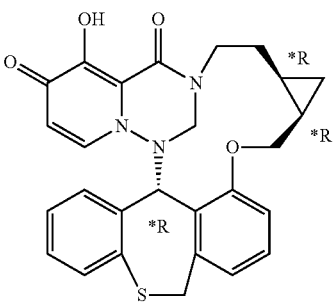

| 144BA | 146B |
|---|---|
| 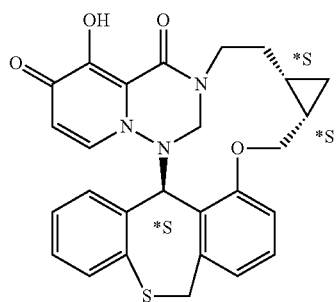 | 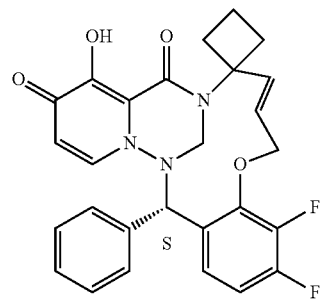 |
| 144BB | 147A |
| 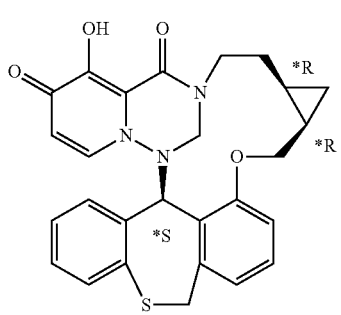 | 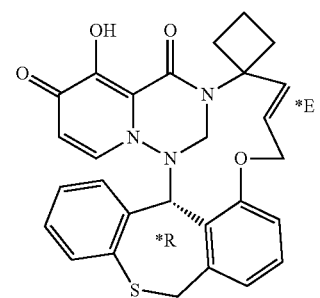 |
| 145A | 147B |
| 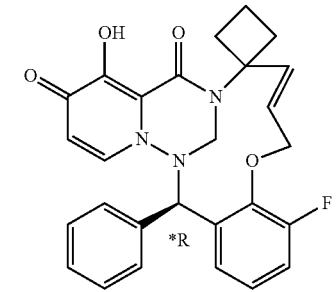 | 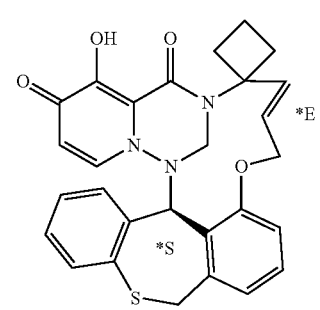 |
| 145B | 148AA |
| 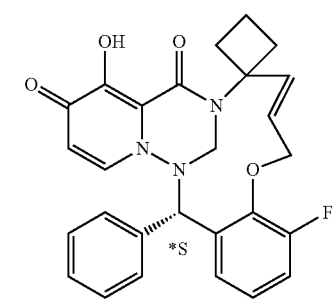 | 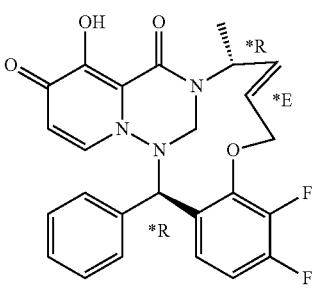 |
| 146A | 148AB |
| 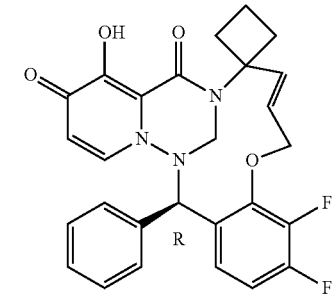 | 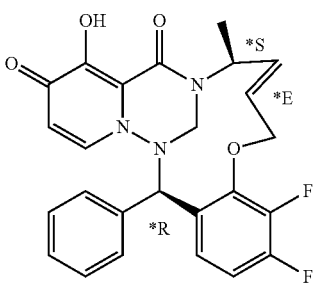 |

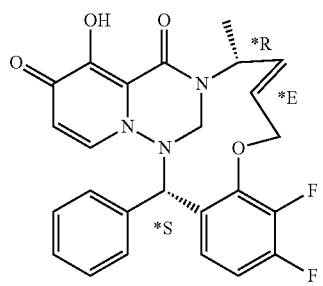 [SMILES: C[C@@H]1/C=C/COc2c(ccc(F)c2F)[C@H](c2ccccc2)N2CN1C(=O)c1c(O)c(=O)ccn12] 148BA
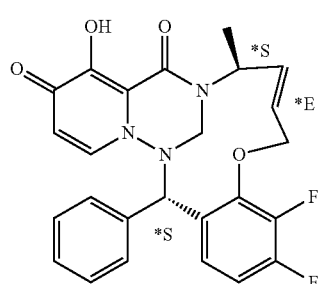 148BB
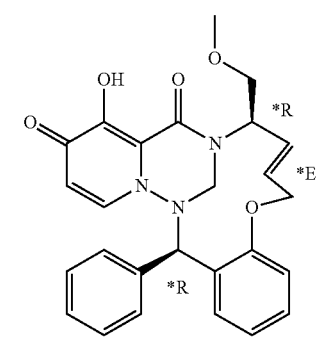 150A
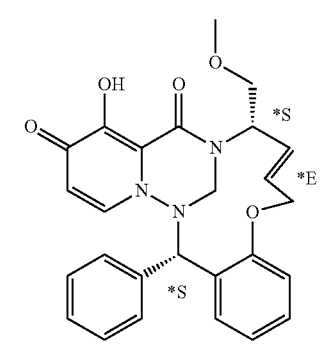 150B
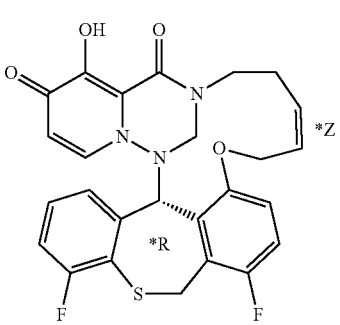 151A
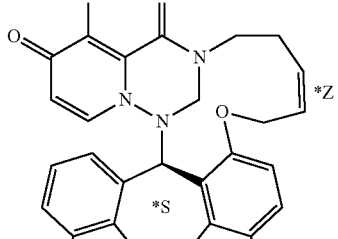 151B
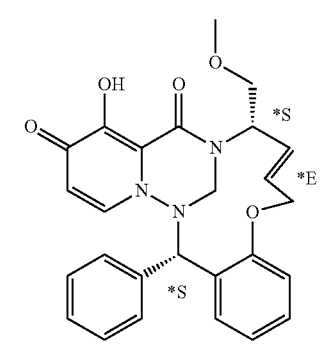 152AA
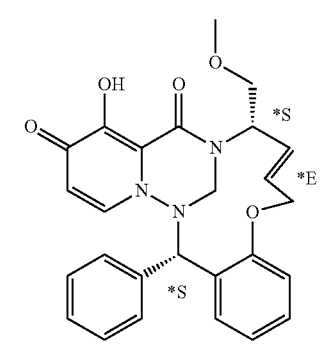 152AB
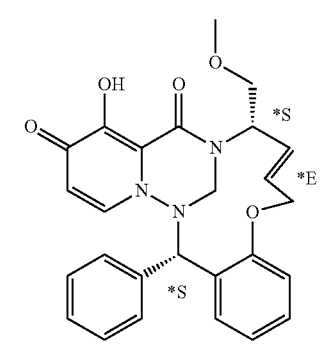 152BA
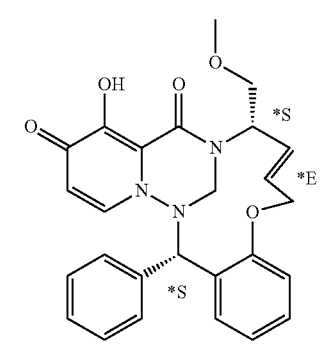 152BB 153AA 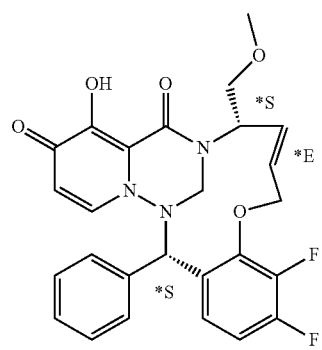
153AB 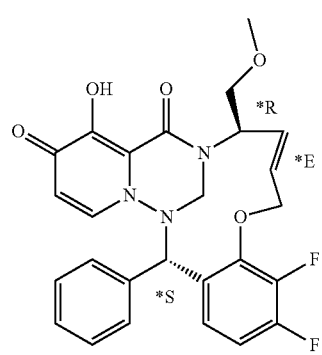
153BA 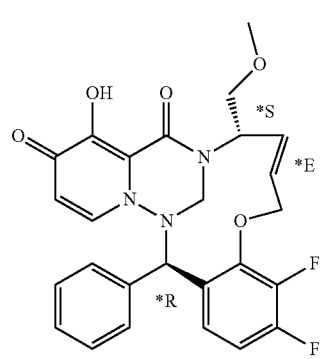
153BB 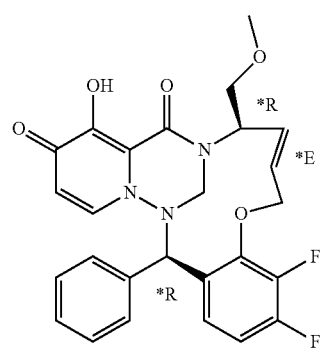
154AA 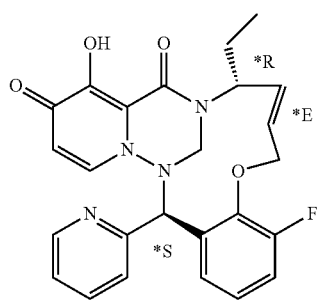
154AB 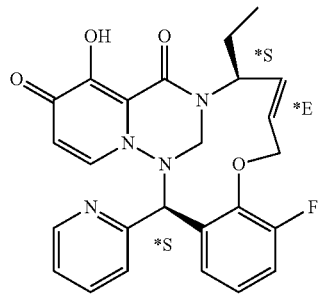
154BA 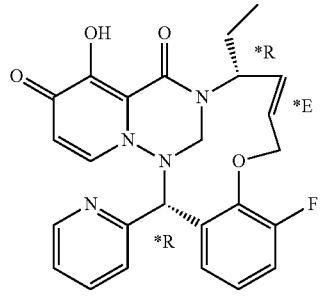
154BB 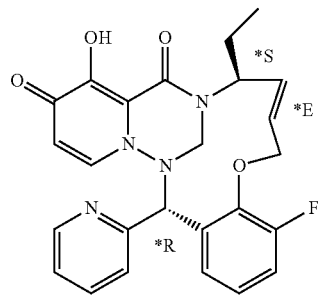
155A 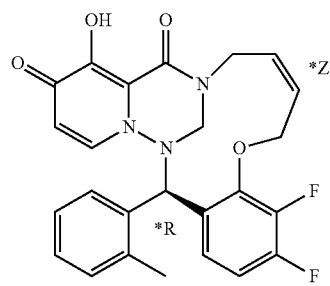

| 155B | 158B |
|---|---|
| 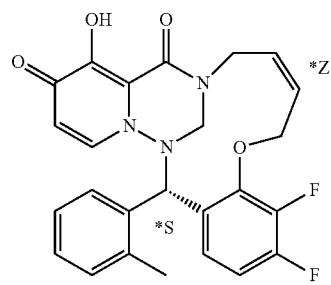 | 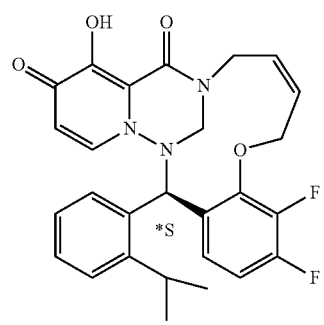 [SMILES: CC(C)c1ccccc1[C@@H]1c2ccc(F)c(F)c2OC/C=C\CN2CN1n1ccc(=O)c(O)c1C2=O] |
| 156A | 159A |
| 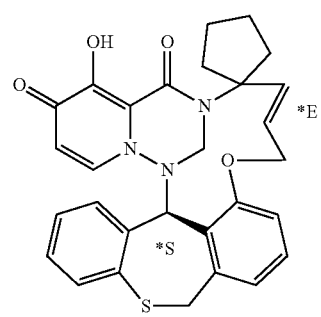 | 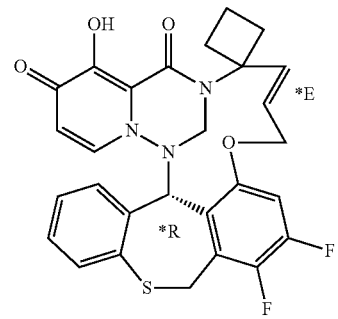 |
| 157A | 159B |
| 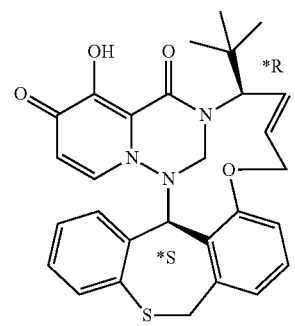 | 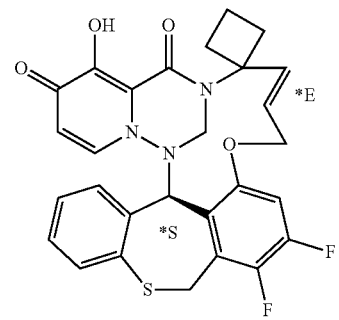 [SMILES: O=C1c2c(O)c(=O)ccn2N2CN1C1(/C=C/COc3cc(F)c(F)c4c3[C@H]2c2ccccc2SC4)CCC1] |
| 157B | 160AA |
| 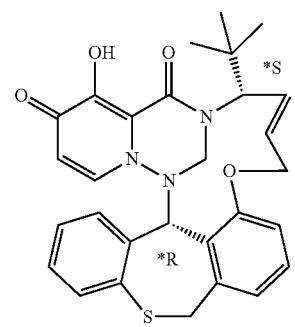 | 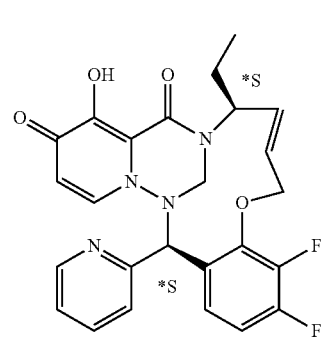 |
| 158A | 160AB |
| 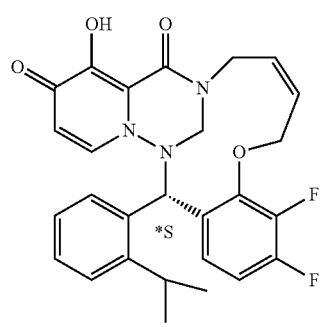 | 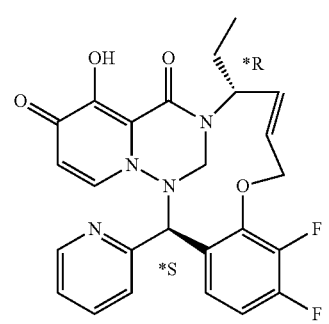 [SMILES: CC[C@@H]1/C=C/COc2c(ccc(F)c2F)[C@@H](c2ccccn2)N2CN1C(=O)c1c(O)c(=O)ccn12] |

160BA
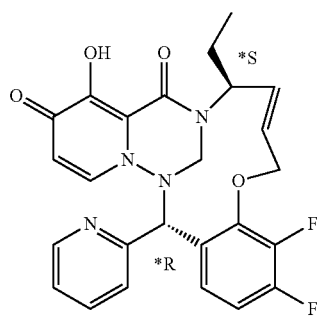
160BB
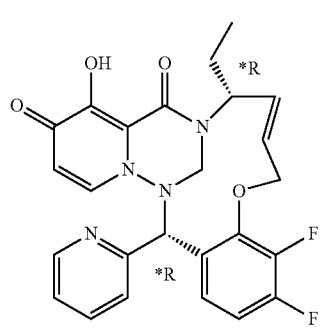
161A
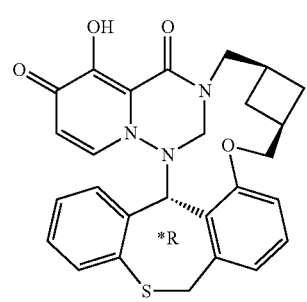
161B
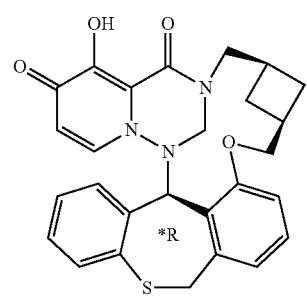
162A
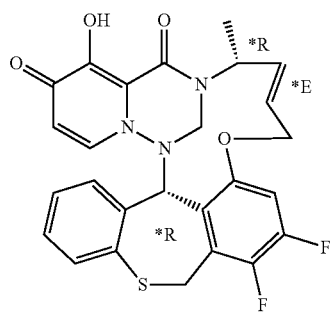
162B
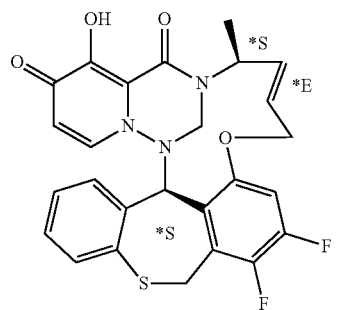
162C
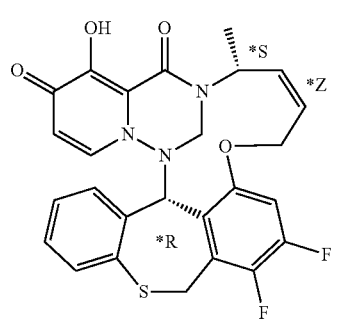 [SMILES: C[C@@H]1/C=C\COc2cc(F)c(F)c3c2[C@H](c2ccccc2SC3)N2CN1C(=O)c1c(O)c(=O)ccn12]
162D
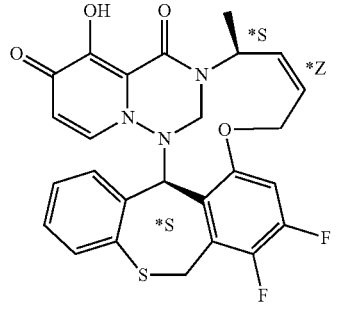
163AA
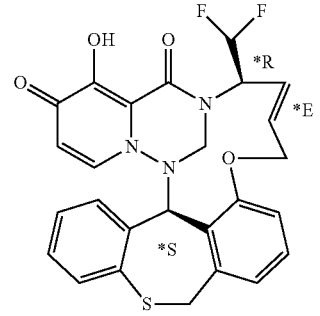
163BA
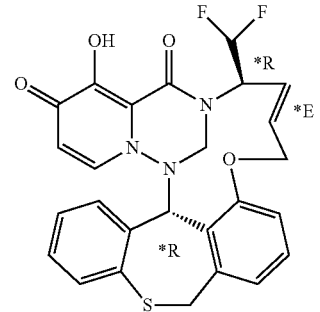

163BB
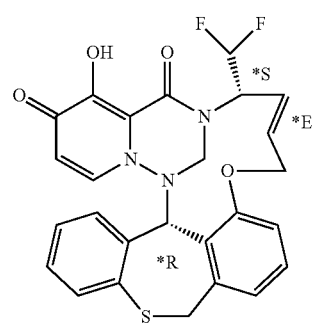
164A
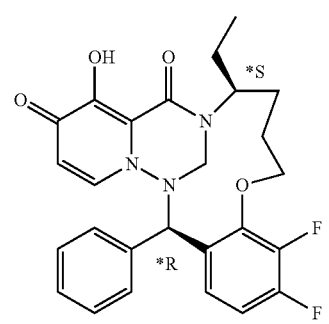
164B
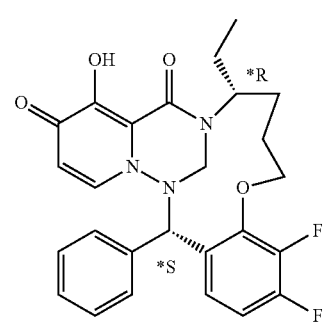
165A
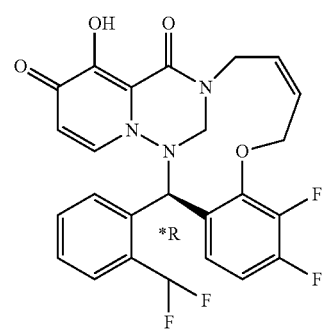
165B
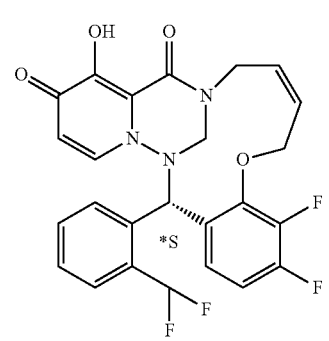
166A
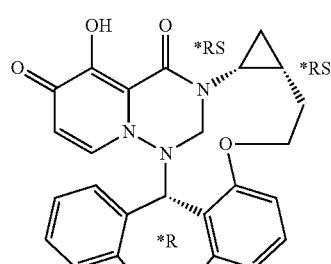
166B
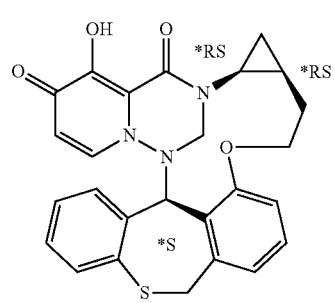
167AA
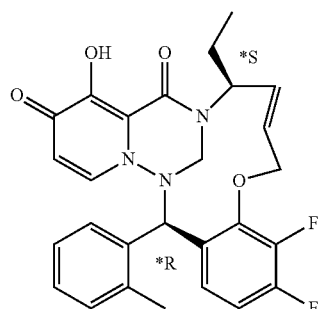
167AB
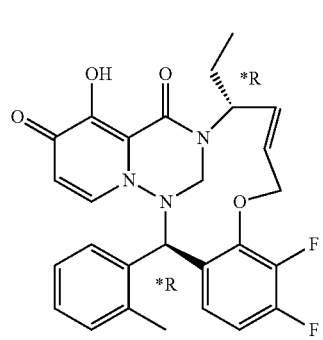
167BA
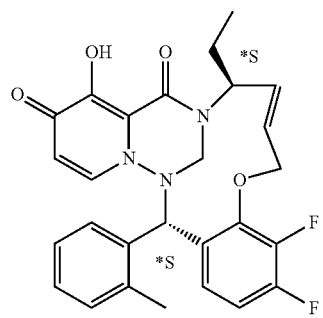

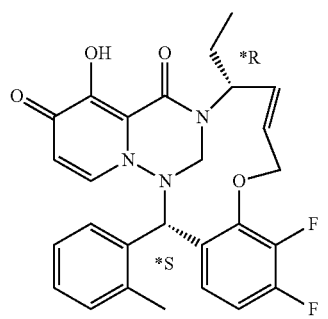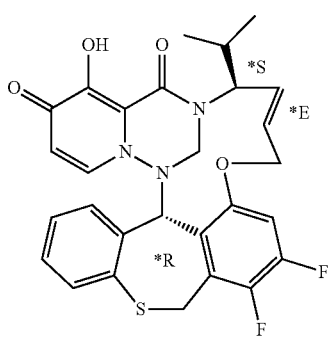 [SMILES: CC(C)[C@H]1/C=C/COc2cc(F)c(F)c3c2[C@H](c2ccccc2SC3)N2CN1C(=O)c1c(O)c(=O)ccn12]

703
-continued
170BB
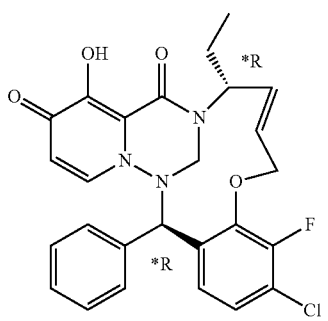
171A
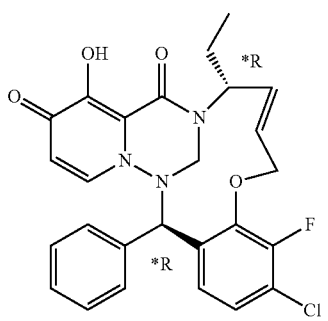
171B
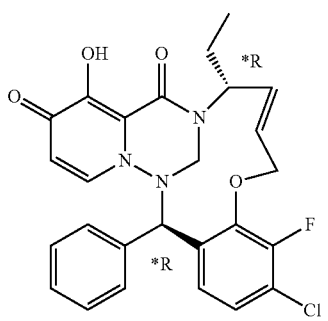
172A
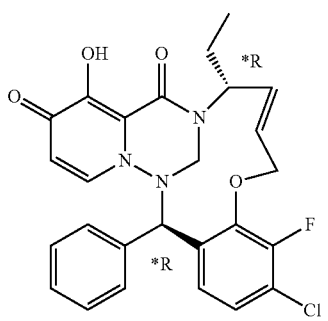
172B
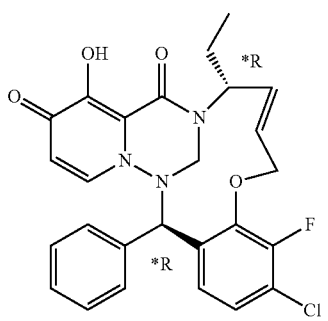
704
-continued
173AA
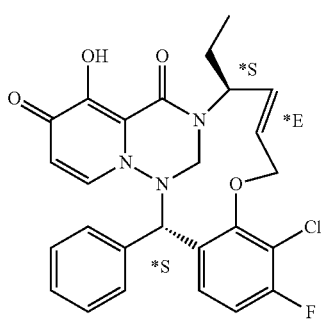
173AB
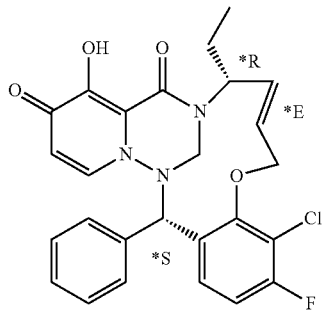
173BA
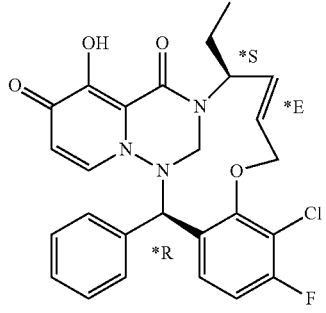
173BB
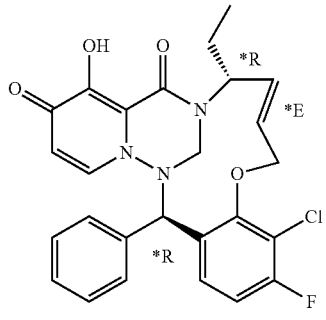
174A
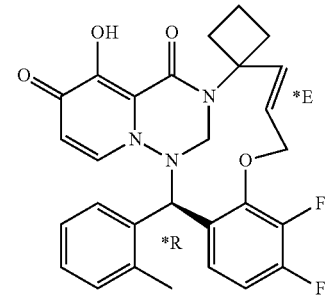 [SMILES: Cc1ccccc1[C@@H]1c2ccc(F)c(F)c2OC/C=C/C2(CCC2)N2CN1n1ccc(=O)c(O)c1C2=O]

174B
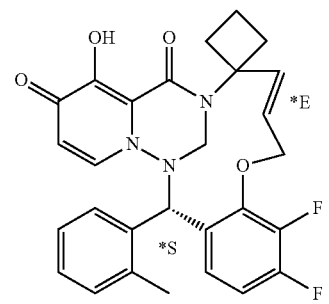 [SMILES: Cc1ccccc1[C@H]1c2ccc(F)c(F)c2OC/C=C/C2(CCC2)N2CN1n1ccc(=O)c(O)c1C2=O]
175A
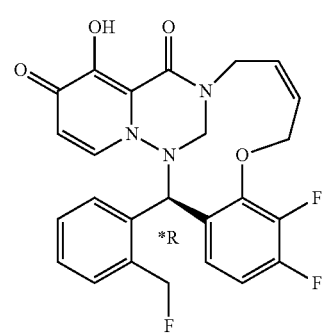 [SMILES: O=C1c2c(O)c(=O)ccn2N2CN1C/C=C\COc1c(ccc(F)c1F)[C@H]2c1ccccc1CF]
175B
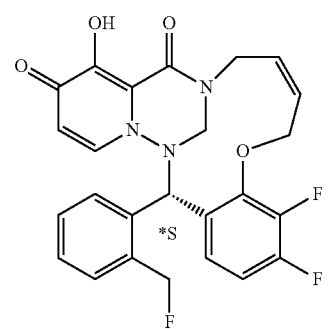
176AA
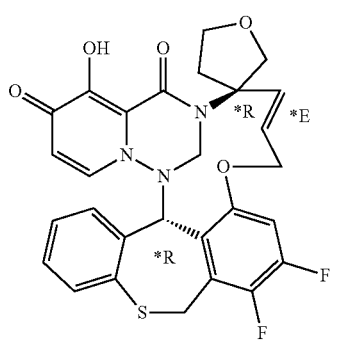
176AB
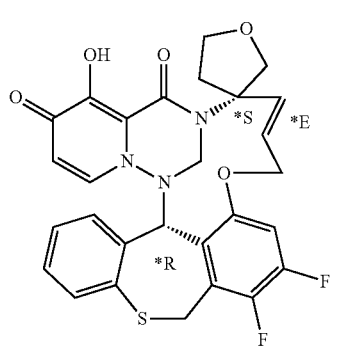
176BA
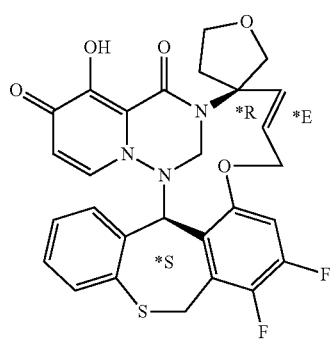
176BB
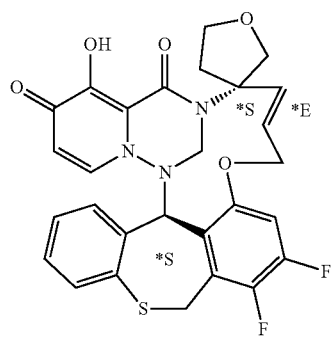
177AA
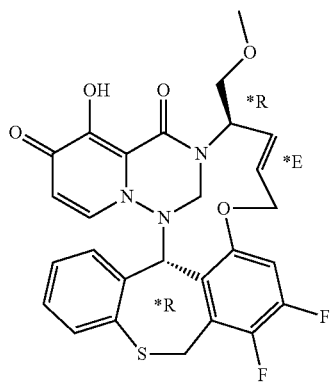
177AB
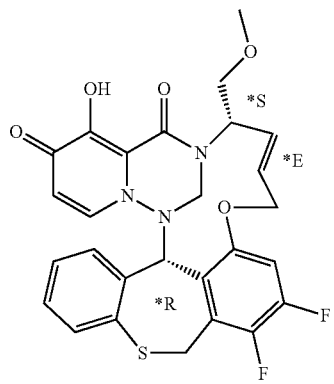

707
-continued
177BA
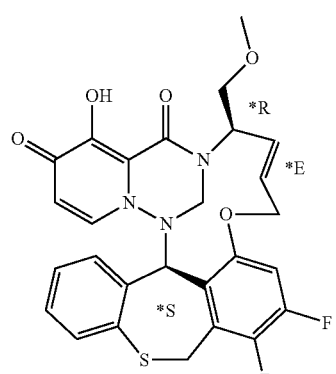
177BB
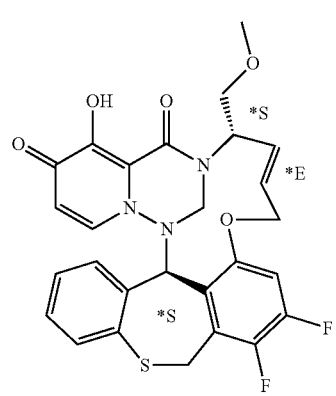
178
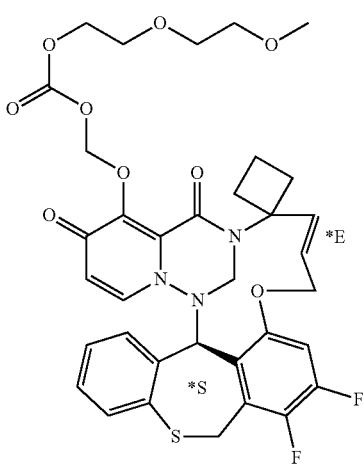 [SMILES: COCCOCCOC(=O)OCOc1c2n(ccc1=O)N1CN(C2=O)C2(/C=C/COc3cc(F)c(F)c4c3[C@H]1c1ccccc1SC4)CCC2]
708
-continued
179
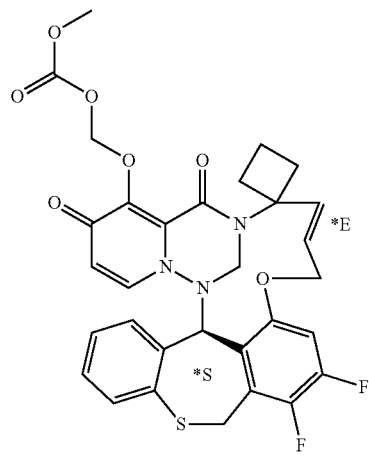 [SMILES: COC(=O)OCOc1c2n(ccc1=O)N1CN(C2=O)C2(/C=C/COc3cc(F)c(F)c4c3[C@H]1c1ccccc1SC4)CCC2]
180A
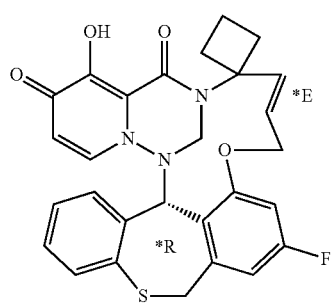
180B
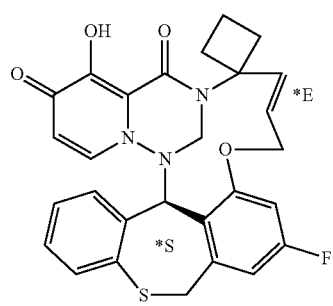
181
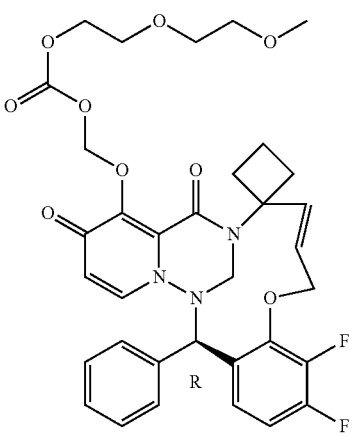

182

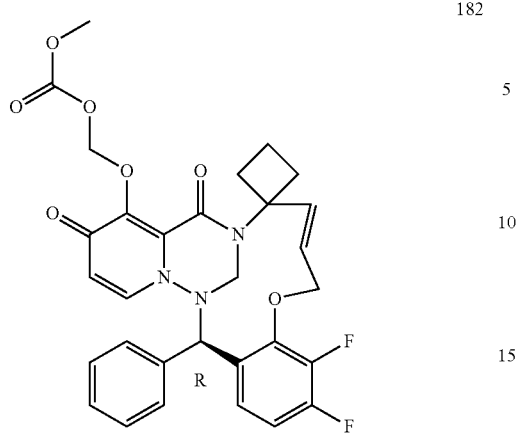

and pharmaceutically acceptable salts, polymorphs, and solvates thereof.

15. A method of treating an influenza viral infection in a subject in need thereof comprising administering to the subject a therapeutically effective amount of a compound according to claim 1 or a pharmaceutically acceptable salt, polymorph, or solvate thereof.

16. The method according to claim 15, wherein the influenza viral infection is an influenza A viral infection, and influenza B viral infection, or a combination thereof.

* * * * *